US011591342B2

United States Patent
Hu et al.

(10) Patent No.: US 11,591,342 B2
(45) Date of Patent: Feb. 28, 2023

(54) HETEROCYCLIC COMPOUND, APPLICATION THEREOF AND PHARMACEUTICAL COMPOSITION COMPRISING SAME

(71) Applicant: SUZHOU SINOVENT PHARMACEUTICALS CO., LTD., Suzhou (CN)

(72) Inventors: Yonghan Hu, Suzhou (CN); Dongdong Wu, Suzhou (CN); Wei Peng, Suzhou (CN); Xin Li, Suzhou (CN); Fan Hu, Suzhou (CN); Bin Huang, Suzhou (CN); Jinlian Zhu, Suzhou (CN); Yuchuan Wu, Suzhou (CN)

(73) Assignee: SUZHOU SINOVENT PHARMACEUTICALS CO., LTD., Jiangsu (CN)

( * ) Notice: Subject to any disclaimer, the term of this patent is extended or adjusted under 35 U.S.C. 154(b) by 14 days.

(21) Appl. No.: 16/969,183

(22) PCT Filed: Feb. 14, 2019

(86) PCT No.: PCT/CN2019/075058
§ 371 (c)(1),
(2) Date: Aug. 11, 2020

(87) PCT Pub. No.: WO2019/158107
PCT Pub. Date: Aug. 22, 2019

(65) Prior Publication Data
US 2020/0369676 A1  Nov. 26, 2020

(30) Foreign Application Priority Data

Feb. 14, 2018  (CN) .......................... 201810151433.5
May 8, 2018   (CN) .......................... 201810433630.6

(51) Int. Cl.
| C07D 487/04 | (2006.01) |
| C07D 491/048 | (2006.01) |
| C07D 401/14 | (2006.01) |
| C07D 403/14 | (2006.01) |
| C07D 417/14 | (2006.01) |
| C07D 471/04 | (2006.01) |

(52) U.S. Cl.
CPC ....... *C07D 491/048* (2013.01); *C07D 401/14* (2013.01); *C07D 403/14* (2013.01); *C07D 417/14* (2013.01); *C07D 471/04* (2013.01); *C07D 487/04* (2013.01)

(58) Field of Classification Search
CPC .................................................. C07D 487/04
See application file for complete search history.

(56) References Cited

U.S. PATENT DOCUMENTS

| 9,249,141 B2 | 2/2016 | Desroy et al. |
| 9,796,719 B2 | 10/2017 | Desroy et al. |
| 11,040,972 B2 * | 6/2021 | Jin ....................... A61K 9/0019 |

FOREIGN PATENT DOCUMENTS

| CN | 105143221 A | 12/2015 |
| CN | 105339370 A | 2/2016 |

OTHER PUBLICATIONS

Extended EP Search Report dated May 27, 2021 from EP 19754118.8.
May 15, 2019 International Search Report issued in International Patent Application No. PCT/CN2019/075058.
May 15, 2019 Written Opinion of the International Searching Authority issued in International Patent Application No. PCT/CN2019/075058.
Nicolas Desroy et al. "Discovery of 2-[[2-Ethyl-6-[-4-[2-(3-hydroxyazetidin-1-yl)-2-oxoethyl]piperazin-1-yl]-8-methylimidazo[1,2-a]pyridin-3-yl]methylamino]-4-(4-fluorophenyl)thiazole-5-carbonitrile (GLPG1690), a First-in-Class Autotaxin Inhibitor Undergoing Clinical Evaluation for the Treatment of Idiopathic Pulmonary Fibrosis", Journal of Medicinal Chemistry, vol. 60, No. 9, Apr. 17, 2017 (Apr. 17, 2017), pp. 3580-3590.
Agnes Joncour et al. "Discovery, Structure-Activity Relationship, and Binding Mode of an Imidazo[1,2-a]pyridine Series of Autotaxin Inhibitors", Journal of Medicinal Chemistry, vol. 60, No. 17, Jun. 21, 2017 (Jun. 21, 2017), pp. 7371-7392.
Berge et al., "Pharmaceutical Salts", Journal of Pharmaceutical Science 66: 1-19 (1977).

* cited by examiner

*Primary Examiner* — Brian E McDowell
(74) *Attorney, Agent, or Firm* — SZDC Law P.C.

(57) ABSTRACT

Disclosed in the present invention are a heterocyclic compound, an application thereof and a pharmaceutical composition comprising the same. Provided by the present invention are a heterocyclic compound represented by formula I or a pharmaceutically acceptable salt thereof. The compound has a novel structure and a good inhibitory activity against autotaxin (ATX).

14 Claims, No Drawings

HETEROCYCLIC COMPOUND, APPLICATION THEREOF AND PHARMACEUTICAL COMPOSITION COMPRISING SAME

This application is the national stage application of PCT/CN2019/075058, filed on Feb. 14, 2019, which claims priority to China Patent Application No. CN201810151433.5 filed on Feb. 14, 2018 and China Patent Application No. CN201810433630.6 filed on May 8, 2018, which are incorporated herein by reference in entirety.

TECHNICAL FIELD

The invention provides a heterocyclic compound, an application thereof and a pharmaceutical composition comprising the same.

BACKGROUND OF THE INVENTION

Autotaxin (ATX, also known as ENPP2 [ectonucleotide pyrophosphatase/phosphodiesterase 2] or lysophospholipase D) is a secreted lysophospholipase D (lysoPLD) that converts lysophosphatidylcholine (LPC) into bioactive phospholipid derivative lysophosphatidic acid (LPA). LPA exhibits its biological activity by signaling through a specific G protein-coupled receptor ($LPA_{1-6}$). The ATX/LPA axis has triggered considerable interest in the pharmaceutical industry due to its involvement in many physiological and pathophysiological processes. LPA and LPA receptors are involved in a variety of diseases such as fibrotic diseases (e.g. idiopathic pulmonary fibrosis, IPF), proliferative diseases, inflammatory diseases, autoimmune diseases, respiratory diseases, cardiovascular diseases, neurodegenerative diseases, dermatological diseases, and diseases associated with abnormal angiogenesis.

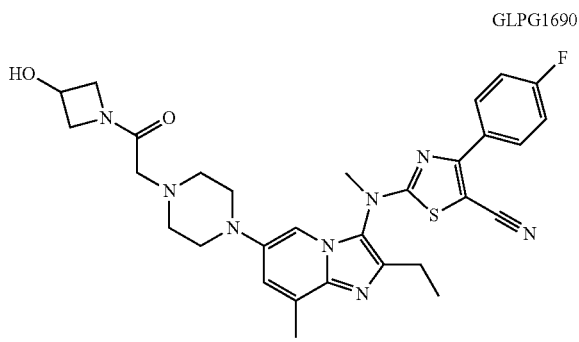 [SMILES: CCc1nc2c(C)cc(N3CCN(CC(=O)N4CC(O)C4)CC3)cn2c1N(C)c1nc(-c2ccc(F)cc2)c(C#N)s1]

GLPG1690

According to Galapagos Publication No. GLPG1690, they have an inhibitory effect on ATX and are useful for the treatment of idiopathic pulmonary fibrosis (IPF).

Therefore, there is an urgent need in the art for compounds with novel structures and good ATX inhibitory activities.

SUMMARY OF THE INVENTION

To overcome issues that might arise from the homogeneous structure of existing ATX inhibitors, the present invention provides a heterocyclic compound, an application thereof and a pharmaceutical composition comprising the same. The compound has a novel structure and good ATX inhibitory activity.

The invention provides a heterocyclic compound of formula I or a pharmaceutically acceptable salt thereof; wherein,

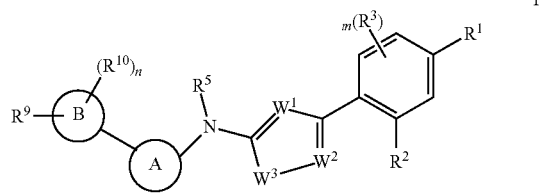

I $R^1$ is hydrogen, cyano, or halogen (for example, fluorine, chlorine, bromine, or iodine, and preferably, for example, fluorine), $C_1$-$C_4$ alkyl, halogen-substituted $C_1$-$C_4$ alkyl (there can be one or more, such as 2, 3 or 4, halogens, and in case that there are a plurality of halogens, the plurality of halogens are the same or different; the halogens are independently selected from fluorine, chlorine, bromine, and iodine, and preferably, for example, fluorine; the "$C_1$-$C_4$ alkyl" is, for example, methyl, ethyl, n-propyl, isopropyl, n-butyl, isobutyl, sec-butyl, or tert-butyl, and preferably, for example, methyl or ethyl; and the "halogen-substituted $C_1$-$C_4$ alkyl" is, for example, 2-fluoroethyl, 2,2-difluoroethyl, or 2,2,2-trifluoroethyl), $C_1$-$C_4$ alkoxy, or halogen-substituted $C_1$-$C_4$ alkoxy (there can be one or more, such as 2, 3 or 4, halogens, and in case that there are a plurality of halogens, the plurality of halogens are the same or different; the halogens are independently selected from, e.g., fluorine, chlorine, bromine, and iodine, and preferably, e.g., fluorine; the "$C_1$-$C_4$ alkoxy" is, for example, methoxy, ethoxy, n-propoxy, isopropoxy, n-butoxy, isobutoxy, sec-butoxy or tert-butoxy, and preferably, for example, methoxy or ethoxy; and the "halogen-substituted $C_1$-$C_4$ alkoxy" is, for example, 2-fluoroethoxy, 2,2-difluoroethoxy, or 2,2,2-trifluoroethoxy);

m is 0, 1, 2, or 3, and $R^3$ is independently selected from halogen (e.g., fluorine, chlorine, bromine, or iodine, and preferably, e.g., fluorine), cyano, $R^{3-1}$-substituted or unsubstituted $C_1$-$C_4$ alkyl (there are one or more $R^{3-1}$, and in case that there are a plurality of $R^{3-1}$, the plurality of $R^{3-1}$ are the same or different; and the "$C_1$-$C_4$ alkyl" is, e.g., methyl, ethyl, n-propyl, isopropyl, n-butyl, isobutyl, sec-butyl, or tert-butyl, and preferably, e.g., methyl), and $R^{3-2}$-substituted or unsubstituted $C_1$-$C_4$ alkoxy (there can be one or more $R^{3-2}$ and in case that there are a plurality of $R^{3-2}$, the plurality of $R^{3-2}$ are the same or different); $R^{3-1}$ and $R^{3-2}$ are each independently selected from halogens; [$R^3$ may be independently located at the ortho or meta position relative to $R^1$; when m is 1, $R^3$ may be located at the ortho or meta position relative to $R^1$]

$W^1$ is =CH— or =N—;
$W^2$ is =$CR^4$— or =N—;
$W^3$ is —O—, —S—, —NH—, —N=CH—, —CH=N—, or —CH=CH—;

when $W^2$ is =N—, $R^2$ is hydrogen, cyano, halogen (e.g., fluorine, chlorine, bromine, or iodine, preferably, e.g., fluorine), $R^{2-1}$-substituted or unsubstituted $C_1$-$C_4$ alkyl (there can be one or more $R^{2-1}$, and in case that there are a plurality of $R^{2-1}$, the plurality of $R^{2-1}$ are the same or different; and the "$C_1$-$C_4$ alkyl" is, e.g., methyl, ethyl, n-propyl, isopropyl, n-butyl, isobutyl, sec-butyl or tert-butyl, and preferably, e.g., methyl), —C(=O)$CH_3$, —C(=O)$CF_3$, —C(=O)$OCH_3$, —C(=O)NH$_2$, or —NHC(=O)CH$_3$; R$^{2-1}$ is independently selected from hydroxy and cyano;

when W$^2$ is =CR$^4$—, one of R$^2$ or R$^4$, e.g., R$^4$, is hydrogen, cyano, halogen (e.g., fluorine, chlorine, bromine, or iodine, and preferably, e.g., fluorine), R$^{2-2}$-substituted or unsubstituted C$_1$-C$_4$ alkyl (there can be one or more R$^{2-2}$, and in case that there are a plurality of R$^{2-2}$, the plurality of R$^{2-2}$ are the same or different), —C(=O)CH$_3$, —C(=O)CF$_3$, —C(=O)OCH$_3$, —C(=O)NH$_2$, or —NHC(=O)CH$_3$, and the other one, such as R$^2$, is hydrogen or C$_1$-C$_4$ alkyl; R$^{2-2}$ is independently selected from hydroxy and cyano;

R$^5$ is halogen-substituted C$_1$-C$_4$ alkyl (there can be one or more, such as 2, 3, or 4, halogens, and in case that there are a plurality of halogens, the plurality of halogens are the same or different; the halogens are independently selected from fluorine, chlorine, bromine, and iodine, and preferably, for example, fluorine; the "C$_1$-C$_4$ alkyl" is, e.g., methyl, ethyl, n-propyl, isopropyl, n-butyl, isobutyl, sec-butyl, or tert-butyl, and preferably, e.g., methyl or ethyl; and the "halogen-substituted C$_1$-C$_4$ alkyl" is, for example, 2-fluoroethyl, 2,2-difluoroethyl, or 2,2,2-trifluoroethyl, and preferably, for example, 2-fluoroethyl or 2,2-difluoroethyl), or C$_1$-C$_4$ alkyl (for example, methyl, ethyl, n-propyl, isopropyl, n-butyl, isobutyl, sec-butyl, or tert-butyl, preferably, for example, methyl or ethyl, and more preferably, for example, ethyl); ring A is

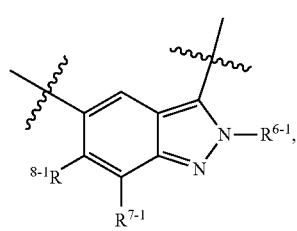

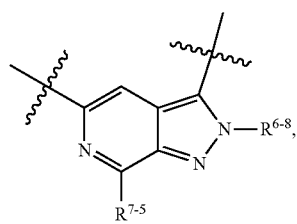

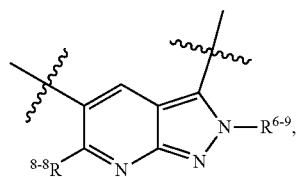

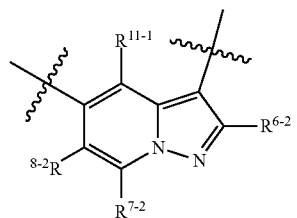

(e.g. 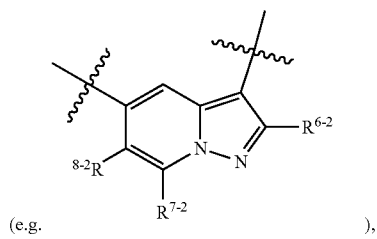 ),

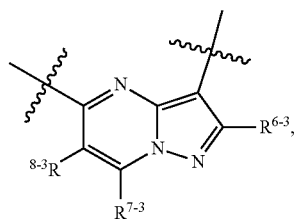

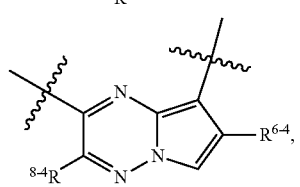

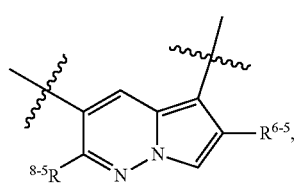

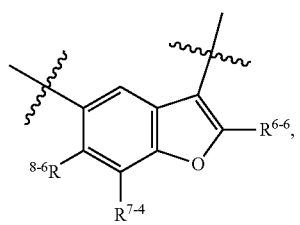

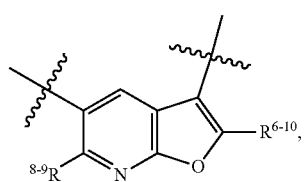

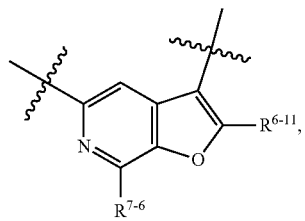

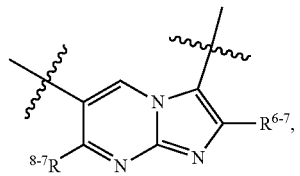

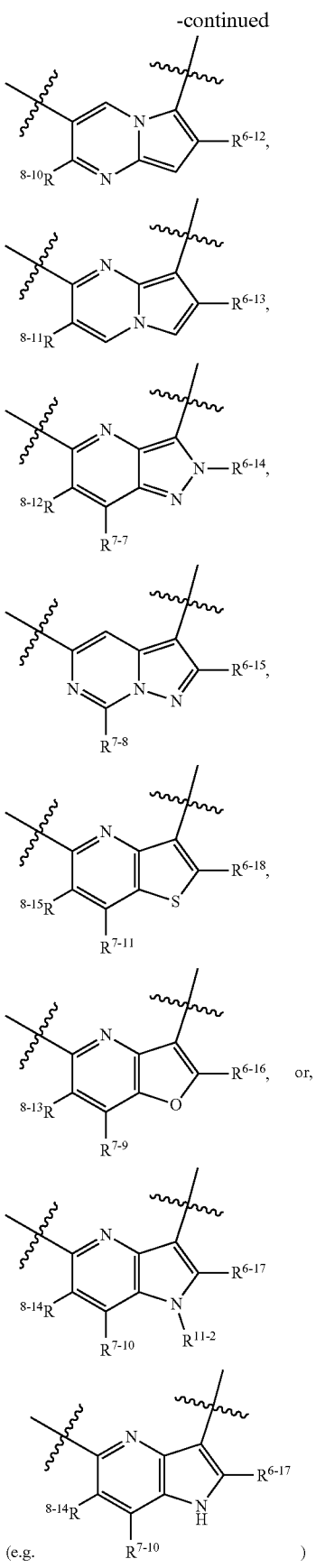

[the left terminus is linked to ring B];

$R^{6-1}$, $R^{6-2}$, $R^{6-3}$, $R^{6-4}$, $R^{6-5}$, $R^{6-6}$, $R^{6-7}$, $R^{6-8}$, $R^{6-9}$, $R^{6-10}$, $R^{6-11}$, $R^{6-12}$, $R^{6-13}$, $R^{6-14}$, $R^{6-15}$, $R^{6-16}$, $R^{6-17}$, and $R^{6-18}$ are each independently selected from hydrogen, $R^{6-1-1}$-substituted or unsubstituted $C_1$-$C_4$ alkyl (there can be one or more $R^{6-1-1}$, and in case that there are a plurality of $R^{6-1-1}$, the plurality of $R^{6-1-1}$ are the same or different; and the "$C_1$-$C_4$alkyl" is, for example, methyl, ethyl, n-propyl, isopropyl, n-butyl, isobutyl, sec-butyl, or tert-butyl, preferably, for example, methyl, ethyl, or isopropyl, and more preferably, for example, methyl or ethyl), and $C_3$-$C_6$ cycloalkyl(e.g., cyclopropyl, cyclobutyl, cyclopentyl, or cyclohexyl, and preferably, e.g., cyclopropyl); $R^{6-1-1}$ is independently selected from hydroxy, cyano, halogen, and —C(=O)NH$_2$;

$R^{7-1}$, $R^{7-2}$, $R^{7-3}$, $R^{7-4}$, $R^{7-5}$, $R^{7-6}$, $R^{7-7}$, $R^{7-8}$, $R^{7-9}$, $R^{7-10}$, and $R^{7-11}$ are each independently selected from hydrogen, cyano, halogen (e.g., fluorine, chlorine, bromine, or iodine, and preferably, e.g., fluorine), $C_1$-$C_4$ alkyl(e.g., methyl, ethyl, n-propyl, isopropyl, n-butyl, isobutyl, sec-butyl, or tert-butyl, and preferably, e.g., methyl), and halogen-substituted $C_1$-$C_4$alkyl (there are one or more, such as 2, 3 or 4, halogens, and in case that there are a plurality of halogens, the plurality of halogens are the same or different; the halogens are independently selected from fluorine, chlorine, bromine, and iodine, and preferably, for example, fluorine; the "$C_1$-$C_4$ alkyl" is, e.g., methyl, ethyl, n-propyl, isopropyl, n-butyl, isobutyl, sec-butyl or tert-butyl, and preferably, e.g., methyl or ethyl; and the "halogen-substituted $C_1$-$C_4$ alkyl" is, for example, 2-fluoroethyl, 2,2-difluoroethyl, or 2,2,2-trifluoroethyl);

$R^{8-1}$, $R^{8-2}$, $R^{8-3}$$R^{8-4}$, $R^{8-5}$$R^{8-6}$, $R^{8-7}$, $R^{8-8}$$R^{8-9}$$R^{8-10}$, $R^{8-11}$, $R^{8-12}$, $R^{8-13}$, $R^{8-14}$, and $R^{8-15}$ are each independently selected from hydrogen, cyano, halogen (e.g., fluorine, chlorine, bromine, and iodine, and preferably, e.g., fluorine), $C_1$-$C_4$ alkyl (e.g., methyl, ethyl, n-propyl, isopropyl, n-butyl, isobutyl, sec-butyl, or tert-butyl, and preferably, e.g., methyl), and halogen-substituted $C_1$-$C_4$ alkyl (there are one or more, such as 2, 3, or 4, halogens, and in case that there are a plurality of halogens, the plurality of halogens are the same or different; the halogens are independently selected from fluorine, chlorine, bromine, and iodine, and preferably, for example, fluorine; the "$C_1$-$C_4$ alkyl" is, e.g., methyl, ethyl, n-propyl, isopropyl, n-butyl, isobutyl, sec-butyl or tert-butyl, and preferably, e.g., methyl or ethyl; and the "halogen-substituted $C_1$-$C_4$ alkyl" is, for example, 2-fluoroethyl, 2,2-difluoroethyl, or 2,2,2-trifluoroethyl);

$R^{11-1}$ is hydrogen or halogen (e.g., fluorine, chlorine, bromine, or iodine, and preferably, e.g., fluorine);

$R^{11-2}$ is hydrogen, $C_1$-$C_4$ alkyl (e.g., methyl, ethyl, n-propyl, isopropyl, n-butyl, isobutyl, sec-butyl, or tert-butyl, and preferably, e.g., methyl), or halogen-substituted $C_1$-$C_4$ alkyl (there can be one or more, such as 2, 3 or 4, halogens, and in case that there are a plurality of halogens, the halogens are the same or different; the halogen is independently selected from fluorine, chlorine, bromine, and iodine, and preferably, for example, fluorine; the "$C_1$-$C_4$ alkyl" is, e.g., methyl, ethyl, n-propyl, isopropyl, n-butyl, isobutyl, sec-butyl, or tert-butyl, and preferably, e.g., methyl or ethyl; and the "halogen-substituted $C_1$-$C_4$ alkyl" is, for example, 2-fluoroethyl, 2,2-difluoroethyl, or 2,2,2-trifluoroethyl);

ring B is $C_3$-$C_{10}$ cycloalkyl (e.g., $C_3$-$C_6$ cycloalkyl, preferably, e.g., $C_5$-$C_6$ cycloalkyl), $C_4$-$C_7$ cycloalkenyl (e.g., $C_5$-$C_6$ cycloalkenyl, preferably, e.g., cyclohexenyl, preferably, e.g.,

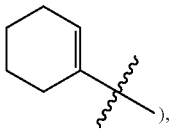

"4-10 membered monocyclic or bicyclic heterocycloalkyl having 1-3 heteroatoms selected from one or more of O, N, and S" (e.g., "4-7 membered monocyclic heterocycloalkyl having 1-2 heteroatoms selected from one or more of O, N, and S", preferably, e.g., "5-6 membered monocyclic heterocycloalkyl having 1-2 heteroatoms selected from one or more of O, N, and S", more preferably, e.g., "

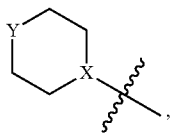

wherein X is N or CH and Y is NH or $CH_2$, which are not both carbon", most preferably, e.g.,

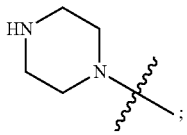

and the heterocycloalkyl may be linked to ring A via a carbon atom or a nitrogen atom, and preferably may be linked to ring A via a nitrogen atom), or "4-7 membered heterocycloalkenyl having 1 double bond and 1-3 heteroatoms selected from one or more of O, N, and S" (e.g., "5-6 membered heterocycloalkenyl having 1 double bond and 1-2 heteroatoms selected from one or more of O, N, and S", preferably, e.g.,

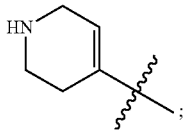

and the heterocycloalkenyl may be linked to ring A via a carbon atom or nitrogen atom [unless otherwise stated, the "carbon atom or nitrogen atom" used herein refers to an atom of ring B], and preferably via a nitrogen atom);

$R^9$ is -$L^1$-$L^2$-$L^3$; [when ring B is 6-membered heterocycloalkyl or heterocycloalkenyl, $R^9$ may be located at the ortho, the meta, or the para position relative to ring A, preferably at the para position relative to ring A; and $R^9$ may be linked to a carbon atom or a nitrogen atom of ring B (i.e., replacing a hydrogen on the carbon atom or the nitrogen atom), preferably linked to a nitrogen atom of ring B].

$L^1$ is a single bond (i.e., $L^2$ and ring B are directly linked), or $C_1$-$C_4$ alkylene (for example, —$CH_2$—, —$CH_2CH_2$—, —$CH(CH_3)$— [wherein the chiral carbon atom may be in R configuration or S configuration], —$CH_2CH_2CH_2$—, or —$CH_2CH(CH_3)$— [wherein the chiral carbon atom may be in R configuration or S configuration]);

$L^2$ is —O—, —C(=O)O—, —OC(=O)—, —C(=O)—$CH_2$— [the left terminus of which is linked to $L^1$], —C(=O)—C(=O)—, —C(=O)—C(=O)$NR^{L-1}$—, —$NR^{L-2}$—, —C(=O)$NR^{L-3}$—, —$NR^{L-4}$C(O)—, —$NR^{L-5}$C(O)O—, —$SO_2$—, —$SO_2NR^{L-6}$—, or —$NR^{L-7}SO_2$— [the left terminus of which is linked to $L^1$]; $R^{L-1}$, $R^{L-2}$, $R^{L-3}$, $R^{L-4}$, $R^{L-5}$, $R^{L-6}$ and $R^{L-7}$ are each independently selected from hydrogen and $C_1$-$C_4$ alkyl (e.g., methyl, ethyl, n-propyl, isopropyl, n-butyl, isobutyl, sec-butyl, or tert-butyl, preferably, e.g., methyl);

$L^3$ is hydrogen, cyano, $R^{L-8}$-substituted or unsubstituted $C_1$-$C_4$ alkyl (there can be one or more $R^{L-8}$, and in case that there are a plurality of $R^{L-8}$, the plurality of $R^{L-8}$ are the same or different; and the $C_1$-$C_4$ alkyl is, e.g., methyl, ethyl, n-propyl, isopropyl, n-butyl, isobutyl, sec-butyl or tert-butyl, and preferably, e.g., methyl or ethyl), amino-substituted or unsubstituted $C_3$-$C_7$ cycloalkyl (there can be one or more aminos), "4-10 membered monocyclic, bicyclic or spirocyclic heterocycloalkyl having 1-3 heteroatoms selected from one or more of O, N, and S" which is substituted or unsubstituted with $R^{L-9}$ (the "4-10 membered monocyclic, bicyclic or spirocyclic heterocycloalkyl having 1-3 heteroatoms selected from one or more of O, N, and S" is, e.g., "4-10 membered monocyclic heterocycloalkyl having 1-2 heteroatoms selected from one or more of O, N and S", preferably, e.g., "4-6 membered monocyclic heterocycloalkyl having 1-2 heteroatoms selected from one or more of O, N, and S", and more preferably, e.g.,

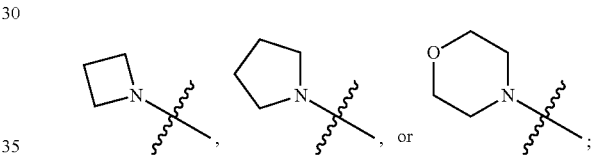

the "4-10 membered monocyclic, bicyclic or spirocyclic heterocycloalkyl having 1-3 heteroatoms selected from one or more of O, N, and S" which is substituted with $R^{L-9}$ is, e.g.,

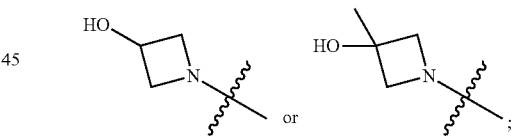

there can be one or more, such as 2, 3, or 4, $R^{L-9}$, and in case that there are a plurality of $R^{L-9}$, the plurality of $R^{L-9}$ are the same or different; and the heterocycloalkyl can be linked to $L^2$ via a carbon atom or a nitrogen atom [unless otherwise stated, the "carbon atom or nitrogen atom" used herein refers to an atom on the heterocycloalkyl], and preferably via a nitrogen atom), "5-6 membered heterocycloalkenyl having 1 double bond and 1-3 heteroatoms selected from one or more of O, N and S" which is substituted or unsubstituted with $R^{L-10}$ (the "5-6 membered heterocycloalkenyl having 1 double bond and 1-3 heteroatoms selected from one or more of O, N, and S" is, e.g., "5-6 membered heterocycloalkenyl having 1 double bond and 1-2 heteroatoms selected from one or more of O, N, and S"; there can be one or more $R^{L-10}$, and in case that there are a plurality of $R^{L-10}$, the plurality of $R^{L-10}$ are the same or different; the heterocycloalkenyl may be linked to $L^2$ via a carbon atom or a nitrogen atom [unless otherwise stated, the "carbon atom or nitrogen atom" used herein refers to an atom on the heterocycloalkenyl], and preferably via a nitrogen atom), or "5-6 membered heteroaryl having 1-3 heteroatoms selected from one or more of O, N, and S" which is substituted or unsubstituted with $R^{L-1}$ (the "5-6 membered heteroaryl having 1-3 heteroatoms selected from one or more of O, N, and S" is, e.g., "5-6 membered heteroaryl having 1-2 heteroatoms selected from one or more of O, N, and S"; there can be one or more $R^{L-1}$, and in case that there are a plurality of $R^{L-1}$, the plurality of $R^{L-1}$ are the same or different; the heteroaryl may be linked to $L^2$ via a carbon atom or a nitrogen atom [unless otherwise stated, the "carbon atom or nitrogen atom" used herein refers to an atom on the heteroaryl], and preferably via a nitrogen atom);

$R^{L-8}$ is independently selected from hydroxy, cyano, halogen, and phenyl;

$R^{L-9}$ is independently selected from oxo, hydroxy, cyano, halogen (e.g., fluorine, chlorine, bromine, or iodine, and preferably, e.g., fluorine), phenyl, $C_1$-$C_4$ alkyl (e.g., methyl, ethyl, n-propyl, isopropyl, n-butyl, isobutyl, sec-butyl, or tert-butyl, and preferably, e.g., methyl), hydroxy-substituted $C_1$-$C_4$ alkyl (there can be one or more hydroxys; the "$C_1$-$C_4$ alkyl" is, e.g., methyl, ethyl, n-propyl, isopropyl, n-butyl, isobutyl, sec-butyl, or tert-butyl, and preferably, e.g., methyl; and the hydroxy-substituted "$C_1$-$C_4$ alkyl" is, e.g., hydroxymethyl), —$SO_2CH_3$, —$C(=O)R^{L-9-1}$, and —$NR^{L-9-2}C(=O)R^{L-9-3}$; $R^{L-9-1}$ is independently selected from $C_1$-$C_4$ alkyl and $C_1$-$C_4$ alkoxy; $R^{L-9-2}$ is independently selected from hydrogen and $C_1$-$C_4$ alkyl; $R^{L-9-3}$ is independently selected from $C_1$-$C_4$ alkyl; [$R^{L-9}$ may be linked to a carbon atom or a nitrogen atom in heterocycloalkyl; the carbon atom in the heterocycloalkyl, linked to $R^{L-9}$, can be independently selected from a chiral carbon atom in either R configuration or S configuration]

$R^{L-10}$ is independently selected from oxo, hydroxy, cyano, halogen, phenyl, —$SO_2CH_3$, —$C(=O)R^{L-10-1}$ and —$NR^{L-10-2}C(=O)R^{L-10-3}$; $R^{L-10-1}$ is independently selected from $C_1$-$C_4$ alkyl and $C_1$-$C_4$ alkoxy; $R^{L-10-2}$ is independently selected from hydrogen and $C_1$-$C_4$ alkyl; $R^{L-10-3}$ is independently selected from $C_1$-$C_4$ alkyl; [$R^{L-10}$ may be linked to a carbon atom or a nitrogen atom of heterocycloalkenyl; the carbon atom, linked to $R^{L-10}$, of the heterocycloalkenyl may be independently selected from a chiral carbon atom, either in R configuration or S configuration]

$R^{L-11}$ is independently selected from hydroxy, cyano, halogen, phenyl, —$SO_2CH_3$, —$C(=O)R^{L-11-1}$ and —$NR^{L-11-2}C(=O)R^{L-11-3}$; $R^{L-11-1}$ is independently selected from $C_1$-$C_4$ alkyl and $C_1$-$C_4$ alkoxy; $R^{L-11-2}$ is independently selected from hydrogen and $C_1$-$C_4$ alkyl; $R^{L-11-3}$ is independently selected from $C_1$-$C_4$ alkyl; and n is 0, 1, 2, 3, or 4, $R^{10}$ is independently selected from hydroxy, halogen (e.g., fluorine, chlorine, bromine, or iodine, and preferably, e.g., fluorine), oxo, and $R^{10-1}$-substituted or unsubstituted $C_1$-$C_4$ alkyl (there can be one or more $R^{10-1}$, and in case that there are a plurality of $R^{10-1}$, the plurality of $R^{10-1}$ are the same or different; the "$C_1$-$C_4$ alkyl" is, e.g., methyl, ethyl, n-propyl, isopropyl, n-butyl, isobutyl, sec-butyl, or tert-butyl, and preferably, e.g., methyl; and the "$R^{10-1}$-substituted $C_1$-$C_4$ alkyl" is, e.g., trifluoromethyl); $R^{10-1}$ is independently selected from halogen (e.g., fluorine, chlorine, bromine, or iodine, and preferably, e.g., fluorine), hydroxy, and $C_1$-$C_4$ alkoxy. [$R^{10}$ may be independently located at the ortho, meta, or para position relative to ring A, and preferably at the ortho or meta position relative to ring A; when n is 1, $R^{10}$ may be located at the ortho or the meta position relative to ring A; $R^{10}$ may be linked to a carbon atom or a nitrogen atom of ring B; and the carbon atom of ring B, linked to $R^{10}$, may be independently selected from a chiral carbon atom, either in R configuration or S configuration]

In one embodiment, certain groups of compound of formula I are defined as follows, and groups not mentioned are defined in any of the above embodiments:

$R^1$ is hydrogen, cyano, halogen (for example, fluorine, chlorine, bromine, or iodine, and preferably, for example, fluorine), halogen-substituted $C_1$-$C_4$ alkyl (there can be one or more, such as 2, 3, or 4, halogens, and in case that there are a plurality of halogens, the plurality of halogens are the same or different; the halogens are independently selected from fluorine, chlorine, bromine, and iodine, and preferably, for example, fluorine; the "$C_1$-$C_4$ alkyl" is, for example, methyl, ethyl, n-propyl, isopropyl, n-butyl, isobutyl, sec-butyl, or tert-butyl, and preferably, for example, methyl or ethyl; and the "halogen-substituted $C_1$-$C_4$ alkyl" is, for example, 2-fluoroethyl, 2,2-difluoroethyl, or 2,2,2-trifluoroethyl), or halogen-substituted $C_1$-$C_4$ alkoxy (there can be one or more, such as 2, 3 or 4, halogens, and in case that there are a plurality of halogens, the plurality of halogens are the same or different; the halogens are independently selected from, e.g., fluorine, chlorine, bromine, and iodine, and preferably, e.g., fluorine; the "$C_1$-$C_4$ alkoxy" is, for example, methoxy, ethoxy, n-propoxy, isopropoxy, n-butoxy, isobutoxy, sec-butoxy or tert-butoxy, and preferably, for example, methoxy or ethoxy; and the "halogen-substituted $C_1$-$C_4$ alkoxy" is, for example, 2-fluoroethoxy, 2,2-difluoroethoxy, or 2,2,2-trifluoroethoxy).

In one embodiment, certain groups of compound of formula I are defined as follows, and groups not mentioned are defined in any of the above embodiments:

$R^1$ is halogen (e.g., fluorine, chlorine, bromine, or iodine, and preferably, e.g., fluorine).

In one embodiment, certain groups of compound of formula I are defined as follows, and groups not mentioned are defined in any of the above embodiments:

m is 0 or 1, and $R^3$ is halogen (e.g., fluorine, chlorine, bromine, or iodine, and preferably, e.g., fluorine). [when m is 1, $R^3$ may be located at the ortho position or the meta position relative to $R^1$]

In one embodiment, certain groups of compound of formula I are defined as follows, and groups not mentioned are defined in any of the above embodiments:

$W^1$ is =N—.

In one embodiment, certain groups of compound of formula I are defined as follows, and groups not mentioned are defined in any of the above embodiments:

$W^2$ is =$CR^4$—.

In one embodiment, certain groups of compound of formula I are defined as follows, and groups not mentioned are defined in any of the above embodiments:

when $W^2$ is =N—, $R^2$ is hydrogen.

In one embodiment, certain groups of compound of formula I are defined as follows, and groups not mentioned are defined in any of the above embodiments:

when $W^2$ is =$CR^4$—, one of $R^2$ and $R^4$, such as $R^4$, is hydrogen or cyano, and the other one, such as $R^2$, is hydrogen.

In one embodiment, certain groups of compound of formula I are defined as follows, and groups not mentioned are defined in any of the above embodiments:

when $W^2$ is =$CR^4$—, one of $R^2$ and $R^4$, such as $R^4$, is cyano, and the other one, such as $R^2$, is hydrogen.

In one embodiment, certain groups of compound of formula I are defined as follows, and groups not mentioned are defined in any of the above embodiments:

when $W^2$ is $=CR^4-$, $R^2$ is hydrogen, and $R^4$ is cyano.

In one embodiment, certain groups of compound of formula I are defined as follows, and groups not mentioned are defined in any of the above embodiments:

$W^3$ is $-O-$, $-S-$, or $-NH-$.

In one embodiment, certain groups of compound of formula I are defined as follows, and groups not mentioned are defined in any of the above embodiments:

$W^3$ is $-S-$.

In one embodiment, certain groups of compound of formula I are defined as follows, and groups not mentioned are defined in any of the above embodiments:

$R^5$ is methyl, ethyl, 2-fluoroethyl, or 2,2-difluoroethyl.

In one embodiment, certain groups of compound of formula I are defined as follows, and groups not mentioned are defined in any of the above embodiments:

$R^5$ is ethyl, 2-fluoroethyl, or 2,2-difluoroethyl.

In one embodiment, certain groups of compound of formula I are defined as follows, and groups not mentioned are defined in any of the above embodiments:

ring A is

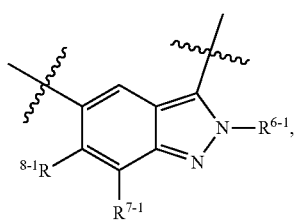

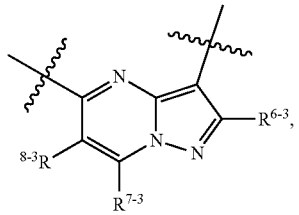

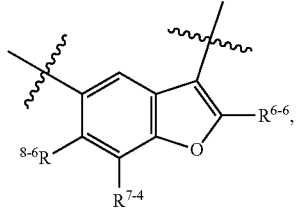

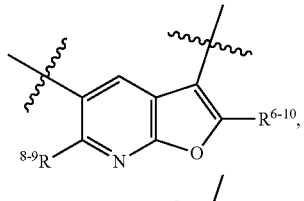

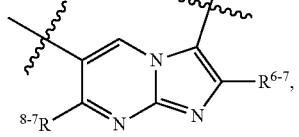

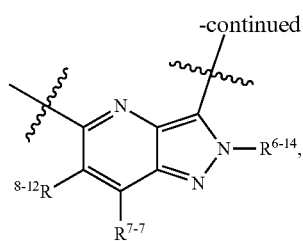

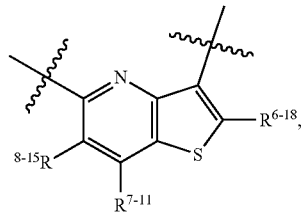

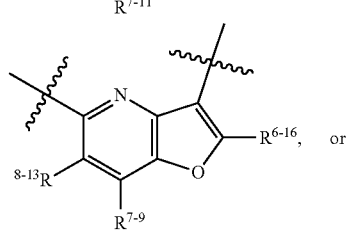

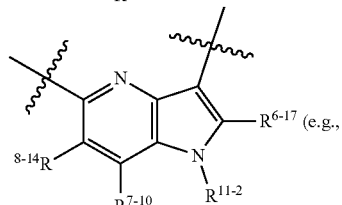

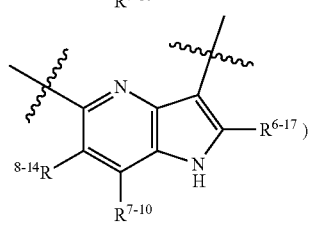

[the left terminus of which is linked to ring B];

$R^{6-1}$, $R^{6-3}$, $R^{6-6}$, $R^{6-7}$, $R^{6-10}$, $R^{6-14}$, $R^{6-16}$, $R^{6-17}$, and $R^{6-18}$ are each independently selected from $C_1$-$C_4$ alkyl (e.g., methyl, ethyl, n-propyl, isopropyl, n-butyl, isobutyl, sec-butyl, or tert-butyl, preferably, e.g., methyl, ethyl, or isopropyl, and more preferably, e.g., methyl or ethyl), and $C_3$-$C_6$ cycloalkyl (e.g., cyclopropyl, cyclobutyl, cyclopentyl, or cyclohexyl, and preferably, e.g., cyclopropyl);

$R^{7-1}$, $R^{7-3}$, $R^{7-4}$, $R^{7-7}$, $R^{7-9}$, $R^{7-10}$, and $R^{7-11}$ are each independently selected from hydrogen, halogen (e.g., fluorine, chlorine, bromine, or iodine, and preferably, e.g., fluorine), $C_1$-$C_4$ alkyl (e.g., methyl, ethyl, n-propyl, isopropyl, n-butyl, isobutyl, sec-butyl, or tert-butyl, and preferably, e.g., methyl), and halogen-substituted $C_1$-$C_4$ alkyl (there can be one or more, such as 2, 3, or 4, halogens, and in case that there are a plurality of halogens, the plurality of halogens are the same or different; the halogens are independently selected from fluorine, chlorine, bromine, and iodine, and preferably, e.g., fluorine; the "$C_1$-$C_4$ alkyl" is, e.g., methyl, ethyl, n-propyl, isopropyl, n-butyl, isobutyl, sec-butyl, or tert-butyl, and preferably, e.g., methyl or ethyl; and the "halogen-substituted $C_1$-$C_4$ alkyl" is, e.g., 2-fluoroethyl, 2,2-difluoroethyl, or 2,2,2-trifluoroethyl);

$R^{8-1}$, $R^{8-3}$, $R^{8-6}$, $R^{8-7}$, $R^{8-9}$, $R^{8-12}$, $R^{8-13}$, $R^{8-14}$, and $R^{8-15}$ are each independently selected from hydrogen and halogen-substituted C$_1$-C$_4$ alkyl (there can be one or more, such as 2, 3 or 4, halogens, and in case that there are a plurality of halogens, the plurality of halogens are the same or different; the halogens are independently selected from fluorine, chlorine, bromine, and iodine, and preferably, e.g., fluorine; the "C$_1$-C$_4$ alkyl" is, e.g., methyl, ethyl, n-propyl, isopropyl, n-butyl, isobutyl, sec-butyl, or tert-butyl, and preferably, e.g., methyl or ethyl; and the "halogen-substituted C$_1$-C$_4$ alkyl" is, e.g., 2-fluoroethyl, 2,2-difluoroethyl, or 2,2,2-trifluoroethyl); and R$^{11-2}$ is hydrogen, C$_1$-C$_4$ alkyl (e.g., methyl, ethyl, n-propyl, isopropyl, n-butyl, isobutyl, sec-butyl, or tert-butyl, and preferably, e.g., methyl), or halogen-substituted C$_1$-C$_4$ alkyl (there can be one or more, such as 2, 3, or 4, halogens, and in case that there are a plurality of halogens, the plurality of halogens are the same or different; the halogen is independently selected from fluorine, chlorine, bromine, and iodine, and preferably, for example, fluorine; the "C$_1$-C$_4$ alkyl" is, e.g., methyl, ethyl, n-propyl, isopropyl, n-butyl, isobutyl, sec-butyl, or tert-butyl, and preferably, e.g., methyl or ethyl; and the "halogen-substituted C$_1$-C$_4$ alkyl" is, for example, 2-fluoroethyl, 2,2-difluoroethyl, or 2,2,2-trifluoroethyl).

In one embodiment, certain groups of compound of formula I are defined as follows, and groups not mentioned are defined in any of the above embodiments:

ring A is

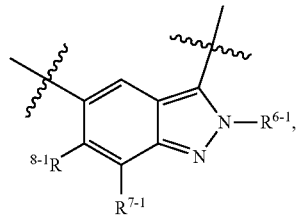

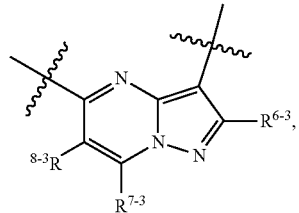

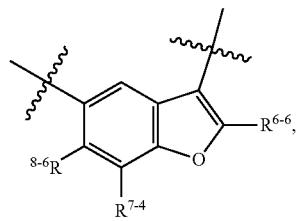

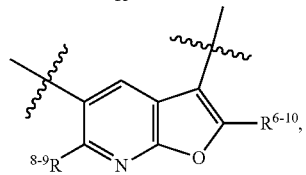

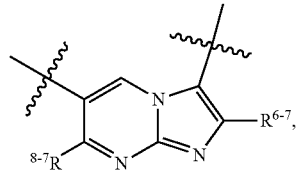

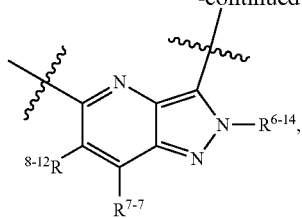

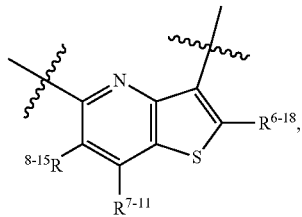

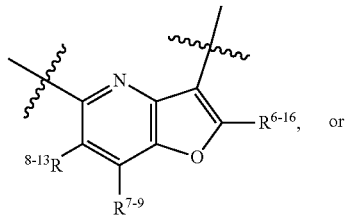

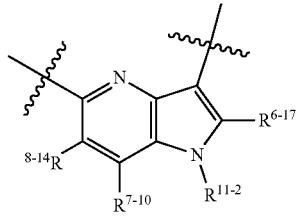

(e.g., 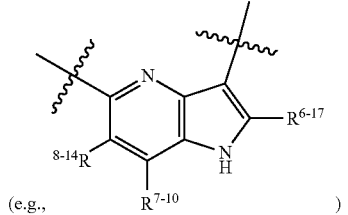 )

[the left terminus of which is linked to ring B];

R$^{6-1}$, R$^{6-3}$, R$^{6-6}$, R$^{6-7}$, R$^{6-10}$, R$^{6-14}$, R$^{6-16}$, R$^{6-17}$, and R$^{6-18}$ are each independently selected from C$_1$-C$_4$ alkyl (e.g., methyl, ethyl, n-propyl, isopropyl, n-butyl, isobutyl, sec-butyl, or tert-butyl, preferably, e.g., methyl, ethyl, or isopropyl, and more preferably, e.g., methyl or ethyl), and C$_3$-C$_6$ cycloalkyl (e.g., cyclopropyl, cyclobutyl, cyclopentyl, or cyclohexyl, and preferably, e.g., cyclopropyl);

R$^{7-1}$, R$^{7-3}$, R$^{7-4}$, R$^{7-7}$, R$^{7-9}$, R$^{7-10}$, and R$^{7-11}$ are each independently selected from hydrogen, fluorine, C$_1$-C$_4$ alkyl (e.g., methyl, ethyl, n-propyl, isopropyl, n-butyl, isobutyl, sec-butyl, or tert-butyl, and preferably, e.g., methyl), and halogen-substituted C$_1$-C$_4$ alkyl (there can be one or more, such as 2, 3, or 4, halogens, and in case that there are a plurality of halogens, the plurality of halogens are the same or different; the halogens are independently selected from fluorine, chlorine, bromine, and iodine, and preferably, e.g., fluorine; the "C$_1$-C$_4$ alkyl" is, e.g., methyl, ethyl, n-propyl, isopropyl, n-butyl, isobutyl, sec-butyl, or tert-butyl, and preferably, e.g., methyl or ethyl; and the "halogen-substituted C$_1$-C$_4$ alkyl" is, e.g., 2-fluoroethyl, 2,2-difluoroethyl, or 2,2,2-trifluoroethyl);

R$^{8-1}$, R$^{8-3}$, R$^{8-6}$, R$^{8-7}$, R$^{8-9}$, R$^{8-12}$, R$^{8-13}$, R$^{8-14}$, and R$^{8-15}$ are each independently selected from hydrogen and halogen-substituted $C_1$-$C_4$ alkyl (there can be one or more, such as 2, 3 or 4, halogens, and in case that there are a plurality of halogens, the plurality of halogens are the same or different; the halogens are independently selected from fluorine, chlorine, bromine, and iodine, and preferably, e.g., fluorine; the "$C_1$-$C_4$ alkyl" is, e.g., methyl, ethyl, n-propyl, isopropyl, n-butyl, isobutyl, sec-butyl, or tert-butyl, and preferably, e.g., methyl or ethyl; and the "halogen-substituted $C_1$-$C_4$ alkyl" is, e.g., 2-fluoroethyl, 2,2-difluoroethyl, or 2,2,2-trifluoroethyl); and $R^{11\text{-}2}$ is hydrogen, $C_1$-$C_4$ alkyl (e.g., methyl, ethyl, n-propyl, isopropyl, n-butyl, isobutyl, sec-butyl, or tert-butyl, and preferably, e.g., methyl), or halogen-substituted $C_1$-$C_4$ alkyl (there can be one or more, such as 2, 3, or 4, halogens, and in case that there are a plurality of halogens, the plurality of halogens are the same or different; the halogen is independently selected from fluorine, chlorine, bromine, and iodine, and preferably, for example, fluorine; the "$C_1$-$C_4$ alkyl" is, e.g., methyl, ethyl, n-propyl, isopropyl, n-butyl, isobutyl, sec-butyl, or tert-butyl, and preferably, e.g., methyl or ethyl; and the "halogen-substituted $C_1$-$C_4$ alkyl" is, for example, 2-fluoroethyl, 2,2-difluoroethyl, or 2,2,2-trifluoroethyl).

In one embodiment, certain groups of compound of formula I are defined as follows, and groups not mentioned are defined in any of the above embodiments:

ring A

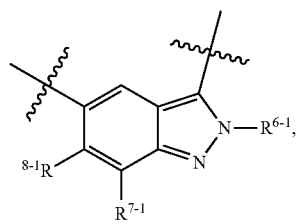

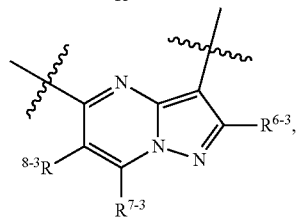

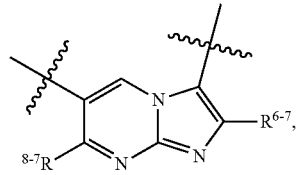

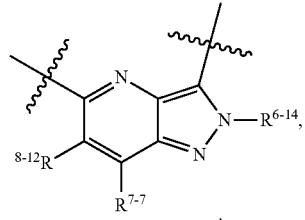

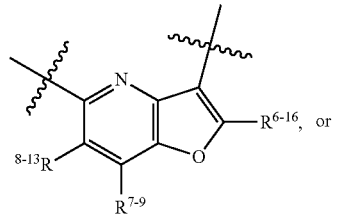

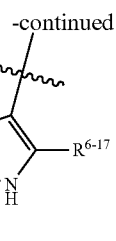

[the left terminus of which is linked to ring B];

$R^{6\text{-}1}$, $R^{6\text{-}3}$, $R^{6\text{-}7}$, $R^{6\text{-}14}$, $R^{6\text{-}16}$, and $R^{6\text{-}17}$ are independently selected from $C_1$-$C_4$ alkyl (e.g., methyl, ethyl, n-propyl, isopropyl, n-butyl, isobutyl, sec-butyl, or tert-butyl, preferably, e.g., methyl, ethyl, or isopropyl, and more preferably, e.g., methyl or ethyl), and $C_3$-$C_6$ cycloalkyl (e.g., cyclopropyl, cyclobutyl, cyclopentyl, or cyclohexyl, preferably, e.g., cyclopropyl);

$R^{7\text{-}1}$, $R^{7\text{-}3}$, $R^{7\text{-}7}$, $R^{7\text{-}9}$, and $R^{7\text{-}10}$ are each independently selected from hydrogen, fluorine, $C_1$-$C_4$ alkyl (e.g., methyl, ethyl, n-propyl, isopropyl, n-butyl, isobutyl, sec-butyl, or tert-butyl, and preferably, e.g., methyl), and halogen-substituted $C_1$-$C_4$ alkyl (there can be one or more, such as 2, 3 or 4, halogens, and in case that there are a plurality of halogens, the plurality of halogens are the same or different; the halogens are independently selected from fluorine, chlorine, bromine, and iodine, and preferably, e.g., fluorine; the "$C_1$-$C_4$ alkyl" is, e.g., methyl, ethyl, n-propyl, isopropyl, n-butyl, isobutyl, sec-butyl, or tert-butyl, and preferably, e.g., methyl or ethyl; and the "halogen-substituted $C_1$-$C_4$ alkyl" is, e.g., 2-fluoroethyl, 2,2-difluoroethyl, or 2,2,2-trifluoroethyl); and $R^{8\text{-}1}$, $R^{8\text{-}3}$, $R^{8\text{-}7}$, $R^{8\text{-}12}$, $R^{8\text{-}13}$, and $R^{8\text{-}14}$ are each independently selected from hydrogen and halogen-substituted $C_1$-$C_4$ alkyl (there can be one or more, such as 2, 3 or 4, halogens, and in case that there are a plurality of halogens, the plurality of halogens are be the same or different; the halogens are independently selected from fluorine, chlorine, bromine, and iodine, and preferably, e.g., fluorine; the "$C_1$-$C_4$ alkyl" is, e.g., methyl, ethyl, n-propyl, isopropyl, n-butyl, isobutyl, sec-butyl or tert-butyl, and preferably, e.g., methyl or ethyl; and the "halogen-substituted $C_1$-$C_4$ alkyl" is, e.g., 2-fluoroethyl, 2,2-difluoroethyl, or 2,2,2-trifluoroethyl).

In one embodiment, certain groups of compound of formula I are defined as follows, and groups not mentioned are defined in any of the above embodiments:

ring A is

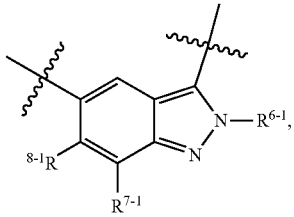

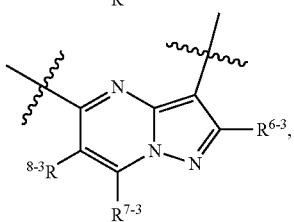

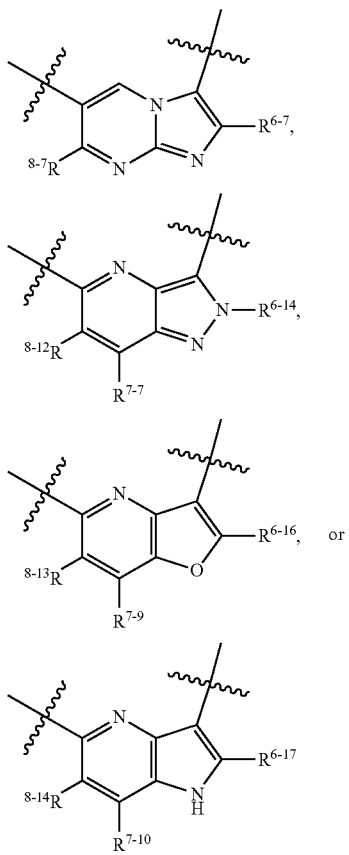

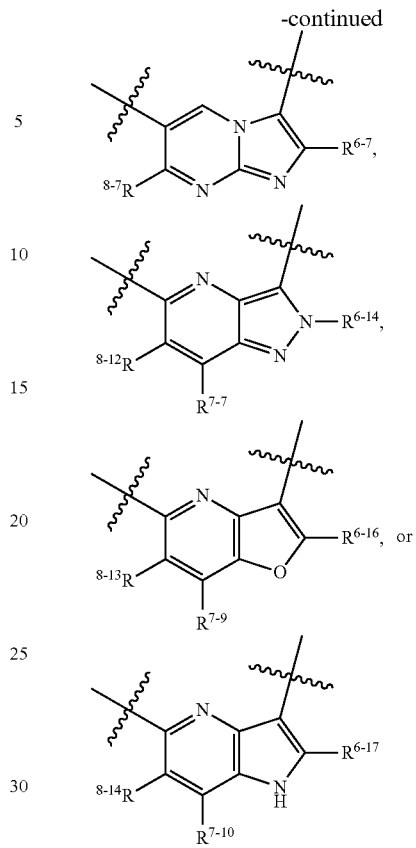

[the left terminus of which is linked to ring B];

$R^{6-1}$, $R^{6-3}$, $R^{6-7}$, $R^{6-14}$, $R^{6-16}$, and $R^{6-17}$ are independently selected from $C_1$-$C_4$ alkyl (e.g., methyl, ethyl, n-propyl, isopropyl, n-butyl, isobutyl, sec-butyl, or tert-butyl, preferably, e.g., methyl, ethyl, or isopropyl, and more preferably, e.g., methyl or ethyl), and $C_3$-$C_6$ cycloalkyl (e.g., cyclopropyl, cyclobutyl, cyclopentyl, or cyclohexyl, preferably, e.g., cyclopropyl);

$R^{7-1}$, $R^{7-3}$, $R^{7-7}$, $R^{7-9}$, and $R^{7-10}$ are independently selected from hydrogen, fluorine, and $C_1$-$C_4$ alkyl (e.g., methyl, ethyl, n-propyl, isopropyl, n-butyl, isobutyl, sec-butyl, or tert-butyl, and preferably, e.g., methyl);

$R^{8-1}$, $R^{8-3}$, $R^{8-7}$, $R^{8-12}$, $R^{8-13}$, and $R^{8-14}$ are independently selected from hydrogen.

In one embodiment, certain groups of compound of formula I are defined as follows, and groups not mentioned are defined in any of the above embodiments:

ring A is

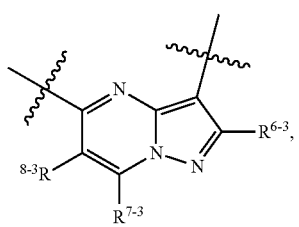

[the left terminus of which is linked to ring B];

$R^{6-3}$, $R^{6-7}$, $R^{6-14}$, $R^{6-16}$, and $R^{6-17}$ are independently selected from $C_1$-$C_4$ alkyl (e.g., methyl, ethyl, n-propyl, isopropyl, n-butyl, isobutyl, sec-butyl, or tert-butyl, preferably, e.g., methyl, ethyl, or isopropyl, more preferably, e.g., methyl or ethyl), and $C_3$-$C_6$ cycloalkyl (e.g., cyclopropyl, cyclobutyl, cyclopentyl, or cyclohexyl, preferably, e.g., cyclopropyl);

$R^{7-3}$, $R^{7-7}$, $R^{7-9}$, and $R^{7-10}$ are independently selected from hydrogen, fluorine, and $C_1$-$C_4$ alkyl (e.g., methyl, ethyl, n-propyl, isopropyl, n-butyl, isobutyl, sec-butyl, or tert-butyl, and preferably, e.g., methyl);

and $R^{8-3}$, $R^{8-7}$, $R^{8-12}$, $R^{8-13}$, and $R^{8-14}$ are independently selected from hydrogen.

In one embodiment, certain groups of compound of formula I are defined as follows, and groups not mentioned are defined in any of the above embodiments:

ring A is

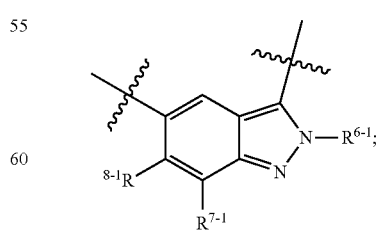

$R^{6-1}$ is $C_1$-$C_4$ alkyl (e.g., methyl, ethyl, n-propyl, isopropyl, n-butyl, isobutyl, sec-butyl, or tert-butyl, preferably, e.g., methyl, ethyl, or isopropyl, more preferably, e.g., methyl or ethyl), and $C_3$-$C_6$ cycloalkyl (e.g., cyclopropyl, cyclobutyl, cyclopentyl, or cyclohexyl, preferably, e.g., cyclopropyl);

$R^{7-1}$ is hydrogen, halogen (e.g., fluorine, chlorine, bromine, or iodine, preferably, e.g., fluorine), or $C_1$-$C_4$ alkyl (e.g., methyl, ethyl, n-propyl, isopropyl, n-butyl, isobutyl, sec-butyl, or tert-butyl, and preferably, e.g., methyl);

and $R^{8-1}$ is hydrogen.

In one embodiment, certain groups of compound of formula I are defined as follows, and groups not mentioned are defined in any of the above embodiments:

ring A is

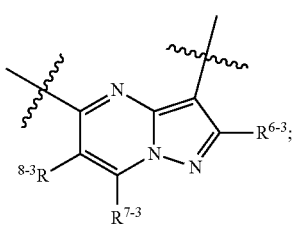

$R^{6-3}$ is $C_1$-$C_4$ alkyl (e.g., methyl, ethyl, n-propyl, isopropyl, n-butyl, isobutyl, sec-butyl, or tert-butyl, preferably, e.g., methyl, ethyl, or isopropyl, and more preferably, e.g., methyl or ethyl), and $C_3$-$C_6$ cycloalkyl (e.g., cyclopropyl, cyclobutyl, cyclopentyl, or cyclohexyl, preferably, e.g., cyclopropyl);

$R^{7-3}$ is hydrogen, halogen (e.g., fluorine, chlorine, bromine, or iodine, and preferably, e.g., fluorine), or $C_1$-$C_4$ alkyl (e.g., methyl, ethyl, n-propyl, isopropyl, n-butyl, isobutyl, sec-butyl, or tert-butyl, and preferably, e.g., methyl); and $R^{8-3}$ is hydrogen.

In one embodiment, certain groups of compound of formula I are defined as follows, and groups not mentioned are defined in any of the above embodiments:

ring A is

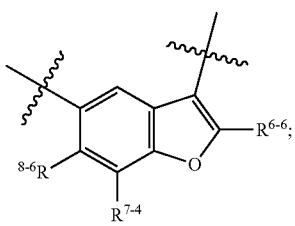

$R^{6-6}$ is $C_1$-$C_4$ alkyl (e.g., methyl, ethyl, n-propyl, isopropyl, n-butyl, isobutyl, sec-butyl, or tert-butyl, preferably, e.g., methyl, ethyl, or isopropyl, and more preferably, e.g., methyl or ethyl), and $C_3$-$C_6$ cycloalkyl (e.g., cyclopropyl, cyclobutyl, cyclopentyl, or cyclohexyl, and preferably, e.g., cyclopropyl);

$R^{7-4}$ is hydrogen, halogen (e.g., fluorine, chlorine, bromine, or iodine, and preferably, e.g., fluorine), or $C_1$-$C_4$ alkyl (e.g., methyl, ethyl, n-propyl, isopropyl, n-butyl, isobutyl, sec-butyl, or tert-butyl, and preferably, e.g., methyl); and $R^{8-6}$ is hydrogen.

In one embodiment, certain groups of compound of formula I are defined as follows, and groups not mentioned are defined in any of the above embodiments:

ring A is

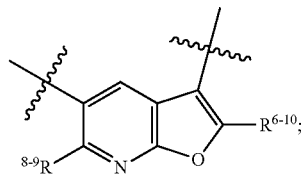

$R^{6-10}$ is $C_1$-$C_4$ alkyl (e.g., methyl, ethyl, n-propyl, isopropyl, n-butyl, isobutyl, sec-butyl, or tert-butyl, preferably, e.g., methyl, ethyl, or isopropyl, and more preferably, e.g., methyl or ethyl), and $C_3$-$C_6$ cycloalkyl (e.g., cyclopropyl, cyclobutyl, cyclopentyl, or cyclohexyl, and preferably, e.g., cyclopropyl); and $R^{8-9}$ is hydrogen.

In one embodiment, certain groups of compound of formula I are defined as follows, and groups not mentioned are defined in any of the above embodiments:

ring A is

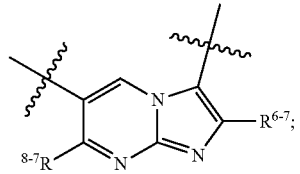

$R^{6-7}$ is $C_1$-$C_4$ alkyl (e.g., methyl, ethyl, n-propyl, isopropyl, n-butyl, isobutyl, sec-butyl, or tert-butyl, preferably, e.g., methyl, ethyl, or isopropyl, and more preferably, e.g., methyl or ethyl), and $C_3$-$C_6$ cycloalkyl (e.g., cyclopropyl, cyclobutyl, cyclopentyl, or cyclohexyl, and preferably, e.g., cyclopropyl); and $R^{8-7}$ is hydrogen.

In one embodiment, certain groups of compound of formula I are defined as follows, and groups not mentioned are defined in any of the above embodiments:

ring A is

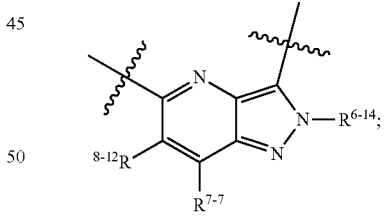

$R^{6-14}$ is $C_1$-$C_4$ alkyl (e.g., methyl, ethyl, n-propyl, isopropyl, n-butyl, isobutyl, sec-butyl, or tert-butyl, preferably, e.g., methyl, ethyl, or isopropyl, and more preferably, e.g., methyl or ethyl), and $C_3$-$C_6$ cycloalkyl (e.g., cyclopropyl, cyclobutyl, cyclopentyl, or cyclohexyl, and preferably, e.g., cyclopropyl);

$R^{7-7}$ is hydrogen, halogen (e.g., fluorine, chlorine, bromine, or iodine, and preferably, e.g., fluorine), or $C_1$-$C_4$ alkyl (e.g., methyl, ethyl, n-propyl, isopropyl, n-butyl, isobutyl, sec-butyl, or tert-butyl, and preferably, e.g., methyl); and $R^{8-12}$ is hydrogen.

In one embodiment, certain groups of compound of formula I are defined as follows, and groups not mentioned are defined in any of the above embodiments:

ring A is

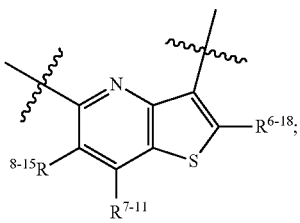

$R^{6-18}$ is $C_1$-$C_4$ alkyl (e.g., methyl, ethyl, n-propyl, isopropyl, n-butyl, isobutyl, sec-butyl, or tert-butyl, preferably, e.g., methyl, ethyl, or isopropyl, and more preferably, e.g., methyl or ethyl), and $C_3$-$C_6$ cycloalkyl (e.g., cyclopropyl, cyclobutyl, cyclopentyl, or cyclohexyl, and preferably, e.g., cyclopropyl);

$R^{7-11}$ is hydrogen, halogen (e.g., fluorine, chlorine, bromine, or iodine, and preferably, e.g., fluorine), or $C_1$-$C_4$ alkyl (e.g., methyl, ethyl, n-propyl, isopropyl, n-butyl, isobutyl, sec-butyl, or tert-butyl, and preferably, e.g., methyl); and $R^{8-15}$ is hydrogen.

In one embodiment, certain groups of compound of formula I are defined as follows, and groups not mentioned are defined in any of the above embodiments:

ring A is

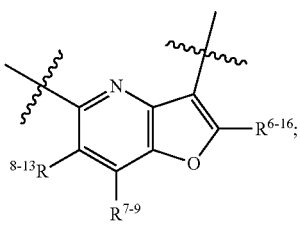

$R^{6-16}$ is $C_1$-$C_4$ alkyl (e.g., methyl, ethyl, n-propyl, isopropyl, n-butyl, isobutyl, sec-butyl, or tert-butyl, preferably, e.g., methyl, ethyl, or isopropyl, and more preferably, e.g., methyl or ethyl), and $C_3$-$C_6$ cycloalkyl (e.g., cyclopropyl, cyclobutyl, cyclopentyl, or cyclohexyl, and preferably, e.g., cyclopropyl);

$R^{7-9}$ is hydrogen, halogen (e.g., fluorine, chlorine, bromine, or iodine, and preferably, e.g., fluorine), or $C_1$-$C_4$ alkyl (e.g., methyl, ethyl, n-propyl, isopropyl, n-butyl, isobutyl, sec-butyl, or tert-butyl, and preferably, e.g., methyl); and $R^{8-13}$ is hydrogen.

In one embodiment, certain groups of compound of formula I are defined as follows, and groups not mentioned are defined in any of the above embodiments:

ring A is

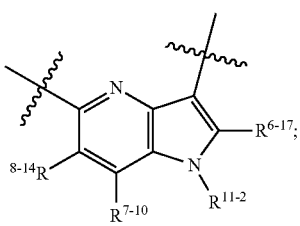

-continued

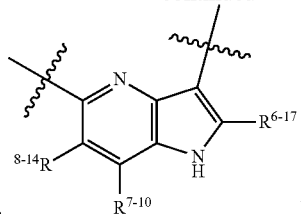

(e.g., );

$R^{6-17}$ is $C_1$-$C_4$ alkyl (e.g., methyl, ethyl, n-propyl, isopropyl, n-butyl, isobutyl, sec-butyl, or tert-butyl, preferably, e.g., methyl, ethyl, or isopropyl, and more preferably, e.g., methyl or ethyl), and $C_3$-$C_6$ cycloalkyl (e.g., cyclopropyl, cyclobutyl, cyclopentyl, or cyclohexyl, and preferably, e.g., cyclopropyl);

$R^{7-10}$ is hydrogen, halogen (e.g., fluorine, chlorine, bromine, or iodine, and preferably, e.g., fluorine), or $C_1$-$C_4$ alkyl (e.g., methyl, ethyl, n-propyl, isopropyl, n-butyl, isobutyl, sec-butyl, or tert-butyl, and preferably, e.g., methyl);

$R^{8-14}$ is hydrogen; and $R^{11-2}$ is hydrogen or $C_1$-$C_4$ alkyl (e.g., methyl, ethyl, n-propyl, isopropyl, n-butyl, isobutyl, sec-butyl, or tert-butyl, and preferably, e.g., methyl).

In one embodiment, certain groups of compound of formula I are defined as follows, and groups not mentioned are defined in any of the above embodiments:

ring B is "4-10 membered monocyclic or bicyclic heterocycloalkyl having 1-3 heteroatoms selected from one or more of O, N, and S" (e.g., "4-7 membered monocyclic heterocycloalkyl having 1-2 heteroatoms selected from one or more of O, N, and S", preferably, e.g., "5-6 membered monocyclic heterocycloalkyl having 1-2 heteroatoms selected from one or more of O, N, and S", and more preferably, e.g., "

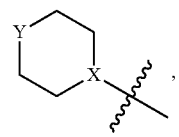

wherein X is N or CH and Y is NH or $CH_2$, which are not both carbon", and most preferably, e.g.,

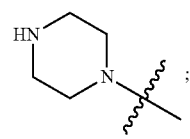 [SMILES: *N1CCNCC1]

the heterocycloalkyl may be linked to ring A via a carbon atom or a nitrogen atom, and preferably via a nitrogen atom);

n is 0 or 1, $R^{10}$ is oxo, or $R^{10-1}$-substituted or unsubstituted $C_1$-$C_4$ alkyl (there can be one or more $R^{10-1}$ and in case that there are a plurality of $R^{10-1}$, the plurality of $R^{10-1}$ are the same or different; the "$C_1$-$C_4$ alkyl" is, e.g., methyl, ethyl, n-propyl, isopropyl, n-butyl, isobutyl, sec-butyl, or tert-butyl, and preferably, e.g., methyl; the "$R^{10-1}$-substituted $C_1$-$C_4$ alkyl" is, e.g., trifluoromethyl); [$R^{10}$ may be independently located at the ortho, meta, or para position relative to ring A, and preferably at the ortho or meta position relative to ring A; when n is 1, $R^{10}$ may be located at the ortho or meta position relative to ring A; $R^{10}$ may be linked to a carbon atom or a nitrogen atom of ring B; and the carbon atom of ring B, linked to $R^{10}$, may be independently selected from a chiral carbon atom, either in R configuration or S configuration]; and $R^{10-1}$ is independently selected from halogens (e.g. fluorine, chlorine, bromine, or iodine, and preferably, e.g., fluorine).

In one embodiment, certain groups of compound of formula I are defined as follows, and groups not mentioned are defined in any of the above embodiments:

ring B is "4-7 membered monocyclic heterocycloalkyl having 1-2 heteroatoms selected from one or more of O, N, and S" (e.g., "5-6 membered monocyclic heterocycloalkyl having 1-2 heteroatoms selected from one or more of O, N, and S", preferably, e.g., "

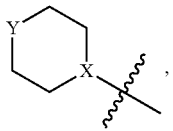

wherein X is N or CH and Y is NH or $CH_2$, which are not both carbon", more preferably, e.g.,

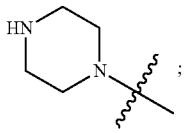

the heterocycloalkyl may be linked to ring A via a carbon atom or a nitrogen atom, and preferably via a nitrogen atom);

n is 0 or 1, $R^{10}$ is $R^{10-1}$-substituted or unsubstituted $C_1$-$C_4$ alkyl (there can be one or more $R^{10-1}$, and in case that there are a plurality of $R^{10-1}$, the plurality of $R^{10-1}$ are the same or different; the "$C_1$-$C_4$ alkyl" is, e.g., methyl, ethyl, n-propyl, isopropyl, n-butyl, isobutyl, sec-butyl, or tert-butyl, and preferably, e.g., methyl; the "$R^{10-1}$-substituted $C_1$-$C_4$ alkyl" is, e.g., trifluoromethyl); [$R^{10}$ may be independently located at the ortho, meta, or para position relative to ring A, and preferably at the ortho or meta position relative to ring A; when n is 1, $R^{10}$ may be located at the ortho or meta position relative to ring A; $R^{10}$ may be linked to a carbon atom or a nitrogen atom of ring B; and the carbon atom of ring B, linked to $R^{10}$, may be independently selected from a chiral carbon atom, either in R configuration or S configuration]; and $R^{10-1}$ is independently selected from halogens (e.g. fluorine, chlorine, bromine, or iodine, and preferably, e.g., fluorine).

In one embodiment, certain groups of compound of formula I are defined as follows, and groups not mentioned are defined in any of the above embodiments:

$L^1$ is $C_1$-$C_4$ alkylene, e.g., —$CH_2$—, —$CH_2CH_2$—, —CH($CH_3$)— (wherein the chiral carbon atom can be in R configuration or S configuration), —$CH_2CH_2CH_2$—, or —$CH_2CH(CH_3)$— (wherein the chiral carbon atom can be in R configuration or S configuration).

In one embodiment, certain groups of compound of formula I are defined as follows, and groups not mentioned are defined in any of the above embodiments:

$L^2$ is —C(=O)—, —C(=O)—$CH_2$— (the left terminus of which is linked to L), —C(=O)—C(=O)—, or —$SO_2$—.

In one embodiment, certain groups of compound of formula I are defined as follows, and groups not mentioned are defined in any of the above embodiments:

$L^2$ is —C(=O)—.

In one embodiment, certain groups of compound of formula I are defined as follows, and groups not mentioned are defined in any of the above embodiments:

$L^3$ is $R^{L-8}$-substituted or unsubstituted $C_1$-$C_4$ alkyl (there can be one or more $R^{L-8}$, and in case that there are a plurality of $R^{L-8}$, the plurality of $R^{L-8}$ are the same or different; and the $C_1$-$C_4$ alkyl is, e.g., methyl, ethyl, n-propyl, isopropyl, n-butyl, isobutyl, sec-butyl, or tert-butyl, and preferably, e.g., methyl), or "4-10 membered monocyclic, bicyclic or spirocyclic heterocycloalkyl having 1-3 heteroatoms selected from one or more of O, N and S" which is substituted or unsubstituted with $R^{L-9}$ (the "4-10 membered monocyclic, bicyclic or spirocyclic heterocycloalkyl having 1-3 heteroatoms selected from one or more of O, N and S" is, e.g., "4-10 membered monocyclic heterocycloalkyl having 1-2 heteroatoms selected from one or more of O, N and S", preferably, e.g., "4-6 membered monocyclic heterocycloalkyl having 1-2 heteroatoms selected from one or more of O, N, and S", and more preferably, e.g.,

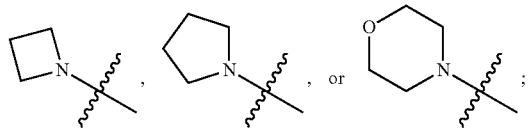 [SMILES: *N1CCC1 ; *N1CCCC1 ; *N1CCOCC1]

the "4-10 membered monocyclic, bicyclic or spirocyclic heterocycloalkyl having 1-3 heteroatoms selected from one or more of O, N and S" which is substituted with $R^{L-9}$ is, e.g.,

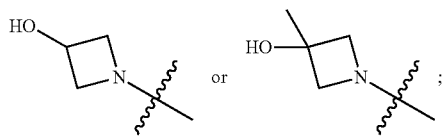

there can be one or more $R^{L-9}$, and in case that there are a plurality of $R^{L-9}$, the plurality of $R^{L-9}$ are the same or different; the heterocycloalkyl can be linked to $L^2$ via a carbon atom or a nitrogen atom, and preferably via a nitrogen atom);

$R^{L-8}$ is independently selected from hydroxy;

$R^{L-9}$ is independently selected from hydroxy and $C_1$-$C_4$ alkyl (e.g., methyl, ethyl, n-propyl, isopropyl, n-butyl, isobutyl, sec-butyl, or tert-butyl, and preferably, e.g., methyl). [The carbon atom in the heterocycloalkyl, linked to $R^{L-9}$, may be independently selected from a chiral carbon atom, either in R configuration or S configuration]

In one embodiment, certain groups of compound of formula I are defined as follows, and groups not mentioned are defined in any of the above embodiments:

$L^3$ is "4-10 membered monocyclic, bicyclic, or spirocyclic heterocycloalkyl having 1-3 heteroatoms selected from one or more of O, N, and S" which is substituted or unsubstituted with $R^{L-9}$ (the "4-10 membered monocyclic, bicyclic, or spirocyclic heterocycloalkyl having 1-3 heteroatoms selected from one or more of O, N, and S" is, e.g., "4-10 membered monocyclic heterocycloalkyl having 1-2 heteroatoms selected from one or more of O, N, and S", preferably, e.g., "4-6 membered monocyclic heterocycloalkyl having 1-2 heteroatoms selected from one or more of O, N, and S", and more preferably, e.g.,

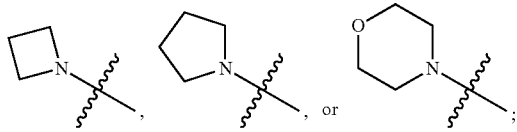

the "4-10 membered monocyclic, bicyclic, or spirocyclic heterocycloalkyl having 1-3 heteroatoms selected from one or more of O, N, and S" which is substituted with $R^{L-9}$ is, e.g.,

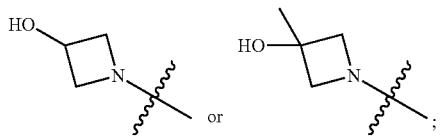

there can be one or more $R^{L-9}$, and in case that there are a plurality of $R^{L-9}$, the plurality of $R^{L-9}$ are the same or different; and the heterocycloalkyl can be linked to $L^2$ via a carbon atom or a nitrogen atom, and preferably via a nitrogen atom);

$R^{L-9}$ is independently selected from hydroxy and $C_1$-$C_4$ alkyl (e.g., methyl, ethyl, n-propyl, isopropyl, n-butyl, isobutyl, sec-butyl, or tert-butyl, and preferably, e.g., methyl). [The carbon atom in the heterocycloalkyl, linked to $R^{L-9}$, may be independently selected from a chiral carbon atom, either in R configuration or S configuration]

In one embodiment, certain groups of compound of formula I are defined as follows, and groups not mentioned are defined in any of the above embodiments:

$L^3$ is "4-6 membered monocyclic heterocycloalkyl having 1-2 heteroatoms selected from one or more of O, N, and S" which is substituted or unsubstituted with $R^{L-9}$ (the "4-6 membered monocyclic heterocycloalkyl having 1-2 heteroatoms selected from one or more of O, N, and S" is, e.g.,

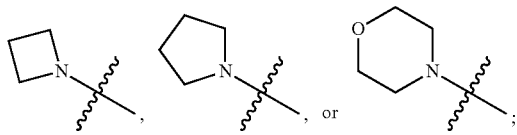

the "4-6 membered monocyclic heterocycloalkyl having 1-2 heteroatoms selected from one or more of O, N, and S" which is substituted with $R^{L-9}$ is, e.g.,

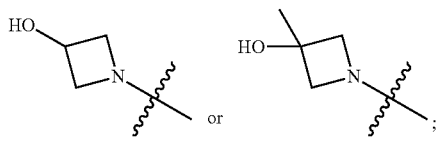

there can be one or more $R^{L-9}$, and in case that there are a plurality of $R^{L-9}$, the plurality of $R^{L-9}$ are the same or different; and the heterocycloalkyl can be linked to $L^2$ via a carbon atom or a nitrogen atom, and preferably via a nitrogen atom);

$R^{L-9}$ is independently selected from hydroxy and $C_1$-$C_4$ alkyl (e.g., methyl, ethyl, n-propyl, isopropyl, n-butyl, isobutyl, sec-butyl, or tert-butyl, and preferably, e.g., methyl). [The carbon atom in the heterocycloalkyl, linked to $R^{L-9}$, may be independently selected from a chiral carbon atom, either in R configuration or S configuration]

In one embodiment, certain groups of compound of formula I are defined as follows, and groups not mentioned are defined in any of the above embodiments:

$R^1$ is halogen (e.g., fluorine, chlorine, bromine, or iodine, and preferably, e.g., fluorine), halogen-substituted $C_1$-$C_4$ alkyl (there can be one or more, such as 2, 3, or 4, halogens, and in case that there are a plurality of halogens, the plurality of halogens are the same or different; the halogens are independently selected from fluorine, chlorine, bromine, and iodine, and preferably, e.g., fluorine; the "$C_1$-$C_4$ alkyl" is, e.g., methyl, ethyl, n-propyl, isopropyl, n-butyl, isobutyl, sec-butyl, or tert-butyl, and preferably, e.g., methyl or ethyl; and the "halogen-substituted $C_1$-$C_4$ alkyl" is, e.g., 2-fluoroethyl, 2,2-difluoroethyl, or 2,2,2-trifluoroethyl), or halogen-substituted $C_1$-$C_4$ alkoxy (there can be one or more, e.g., 2, 3, or 4, halogens, and in case that there are a plurality of halogens, the plurality of halogens can be the same or different; the halogens are independently selected from fluorine, chlorine, bromine, and iodine, and preferably, e.g., fluorine; the "$C_1$-$C_4$ alkoxy" is, e.g., methoxy, ethoxy, n-propoxy, isopropoxy, n-butoxy, isobutoxy, sec-butoxy, or tert-butoxy, and preferably, e.g., methoxy or ethoxy; and the halogen-substituted $C_1$-$C_4$ alkoxy is, e.g., 2-fluoroethoxy, 2,2-difluoroethoxy, or 2,2,2-trifluoroethoxy);

m is 0 or 1, $R^3$ is halogen (e.g., fluorine, chlorine, bromine, or iodine, and preferably, e.g., fluorine); [when m is 1, $R^3$ can be located at the ortho position or meta position relative to $R^1$]

$W^1$ is =N—;
$W^2$ is =CR$^4$— or =N—;
$W^3$ is —O—, —S—, —NH—, —N=CH—, —CH=N—, or —CH=CH—;

when $W^2$ is =N—, $R^2$ is hydrogen;

when $W^2$ is =CR$^4$—, one (e.g., $R^4$) of $R^2$ and $R^4$ is hydrogen or cyano, and the other (e.g., $R^2$) is hydrogen;

$R^5$ is halogen-substituted $C_1$-$C_4$ alkyl (there can be one or more, such as 2, 3, or 4, halogens, and in case that there are a plurality of halogens, the plurality of halogens are the same or different; the halogens are independently selected from fluorine, chlorine, bromine, and iodine, and preferably, for example, fluorine; the "$C_1$-$C_4$ alkyl" is, e.g., methyl, ethyl, n-propyl, isopropyl, n-butyl, isobutyl, sec-butyl, or tert-butyl, and preferably, e.g., methyl or ethyl; and the "halogen-substituted $C_1$-$C_4$ alkyl" is, for example, 2-fluoroethyl, 2,2-difluoroethyl, or 2,2,2-trifluoroethyl, and preferably, for example, 2-fluoroethyl or 2,2-difluoroethyl), or $C_1$-$C_4$ alkyl (for example, methyl, ethyl, n-propyl, isopropyl, n-butyl, isobutyl, sec-butyl, or tert-butyl, preferably, for example, methyl or ethyl, and more preferably, for example, ethyl);

ring A is

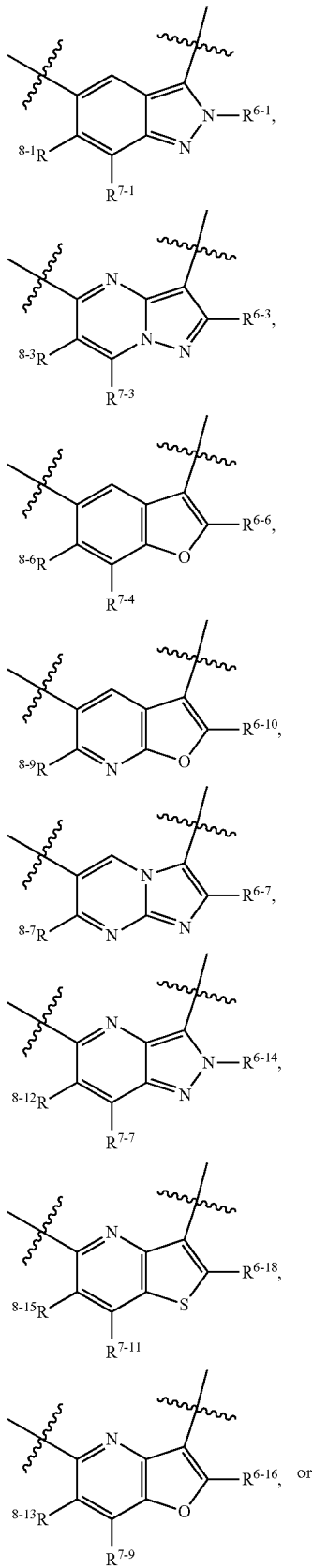

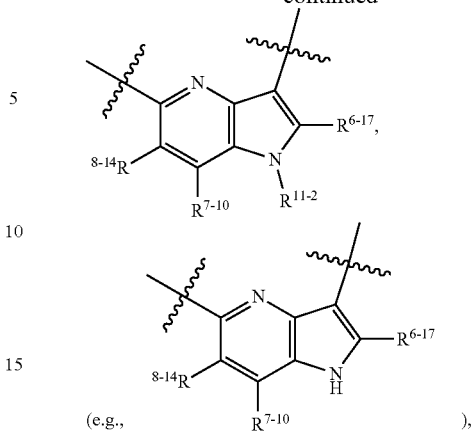

(e.g., ),

[the left terminus of which is linked to ring B];

$R^{6-1}$, $R^{6-3}$, $R^{6-6}$, $R^{6-7}$, $R^{6-10}$, $R^{6-14}$, $R^{6-16}$, $R^{6-17}$, and $R^{6-18}$ are each independently selected from $C_1$-$C_4$ alkyl (e.g., methyl, ethyl, n-propyl, isopropyl, n-butyl, isobutyl, sec-butyl, or tert-butyl, preferably, e.g., methyl, ethyl, or isopropyl, and more preferably, e.g., methyl or ethyl), and $C_3$-$C_6$ cycloalkyl (e.g., cyclopropyl, cyclobutyl, cyclopentyl, or cyclohexyl, and preferably, e.g., cyclopropyl);

$R^{7-1}$, $R^{7-3}$, $R^{7-4}$, $R^{7-7}$, $R^{7-9}$, $R^{7-10}$, and $R^{7-11}$ are each independently selected from hydrogen, halogen (e.g., fluorine, chlorine, bromine, or iodine, and preferably, e.g., fluorine), $C_1$-$C_4$ alkyl (e.g., methyl, ethyl, n-propyl, isopropyl, n-butyl, isobutyl, sec-butyl, or tert-butyl, and preferably, e.g., methyl), and halogen-substituted $C_1$-$C_4$ alkyl (there can be one or more, such as 2, 3, or 4, halogens, and in case that there are a plurality of halogens, the plurality of halogens are the same or different; the halogens are independently selected from fluorine, chlorine, bromine, and iodine, and preferably, e.g., fluorine; the "$C_1$-$C_4$ alkyl" is, e.g., methyl, ethyl, n-propyl, isopropyl, n-butyl, isobutyl, sec-butyl, or tert-butyl, and preferably, e.g., methyl or ethyl; and the "halogen-substituted $C_1$-$C_4$ alkyl" is, e.g., 2-fluoroethyl, 2,2-difluoroethyl, or 2,2,2-trifluoroethyl);

$R^{8-1}$, $R^{8-3}$, $R^{8-6}$, $R^{8-7}$, $R^{8-9}$, $R^{8-12}$, $R^{8-13}$, $R^{8-14}$, and $R^{8-15}$ are each independently selected from hydrogen and halogen-substituted $C_1$-$C_4$ alkyl (there can be one or more, such as 2, 3 or 4, halogens, and in case that there are a plurality of halogens, the plurality of halogens are the same or different; the halogens are independently selected from fluorine, chlorine, bromine, and iodine, and preferably, e.g., fluorine; the "$C_1$-$C_4$ alkyl" is, e.g., methyl, ethyl, n-propyl, isopropyl, n-butyl, isobutyl, sec-butyl, or tert-butyl, and preferably, e.g., methyl or ethyl; and the "halogen-substituted $C_1$-$C_4$ alkyl" is, e.g., 2-fluoroethyl, 2,2-difluoroethyl, or 2,2,2-trifluoroethyl); and $R^{11-2}$ is hydrogen, $C_1$-$C_4$ alkyl (e.g., methyl, ethyl, n-propyl, isopropyl, n-butyl, isobutyl, sec-butyl, or tert-butyl, and preferably, e.g., methyl), or halogen-substituted $C_1$-$C_4$ alkyl (there can be one or more, such as 2, 3 or 4, halogens, and in case that there are a plurality of halogens, the halogens are the same or different; the halogen is independently selected from fluorine, chlorine, bromine, and iodine, and preferably, for example, fluorine; the "$C_1$-$C_4$ alkyl" is, e.g., methyl, ethyl, n-propyl, isopropyl, n-butyl, isobutyl, sec-butyl, or tert-butyl, and preferably, e.g., methyl or ethyl; and the "halogen-substituted $C_1$-$C_4$ alkyl" is, for example, 2-fluoroethyl, 2,2-difluoroethyl, or 2,2,2-trifluoroethyl);

ring B is "4-10 membered monocyclic or bicyclic heterocycloalkyl having 1-3 heteroatoms selected from one or more of O, N, and S" (e.g., "4-7 membered monocyclic heterocycloalkyl having 1-2 heteroatoms selected from one or more of O, N, and S", preferably, e.g., "5-6 membered monocyclic heterocycloalkyl having 1-2 heteroatoms selected from one or more of O, N, and S", and more preferably, e.g., "

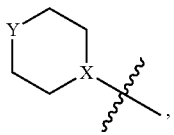

wherein X is N or CH and Y is NH or $CH_2$, which are not both carbon", and most preferably, e.g.,

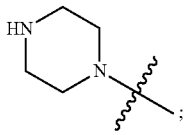

the heterocycloalkyl may be linked to ring A via a carbon atom or a nitrogen atom, and preferably via a nitrogen atom);

$R^9$ is -$L^1$-$L^2$-$L^3$; [when ring B is 6-membered heterocycloalkyl, $R^9$ can be located at the ortho, meta, or para position relative to ring A, and preferably at the para position relative to ring A; and $R^9$ can be linked to a carbon atom or a nitrogen atom of ring B, and preferably linked to a nitrogen atom of ring B]

$L^1$ is a single bond (i.e., $L^2$ and ring B are directly linked), or $C_1$-$C_4$ alkylene (for example, —$CH_2$—, —$CH_2CH_2$—, —$CH(CH_3)$— [wherein the chiral carbon atom may be in R configuration or S configuration], —$CH_2CH_2CH_2$—, or —$CH_2CH(CH_3)$— [wherein the chiral carbon atom may be in R configuration or S configuration]);

$L^2$ is —C(=O)—, —C(=O)—$CH_2$— [the left terminus of which is linked to $L^1$], —C(=O)—C(=O)—, or —$SO_2$—;

$L^3$ is $R^{L-8}$-substituted or unsubstituted $C_1$-$C_4$ alkyl (there can be one or more $R^{L-8}$, and in case that there are a plurality of $R^{L-8}$, the plurality of $R^{L-8}$ are the same or different; and the $C_1$-$C_4$ alkyl is, e.g., methyl, ethyl, n-propyl, isopropyl, n-butyl, isobutyl, sec-butyl, or tert-butyl, and preferably, e.g., methyl), or "4-10 membered monocyclic, bicyclic or spirocyclic heterocycloalkyl having 1-3 heteroatoms selected from one or more of O, N and S" which is substituted or unsubstituted with $R^{L-9}$ (the "4-10 membered monocyclic, bicyclic or spirocyclic heterocycloalkyl having 1-3 heteroatoms selected from one or more of O, N and S" is, e.g., "4-10 membered monocyclic heterocycloalkyl having 1-2 heteroatoms selected from one or more of O, N and S", preferably, e.g., "4-6 membered monocyclic heterocycloalkyl having 1-2 heteroatoms selected from one or more of O, N, and S", and more preferably, e.g.,

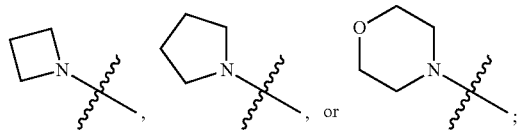

the "4-10 membered monocyclic, bicyclic or spirocyclic heterocycloalkyl having 1-3 heteroatoms selected from one or more of O, N and S" which is substituted with $R^{L-9}$ is, e.g.,

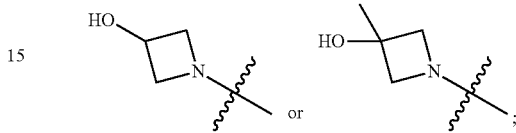

there can be one or more $R^{L-9}$, and in case that there are a plurality of $R^{L-9}$, the plurality of $R^{L-9}$ are the same or different; the heterocycloalkyl can be linked to $L^2$ via a carbon atom or a nitrogen atom, and preferably via a nitrogen atom);

$R^{L-8}$ is independently selected from hydroxy;

$R^{L-9}$ is independently selected from hydroxy and $C_1$-$C_4$ alkyl (e.g., methyl, ethyl, n-propyl, isopropyl, n-butyl, isobutyl, sec-butyl, or tert-butyl, and preferably, e.g., methyl); [the carbon atom in the heterocycloalkyl, linked to $R^{L-9}$, can be independently selected from a chiral carbon atom, either in R configuration or S configuration]

n is 0 or 1, $R^1$ is oxo, or $R^{10-1}$-substituted or unsubstituted $C_1$-$C_4$ alkyl (there can be one or more $R^{10-1}$ and in case that there are a plurality of $R^{10-1}$, the plurality of $R^{10-1}$ are the same or different; the "$C_1$-$C_4$ alkyl" is, e.g., methyl, ethyl, n-propyl, isopropyl, n-butyl, isobutyl, sec-butyl, or tert-butyl, and preferably, e.g., methyl; the "$R^{10-1}$-substituted $C_1$-$C_4$ alkyl" is, e.g., trifluoromethyl); [$R^1$ may be independently located at the ortho, meta, or para position relative to ring A, and preferably at the ortho or meta position relative to ring A; when n is 1, $R^1$ may be located at the ortho or meta position relative to ring A; $R^1$ may be linked to a carbon atom or a nitrogen atom of ring B; and the carbon atom of ring B, linked to $R^{10}$, may be independently selected from a chiral carbon atom, either in R configuration or S configuration]; and $R^{10-1}$ is independently selected from halogens (e.g. fluorine, chlorine, bromine, or iodine, and preferably, e.g., fluorine).

In one embodiment, certain groups of compound of formula I are defined as follows, and groups not mentioned are defined in any of the above embodiments:

$R^1$ is halogen (e.g., fluorine, chlorine, bromine, or iodine, and preferably, e.g., fluorine), halogen-substituted $C_1$-$C_4$ alkyl (there can be one or more, such as 2, 3, or 4, halogens, and in case that there are a plurality of halogens, the plurality of halogens are the same or different; the halogens are independently selected from fluorine, chlorine, bromine, and iodine, and preferably, e.g., fluorine; the "$C_1$-$C_4$ alkyl" is, e.g., methyl, ethyl, n-propyl, isopropyl, n-butyl, isobutyl, sec-butyl, or tert-butyl, and preferably, e.g., methyl or ethyl; and the "halogen-substituted $C_1$-$C_4$ alkyl" is, e.g., 2-fluoroethyl, 2,2-difluoroethyl, or 2,2,2-trifluoroethyl), or halogen-substituted $C_1$-$C_4$ alkoxy (there can be one or more, e.g., 2, 3, or 4, halogens, and in case that there are a plurality of halogens, the plurality of halogens can be the same or different; the halogens are independently selected from fluorine, chlorine, bromine, and iodine, and preferably, e.g., fluorine; the "$C_1$-$C_4$ alkoxy" is, e.g., methoxy, ethoxy, n-propoxy, isopropoxy, n-butoxy, isobutoxy, sec-butoxy, or tert-butoxy, and preferably, e.g., methoxy or ethoxy; and the halogen-substituted $C_1$-$C_4$ alkoxy is, e.g., 2-fluoroethoxy, 2,2-difluoroethoxy, or 2,2,2-trifluoroethoxy);

m is 0 or 1, $R^3$ is halogen (e.g., fluorine, chlorine, bromine, or iodine, and preferably, e.g., fluorine); [when m is 1, $R^3$ can be located at the ortho position or meta position relative to $R^1$]

$W^1$ is =N—;

$W^2$ is =$CR^4$—;

$W^3$ is —O—, —S—, or —NH—;

when $W^2$ is =$CR^4$—, one (e.g., $R^4$) of $R^2$ and $R^4$ is cyano, and the other (e.g., $R^2$) is hydrogen;

$R^5$ is halogen-substituted $C_1$-$C_4$ alkyl (there can be one or more, such as 2, 3, or 4, halogens, and in case that there are a plurality of halogens, the plurality of halogens are the same or different; the halogens are independently selected from fluorine, chlorine, bromine, and iodine, and preferably, for example, fluorine; the "$C_1$-$C_4$ alkyl" is, e.g., methyl, ethyl, n-propyl, isopropyl, n-butyl, isobutyl, sec-butyl, or tert-butyl, and preferably, e.g., methyl or ethyl; and the "halogen-substituted $C_1$-$C_4$ alkyl" is, for example, 2-fluoroethyl, 2,2-difluoroethyl, or 2,2,2-trifluoroethyl, and preferably, for example, 2-fluoroethyl or 2,2-difluoroethyl), or $C_1$-$C_4$ alkyl (for example, methyl, ethyl, n-propyl, isopropyl, n-butyl, isobutyl, sec-butyl, or tert-butyl, preferably, for example, methyl or ethyl, and more preferably, for example, ethyl);

ring A is

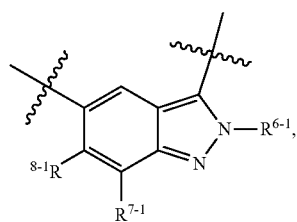

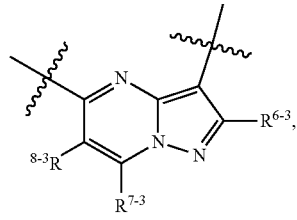

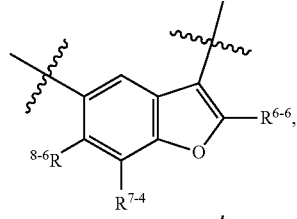

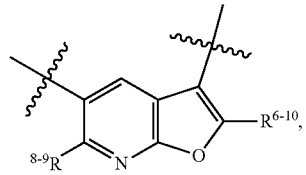

-continued

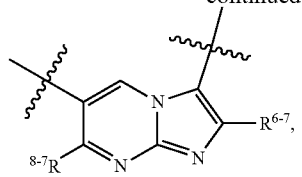

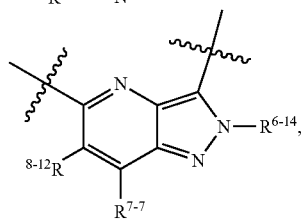

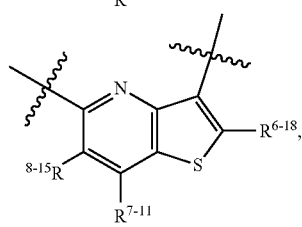

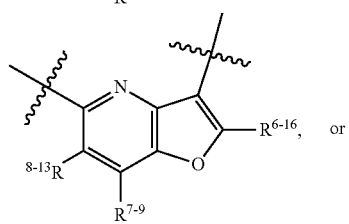

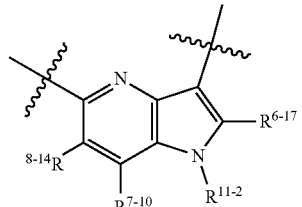

or

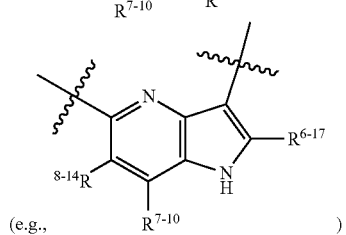

(e.g., )

[the left terminus of which is linked to ring B];

$R^{6-1}$, $R^{6-3}$, $R^{6-6}$, $R^{6-7}$, $R^{6-10}$, $R^{6-14}$, $R^{6-16}$, $R^{6-17}$, and $R^{6-18}$ are each independently selected from $C_1$-$C_4$ alkyl (e.g., methyl, ethyl, n-propyl, isopropyl, n-butyl, isobutyl, sec-butyl, or tert-butyl, preferably, e.g., methyl, ethyl, or isopropyl, and more preferably, e.g., methyl or ethyl), and $C_3$-$C_6$ cycloalkyl (e.g., cyclopropyl, cyclobutyl, cyclopentyl, or cyclohexyl, and preferably, e.g., cyclopropyl);

$R^{7-1}$, $R^{7-3}$, $R^{7-4}$, $R^{7-7}$, $R^{7-9}$, $R^{7-10}$, and $R^{7-11}$ are each independently selected from hydrogen, fluorine, $C_1$-$C_4$ alkyl (e.g., methyl, ethyl, n-propyl, isopropyl, n-butyl, isobutyl, sec-butyl, or tert-butyl, and preferably, e.g., methyl), and halogen-substituted $C_1$-$C_4$ alkyl (there can be one or more, such as 2, 3, or 4, halogens, and in case that there are a plurality of halogens, the plurality of halogens are the same or different; the halogens are independently selected from fluorine, chlorine, bromine, and iodine, and preferably, e.g., fluorine; the "$C_1$-$C_4$ alkyl" is, e.g., methyl, ethyl, n-propyl, isopropyl, n-butyl, isobutyl, sec-butyl, or tert-butyl, and preferably, e.g., methyl or ethyl; and the "halogen-substituted $C_1$-$C_4$ alkyl" is, e.g., 2-fluoroethyl, 2,2-difluoroethyl, or 2,2,2-trifluoroethyl);

$R^{8-1}$, $R^{8-3}$, $R^{8-6}$, $R^{8-7}$, $R^{8-9}$, $R^{8-12}$, $R^{8-13}$, $R^{8-14}$, and $R^{8-15}$ are each independently selected from hydrogen and halogen-substituted $C_1$-$C_4$ alkyl (there can be one or more, such as 2, 3 or 4, halogens, and in case that there are a plurality of halogens, the plurality of halogens are the same or different; the halogens are independently selected from fluorine, chlorine, bromine, and iodine, and preferably, e.g., fluorine; the "$C_1$-$C_4$ alkyl" is, e.g., methyl, ethyl, n-propyl, isopropyl, n-butyl, isobutyl, sec-butyl, or tert-butyl, and preferably, e.g., methyl or ethyl; and the "halogen-substituted $C_1$-$C_4$ alkyl" is, e.g., 2-fluoroethyl, 2,2-difluoroethyl, or 2,2,2-trifluoroethyl); and $R^{11-2}$ is hydrogen, $C_1$-$C_4$ alkyl (e.g., methyl, ethyl, n-propyl, isopropyl, n-butyl, isobutyl, sec-butyl, or tert-butyl, and preferably, e.g., methyl), or halogen-substituted $C_1$-$C_4$ alkyl (there can be one or more, such as 2, 3 or 4, halogens, and in case that there are a plurality of halogens, the halogens are the same or different; the halogen is independently selected from fluorine, chlorine, bromine, and iodine, and preferably, for example, fluorine; the "$C_1$-$C_4$ alkyl" is, e.g., methyl, ethyl, n-propyl, isopropyl, n-butyl, isobutyl, sec-butyl, or tert-butyl, and preferably, e.g., methyl or ethyl; and the "halogen-substituted $C_1$-$C_4$ alkyl" is, for example, 2-fluoroethyl, 2,2-difluoroethyl, or 2,2,2-trifluoroethyl);

ring B is "4-10 membered monocyclic or bicyclic heterocycloalkyl having 1-3 heteroatoms selected from one or more of O, N, and S" (e.g., "4-7 membered monocyclic heterocycloalkyl having 1-2 heteroatoms selected from one or more of O, N, and S", preferably, e.g., "5-6 membered monocyclic heterocycloalkyl having 1-2 heteroatoms selected from one or more of O, N, and S", and more preferably, e.g., "

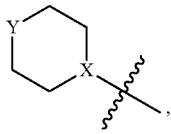

wherein X is N or CH and Y is NH or $CH_2$, which are not both carbon", and most preferably, e.g.,

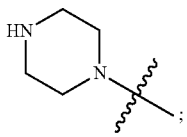

the heterocycloalkyl may be linked to ring A via a carbon atom or a nitrogen atom, and preferably via a nitrogen atom);

$R^9$ is -$L^1$-$L^2$-$L^3$; [when ring B is 6-membered heterocycloalkyl, $R^9$ can be located at the ortho, meta, or para position relative to ring A, and preferably at the para position relative to ring A; and $R^9$ can be linked to a carbon atom or a nitrogen atom of ring B, and preferably linked to a nitrogen atom of ring B]

$L^1$ is $C_1$-$C_4$ alkylene, e.g., —$CH_2$—, —$CH_2CH_2$—, —CH($CH_3$)— (wherein the chiral carbon atom can be in R configuration or S configuration), —$CH_2CH_2CH_2$—, or —$CH_2CH(CH_3)$— (wherein the chiral carbon atom can be in R configuration or S configuration);

$L^2$ is —C(=O)—;

$L^3$ is "4-10 membered monocyclic, bicyclic, or spirocyclic heterocycloalkyl having 1-3 heteroatoms selected from one or more of O, N, and S" which is substituted or unsubstituted with $R^{L-9}$ (the "4-10 membered monocyclic, bicyclic, or spirocyclic heterocycloalkyl having 1-3 heteroatoms selected from one or more of O, N, and S" is, e.g., "4-10 membered monocyclic heterocycloalkyl having 1-2 heteroatoms selected from one or more of O, N, and S", preferably, e.g., "4-6 membered monocyclic heterocycloalkyl having 1-2 heteroatoms selected from one or more of O, N, and S", and more preferably, e.g.,

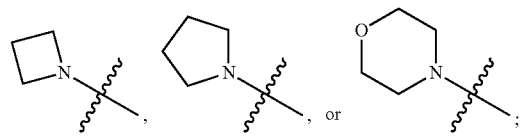

the "4-10 membered monocyclic, bicyclic, or spirocyclic heterocycloalkyl having 1-3 heteroatoms selected from one or more of O, N, and S" which is substituted with $R^{L-9}$ is, e.g.,

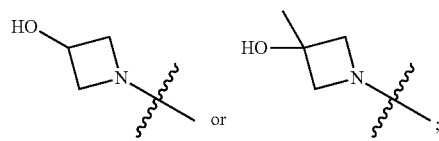

there can be one or more $R^{L-9}$, and in case that there are a plurality of $R^{L-9}$, the plurality of $R^{L-9}$ are the same or different; and the heterocycloalkyl can be linked to $L^2$ via a carbon atom or a nitrogen atom, and preferably via a nitrogen atom);

$R^{L-9}$ is independently selected from hydroxy and $C_1$-$C_4$ alkyl (e.g., methyl, ethyl, n-propyl, isopropyl, n-butyl, isobutyl, sec-butyl, or tert-butyl, and preferably, e.g., methyl); [the carbon atom in the heterocycloalkyl, linked to $R^{L-9}$, can be independently selected from a chiral carbon atom, either in R configuration or S configuration]

n is 0 or 1, $R^{10}$ is $R^{10-1}$-substituted or unsubstituted $C_1$-$C_4$ alkyl (there can be one or more $R^{10-1}$, and in case that there are a plurality of $R^{10-1}$, the plurality of $R^{10-1}$ are the same or different; the "$C_1$-$C_4$ alkyl" is, e.g., methyl, ethyl, n-propyl, isopropyl, n-butyl, isobutyl, sec-butyl, or tert-butyl, and preferably, e.g., methyl; the "$R^{10-1}$-substituted $C_1$-$C_4$ alkyl" is, e.g., trifluoromethyl); [$R^{10}$ may be independently located at the ortho, meta, or para position relative to ring A, and preferably at the ortho or meta position relative to ring A; when n is 1, $R^{10}$ may be located at the ortho or meta position relative to ring A; $R^{10}$ may be linked to a carbon atom or a nitrogen atom of ring B; and the carbon atom of ring B, linked to $R^{10}$, may be independently selected from a chiral carbon atom, either in R configuration or S configuration]; and $R^{10-1}$ is independently selected from halogens (e.g. fluorine, chlorine, bromine, or iodine, and preferably, e.g., fluorine).

In one embodiment, certain groups of compound of formula I are defined as follows, and groups not mentioned are defined in any of the above embodiments:

$R^1$ is halogen (e.g., fluorine, chlorine, bromine, or iodine, and preferably, e.g., fluorine);

m is 0 or 1, $R^3$ is halogen (e.g., fluorine, chlorine, bromine, or iodine, and preferably, e.g., fluorine); [when m is 1, $R^3$ can be located at the ortho position or meta position relative to $R^1$]

$W^1$ is =N—;
$W^2$ is =$CR^4$—;
$W^3$ is —O—, —S—, or —NH—;

when $W^2$ is =$CR^4$—, one (e.g., $R^4$) of $R^2$ and $R^4$ is cyano, and the other (e.g., $R^2$) is hydrogen;

$R^5$ is methyl, ethyl, 2-fluoroethyl, or 2,2-difluoroethyl;

ring A is

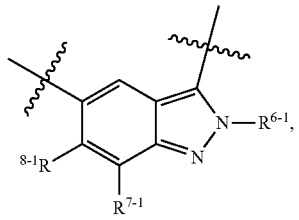

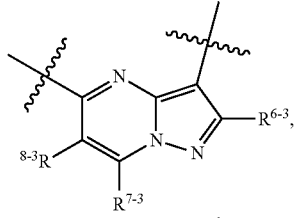

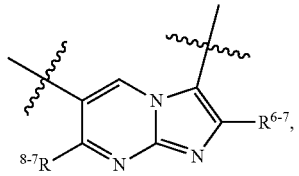

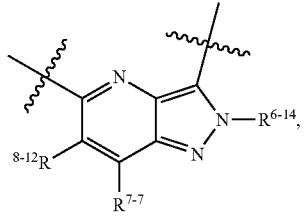

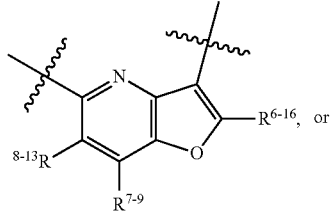

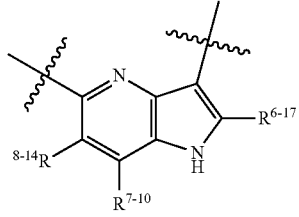

[the left terminus of which is linked to ring B];

$R^{6-1}$, $R^{6-3}$, $R^{6-7}$, $R^{6-14}$, $R^{6-16}$, and $R^{6-17}$ are independently selected from $C_1$-$C_4$ alkyl (e.g., methyl, ethyl, n-propyl, isopropyl, n-butyl, isobutyl, sec-butyl, or tert-butyl, preferably, e.g., methyl, ethyl, or isopropyl, and more preferably, e.g., methyl or ethyl), and $C_3$-$C_6$ cycloalkyl (e.g., cyclopropyl, cyclobutyl, cyclopentyl, or cyclohexyl, preferably, e.g., cyclopropyl);

$R^{7-1}$, $R^{7-3}$, $R^{7-7}$, $R^{7-9}$, and $R^{7-10}$ are independently selected from hydrogen, fluorine, and $C_1$-$C_4$ alkyl (e.g., methyl, ethyl, n-propyl, isopropyl, n-butyl, isobutyl, sec-butyl, or tert-butyl, and preferably, e.g., methyl);

$R^{8-1}$, $R^{8-3}$, $R^{8-7}$, $R^{8-12}$, $R^{8-13}$, and $R^{8-14}$ are each independently selected from hydrogen;

ring B is "4-7 membered monocyclic heterocycloalkyl having 1-2 heteroatoms selected from one or more of O, N, and S" (e.g., "5-6 membered monocyclic heterocycloalkyl having 1-2 heteroatoms selected from one or more of O, N, and S", preferably, e.g., "

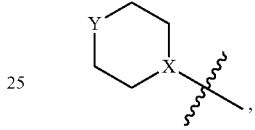

wherein X is N or CH and Y is NH or $CH_2$, which are not both carbon", more preferably, e.g.,

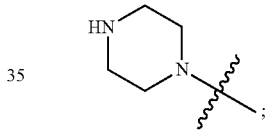

the heterocycloalkyl may be linked to ring A via a carbon atom or a nitrogen atom, and preferably via a nitrogen atom);

$R^9$ is -$L^1$-$L^2$-$L^3$; [when ring B is 6-membered heterocycloalkyl, $R^9$ can be located at the ortho, meta, or para position relative to ring A, and preferably at the para position relative to ring A; and $R^9$ can be linked to a carbon atom or a nitrogen atom of ring B, and preferably linked to a nitrogen atom of ring B]

$L^1$ is $C_1$-$C_4$ alkylene, e.g., —$CH_2$—, —$CH_2CH_2$—, —CH($CH_3$)— (wherein the chiral carbon atom can be in R configuration or S configuration), —$CH_2CH_2CH_2$—, or —$CH_2CH(CH_3)$— (wherein the chiral carbon atom can be in R configuration or S configuration);

$L^2$ is —C(=O)—;

$L^3$ is "4-6 membered monocyclic heterocycloalkyl having 1-2 heteroatoms selected from one or more of O, N, and S" which is substituted or unsubstituted with $R^{L-9}$ (the "4-6 membered monocyclic heterocycloalkyl having 1-2 heteroatoms selected from one or more of O, N, and S" is, e.g.,

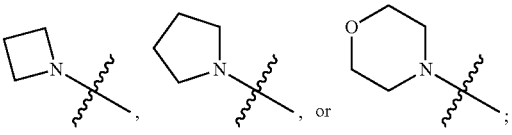

the "4-6 membered monocyclic heterocycloalkyl having 1-2 heteroatoms selected from one or more of O, N, and S" which is substituted with $R^{L-9}$ is, e.g.,

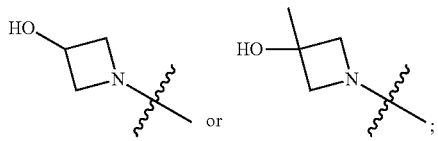

there can be one or more $R^{L-9}$, and in case that there are a plurality of $R^{L-9}$, the plurality of $R^{L-9}$ are the same or different; and the heterocycloalkyl can be linked to $L^2$ via a carbon atom or a nitrogen atom, and preferably via a nitrogen atom);

$R^{L-9}$ is independently selected from hydroxy and $C_1$-$C_4$ alkyl (e.g., methyl, ethyl, n-propyl, isopropyl, n-butyl, isobutyl, sec-butyl, or tert-butyl, and preferably, e.g., methyl); [the carbon atom in the heterocycloalkyl, linked to $R^{L-9}$, can be independently selected from a chiral carbon atom, either in R configuration or S configuration]

n is 0 or 1, $R^{10}$ is $R^{10-1}$-substituted or unsubstituted $C_1$-$C_4$ alkyl (there can be one or more $R^{10-1}$, and in case that there are a plurality of $R^{10-1}$, the plurality of $R^{10-1}$ are the same or different; the "$C_1$-$C_4$ alkyl" is, e.g., methyl, ethyl, n-propyl, isopropyl, n-butyl, isobutyl, sec-butyl, or tert-butyl, and preferably, e.g., methyl; the "$R^{10-1}$-substituted $C_1$-$C_4$ alkyl" is, e.g., trifluoromethyl); [$R^{10}$ may be independently located at the ortho, meta, or para position relative to ring A, and preferably at the ortho or meta position relative to ring A; when n is 1, $R^{10}$ may be located at the ortho or meta position relative to ring A; $R^{10}$ may be linked to a carbon atom or a nitrogen atom of ring B; and the carbon atom of ring B, linked to $R^{10}$, may be independently selected from a chiral carbon atom, either in R configuration or S configuration]; and $R^{10-1}$ is independently selected from halogens (e.g. fluorine, chlorine, bromine, or iodine, and preferably, e.g., fluorine).

In one embodiment, certain groups of compound of formula I are defined as follows, and groups not mentioned are defined in any of the above embodiments:

$R^1$ is halogen (e.g., fluorine, chlorine, bromine, or iodine, and preferably, e.g., fluorine);

m is 0 or 1, $R^3$ is halogen (e.g., fluorine, chlorine, bromine, or iodine, and preferably, e.g., fluorine); [when m is 1, $R^3$ can be located at the ortho position or meta position relative to $R^1$]

$W^1$ is =N—;
$W^2$ is =CR$^4$—;
$W^3$ is —O—, —S—, or —NH—;
when $W^2$ is =CR$^4$—, one (e.g., $R^4$) of $R^2$ and $R^4$ is cyano, and the other (e.g., $R^2$) is hydrogen;

$R^5$ is methyl, ethyl, 2-fluoroethyl, or 2,2-difluoroethyl; ring A is

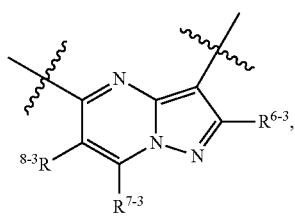

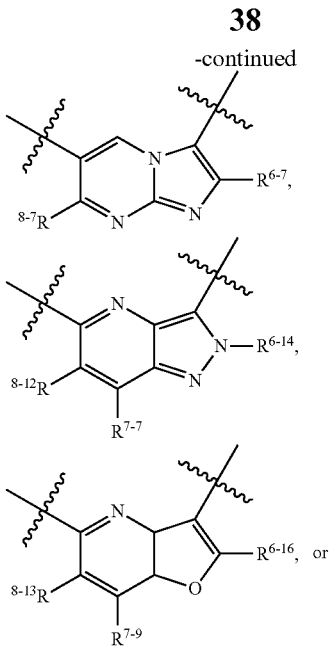

[the left terminus of which is linked to ring B];

$R^{6-3}$, $R^{6-7}$, $R^{6-14}$, $R^{6-16}$, and $R^{6-17}$ are independently selected from $C_1$-$C_4$ alkyl (e.g., methyl, ethyl, n-propyl, isopropyl, n-butyl, isobutyl, sec-butyl, or tert-butyl, preferably, e.g., methyl, ethyl, or isopropyl, more preferably, e.g., methyl or ethyl), and $C_3$-$C_6$ cycloalkyl (e.g., cyclopropyl, cyclobutyl, cyclopentyl, or cyclohexyl, preferably, e.g., cyclopropyl);

$R^{7-3}$, $R^{7-7}$, $R^{7-9}$, and $R^{7-10}$ are independently selected from hydrogen, fluorine, and $C_1$-$C_4$ alkyl (e.g., methyl, ethyl, n-propyl, isopropyl, n-butyl, isobutyl, sec-butyl, or tert-butyl, and preferably, e.g., methyl);

$R^{8-3}$, $R^{8-7}$, $R^{8-12}$, $R^{8-13}$, and $R^{8-14}$ are each independently selected from hydrogen;

ring B is "4-7 membered monocyclic heterocycloalkyl having 1-2 heteroatoms selected from one or more of O, N, and S" (e.g., "5-6 membered monocyclic heterocycloalkyl having 1-2 heteroatoms selected from one or more of O, N, and S", preferably, e.g., "

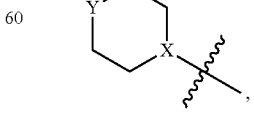

wherein X is N or CH and Y is NH or $CH_2$, which are not both carbon", more preferably, e.g.,

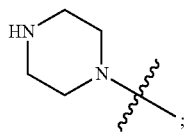

the heterocycloalkyl may be linked to ring A via a carbon atom or a nitrogen atom, and preferably via a nitrogen atom);

$R^9$ is -$L^1$-$L^2$-$L^3$; [when ring B is 6-membered heterocycloalkyl, $R^9$ can be located at the ortho, meta, or para position relative to ring A, and preferably at the para position relative to ring A; and $R^9$ can be linked to a carbon atom or a nitrogen atom of ring B, and preferably linked to a nitrogen atom of ring B]

$L^1$ is $C_1$-$C_4$ alkylene, e.g., —$CH_2$—, —$CH_2CH_2$—, —CH($CH_3$)— (wherein the chiral carbon atom can be in R configuration or S configuration), —$CH_2CH_2CH_2$—, or —$CH_2CH(CH_3)$— (wherein the chiral carbon atom can be in R configuration or S configuration);

$L^2$ is —C(=O)—;

$L^3$ is "4-6 membered monocyclic heterocycloalkyl having 1-2 heteroatoms selected from one or more of O, N, and S" which is substituted or unsubstituted with $R^{L\text{-}9}$ (the "4-6 membered monocyclic heterocycloalkyl having 1-2 heteroatoms selected from one or more of O, N, and S" is, e.g.,

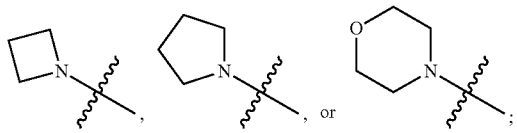

the "4-6 membered monocyclic heterocycloalkyl having 1-2 heteroatoms selected from one or more of O, N, and S" which substituted with $R^{L\text{-}9}$ is, e.g.,

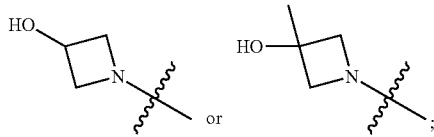

there can be one or more $R^{L\text{-}9}$, and in case that there are a plurality of $R^{L\text{-}9}$, the plurality of $R^{L\text{-}9}$ are the same or different; and the heterocycloalkyl can be linked to $L^2$ via a carbon atom or a nitrogen atom, and preferably via a nitrogen atom);

$R^{L\text{-}9}$ is independently selected from hydroxy and $C_1$-$C_4$ alkyl (e.g., methyl, ethyl, n-propyl, isopropyl, n-butyl, isobutyl, sec-butyl, or tert-butyl, and preferably, e.g., methyl); [the carbon atom in the heterocycloalkyl, linked to $R^{L\text{-}9}$, can be independently selected from a chiral carbon atom, either in R configuration or S configuration]

n is 0 or 1, $R^{10}$ is $R^{10\text{-}1}$-substituted or unsubstituted $C_1$-$C_4$ alkyl (there can be one or more $R^{10\text{-}1}$, and in case that there are a plurality of $R^{10\text{-}1}$, the plurality of $R^{10\text{-}1}$ are the same or different; the "$C_1$-$C_4$ alkyl" is, e.g., methyl, ethyl, n-propyl, isopropyl, n-butyl, isobutyl, sec-butyl, or tert-butyl, and preferably, e.g., methyl; the "$R^{10\text{-}1}$-substituted $C_1$-$C_4$ alkyl" is, e.g., trifluoromethyl); [$R^{10}$ may be independently located at the ortho, meta, or para position relative to ring A, and preferably at the ortho or meta position relative to ring A; when n is 1, $R^{10}$ may be located at the ortho or meta position relative to ring A; $R^{10}$ may be linked to a carbon atom or a nitrogen atom of ring B; and the carbon atom of ring B, linked to $R^{10}$, may be independently selected from a chiral carbon atom, either in R configuration or S configuration]; and $R^{10\text{-}1}$ is independently selected from halogens (e.g. fluorine, chlorine, bromine, or iodine, and preferably, e.g., fluorine).

In one embodiment, certain groups of compound of formula I are defined as follows, and groups not mentioned are defined in any of the above embodiments:

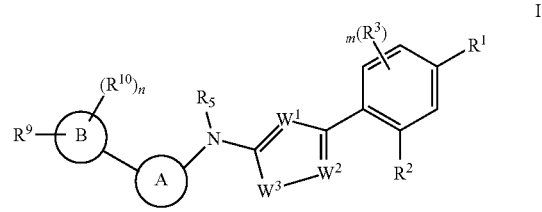

$R^1$ is independently selected from hydrogen, cyano, halogen (e.g., fluorine, chlorine, bromine, or iodine, and preferably, e.g., fluorine), $C_1$-$C_4$ alkyl, and $C_1$-$C_4$ alkoxy;

m is 0, 1, 2, or 3, and $R^3$ is independently selected from halogen (e.g., fluorine, chlorine, bromine, or iodine, and preferably, e.g., fluorine), cyano, $R^{3\text{-}1}$-substituted or unsubstituted $C_1$-$C_4$ alkyl (there are one or more $R^{3\text{-}1}$, and in case that there are a plurality of $R^{3\text{-}1}$, the plurality of $R^{3\text{-}1}$ are the same or different; and the "$C_1$-$C_4$ alkyl" is, e.g., methyl, ethyl, n-propyl, isopropyl, n-butyl, isobutyl, sec-butyl, or tert-butyl, and preferably, e.g., methyl), and $R^{3\text{-}2}$-substituted or unsubstituted $C_1$-$C_4$ alkoxy (there can be one or more $R^{3\text{-}2}$, and in case that there are a plurality of $R^{3\text{-}2}$, the plurality of $R^{3\text{-}2}$ are the same or different); $R^{3\text{-}1}$ and $R^{3\text{-}2}$ are each independently selected from halogens; [$R^3$ may be independently located at the ortho or meta position relative to $R^1$; when m is 1, $R^3$ may be located at the ortho or meta position relative to $R^1$]

$W^1$ is =CH— or =N—;

$W^2$ is =$CR^4$— or =N—;

$W^3$ is —O—, —S—, —NH—, —N=CH—, —CH=N—, or —CH=CH—;

when $W^2$ is =N—, $R^2$ is hydrogen, cyano, halogen (e.g., fluorine, chlorine, bromine, or iodine, preferably, e.g., fluorine), $R^{2\text{-}1}$-substituted or unsubstituted $C_1$-$C_4$ alkyl (there can be one or more $R^{2\text{-}1}$, and in case that there are a plurality of $R^{2\text{-}1}$, the plurality of $R^{2\text{-}1}$ are the same or different; and the "$C_1$-$C_4$ alkyl" is, e.g., methyl, ethyl, n-propyl, isopropyl, n-butyl, isobutyl, sec-butyl or tert-butyl, and preferably, e.g., methyl), —C(=O)$CH_3$, —C(=O)$CF_3$, —C(=O)$OCH_3$, —C(=O)$NH_2$, or —NHC(=O)$CH_3$; $R^{2\text{-}1}$ is independently selected from hydroxy and cyano;

when $W^2$ is =$CR^4$—, one of $R^2$ or $R^4$, e.g., $R^4$, is hydrogen, cyano, halogen (e.g., fluorine, chlorine, bromine, or iodine, and preferably, e.g., fluorine), $R^{2\text{-}2}$-substituted or unsubstituted $C_1$-$C_4$ alkyl (there can be one or more $R^{2\text{-}2}$, and in case that there are a plurality of $R^2$, the plurality of $R^{2\text{-}2}$ are the same or different), —C(=O)$CH_3$, —C(=O)$CF_3$, —C(=O)$OCH_3$, —C(=O)$NH_2$, or —NHC(=O)$CH_3$, and the other one, such as $R^2$, is hydrogen or $C_1$-$C_4$ alkyl; $R^{2\text{-}2}$ is independently selected from hydroxy and cyano;

$R^5$ is $C_1$-$C_4$ alkyl (e.g., methyl, ethyl, n-propyl, isopropyl, n-butyl, isobutyl, sec-butyl, or tert-butyl, and preferably, e.g., methyl);
ring A is
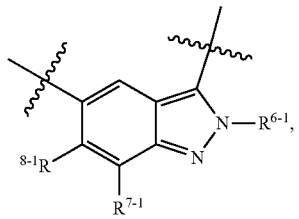
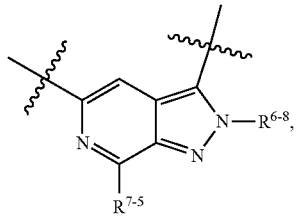
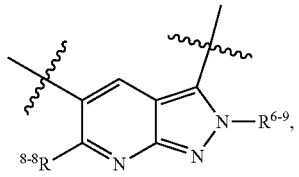
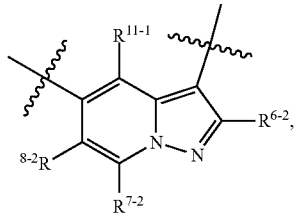
(e.g., 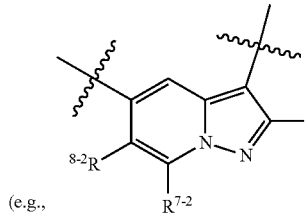),
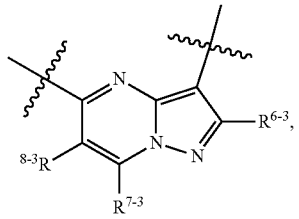
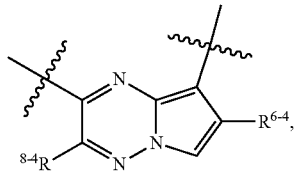
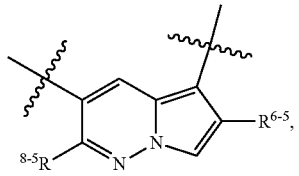
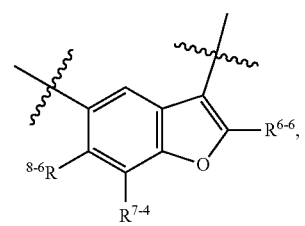
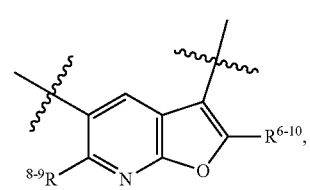
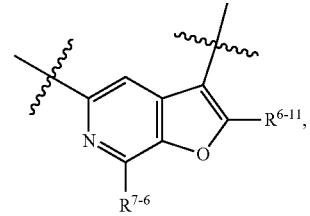
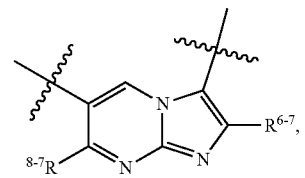
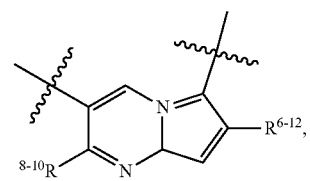
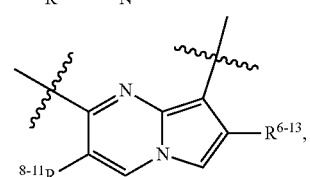
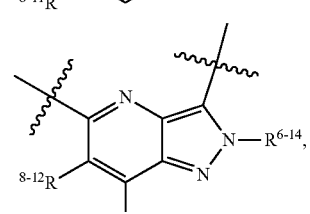
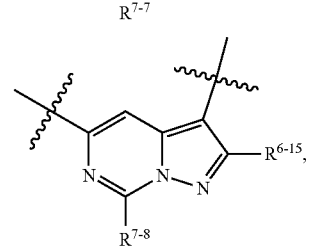

-continued

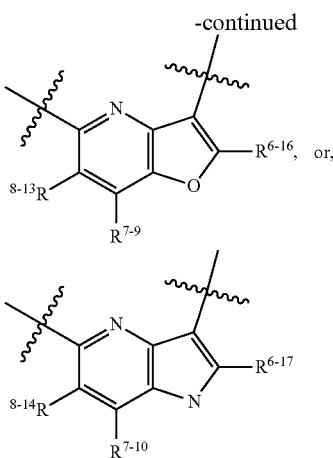

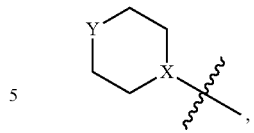

wherein X is N or CH, and Y is NH or CH$_2$, but X and Y are not both carbon", and yet more preferably, e.g.,

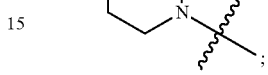

and the heterocycloalkyl can be linked to ring A via a carbon atom or a nitrogen atom, and preferably via a nitrogen atom), or "4-7 membered heterocycloalkenyl having 1 double bond and 1-3 heteroatoms selected from one or more of O, N, and S" (e.g., "5-6 membered heterocycloalkenyl having 1 double bond and 1-2 heteroatoms selected from one or more of O, N, and S", and preferably, e.g.,

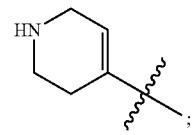 [SMILES: *C1=CCNCC1 ; ";"]

and the heterocycloalkenyl can be linked to ring A via a carbon atom or a nitrogen atom, and preferably via a nitrogen atom);

(the left terminus of which is linked to ring B);

$R^{6-1}$, $R^{6-2}$, $R^{63}$, $R^{6-4}$, $R^{6-5}$, $R^6$, $R^{6-7}$, $R^{6-8}$, $R^{6-9}$, $R^{6-10}$, $R^{6-11}$, $R^{6-12}$, $R^{6-13}$, $R^{6-14}$, $R^{6-15}$, $R^{6-16}$, and $R^{6-17}$ each independently selected from hydrogen and $R^{6-1-1}$-substituted or unsubstituted $C_1$-$C_4$ alkyl (there are one or more $R^{6-1-1}$, and in case that there are a plurality of $R^{6-1}$, the plurality of $R^{6-1-1}$ are the same or different; and the "$C_1$-$C_4$ alkyl" is, e.g., methyl, ethyl, n-propyl, isopropyl, n-butyl, isobutyl, sec-butyl, or tert-butyl, and preferably, e.g., methyl or ethyl); and $R^{6-1-1}$ is independently selected from hydroxy, cyano, halogen, and —C(=O)NH$_2$;

$R^{7-1}$, $R^{7-2}$, $R^{7-3}$, $R^{7-4}$, $R^{7-5}$, $R^{7-6}$, $R^{7-7}$, $R^{7-8}$, $R^{7-9}$, and $R^{7-10}$ are each independently selected from hydrogen, cyano, halogen (e.g., fluorine, chlorine, bromine, or iodine, and preferably, e.g., fluorine), and $C_1$-$C_4$ alkyl (e.g., methyl, ethyl, n-propyl, isopropyl, n-butyl, isobutyl, sec-butyl, or tert-butyl, and preferably, e.g., methyl);

$R^{8-1}$, $R^{8-2}$, $R^{8-3}$, $R^{8-4}$, $R^{8-5}$, $R^{8-6}$, $R^{8-7}$, $R^{8-8}$, $R^{8-9}$, $R^{8-10}$, $R^{8-11}$, $R^{8-12}$, $R^{8-13}$, and $R^{8-14}$ are each independently selected from hydrogen, cyano, halogen (e.g., fluorine, chlorine, bromine, or iodine, and preferably, e.g., fluorine), and $C_1$-$C_4$ alkyl (e.g., methyl, ethyl, n-propyl, isopropyl, n-butyl, isobutyl, sec-butyl, or tert-butyl, and preferably, e.g., methyl);

$R^{11-1}$ is hydrogen or halogen (e.g., fluorine, chlorine, bromine, or iodine, and preferably, e.g., fluorine);

ring B is $C_3$-$C_{10}$ cycloalkyl (e.g., $C_3$-$C_6$ cycloalkyl, and preferably, e.g., $C_5$-$C_6$ cycloalkyl), $C_4$-$C_7$ cycloalkenyl (e.g., $C_5$-$C_6$ cycloalkenyl, preferably, e.g., cyclohexenyl, and more preferably, e.g.,

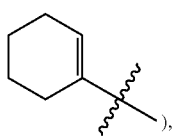),

"4-10 membered monocyclic or bicyclic heterocycloalkyl having 1-3 heteroatoms selected from one or more of O, N, and S" (e.g., "4-7 membered monocyclic heterocycloalkyl having 1-2 heteroatoms selected from one or more of O, N, and S", preferably, e.g., "5-6 membered monocyclic heterocycloalkyl having 1-2 heteroatoms selected from one or more of O, N, and S", more preferably, e.g., "

$R^9$ is -L$^1$-L$^2$-L$^3$; [when ring B is 6-membered heterocycloalkyl or heterocycloalkenyl, $R^9$ can be located at the ortho, meta, or para position relative to ring A, and preferably at the para position relative to ring A; and $R^9$ can be linked to a carbon atom or a nitrogen atom of ring B, and preferably linked to a nitrogen atom of ring B]

L$^1$ is a single bond (i.e., L$^2$ and ring B are directly linked), or $C_1$-$C_4$ alkylene (for example, —CH$_2$—, —CH$_2$CH$_2$—, —CH(CH$_3$)— [wherein the chiral carbon atom may be in R configuration or S configuration], —CH$_2$CH$_2$CH$_2$—, or —CH$_2$CH(CH$_3$)— [wherein the chiral carbon atom may be in R configuration or S configuration]);

L$^2$ is —O—, —C(=O)—, —C(=O)O—, —OC(=O)—, —C(=O)—C(=O)—, —C(=O)—C(=O)NR$^{L-1}$—, —NR$^{L-2}$—, —C(=O)NR$^{L-3}$—, —NR$^{L-4}$C(=O)—, —NR$^{L-5}$C(O)O—, —SO$_2$—, —SO$_2$NR$^{L-6}$—, or —NR$^{L-7}$SO$_2$— (the left terminus of which is linked to L$^1$);

R$^{L-1}$, R$^{L-2}$, R$^{L-3}$, R$^{L-4}$, R$^{L-5}$, R$^{L-6}$, and R$^{L-7}$ are each independently selected from hydrogen and $C_1$-$C_4$ alkyl (e.g., methyl, ethyl, n-propyl, isopropyl, n-butyl, isobutyl, sec-butyl, or tert-butyl, and preferably, e.g., methyl);

L$^3$ is hydrogen, cyano, R$^{L-8}$-substituted or unsubstituted $C_1$-$C_4$ alkyl (there can be one or more R$^{L-8}$, and in case that there are a plurality of R$^{L-8}$, the plurality of R$^{L-8}$ are the same or different; and the $C_1$-$C_4$ alkyl is, e.g., methyl, ethyl, n-propyl, isopropyl, n-butyl, isobutyl, sec-butyl or tert-butyl, and preferably, e.g., methyl), amino-substituted or unsubstituted $C_3$-$C_7$ cycloalkyl (there can be one or more aminos), "4-10 membered monocyclic, bicyclic, or spirocyclic heterocycloalkyl having 1-3 heteroatoms selected from one or more of O, N, and S" which is substituted or unsubstituted with $R^{L-9}$ (the "4-10 membered monocyclic, bicyclic, or spirocyclic heterocycloalkyl having 1-3 heteroatoms selected from one or more of O, N, and S" is, e.g., "4-10 membered monocyclic heterocycloalkyl having 1-2 heteroatoms selected from one or more of O, N, and S", preferably, e.g., "4-6 membered monocyclic heterocycloalkyl having 1-2 heteroatoms selected from one or more of O, N, and S", and more preferably, e.g.,

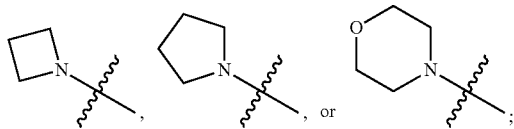
, , or ;

the "4-10 membered monocyclic, bicyclic, or spirocyclic heterocycloalkyl having 1-3 heteroatoms selected from one or more of O, N, and S" which is substituted with $R^{L-9}$ is, e.g.,

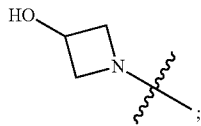
;

there can be one or more $R^{L-9}$, and in case that there are a plurality of $R^{L-9}$, the plurality of $R^{L-9}$ are the same or different; and the heterocycloalkyl can be linked to $L^2$ via a carbon atom or a nitrogen atom, and preferably via a nitrogen atom), "5-6 membered heterocycloalkenyl having 1 double bond and 1-3 heteroatoms selected from one or more of O, N, and S" which is substituted or unsubstituted with $R^{L-10}$ (the "5-6 membered heterocycloalkenyl having 1 double bond and 1-3 heteroatoms selected from one or more of O, N, and S" is, e.g., "5-6 membered heterocycloalkenyl having 1 double bond and 1-2 heteroatoms selected from one or more of O, N, and S"; there can be one or more $R^{L-10}$, and in case that there are a plurality of $R^{L-10}$, the plurality of $R^{L-10}$ are the same or different; and the heterocycloalkenyl can be linked to $L^2$ via a carbon atom or a nitrogen atom, and preferably via a nitrogen atom), or "5-6 membered heteroaryl having 1-3 heteroatoms selected from one or more of O, N, and S" which is substituted or unsubstituted with $R^{L-10}$ (the "5-6 membered heteroaryl having 1-3 heteroatoms selected from one or more of O, N, and S" is, e.g., "5-6 membered heteroaryl having 1-2 heteroatoms selected from one or more of O, N, and S"; there can be one or more $R^{L-10}$, and in case that there are a plurality of $R^{L-11}$, $R^{L-11}$ are the same or different; and the heteroaryl can be linked to $L^2$ via a carbon atom or a nitrogen atom, and preferably via a nitrogen atom);

$R^{L-8}$ is independently selected from hydroxy, cyano, halogen, and phenyl;

$R^{L-9}$ is independently selected from oxo, hydroxy, cyano, halogen (e.g., fluorine, chlorine, bromine, or iodine, and preferably, e.g., fluorine), phenyl, hydroxy-substituted $C_1$-$C_4$ alkyl (there can be one or more hydroxys; the "$C_1$-$C_4$ alkyl" is, e.g., methyl, ethyl, n-propyl, isopropyl, n-butyl, isobutyl, sec-butyl, or tert-butyl, and preferably, e.g., methyl; and the "hydroxy-substituted $C_1$-$C_4$ alkyl" is, e.g., hydroxymethyl), —$SO_2CH_3$, —C(=O)$R^{L-9-1}$, and —$NR^{L-9-2}$C(=O)$R^{L-9-3}$; $R^{L-9-1}$ is independently selected from $C_1$-$C_4$ alkyl and $C_1$-$C_4$ alkoxy; $R^{L-9-2}$ is independently selected from hydrogen and $C_1$-$C_4$ alkyl; and $R^{L-9-3}$ is independently selected from $C_1$-$C_4$ alkyl; [the carbon atom in the heterocycloalkyl, linked to $R^{L-9}$, can be independently selected from a chiral carbon atom, either in R or S configuration]

$R^{L-10}$ is independently selected from oxo, hydroxy, cyano, halogen, phenyl, —$SO_2CH_3$, —C(=O)$R^{L-10-1}$ and —$NR^{L-10-2}$C(=O)$R^{L-10-3}$; $R^{L-10-1}$ is independently selected from $C_1$-$C_4$ alkyl and $C_1$-$C_4$ alkoxy; $R^{L-10-2}$ is independently selected from hydrogen and $C_1$-$C_4$ alkyl; and $R^{L-10-3}$ is independently selected from $C_1$-$C_4$ alkyl; [the carbon atom in the heterocycloalkenyl, linked to $R^{L-10}$, can be independently selected from a chiral carbon atom, either in R configuration or S configuration]

$R^{L-11}$ is independently selected from hydroxy, cyano, halogen, phenyl, —$SO_2CH_3$, —C(=O)$R^{L-10-1}$ and —$NR^{L-11-2}$C(=O)$R^{L-11-3}$; $R^{L-10-1}$ is independently selected from $C_1$-$C_4$ alkyl and $C_1$-$C_4$ alkoxy; $R^{L-10-2}$ is independently selected from hydrogen and $C_1$-$C_4$ alkyl; $R^{L-11-3}$ is independently selected from $C_1$-$C_4$ alkyl; and n is 0, 1, 2, 3, or 4, $R^{10}$ is independently selected from hydroxy, halogen (e.g., fluorine, chlorine, bromine, or iodine, and preferably e.g., fluorine), oxo, and $R^{10-1}$-substituted or unsubstituted $C_1$-$C_4$ alkyl (there can be one or more $R^{10-1}$, and in case that there are a plurality of $R^{10-1}$, the plurality of $R^{10-1}$ are the same or different; and the "$C_1$-$C_4$ alkyl" is, e.g., methyl, ethyl, n-propyl, isopropyl, n-butyl, isobutyl, sec-butyl, or tert-butyl, and preferably, e.g., methyl); and $R^{10-1}$ is independently selected from hydroxy and $C_1$-$C_4$ alkoxy. [The $R^1$ can be independently located at the ortho, meta or para position relative to ring A, and preferably at the ortho or meta position relative to ring A; when n is 1, $R^{10}$ can be located at the ortho or meta position relative to ring A; $R^1$ can be linked to a carbon atom or a nitrogen atom of ring B; and the carbon atom of ring B, linked to $R^{10}$, can be independently selected from a chiral carbon atom, either in R configuration or S configuration]

In one embodiment, certain groups of compound of formula I are defined as follows, and groups not mentioned are defined in any of the above embodiments:

$R^1$ can be halogen.

In one embodiment, certain groups of compound of formula I are defined as follows, and groups not mentioned are defined in any of the above embodiments:

m can be 0 or 1, and preferably 0.

In one embodiment, certain groups of compound of formula I are defined as follows, and groups not mentioned are defined in any of the above embodiments:

$R^3$ can be halogen.

In one embodiment, certain groups of compound of formula I are defined as follows, and groups not mentioned are defined in any of the above embodiments:

$W^1$ may be =N—.

In one embodiment, certain groups of compound of formula I are defined as follows, and groups not mentioned are defined in any of the above embodiments:

$W^2$ may be =$CR^4$—.

In one embodiment, certain groups of compound of formula I are defined as follows, and groups not mentioned are defined in any of the above embodiments:

$W^3$ may be —S— or —CH=CH—.

In one embodiment, certain groups of compound of formula I are defined as follows, and groups not mentioned are defined in any of the above embodiments:

$W^2$ may be =$CR^4$— or =N—.

In one embodiment, certain groups of compound of formula I are defined as follows, and groups not mentioned are defined in any of the above embodiments:

W³ may be —S—, —CH═CH—, or —N═CH—.

In one embodiment, certain groups of compound of formula I are defined as follows, and groups not mentioned are defined in any of the above embodiments:

when W² is ═N—, R² can be cyano, halogen, or $C_1$-$C_4$ alkyl.

In one embodiment, certain groups of compound of formula I are defined as follows, and groups not mentioned are defined in any of the above embodiments:

when W² is ═CR⁴—, one of R² and R⁴ is cyano, and the other is hydrogen.

In one embodiment, certain groups of compound of formula I are defined as follows, and groups not mentioned are defined in any of the above embodiments:

when W² is ═CR⁴—, R⁴ may be cyano, and R² may be hydrogen.

In one embodiment, certain groups of compound of formula I are defined as follows, and groups not mentioned are defined in any of the above embodiments:

ring A may be

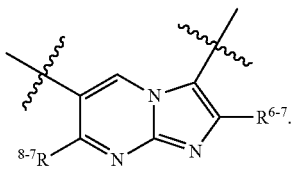

In one embodiment, certain groups of compound of formula I are defined as follows, and groups not mentioned are defined in any of the above embodiments:

ring A may be

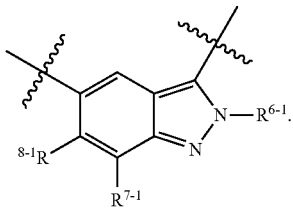

In one embodiment, certain groups of compound of formula I are defined as follows, and groups not mentioned are defined in any of the above embodiments:

ring A may be

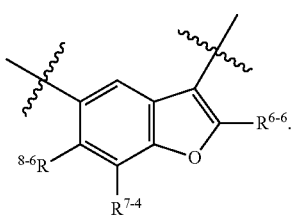

In one embodiment, certain groups of compound of formula I are defined as follows, and groups not mentioned are defined in any of the above embodiments:

ring A may be

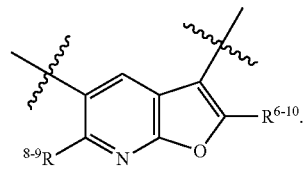

In one embodiment, certain groups of compound of formula I are defined as follows, and groups not mentioned are defined in any of the above embodiments:

ring A may be

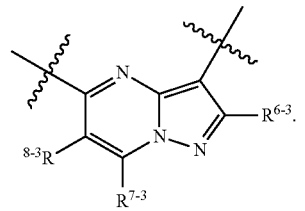

In one embodiment, certain groups of compound of formula I are defined as follows, and groups not mentioned are defined in any of the above embodiments:

ring A may be

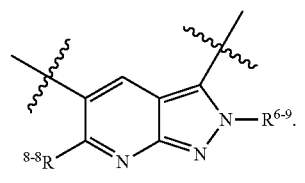

In one embodiment, certain groups of compound of formula I are defined as follows, and groups not mentioned are defined in any of the above embodiments:

ring A may be

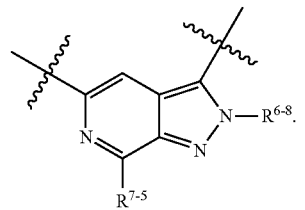

In one embodiment, certain groups of compound of formula I are defined as follows, and groups not mentioned are defined in any of the above embodiments:

ring A may be

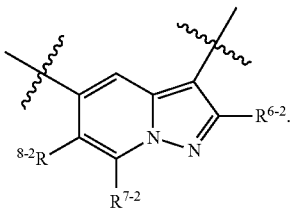

In one embodiment, certain groups of compound of formula I are defined as follows, and groups not mentioned are defined in any of the above embodiments:

ring A may be

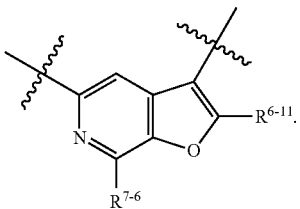

In one embodiment, certain groups of compound of formula I are defined as follows, and groups not mentioned are defined in any of the above embodiments:

ring A may be

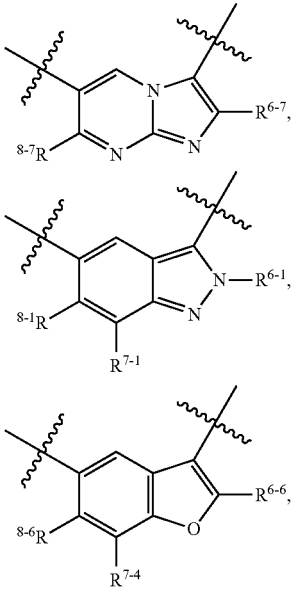

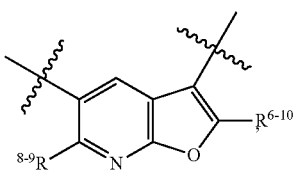

-continued

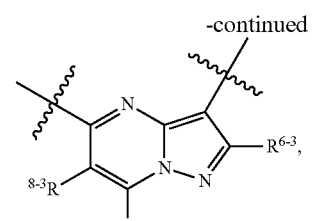

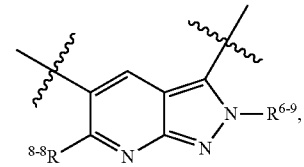

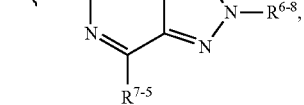

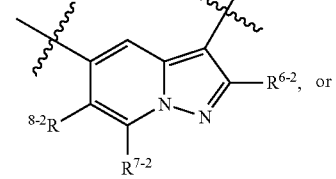

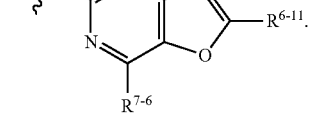

In one embodiment, certain groups of compound of formula I are defined as follows, and groups not mentioned are defined in any of the above embodiments:

$R^{6-1}$, $R^{6-2}$, $R^{6-3}$, $R^{6-4}$, $R^{6-5}$, $R^{6-6}$, $R^{6-7}$, $R^{6-8}$, $R^{6-9}$, $R^{6-10}$, $R^{6-11}$, $R^{6-12}$, $R^{6-13}$, $R^{6-14}$, $R^{6-15}$, $R^{6-16}$, and $R^{6-17}$ can be independently selected from $C_1$-$C_4$ alkyl.

In one embodiment, certain groups of compound of formula I are defined as follows, and groups not mentioned are defined in any of the above embodiments:

at least one of $R^{7-1}$ and $R^{8-1}$ is hydrogen (e.g., only one of the two is hydrogen).

In one embodiment, certain groups of compound of formula I are defined as follows, and groups not mentioned are defined in any of the above embodiments:

at least one of $R^{7-2}$ and $R^{8-2}$ is hydrogen (e.g., only one of the two is hydrogen).

In one embodiment, certain groups of compound of formula I are defined as follows, and groups not mentioned are defined in any of the above embodiments:

at least one of $R^{7-3}$ and $R^{8-3}$ is hydrogen (e.g., only one of the two is hydrogen).

In one embodiment, certain groups of compound of formula I are defined as follows, and groups not mentioned are defined in any of the above embodiments:

at least one of $R^{7-4}$ and $R^{8-6}$ is hydrogen (e.g., only one of the two is hydrogen).

In one embodiment, certain groups of compound of formula I are defined as follows, and groups not mentioned in any of the above embodiments:

$R^{7-1}$, $R^{7-2}$, $R^{7-3}$, $R^{7-4}$, $R^{7-5}$, $R^{7-6}$, $R^{7-7}$, $R^{7-8}$, $R^{7-9}$ and $R^{7-10}$ can be independently selected from hydrogen, halogen, or $C_1$-$C_4$ alkyl.

In one embodiment, certain groups of compound of formula I are defined as follows, and groups not mentioned in any of the above embodiments:

$R^1$, $R^{8-2}$, $R^{8-3}$, $R^{8-4}$, $R^{8-5}$, $R^{8-6}$, $R^{8-7}$, $R^{8-8}$, $R^{8-9}$, $R^{8-10}$, $R^{8-11}$, $R^{8-12}$, $R^{8-13}$, and $R^{8-14}$ can be independently selected from hydrogen and halogen.

In one embodiment, certain groups of compound of formula I are defined as follows, and groups not mentioned in any of the above embodiments:

ring B may be "4-10 membered monocyclic or bicyclic heterocycloalkyl having 1-3 heteroatoms selected from one or more of O, N, and S", or "4-7 membered heterocycloalkenyl having 1 double bond and 1-3 heteroatoms selected from one or more of O, N, and S".

In one embodiment, certain groups of compound of formula I are defined as follows, and groups not mentioned in any of the above embodiments:

$L^1$ may be $C_1$-$C_4$ alkylene.

In one embodiment, certain groups of compound of formula I are defined as follows, and groups not mentioned in any of the above embodiments:

$L^2$ may be —C(=O)— or —SO$_2$—, and preferably —C(=O)—.

In one embodiment, certain groups of compound of formula I are defined as follows, and groups not mentioned in any of the above embodiments:

$L^3$ may be "4-10 membered monocyclic, bicyclic, or spirocyclic heterocycloalkyl having 1-3 heteroatoms selected from one or more of O, N, and S" which is substituted or unsubstituted with $R^{L-9}$ In one embodiment, certain groups of compound of formula I are defined as follows, and groups not mentioned in any of the above embodiments:

$R^{L-9}$ may be independently selected from hydroxy and halogen.

In one embodiment, certain groups of compound of formula I are defined as follows, and groups not mentioned in any of the above embodiments:

n can be 0 or 1, and preferably 0.

In one embodiment, certain groups of compound of formula I are defined as follows, and groups not mentioned in any of the above embodiments:

$R^{10}$ is independently selected from hydroxy and $C_1$-$C_4$ alkyl.

In one embodiment, certain groups of compound of formula I are defined as follows, and groups not mentioned in any of the above embodiments:

$R^1$ is cyano or halogen (e.g., fluorine, chlorine, bromine, or iodine, and preferably, e.g., fluorine);
m is 0;
$W^1$ is =N—;
$W^2$ is =CR$^4$— or =N—;
$W^3$ is —S—;
when $W^2$ is =N—, $R^2$ is hydrogen, cyano, or methyl;
when $W^2$ is =CR$^4$—, "$R^4$ is cyano and $R^2$ is hydrogen", or, "$R^4$ is hydrogen and $R^2$ is cyano";
$R^5$ is $C_1$-$C_4$ alkyl (e.g., methyl, ethyl, n-propyl, isopropyl, n-butyl, isobutyl, sec-butyl, or tert-butyl, and preferably, e.g., methyl);

ring A is

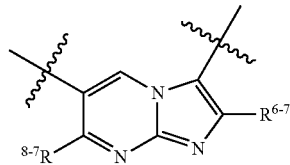

[the left terminus of which is linked to ring B];
$R^{6-7}$ is $R^{6-1-1}$-substituted or unsubstituted $C_1$-$C_4$ alkyl (there can be one or more $R^{6-1-1}$, and in case that there are a plurality of $R^{6-1}$—, the plurality of $R^{6-1-1}$ are the same or different; and the "$C_1$-$C_4$ alkyl" is, e.g., methyl, ethyl, n-propyl, isopropyl, n-butyl, isobutyl, sec-butyl, or tert-butyl, and preferably, e.g., ethyl), and $R^{6-1-1}$ is independently selected from hydroxy, cyano, halogen, or —C(=O)NH$_2$;
$R^{8-7}$ is hydrogen; and
ring B is "4-10 membered monocyclic or bicyclic heterocycloalkyl having 1-3 heteroatoms selected from one or more of O, N, and S" (e.g., "4-7 membered monocyclic heterocycloalkyl having 1-2 heteroatoms selected from one or more of O, N, and S", preferably, e.g., "5-6 membered monocyclic heterocycloalkyl having 1-2 heteroatoms selected from one or more of O, N, and S", and more preferably, e.g., "

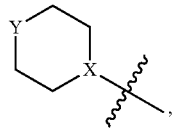

wherein X is N or CH and Y is NH or CH$_2$, which are not both carbon", and most preferably, e.g.,

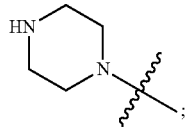 [SMILES: *N1CCNCC1 ; ";"]

the heterocycloalkyl may be linked to ring A via a carbon atom or a nitrogen atom, and preferably via a nitrogen atom);
$R^9$ is -$L^1$-$L^2$-$L^3$; [when ring B is 6-membered heterocycloalkyl, $R^9$ can be located at the ortho, meta, or para position relative to ring A, and preferably at the para position relative to ring A; and $R^9$ can be linked to a carbon atom or a nitrogen atom of ring B, and preferably linked to a nitrogen atom of ring B]
$L^1$ is $C_1$-$C_4$ alkylene, e.g., —CH$_2$—, —CH$_2$CH$_2$—, —CH(CH$_3$)— (wherein the chiral carbon atom can be in R configuration or S configuration), —CH$_2$CH$_2$CH$_2$—, or —CH$_2$CH(CH$_3$)— (wherein the chiral carbon atom can be in R configuration or S configuration);
$L^2$ is —C(=O)—;
$L^3$ is "4-10 membered monocyclic, bicyclic, or spirocyclic heterocycloalkyl having 1-3 heteroatoms selected from one or more of O, N, and S" which is substituted or unsubstituted with $R^{L-9}$ (the "4-10 membered monocyclic, bicyclic, or spirocyclic heterocycloalkyl having 1-3 heteroatoms selected from one or more of O, N, and S" is, e.g., "4-10 membered monocyclic heterocycloalkyl having 1-2 heteroatoms selected from one or more of O, N, and S", preferably, e.g., "4-6 membered monocyclic heterocycloalkyl having 1-2 heteroatoms selected from one or more of O, N, and S", and more preferably, e.g.,

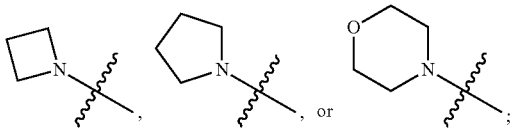

the "4-10 membered monocyclic, bicyclic, or spirocyclic heterocycloalkyl having 1-3 heteroatoms selected from one or more of O, N, and S" which is substituted with $R^{L-9}$ is, e.g.,

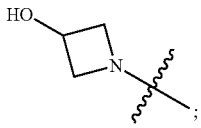

there can be one or more $R^{L-9}$, and in case that there are a plurality of $R^{L-9}$, the plurality of $R^{L-9}$ are the same or different; and the heterocycloalkyl can be linked to $L^2$ via a carbon atom or a nitrogen atom, and preferably via a nitrogen atom);

$R^{L-9}$ is independently selected from oxo, hydroxy, cyano, halogen (e.g., fluorine, chlorine, bromine, or iodine, and preferably, e.g., fluorine), phenyl, hydroxy-substituted $C_1$-$C_4$ alkyl (the "$C_1$-$C_4$ alkyl" is, e.g., methyl, ethyl, n-propyl, isopropyl, n-butyl, isobutyl, sec-butyl, or tert-butyl, and preferably, e.g., methyl; and the "hydroxy-substituted $C_1$-$C_4$ alkyl" is, e.g., hydroxymethyl), —SO$_2$CH$_3$, —C(=O)$R^{L-9-1}$ and —NR$^{L-9-2}$C(=O)$R^{L-9-3}$; $R^{L-9-1}$ is independently selected from $C_1$-$C_4$ alkyl and $C_1$-$C_4$ alkoxy, $R^{L-9-2}$ is independently selected from hydrogen and $C_1$-$C_4$ alkyl, $R^{L-9-3}$ is independently selected from $C_1$-$C_4$ alkyl (the carbon atom in the heterocycloalkyl, linked to $R^{L-9}$, may be independently a chiral carbon atom, either in R or S configuration); and n is 0.

In one embodiment, certain groups of compound of formula I are defined as follows, and groups not mentioned are defined in any of the above embodiments:

$R^1$ is cyano or halogen (e.g., fluorine, chlorine, bromine, or iodine, and preferably, e.g., fluorine);

m is 0;

$W^1$ is =N—;

$W^2$ is =CR$^4$— or =N—;

$W^3$ is —S—;

when $W^2$ is =N—, $R^2$ is hydrogen, cyano, or methyl;

when $W^2$ is =CR$^4$—, "$R^4$ is cyano and $R^2$ is hydrogen", or, "$R^4$ is hydrogen and $R^2$ is cyano";

$R^5$ is $C_1$-$C_4$ alkyl (e.g., methyl, ethyl, n-propyl, isopropyl, n-butyl, isobutyl, sec-butyl, or tert-butyl, and preferably, e.g., methyl);

ring A is

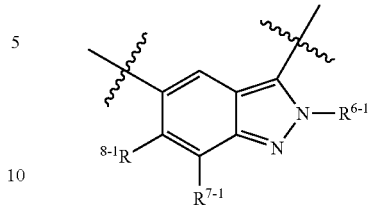

[the left terminus of which is linked to ring B];

$R^{6-1}$ is $R^{6-1-1}$-substituted or unsubstituted $C_1$-$C_4$ alkyl (there can be one or more $R^{6-1-1}$, and in case that there are a plurality of $R^{6-1-1}$, the plurality of $R^{6-1-1}$ are the same or different; and the "$C_1$-$C_4$ alkyl" is, e.g., methyl, ethyl, n-propyl, isopropyl, n-butyl, isobutyl, sec-butyl, or tert-butyl, and preferably, e.g., ethyl), and $R^{6-1-1}$ is independently selected from hydroxy, cyano, halogen, or —C(=O)NH$_2$;

$R^{7-1}$ is halogen (e.g., fluorine, chlorine, bromine, or iodine, and preferably, e.g., fluorine);

$R^{8-1}$ is hydrogen; and ring B is "4-10 membered monocyclic or bicyclic heterocycloalkyl having 1-3 heteroatoms selected from one or more of O, N, and S" (e.g., "4-7 membered monocyclic heterocycloalkyl having 1-2 heteroatoms selected from one or more of O, N, and S", preferably, e.g., "5-6 membered monocyclic heterocycloalkyl having 1-2 heteroatoms selected from one or more of O, N, and S", and more preferably, e.g., "

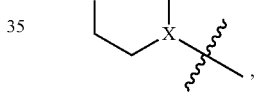

wherein X is N or CH and Y is NH or CH$_2$, which are not both carbon", and most preferably, e.g.,

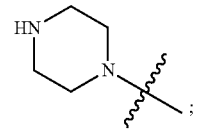

the heterocycloalkyl may be linked to ring A via a carbon atom or a nitrogen atom, and preferably via a nitrogen atom);

$R^9$ is -$L^1$-$L^2$-$L^3$; [when ring B is 6-membered heterocycloalkyl, $R^9$ can be located at the ortho, meta, or para position relative to ring A, and preferably at the para position relative to ring A; and $R^9$ can be linked to a carbon atom or a nitrogen atom of ring B, and preferably linked to a nitrogen atom of ring B]

$L^1$ is $C_1$-$C_4$ alkylene, e.g., —CH$_2$—, —CH$_2$CH$_2$—, —CH(CH$_3$)— (wherein the chiral carbon atom can be in R configuration or S configuration), —CH$_2$CH$_2$CH$_2$—, or —CH$_2$CH(CH$_3$)— (wherein the chiral carbon atom can be in R configuration or S configuration);

$L^2$ is —C(=O)—;

$L^3$ is "4-10 membered monocyclic, bicyclic, or spirocyclic heterocycloalkyl having 1-3 heteroatoms selected from one or more of O, N, and S" which is substituted or unsubstituted with $R^{L-9}$ (the "4-10 membered monocyclic, bicyclic, or spirocyclic heterocycloalkyl having 1-3 heteroatoms selected from one or more of O, N, and S" is, e.g., "4-10 membered monocyclic heterocycloalkyl having 1-2 heteroatoms selected from one or more of O, N, and S", preferably, e.g., "4-6 membered monocyclic heterocycloalkyl having 1-2 heteroatoms selected from one or more of O, N, and S", and more preferably, e.g.,

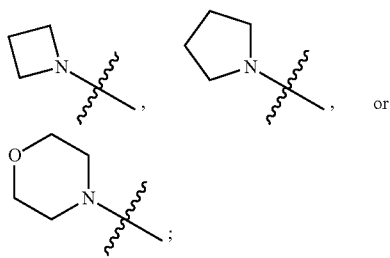

the "4-10 membered monocyclic, bicyclic, or spirocyclic heterocycloalkyl having 1-3 heteroatoms selected from one or more of O, N, and S" which is substituted with $R^{L-9}$ is, e.g.,

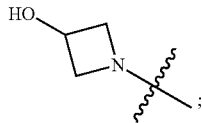 [SMILES: *N1CC(O)C1]

there can be one or more $R^{L-9}$, and in case that there are a plurality of $R^{L-9}$, the plurality of $R^{L-9}$ are the same or different; and the heterocycloalkyl can be linked to $L^2$ via a carbon atom or a nitrogen atom, and preferably via a nitrogen atom);

$R^{L-9}$ is independently selected from oxo, hydroxy, cyano, halogen (e.g., fluorine, chlorine, bromine, or iodine, and preferably, e.g., fluorine), phenyl, hydroxy-substituted $C_1$-$C_4$ alkyl (the "$C_1$-$C_4$ alkyl" is, e.g., methyl, ethyl, n-propyl, isopropyl, n-butyl, isobutyl, sec-butyl, or tert-butyl, and preferably, e.g., methyl; and the "hydroxy-substituted $C_1$-$C_4$ alkyl" is, e.g., hydroxymethyl), —$SO_2CH_3$, —C(=O)$R^{L-9-1}$ and —$NR^{L-9-2}$C(=O)$R^{L-9-3}$; $R^{L-9-1}$ is independently selected from $C_1$-$C_4$ alkyl and $C_1$-$C_4$ alkoxy, $R^{L-9-2}$ is independently selected from hydrogen and $C_1$-$C_4$ alkyl, $R^{L-9-3}$ is independently selected from $C_1$-$C_4$ alkyl (the carbon atom in the heterocycloalkyl, linked to $R^{L-9}$, may be independently a chiral carbon atom, either in R or S configuration); and n is 0.

In one embodiment, certain groups of compound of formula I are defined as follows, and groups not mentioned are defined in any of the above embodiments:

$R^1$ is cyano or halogen (e.g., fluorine, chlorine, bromine, or iodine, and preferably, e.g., fluorine);

m is 0;

$W^1$ is =N—;

$W^2$ is =$CR^4$— or =N—;

$W^3$ is —S—;

when $W^2$ is =N—, $R^2$ is hydrogen, cyano, or methyl;

when $W^2$ is =$CR^4$—, "$R^4$ is cyano and $R^2$ is hydrogen", or, "$R^4$ is hydrogen and $R^2$ is cyano";

$R^5$ is $C_1$-$C_4$ alkyl (e.g., methyl, ethyl, n-propyl, isopropyl, n-butyl, isobutyl, sec-butyl, or tert-butyl, and preferably, e.g., methyl);

ring A is

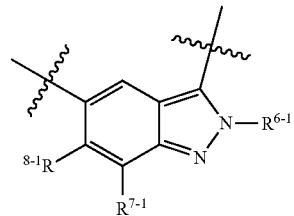

[the left terminus of which is linked to ring B];

$R^{6-1}$ is $R^{6-1-1}$-substituted or unsubstituted $C_1$-$C_4$ alkyl (there can be one or more $R^{6-1-1}$, and in case that there are a plurality of $R^{6-1-1}$, the plurality of $R^{6-1-1}$ are the same or different; and the "$C_1$-$C_4$ alkyl" is, e.g., methyl, ethyl, n-propyl, isopropyl, n-butyl, isobutyl, sec-butyl, or tert-butyl, and preferably, e.g., ethyl), and $R^{6-1-1}$ is independently selected from hydroxy, cyano, halogen, or —C(=O)$NH_2$;

$R^{7-1}$ is fluorine;

$R^{8-1}$ is hydrogen; and ring B is "4-10 membered monocyclic or bicyclic heterocycloalkyl having 1-3 heteroatoms selected from one or more of O, N, and S" (e.g., "4-7 membered monocyclic heterocycloalkyl having 1-2 heteroatoms selected from one or more of O, N, and S", preferably, e.g., "5-6 membered monocyclic heterocycloalkyl having 1-2 heteroatoms selected from one or more of O, N, and S", and more preferably, e.g., "

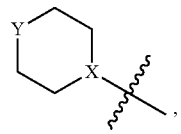

wherein X is N or CH and Y is NH or $CH_2$, which are not both carbon", and most preferably, e.g.,

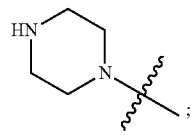

the heterocycloalkyl may be linked to ring A via a carbon atom or a nitrogen atom, and preferably via a nitrogen atom);

$R^9$ is -$L^1$-$L^2$-$L^3$; [when ring B is 6-membered heterocycloalkyl, $R^9$ can be located at the ortho, meta, or para position relative to ring A, and preferably at the para position relative to ring A; and $R^9$ can be linked to a carbon atom or a nitrogen atom of ring B, and preferably linked to a nitrogen atom of ring B]

$L^1$ is $C_1$-$C_4$ alkylene, e.g., —$CH_2$—, —$CH_2CH_2$—, —CH($CH_3$)— (wherein the chiral carbon atom can be in R configuration or S configuration), —$CH_2CH_2CH_2$—, or —$CH_2CH(CH_3$)— (wherein the chiral carbon atom can be in R configuration or S configuration);

$L^2$ is —C(=O)—;

$L^3$ is "4-10 membered monocyclic, bicyclic, or spirocyclic heterocycloalkyl having 1-3 heteroatoms selected from one or more of O, N, and S" which is substituted or unsubstituted with $R^{L-9}$ (the "4-10 membered monocyclic, bicyclic, or spirocyclic heterocycloalkyl having 1-3 heteroatoms selected from one or more of O, N, and S" is, e.g., "4-10 membered monocyclic heterocycloalkyl having 1-2 heteroatoms selected from one or more of, N, and", preferably, e.g., "4-6 membered monocyclic heterocycloalkyl having 1-2 heteroatoms selected from one or more of O, N, and S", and more preferably, e.g.,

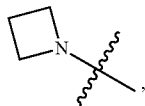

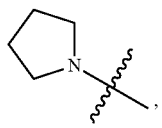 or 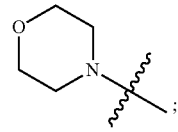;

the "4-10 membered monocyclic, bicyclic, or spirocyclic heterocycloalkyl having 1-3 heteroatoms selected from one or more of O, N, and S" which is substituted with $R^{L-9}$ is, e.g.,

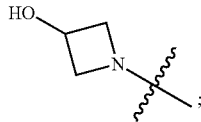 [SMILES: *N1CC(O)C1];

there can be one or more $R^{L-9}$, and in case that there are a plurality of $R^{L-9}$, the plurality of $R^{L-9}$ are the same or different; and the heterocycloalkyl can be linked to $L^2$ via a carbon atom or a nitrogen atom, and preferably via a nitrogen atom);

$R^{L-9}$ is independently selected from oxo, hydroxy, cyano, halogen (e.g., fluorine, chlorine, bromine, or iodine, and preferably, e.g., fluorine), phenyl, hydroxy-substituted $C_1$-$C_4$ alkyl (the "$C_1$-$C_4$ alkyl" is, e.g., methyl, ethyl, n-propyl, isopropyl, n-butyl, isobutyl, sec-butyl, or tert-butyl, and preferably, e.g., methyl; and the "hydroxy-substituted $C_1$-$C_4$ alkyl" is, e.g., hydroxymethyl), —SO$_2$CH$_3$, —C(=O)$R^{L-9-1}$ and —NR$^{L-9-2}$C(=O)R$^{L-9-3}$; $R^{L-9-1}$ is independently selected from $C_1$-$C_4$ alkyl and $C_1$-$C_4$ alkoxy, $R^{L-9-2}$ is independently selected from hydrogen and $C_1$-$C_4$ alkyl, $R^{L-9-3}$ is independently selected from $C_1$-$C_4$ alkyl (the carbon atom in the heterocycloalkyl, linked to $R^{L-9}$, may be independently a chiral carbon atom, either in R or S configuration); and n is 0.

In one embodiment, certain groups of compound of formula I are defined as follows, and groups not mentioned are defined in any of the above embodiments:

$R^1$ is cyano or halogen (e.g., fluorine, chlorine, bromine, or iodine, and preferably, e.g., fluorine);

m is 0;

$W^1$ is —N—;

$W^2$ is —CR$^4$— or —N—;

$W^3$ is —S—;

when $W^2$ is =N—, $R^2$ is hydrogen, cyano, or methyl;

when $W^2$ is —CR$^4$—, "$R^4$ is cyano and $R^2$ is hydrogen", or, "$R^4$ is hydrogen and $R^2$ is cyano";

$R^5$ is $C_1$-$C_4$ alkyl (e.g., methyl, ethyl, n-propyl, isopropyl, n-butyl, isobutyl, sec-butyl, or tert-butyl, and preferably, e.g., methyl);

ring A is

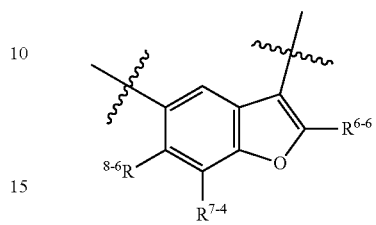

[the left terminus of which is linked to ring B];

$R^{6-6}$ is $R^{6-1-1}$-substituted or unsubstituted $C_1$-$C_4$ alkyl (there can be one or more $R^{6-1-1}$, and in case that there are a plurality of $R^{6-1-1}$, the plurality of $R^{6-1-1}$ are the same or different; and the "$C_1$-$C_4$ alkyl" is, e.g., methyl, ethyl, n-propyl, isopropyl, n-butyl, isobutyl, sec-butyl, or tert-butyl, and preferably, e.g., ethyl), and $R^{6-1-1}$ is independently selected from hydroxy, cyano, halogen, or —C(=O)NH$_2$;

$R^{7-4}$ is hydrogen or halogen (e.g., fluorine, chlorine, bromine, or iodine, and preferably, e.g., fluorine or chlorine);

$R^{8-6}$ is hydrogen; and ring B is "4-10 membered monocyclic or bicyclic heterocycloalkyl having 1-3 heteroatoms selected from one or more of O, N, and S" (e.g., "4-7 membered monocyclic heterocycloalkyl having 1-2 heteroatoms selected from one or more of O, N, and S", preferably, e.g., "5-6 membered monocyclic heterocycloalkyl having 1-2 heteroatoms selected from one or more of O, N, and S", and more preferably, e.g., "

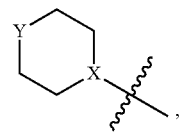, wherein X is N or CH and Y is NH or CH$_2$, which are not both carbon", and most preferably, e.g.,

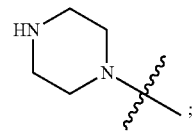;

the heterocycloalkyl may be linked to ring A via a carbon atom or a nitrogen atom, and preferably via a nitrogen atom);

$R^9$ is -$L^1$-$L^2$-$L^3$; [when ring B is 6-membered heterocycloalkyl, $R^9$ can be located at the ortho, meta, or para position relative to ring A, and preferably at the para position relative to ring A; and $R^9$ can be linked to a carbon atom or a nitrogen atom of ring B, and preferably linked to a nitrogen atom of ring B]

$L^1$ is $C_1$-$C_4$ alkylene, e.g., —CH$_2$—, —CH$_2$CH$_2$—, —CH(CH$_3$)— (wherein the chiral carbon atom can be in R configuration or S configuration), —CH$_2$CH$_2$CH$_2$—, or —CH$_2$CH(CH$_3$)— (wherein the chiral carbon atom can be in R configuration or S configuration);

L$^2$ is —C(═O)—;

L$^3$ is "4-10 membered monocyclic, bicyclic, or spirocyclic heterocycloalkyl having 1-3 heteroatoms selected from one or more of O, N, and S" which is substituted or unsubstituted with R$^{L-9}$ (the "4-10 membered monocyclic, bicyclic, or spirocyclic heterocycloalkyl having 1-3 heteroatoms selected from one or more of O, N, and S" is, e.g., "4-10 membered monocyclic heterocycloalkyl having 1-2 heteroatoms selected from one or more of O, N, and S", preferably, e.g., "4-6 membered monocyclic heterocycloalkyl having 1-2 heteroatoms selected from one or more of O, N, and S", and more preferably, e.g.,

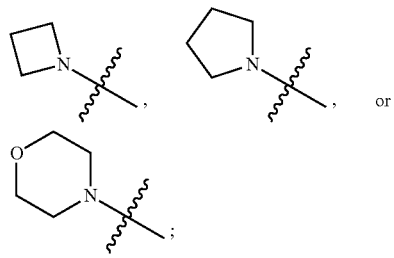

the "4-10 membered monocyclic, bicyclic, or spirocyclic heterocycloalkyl having 1-3 heteroatoms selected from one or more of O, N, and S" which is substituted with R$^{L-9}$ is, e.g.,

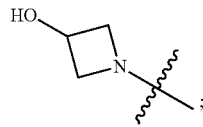 [SMILES: *N1CC(O)C1]

there can be one or more R$^{L-9}$, and in case that there are a plurality of R$^{L-9}$, the plurality of R$^{L-9}$ are the same or different; and the heterocycloalkyl can be linked to L$^2$ via a carbon atom or a nitrogen atom, and preferably via a nitrogen atom);

R$^{L-9}$ is independently selected from oxo, hydroxy, cyano, halogen (e.g., fluorine, chlorine, bromine, or iodine, and preferably, e.g., fluorine), phenyl, hydroxy-substituted C$_1$-C$_4$ alkyl (the "C$_1$-C$_4$ alkyl" is, e.g., methyl, ethyl, n-propyl, isopropyl, n-butyl, isobutyl, sec-butyl, or tert-butyl, and preferably, e.g., methyl; and the "hydroxy-substituted C$_1$-C$_4$ alkyl" is, e.g., hydroxymethyl), —SO$_2$CH$_3$, —C(═O)R$^{L-9-1}$ and —NR$^{L-9-2}$C(═O)R$^{L-9-3}$; R$^{L-9-1}$ is independently selected from C$_1$-C$_4$ alkyl and C$_1$-C$_4$ alkoxy, R$^{L-9-2}$ is independently selected from hydrogen and C$_1$-C$_4$ alkyl, R$^{L-9-3}$ is independently selected from C$_1$-C$_4$ alkyl (the carbon atom in the heterocycloalkyl, linked to R$^{L-9}$, may be independently a chiral carbon atom, either in R or S configuration); and n is 0.

In one embodiment, certain groups of compound of formula I are defined as follows, and groups not mentioned are defined in any of the above embodiments:

R$^1$ is cyano or halogen (e.g., fluorine, chlorine, bromine, or iodine, and preferably, e.g., fluorine);

m is 0;

W$^1$ is ═N—;

W$^2$ is ═CR$^4$— or ═N—;

W$^3$ is —S—;

when W$^2$ is ═N—, R$^2$ is hydrogen, cyano, or methyl;

when W$^2$ is ═CR$^4$—, "R$^4$ is cyano and R$^2$ is hydrogen", or, "R$^4$ is hydrogen and R$^2$ is cyano";

R$^5$ is C$_1$-C$_4$ alkyl (e.g., methyl, ethyl, n-propyl, isopropyl, n-butyl, isobutyl, sec-butyl, or tert-butyl, and preferably, e.g., methyl);

ring A is

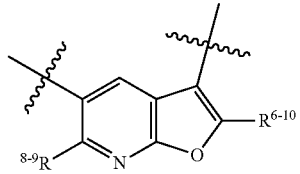

[the left terminus of which is linked to ring B];

R$^{6-10}$ is R$^{6-1-1}$-substituted or unsubstituted C$_1$-C$_4$ alkyl (there can be one or more R$^{6-1-1}$, and in case that there are a plurality of R$^{6-1-1}$, the plurality of R$^{6-1-1}$ are the same or different; and the "C$_1$-C$_4$ alkyl" is, e.g., methyl, ethyl, n-propyl, isopropyl, n-butyl, isobutyl, sec-butyl, or tert-butyl, and preferably, e.g., ethyl), and R$^{6-1-1}$ is independently selected from hydroxy, cyano, halogen, or —C(═O)NH$_2$;

R$^{8-9}$ is hydrogen; and ring B is "4-10 membered monocyclic or bicyclic heterocycloalkyl having 1-3 heteroatoms selected from one or more of O, N, and S" (e.g., "4-7 membered monocyclic heterocycloalkyl having 1-2 heteroatoms selected from one or more of O, N, and S", preferably, e.g., "5-6 membered monocyclic heterocycloalkyl having 1-2 heteroatoms selected from one or more of O, N, and S", and more preferably, e.g., "

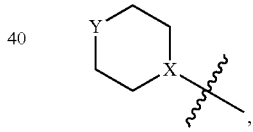

wherein X is N or CH and Y is NH or CH$_2$, which are not both carbon", and most preferably, e.g.,

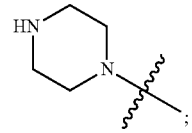

the heterocycloalkyl may be linked to ring A via a carbon atom or a nitrogen atom, and preferably via a nitrogen atom);

R$^9$ is -L$^1$-L$^2$-L; [when ring B is 6-membered heterocycloalkyl, R$^9$ can be located at the ortho, meta, or para position relative to ring A, and preferably at the para position relative to ring A; and R$^9$ can be linked to a carbon atom or a nitrogen atom of ring B, and preferably linked to a nitrogen atom of ring B]

L$^1$ is C$_1$-C$_4$ alkylene, e.g., —CH$_2$—, —CH$_2$CH$_2$—, —CH(CH$_3$)— (wherein the chiral carbon atom can be in R configuration or S configuration), —CH$_2$CH$_2$CH$_2$—, or —CH$_2$CH(CH$_3$)— (wherein the chiral carbon atom can be in R configuration or S configuration);

L$^2$ is —C(=O)—;

L$^3$ is "4-10 membered monocyclic, bicyclic, or spirocyclic heterocycloalkyl having 1-3 heteroatoms selected from one or more of O, N, and S" which is substituted or unsubstituted with R$^{L-9}$ (the "4-10 membered monocyclic, bicyclic, or spirocyclic heterocycloalkyl having 1-3 heteroatoms selected from one or more of O, N, and S" is, e.g., "4-10 membered monocyclic heterocycloalkyl having 1-2 heteroatoms selected from one or more of O, N, and S", preferably, e.g., "4-6 membered monocyclic heterocycloalkyl having 1-2 heteroatoms selected from one or more of O, N, and S", and more preferably, e.g.,

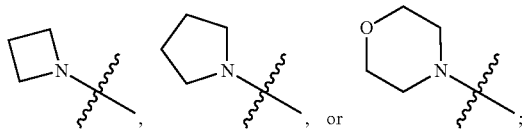 [SMILES: *N1CCC1 ; *N1CCCC1 ; *N1CCOCC1]

the "4-10 membered monocyclic, bicyclic, or spirocyclic heterocycloalkyl having 1-3 heteroatoms selected from one or more of O, N, and S" which is substituted with R$^{L-9}$ is, e.g.,

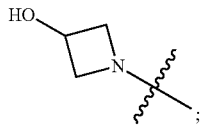

there can be one or more R$^{L-9}$, and in case that there are a plurality of R$^{L-9}$, the plurality of R$^{L-9}$ are the same or different; and the heterocycloalkyl can be linked to L$^2$ via a carbon atom or a nitrogen atom, and preferably via a nitrogen atom);

R$^{L-9}$ is independently selected from oxo, hydroxy, cyano, halogen (e.g., fluorine, chlorine, bromine, or iodine, and preferably, e.g., fluorine), phenyl, hydroxy-substituted C$_1$-C$_4$ alkyl (the "C$_1$-C$_4$ alkyl" is, e.g., methyl, ethyl, n-propyl, isopropyl, n-butyl, isobutyl, sec-butyl, or tert-butyl, and preferably, e.g., methyl; and the "hydroxy-substituted C$_1$-C$_4$ alkyl" is, e.g., hydroxymethyl), —SO$_2$CH$_3$, —C(=O)R$^{L-9-1}$ and —NR$^{L-9-2}$C(=O)R$^{L-9-3}$; R$^{L-9-1}$ is independently selected from C$_1$-C$_4$ alkyl and C$_1$-C$_4$ alkoxy, R$^{L-9-2}$ is independently selected from hydrogen and C$_1$-C$_4$ alkyl, R$^{L-9-3}$ is independently selected from C$_1$-C$_4$ alkyl (the carbon atom in the heterocycloalkyl, linked to R$^{L-9}$, may be independently a chiral carbon atom, either in R or S configuration); and n is 0.

In one embodiment, certain groups of compound of formula I are defined as follows, and groups not mentioned are defined in any of the above embodiments:

R$^1$ is cyano or halogen (e.g., fluorine, chlorine, bromine, or iodine, and preferably, e.g., fluorine);

m is 0;

W$^1$ is =N—;

W$^2$ is =CR$^4$— or =N—;

W$^3$ is —S—;

when W$^2$ is =N—, R$^2$ is hydrogen, cyano, or methyl;

when W$^2$ is =CR$^4$—, "R$^4$ is cyano and R$^2$ is hydrogen", or, "R$^4$ is hydrogen and R$^2$ is cyano";

R$^5$ is C$_1$-C$_4$ alkyl (e.g., methyl, ethyl, n-propyl, isopropyl, n-butyl, isobutyl, sec-butyl, or tert-butyl, and preferably, e.g., methyl); ring A is

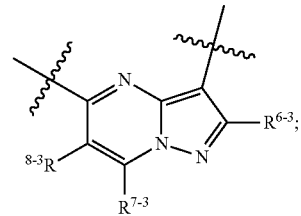

R$^{6-3}$ is R$^{6-1-1}$-substituted or unsubstituted C$_1$-C$_4$ alkyl (there can be one or more R$^{6-1-1}$, and in case that there are a plurality of R$^{6-1-1}$, the plurality of R$^{6-1-1}$ are the same or different; and the "C$_1$-C$_4$ alkyl" is, e.g., methyl, ethyl, n-propyl, isopropyl, n-butyl, isobutyl, sec-butyl, or tert-butyl, and preferably, e.g., ethyl), and R$^{6-1-1}$ is independently selected from hydroxy, cyano, halogen, or —C(=O)NH$_2$;

R$^{7-3}$ is hydrogen, fluorine, or C$_1$-C$_4$ alkyl (the "C$_1$-C$_4$ alkyl" is, e.g., methyl, ethyl, n-propyl, isopropyl, n-butyl, isobutyl, sec-butyl, or tert-butyl, and preferably, e.g., methyl);

R$^{8-3}$ is hydrogen or fluorine;

ring B is "4-10 membered monocyclic or bicyclic heterocycloalkyl having 1-3 heteroatoms selected from one or more of O, N, and S" (e.g., "4-7 membered monocyclic heterocycloalkyl having 1-2 heteroatoms selected from one or more of O, N, and S", preferably, e.g., "5-6 membered monocyclic heterocycloalkyl having 1-2 heteroatoms selected from one or more of O, N, and S", and more preferably, e.g., "

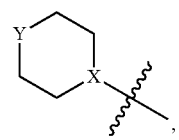

wherein X is N or CH and Y is NH or CH$_2$, which are not both carbon", and most preferably, e.g.,

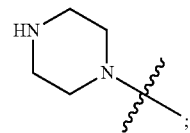

the heterocycloalkyl may be linked to ring A via a carbon atom or a nitrogen atom, and preferably via a nitrogen atom);

R$^9$ is -L$^1$-L$^2$-L$^3$; [when ring B is 6-membered heterocycloalkyl, R$^9$ can be located at the ortho, meta, or para position relative to ring A, and preferably at the para position relative to ring A; and R$^9$ can be linked to a carbon atom or a nitrogen atom of ring B, and preferably linked to a nitrogen atom of ring B]

L$^1$ is C$_1$-C$_4$ alkylene, e.g., —CH$_2$—, —CH$_2$CH$_2$—, —CH(CH$_3$)— (wherein the chiral carbon atom can be in R configuration or S configuration), —CH$_2$CH$_2$CH$_2$—, or —CH$_2$CH(CH$_3$)— (wherein the chiral carbon atom can be in R configuration or S configuration);

L$^2$ is —C(=O)—;

L$^3$ is "4-10 membered monocyclic, bicyclic, or spirocyclic heterocycloalkyl having 1-3 heteroatoms selected from one or more of O, N, and S" which is substituted or unsubstituted with R$^{L-9}$ (the "4-10 membered monocyclic, bicyclic, or spirocyclic heterocycloalkyl having 1-3 heteroatoms selected from one or more of O, N, and S" is, e.g., "4-10 membered monocyclic heterocycloalkyl having 1-2 heteroatoms selected from one or more of O, N, and S", preferably, e.g., "4-6 membered monocyclic heterocycloalkyl having 1-2 heteroatoms selected from one or more of O, N, and S", and more preferably, e.g.,

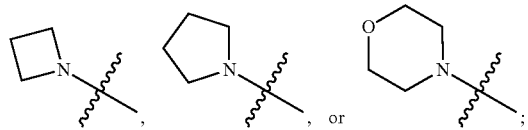 [SMILES: *N1CCC1 ; *N1CCCC1 ; *N1CCOCC1]

the "4-10 membered monocyclic, bicyclic, or spirocyclic heterocycloalkyl having 1-3 heteroatoms selected from one or more of O, N, and S" which is substituted with R$^{L-9}$ is, e.g.,

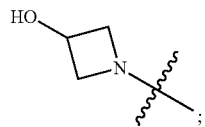

there can be one or more R$^{L-9}$, and in case that there are a plurality of R$^{L-9}$, the plurality of R$^{L-9}$ are the same or different; and the heterocycloalkyl can be linked to L$^2$ via a carbon atom or a nitrogen atom, and preferably via a nitrogen atom);

R$^{L-9}$ is independently selected from oxo, hydroxy, cyano, halogen (e.g., fluorine, chlorine, bromine, or iodine, and preferably, e.g., fluorine), phenyl, hydroxy-substituted C$_1$-C$_4$ alkyl (the "C$_1$-C$_4$ alkyl" is, e.g., methyl, ethyl, n-propyl, isopropyl, n-butyl, isobutyl, sec-butyl, or tert-butyl, and preferably, e.g., methyl; and the "hydroxy-substituted C$_1$-C$_4$ alkyl" is, e.g., hydroxymethyl), —SO$_2$CH$_3$, —C(=O)R$^{L-9-1}$ and —NR$^{L-9-2}$C(=O)R$^{L-9-3}$; R$^{L-9-1}$ is independently selected from C$_1$-C$_4$ alkyl and C$_1$-C$_4$ alkoxy, R$^{L-9-2}$ is independently selected from hydrogen and C$_1$-C$_4$ alkyl, R$^{L-9-3}$ is independently selected from C$_1$-C$_4$ alkyl (the carbon atom in the heterocycloalkyl, linked to R$^{L-9}$, may be independently a chiral carbon atom, either in R or S configuration); and n is 0.

In one embodiment, certain groups of compound of formula I are defined as follows, and groups not mentioned are defined in any of the above embodiments:

R$^1$ is cyano or halogen (e.g., fluorine, chlorine, bromine, or iodine, and preferably, e.g., fluorine);

m is 0;

W$^1$ is =N—;

W$^2$ is =CR$^4$— or =N—;

W$^3$ is —S—;

when W$^2$ is =N—, R$^2$ is hydrogen, cyano, or methyl;

when W$^2$ is =CR$^4$—, "R$^4$ is cyano and R$^2$ is hydrogen", or, "R$^4$ is hydrogen and R$^2$ is cyano";

R$^5$ is C$_1$-C$_4$ alkyl (e.g., methyl, ethyl, n-propyl, isopropyl, n-butyl, isobutyl, sec-butyl, or tert-butyl, and preferably, e.g., methyl);

ring A is

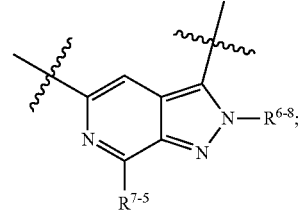

R$^{6-8}$ is R$^{6-1-1}$-substituted or unsubstituted C$_1$-C$_4$ alkyl (there can be one or more R$^{6-1-1}$, and in case that there are a plurality of R$^{6-1-1}$, the plurality of R$^{6-1-1}$ are the same or different; and the "C$_1$-C$_4$ alkyl" is, e.g., methyl, ethyl, n-propyl, isopropyl, n-butyl, isobutyl, sec-butyl, or tert-butyl, and preferably, e.g., ethyl), and R$^{6-1-1}$ is independently selected from hydroxy, cyano, halogen, or —C(=O)NH$_2$;

R$^{7-5}$ is hydrogen; and ring B is "4-10 membered monocyclic or bicyclic heterocycloalkyl having 1-3 heteroatoms selected from one or more of O, N, and S" (e.g., "4-7 membered monocyclic heterocycloalkyl having 1-2 heteroatoms selected from one or more of O, N, and S", preferably, e.g., "5-6 membered monocyclic heterocycloalkyl having 1-2 heteroatoms selected from one or more of O, N, and S", and more preferably, e.g., "

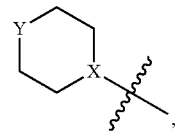

wherein X is N or CH and Y is NH or CH$_2$, which are not both carbon", and most preferably, e.g.,

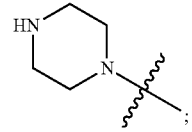

the heterocycloalkyl may be linked to ring A via a carbon atom or a nitrogen atom, and preferably via a nitrogen atom);

R$^9$ is -L$^1$-L$^2$-L$^3$; [when ring B is 6-membered heterocycloalkyl, R$^9$ can be located at the ortho, meta, or para position relative to ring A, and preferably at the para position relative to ring A; and R$^9$ can be linked to a carbon atom or a nitrogen atom of ring B, and preferably linked to a nitrogen atom of ring B]

L$^1$ is C$_1$-C$_4$ alkylene, e.g., —CH$_2$—, —CH$_2$CH$_2$—, —CH(CH$_3$)— (wherein the chiral carbon atom can be in R configuration or S configuration), —CH$_2$CH$_2$CH$_2$—, or —CH$_2$CH(CH$_3$)— (wherein the chiral carbon atom can be in R configuration or S configuration);

L² is —C(=O)—;

L³ is "4-10 membered monocyclic, bicyclic, or spirocyclic heterocycloalkyl having 1-3 heteroatoms selected from one or more of O, N, and S" which is substituted or unsubstituted with $R^{L-9}$ (the "4-10 membered monocyclic, bicyclic, or spirocyclic heterocycloalkyl having 1-3 heteroatoms selected from one or more of O, N, and S" is, e.g., "4-10 membered monocyclic heterocycloalkyl having 1-2 heteroatoms selected from one or more of O, N, and S", preferably, e.g., "4-6 membered monocyclic heterocycloalkyl having 1-2 heteroatoms selected from one or more of O, N, and S", and more preferably, e.g.,

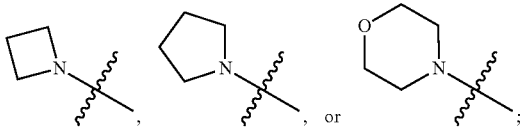 [SMILES: *N1CCC1 ; *N1CCCC1 ; *N1CCOCC1]

the "4-10 membered monocyclic, bicyclic, or spirocyclic heterocycloalkyl having 1-3 heteroatoms selected from one or more of O, N, and S" which is substituted with $R^{L-9}$ is, e.g.,

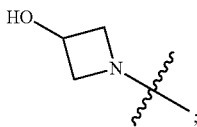

there can be one or more $R^{L-9}$, and in case that there are a plurality of $R^{L-9}$, the plurality of $R^{L-9}$ are the same or different; and the heterocycloalkyl can be linked to L² via a carbon atom or a nitrogen atom, and preferably via a nitrogen atom);

$R^{L-9}$ is independently selected from oxo, hydroxy, cyano, halogen (e.g., fluorine, chlorine, bromine, or iodine, and preferably, e.g., fluorine), phenyl, hydroxy-substituted $C_1$-$C_4$ alkyl (the "$C_1$-$C_4$ alkyl" is, e.g., methyl, ethyl, n-propyl, isopropyl, n-butyl, isobutyl, sec-butyl, or tert-butyl, and preferably, e.g., methyl; and the "hydroxy-substituted $C_1$-$C_4$ alkyl" is, e.g., hydroxymethyl), —SO₂CH₃, —C(=O)$R^{L-9-1}$ and —$NR^{L-9-2}C(=O)R^{L-9-3}$; $R^{L-9-1}$ is independently selected from $C_1$-$C_4$ alkyl and $C_1$-$C_4$ alkoxy, $R^{L-9-2}$ is independently selected from hydrogen and $C_1$-$C_4$ alkyl, $R^{L-9-3}$ is independently selected from $C_1$-$C_4$ alkyl (the carbon atom in the heterocycloalkyl, linked to $R^{L-9}$, may be independently a chiral carbon atom, either in R or S configuration); and n is 0.

In one embodiment, certain groups of compound of formula I are defined as follows, and groups not mentioned are defined in any of the above embodiments:

$R^1$ is cyano or halogen (e.g., fluorine, chlorine, bromine, or iodine, and preferably, e.g., fluorine);

m is 0;

$W^1$ is =N—;

$W^2$ is =CR⁴— or =N—;

$W^3$ is —S—;

when $W^2$ is =N—, $R^2$ is hydrogen, cyano, or methyl;

when $W^2$ is =CR⁴—, "$R^4$ is cyano and $R^2$ is hydrogen", or, "$R^4$ is hydrogen and $R^2$ is cyano";

$R^5$ is $C_1$-$C_4$ alkyl (e.g., methyl, ethyl, n-propyl, isopropyl, n-butyl, isobutyl, sec-butyl, or tert-butyl, and preferably, e.g., methyl);

ring A is

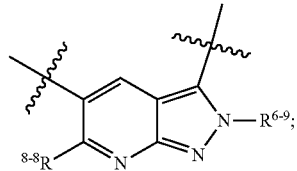

$R^{6-9}$ is $R^{6-1-1}$-substituted or unsubstituted $C_1$-$C_4$ alkyl (there can be one or more $R^{6-1-1}$, and in case that there are a plurality of $R^{6-1-1}$, the plurality of $R^{6-1-1}$ are the same or different; and the "$C_1$-$C_4$ alkyl" is, e.g., methyl, ethyl, n-propyl, isopropyl, n-butyl, isobutyl, sec-butyl, or tert-butyl, and preferably, e.g., ethyl), and $R^{6-1-1}$ is independently selected from hydroxy, cyano, halogen, or —C(=O)NH₂;

$R^{8-8}$ is hydrogen; and ring B is "4-10 membered monocyclic or bicyclic heterocycloalkyl having 1-3 heteroatoms selected from one or more of O, N, and S" (e.g., "4-7 membered monocyclic heterocycloalkyl having 1-2 heteroatoms selected from one or more of O, N, and S", preferably, e.g., "5-6 membered monocyclic heterocycloalkyl having 1-2 heteroatoms selected from one or more of O, N, and S", and more preferably, e.g., "

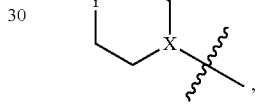

wherein X is N or CH and Y is NH or CH₂, which are not both carbon", and most preferably, e.g.,

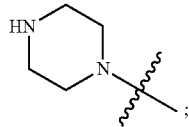

the heterocycloalkyl may be linked to ring A via a carbon atom or a nitrogen atom, and preferably via a nitrogen atom);

$R^9$ is -L¹-L²-L³; [when ring B is 6-membered heterocycloalkyl, $R^9$ can be located at the ortho, meta, or para position relative to ring A, and preferably at the para position relative to ring A; and $R^9$ can be linked to a carbon atom or a nitrogen atom of ring B, and preferably linked to a nitrogen atom of ring B]

L¹ is $C_1$-$C_4$ alkylene, e.g., —CH₂—, —CH₂CH₂—, —CH(CH₃)— (wherein the chiral carbon atom can be in R configuration or S configuration), —CH₂CH₂CH₂—, or —CH₂CH(CH₃)— (wherein the chiral carbon atom can be in R configuration or S configuration);

L² is —C(=O)—;

L³ is "4-10 membered monocyclic, bicyclic, or spirocyclic heterocycloalkyl having 1-3 heteroatoms selected from one or more of O, N, and S" which is substituted or unsubstituted with $R^{L-9}$ (the "4-10 membered monocyclic, bicyclic, or spirocyclic heterocycloalkyl having 1-3 heteroatoms selected from one or more of O, N, and S" is, e.g., "4-10 membered monocyclic heterocycloalkyl having 1-2 heteroatoms selected from one or more of O, N, and S", preferably, e.g., "4-6 membered monocyclic heterocycloalkyl having 1-2 heteroatoms selected from one or more of O, N, and S", and more preferably, e.g.,

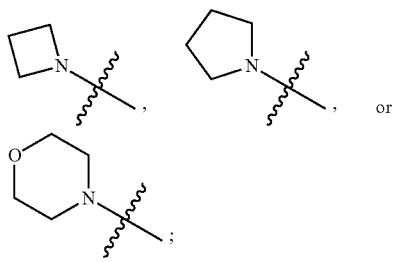

the "4-10 membered monocyclic, bicyclic, or spirocyclic heterocycloalkyl having 1-3 heteroatoms selected from one or more of O, N, and S" which is substituted with $R^{L-9}$ is, e.g.,

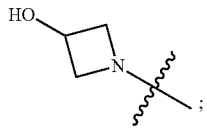

there can be one or more $R^{L-9}$, and in case that there are a plurality of $R^{L-9}$, the plurality of $R^{L-9}$ are the same or different; and the heterocycloalkyl can be linked to $L^2$ via a carbon atom or a nitrogen atom, and preferably via a nitrogen atom);

$R^{L-9}$ is independently selected from oxo, hydroxy, cyano, halogen (e.g., fluorine, chlorine, bromine, or iodine, and preferably, e.g., fluorine), phenyl, hydroxy-substituted $C_1$-$C_4$ alkyl (the "$C_1$-$C_4$ alkyl" is, e.g., methyl, ethyl, n-propyl, isopropyl, n-butyl, isobutyl, sec-butyl, or tert-butyl, and preferably, e.g., methyl; and the "hydroxy-substituted $C_1$-$C_4$ alkyl" is, e.g., hydroxymethyl), —$SO_2CH_3$, —$C(=O)R^{L-9-1}$ and —$NR^{L-9-2}C(=O)R^{L-9-3}$; $R^{L-9-1}$ is independently selected from $C_1$-$C_4$ alkyl and $C_1$-$C_4$ alkoxy, $R^{L-9-2}$ is independently selected from hydrogen and $C_1$-$C_4$ alkyl, $R^{L-9-3}$ is independently selected from $C_1$-$C_4$ alkyl (the carbon atom in the heterocycloalkyl, linked to $R^{L-9}$, may be independently a chiral carbon atom, either in R or S configuration); and n is 0.

In one embodiment, certain groups of compound of formula I are defined as follows, and groups not mentioned are defined in any of the above embodiments:

$R^1$ is cyano or halogen (e.g., fluorine, chlorine, bromine, or iodine, and preferably, e.g., fluorine);

m is 1;

$R^3$ is cyano or halogen (e.g., fluorine, chlorine, bromine, or iodine, and preferably, e.g., fluorine);

$W^1$ is =N—;

$W^2$ is =$CR^4$— or =N—;

$W^3$ is —S—;

when $W^2$ is =N—, $R^2$ is hydrogen, cyano, or methyl;

when $W^2$ is =$CR^4$—, "$R^4$ is cyano and $R^2$ is hydrogen", or, "$R^4$ is hydrogen and $R^2$ is cyano";

$R^5$ is $C_1$-$C_4$ alkyl (e.g., methyl, ethyl, n-propyl, isopropyl, n-butyl, isobutyl, sec-butyl, or tert-butyl, and preferably, e.g., methyl);

ring A is

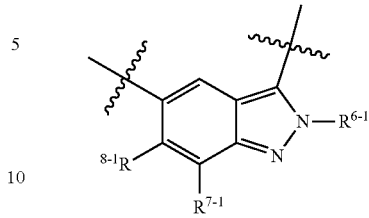

[the left terminus of which is linked to ring B];

$R^{6-1}$ is $R^{6-1-1}$-substituted or unsubstituted $C_1$-$C_4$ alkyl (there can be one or more $R^{6-1-1}$, and in case that there are a plurality of $R^{6-1}$—, the plurality of $R^{6-1-1}$ are the same or different; and the "$C_1$-$C_4$ alkyl" is, e.g., methyl, ethyl, n-propyl, isopropyl, n-butyl, isobutyl, sec-butyl, or tert-butyl, and preferably, e.g., ethyl), and $R^{6-1-1}$ is independently selected from hydroxy, cyano, halogen, or —$C(=O)NH_2$;

$R^{7-1}$ is halogen (e.g., fluorine, chlorine, bromine, or iodine, and preferably, e.g., fluorine);

$R^{8-1}$ is hydrogen; and ring B is "4-10 membered monocyclic or bicyclic heterocycloalkyl having 1-3 heteroatoms selected from one or more of O, N, and S" (e.g., "4-7 membered monocyclic heterocycloalkyl having 1-2 heteroatoms selected from one or more of O, N, and S", preferably, e.g., "5-6 membered monocyclic heterocycloalkyl having 1-2 heteroatoms selected from one or more of O, N, and S", and more preferably, e.g., "

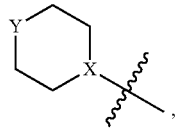

wherein X is N or CH and Y is NH or $CH_2$, which are not both carbon", and most preferably, e.g.,

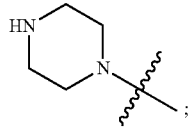

the heterocycloalkyl may be linked to ring A via a carbon atom or a nitrogen atom, and preferably via a nitrogen atom);

$R^9$ is -$L^1$-$L^2$-$L^3$; [when ring B is 6-membered heterocycloalkyl, $R^9$ can be located at the ortho, meta, or para position relative to ring A, and preferably at the para position relative to ring A; and $R^9$ can be linked to a carbon atom or a nitrogen atom of ring B, and preferably linked to a nitrogen atom of ring B]

$L^1$ is $C_1$-$C_4$ alkylene, e.g., —$CH_2$—, —$CH_2CH_2$—, —CH($CH_3$)— (wherein the chiral carbon atom can be in R configuration or S configuration), —$CH_2CH_2CH_2$—, or —$CH_2CH(CH_3)$— (wherein the chiral carbon atom can be in R configuration or S configuration);

$L^2$ is —$C(=O)$—;

$L^3$ is "4-10 membered monocyclic, bicyclic, or spirocyclic heterocycloalkyl having 1-3 heteroatoms selected from one or more of O, N, and S" which is substituted or unsubstituted with $R^{L-9}$ (the "4-10 membered monocyclic, bicyclic, or spirocyclic heterocycloalkyl having 1-3 heteroatoms selected from one or more of O, N, and S" is, e.g., "4-10 membered monocyclic heterocycloalkyl having 1-2 heteroatoms selected from one or more of O, N, and S", preferably, e.g., "4-6 membered monocyclic heterocycloalkyl having 1-2 heteroatoms selected from one or more of O, N, and S", and more preferably, e.g.,

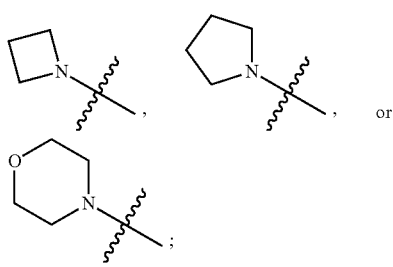

the "4-10 membered monocyclic, bicyclic, or spirocyclic heterocycloalkyl having 1-3 heteroatoms selected from one or more of O, N, and S" which is substituted with $R^{L-9}$ is, e.g.,

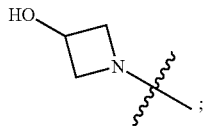 [SMILES: *N1CC(O)C1]

there can be one or more $R^{L-9}$, and in case that there are a plurality of $R^{L-9}$, the plurality of $R^{L-9}$ are the same or different; and the heterocycloalkyl can be linked to $L^2$ via a carbon atom or a nitrogen atom, and preferably via a nitrogen atom);

$R^{L-9}$ is independently selected from oxo, hydroxy, cyano, halogen (e.g., fluorine, chlorine, bromine, or iodine, and preferably, e.g., fluorine), phenyl, hydroxy-substituted $C_1$-$C_4$ alkyl (the "$C_1$-$C_4$ alkyl" is, e.g., methyl, ethyl, n-propyl, isopropyl, n-butyl, isobutyl, sec-butyl, or tert-butyl, and preferably, e.g., methyl; and the "hydroxy-substituted $C_1$-$C_4$ alkyl" is, e.g., hydroxymethyl), —$SO_2CH_3$, —C(=O)$R^{L-9-1}$ and —$NR^{L-9-2}$C(=O)$R^{L-9-3}$; $R^{L-9-1}$ is independently selected from $C_1$-$C_4$ alkyl and $C_1$-$C_4$ alkoxy, $R^{L-9-2}$ is independently selected from hydrogen and $C_1$-$C_4$ alkyl, $R^{L-9-3}$ is independently selected from $C_1$-$C_4$ alkyl (the carbon atom in the heterocycloalkyl, linked to $R^{L-9}$, may be independently a chiral carbon atom, either in R or S configuration); and n is 0.

In one embodiment, certain groups of compound of formula I are defined as follows, and groups not mentioned are defined in any of the above embodiments:

$R^1$ is hydrogen, cyano, halogen (e.g., fluorine, chlorine, bromine, or iodine, and preferably, e.g., fluorine), or $C_1$-$C_4$ alkyl;

m is 0, 1, 2, or 3, and $R^3$ is independently selected from halogen (e.g., fluorine, chlorine, bromine, or iodine, and preferably, e.g., fluorine), cyano, $R^{3-1}$-substituted or unsubstituted $C_1$-$C_4$ alkyl (there are one or more $R^{3-1}$, and in case that there are a plurality of $R^{3-1}$, the plurality of $R^{3-1}$ are the same or different; and the "$C_1$-$C_4$ alkyl" is, e.g., methyl, ethyl, n-propyl, isopropyl, n-butyl, isobutyl, sec-butyl, or tert-butyl, and preferably, e.g., methyl), and $R^{3-2}$-substituted or unsubstituted $C_1$-$C_4$ alkoxy (there can be one or more $R^{3-2}$, and in case that there are a plurality of $R^{3-2}$, the plurality of $R^{3-2}$ are the same or different); $R^{3-1}$ and $R^{3-2}$ are each independently selected from halogens; [$R^3$ may be independently located at the ortho or meta position relative to $R^1$; when m is 1, $R^3$ may be located at the ortho or meta position relative to $R^1$]

$W^1$ is =CH— or =N—;
$W^2$ is =$CR^4$— or =N—;
$W^3$ is —O—, —S—, —NH—, —N=CH—, —CH=N—, or —CH=CH—;

when $W^2$ is =N—, $R^2$ is hydrogen, cyano, halogen (e.g., fluorine, chlorine, bromine, or iodine, preferably, e.g., fluorine), $R^{2-1}$-substituted or unsubstituted $C_1$-$C_4$ alkyl (there can be one or more $R^{2-1}$, and in case that there are a plurality of $R^{2-1}$, the plurality of $R^{2-1}$ are the same or different; and the "$C_1$-$C_4$ alkyl" is, e.g., methyl, ethyl, n-propyl, isopropyl, n-butyl, isobutyl, sec-butyl or tert-butyl, and preferably, e.g., methyl), —C(=O)$CH_3$, —C(=O)$CF_3$, —C(=O)$OCH_3$, —C(=O)$NH_2$, or —NHC(=O)$CH_3$; $R^{2-1}$ is independently selected from hydroxy and cyano;

when $W^2$ is =$CR^4$—, one of $R^2$ or $R^4$, e.g., $R^4$, is hydrogen, cyano, halogen (e.g., fluorine, chlorine, bromine, or iodine, and preferably, e.g., fluorine), $R^{2-2}$-substituted or unsubstituted $C_1$-$C_4$ alkyl (there can be one or more $R^{2-2}$, and in case that there are a plurality of $R^{2-2}$, the plurality of $R^{2-2}$ are the same or different), —C(=O)$CH_3$, —C(=O)$CF_3$, —C(=O)$OCH_3$, —C(=O)$NH_2$, or —NHC(=O)$CH_3$, and the other one, such as $R^2$, is hydrogen or $C_1$-$C_4$ alkyl; $R^{2-2}$ is independently selected from hydroxy and cyano;

$R^5$ is $C_1$-$C_4$ alkyl (e.g., methyl, ethyl, n-propyl, isopropyl, n-butyl, isobutyl, sec-butyl, or tert-butyl, and preferably, e.g., methyl);

ring A is

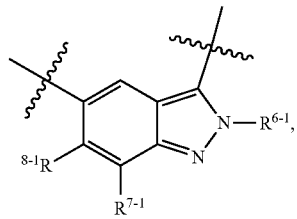

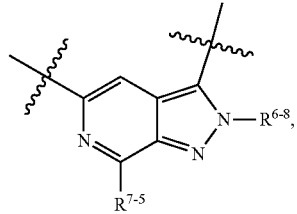

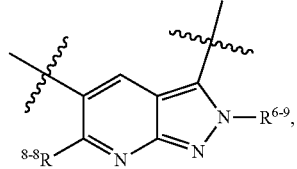

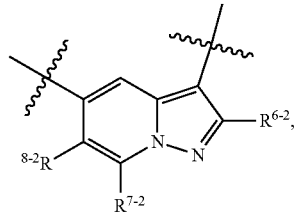

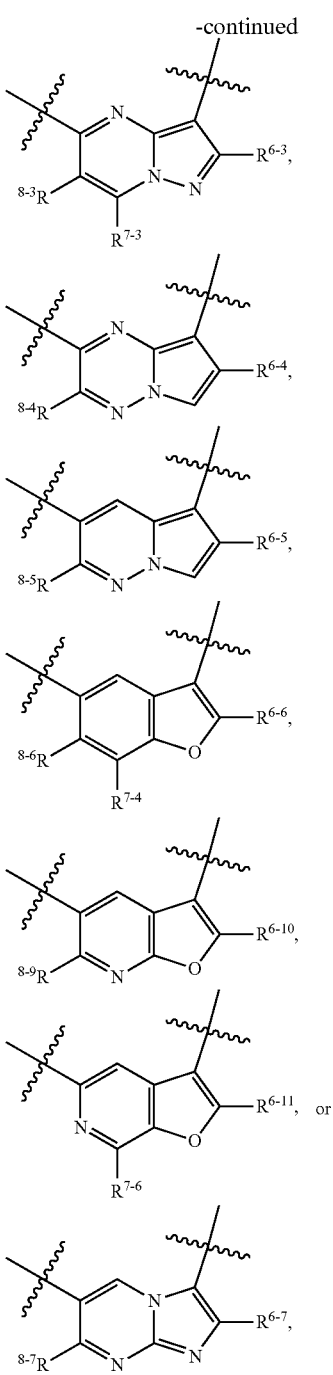

[the left terminus of which is linked to ring B];

$R^{6-1}$, $R^{6-2}$, $R^{6-3}$, $R^{6-4}$, $R^{6-5}$, $R^6$, $R^{6-7}$, $R^{6-8}$, $R^{6-9}$, $R^{6-10}$, and $R^{6-11}$ are each independently selected from hydrogen and $R^{6-1-1}$-substituted or unsubstituted $C_1$-$C_4$ alkyl (there can be one or more $R^{6-1}$—, and in case that there are a plurality of $R^{6-1-1}$, the plurality of $R^{6-1-1}$ are the same or different; and the "$C_1$-$C_4$ alkyl" is, e.g., methyl, ethyl, n-propyl, isopropyl, n-butyl, isobutyl, sec-butyl, or tert-butyl, and preferably, e.g., methyl or ethyl); and $R^{6-1-1}$ is independently selected from hydroxy, cyano, halogen, and —C(=O)NH$_2$;

$R^{7-1}$, $R^{7-2}$, $R^{7-3}$, $R^{7-4}$, $R^{7-5}$, and $R^{7-6}$ are each independently selected from hydrogen, cyano, halogen (e.g., fluorine, chlorine, bromine, or iodine, and preferably, e.g., fluorine), and $C_1$-$C_4$ alkyl (e.g., methyl, ethyl, n-propyl, isopropyl, n-butyl, isobutyl, sec-butyl, or tert-butyl, and preferably, e.g., methyl);

$R^{8-1}$, $R^{8-2}$, $R^{8-3}$, $R^{8-4}$, $R^{8-5}$, $R^{8-6}$, $R^{8-7}$, $R^{8-8}$, and $R^{8-9}$ are each independently selected from hydrogen, cyano, halogen (e.g., fluorine, chlorine, bromine, or iodine, and preferably, e.g., fluorine), and $C_1$-$C_4$ alkyl (e.g., methyl, ethyl, n-propyl, isopropyl, n-butyl, isobutyl, sec-butyl, or tert-butyl, and preferably, e.g., methyl);

ring B is $C_3$-$C_{10}$ cycloalkyl (e.g., $C_3$-$C_6$ cycloalkyl, and preferably, e.g., $C_5$-$C_6$ cycloalkyl), $C_4$-$C_7$ cycloalkenyl (e.g., $C_5$-$C_6$ cycloalkenyl, preferably, e.g., cyclohexenyl, and more preferably, e.g.,

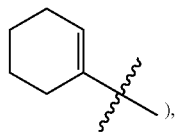 [SMILES: *C1=CCCCC1]),

"4-10 membered monocyclic or bicyclic heterocycloalkyl having 1-3 heteroatoms selected from one or more of O, N, and S" (e.g., "4-7 membered monocyclic heterocycloalkyl having 1-2 heteroatoms selected from one or more of O, N, and S", preferably, e.g., "5-6 membered monocyclic heterocycloalkyl having 1-2 heteroatoms selected from one or more of O, N, and S", more preferably, e.g., "

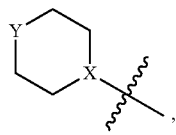, wherein X is N or CH, and Y is NH or CH$_2$, but X and Y are not both carbon", and yet more preferably, e.g.,

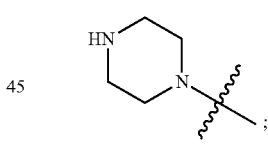;

and the heterocycloalkyl can be linked to ring A via a carbon atom or a nitrogen atom, and preferably via a nitrogen atom), or "4-7 membered heterocycloalkenyl having 1 double bond and 1-3 heteroatoms selected from one or more of O, N, and S" (e.g., "5-6 membered heterocycloalkenyl having 1 double bond and 1-2 heteroatoms selected from one or more of O, N, and S", and preferably, e.g.,

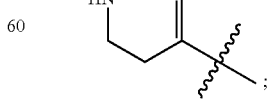;

and the heterocycloalkenyl can be linked to ring A via a carbon atom or a nitrogen atom, and preferably via a nitrogen atom);

R⁹ is -L¹-L²-L³; [when ring B is 6-membered heterocycloalkyl or heterocycloalkenyl, R⁹ can be located at the ortho, meta, or para position relative to ring A, and preferably at the para position relative to ring A; and R⁹ can be linked to a carbon atom or a nitrogen atom of ring B, and preferably linked to a nitrogen atom of ring B]

L¹ is a single bond (i.e., L² and ring B are directly linked), or C₁-C₄ alkylene (for example, —CH₂—, —CH₂CH₂—, —CH(CH₃)— [wherein the chiral carbon atom may be in R configuration or S configuration], —CH₂CH₂CH₂—, or —CH₂CH(CH₃)— [wherein the chiral carbon atom may be in R configuration or S configuration]);

L² is —O—, —C(=O)—, —C(=O)O—, —OC(=O)—, —C(=O)—C(=O)—, —C(=O)—C(=O)NR$^{L-1}$—, —NR$^{L-2}$—, —C(=O)NR$^{L-3}$—, —NR$^{L-4}$C(=O)—, —NR$^{L-5}$C(=O)O—, —SO₂—, —SO₂NR$^{L-6}$—, or —NR$^{L-7}$SO₂— (the left terminus of which is linked to L); R$^{L-1}$, R$^{L-2}$, R$^{L-3}$, R$^{L-4}$, R$^{L-5}$, R$^{L-6}$, and R$^{L-7}$ are each independently selected from hydrogen and C₁-C₄ alkyl (e.g., methyl, ethyl, n-propyl, isopropyl, n-butyl, isobutyl, sec-butyl, or tert-butyl, and preferably, e.g., methyl);

L³ is hydrogen, cyano, R$^{L-8}$-substituted or unsubstituted C₁-C₄ alkyl (there can be one or more R$^{L-8}$, and in case that there are a plurality of R$^{L-8}$, the plurality of R$^{L-8}$ are the same or different; and the C₁-C₄ alkyl is, e.g., methyl, ethyl, n-propyl, isopropyl, n-butyl, isobutyl, sec-butyl, or tert-butyl, and preferably, e.g., methyl), amino-substituted or unsubstituted C₃-C₇ cycloalkyl (there can be one or more amino), "4-10 membered monocyclic, bicyclic, or spirocyclic heterocycloalkyl having 1-3 heteroatoms selected from one or more of O, N, and S" which is substituted or unsubstituted with R$^{L-9}$ (the "4-10 membered monocyclic, bicyclic, or spirocyclic heterocycloalkyl having 1-3 heteroatoms selected from one or more of O, N, and S" is, e.g., "4-10 membered monocyclic heterocycloalkyl having 1-2 heteroatoms selected from one or more of O, N, and S", preferably, e.g., "4-6 membered monocyclic heterocycloalkyl having 1-2 heteroatoms selected from one or more of O, N, and S", and more preferably, e.g.,

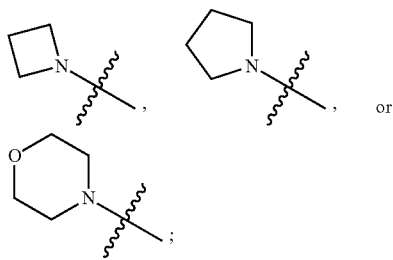

the "4-10 membered monocyclic, bicyclic, or spirocyclic heterocycloalkyl having 1-3 heteroatoms selected from one or more of O, N, and S" which is substituted with R$^{L-9}$ is, e.g.,

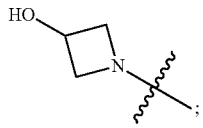

there can be one or more R$^{L-9}$, and in case that there are a plurality of R$^{L-9}$, the plurality of R$^{L-9}$ are the same or different; and the heterocycloalkyl can be linked to L² via a carbon atom or a nitrogen atom, and preferably via a nitrogen atom), "5-6 membered heterocycloalkenyl containing 1 double bond and 1-3 heteroatoms selected from one or more of O, N, and S" which is substituted or unsubstituted with R$^{L-10}$ (the "5-6 membered heterocycloalkenyl containing 1 double bond and 1-3 heteroatoms selected from one or more of O, N, and S" is, e.g., "5-6 membered heterocycloalkenyl containing 1 double bond and 1-2 heteroatoms selected from one or more of O, N, and S"; there can be one or more R$^{L-10}$, and in case that there are a plurality of R$^{L-10}$, the plurality of R$^{L-10}$ are the same or different; and the heterocycloalkenyl can be linked to L² via a carbon atom or a nitrogen atom, and preferably via a nitrogen atom), or "5-6 membered heteroaryl having 1-3 heteroatoms selected from one or more of O, N, and S" which is substituted or unsubstituted with R$^{L-11}$ (the "5-6 membered heteroaryl having 1-3 heteroatoms selected from one or more of O, N, and S" is, e.g., "5-6 membered heteroaryl having 1-2 heteroatoms selected from one or more of O, N, and S"; there can one or more R$^{L-10}$, and in case that there are a plurality of R$^{L-11}$, the plurality of R$^{L-11}$ are the same or different; and the heteroaryl can be linked to L² via a carbon atom or a nitrogen atom, and preferably via a nitrogen atom);

R$^{L-8}$ is independently selected from hydroxy, cyano, halogen, and phenyl;

R$^{L-9}$ is independently selected from oxo, hydroxy, cyano, halogen (e.g., fluorine, chlorine, bromine, or iodine, and preferably, e.g., fluorine), phenyl, hydroxy-substituted C₁-C₄ alkyl (there can be one or more hydroxys; the "C₁-C₄ alkyl" is, e.g., methyl, ethyl, n-propyl, isopropyl, n-butyl, isobutyl, sec-butyl, or tert-butyl, and preferably, e.g., methyl; and the "hydroxy-substituted C₁-C₄ alkyl" is, e.g., hydroxymethyl), —SO₂CH₃, —C(=O)R$^{L-9-1}$, and —NR$^{L-9-2}$C(=O)R$^{L-9-3}$; R$^{L-9-1}$ is independently selected from C₁-C₄ alkyl and C₁-C₄ alkoxy; R$^{L-9-2}$ is independently selected from hydrogen and C₁-C₄ alkyl; and R$^{L-9-3}$ is independently selected from C₁-C₄ alkyl; [the carbon atom in the heterocycloalkyl, linked to R$^{L-9}$, can be independently selected from a chiral carbon atom, either in R or S configuration]

R$^{L-10}$ is independently selected from oxo, hydroxy, cyano, halogen, phenyl, —SO₂CH₃, —C(=O)R$^{L-10-1}$ and —NR$^{L-10-2}$C(=O)R$^{L-10-3}$; R$^{L-10-1}$ is independently selected from C₁-C₄ alkyl and C₁-C₄ alkoxy; R$^{L-10-2}$ is independently selected from hydrogen and C₁-C₄ alkyl; and R$^{L-10-3}$ is independently selected from C₁-C₄ alkyl; [the carbon atom in the heterocycloalkenyl, linked to R$^{L-10}$, can be independently selected from a chiral carbon atom, either in R configuration or S configuration]

R$^{L-11}$ is independently selected from hydroxy, cyano, halogen, phenyl, —SO₂CH₃, —C(=O)R$^{L-1-1}$ and —NR$^{L-11-2}$C(=O)R$^{L-11-3}$; R$^{L-11-1}$ is independently selected from C₁-C₄ alkyl and C₁-C₄ alkoxy; R$^{L-11-2}$ is independently selected from hydrogen and C₁-C₄ alkyl; R$^{L-11-3}$ is independently selected from C₁-C₄ alkyl; and n is 0, 1, 2, 3, or 4, R¹⁰ is independently selected from hydroxy, halogen (e.g., fluorine, chlorine, bromine, or iodine, and preferably, e.g., fluorine), oxo, and R$^{10-1}$-substituted or unsubstituted C₁-C₄ alkyl (there can be one or more R$^{10-1}$, and in case that there are a plurality of R$^{10-1}$, the plurality of R$^{10-1}$ are the same or different; e.g., methyl, ethyl, n-propyl, isopropyl, n-butyl, isobutyl, sec-butyl, or tert-butyl, and preferably, e.g., methyl), and R$^{10-1}$ is independently selected from hydroxy and C₁-C₄ alkoxy. [The R¹⁰ can be independently located at the ortho, meta or para position relative to ring A, and preferably at the ortho or meta position relative to ring A; when n is 1, $R^{10}$ can be located at the ortho or meta position relative to ring A; $R^{10}$ can be linked to a carbon atom or a nitrogen atom of ring B; and the carbon atom of ring B, linked to $R^{10}$, can be independently selected from a chiral carbon atom, either in R configuration or S configuration]

In one embodiment, certain groups of compound of formula I are defined as follows, and groups not mentioned are defined in any of the above embodiments:

$R^1$ can be halogen.

In one embodiment, certain groups of compound of formula I are defined as follows, and groups not mentioned are defined in any of the above embodiments:

m can be 0 or 1, and preferably 0.

In one embodiment, certain groups of compound of formula I are defined as follows, and groups not mentioned are defined in any of the above embodiments:

$R^3$ can be halogen.

In one embodiment, certain groups of compound of formula I are defined as follows, and groups not mentioned are defined in any of the above embodiments:

$W^1$ may be =N—.

In one embodiment, certain groups of compound of formula I are defined as follows, and groups not mentioned are defined in any of the above embodiments:

$W^2$ may be =CR$^4$—.

In one embodiment, certain groups of compound of formula I are defined as follows, and groups not mentioned are defined in any of the above embodiments:

$W^3$ may be —S— or —CH=CH—.

In one embodiment, certain groups of compound of formula I are defined as follows, and groups not mentioned are defined in any of the above embodiments:

when $W^2$ is =N—, $R^2$ can be cyano, halogen, or $C_1$-$C_4$ alkyl.

In one embodiment, certain groups of compound of formula I are defined as follows, and groups not mentioned are defined in any of the above embodiments:

when $W^2$ is =CR$^4$—, one of $R^2$ and $R^4$ is cyano, and the other is hydrogen.

In one embodiment, certain groups of compound of formula I are defined as follows, and groups not mentioned are defined in any of the above embodiments:

when $W^2$ is =CR$^4$—, $R^4$ may be cyano, and $R^2$ may be hydrogen.

In one embodiment, certain groups of compound of formula I are defined as follows, and groups not mentioned are defined in any of the above embodiments:

ring A may be

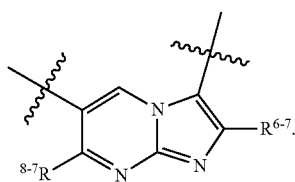

In one embodiment, certain groups of compound of formula I are defined as follows, and groups not mentioned are defined in any of the above embodiments:

ring A may be

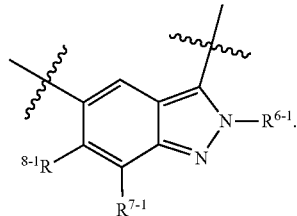

In one embodiment, certain groups of compound of formula I are defined as follows, and groups not mentioned are defined in any of the above embodiments:

$R^{6-1}$, $R^{6-2}$, $R^{6-3}$, $R^{6-4}$, $R^{6-5}$, $R^6$, $R^{6-7}$, $R^{6-8}$, $R^{6-9}$, $R^{6-10}$, and $R^{6-11}$ can be independently selected from $C_1$-$C_4$ alkyl.

In one embodiment, certain groups of compound of formula I are defined as follows, and groups not mentioned are defined in any of the above embodiments:

at least one of $R^{7-1}$ and $R^{8-1}$ is hydrogen (e.g., only one of the two is hydrogen).

In one embodiment, certain groups of compound of formula I are defined as follows, and groups not mentioned are defined in any of the above embodiments:

at least one of $R^{7-2}$ and $R^{8-2}$ is hydrogen (e.g., only one of the two is hydrogen).

In one embodiment, certain groups of compound of formula I are defined as follows, and groups not mentioned are defined in any of the above embodiments:

at least one of $R^{7-3}$ and $R^{8-3}$ is hydrogen (e.g., only one of the two is hydrogen).

In one embodiment, certain groups of compound of formula I are defined as follows, and groups not mentioned are defined in any of the above embodiments:

at least one of $R^{7-4}$ and $R^{8-6}$ is hydrogen (e.g., only one of the two is hydrogen).

In one embodiment, certain groups of compound of formula I are defined as follows, and groups not mentioned are defined in any of the above embodiments:

$R^{7-1}$, $R^{7-2}$, $R^{7-3}$, $R^{7-4}$, $R^{7-5}$, and $R^{7-6}$ can be independently selected hydrogen, halogen, and $C_1$-$C_4$ alkyl.

In one embodiment, certain groups of compound of formula I are defined as follows, and groups not mentioned are defined in any of the above embodiments:

$R^{8-1}$, $R^{8-2}$, $R^{8-3}$, $R^{8-4}$, $R^{8-5}$, $R^{8-6}$, $R^{8-7}$, $R^{8-8}$, and $R^{8-9}$ can be independently selected from hydrogen and halogen.

In one embodiment, certain groups of compound of formula I are defined as follows, and groups not mentioned are defined in any of the above embodiments:

ring B may be "4-10 membered monocyclic or bicyclic heterocycloalkyl having 1-3 heteroatoms selected from one or more of O, N, and S", or "4-7 membered heterocycloalkenyl having 1 double bond and 1-3 heteroatoms selected from one or more of O, N, and S".

In one embodiment, certain groups of compound of formula I are defined as follows, and groups not mentioned are defined in any of the above embodiments:

$L^1$ may be $C_1$-$C_4$ alkylene.

In one embodiment, certain groups of compound of formula I are defined as follows, and groups not mentioned are defined in any of the above embodiments:

$L^2$ may be —C(=O)— or —SO$_2$—, and preferably —C(=O)—.

In one embodiment, certain groups of compound of formula I are defined as follows, and groups not mentioned are defined in any of the above embodiments:

$L^3$ may be "4-10 membered monocyclic, bicyclic, or spirocyclic heterocycloalkyl having 1-3 heteroatoms selected from one or more of O, N, and S" which is substituted or unsubstituted with $R^{L-9}$ In one embodiment, certain groups of compound of formula I are defined as follows, and groups not mentioned are defined in any of the above embodiments:

$R^{L-9}$ may be independently selected from hydroxy and halogen.

In one embodiment, certain groups of compound of formula I are defined as follows, and groups not mentioned are defined in any of the above embodiments:

n can be 0 or 1, and preferably 0.

In one embodiment, certain groups of compound of formula I are defined as follows, and groups not mentioned are defined in any of the above embodiments:

$R^{10}$ is independently selected from hydroxy and $C_1$-$C_4$ alkyl.

In one embodiment, certain groups of compound of formula I are defined as follows, and groups not mentioned are defined in any of the above embodiments:

$R^1$ is cyano or halogen (e.g., fluorine, chlorine, bromine, or iodine, and preferably, e.g., fluorine);

m is 0;

$W^1$ is =N—;

$W^2$ is =$CR^4$— or =N—;

$W^3$ is —S—;

when $W^2$ is =N—, $R^2$ is hydrogen, cyano, or methyl;

when $W^2$ is =$CR^4$—, "$R^4$ is cyano and $R^2$ is hydrogen", or, "$R^4$ is hydrogen and $R^2$ is cyano";

$R^5$ is $C_1$-$C_4$ alkyl (e.g., methyl, ethyl, n-propyl, isopropyl, n-butyl, isobutyl, sec-butyl, or tert-butyl, and preferably, e.g., methyl);

ring A is

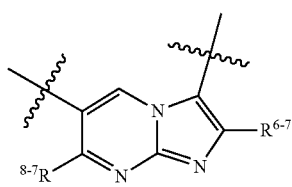

[the left terminus of which is linked to ring B];

$R^{6-7}$ is $R^{6-1-1}$-substituted or unsubstituted $C_1$-$C_4$ alkyl (there can be one or more $R^{6-1-1}$, and in case that there are a plurality of $R^{6-1}$—, the plurality of $R^{6-1-1}$ are the same or different; and the "$C_1$-$C_4$ alkyl" is, e.g., methyl, ethyl, n-propyl, isopropyl, n-butyl, isobutyl, sec-butyl, or tert-butyl, and preferably, e.g., ethyl), and $R^{6-1-1}$ is independently selected from hydroxy, cyano, halogen, or —C(=O)NH$_2$;

$R^{8-7}$ is hydrogen; and ring B is "4-10 membered monocyclic or bicyclic heterocycloalkyl having 1-3 heteroatoms selected from one or more of O, N, and S" (e.g., "4-7 membered monocyclic heterocycloalkyl having 1-2 heteroatoms selected from one or more of O, N, and S", preferably, e.g., "5-6 membered monocyclic heterocycloalkyl having 1-2 heteroatoms selected from one or more of O, N, and S", and more preferably, e.g., "

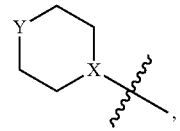

wherein X is N or CH and Y is NH or CH$_2$, which are not both carbon", and most preferably, e.g.,

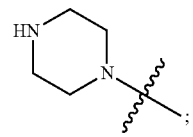 [SMILES: *N1CCNCC1]

the heterocycloalkyl may be linked to ring A via a carbon atom or a nitrogen atom, and preferably via a nitrogen atom);

$R^9$ is -$L^1$-$L^2$-$L^3$; [when ring B is 6-membered heterocycloalkyl, $R^9$ can be located at the ortho, meta, or para position relative to ring A, and preferably at the para position relative to ring A; and $R^9$ can be linked to a carbon atom or a nitrogen atom of ring B, and preferably linked to a nitrogen atom of ring B]

$L^1$ is $C_1$-$C_4$ alkylene, e.g., —CH$_2$—, —CH$_2$CH$_2$—, —CH(CH$_3$)— (wherein the chiral carbon atom can be in R configuration or S configuration), —CH$_2$CH$_2$CH$_2$—, or —CH$_2$CH(CH$_3$)— (wherein the chiral carbon atom can be in R configuration or S configuration);

$L^2$ is —C(=O)—;

$L^3$ is "4-10 membered monocyclic, bicyclic, or spirocyclic heterocycloalkyl having 1-3 heteroatoms selected from one or more of O, N, and S" which is substituted or unsubstituted with $R^{L-9}$ (the "4-10 membered monocyclic, bicyclic, or spirocyclic heterocycloalkyl having 1-3 heteroatoms selected from one or more of O, N, and S" is, e.g., "4-10 membered monocyclic heterocycloalkyl having 1-2 heteroatoms selected from one or more of O, N, and S", preferably, e.g., "4-6 membered monocyclic heterocycloalkyl having 1-2 heteroatoms selected from one or more of O, N, and S", and more preferably, e.g.,

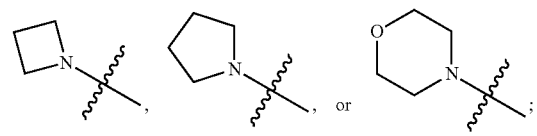 [SMILES: *N1CCC1 ; *N1CCCC1 ; *N1CCOCC1]

the "4-10 membered monocyclic, bicyclic, or spirocyclic heterocycloalkyl having 1-3 heteroatoms selected from one or more of O, N, and S" which is substituted with $R^{L-9}$ is, e.g.,

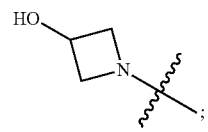

there can be one or more $R^{L-9}$, and in case that there are a plurality of $R^{L-9}$, the plurality of $R^{L-9}$ are the same or different; and the heterocycloalkyl can be linked to $L^2$ via a carbon atom or a nitrogen atom, and preferably via a nitrogen atom);

$R^{L-9}$ is independently selected from oxo, hydroxy, cyano, halogen (e.g., fluorine, chlorine, bromine, or iodine, and preferably, e.g., fluorine), phenyl, hydroxy-substituted $C_1$-$C_4$ alkyl (the "$C_1$-$C_4$ alkyl" is, e.g., methyl, ethyl, n-propyl, isopropyl, n-butyl, isobutyl, sec-butyl, or tert-butyl, and preferably, e.g., methyl; and the "hydroxy-substituted $C_1$-$C_4$ alkyl" is, e.g., hydroxymethyl), —SO$_2$CH$_3$, —C(=O)R$^{L-9-1}$ and —NR$^{L-9-2}$C(=O)R$^{L-9-3}$; R$^{L-9-1}$ is independently selected from $C_1$-$C_4$ alkyl and $C_1$-$C_4$ alkoxy, R$^{L-9-2}$ is independently selected from hydrogen and $C_1$-$C_4$ alkyl, R$^{L-9-3}$ is independently selected from $C_1$-$C_4$ alkyl (the carbon atom in the heterocycloalkyl, linked to R$^{L-9}$, may be independently a chiral carbon atom, either in R or S configuration); and n is 0.

In one embodiment, certain groups of compound of formula I are defined as follows, and groups not mentioned are defined in any of the above embodiments:

$R^1$ is cyano or halogen (e.g., fluorine, chlorine, bromine, or iodine, and preferably, e.g., fluorine);

m is 0;

$W^1$ is =N—;

$W^2$ is =CR$^4$— or =N—;

$W^3$ is —S—;

when $W^2$ is =N—, $R^2$ is hydrogen, cyano, or methyl;

when $W^2$ is =CR$^4$—, "$R^4$ is cyano and $R^2$ is hydrogen", or, "$R^4$ is hydrogen and $R^2$ is cyano";

$R^5$ is $C_1$-$C_4$ alkyl (e.g., methyl, ethyl, n-propyl, isopropyl, n-butyl, isobutyl, sec-butyl, or tert-butyl, and preferably, e.g., methyl);

ring A is

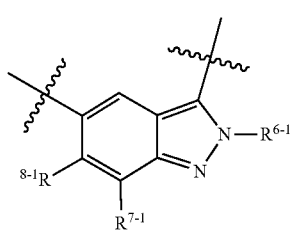

[the left terminus of which is linked to ring B];

$R^{6-1}$ is $R^{6-1-1}$-substituted or unsubstituted $C_1$-$C_4$ alkyl (there can be one or more $R^{6-1-1}$, and in case that there are a plurality of $R^{6-1-1}$, the plurality of $R^{6-1-1}$ are the same or different; and the "$C_1$-$C_4$ alkyl" is, e.g., methyl, ethyl, n-propyl, isopropyl, n-butyl, isobutyl, sec-butyl, or tert-butyl, and preferably, e.g., ethyl), and $R^{6-1-1}$ is independently selected from hydroxy, cyano, halogen, and —C(=O)NH$_2$;

$R^{7-1}$ is halogen (e.g., fluorine, chlorine, bromine, or iodine, and preferably, e.g., fluorine);

$R^{8-1}$ is hydrogen; and ring B is "4-10 membered monocyclic or bicyclic heterocycloalkyl having 1-3 heteroatoms selected from one or more of O, N, and S" (e.g., "4-7 membered monocyclic heterocycloalkyl having 1-2 heteroatoms selected from one or more of O, N, and S", preferably, e.g., "5-6 membered monocyclic heterocycloalkyl having 1-2 heteroatoms selected from one or more of O, N, and S", and more preferably, e.g., "

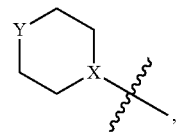

wherein X is N or CH and Y is NH or CH$_2$, which are not both carbon", and most preferably, e.g.,

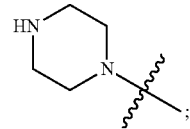

the heterocycloalkyl may be linked to ring A via a carbon atom or a nitrogen atom, and preferably via a nitrogen atom);

$R^9$ is -$L^1$-$L^2$-$L^3$; [when ring B is 6-membered heterocycloalkyl, $R^9$ can be located at the ortho, meta, or para position relative to ring A, and preferably at the para position relative to ring A; and $R^9$ can be linked to a carbon atom or a nitrogen atom of ring B, and preferably linked to a nitrogen atom of ring B]

$L^1$ is $C_1$-$C_4$ alkylene, e.g., —CH$_2$—, —CH$_2$CH$_2$—, —CH(CH$_3$)— (wherein the chiral carbon atom can be in R configuration or S configuration), —CH$_2$CH$_2$CH$_2$—, or —CH$_2$CH(CH$_3$)— (wherein the chiral carbon atom can be in R configuration or S configuration);

$L^2$ is —C(=O)—;

$L^3$ is "4-10 membered monocyclic, bicyclic, or spirocyclic heterocycloalkyl having 1-3 heteroatoms selected from one or more of O, N, and S" which is substituted or unsubstituted with $R^{L-9}$ (the "4-10 membered monocyclic, bicyclic, or spirocyclic heterocycloalkyl having 1-3 heteroatoms selected from one or more of O, N, and S" is, e.g., "4-10 membered monocyclic heterocycloalkyl having 1-2 heteroatoms selected from one or more of O, N, and S", preferably, e.g., "4-6 membered monocyclic heterocycloalkyl having 1-2 heteroatoms selected from one or more of O, N, and S", and more preferably, e.g.,

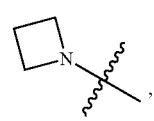 , 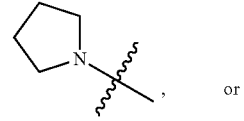 or

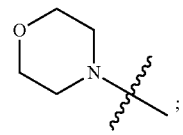 ;

the "4-10 membered monocyclic, bicyclic, or spirocyclic heterocycloalkyl having 1-3 heteroatoms selected from one or more of O, N, and S" which is substituted with $R^{L-9}$ is, e.g.,

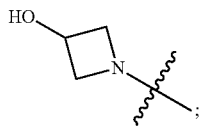

there can be one or more $R^{L-9}$ and in case that there are a plurality of $R^{L-9}$, the plurality of $R^{L-9}$ are the same or different; and the heterocycloalkyl can be linked to $L^2$ via a carbon atom or a nitrogen atom, and preferably via a nitrogen atom);

$R^{L-9}$ is independently selected from oxo, hydroxy, cyano, halogen (e.g., fluorine, chlorine, bromine, or iodine, and preferably, e.g., fluorine), phenyl, hydroxy-substituted $C_1$-$C_4$ alkyl (the "$C_1$-$C_4$ alkyl" is, e.g., methyl, ethyl, n-propyl, isopropyl, n-butyl, isobutyl, sec-butyl, or tert-butyl, and preferably, e.g., methyl; and the "hydroxy-substituted $C_1$-$C_4$ alkyl" is, e.g., hydroxymethyl), —$SO_2CH_3$, —$C(=O)R^{L-9-1}$ and —$NR^{L-9-2}C(=O)R^{L-9-3}$; $R^{L-9-1}$ is independently selected from $C_1$-$C_4$ alkyl and $C_1$-$C_4$ alkoxy, $R^{L-9-2}$ is independently selected from hydrogen and $C_1$-$C_4$ alkyl, $R^{L-9-3}$ is independently selected from $C_1$-$C_4$ alkyl (the carbon atom in the heterocycloalkyl, linked to $R^{L-9}$, may be independently a chiral carbon atom, either in R or S configuration); and n is 0.

In a certain embodiment, the heterocyclic compound of formula I may be any one of the following compounds:

S-0021: 2-((2-ethyl-6-(4-(2-(3-hydroxyazetidin-1-yl)-2-oxoethyl)piperazin-1-yl)imidazo [1,2-a]pyrimidin-3-yl)(methyl)amino)-4-(4-fluorophenyl)thiazole-5-carbonitrile S-0058: 2-(ethyl(2-ethyl-6-(4-(2-(3-hydroxyazetidin-1-yl)-2-oxoethyl)piperazin-1-yl) imidazo[1,2-a]pyrimidin-3-yl)amino)-4-(4-fluorophenyl)thiazole-5-carbonitrile S-0025: 2-((2-ethyl-7-fluoro-5-(4-(2-(3-hydroxyazetidin-1-yl)-2-oxoethyl)piperazin-1-yl)-2H-indazol-3-yl)(methyl)amino)-4-(4-fluorophenyl)thiazole-5-carbonitrile S-0027: 4-(3,4-difluorophenyl)-2-((2-ethyl-7-fluoro-5-(4-(2-(3-hydroxyazetidin-1-yl)-2-oxoethyl)piperazin-1-yl)-2H-indazol-3-yl)(methyl)amino)thiazole-5-carbonitrile S-0122: 2-(ethyl(2-ethyl-7-fluoro-5-(4-(2-(3-hydroxyazetidin-1-yl)-2-oxoethyl)piperazin-1-yl)-2H-indazol-3-yl)amino)-4-(4-fluorophenyl)thiazole-5-carbonitrile S-0123: 4-(3,4-difluorophenyl)-2-(ethyl(2-ethyl-7-fluoro-5-(4-(2-(3-hydroxyazetidin-1-yl)-2-oxoethyl)piperazin-1-yl)-2H-indazol-3-yl)amino)thiazole-5-carbonitrile S-0125: 2-((7-fluoro-5-(4-(2-(3-hydroxyazetidin-1-yl)-2-oxoethyl)piperazin-1-yl)-2-isopropyl-2H-indazol-3-yl)(methyl)amino)-4-(4-fluorophenyl)thiazole-5-carbonitrile S-0126: 2-((2-cyclopropyl-7-fluoro-5-(4-(2-(3-hydroxyazetidin-1-yl)-2-oxoethyl) piperazin-1-yl)-2H-indazol-3-yl)(methyl)amino)-4-(4-fluorophenyl)thiazole-5-carbonitrile S-0131: 2-((2-ethyl-7-fluoro-5-(4-(2-(3-hydroxyazetidin-1-yl)-2-oxoethyl)-2-(trifluoromethyl)piperazin-1-yl)-2H-indazol-3-yl)(methyl)amino)-4-(4-fluorophenyl)thiazole-5-carbonitrile S-0134: 2-(ethyl(2-ethyl-7-fluoro-5-(4-(2-(3-hydroxyazetidin-1-yl)-2-oxoethyl)-2-(trifluoromethyl)piperazin-1-yl)-2H-indazol-3-yl)amino)-4-(4-fluorophenyl)thiazole-5-carbonitrile S-0029: 2-(4-(2-ethyl-7-fluoro-3-((3-(4-fluorophenyl)-1,2,4-thiadiazol-5-yl)(methyl) amino)-2H-indazol-5-yl)piperazin-1-yl)-1-(3-hydroxyazetidin-1-yl)ethyl-1-one S-0030: 6-((2-ethyl-7-fluoro-5-(4-(2-(3-hydroxyazetidin-1-yl)-2-oxoethyl)piperazin-1-yl)-2H-indazol-3-yl)(methyl)amino)-2-(4-fluorophenyl)nicotinonitrile S-0080: 2-(4-(2-ethyl-7-fluoro-3-((4-(4-fluorophenyl)pyrimidin-2-yl)(methyl)amino)-2H-indazol-5-yl)piperazin-1-yl)-1-(3-hydroxyazetidin-1-yl)ethyl-1-one S-0135: 2-(ethyl(2-ethyl-7-fluoro-5-(4-(2-(3-hydroxyazetidin-1-yl)-2-oxoethyl)-3-(trifluoromethyl)piperazin-1-yl)-2H-indazol-3-yl)amino)-4-(4-fluorophenyl)thiazole-5-carbonitrile S-0022: 2-((2-ethyl-5-(4-(2-(3-hydroxyazetidin-1-yl)-2-oxoethyl)piperazin-1-yl)-7-methyl-2H-indazol-3-yl)(methyl)amino)-4-(4-fluorophenyl)thiazole-5-carbonitrile S-103: 2-((7-chloro-2-ethyl-5-(4-(2-(3-hydroxyazetidin-1-yl)-2-oxoethyl)piperazin-1-yl)-2H-indazol-3-yl)(methyl)amino)-4-(4-fluorophenyl)thiazole-5-carbonitrile S-0094: 2-((2-ethyl-5-(4-(2-(3-hydroxyazetidin-1-yl)-2-oxoethyl)piperazin-1-yl)-2H-pyrazolo[4,3-b]pyridin-3-yl)(methyl)amino)-4-(4-fluorophenyl)thiazole-5-carbonitrile S-0117: 2-(ethyl(2-ethyl-5-(4-(2-(3-hydroxyazetidin-1-yl)-2-oxoethyl)piperazin-1-yl)-2H-pyrazolo[4,3-b]pyridin-3-yl)amino)-4-(4-fluorophenyl)thiazole-5-carbonitrile S-0095: 2-((2-ethyl-5-(4-(2-(3-hydroxyazetidin-1-yl)-2-oxoethyl)piperazin-1-yl)-7-methyl-2H-pyrazolo[4,3-b]pyridin-3-yl)(methyl)amino)-4-(4-fluorophenyl)thiazole-5-carbonitrile S-0124: 2-(ethyl(2-ethyl-5-(4-(2-(3-hydroxyazetidin-1-yl)-2-oxoethyl)piperazin-1-yl)-7-methyl-2H-pyrazolo[4,3-b]pyridin-3-yl)amino)-4-(4-fluorophenyl)thiazole-5-carbonitrile S-0140: 2-((2-ethyl-5-(4-(2-(3-hydroxyazetidin-1-yl)-2-oxoethyl)piperazin-1-yl)-7-methyl-2H-pyrazolo[4,3-b]pyridin-3-yl)(2,2,2-trifluoroethyl)amino)-4-(4-fluorophenyl) thiazole-5-carbonitrile S-0141: 2-((2,2-difluoroethyl)(2-ethyl-5-(4-(2-(3-hydroxyazetidin-1-yl)-2-oxoethyl) piperazin-1-yl)-7-methyl-2H-pyrazolo[4,3-b]pyridin-3-yl)amino)-4-(4-fluorophenyl)thiazole-5-carbonitrile S-0144: 2-((2-ethyl-5-(4-(2-(3-hydroxyazetidin-1-yl)-2-oxoethyl)piperazin-1-yl)-7-methyl-2H-pyrazolo[4,3-b]pyridin-3-yl)(2-fluoroethyl)amino)-4-(4-fluorophenyl) thiazole-5-carbonitrile S-0043: 2-((2-ethyl-5-(4-(2-(3-hydroxyazetidin-1-yl)-2-oxoethyl)piperazin-1-yl)-2H-pyrazolo[3,4-b]pyridin-3-yl)(methyl)amino)-4-(4-fluorophenyl)thiazole-5-carbonitrile S-0044: 2-((2-ethyl-5-(4-(2-(3-hydroxyazetidin-1-yl)-2-oxoethyl)piperazin-1-yl)-2H-pyrazolo[3,4-c]pyridin-3-yl)(methyl)amino)-4-(4-fluorophenyl)thiazole-5-carbonitrile S-0024: 2-((2-ethyl-7-fluoro-5-(4-(2-(3-hydroxyazetidin-1-yl)-2-oxoethyl)piperazin-1-yl) benzofuran-3-yl)(methyl)amino)-4-(4-fluorophenyl)thiazole-5-carbonitrile S-0045: 2-((2-ethyl-5-(4-(2-(3-hydroxyazetidin-1-yl)-2-oxoethyl)piperazin-1-yl)furo [2,3-b]pyridin-3-yl)(methyl)amino)-4-(4-fluorophenyl)thiazole-5-carbonitrile S-0097: 2-((2-ethyl-5-(4-(2-(3-hydroxyazetidin-1-yl)-2-oxoethyl)piperazin-1-yl)furo [3,2-b]pyridin-3-yl)(methyl)amino)-4-(4-fluorophenyl)thiazole-5-carbonitrile S-0105CP: 2-(ethyl(2-ethyl-5-(4-(2-(3-hydroxyazetidin-1-yl)-2-oxoethyl)piperazin-1-yl) furo[3,2-b]pyridin-3-yl)amino)-4-(4-fluorophenyl)thiazole-5-carbonitrile S-0046: 2-((2-ethyl-5-(4-(2-(3-hydroxyazetidin-1-yl)-2-oxoethyl)piperazin-1-yl)furo [2,3-c]pyridin-3-yl)(methyl)amino)-4-(4-fluorophenyl)thiazole-5-carbonitrile S-0098: 2-((2-ethyl-5-(4-(2-(3-hydroxyazetidin-1-yl)-2-oxoethyl)piperazin-1-yl)-1H-pyrrolo[3,2-b]pyridin-3-yl)(methyl)amino)-4-(4-fluorophenyl)thiazole-5-carbonitrile 2-((2-ethyl-5-(4-(2-(3-hydroxyazetidin-1-yl)-2-oxoethyl) piperazin-1-yl)-1H-pyrrolo [3,2-b]pyridin-3-yl)(methyl) amino)-4-(4-fluorophenyl)thiazole-5-carbonitrile S-0128: 2-((2-ethyl-5-(4-(2-(3-hydroxyazetidin-1-yl)-2-oxoethyl)piperazin-1-yl)-1-methyl-1H-pyrrolo[3,2-b] pyridin-3-yl)(methyl)amino)-4-(4-fluorophenyl)thiazole-5-carbonitrile S-0129: 2-((2-ethyl-5-(4-(2-(3-hydroxyazetidin-1-yl)-2-oxoethyl)piperazin-1-yl)thieno [3,2-b]pyridin-3-yl) (methyl)amino)-4-(4-fluorophenyl)thiazole-5-carbonitrile S-0035: 2-((2-ethyl-5-(4-(2-(3-hydroxyazetidin-1-yl)-2-oxoethyl)piperazin-1-yl)-7-methylpyrazolo[1,5-a]pyrimidin-3-yl)(methyl)amino)-4-(4-fluorophenyl)thiazole-5-carbonitrile S-0068: 4-(3,4-difluorophenyl)-2-((2-ethyl-5-(4-(2-(3-hydroxyazetidin-1-yl)-2-oxoethyl) piperazin-1-yl)-7-methylpyrazolo[1,5-a]pyrimidin-3-yl)(methyl)amino)thiazole-5-carbonitrile S-0069: 2-(ethyl(2-ethyl-5-(4-(2-(3-hydroxyazetidin-1-yl)-2-oxoethyl)piperazine-1-yl)-7-methylpyrazolo[1,5-a]pyrimidin-3-yl)amino)-4-(4-fluorophenyl)thiazole-5-carbonitrile S-0070: (R)-2-((2-ethyl-5-(4-(2-(3-hydroxyazetidin-1-yl)-2-oxoethyl)-2-methylpiperazin-1-yl)-7-methylpyrazolo[1,5-a]pyrimidin-3-yl)(methyl)amino)-4-(4-fluorophenyl) thiazole-5-carbonitrile S-0071: (S)-2-((2-ethyl-5-(4-(2-(3-hydroxyazetidin-1-yl)-2-oxoethyl)-2-methylpiperazin-1-yl)-7-methylpyrazolo[1,5-a]pyrimidin-3-yl)(methyl)amino)-4-(4-fluorophenyl) thiazole-5-carbonitrile S-0074: (R)-2-((2-ethyl-5-(4-(2-(3-hydroxyazetidin-1-yl)-2-oxoethyl)-3-methylpiperazin-1-yl)-7-methylpyrazolo[1,5-a]pyrimidin-3-yl)(methyl)amino)-4-(4-fluorophenyl) thiazole-5-carbonitrile S-0075: (S)-2-((2-ethyl-5-(4-(2-(3-hydroxyazetidin-1-yl)-2-oxoethyl)-3-methylpiperazin-1-yl)-7-methylpyrazolo[1,5-a]pyrimidin-3-yl)(methyl)amino)-4-(4-fluorophenyl) thiazole-5-carbonitrile S-0099: 2-((2-ethyl-5-(4-(2-(3-hydroxyazetidin-1-yl)-2-oxoacetyl)piperazin-1-yl)-7-methylpyrazolo[1,5-a]pyrimidin-3-yl)(methyl)amino)-4-(4-fluorophenyl)thiazole-5-carbonitrile S-0100CP: 2-((2-ethyl-5-(4-(2-(3-hydroxyazetidin-1-yl) acetyl)piperazin-1-yl)-7-methylpyrazolo[1,5-a]pyrimidin-3-yl)(methyl)amino)-4-(4-fluorophenyl)thiazole-5-carbonitrile S-0041: 2-((2-ethyl-5-(4-(2-(3-hydroxyazetidin-1-yl)-2-oxoethyl)piperazin-1-yl)pyrazolo [1,5-a]pyrimidin-3-yl) (methyl)amino)-4-(4-fluorophenyl)thiazole-5-carbonitrile S-0082: 2-(ethyl(2-ethyl-5-(4-(2-(3-hydroxyazetidin-1-yl)-2-oxoethyl)piperazin-1-yl) pyrazolo[1,5-a]pyrimidin-3-yl)amino)-4-(4-fluorophenyl)thiazole-5-carbonitrile S-0104CP: 2-((2-ethyl-5-(4-(2-(3-hydroxyazetidin-1-yl)-2-oxoethyl)-3-oxopiperazin-1-yl) pyrazolo[1,5-a]pyrimidin-3-yl)(methyl)amino)-4-(4-fluorophenyl)thiazole-5-carbonitrile S-0120: 2-((2-ethyl-5-(4-(2-(3-hydroxy-3-methylazetidin-1-yl)-2-oxoethyl)piperazin-1-yl) pyrazolo[1,5-a]pyrimidin-3-yl)(methyl)amino)-4-(4-fluorophenyl)thiazole-5-carbonitrile S-0121: 4-(3,4-difluorophenyl)-2-((2-ethyl-5-(4-(2-(3-hydroxyazetidin-1-yl)-2-oxoethyl) piperazin-1-yl)pyrazolo [1,5-a]pyrimidin-3-yl)(methyl)amino)thiazole-5-carbonitrile S-0102CP: 2-((2-ethyl-5-(4-(2-hydroxyethylsulfonyl)piperazin-1-yl)pyrazolo[1,5-a]pyrimidin-3-yl)(methyl)amino)-4-(4-fluorophenyl)thiazole-5-carbonitrile S-0103 CP: 2-((2-ethyl-5-(4-(ethylsulfonyl)piperazin-1-yl) pyrazolo[1,5-a]pyrimidin-3-yl) (methyl)amino)-4-(4-fluorophenyl)thiazole-5-carbonitrile S-0040: 2-((2-ethyl-5-(4-(2-(3-hydroxyazetidin-1-yl)-2-oxoethyl)piperazin-1-yl)pyrazolo [1,5-a]pyridin-3-yl) (methyl)amino)-4-(4-fluorophenyl)thiazole-5-carbonitrile S-0023: 2-((2-ethyl-5-(4-(2-(3-hydroxyazetidin-1-yl)-2-oxoethyl)piperazin-1-yl)-7-methylbenzofuran-3-yl) (methyl)amino)-4-(4-fluorophenyl)thiazole-5-carbonitrile S-0149: 2-(4-(2-ethyl-3-(ethyl(4-(4-fluorophenyl)thiazol-2-yl)amino)-7-fluoro-2H-indazol-5-yl)piperazin-1-yl)-1-(3-hydroxyazetidin-1-yl)ethanone S-0151: 2-(4-(2-ethyl-3-(ethyl(4-(4-fluorophenyl)thiazol-2-yl)amino)-7-methyl-2H-pyrazolo[4,3-b]pyridin-5-yl)piperazin-1-yl)-1-(3-hydroxyazetidin-1-yl)ethanone In a certain embodiment, the heterocyclic compound of formula I can further be any one of the following compounds:

2-((2-ethyl-7-fluoro-5-(4-(2-(3-hydroxyazetidin-1-yl)-2-oxoethyl)-2-(trifluoromethyl)piperazin-1-yl)-2H-indazol-3-yl)(methyl)amino)-4-(4-fluorophenyl)thiazole-5-carbonitrile having a retention time of 3.87 min or 5.09 min under the following analytical conditions: column: AD-H, 4.6*100 mm, 5 µm; mobile phase: ethanol (containing 1% of a solution of ammonia in methanol);

2-(ethyl(2-ethyl-7-fluoro-5-(4-(2-(3-hydroxyazetidin-1-yl)-2-oxoethyl)-2-(trifluoromethyl)piperazin-1-yl)-2H-indazol-3-yl)amino)-4-(4-fluorophenyl)thiazole-5-carbonitrile having a retention time of 3.05 min or 4.26 min under the following analytical conditions: column: AD-H, 4.6*100 mm, 5 µm; mobile phase: ethanol (containing 1% of a solution of ammonia in methanol); and 2-(ethyl(2-ethyl-7-fluoro-5-(4-(2-(3-hydroxyazetidin-1-yl)-2-oxoethyl)-3-(trifluoromethyl)piperazin-1-yl)-2H-indazol-3-yl)amino)-4-(4-fluorophenyl)thiazole-5-carbonitrile having a retention time of 10.04 min or 11.09 min under the following analytical conditions: column: OD-H, 4.6*250 mm, 5 µm; mobile phase: hexane (containing 0.1% diethanolamine): ethanol (containing 0.1% diethanolamine)=80:20.

The invention further provides an application of the compound of formula I or the pharmaceutically acceptable salt thereof described above in the preparation of Autotaxin (ATX) inhibitors.

The invention further provides an application of the compound of formula I or the pharmaceutically acceptable salt thereof described above in the preparation of drugs for preventing and/or treating diseases associated with Autotaxin (ATX).

The invention further provides an application of the compound of formula I or the pharmaceutically acceptable salt thereof described above in the preparation of drugs for preventing and/or treating one or more of a fibrotic disease (e.g., idiopathic pulmonary fibrosis or nonalcoholic steatohepatitis), a proliferative disease (e.g., cancer), an inflammatory disease (e.g., chronic obstructive pulmonary disease or pain (such as osteoarthritis pain)), an autoimmune disease, a respiratory disease, a cardiovascular disease, a neurodegenerative disease, a dermatological disease, and a disease associated with abnormal angiogenesis.

The invention further provides a pharmaceutical composition comprising the compound of formula I or the pharmaceutically acceptable salt thereof described above and a pharmaceutical excipient.

The pharmaceutical composition can consist of the compound of formula I or the pharmaceutically acceptable salt thereof and the pharmaceutical excipient.

The invention further provides an application of the compound of formula I or the pharmaceutically acceptable salt thereof described above in the preparation of drugs used, in combination with another therapeutic agent, for preventing and/or treating a disease associated with Autotaxin (e.g., one or more of a fibrotic disease (e.g., idiopathic pulmonary fibrosis or nonalcoholic steatohepatitis), a proliferative disease (e.g., cancer), an inflammatory disease (e.g., chronic obstructive pulmonary disease or pain (such as osteoarthritis pain)), an autoimmune disease, a respiratory disease, a cardiovascular disease, a neurodegenerative disease, a dermatological disease, and a disease associated with abnormal angiogenesis).

The "another therapeutic agent" can be a therapeutic agent for preventing and/or treating "one or more of a fibrotic disease (e.g., idiopathic pulmonary fibrosis or nonalcoholic steatohepatitis), a proliferative disease (e.g., cancer), an inflammatory disease (e.g., chronic obstructive pulmonary disease or pain (such as osteoarthritis pain)), an autoimmune disease, a respiratory disease, a cardiovascular disease, a neurodegenerative disease, a dermatological disease, and a disease associated with abnormal angiogenesis", for example, "substance A, which is nintedanib or a pharmaceutically acceptable salt thereof, and/or pirfenidone or a pharmaceutically acceptable salt thereof".

The pharmaceutically acceptable salt of nintedanib is, for example, nintedanib ethanesulfonate salt.

The invention further provides an application of nintedanib or a pharmaceutically acceptable salt thereof in the preparation of drugs used, in combination with the compound of formula I or the pharmaceutically acceptable salt thereof described above, for preventing and/or treating a disease associated with Autotaxin (e.g., one or more of a fibrotic disease (e.g., idiopathic pulmonary fibrosis or nonalcoholic steatohepatitis), a proliferative disease (e.g., cancer), an inflammatory disease (e.g., chronic obstructive pulmonary disease or pain (such as osteoarthritis pain)), an autoimmune disease, a respiratory disease, a cardiovascular disease, a neurodegenerative disease, a dermatological disease, and a disease associated with abnormal angiogenesis).

The pharmaceutically acceptable salt of nintedanib is, for example, nintedanib ethanesulfonate salt.

The invention further provides an application of nintedanib or a pharmaceutically acceptable salt thereof in the preparation of drugs used, in combination with a substance B, for preventing and/or treating a disease associated with Autotaxin (e.g., one or more of a fibrotic disease (e.g., idiopathic pulmonary fibrosis or nonalcoholic steatohepatitis), a proliferative disease (e.g., cancer), an inflammatory disease (e.g., chronic obstructive pulmonary disease or pain (such as osteoarthritis pain)), an autoimmune disease, a respiratory disease, a cardiovascular disease, a neurodegenerative disease, a dermatological disease, and a disease associated with abnormal angiogenesis). The substance B refers to the compound of formula I or the pharmaceutically acceptable salt thereof described above, and pirfenidone or a pharmaceutically acceptable salt thereof.

The pharmaceutically acceptable salt of nintedanib is, for example, nintedanib ethanesulfonate salt.

The invention further provides an application of pirfenidone or a pharmaceutically acceptable salt thereof in the preparation of drugs used, in combination with the compound of formula I or the pharmaceutically acceptable salt thereof described above, for preventing and/or treating a disease associated with Autotaxin (e.g., one or more of a fibrotic disease (e.g., idiopathic pulmonary fibrosis or nonalcoholic steatohepatitis), a proliferative disease (e.g., cancer), an inflammatory disease (e.g., chronic obstructive pulmonary disease or pain (such as osteoarthritis pain)), an autoimmune disease, a respiratory disease, a cardiovascular disease, a neurodegenerative disease, a dermatological disease, and a disease associated with abnormal angiogenesis).

The pharmaceutically acceptable salt of nintedanib is, for example, nintedanib ethanesulfonate salt.

The invention further provides an application of pirfenidone or a pharmaceutically acceptable salt thereof in the preparation of drugs used, in combination with a substance C, for preventing and/or treating a disease associated with Autotaxin (e.g., one or more of a fibrotic disease (e.g., idiopathic pulmonary fibrosis or nonalcoholic steatohepatitis), a proliferative disease (e.g., cancer), an inflammatory disease (e.g., chronic obstructive pulmonary disease or pain (such as osteoarthritis pain)), an autoimmune disease, a respiratory disease, a cardiovascular disease, a neurodegenerative disease, a dermatological disease, and a disease associated with abnormal angiogenesis). The substance C refers to the compound of formula I or the pharmaceutically acceptable salt thereof described above, and nintedanib or a pharmaceutically acceptable salt thereof.

The pharmaceutically acceptable salt of nintedanib is, for example, nintedanib ethanesulfonate salt.

The invention further provides a combination comprising the compound of formula I or the pharmaceutically acceptable salt thereof described above and another therapeutic agent.

The "another therapeutic agent" can be a therapeutic agent for preventing and/or treating "one or more of a fibrotic disease (e.g., idiopathic pulmonary fibrosis or nonalcoholic steatohepatitis), a proliferative disease (e.g., cancer), an inflammatory disease (e.g., chronic obstructive pulmonary disease or pain (such as osteoarthritis pain)), an autoimmune disease, a respiratory disease, a cardiovascular disease, a neurodegenerative disease, a dermatological disease, and a disease associated with abnormal angiogenesis", for example, "substance A, which is nintedanib or a pharmaceutically acceptable salt thereof, and/or pirfenidone or a pharmaceutically acceptable salt thereof".

The combination may consist of the compound of formula I or the pharmaceutically acceptable salt thereof and the "another therapeutic agent".

The pharmaceutically acceptable salt of nintedanib is, for example, nintedanib ethanesulfonate salt.

The components of the combination may be used simultaneously or separately (e.g., sequentially).

When used simultaneously, the components of the combination can be well mixed (i.e., used as a mixture of the components).

The components of the combination may be prepared into a single pharmaceutical composition for simultaneous use, or may be prepared into separate pharmaceutical compositions that can be used simultaneously or separately (e.g., sequentially).

The invention further provides a pharmaceutical composition comprising the combination described above and a pharmaceutical excipient.

The pharmaceutical composition can consist of the combination and the pharmaceutical excipient.

The invention further provides a combination kit comprising a pharmaceutical composition A and a pharmaceutical composition B;

the pharmaceutical composition A comprises the compound of formula I or the pharmaceutically acceptable salt thereof described above and a pharmaceutical excipient; and the pharmaceutical composition B comprises nintedanib or a pharmaceutically acceptable salt thereof and a pharmaceutical excipient.

The combination kit can consist of the pharmaceutical composition A and the pharmaceutical composition B.

The pharmaceutically acceptable salt of nintedanib is, for example, nintedanib ethanesulfonate salt.

The pharmaceutical composition A can consist of the compound of formula I or the pharmaceutically acceptable salt thereof and the pharmaceutical excipient.

The pharmaceutical composition B can consist of nintedanib or the pharmaceutically acceptable salt thereof and the pharmaceutical excipient.

The combination kit may further comprise a pharmaceutical composition C.

The pharmaceutical composition C comprises pirfenidone or a pharmaceutically acceptable salt thereof and a pharmaceutical excipient.

The pharmaceutical composition C can consist of pirfenidone or the pharmaceutically acceptable salt thereof and the pharmaceutical excipient.

The combination kit can consist of the pharmaceutical composition A, the pharmaceutical composition B, and the pharmaceutical composition C.

The pharmaceutical compositions in the combination kit may be used simultaneously or separately (e.g., sequentially).

The invention further provides a combination kit comprising a pharmaceutical composition A and a pharmaceutical composition C;

the pharmaceutical composition A comprises the compound of formula I or the pharmaceutically acceptable salt thereof described above and a pharmaceutical excipient; and The pharmaceutical composition C comprises pirfenidone or a pharmaceutically acceptable salt thereof and a pharmaceutical excipient.

The combination kit can consist of the pharmaceutical composition A and the pharmaceutical composition C.

The pharmaceutical composition A can consist of the compound of formula I or the pharmaceutically acceptable salt thereof and the pharmaceutical excipient.

The pharmaceutical composition C can consist of pirfenidone or the pharmaceutically acceptable salt thereof and the pharmaceutical excipient.

The pharmaceutical compositions in the combination kit may be used simultaneously or separately (e.g., sequentially).

The invention further provides a combination kit comprising a pharmaceutical composition A and a pharmaceutical composition D;

the pharmaceutical composition A comprises the compound of formula I or the pharmaceutically acceptable salt thereof described above and a pharmaceutical excipient; and the pharmaceutical composition D comprises another therapeutic agent and a pharmaceutical excipient.

The combination kit can consist of the pharmaceutical composition A and the pharmaceutical composition D.

The pharmaceutical composition A can consist of the compound of formula I or the pharmaceutically acceptable salt thereof and the pharmaceutical excipient.

The "another therapeutic agent" may be a therapeutic agent for preventing and/or treating "one or more of a fibrotic disease (e.g., idiopathic pulmonary fibrosis or nonalcoholic steatohepatitis), a proliferative disease (e.g., cancer), an inflammatory disease (e.g., chronic obstructive pulmonary disease or pain (such as osteoarthritis pain)), an autoimmune disease, a respiratory disease, a cardiovascular disease, a neurodegenerative disease, a dermatological disease, and a disease associated with abnormal angiogenesis".

The pharmaceutical composition D can consist of the another therapeutic agent and the pharmaceutical excipient.

A method for inhibiting Autotaxin (ATX) comprises: employing the compound of formula I or the pharmaceutically acceptable salt thereof described above.

A method for preventing and/or treating a disease associated with Autotaxin (ATX) comprises: administering to a subject (e.g., a patient) an effective amount of the compound of formula I or the pharmaceutically acceptable salt thereof described above.

A method for preventing and/or treating a disease comprises: administering to a subject (e.g., a patient) an effective amount of the compound of formula I or the pharmaceutically acceptable salt thereof described above.

The disease is one or more of a fibrotic disease (e.g., idiopathic pulmonary fibrosis or nonalcoholic steatohepatitis), a proliferative disease (e.g., cancer), an inflammatory disease (e.g., chronic obstructive pulmonary disease or pain (such as osteoarthritis pain)), an autoimmune disease, a respiratory disease, a cardiovascular disease, a neurodegenerative disease, a dermatological disease, and a disease associated with abnormal angiogenesis.

A method for preventing and/or treating a disease associated with Autotaxin (ATX) comprises: administering to a subject (e.g., a patient) an effective amount of "the compound of formula I or the pharmaceutically acceptable salt thereof described above" and another therapeutic agent.

The "another therapeutic agent" can be a therapeutic agent for preventing and/or treating "one or more of a fibrotic disease (e.g., idiopathic pulmonary fibrosis or nonalcoholic steatohepatitis), a proliferative disease (e.g., cancer), an inflammatory disease (e.g., chronic obstructive pulmonary disease or pain (such as osteoarthritis pain)), an autoimmune disease, a respiratory disease, a cardiovascular disease, a neurodegenerative disease, a dermatological disease, and a disease associated with abnormal angiogenesis", for example, "substance A, which is nintedanib or a pharmaceutically acceptable salt thereof, and/or pirfenidone or a pharmaceutically acceptable salt thereof".

The pharmaceutically acceptable salt of nintedanib is, for example, nintedanib ethanesulfonate salt.

A method for preventing and/or treating a disease comprises: administering to a subject (e.g., a patient) an effective amount of "the compound of formula I or the pharmaceutically acceptable salt thereof described above" and another therapeutic agent.

The disease is one or more of a fibrotic disease (e.g., idiopathic pulmonary fibrosis or nonalcoholic steatohepatitis), a proliferative disease (e.g., cancer), an inflammatory disease (e.g., chronic obstructive pulmonary disease or pain (such as osteoarthritis pain)), an autoimmune disease, a respiratory disease, a cardiovascular disease, a neurodegenerative disease, a dermatological disease, and a disease associated with abnormal angiogenesis.

The "another therapeutic agent" can be a therapeutic agent for preventing and/or treating "one or more of a fibrotic disease (e.g., idiopathic pulmonary fibrosis or nonalcoholic steatohepatitis), a proliferative disease (e.g., cancer), an inflammatory disease (e.g., chronic obstructive pulmonary disease or pain (such as osteoarthritis pain)), an autoimmune disease, a respiratory disease, a cardiovascular disease, a neurodegenerative disease, a dermatological disease, and a disease associated with abnormal angiogenesis", for example, "substance A, which is nintedanib or a pharmaceutically acceptable salt thereof, and/or pirfenidone or a pharmaceutically acceptable salt thereof".

The pharmaceutically acceptable salt of nintedanib is, for example, nintedanib ethanesulfonate salt.

The invention further provides a compound of formula I described above or a pharmaceutically acceptable salt thereof used as an Autotaxin (ATX) inhibitor.

The invention further provides a compound of formula I described above or a pharmaceutically acceptable salt thereof for preventing and/or treating diseases.

The invention further provides a compound of formula I described above or a pharmaceutically acceptable salt thereof for preventing and/or treating diseases associated with Autotaxin (ATX).

The invention further provides a compound of formula I described above or a pharmaceutically acceptable salt thereof for preventing and/or treating one or more of a fibrotic disease (e.g., idiopathic pulmonary fibrosis or nonalcoholic steatohepatitis), a proliferative disease (e.g., cancer), an inflammatory disease (e.g., chronic obstructive pulmonary disease or pain (such as osteoarthritis pain)), an autoimmune disease, a respiratory disease, a cardiovascular disease, a neurodegenerative disease, a dermatological disease, and a disease associated with abnormal angiogenesis.

The invention further provides a compound of formula I described above or a pharmaceutically acceptable salt thereof for preventing and/or treating a disease in combination with another therapeutic agent.

The "another therapeutic agent" can be a therapeutic agent for preventing and/or treating "one or more of a fibrotic disease (e.g., idiopathic pulmonary fibrosis or nonalcoholic steatohepatitis), a proliferative disease (e.g., cancer), an inflammatory disease (e.g., chronic obstructive pulmonary disease or pain (such as osteoarthritis pain)), an autoimmune disease, a respiratory disease, a cardiovascular disease, a neurodegenerative disease, a dermatological disease, and a disease associated with abnormal angiogenesis", for example, "substance A, which is nintedanib or a pharmaceutically acceptable salt thereof, and/or pirfenidone or a pharmaceutically acceptable salt thereof".

The pharmaceutically acceptable salt of nintedanib is, for example, nintedanib ethanesulfonate salt.

The invention further provides a compound of formula I described above or a pharmaceutically acceptable salt thereof for preventing and/or treating diseases associated with Autotaxin (ATX) in combination with another therapeutic agent.

The "another therapeutic agent" can be a therapeutic agent for preventing and/or treating "one or more of a fibrotic disease (e.g., idiopathic pulmonary fibrosis or nonalcoholic steatohepatitis), a proliferative disease (e.g., cancer), an inflammatory disease (e.g., chronic obstructive pulmonary disease or pain (such as osteoarthritis pain)), an autoimmune disease, a respiratory disease, a cardiovascular disease, a neurodegenerative disease, a dermatological disease, and a disease associated with abnormal angiogenesis", for example, "substance A, which is nintedanib or a pharmaceutically acceptable salt thereof, and/or pirfenidone or a pharmaceutically acceptable salt thereof".

The pharmaceutically acceptable salt of nintedanib is, for example, nintedanib ethanesulfonate salt.

The invention further provides a compound of formula I described above or a pharmaceutically acceptable salt thereof used, in combination with another therapeutic agent, for preventing and/or treating one or more of a fibrotic disease (e.g., idiopathic pulmonary fibrosis or nonalcoholic steatohepatitis), a proliferative disease (e.g., cancer), an inflammatory disease (e.g., chronic obstructive pulmonary disease or pain (such as osteoarthritis pain)), an autoimmune disease, a respiratory disease, a cardiovascular disease, a neurodegenerative disease, a dermatological disease, and a disease associated with abnormal angiogenesis.

The "another therapeutic agent" can be a therapeutic agent for preventing and/or treating "one or more of a fibrotic disease (e.g., idiopathic pulmonary fibrosis or nonalcoholic steatohepatitis), a proliferative disease (e.g., cancer), an inflammatory disease (e.g., chronic obstructive pulmonary disease or pain (such as osteoarthritis pain)), an autoimmune disease, a respiratory disease, a cardiovascular disease, a neurodegenerative disease, a dermatological disease, and a disease associated with abnormal angiogenesis", for example, "substance A, which is nintedanib or a pharmaceutically acceptable salt thereof, and/or pirfenidone or a pharmaceutically acceptable salt thereof".

The pharmaceutically acceptable salt of nintedanib is, for example, nintedanib ethanesulfonate salt.

The invention further provides nintedanib or a pharmaceutically acceptable salt thereof used, in combination with the compound of formula I or the pharmaceutically acceptable salt thereof described above, for preventing and/or treating a disease associated with Autotaxin (e.g., one or more of a fibrotic disease (e.g., idiopathic pulmonary fibrosis or nonalcoholic steatohepatitis), a proliferative disease (e.g., cancer), an inflammatory disease (e.g., chronic obstructive pulmonary disease or pain (such as osteoarthritis pain)), an autoimmune disease, a respiratory disease, a cardiovascular disease, a neurodegenerative disease, a dermatological disease, and a disease associated with abnormal angiogenesis).

The pharmaceutically acceptable salt of nintedanib is, for example, nintedanib ethanesulfonate salt.

The invention further provides nintedanib or a pharmaceutically acceptable salt thereof used, in combination with a substance B, for preventing and/or treating a disease associated with Autotaxin (e.g., one or more of a fibrotic disease (e.g., idiopathic pulmonary fibrosis or nonalcoholic steatohepatitis), a proliferative disease (e.g., cancer), an inflammatory disease (e.g., chronic obstructive pulmonary disease or pain (such as osteoarthritis pain)), an autoimmune disease, a respiratory disease, a cardiovascular disease, a neurodegenerative disease, a dermatological disease, and a disease associated with abnormal angiogenesis).

The substance B refers to the compound of formula I or the pharmaceutically acceptable salt thereof described above, and pirfenidone or a pharmaceutically acceptable salt thereof.

The pharmaceutically acceptable salt of nintedanib is, for example, nintedanib ethanesulfonate salt.

The invention further provides pirfenidone or a pharmaceutically acceptable salt thereof used, in combination with the compound of formula I or the pharmaceutically acceptable salt thereof described above, for preventing and/or treating a disease associated with Autotaxin (e.g., one or more of a fibrotic disease (e.g., idiopathic pulmonary fibrosis or nonalcoholic steatohepatitis), a proliferative disease (e.g., cancer), an inflammatory disease (e.g., chronic obstructive pulmonary disease or pain (such as osteoarthritis pain)), an autoimmune disease, a respiratory disease, a cardiovascular disease, a neurodegenerative disease, a dermatological disease, and a disease associated with abnormal angiogenesis).

The pharmaceutically acceptable salt of nintedanib is, for example, nintedanib ethanesulfonate salt.

The invention further provides pirfenidone or a pharmaceutically acceptable salt thereof used, in combination with a substance C, for preventing and/or treating a disease associated with Autotaxin (e.g., one or more of a fibrotic disease (e.g., idiopathic pulmonary fibrosis or nonalcoholic steatohepatitis), a proliferative disease (e.g., cancer), an inflammatory disease (e.g., chronic obstructive pulmonary disease or pain (such as osteoarthritis pain)), an autoimmune disease, a respiratory disease, a cardiovascular disease, a neurodegenerative disease, a dermatological disease, and a disease associated with abnormal angiogenesis). The substance C refers to the compound of formula I or the pharmaceutically acceptable salt thereof described above, and nintedanib or a pharmaceutically acceptable salt thereof.

The pharmaceutically acceptable salt of nintedanib is, for example, nintedanib ethanesulfonate salt.

Unless otherwise specified, the terms in this application are defined as follows.

The term "alkyl" refers to linear or branched aliphatic hydrocarbyl having a specified number of carbon atoms. Specifically, the alkyl has 1 to 8 carbon atoms. More specifically, the alkyl is lower alkyl having 1 to 6 carbon atoms. Yet more specifically, the group has 1 to 4 carbon atoms. Exemplary linear groups include methyl, ethyl, n-propyl, and n-butyl. "branched" means that one or more lower alkyls (e.g., methyl, ethyl, propyl, or butyl) are linked to linear alkyl. Exemplary branched groups include isopropyl, isobutyl, tert-butyl, and isopentyl.

The term "alkoxy" refers to the group of —OR$^{26}$, wherein the R$^{26}$ is alkyl having a specified number of carbon atoms. Specifically, the alkoxy is methoxy, ethoxy, n-propoxy, isopropoxy, n-butoxy, tert-butoxy, sec-butoxy, n-pentoxy, n-hexyloxy, or 1,2-dimethylbutoxy. More specifically, the alkoxy is lower alkoxy, i.e., having 1 to 6 carbon atoms. Yet more specifically, the alkoxy has 1 to 4 carbon atoms.

The term "alkylene" refers to a divalent olefinic group having a specified number of carbon atoms, particularly, having 1 to 6 carbon atoms, and more particularly, having 1 to 4 carbon atoms, which may be linear or branched. The term refers to, e.g., methylene (—CH$_2$—), ethylidene (—CH$_2$—CH$_2$—) or —CH(CH$_3$)—, or the like.

The term "cycloalkyl" refers to a non-aromatic hydrocarbyl ring structure (monocyclic or polycyclic) having a specified number of ring atoms. The cycloalkyl may have 3 to 10 carbon atoms, and in particular, 3 to 7 carbon atoms. The cycloalkyl includes, for example, a monocyclic structure such as cyclopropyl, cyclobutyl, cyclopentyl, cyclohexyl, and cycloheptyl.

The term "heteroaryl" refers to an aromatic ring structure (monocyclic or polycyclic) containing one or more heteroatoms independently selected from O, N, and S and having a specified number of ring atoms. In particular, the aromatic ring structure may have 5 to 10 ring members. The heteroaryl may be, for example, a 5-membered or 6-membered monocyclic ring, or a bicyclic structure which is formed by fusing a 5-membered ring with a 6-membered ring, by fusing two 6-membered rings, or by fusing (as a further example) two 5-membered rings. Each ring may contain up to four heteroatoms typically selected from nitrogen, sulfur, and oxygen atoms. The heteroaryl ring typically contains up to 4 heteroatoms, more typically up to 3 heteroatoms, and much more typically up to 2 heteroatoms, for example, a single heteroatom.

The term "heterocycloalkyl" refers to a stable non-aromatic ring structure (monocyclic or polycyclic) containing one or more heteroatoms independently selected from O, N, and S and having a specified number of ring atoms. The non-aromatic ring structure may have 4 to 10 ring members, and in particular, 4 to 7 ring members. A fused heterocyclic ring system may contain carbocyclic rings and need only contain one heterocyclic ring.

The term "heterocycloalkenyl" refers to a stable non-aromatic ring structure (monocyclic or polycyclic) containing one or more heteroatoms independently selected from O, N, and S, a specified number of ring atoms, and at least one double bond. The non-aromatic ring structure may have 4 to 10 ring members, and in particular, 4 to 7 ring members. A fused heterocyclic ring system may contain carbocyclic rings and need only contain one heterocyclic ring.

The term "one or more" refers to one to four. In an embodiment, it refers to one to three. In a further embodiment, it refers to one or two. In a still further embodiment, it refers to one.

One skilled in the art of organic synthesis will recognize that the maximum number of heteroatoms in a stable, chemically feasible heterocyclic ring, whether the heterocyclic ring is aromatic or non-aromatic, is determined by the size of the ring, the degree of unsaturation, and the heteroatom valency. In general, the heterocyclic ring may have one to four heteroatoms as long as the heteroaromatic ring is chemically feasible and stable.

The term "pharmaceutically acceptable salt" refers to a salt of the compound disclosed herein, which is prepared from the compound having particular substituents disclosed herein and a relatively nontoxic acid or base. When the compound disclosed herein contains a relatively acidic functional group, a base addition salt can be obtained by contacting the neutral form of such a compound with a sufficient amount of a base in a neat solution or a suitable inert solvent. Pharmaceutically acceptable base addition salts include sodium, potassium, calcium, ammonium, organic amine, or magnesium salts, or similar salts. When the compound disclosed herein contains a relatively basic functional group, an acid addition salt can be obtained by contacting the neutral form of such a compound with a sufficient amount of an acid in a neat solution or a suitable inert solvent. Examples of pharmaceutically acceptable acid addition salts include those derived from inorganic acids, such as hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and salts derived from organic acids, such as acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, methanesulfonic acid, and the like). Also included are salts of amino acids (e.g., arginine, etc.) and salts of organic acids such as glucuronic acid (see Berge et al., "Pharmaceutical Salts", Journal of Pharmaceutical Science 66: 1-19 (1977)). Certain specific compounds disclosed herein contain both basic and acidic functional groups that allow the compounds to be converted into either base or acid addition salts. Preferably, the neutral form of a compound is regenerated by contacting the salt with a base or acid and isolating the parent compound in the conventional manner. The parent form of the compound differs from the various salt forms thereof in certain physical properties, such as solubility in a polar solvent.

The term "pharmaceutical excipient" may be those widely used in the field of pharmaceutical production. An excipient is primarily used to provide a safe, stable and functional pharmaceutical composition and may also provide a method for dissolving the active ingredients at a desired rate or for promoting the effective absorption of the active ingredients after administration of the composition to a subject. The pharmaceutical excipient may be an inert filler or provide a function such as stabilizing the overall pH of the composition or preventing degradation of the active ingredients of the composition. The pharmaceutical excipient may include one or more of the following excipients: binder, suspending agent, emulsifier, diluent, filler, granulating agent, sizing agent, disintegrating agent, lubricant, antiadherent, glidant, wetting agent, gelling agent, absorption delaying agent, dissolution inhibitor, reinforcing agent, adsorbent, buffering agent, chelating agent, preservative, colorant, flavoring agent, and sweetener.

The term "component" refers to "the compound of formula I or the pharmaceutically acceptable salt thereof described above", "nintedanib or a pharmaceutically acceptable salt thereof", or "pirfenidone or a pharmaceutically acceptable salt thereof".

The term "preventing" refers to a reduction in the risk of acquiring or developing a disease or disorder (i.e., causing at least one of the clinical symptoms of the disease not to occur in a subject who may be exposed to a disease-inducing agent or who are susceptible to the disease prior to the onset of the disease).

The term "preventing" is related to "keeping off" and refers to a measure or method directed to preventing, rather than treating or curing, a disease. Non-limiting examples of preventing measures may include administration of a vaccine; administering low-molecular-weight heparin to a hospitalized patient at risk for thrombosis due to immobilization; and administering antimalarial drugs, such as chloroquine, to an individual before the individual visits a geographical area where malaria prevails or the risk of exposure to malaria is high.

The term "treating" any disease or disorder in an embodiment refers to ameliorating the disease or disorder (i.e., arresting the disease or reducing the manifestation, and the degree or severity of clinical symptoms thereof). In another embodiment, "treating" refers to improving at least one physical parameter, which may not be perceived by a subject. In another embodiment, "treating" refers to modulating the disease or disorder, either physically (e.g., stabilizing distinguishable symptoms), or physiologically (e.g., stabilizing physical parameters), or both. In another embodiment, "treating" refers to slowing the disease progression.

The term "fibrotic disease" refers to conditions characterized by excessive scarring due to overproduction, deposition and contraction of extracellular matrix and associated with abnormal accumulation of cells and/or fibronectin and/or collagen and/or increased fibroblast recruitment, and includes, but is not limited to, fibrosis of an individual organ or tissue, such as heart, kidney, liver, joint, lung, pleural tissue, peritoneal tissue, skin, cornea, retina, musculoskeletal tissue, and digestive tract. In particular, the term "fibrotic disease" refers to idiopathic pulmonary fibrosis (IPF); cystic fibrosis; other diffuse interstitial lung diseases of different pathogenesis, including iatrogenic drug-induced fibrosis, occupational and/or environmental induced fibrosis; granulomatosis (sarcoidosis, and hypersensitivity pneumonitis), collagen vascular disease, pulmonary alveolar proteinosis, Langerhans cell granulomatosis, lymphangioleiomyomatosis, genetic diseases (Hermansky-Pudlak syndrome, tuberous sclerosis, neurofibromatosis, metabolic storage disease, and familial interstitial lung disease); radiation-induced fibrosis; chronic obstructive pulmonary disease (COPD); scleroderma; bleomycin-induced pulmonary fibrosis; chronic asthma; silicosis; asbestos-induced pulmonary fibrosis; acute respiratory distress syndrome (ARDS); renal fibrosis; tubulointerstitial renal fibrosis; glomerulonephritis; focal segmental glomerulosclerosis; IgA nephropathy; hypertension; Alport; intestinal fibrosis; liver fibrosis; cirrhosis; alcohol-induced liver fibrosis; toxin/drug induced liver fibrosis; hemochromatosis; nonalcoholic steatohepatitis (NASH); bile duct injury; primary biliary cirrhosis; infection-induced liver fibrosis; virus-induced liver fibrosis; autoimmune hepatitis; corneal scarring; hypertrophic scar; Dupuytren's disease, keloid, skin fibrosis; cutaneous scleroderma; systemic sclerosis, spinal cord injury/fibrosis; myelofibrosis; vascular restenosis; atherosclerosis; arteriosclerosis; Wegener's granulomatosis; and Peyronie's disease; or chronic lymphocytic disease. More specifically, the term "fibrotic disease" refers to idiopathic pulmonary fibrosis (IPF).

The term "proliferative disease" refers to conditions such as cancer (e.g., uterine leiomyosarcoma or prostate cancer), myeloproliferative diseases (e.g., polycythemia vera, essential thrombocythemia, and myelofibrosis), leukemia (e.g., acute myelogenous leukemia, acute and chronic lymphoblastic leukemia), multiple myeloma, psoriasis, restenosis, scleroderma, or fibrosis. Specifically, the term refers to cancer, leukemia, multiple myeloma, and psoriasis. The term "proliferative disease" as used herein refers to conditions such as cancer (e.g., uterine leiomyosarcoma or prostate cancer), myeloproliferative diseases (e.g., polycythemia vera, essential thrombocythemia and myelofibrosis), leukemia (e.g., acute myelogenous leukemia, acute and chronic lymphoblastic leukemia), multiple myeloma, psoriasis, restenosis, scleroderma, or fibrosis. Specifically, the term refers to cancer, leukemia, multiple myeloma, and psoriasis.

The term "cancer" refers to a malignant or benign growth of cells in the skin or body organs, such as, but not limited to, breast, prostate, lung, kidney, pancreas, stomach, or intestine. Cancer tends to infiltrate adjacent tissues and spread (metastasize) to distant organs, such as bone, liver, lung, or brain. The term "cancer" as used herein includes metastatic tumor cell types (such as, but not limited to, melanoma, lymphoma, leukemia, fibrosarcoma, rhabdomyosarcoma, and mast cell tumor) and tissue cancer types (such as, but not limited to, colorectal cancer, prostate cancer, small cell lung cancer and non-small cell lung cancer, breast cancer, pancreatic cancer, bladder cancer, kidney cancer, gastric cancer, glioblastoma, primary liver cancer, ovarian cancer, prostate cancer, and uterine leiomyosarcoma). In particular, the term "cancer" refers to acute lymphoblastic leukemia, acute myeloid leukemia, adrenocortical carcinoma, anal cancer, appendiceal tumor, astrocytoma, atypical teratoid/rhabdoid tumors, basal cell carcinoma, cholangiocarcinoma, bladder cancer, bone cancer (osteosarcoma and malignant fibrous histiocytoma), brain stem glioma, brain tumor, brain and spinal cord tumor, breast cancer, bronchial tumor, Burkitt lymphoma, cervical cancer, chronic lymphocytic leukemia, chronic myelogenous leukemia, colon cancer, colorectal cancer, craniopharyngioma, cutaneous T-cell lymphoma, embryonal tumor, endometrial cancer, ependymoblastoma, ependymoma, esophageal cancer, the Ewing sarcoma family of tumors, eye cancer, retinoblastoma, gallbladder cancer, stomach (gastric) cancer, gastrointestinal carcinoid tumor, gastrointestinal stromal tumor (GIST), gastrointestinal stromal cell tumor, blastoma, glioma, hairy cell leukemia, head and neck cancer, liver cell (liver) cancer, Hodgkin's lymphoma, hypopharyngeal cancer, intraocular melanoma, islet cell tumor (endocrine pancreas), Kaposi's sarcoma, kidney cancer, Langerhans cell proliferative disorder, laryngeal cancer, leukemia, acute lymphoblastic leukemia, acute myelogenous leukemia, chronic lymphocytic leukemia, chronic myelogenous leukemia, hairy cell leukemia, liver cancer, non-small cell lung cancer, small cell lung cancer, Burkitt's lymphoma, cutaneous T-cell lymphoma, Hodgkin's lymphoma, non-Hodgkin's lymphoma, lymphoma, Waldenstrom macroglobulinemia, medulloblastoma, medulloepithelioma, melanoma, mesothelioma, oral cancer, chronic myelogenous leukemia, myeloid leukemia, multiple myeloma, nasopharyngeal cancer, neuroblastoma, non-small cell lung cancer, mouth cancer, oropharyngeal cancer, osteosarcoma, malignant fibrous histiocytoma of bone, ovarian cancer, ovarian epithelial tumor, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pinealoblastoma and supratentorial primitive neuroectodermal tumors, pituitary tumor, plasma cell tumor/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, the Ewing sarcoma family of tumors, sarcoma, Kaposi's sarcoma, Sezary syndrome, skin cancer, small cell lung cancer, small bowel cancer, soft tissue sarcoma, squamous cell cancer, stomach (gastric) cancer, supratentorial primitive neuroectodermal tumors, T-cell lymphoma, testicular cancer, laryngeal cancer, thymoma and thymus cancer, thyroid cancer, urethral cancer, uterine cancer, uterine sarcoma, vaginal cancer, vulvar cancer, Waldenstrom macroglobulinemia, and Wilms tumor.

The term "leukemia" refers to neoplastic diseases of the blood and blood-forming organs. Such diseases can lead to bone marrow and immune system dysfunction, which renders the host highly susceptible to infection and bleeding. In particular, the term "leukemia" refers to acute myelogenous leukemia (AML), acute lymphoblastic leukemia (ALL), and chronic lymphoblastic leukemia (CLL).

The term "inflammatory disease" refers to a group of disorders including rheumatoid arthritis, osteoarthritis, juvenile idiopathic arthritis, psoriasis, psoriatic arthritis, allergic respiratory disease (e.g., asthma and rhinitis), chronic obstructive pulmonary disease (COPD), inflammatory bowel disease (e.g., Crohn's disease and ulcerative colitis), endotoxin-driven conditions (e.g., complications after coronary artery bypass surgery or chronic endotoxin status contributing to, e.g., chronic heart failure), and disease associated with cartilage, such as arthropathy. Specifically, the term refers to rheumatoid arthritis, osteoarthritis, allergic respiratory disease (e.g., asthma), COPD and inflammatory bowel disease (e.g., Crohn's disease, and ulcerative colitis). More specifically, the term refers to rheumatoid arthritis and COPD.

The term "autoimmune disease" refers to a group of diseases, including obstructive airways disease, which includes disorders such as COPD and asthma (e.g., intrinsic asthma, extrinsic asthma, dust allergic asthma, and pediatric asthma), in particular chronic or persistent asthma (e.g., late asthma and airway hyperresponsiveness); bronchitis, including bronchial asthma; systemic lupus erythematosus (SLE); cutaneous lupus erythematosus; lupus nephritis; dermatomyositis; Sjogren's syndrome; multiple sclerosis; psoriasis; xerophthalmia; type I diabetes and associated complications; atopic eczema (atopic dermatitis); thyroiditis (Hashimoto's thyroiditis and autoimmune thyroiditis); contact dermatitis, and other eczematous dermatitis; inflammatory bowel disease (e.g., Crohn's disease and ulcerative colitis); atherosclerosis; and amyotrophic lateral sclerosis. Specifically, the term refers to COPD, asthma, systemic lupus erythematosus, type I diabetes, and inflammatory bowel disease.

The term "respiratory disease" refers to a disease affecting organs involved in breathing, such as the nose, throat, larynx, eustachian tube, trachea, bronchi, lungs, associated muscles (e.g., septum and intercostals) and nerves. Specifically, examples of respiratory diseases include asthma, adult respiratory distress syndrome, allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, childhood-onset asthma, adult-onset asthma, cough variant asthma, occupational asthma, steroid resistant asthma, seasonal asthma, seasonal allergic rhinitis, perennial allergic rhinitis, chronic obstructive pulmonary diseases including chronic bronchitis or emphysema, pulmonary arterial hypertension, interstitial pulmonary fibrosis and/or airway inflammation, cystic fibrosis, and hypoxia.

The term "asthma" refers to any disorder characterized by changes in pulmonary airflow associated with airway narrowing of any cause (intrinsic, extrinsic, or both; allergic or non-allergic). It may be used in conjunction with one or more adjectives to indicate a cause.

The term "cardiovascular disease" refers to a disease affecting the heart or blood vessels, or both.

Specifically, cardiovascular diseases include cardiac arrhythmias (atrial or ventricular or both); atherosclerosis and its sequelae; angina; cardiac arrhythmia; myocardial ischemia; myocardial infarction; cardiac or vascular aneurysms; vasculitis, stroke, and arterial occlusive disease around limbs, organs, or tissue; reperfusion injury following ischemia in brain, heart, kidney, other organs, or tissue; endotoxin, and surgical or traumatic shock; hypertension, valvular heart disease, heart failure, and abnormal blood pressure; vasoconstriction (including vasoconstriction associated with migraine); and vascular abnormalities, inflammation, and functional insufficiency limited to a single organ or tissue.

The term "neurodegenerative disease" refers to disorders associated with atrophy of affected central or peripheral nervous system structures. In particular, the term "neurodegenerative disease" refers to such diseases as Alzheimer's disease and other dementias, degenerative neurological disease, encephalitis, epilepsy, genetic brain disorders, head and brain malformations, hydrocephalus, stroke, Parkinson's disease, multiple sclerosis, amyotrophic lateral sclerosis (ALS or LouGehrig's disease), Huntington's disease, and prion disease.

The term "dermatological disease" refers to a skin condition. In particular, dermatological diseases include proliferative or inflammatory disorders of the skin, such as atopic dermatitis, bullous disease, collagenosis, psoriasis, psoriatic lesions, dermatitis, contact dermatitis, eczema, pruritus, rosacea, scleroderma, wound healing, scars, hypertrophic scars, keloids, Kawasaki's disease, rosacea, Sjogren-Larsso syndrome, or urticaria.

The term "disease associated with neoangiogenesis" refers to a disease resulting from dysregulation of processes that mediate angiogenesis. In particular, diseases associated with neoangiogenesis include atherosclerosis, hypertension, tumor growth, inflammation, rheumatoid arthritis, wet macular degeneration, choroidal neovascularization, retinal neovascularization, and diabetic retinopathy.

The above preferred conditions may be combined arbitrarily to obtain preferred embodiments of the present invention without departing from the general knowledge in the art.

The reagents and starting materials used in the present invention are commercially available.

The advantages of the invention are as follows: the compounds of the invention have novel structures and better inhibitory activity on ATX.

DETAILED DESCRIPTION

The invention is further illustrated, but not restricted, by the following examples. The compounds of the invention can be prepared from readily available starting materials using the methods and procedures in the examples. Unless otherwise stated, methods in the following examples are implemented according to conventional practice and conditions, or according to product instructions or standard procedures.

LCMS measurement was performed on Agilent 1200 HPLC/6100 SQ System using the follow conditions:

Method A: Mobile Phase: A: Water (0.01% TFA) B: Acetonitrile (0.01% TFA); Gradient: 5% B to 95% B within 1.4 min, 95% B for 1.6 min (total runtime: 1.6 min); Flow Rate: 2.3 mL/min; Column: SunFire C18, 4.6*50 mm, 3.5 μm; Column Temperature: 50° C.; Detectors: ADC ELSD, DAD (214 nm and 254 nm), ES-API.

Method B: Mobile Phase: A: Water (10 mM NH$_4$HCO$_3$) B: Acetonitrile; Gradient: 10% B to 95% B within 1.5 min, 95% B for 1.5 min (total runtime: 3 min); Flow Rate: 1.8 mL/min; Column: XBridge C18, 4.6*50 mm, 3.5 μm; Column Temperature: 50° C.; Detectors: ADC ELSD, DAD (214 nm and 254 nm), MSD (ES-API).

Method C: Mobile Phase: A: Water (0.01% TFA) B: Acetonitrile (0.01% TFA); Gradient: 5% B to 95% B within 1.2 min, 95% B for 13.8 min (total runtime: 15 min); Flow Rate: 2 mL/min; Column: SunFire C18, 4.6*50 mm, 3.5 μm; Column Temperature: 50° C.; Detectors: UV (214 nm and 254 nm), MS (ESI, Pos mode, 132 to 1500 amu).

Method D: Mobile Phase: A: Water (10 mM NH$_4$HCO$_3$) B: Acetonitrile; Gradient: 10% to 95% B within 8 min, 95% B for 7 min (total runtime: 15 min); Flow Rate: 1 mL/min; Column: XBridge C18, 4.6*50 mm, 3.5 μm; Column Temperature: 40° C.; Detectors: UV (214 nm and 4 nm), MS (ESI, Pos mode, 132 to 1500 amu).

Method E: Mobile Phase: A: Water (0.01% TFA) B: Acetonitrile (0.01% TFA); Gradient Phase: 5% B to 95% B within 1.2 min, 95% B for 1.8 min, back to 5% B within 0.01 min (total runtime: 15 min); Flow Rate: 2 mL/min; Column: SunFire C18, 4.6*50 mm, 3.5 μm; Column Temperature: 40° C.; Detectors: UV (214 nm and 4 nm), MS (ESI, Pos mode, 132 to 1500 amu).

Preparation Example 1: Synthesis Methods of Intermediates

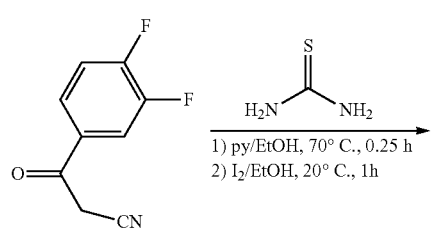

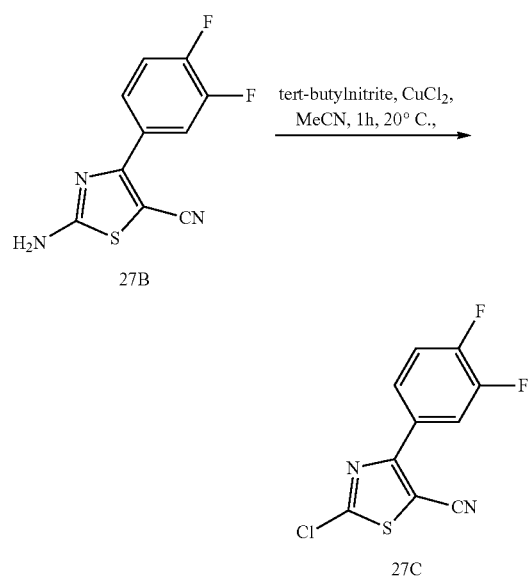

Step 1: 2-amino-4-(3,4-difluorophenyl)thiazole-5-carbonitrile

Pyridine (0.60 g, 7.63 mmol) was added to a solution of 3-(3,4-difluorophenyl)-3-oxopropanenitrile (1.38 g, 7.63 mmol) in ethanol (18 mL). The mixture was stirred at 70° C. for 15 min and then cooled to room temperature. Then a mixture of thiourea (1.18 g, 215.52 mmol) and iodine (1.96 g, 7.63 mmol) in ethanol (18 mL) was slowly added dropwise. The resulting mixture was stirred at room temperature for 1 h, and the reaction was quenched with a cold sodium thiosulfate solution (10 mL). The reaction solution was filtered, and the filter cake was washed with water and dried to give 2-amino-4-(3,4-difluorophenyl)thiazole-5-carbonitrile (1.50 g, 82.9%) in the form of a off-white solid. $^1$H NMR (400 MHz, DMSO-d$_6$) δ 8.28 (s, 2H), 7.89-7.83 (m, 1H), 7.82-7.78 (m, 1H), 7.65-7.58 (m, 1H).

Step 2: 2-chloro-4-(3,4-difluorophenyl)thiazole-5-carbonitrile

Tert-butyl nitrite (1.37 g, 13.29 mmol) was slowly added dropwise to a solution of copper (II) chloride dihydrate (1.8 g, 10.56 mmol) in acetonitrile (90 mL). The mixture was stirred at room temperature for 0.5 h, and then 2-amino-4-(3,4-difluorophenyl)thiazole-5-carbonitrile (2.1 g, 8.85 mmol) was added. The resulting mixture was stirred at room temperature for 1 h. The reaction was quenched with a 1 N hydrochloric acid solution (1 M, 31 mL) added slowly, and ethyl acetate (50 mL×3) was added for extraction. The organic phases were combined, washed with saturated brine (20 mL×2), dried over anhydrous sodium sulfate, filtered and concentrated to give 2-chloro-4-(3,4-difluorophenyl)thiazole-5-carbonitrile in the form of a yellow solid (2.0 g, 87.2%). H NMR (400 MHz, DMSO-d$_6$) δ 7.98-7.93 (m, 1H), 7.87-7.83 (m, 1H), 7.72-7.65 (nm, 1H).

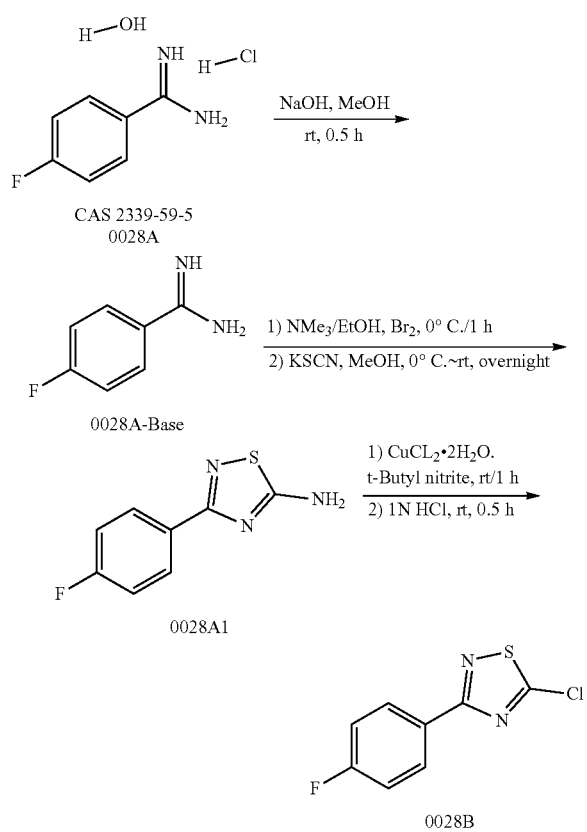

and concentrated to give a yellow solid (1.02 g, purity detected by HPLC: 95.6%), which was directly used in the next step without further purification.

Step 3:
5-chloro-3-(4-fluorophenyl)-1,2,4-thiadiazole

Anhydrous acetonitrile (20 mL) was added to a 100 mL single-neck flask and then copper (II) chloride dihydrate (2.2 g, 12.9 mmol, 1.2 eq.) was added at room temperature with stirring, and during this process, the system became brown and cloudy from green and clear. Tert-butyl nitrite (1.6 g, 16.1 mmol, 1.5 eq.) was added, and then the solid obtained in the last step was added in batches. The reaction system was stirred at room temperature for 1 h until the reaction was completed as detected by TLC, and then concentrated at 40° C. to remove acetonitrile. 20 mL of water was added to the residue. Ethyl acetate (20 mL×2) was added for extraction, and the aqueous phases were removed. The organic phases were combined, washed once with water (20 mL), and concentrated to dryness. The crude product was purified by flash chromatography (ethyl acetate/n-heptane=0%-30%) to give 5-chloro-3-(4-fluorophenyl)-1,2,4-thiadiazole in the form of a light yellow crystal (770 mg, total yield over three steps: 34.5%, purity detected by HPLC: 98.4%). $^1$HNMR (400 MHz, DMSO-$d_6$) δ 8.19-8.23 (m, 2H), 7.37-7.41 (m, 2H). LC-MS: 215.0 (M+H)$^+$.

Step 1: 4-fluorobenzimidamide

Anhydrous methanol (20 mL) was added to a 50 mL single-neck flask. A solid of sodium hydroxide (0.5 g, 12.5 mmol, 1.2 eq.) was added to the anhydrous methanol with stirring, and 4-fluorobenzimidamide hydrochloride monohydrate (2.0 g, 10.4 mmol, 1.0 eq.) was added in one portion. The reaction system was stirred at room temperature for 1 h, and then filtered under vacuum. The filtrate was concentrated to dryness to give a white solid, which was directly used in the next step.

Step 2: 3-(4-fluorophenyl)-1,2,4-thiadiazol-5-amine

The white solid obtained in the last step was dispersed in anhydrous methanol (10 mL) under a 0° C. ice bath. A solution of 33% trimethylamine in ethanol (9.6 g, 54 mmol, 5.2 eq.) was added dropwise with stirring. Then bromine (1.66 g, 10.4 mmol, 1.0 eq.) was added dropwise, resulting in a yellow solution temporarily, and the mixture solution became colourless immediately after addition. The reaction system was stirred for 10 min under an ice bath. Potassium thiocyanate (1.1 g, 11.4 mmol, 1.1 eq.) was added in one portion and the reaction system was stirred at room temperature overnight. After no reduction in raw materials was detected by TLC, a 1 N dilute aqueous hydrochloric acid solution was added to the reaction solution with stirring to adjust pH to 7, and the resulting solution was clear. The reaction solution was concentrated at 40° C. to remove methanol and 20 mL water was added to the residue. Ethyl acetate (20 mL×2) was added for extraction. The organic phases were combined, washed once with water (20 mL),

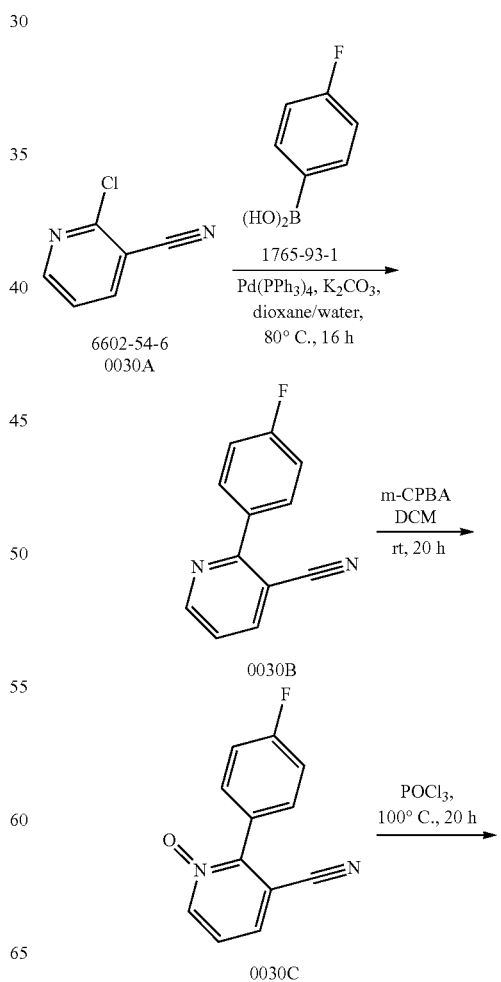

-continued

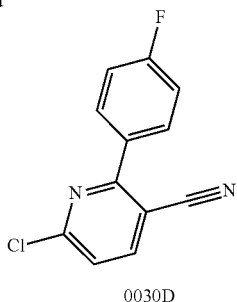

0030D

Step 1: 3-cyano-2-(4-fluorophenyl)pyridine 2-chloro-3-cyanopyridine (1.38 g, 10.0 mmol, 1.0 eq), (4-fluorophenyl)boronic acid (1.54 g, 11.0 mmol, 1.1 eq.), tetrakis(triphenylphosphine)palladium(0) (0.6 g, 0.5 mmol, 0.05 eq.), potassium carbonate (3.45 g, 25.0 mmol, 2.5 eq.), 1,4-dioxane (24 mL) and water (5 mL) were added to a 50 mL single-neck flask, and the atmosphere in the flask was replaced with argon three times. The reaction system was stirred overnight at 80° C. After the reaction was completed, the reaction solution was filtered through celite, and the filtrate was concentrated and added with water. Ethyl acetate was added for extraction. The organic phase was washed with water and concentrated to give a crude product, and the crude product was recrystallized with an ethyl acetate-n-heptane system to give a bluish-yellow solid (1.62 g), which was directly used in the next step. $^1$HNMR (400 MHz, DMSO-$d_6$) δ 8.94 (dd, J=2 Hz, J=5.2 Hz, 1H), 8.43 (dd, J=2 Hz, J=8.4 Hz, 1H), 7.92-7.96 (m, 2H), 7.62 (dd, J=4.8 Hz, J=7.6 Hz, 1H), 7.39-7.44 (m, 2H).

Step 2: 3-cyano-2-(4-fluorophenyl)pyridine-N-oxide

The product obtained in the last step (1.62 g) and dichloromethane (60 mL) were added to a 100 mL single-neck flask, and then 3-chloroperbenzoic acid was added in batches with stirring and under an ice bath. The reaction system was stirred overnight at room temperature. After the reaction was completed, sodium hyposulfite was added to the reaction system, and the resulting reaction system was further stirred for 10 min and then separated into layers. Ethyl acetate was added to the aqueous phase for extraction. The organic phases were combined, washed with water, dried, and concentrated to give a crude product. The crude product was recrystallized by an ethyl acetate-n-heptane system to give a gray solid (1.34 g, yield: 76.6%). LC-MS: 214.9 (M+H)$^+$.

Step 3: 2-chloro-6-(4-fluorophenyl)nicotinonitrile

Phosphorus oxychloride (10 mL) was added to a 100 mL single-neck flask and, under an ice bath, 3-cyano-2-(4-fluorophenyl)pyridine-N-oxide (1.3 g) was slowly added in batches with stirring. The reaction solution was stirred overnight at 100° C. After the reaction was completed as detected by TLC, the reaction system was cooled to room temperature. The reaction was quenched with 100 g of ice water slowly added dropwise, then sodium carbonate was added to adjust pH to 8, and ethyl acetate (50 mL×3) was added for extraction. The organic phases were combined, washed with water, dried over anhydrous sodium sulfate, and concentrated to give a crude product. The crude product was purified by silica gel column chromatography (PE/EA=50/1-20/1) to give a product (280 mg, yield: 20.1%), LC-MS: 232.1 (M+H)$^+$.

500 mg 2,4-dichloropyrimidine (3.4 mmol, 1.0 eq.), 520 mg 4-fluorophenylboronic acid (3.7 mmol, 1.1 eq.), 137 mg Pd(dppf)Cl$_2$ DCM (0.17 mmol, 0.05 eq.), 1.4 g potassium carbonate (10.1 mmol, 2.5 eq.), 9 mL toluene and 1 mL DMF were added to a 25 mL single-neck flask, and the atmosphere in the flask was replaced with argon three times. The reaction system was stirred overnight at 120° C. After the reaction was completed, the reaction solution was filtered through celite, and the filtrate was concentrated and separated twice by flash preparative chromatography (ethyl acetate/n-heptane=0%-30%) to give a gray solid (360 mg, yield: 50.8%). $^1$H NMR (400 MHz, CDCl$_3$) δ 8.83 (d, J=5.6 Hz, 1H), 8.26-8.30 (m, 2H), 8.15 (d, J=5.2 Hz, 1H), 7.42 (t, J=8.8 Hz, 2H). LC-MS: 208.9 (M+H)$^+$, 210.9 (M+2H)$^+$.

Example 1. S-0021:2-((2-ethyl-6-(4-(2-(3-hydroxyazetidin-1-yl)-2-oxoethyl) piperazin-1-yl)imidazo[1,2-a]pyrimidin-3-yl)(methyl)amino)-4-(4-fluorophenyl)thiazole-5-carbonitrile

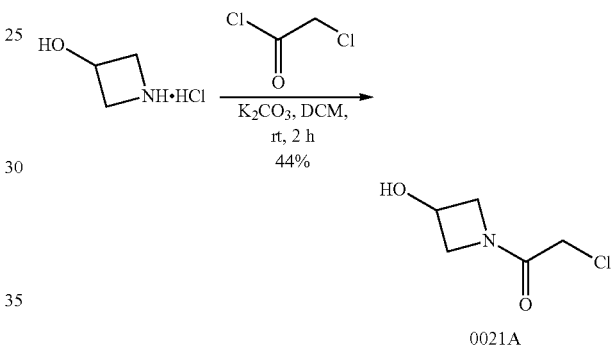

0021A

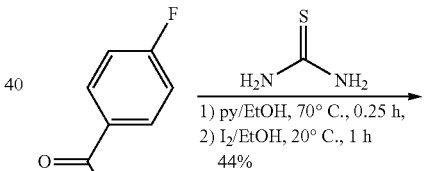

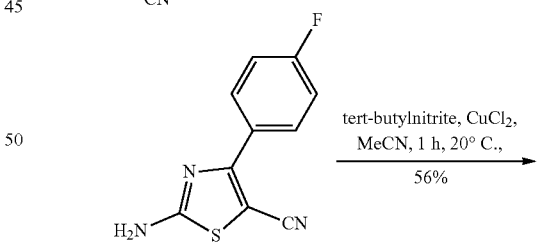

0021B

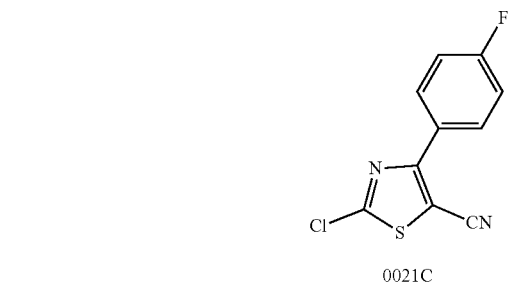

0021C

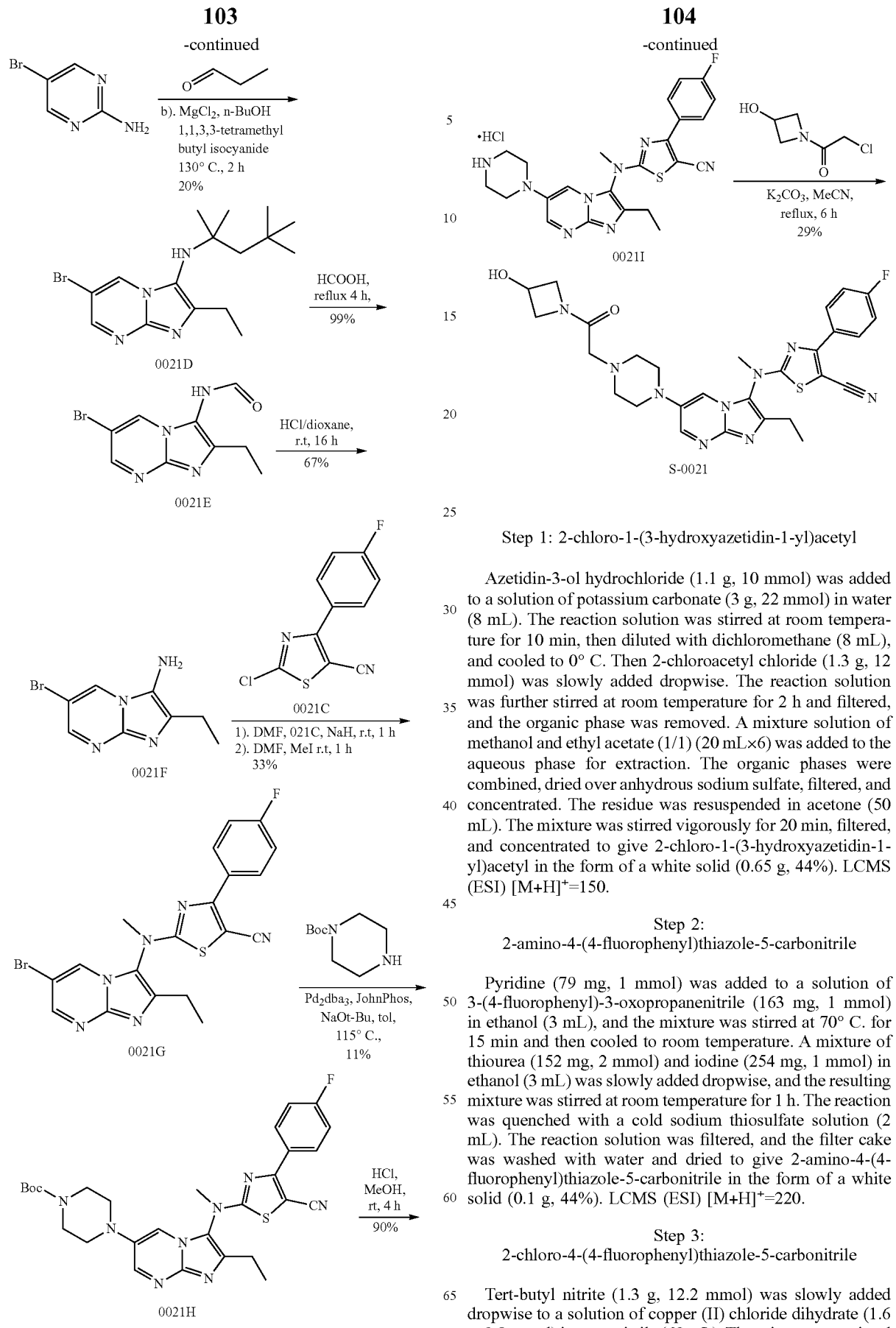

Step 1: 2-chloro-1-(3-hydroxyazetidin-1-yl)acetyl

Azetidin-3-ol hydrochloride (1.1 g, 10 mmol) was added to a solution of potassium carbonate (3 g, 22 mmol) in water (8 mL). The reaction solution was stirred at room temperature for 10 min, then diluted with dichloromethane (8 mL), and cooled to 0° C. Then 2-chloroacetyl chloride (1.3 g, 12 mmol) was slowly added dropwise. The reaction solution was further stirred at room temperature for 2 h and filtered, and the organic phase was removed. A mixture solution of methanol and ethyl acetate (1/1) (20 mL×6) was added to the aqueous phase for extraction. The organic phases were combined, dried over anhydrous sodium sulfate, filtered, and concentrated. The residue was resuspended in acetone (50 mL). The mixture was stirred vigorously for 20 min, filtered, and concentrated to give 2-chloro-1-(3-hydroxyazetidin-1-yl)acetyl in the form of a white solid (0.65 g, 44%). LCMS (ESI) $[M+H]^+=150$.

Step 2: 2-amino-4-(4-fluorophenyl)thiazole-5-carbonitrile

Pyridine (79 mg, 1 mmol) was added to a solution of 3-(4-fluorophenyl)-3-oxopropanenitrile (163 mg, 1 mmol) in ethanol (3 mL), and the mixture was stirred at 70° C. for 15 min and then cooled to room temperature. A mixture of thiourea (152 mg, 2 mmol) and iodine (254 mg, 1 mmol) in ethanol (3 mL) was slowly added dropwise, and the resulting mixture was stirred at room temperature for 1 h. The reaction was quenched with a cold sodium thiosulfate solution (2 mL). The reaction solution was filtered, and the filter cake was washed with water and dried to give 2-amino-4-(4-fluorophenyl)thiazole-5-carbonitrile in the form of a white solid (0.1 g, 44%). LCMS (ESI) $[M+H]^+=220$.

Step 3: 2-chloro-4-(4-fluorophenyl)thiazole-5-carbonitrile

Tert-butyl nitrite (1.3 g, 12.2 mmol) was slowly added dropwise to a solution of copper (II) chloride dihydrate (1.6 g, 9.8 mmol) in acetonitrile (60 mL). The mixture was stirred at room temperature for 0.5 h, and then 2-amino-4-(4-fluorophenyl)thiazole-5-carbonitrile (1.8 g, 8.1 mmol) was added. The resulting mixture was stirred at room temperature for 1 h. The reaction was quenched with a 1 N hydrochloric acid solution (1 M, 20 mL) added slowly, and ethyl acetate (30 mL×3) was added for extraction. The organic phases were combined, washed with saturated brine (10 mL×2), dried over anhydrous sodium sulfate, filtered, and concentrated to give 2-chloro-4-(4-fluorophenyl)thiazole-5-carbonitrile in the form of a yellow solid (1.1 g, 56%). LCMS (ESI) [M+H]$^+$=239.

Step 4: 6-bromo-2-ethyl-N-(2,4,4-trimethylpentan-2-yl)imidazo[1,2-a]pyrimidin-3-amine Magnesium chloride (9 mg, 0.1 mmol) was added to a solution of 5-bromopyrimidin-2-amine (173 mg, 1 mmol), propionaldehyde (174 mg, 3 mmol) and 1,1,3,3-tetramethylbutyl isocyanide (173 mg, 1.24 mmol) in 1-butanol (5 mL). The reaction solution was stirred at 130° C. for 2 h and then concentrated. The residue was purified by flash chromatography (ethyl acetate/petroleum ether=0%-60%) to give 6-bromo-2-ethyl-N-(2,4,4-trimethylpentan-2-yl)imidazo[1,2-a]pyrimidin-3-amine in the form of a yellow solid (0.07 g, 20%). LCMS (ESI) [M+H]$^+$=353.

Step 5: N-(6-bromo-2-ethylimidazo[1,2-a]pyrimidin-3-yl)formamide

A mixture of 6-bromo-2-ethyl-N-(2,4,4-trimethylpentan-2-yl)imidazo[1,2-a]pyrimidin-3-amine (0.07 g, 0.2 mmol) and formic acid (3 mL) was heated to reflux for 4 h, and then concentrated to give N-(6-bromo-2-ethylimidazo[1,2-a]pyrimidin-3-yl)formamide in the form of a yellow solid (50 mg, 99%), which was directly used in the next step without purification. LCMS (ESI) [M+H]$^+$=269. $^1$H NMR (400 MHz, DMSO-d6) δ 10.22 (s, 1H), 8.83 (d, J=2.4 Hz, 1H), 8.55 (d, J=2.4 Hz, 1H), 8.37 (d, J=0.8 Hz, 1H), 2.64 (q, J=8.0 Hz, 2H), 1.23 (t, J=7.6 Hz, 3H).

Step 6: 6-bromo-2-ethylimidazo[1,2-a]pyrimidin-3-amine

A mixture of N-(6-bromo-2-ethylimidazo[1,2-a]pyrimidin-3-yl)formamide (50 mg, 0.2 mmol) and hydrogen chloride (4 N in dioxane, 3 mL) was stirred at room temperature for 16 h and then concentrated. The residue was purified by flash chromatography (methanol/dichloromethane=0%-10%) to give 6-bromo-2-ethylimidazo[1,2-a]pyrimidin-3-amine in the form of a yellow solid (30 mg, 67%). LCMS (ESI) [M+H]$^+$=241.

Step 7: 2-((6-bromo-2-ethylimidazo[1,2-a]pyrimidin-3-yl)(methyl)amino)-4-(4-fluorophenyl)thiazole-5-carbonitrile Sodium hydride (60% in oil, 120 mg, 3 mmol) was slowly added to a solution of 6-bromo-2-ethylimidazo[1,2-a]pyrimidin-3-amine (240 mg, 1.08 mmol) in N,N-dimethylformamide (10 mL), and the reaction solution was stirred at room temperature for 2 h. Then 2-chloro-4-(4-fluorophenyl)thiazole-5-carbonitrile (238 mg, 1 mmol) was added, and the resulting mixture was further stirred at room temperature for 1 h. Then methyl iodide (140 mg, 1 mmol) was added, and the resulting mixture was further stirred at room temperature for 1 h. The reaction was quenched with water (30 mL), and ethyl acetate (30 mL×5) was added for extraction. The organic phases were combined, washed with saturated brine (10 mL×2), dried over anhydrous sodium sulfate, filtered, and concentrated. The residue was purified by flash chromatography (ethyl acetate/petroleum ether=0%-30%) to give 2-((6-bromo-2-ethylimidazo[1,2-a]pyrimidin-3-yl)(methyl)amino)-4-(4-fluorophenyl)thiazole-5-carbonitrile in the form of a yellow solid (150 mg, 33%). LCMS (ESI) [M+H]$^+$=457. $^1$H NMR (400 MHz, CDCl$_3$) δ 8.62 (d, J=2.4 Hz, 1H), 8.24 (d, J=2.8 Hz, 1H), 8.10-8.14 (m, 2H), 7.15-7.20 (m, 2H), 3.64 (s, 3H), 2.81 (q, J=7.6 Hz, 2H), 1.39 (t, J=7.6 Hz, 3H).

Step 8: tert-butyl 4-(3-((5-cyano-4-(4-fluorophenyl)thiazol-2-yl)(methyl)amino)-2-ethylimidazo[1,2-a]pyrimidin-6-yl)piperazine-1-carboxylate 2-((6-bromo-2-ethylimidazo[1,2-a]pyrimidin-3-yl)(methyl)amino)-4-(4-fluorophenyl) thiazole-5-carbonitrile (150 mg, 0.33 mmol), tert-butyl piperazine-1-carboxylate (183 mg, 0.98 mmol), tris(dibenzylideneacetone)dipalladium(0) (30 mg, 0.033 mmol), 2-(di-tert-butylphosphino)biphenyl (20 mg, 0.066 mmol), sodium tert-butoxide (94 mg, 0.98 mmol) and toluene (10 mL) were added to a microwave tube. The reaction solution was heated to 115° C. under a nitrogen atmosphere, then stirred for 5 h, and cooled to room temperature. Ethyl acetate (20 mL×3) was added for extraction. The organic phases were combined, washed with saturated brine (10 mL×2), dried over anhydrous sodium sulfate, filtered and concentrated. The residue was purified by flash chromatography (ethyl acetate/petroleum ether=0%-50%) to give tert-butyl 4-(3-((5-cyano-4-(4-fluorophenyl)thiazol-2-yl)(methyl)amino)-2-ethylimidazo[1,2-a]pyrimidin-6-yl)piperazine-1-carboxylate in the form of a yellow solid (20 mg, 11%). LCMS (ESI) [M+H]$^+$=563.

Step 9: 2-((2-ethyl-6-(piperazin-1-yl)imidazo[1,2-a]pyrimidin-3-yl)(methyl)amino)-4-(4-fluorophenyl)thiazole-5-carbonitrile hydrochloride Hydrogen chloride (4 N in dioxane, 2 mL) was added to a solution of tert-butyl 4-(3-((5-cyano-4-(4-fluorophenyl)thiazol-2-yl)(methyl)amino)-2-ethylimidazo[1,2-a]pyrimidin-6-yl)piperazine-1-carboxylate (20 mg, 0.035 mmol) in dichloromethane (1 mL). The reaction solution was stirred at room temperature for 4 h and then concentrated to give 2-((2-ethyl-6-(piperazin-1-yl)imidazo[1,2-a]pyrimidin-3-yl)(methyl)amino)-4-(4-fluorophenyl)thiazole-5-carbonitrile hydrochloride in the form of a yellow solid (16 mg, 90%). LCMS (ESI) [M−HCl+H]$^+$=463.

Step 10: 2-((2-ethyl-6-(4-(2-(3-hydroxyazetidin-1-yl)-2-oxoethyl)piperazin-1-yl)imidazo [1,2-a]pyrimidin-3-yl)(methyl)amino)-4-(4-fluorophenyl)thiazole-5-carbonitrile (S-0021)

2-chloro-1-(3-hydroxyazetidin-1-yl)acetyl (10 mg, 0.069 mmol) and potassium carbonate (14 mg, 0.1 mmol) were added to a solution of 2-((2-ethyl-6-(piperazin-1-yl)imidazo[1,2-a]pyrimidin-3-yl)(methyl)amino)-4-(4-fluorophenyl)thiazole-5-carbonitrile hydrochloride (16 mg, 0.035 mmol) in acetonitrile (3 mL), and the reaction solution was heated to reflux for 6 h and then concentrated. The residue was purified by Pre-HPLC to give 2-((2-ethyl-6-(4-(2-(3-hydroxyazetidin-1-yl)-2-oxoethyl)piperazin-1-yl)imidazo[1,2-a]pyrimidin-3-yl)(methyl)amino)-4-(4-fluorophenyl)thiazole-5-carbonitrile in the form of a white solid (5.3 mg, 29%). LCMS (ESI) [M+H]$^+$=576; $^1$H NMR (400 MHz, CD$_3$OD) δ

8.74 (d, J=3.2 Hz, 1H), 8.14-8.18 (m, 2H), 7.92 (d, J=2.8 Hz, 1H), 7.25-7.29 (m, 2H), 3.71-4.72 (m, 5H), 3.68 (s, 3H), 3.14-3.24 (m, 6H), 2.70-2.77 (m, 6H), 1.36 (t, J=8.0 Hz, 3H).

Example 2. S-0022: 2-((2-ethyl-5-(4-(2-(3-hydroxyazetidin-1-yl)-2-oxoethyl) piperazin-1-yl)-7-methyl-2H-indazol-3-yl)(methyl)amino)-4-(4-fluorophenyl)thiazole-5-carbonitrile

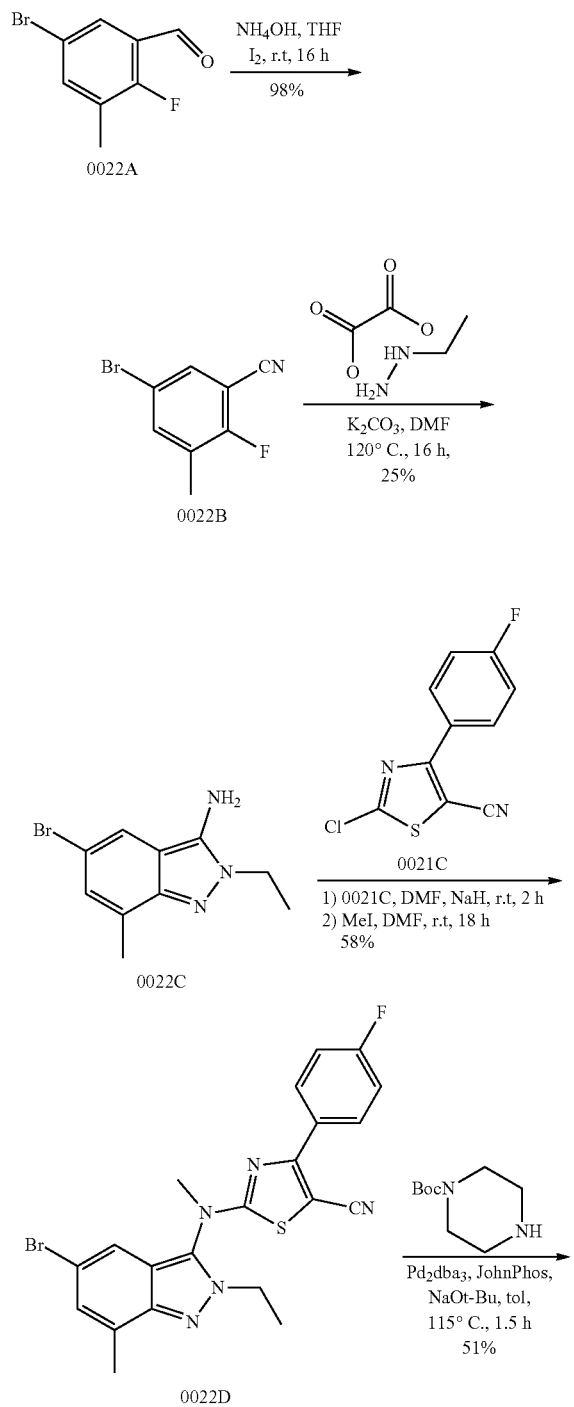

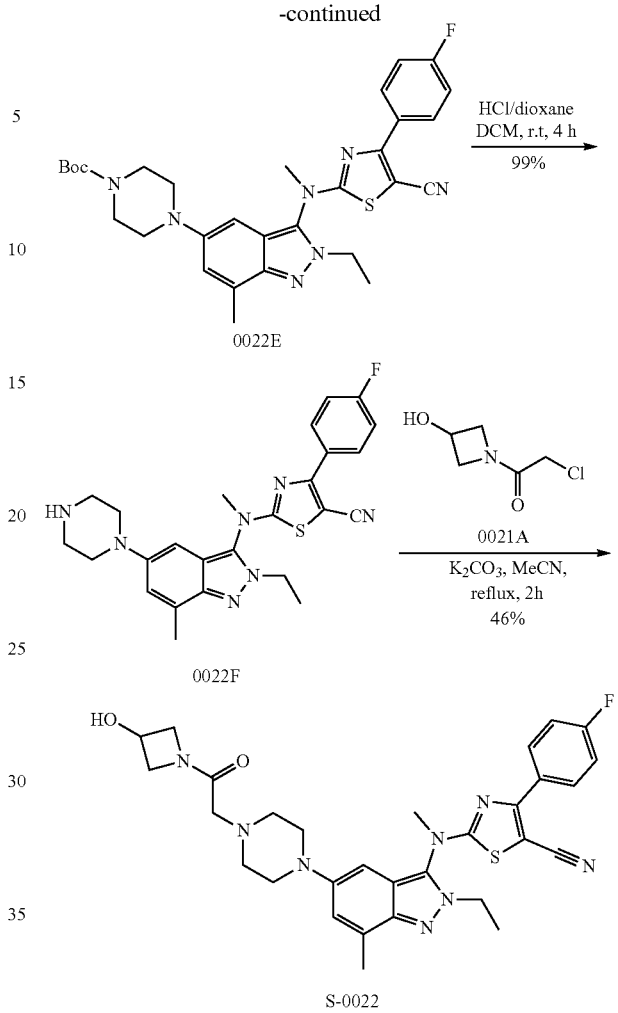

Step 1: 5-bromo-2-fluoro-3-methylbenzonitrile

Iodine (11.67 g, 46.3 mmol) was added to a mixture of 5-bromo-2-fluoro-3-methylbenzaldehyde (5 g, 23.1 mmol) in tetrahydrofuran (20 mL) and ammonium hydroxide (20 mL), and the reaction solution was stirred at room temperature for 16 h. The reaction was quenched with a sodium bisulfite solution (20 mL), and then ethyl acetate (50 mL×2) was added for extraction. The organic phases were combined, washed with saturated brine (10 mL×2), dried over anhydrous sodium sulfate, filtered, and concentrated to give 5-bromo-2-fluoro-3-methylbenzonitrile in the form of a white solid (5 g, 98%), which was directly used in the next step without purification. $^1$H NMR (400 MHz, CDCl$_3$) δ 7.55-7.59 (m, 2H), 2.32 (s, 3H).

Step 2: 5-bromo-2-ethyl-7-methyl-2H-indazol-3-amine 5-bromo-2-fluoro-3-methylbenzonitrile (5 g, 23.4 mmol), ethylhydrazine oxalate (5.28 g, 35.2 mmol) and potassium carbonate (9.68 g, 70.2 mmol) were mixed in N, N-dimethylformamide (50 mL). The reaction solution was heated to 120° C., stirred for 16 h, and then cooled to room temperature. Ethyl acetate (50 mL×3) was added for extraction. The organic phases were combined, washed with saturated brine (10 mL×3), dried over anhydrous sodium sulfate, filtered and concentrated. The residue was purified by flash chromatography (ethyl acetate/petroleum ether=0%-100%) to give 5-bromo-2-ethyl-7-methyl-2H-indazol-3-amine in the form of a yellow solid (1.5 g, yield: 25%). LCMS (ESI) [M+H]$^+$=254. $^1$H NMR (400 MHz, DMSO-d6) δ 7.69 (s, 1H), 6.91 (s, 1H), 6.12 (s, 2H), 4.15 (q, J=7.2 Hz, 2H), 2.32 (s, 3H), 1.32 (t, J=6.8 Hz, 3H).

Step 3:2-((5-bromo-2-ethyl-7-methyl-2H-indazol-3-yl)(methyl)amino)-4-(4-fluorophenyl)thiazole-5-carbonitrile Sodium hydride (60% in oil, 120 mg, 3 mmol) was slowly added to a solution of 5-bromo-2-ethyl-7-methyl-2H-indazol-3-amine (253 mg, 1 mmol) in N, N-dimethylformamide (10 mL); and the mixture was stirred at room temperature for 2 h. Then 2-chloro-4-(4-fluorophenyl)thiazole-5-carbonitrile (238 mg, 1 mmol) was added, and the mixture was further stirred at room temperature for 2 h. Then methyl iodide (280 mg, 2 mmol) was added, and the mixture was further stirred at room temperature for 16 h. The reaction was quenched with water (30 mL), and ethyl acetate (30 mL×5) was added for extraction. The organic phases were combined, washed with saturated brine (10 mL×2), dried over anhydrous sodium sulfate, filtered and concentrated. The residue was purified by flash chromatography (ethyl acetate/petroleum ether=0%-30%) to give 2-((5-bromo-2-ethyl-7-methyl-2H-indazol-3-yl) (methyl)amino)-4-(4-fluorophenyl)thiazole-5-carbonitrile in the form of a red solid (270 mg, 58%). LCMS (ESI) [M+H]$^+$=470. $^1$H NMR (400 MHz, CDCl$_3$) δ 8.11-8.15 (m, 2H), 7.46 (s, 1H), 7.15-7.19 (m, 3H), 4.35 (q, J=7.2 Hz, 2H), 3.67 (s, 3H), 2.63 (s, 3H), 1.60 (t, J=7.2 Hz, 3H).

Step 4: tert-butyl 4-(3-((5-cyano-4-(4-fluorophenyl) thiazol-2-yl)(methyl)amino)-2-ethyl-7-methyl-2H-indazol-5-yl)piperazine-1-carboxylate In a glove box, 2-((5-bromo-2-ethyl-7-methyl-2H-indazol-3-yl)(methyl)amino)-4-(4-fluorophenyl)thiazole-5-carbonitrile (270 mg, 0.57 mmol), tert-butyl piperazine-1-carboxylate (321 mg, 1.73 mmol), tris(dibenzylideneacetone)dipalladium(0) (26 mg, 0.028 mmol), 2-(di-tert-butylphosphino)biphenyl (17 mg, 0.05 mmol), sodium tert-butoxide (110 mg, 1.14 mmol) and toluene (10 mL) were mixed in a microwave tube. The reaction solution was heated to 115° C., stirred for 1.5 h and then cooled to room temperature. Ethyl acetate (20 mL×3) was added for extraction. The organic phases were combined, washed with saturated brine (10 mL×2), dried over anhydrous sodium sulfate, filtered and concentrated. The residue was purified by flash chromatography (ethyl acetate/petroleum ether=0%-50%) to give tert-butyl 4-(3-((5-cyano-4-(4-fluorophenyl)thiazol-2-yl)(methyl)amino)-2-ethyl-7-methyl-2H-indazol-5-yl)piperazine-1-carboxylate in the form of a red solid (170 mg, 51%). LCMS (ESI) [M+H]$^+$=576.

Step 5: 2-((2-ethyl-7-methyl-5-(piperazin-1-yl)-2H-indazol-3-yl)(methyl)amino)-4-(4-fluorophenyl)thiazole-5-carbonitrile Hydrogen chloride (4 N in dioxane, 4 mL) was added to a solution of tert-butyl 4-(3-((5-cyano-4-(4-fluorophenyl)thiazol-2-yl)(methyl)amino)-2-ethyl-7-methyl-2H-indazol-5-yl)piperazine-1-carboxylate (170 mg, 0.292 mmol) in dichloromethane (4 mL). The reaction solution was stirred at room temperature for 4 h and then concentrated. A sodium carbonate solution (20 mL) was added to adjust pH to low alkalinity, and dichloromethane (20 mL×3) was added for extraction. The organic phases were combined, washed with saturated brine (10 mL×2), dried over anhydrous sodium sulfate, filtered, and concentrated to give 2-((2-ethyl-7-methyl-5-(piperazin-1-yl)-2H-indazol-3-yl)(methyl)amino)-4-(4-fluorophenyl)thiazole-5-carbo nitrile in the form of a red solid (140 mg, 99%). LCMS (ESI) [M+H]$^+$=476.

Step 6: 2-((2-ethyl-5-(4-(2-(3-hydroxyazetidin-1-yl)-2-oxoethyl)piperazin-1-yl)-7-methyl-2H-indazol-3-yl)(methyl)amino)-4-(4-fluorophenyl)thiazole-5-carbonitrile (S-0022)

2-chloro-1-(3-hydroxyazetidin-1-yl)acetyl (30 mg, 0.2 mmol) and potassium carbonate (41 mg, 0.3 mmol) were added to a solution of 2-((2-ethyl-7-methyl-5-(piperazin-1-yl)-2H-indazol-3-yl)(methyl)amino)-4-(4-fluorophenyl)thiazole-5-carbonitrile (47 mg, 0.1 mmol) in acetonitrile (5 mL), and the reaction solution was heated to reflux for 2 h and then concentrated. The residue was purified by flash chromatography (methanol/dichloromethane=0%-8%) to give 2-((2-ethyl-5-(4-(2-(3-hydroxyazetidin-1-yl)-2-oxoethyl)piperazin-1-yl)-7-methyl-2H-indazol-3-yl)(methyl)amino)-4-(4-fluorophenyl)thiazole-5-carbonitrile in the form of a purple solid (27 mg, yield: 46%). LCMS (ESI) [M+H]$^+$=589; H NMR (400 MHz, CD$_3$OD) δ 8.12-8.15 (m, 2H), 7.21-7.26 (m, 2H), 7.05 (s, 1H), 6.58 (s, 1H), 4.05-4.59 (m, 6H), 3.77-3.80 (m, 1H), 3.70 (s, 3H), 3.12-3.17 (m, 6H), 2.67-2.69 (m, 4H), 2.58 (s, 3H), 1.56 (t, J=7.6 Hz, 3H).

Example 3. S-0025:2-((2-ethyl-7-fluoro-5-(4-(2-(3-hydroxyazetidin-1-yl)-2-oxoethyl) piperazin-1-yl)-2H-indazol-3-yl)(methyl)amino)-4-(4-fluorophenyl) thiazole-5-carbonitrile

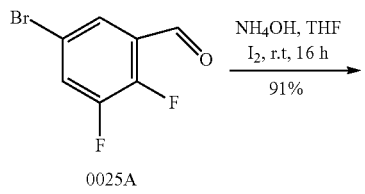

0025A

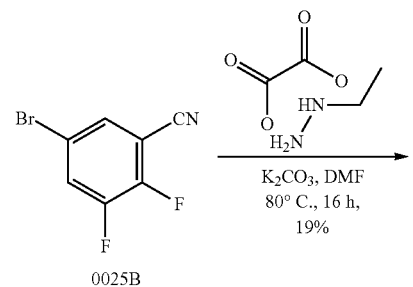

0025B

-continued

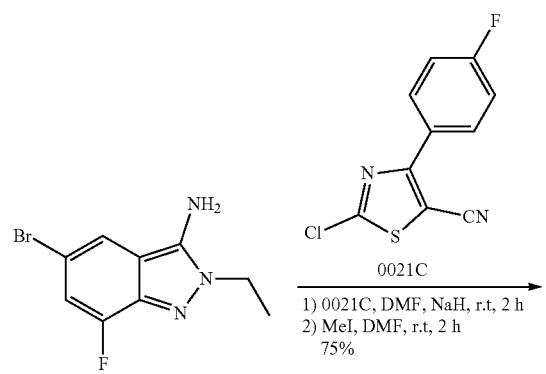
0025C

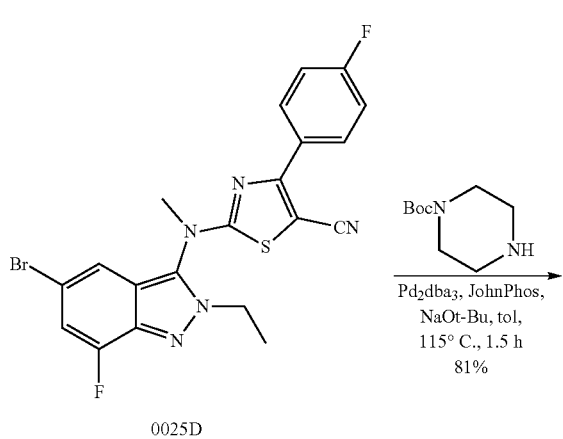
0025D

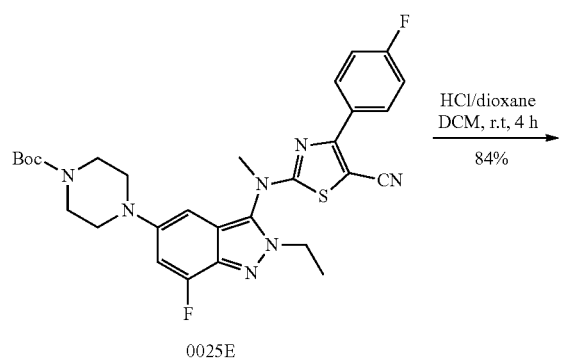
0025E

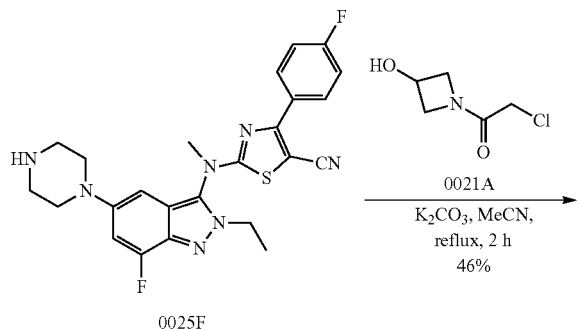
0025F

-continued

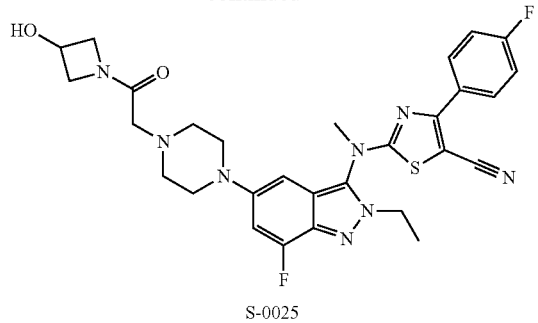
S-0025

Step 1: 5-bromo-2,3-difluorobenzonitrile

Iodine (6.38 g, 25.3 mmol) was added to a mixture of 5-bromo-2,3-difluorobenzaldehyde (2.8 g, 12.67 mmol) in tetrahydrofuran (15 mL) and ammonium hydroxide (15 mL), and the reaction solution was stirred at room temperature for 16 h. The reaction was quenched with a sodium bisulfite solution (20 mL), and then ethyl acetate (50 mL×2) was added for extraction. The organic phases were combined, washed with saturated brine (10 mL×2), dried over anhydrous sodium sulfate, filtered, and concentrated to give 5-bromo-2,3-difluorobenzonitrile in the form of a yellow solid (2.5 g, 91%), which was directly used in the next step without purification. $^1$H NMR (400 MHz, CDCl$_3$) δ 7.51-7.64 (m, 2H).

Step 2: 5-bromo-2-ethyl-7-fluoro-2H-indazol-3-amine 5-bromo-2,3-difluorobenzonitrile (217 mg, 1 mmol), ethylhydrazine oxalate (225 mg, 1.5 mmol) and potassium carbonate (414 mg, 3 mmol) were mixed in dimethyl sulfoxide (5 mL). The reaction solution was heated to 80° C., stirred for 16 h, and then cooled to room temperature. Ethyl acetate (30 mL×3) was added for extraction. The organic phases were combined, washed with saturated brine (10 mL×3), dried over anhydrous sodium sulfate, filtered and concentrated. The residue was purified by flash chromatography (ethyl acetate/petroleum ether=0%-75%) to give 5-bromo-2-ethyl-7-fluoro-2H-indazol-3-amine in the form of a yellow solid (50 mg, 19%). LCMS (ESI) [M+H]$^+$=258. $^1$H NMR (400 MHz, DMSO-d6) δ7.75 (s, 1H), 7.02 (dd, J=7.2 Hz, 1H), 6.39 (bs, 2H), 4.17 (q, J=7.6 Hz, 2H), 1.34 (t, J=7.2 Hz, 3H).

Step 3: 2-((5-bromo-2-ethyl-7-fluoro-2H-indazol-3-yl)(methyl)amino)-4-(4-fluorophenyl) thiazole-5-carbonitrile Sodium hydride (60% in oil, 60 mg, 1.5 mmol) was slowly added to a solution of 5-bromo-2-ethyl-7-fluoro-2H-indazol-3-amine (130 mg, 0.5 mmol) in N, N-dimethylformamide (4 mL). and the mixture was stirred at room temperature for 2 h. Then 2-chloro-4-(4-fluorophenyl)thiazole-5-carbonitrile (120 mg, 0.5 mmol) was added, and the mixture was further stirred at room temperature for 2 h. Then methyl iodide (144 mg, 1 mmol) was added, and the mixture was further stirred at room temperature for 2 h. The reaction was quenched with water (30 mL), and ethyl acetate (30 mL×5) was added for extraction. The organic phases were combined, washed with saturated brine (10 mL×2), dried over anhydrous sodium sulfate, filtered and concentrated. The residue was purified by flash chromatography (ethyl acetate/petroleum ether=0%-50%) to give 2-((5-bromo-2-ethyl-7-fluoro-2H-indazol-3-yl)(methyl)amino)-4-(4-fluorophenyl)thiazole-5-carbonitrile in the form of a yellow solid (180 mg, yield: 75%). H NMR (400 MHz, CDCl₃) δ 8.10-8.13 (m, 2H), 7.44 (s, 1H), 7.12-7.19 (m, 3H), 4.36 (q, J=7.6 Hz, 2H), 3.73 (s, 3H), 1.63 (t, J=7.2 Hz, 3H).

Step 4: tert-butyl 4-(3-((5-cyano-4-(4-fluorophenyl)thiazol-2-yl)(methyl)amino)-2-ethyl-7-fluoro-2H-indazol-5-yl)piperazine-1-carboxylate In a glove box, 2-((5-bromo-2-ethyl-7-fluoro-2H-indazol-3-yl)(methyl)amino)-4-(4-fluorophenyl)thiazole-5-carbonitrile (100 mg, 0.21 mmol), tert-butyl piperazine-1-carboxylate (51 mg, 0.274 mmol), tris(dibenzylideneacetone)dipalladium(0) (19 mg, 0.021 mmol), 2-(di-tert-butylphosphino)biphenyl (12.5 mg, 0.042 mmol), sodium tert-butoxide (40 mg, 0.42 mmol) and toluene (3 mL) were mixed in a microwave tube. The reaction solution was heated to 115° C., stirred for 1.5 h, and then cooled to room temperature. Ethyl acetate (20 mL×3) was added for extraction. The organic phases were combined, washed with saturated brine (10 mL×2), dried over anhydrous sodium sulfate, filtered and concentrated. The residue was purified by flash chromatography (ethyl acetate/petroleum ether=0%-40%) to give tert-butyl 4-(3-((5-cyano-4-(4-fluorophenyl)thiazol-2-yl)(methyl)amino)-2-ethyl-7-methyl-2H-indazol-5-yl)piperazine-1-carboxylate in the form of a yellow solid (70 mg, 81%). LCMS (ESI) [M+H]⁺=580.

Step 5: 2-((2-ethyl-7-fluoro-5-(piperazin-1-yl)-2H-indazol-3-yl)(methyl)amino)-4-(4-fluorophenyl)thiazole-5-carbonitrile Hydrogen chloride (4 N in dioxane, 4 mL) was added to a solution of tert-butyl 4-(3-((5-cyano-4-(4-fluorophenyl)thiazol-2-yl)(methyl)amino)-2-ethyl-7-fluoro-2H-indazol-5-yl)piperazine-1-carboxylate (100 mg, 0.17 mmol) in dichloromethane (5 mL). The reaction solution was stirred at room temperature for 4 h and then concentrated. A sodium carbonate solution (20 mL) was added to adjust pH to low alkalinity, and dichloromethane (20 mL×3) was added for extraction. The organic phases were combined, washed with saturated brine (10 mL×2), dried over anhydrous sodium sulfate, filtered, and concentrated to give 2-((2-ethyl-7-fluoro-5-(piperazin-1-yl)-2H-indazol-3-yl)(methyl)amino)-4-(4-fluorophenyl)thiazole-5-carbonitrile in the form of a yellow solid (70 mg, 84%). LCMS (ESI) [M+H]⁺=480.

Step 6: 2-((2-ethyl-7-fluoro-5-(4-(2-(3-hydroxyazetidin-1-yl)-2-oxoethyl)piperazin-1-yl)-2H-indazol-3-yl)(methyl)amino)-4-(4-fluorophenyl)thiazole-5-carbonitrile (S-0025)

2-chloro-1-(3-hydroxyazetidin-1-yl)acetyl (43 mg, 0.292 mmol) and potassium carbonate (60 mg, 0.438 mmol) were added to a solution of 2-((2-ethyl-7-fluoro-5-(piperazin-1-yl)-2H-indazol-3-yl)(methyl)amino)-4-(4-fluorophenyl)thiazole-5-carbonitrile (70 mg, 0.146 mmol) in acetonitrile (5 mL), and the reaction solution was heated to reflux for 2 h and then concentrated. The residue was purified by flash chromatography (methanol/dichloromethane=0%-8%) to give 2-((2-ethyl-5-(4-(2-(3-hydroxyazetidin-1-yl)-2-oxoethyl)piperazin-1-yl)-7-methyl-2H-indazol-3-yl)(methyl)amino)-4-(4-fluorophenyl)thiazole-5-carbonitrile in the form of a yellow solid (40 mg, 46%). LCMS (ESI) [M+H]⁺=593; ¹H NMR (400 MHz, CD₃OD) δ 8.11-8.15 (m, 2H), 7.22-7.27 (m, 2H), 7.03 (dd, J=13.6 Hz 1H), 6.55 (d, J=2.0 Hz, 1H), 4.06-4.58 (m, 6H), 3.79-3.80 (m, 1H), 3.71 (s, 3H), 3.13-3.20 (m, 6H), 2.66-2.69 (m, 4H), 1.57 (t, J=7.6 Hz, 3H).

Example 4. S-103: 2-((7-chloro-2-ethyl-5-(4-(2-(3-hydroxyazetidin-1-yl)-2-oxoethyl)

piperazin-1-yl)-2H-indazol-3-yl)(methyl)amino)-4-(4-fluorophenyl)thiazole-5-carbonitrile

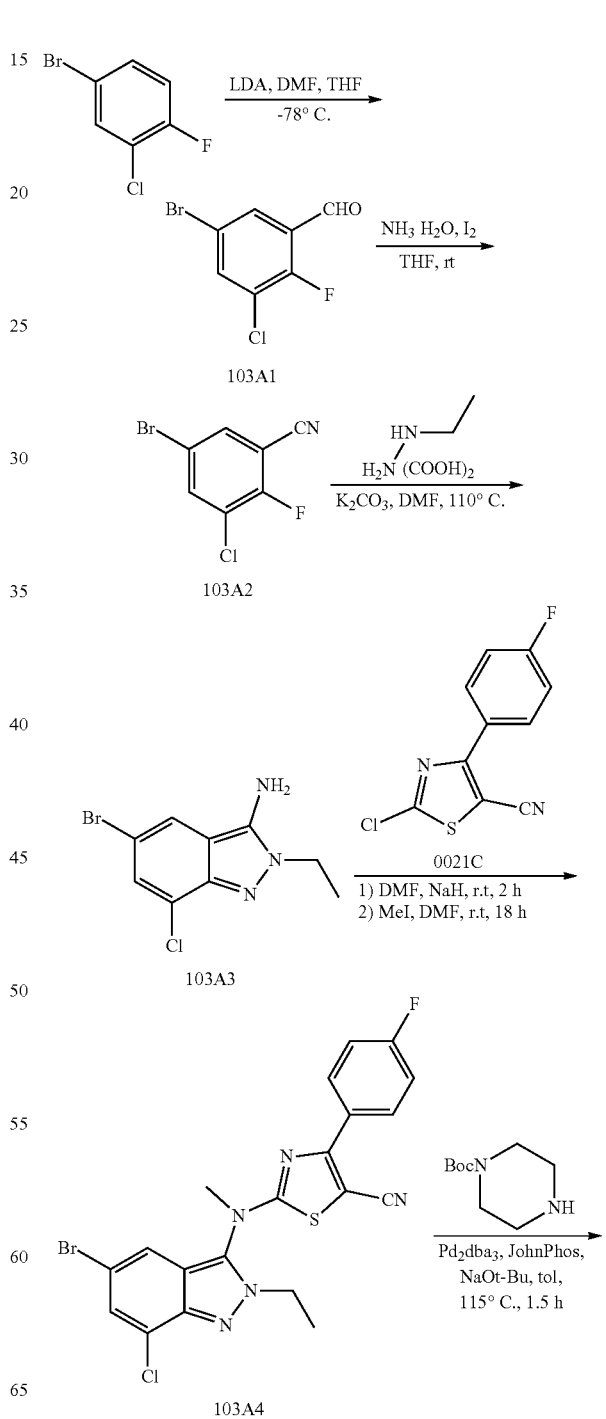

-continued

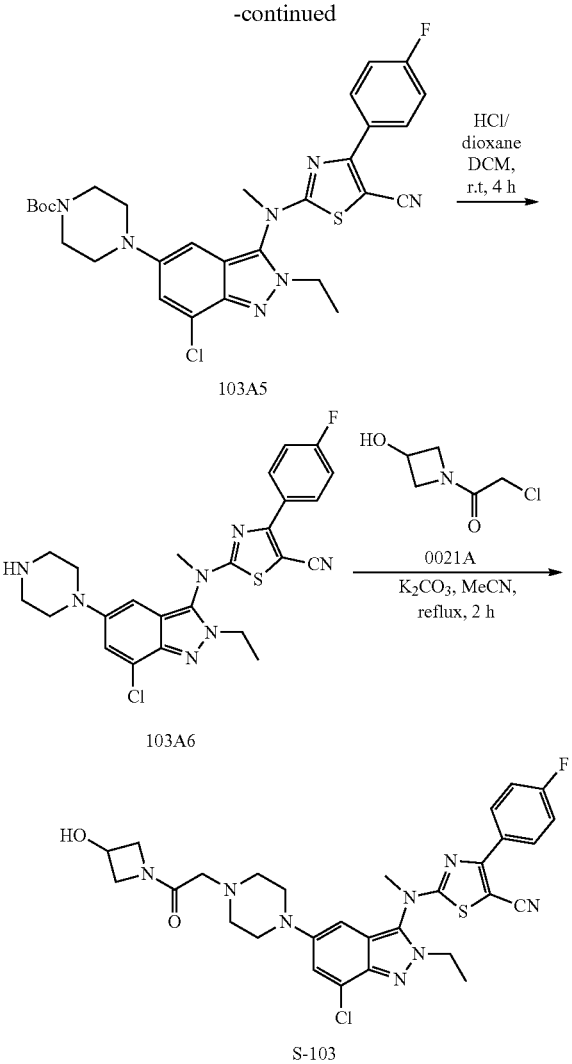

Step 1: 5-bromo-3-chloro-2-fluorobenzaldehyde 3-chloro-4-fluoro bromobenzene (6.3 g, 30 mmol) and tetrahydrofuran (60 mL) were added to a reaction flask, and cooled to −73° C. under an argon atmosphere. A solution of LDA in tetrahydrofuran/n-hexane (2 mol/L, 18 mL, 36 mmol) was added dropwise. The resulting mixture was stirred at a certain temperature for 1.5 h, and then DMF (12.4 mL, 161 mmol) was added dropwise. After the addition, the reaction solution was stirred at a certain temperature until raw materials substantially disappeared as detected by HPLC. The reaction solution was added to a mixture of water (40 mL), concentrated hydrochloric acid (30 mL) and methyl tert-butyl ether (60 mL), and the mixture was separated into layers. Methyl tert-butyl ether (30 mL) was added to the aqueous phase for extraction. The organic phases were combined, and concentrated under reduced pressure to constant weight to give a crude product (7.0 g, yield: 98%), and the crude product became light yellow when cooled to room temperature, which was directly used in the next step.

Step 2: 5-bromo-3-chloro-2-fluorobenzonitrile

Iodine (10.0 g, 40 mmol, 2.0 eq.) was added to a mixture of 5-bromo-3-chloro-2-fluorobenzaldehyde (4.6 g, 20 mmol, 1.0 eq.) in tetrahydrofuran (20 mL) and ammonium hydroxide (20 mL), and the reaction solution was stirred at room temperature for 16 h. The reaction was quenched with a sodium bisulfite solution (20 mL), and then ethyl acetate (50 mL×2) was added for extraction. The organic phases were combined, washed with saturated brine (10 mL×2), dried over anhydrous sodium sulfate, filtered, and concentrated to give 5-bromo-3-chloro-2-fluorobenzonitrile (4.21 g, 93%), which was a yellow solid when cooled, and was directly used in the next step without purification.

Step 3: 5-bromo-7-chloro-2-ethyl-2H-indazol-3-amine 5-bromo-3-chloro-2-fluorobenzonitrile obtained in the last step (4.21 g, 18 mmol, 1.0 eq.), ethylhydrazine oxalate (10.6 g, 72 mmol, 4.0 eq.) and potassium carbonate (10.0 g, 72 mmol, 4.0 eq.) were mixed in DMF (50 mL). The reaction solution was heated to 110° C., stirred for 16 h, and then cooled to room temperature. Ethyl acetate (30 mL×3) was added for extraction. The organic phases were combined, washed with saturated brine (10 mL×3), dried over anhydrous sodium sulfate, filtered and concentrated. The residue was purified by flash chromatography (ethyl acetate/petroleum ether=0%-75%) to give 5-bromo-7-chloro-2-ethyl-2H-indazol-3-amine in the form of a yellow solid (390 mg, 8%). LCMS (ESI) $[M+H]^+$=273.28, $[M+2H]^+$=275.73; H NMR (400 MHz, CDCl$_3$) δ 7.55 (d, J=1.6 Hz, 1H), 7.40 (d, J=1.6 Hz, 1H), 4.55 (q, J=7.2 Hz, 2H), 1.89 (s, 2H), 1.38 (t, J=7.2 Hz, 3H).

Step 4: 2-((5-bromo-7-chloro-2-ethyl-2H-indazol-3-yl)(methyl)amino)-4-(4-fluorophenyl) thiazole-5-carbonitrile Sodium hydride (60% in oil, 171 mg, 4.29 mmol) was slowly added to a solution of 5-bromo-7-chloro-2-ethyl-2H-indazol-3-amine (390 mg, 1.43 mmol, 1.0 eq.) in N, N-dimethylformamide (15 mL), and the mixture was stirred at room temperature for 1 h. Then 2-chloro-4-(4-fluorophenyl) thiazole-5-carbonitrile (340 mg, 1.43 mmol, 1.0 eq.) was added, and the mixture was further stirred at room temperature for 1 h. Then methyl iodide (400 mg, 2.86 mmol, 2.0 eq.) was added, and the resulting reaction solution was stirred at room temperature overnight. The reaction was quenched with water (30 mL), and ethyl acetate (30 mL×5) was added for extraction. The organic phases were combined, washed with saturated brine (10 mL×2), dried over anhydrous sodium sulfate, filtered and concentrated. The residue was purified by flash chromatography (ethyl acetate/petroleum ether=0%-50%) to give 2-((5-bromo-7-chloro-2-ethyl-2H-indazol-3-yl)(methyl)amino)-4-(4-fluorophenyl) thiazole-5-carbonitrile in the form of a yellow solid (30 mg, yield: 4.3%). LCMS (ESI) $[M+H]^+$=258.77, $[M+2H]^+$=260.79.

Step 5: tert-butyl 4-(7-chloro-3-((5-cyano-4-(4-fluorophenyl)thiazol-2-yl)(methyl)amino)-2-ethyl-2H-indazol-5-yl)piperazine-1-carboxylate 2-((5-bromo-7-chloro-2-ethyl-2H-indazol-3-yl)(methyl)amino)-4-(4-fluorophenyl) thiazole-5-carbonitrile (20 mg, 0.04 mmol, 1.0 eq.), tert-butyl piperazine-1-carboxylate (23 mg, 0.12 mmol, 3.0 eq.), tris(dibenzylideneacetone)dipalladium(0)-chloroform adduct (2 mg, 0.002 mmol, 0.05 eq.), 2-(di-tert-butylphosphino)biphenyl (1.2 mg, 0.004 mmol, 0.1 eq.), sodium tert-butoxide (7.8 mg, 0.08 mmol, 2.0 eq.)

and toluene (5 mL) were mixed in a 25 mL reaction flask, and the reaction solution was heated to 115° C., stirred for 16 h, and then cooled to room temperature. Ethyl acetate (20 mL×3) was added for extraction. The organic phases were combined, washed with saturated brine (10 mL×2), dried over anhydrous sodium sulfate, filtered and concentrated. The residue was purified by flash chromatography (ethyl acetate/petroleum ether=0%-40%) to give light-yellow tert-butyl 4-(7-chloro-3-((5-cyano-4-(4-fluorophenyl)thiazol-2-yl)(methyl)amino)-2-ethyl-2H-indazol-5-yl)piperazine-1-carboxylate (10 mg). LCMS (ESI) [M+H]$^+$=596.04, [M+2H]$^+$=598.03.

Step 6: 2-((7-chloro-2-ethyl-5-(piperazin-1-yl)-2H-indazol-3-yl)(methyl)amino)-4-(4-fluorophenyl)thiazole-5-carbonitrile Hydrogen chloride (4 N in dioxane, 4 mL) was added to a solution of tert-butyl 4-(3-((5-cyano-4-(4-fluorophenyl)thiazol-2-yl)(methyl)amino)-2-ethyl-7-fluoro-2H-indazol-5-yl)piperazine-1-carboxylate (140 mg, 0.235 mmol, 1.0 eq.) in dichloromethane (4 mL). The reaction solution was stirred at room temperature for 4 h and then concentrated. A sodium carbonate solution (20 mL) was added to adjust pH to low alkalinity, and dichloromethane (20 mL×3) was added for extraction. The organic phases were combined, washed with saturated brine (10 mL×2), dried over anhydrous sodium sulfate, filtered, and concentrated to give 2-((7-chloro-2-ethyl-5-(piperazin-1-yl)-2H-indazol-3-yl)(methyl)amino)-4-(4-fluorophenyl)thiazole-5-carbonitrile in the form of a yellow solid, which was directly used in the next step. LCMS (ESI) [M+H]$^+$=496.08.

Step 7: 2-((7-chloro-2-ethyl-5-(4-(2-(3-hydroxyazetidin-1-yl)-2-oxoethyl)piperazin-1-yl)-2H-indazol-3-yl)(methyl)amino)-4-(4-fluorophenyl)thiazole-5-carbonitrile (5-103)

2-chloro-1-(3-hydroxyazetidin-1-yl)acetyl (101 mg, 0.68 mmol, 2.0 eq.) and potassium carbonate (141 mg, 1.02 mmol, 3.0 eq.) were added to a solution of 2-((7-chloro-2-ethyl-5-(piperazin-1-yl)-2H-indazol-3-yl)(methyl)amino)-4-(4-fluorophenyl)thiazole-5-carbonitrile in acetonitrile (5 mL), and the reaction solution was heated to reflux and then concentrated. The residue was purified twice by flash chromatography (methanol/water=0%-65%) to give 2-((7-chloro-2-ethyl-5-(4-(2-(3-hydroxyazetidin-1-yl)-2-oxoethyl)piperazin-1-yl)-2H-indazol-3-yl)(methyl)amino)-4-(4-fluorophenyl)thiazole-5-carbonitrile in the form of a light yellow solid (9.4 mg, 4.5%). LCMS (ESI) [M+H]$^+$=609.10; $^1$H NMR (400 MHz, MeOD) δ 8.10-8.14 (m, 2H), 7.22-7.35 (d, J=2.0 Hz, 1H), 7.24 (m, 2H), 6.70 (d, J=2.0 Hz, 1H), 4.55-4.58 (m, 1H), 4.48-4.54 (m, 1H), 4.32-4.39 (m, 2H), 4.19-4.23 (m, 1H), 4.03-4.07 (m, 1H), 3.75-3.78 (m, 1H), 3.70 (s, 3H), 3.14-3.18 (m, 6H), 2.68-2.70 (m, 4H), 1.56 (t, J=7.2 Hz, 3H).

Example 5. S-0023: 2-((2-ethyl-5-(4-(2-(3-hydroxyazetidin-1-yl)-2-oxoethyl)piperazin-1-yl)-7-methylbenzofuran-3-yl)(methyl)amino)-4-(4-fluorophenyl)thiazole-5-carbonitrile

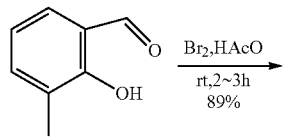

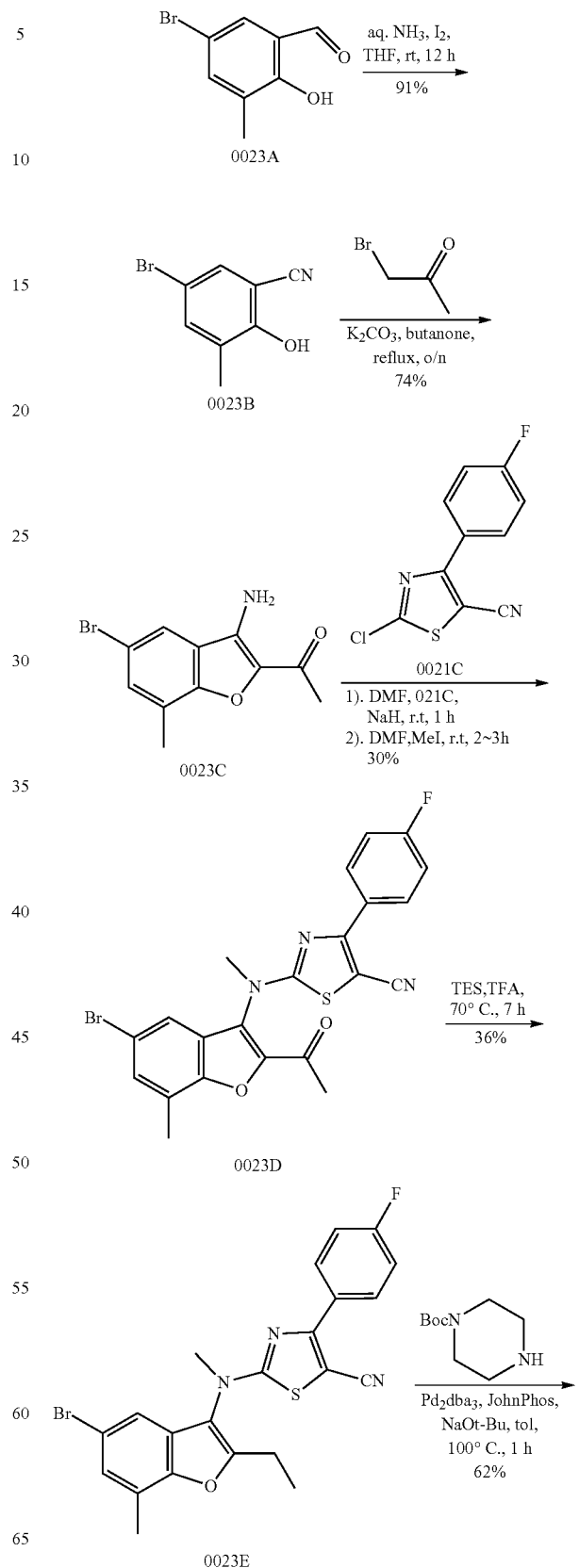

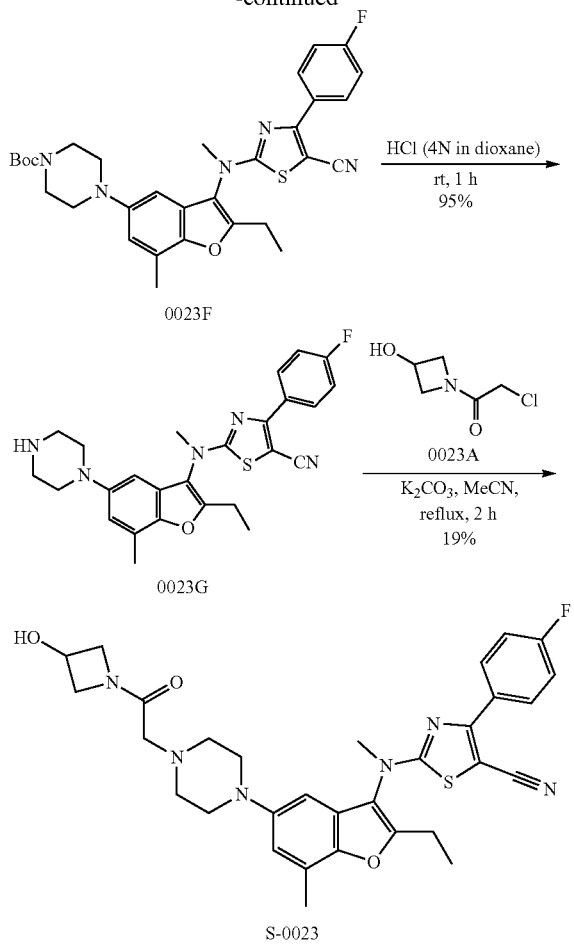

0023F

0023G

S-0023

Step 1: 5-bromo-2-hydroxy-3-methylbenzaldehyde

Under an ice bath, bromine (4.6 g, 28.75 mmol) was added to a solution of 2-hydroxy-3-methylbenzaldehyde (3.4 g, 25.0 mmol) in glacial acetic acid (20 mL), and the reaction solution was stirred at room temperature for 2 h. Water (100 mL) was added to the reaction solution, and the precipitated solid was filtered out. The filter cake was washed with water (100 mL) and dried under vacuum to give 5-bromo-2-hydroxy-3-methylbenzaldehyde (4.8 g, 89%) in the form of a yellow solid, which was directly used in the next step. LCMS (ESI) [M+H]$^+$=216.9; $^1$H NMR (400 MHz, CDCl$_3$) δ 11.19 (s, 1H), 9.82 (s, 1H), 7.66-7.46 (m, 2H), 2.26 (s, 3H).

Step 2: 5-bromo-2-hydroxy-3-methylbenzonitrile

Iodine (5.08 g, 20 mmol) was added to a mixture of 5-bromo-2-hydroxy-3-methylbenzaldehyde (2.15 g, 10.0 mmol) in tetrahydrofuran (20 mL) and ammonium hydroxide (20 mL), and the reaction solution was stirred at room temperature for 16 h. The reaction was quenched with a sodium bisulfite solution (50 mL), and then ethyl acetate (100 mL×2) was added for extraction. The organic phases were combined, washed with saturated brine (100 mL×2), dried over anhydrous sodium sulfate, filtered, and concentrated to give 5-bromo-2-hydroxy-3-methylbenzonitrile in the form of a yellow solid (1.92 g, 91%), which was directly used in the next step without purification. LCMS (ESI) [M+H]$^+$=211.9; $^1$H NMR (400 MHz, CDCl$_3$) δ 7.50-7.42 (m, 2H), 5.99 (s, 1H), 2.27 (s, 3H).

Step 3: 1-(3-amino-5-bromo-7-methylbenzofuran-2-yl)acetyl

A solution of 5-bromo-2-hydroxy-3-methylbenzonitrile (1.92 g, 9.1 mmol), 1-bromoacetone (1.87 g, 13.6 mmol) and potassium carbonate (3.77 g, 27.3 mmol) in butanone (50 mL) was heated to reflux overnight. The reaction was quenched with water (100 mL), and ethyl acetate (150 mL×3) was added for extraction. The organic phases were combined, washed with saturated brine (100 mL×2), dried over anhydrous sodium sulfate, filtered and concentrated. The residue was purified by flash chromatography (ethyl acetate/petroleum ether=0%-25%) to give 1-(3-amino-5-bromo-7-methylbenzofuran-2-yl)acetyl in the form of a yellow solid (1.8 g, yield: 74%). LCMS (ESI) [M+H]$^+$=270.0.

Step 4: 2-((2-acetyl-5-bromo-7-methylbenzofuran-3-yl)(methyl)amino)-4-(4-fluorophenyl)thiazole-5-carbonitrile Sodium hydride (60% in oil, 180 mg, 4.5 mmol) was slowly added to a solution of 1-(3-amino-5-bromo-7-methylbenzofuran-2-yl)acetyl (400 mg, 1.50 mmol) in N,N-dimethylformamide (4 mL), and the mixture was stirred at room temperature for 0.5 h. Then 2-chloro-4-(4-fluorophenyl)thiazole-5-carbonitrile (357 mg, 1.5 mmol) was added, and the mixture was further stirred at room temperature for 1 h. Then methyl iodide (426 mg, 3.0 mmol) was added, and the resulting reaction solution was stirred at room temperature for 3 h. The reaction was quenched with water (30 mL), and ethyl acetate (30 mL×5) was added for extraction. The organic phases were combined, washed with saturated brine (30 mL×2), dried over anhydrous sodium sulfate, filtered and concentrated. The residue was purified by flash chromatography (ethyl acetate/petroleum ether=0%-25%) to give 2-((2-acetyl-5-bromo-7-methylbenzofuran-3-yl)(methyl)amino)-4-(4-fluorophenyl)thiazole-5-carbonitrile in the form of a yellow solid (220 mg, 30%). LCMS (ESI) [M+H]$^+$=483.8.

Step 5: 2-((5-bromo-2-ethyl-7-methylbenzofuran-3-yl)(methyl)amino)-4-(4-fluorophenyl) thiazole-5-carbonitrile A solution of 2-((2-acetyl-5-bromo-7-methylbenzofuran-3-yl)(methyl)amino)-4-(4-fluorophenyl)thiazole-5-carbonitrile (220 mg, 4.55 mmol) and triethylsilane (1 mL) in trifluoroacetic acid (2 mL) was heated to 70° C., stirred for 7 h, and concentrated. The residue was diluted with ethyl acetate (30 mL), washed with saturated brine (30 mL×2), dried over anhydrous sodium sulfate, filtered and concentrated. The residue was purified by flash chromatography (ethyl acetate/petroleum ether=0%-25%) to give 2-((5-bromo-2-ethyl-7-methylbenzofuran-3-yl)(methyl)amino)-4-(4-fluorophenyl)thiazole-5-carbonitrile in the form of a yellow solid (76 mg, 36%). LCMS (ESI) [M+H]$^+$=471.9. $^1$H NMR (400 MHz, CDCl$_3$) δ 8.14-8.11 (m, 2H), 7.33 (m, 1H), 7.17 (t, J=8.7 Hz, 2H), 3.60 (s, 3H), 2.79 (q, J=7.7 Hz, 2H), 2.52 (s, 3H), 1.35 (t, J=7.6 Hz, 3H).

Step 6: tert-butyl 4-(3-((5-cyano-4-(4-fluorophenyl) thiazol-2-yl)(methyl)amino)-2-ethyl-7-methylbenzofuran-5-yl)piperazine-1-carboxylate In a glove box, 2-((5-bromo-2-ethyl-7-methylbenzofuran-3-yl)(methyl)amino)-4-(4-fluorophenyl)thiazole-5-carbonitrile (76 mg, 0.16 mmol), tert-butyl piperazine-1-carboxylate (45 mg, 0.242 mmol), tris(dibenzylideneacetone)dipalladium(0) (7.38 mg, 0.008 mmol), 2-(di-tert-butylphosphino)biphenyl (4.8 mg, 0.016 mmol), sodium tert-butoxide (31 mg, 0.323 mmol) and toluene (3 mL) were mixed in a microwave tube. The mixture was heated to 100° C., stirred for 1 h, and then cooled to room temperature. Then the reaction solution was diluted with ethyl acetate (50 mL), washed with saturated brine (30 mL×2), dried over anhydrous sodium sulfate, filtered and concentrated. The residue was purified by flash chromatography (ethyl acetate/petroleum ether=0%-30%) to give tert-butyl 4-(3-((5-cyano-4-(4-fluorophenyl)thiazol-2-yl)(methyl)amino)-2-ethyl-7-methylbenzofuran-5-yl)piperazine-1-carboxylate in the form of a yellow solid (57 mg, 62%). LCMS (ESI) [M+H]$^+$=576.0.

Step 7: 2-((2-ethyl-7-methyl-5-(piperazin-1-yl)-benzofuran-3-yl)(methyl)amino)-4-(4-fluorophenyl) thiazole-5-carbonitrile Hydrogen chloride (4 N in dioxane, 3 mL) was added to a solution of tert-butyl 4-(3-((5-cyano-4-(4-fluorophenyl)thiazol-2-yl)(methyl)amino)-2-ethyl-7-methylbenzofuran-5-yl)piperazine-1-carboxylate (57 mg, 0.099 mmol) in dichloromethane (4 mL). The reaction solution was stirred at room temperature for 1 h and then concentrated. A sodium carbonate solution (20 mL) was added to adjust pH to low alkalinity, and dichloromethane (20 mL×3) was added for extraction. The organic phases were combined, washed with saturated brine (20 mL×2), dried over anhydrous sodium sulfate, filtered and concentrated to give 2-((2-ethyl-7-methyl-5-(piperazin-1-yl)-benzofuran-3-yl)(methyl)amino)-4-(4-fluorophenyl)thiazole-5-carbonitrile in the form of a yellow solid (45 mg, 95%). LCMS (ESI) [M+H]$^+$=476.0.

Step 8: 2-((2-ethyl-5-(4-(2-(3-hydroxyazetidin-1-yl)-2-oxoethyl)piperazin-1-yl)-7-methylbenzofuran-3-yl)(methyl)amino)-4-(4-fluorophenyl)thiazole-5-carbonitrile (S-0023)

2-chloro-1-(3-hydroxyazetidin-1-yl)acetyl (28 mg, 0.189 mmol) and potassium carbonate (39 mg, 0.284 mmol) were added to a solution of 2-((2-ethyl-7-methyl-5-(piperazin-1-yl)-benzofuran-3-yl)(methyl)amino)-4-(4-fluorophenyl)thiazole-5-carbonitrile (45 mg, 0.095 mmol) in acetonitrile (6 mL), and the reaction solution was heated to reflux for 2 h and then concentrated. The residue was purified by Pre-HPLC to give 2-((2-ethyl-5-(4-(2-(3-hydroxyazetidin-1-yl)-2-oxoethyl)piperazin-1-yl)-7-methylbenzofuran-3-yl)(methyl)amino)-4-(4-fluorophen yl)thiazole-5-carbonitrile in the form of a white solid (10.4 mg, 19%). LCMS (ESI) [M+H]$^+$=589; $^1$H NMR (400 MHz, CD$_3$OD) δ 8.17-8.15 (m, 2H), 7.26 (t, J=8.7 Hz, 2H), 6.92 (s, 1H), 6.76 (s, 1H), 4.58-4.56 (m, 1H), 4.52-4.48 (m, 1H), 4.25-4.21 (m, 1H), 4.09-4.05 (m, 1H), 3.80-3.76 (m, 1H), 3.65 (s, 3H), 3.17 (m, 4H), 3.13 (d, J=3.1 Hz, 2H), 2.81 (q, J=7.5 Hz, 2H), 2.68 (m, 4H), 2.50 (s, 3H), 1.36 (t, J=7.5 Hz, 3H).

Example 6. S-0024: 2-((2-ethyl-7-fluoro-5-(4-(2-(3-hydroxyazetidin-1-yl)-2-oxoethyl) piperazin-1-yl) benzofuran-3-yl)(methyl)amino)-4-(4-fluorophenyl) thiazole-5-carbonitrile

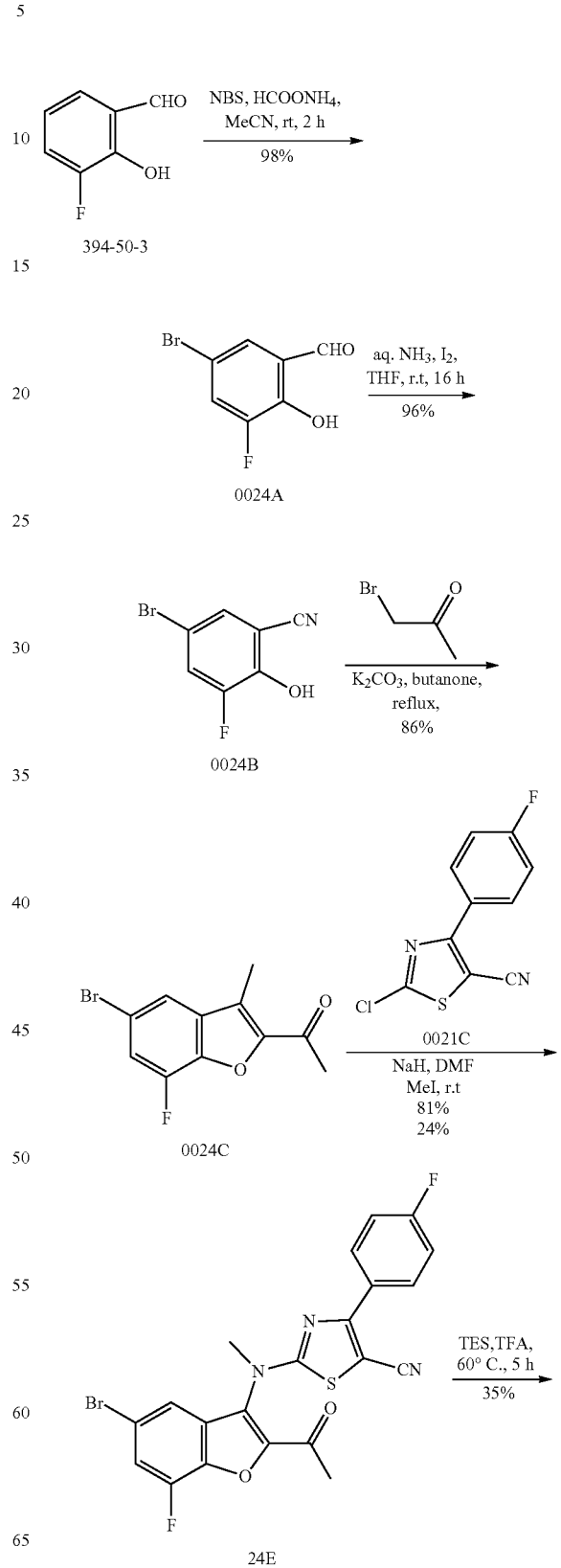

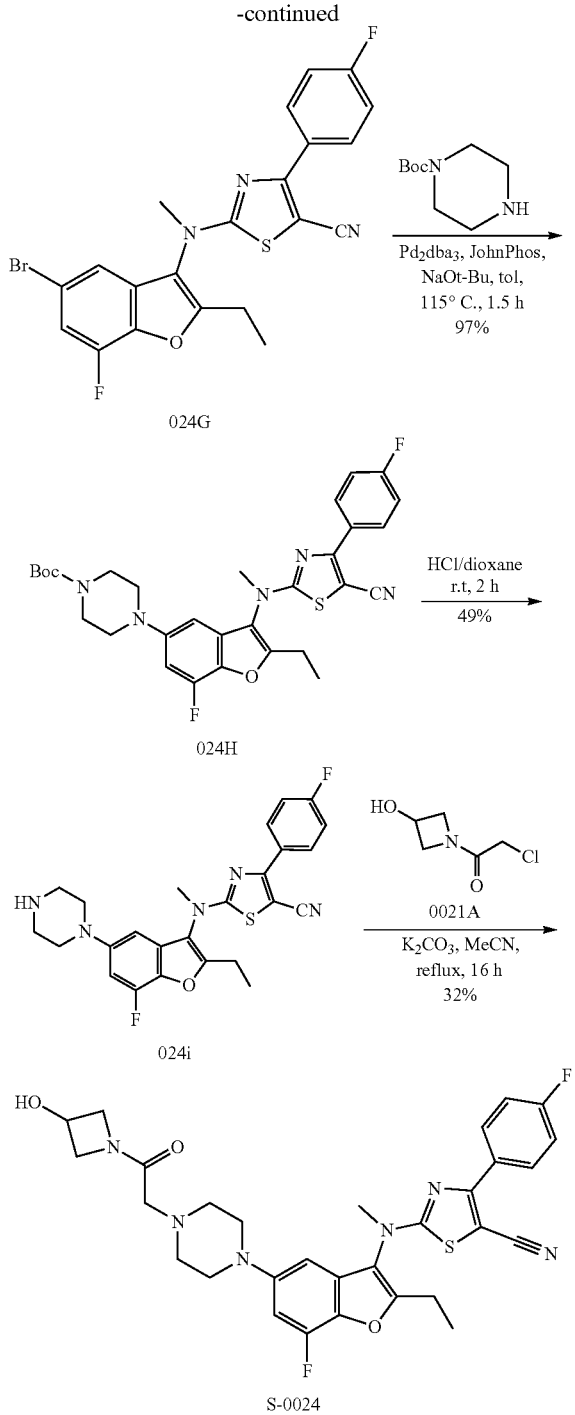

Step 1: 5-bromo-3-fluoro-2-hydroxybenzaldehyde

Bromine (6.57 g, 41.07 mmol) was added to a solution of 3-fluoro-2-hydroxybenzaldehyde (5.0 g, 35.71 mmol) in formic acid (50 mL), and the reaction solution was stirred at room temperature for 2 h. A saturated sodium bicarbonate solution was added to adjust pH to 7, and then ethyl acetate (500 mL×2) was added for extraction. The organic phases were combined, washed with saturated brine (100 mL×2), dried over anhydrous sodium sulfate, filtered and concentrated to give 5-bromo-3-fluoro-2-hydroxybenzaldehyde in the form of a yellow solid (4.9 g, 98%), which was directly used in the next step without purification. $^1$H NMR (400 MHz, DMSO-d6) δ 11.23 (S, 1H), 10.22 (S, 1H), 7.79-7.81 (m, 1H), 7.57 (S, 1H).

Step 2: 5-bromo-3-fluoro-2-hydroxybenzonitrile

Iodide (1155 mg, 4.56 mmol) was added to a mixture of 5-bromo-3-fluoro-2-hydroxybenzaldehyde (500 mg, 2.29 mmol), ammonium hydroxide (10 mL) and tetrahydrofuran (10 mL), and the mixture was stirred at room temperature for 16 h. Then sodium thiosulfate (50 mL) was added, and ethyl acetate (100 mL×3) was added for extraction. The organic phases were combined, washed with saturated brine (100 mL×3), dried over anhydrous sodium sulfate, filtered and concentrated. The residue was purified by flash chromatography (ethyl acetate/petroleum ether=0%-75%) to give 5-bromo-3-fluoro-2-hydroxybenzonitrile in the form of a yellow solid (480 mg, 96%). $^1$H NMR (400 MHz, DMSO-d6) δ 7.27-7.34 (m, 2H).

Step 3: 1-(3-amino-5-bromo-7-fluorobenzofuran-2-yl)ethanone 5-bromo-3-fluoro-2-hydroxybenzonitrile (6.0 g, 28 mmol) was added to butanone (100 mL), and potassium carbonate (11 g, 79 mmol) and bromoacetone (4.95 g, 36.4 mmol) were added. The mixture was heated to reflux for 16 h, and then water (150 mL) was added. Ethyl acetate (500 mL×3) was added for extraction. The organic phases were combined, washed with saturated brine (500 mL×3), dried over anhydrous sodium sulfate, filtered and concentrated. The residue was purified by flash chromatography (ethyl acetate/petroleum ether=0%-75%) to give 1-(3-amino-5-bromo-7-fluorobenzofuran-2-yl)ethanone in the form of a yellow solid (5.2 mg, yield: 86%). LCMS (ESI) [M+H]$^+$=274.

Step 4: 2-((2-acetyl-5-bromo-7-fluoro-2,7a-dihydrobenzofuran-3-yl)(methyl)amino)-4-(4-fluorophenyl)thiazole-5-carbonitrile Sodium hydride (60% in oil, 111.3 mg, 4.64 mmol) was slowly added to a solution of 1-(3-amino-5-bromo-7-fluorobenzofuran-2-yl)ethanone (400 mg, 1.16 mmol) in N,N-dimethylformamide (10 mL), and the mixture was stirred at room temperature for 2 h. Then 2-chloro-4-(4-fluorophenyl)thiazole-5-carbonitrile (276 mg, 1.16 mmol) was added, and the mixture was further stirred at room temperature for 2 h. Then methyl iodide (144 mg, 1 mmol) was added, and the resulting reaction solution was stirred at room temperature for 2 h. The reaction was quenched with water (30 mL), and ethyl acetate (30 mL×5) was added for extraction. The organic phases were combined, washed with saturated brine (10 mL×2), dried over anhydrous sodium sulfate, filtered and concentrated. The residue was purified by flash chromatography (ethyl acetate/petroleum ether=0%-50%) to give 2-((2-acetyl-5-bromo-7-fluoro-2,7a-dihydrobenzofuran-3-yl)(methyl)amino)-4-(4-fluorophenyl)thiazole-5-carbonitrile in the form of a yellow solid (550 mg, yield: 81%). LCMS (ESI) [M+H]$^+$=490.

Step 5: 2-((5-bromo-2-ethyl-7-fluoro-benzofuran-3-yl)(methyl)amino)-4-(4-fluorophenyl) thiazole-5-carbonitrile Trimethylsilyl cyanide (3 mL) was added to a solution of 2-((2-acetyl-5-bromo-7-fluoro-2,7a-dihydrobenzofuran-3- yl)(methyl)amino)-4-(4-fluorophenyl)thiazole-5-carbonitrile (550 mg, 1.12 mmol) in trifluoroacetic acid (9 mL), and the reaction solution was stirred at 60° C. for 6 h. The reaction solution was concentrated to dryness under vacuum, then the reaction was quenched with water (30 mL), and ethyl acetate (100 mL×5) was added for extraction. The organic phases were combined, washed with saturated brine (100 mL×2), dried over anhydrous sodium sulfate, filtered and concentrated. The residue was purified by flash chromatography (ethyl acetate/petroleum ether=0%-50%) to give 2-((5-bromo-2-ethyl-7-fluoro-benzofuran-3-yl)(methyl)amino)-4-(4-fluorophenyl)thiazole-5-carbonitrile in the form of a yellow solid (194 mg, yield: 35%). LCMS (ESI) [M+H]$^+$=476; $^1$H NMR (400 MHz, DMSO-d6) δ 8.03-8.12 (m, 2H), 7.76 (s, 1H), 7.63-7.66 (m, 1H), 7.40-7.44 (m, 2H), 3.59 (s, 3H), 2.83-2.88 (m, 2H), 1.26-1.30 (m, 3H).

Step 6: tert-butyl 4-(3-((5-cyano-4-(4-fluorophenyl)thiazol-2-yl)(methyl)amino)-2-ethyl-7-fluoro-benzofuran-5-yl)piperazine-1-carboxylate In a glove box, 2-((5-bromo-2-ethyl-7-fluoro-benzofuran-3-yl)(methyl)amino)-4-(4-fluorophenyl)thiazole-5-carbonitrile (194 mg, 0.390 mmol), tert-butyl piperazine-1-carboxylate (217 mg, 1.171 mmol), tris(dibenzylideneacetone)dipalladium(0) (17.8 mg, 0.0195 mmol), 2-(di-tert-butylphosphino)biphenyl (11.62 mg, 0.039 mmol), sodium tert-butoxide (74.9 mg, 0.78 mmol) and toluene (6 mL) were mixed in a microwave tube. The reaction solution was heated to 115° C., stirred for 1.5 h, and then cooled to room temperature. Ethyl acetate (20 mL×3) was added for extraction. The organic phases were combined, washed with saturated brine (10 mL×2), dried over anhydrous sodium sulfate, filtered and concentrated. The residue was purified by flash chromatography (ethyl acetate/petroleum ether=0%-40%) to give tert-butyl 4-(3-((5-cyano-4-(4-fluorophenyl)thiazol-2-yl)(methyl) amino)-2-ethyl-7-fluoro-benzofuran-5-yl)piperazine-1-carboxylate in the form of a yellow solid (190 mg, 97%). LCMS (ESI) [M+H]$^+$=580.

Step 7: 2-((2-ethyl-7-fluoro-5-(piperazin-1-yl)benzofuran-3-yl)(methyl)amino)-4-(4-fluorophenyl)thiazole-5-carbonitrile Hydrogen chloride (4 N in dioxane, 5 mL) was added to a solution of tert-butyl 4-(3-((5-cyano-4-(4-fluorophenyl)thiazol-2-yl)(methyl)amino)-2-ethyl-7-fluoro-benzofuran-5-yl)piperazine-1-carboxylate (190 mg, 0.335 mmol) in dichloromethane (4 mL). The reaction solution was stirred at room temperature for 4 h and then concentrated. A sodium carbonate solution (20 mL) was added to adjust pH to low alkalinity, and dichloromethane (20 mL×3) was added for extraction. The organic phases were combined, washed with saturated brine (10 mL×2), dried over anhydrous sodium sulfate, filtered, and concentrated to give 2-((2-ethyl-7-fluoro-5-(piperazin-1-yl)benzofuran-3-yl)(methyl)amino)-4-(4-fluorophenyl)thiazole-5-carbonitrile in the form of a yellow solid (94 mg, 49%). LCMS (ESI) [M+H]$^+$=480.

Step 8: 2-((2-ethyl-7-fluoro-5-(4-(2-(3-hydroxyazetidin-1-yl)-2-oxoethyl)piperazin-1-yl)benzofuran-3-yl)(methyl)amino)-4-(4-fluorophenyl)thiazole-5-carbonitrile (S-0024)

2-chloro-1-(3-hydroxyazetidin-1-yl)acetyl (55 mg, 0.392 mmol) and potassium carbonate (81 mg, 0.588 mmol) were added to a solution of 2-((2-ethyl-7-fluoro-5-(piperazin-1-yl) benzofuran-3-yl)(methyl)amino)-4-(4-fluorophenyl)thiazole-5-carbonitrile (94 mg, 0.196 mmol) in acetonitrile (5 mL), and the reaction solution was heated to reflux for 2 h and then concentrated. The residue was separated by HPLC to give 2-((2-ethyl-7-fluoro-5-(4-(2-(3-hydroxyazetidin-1-yl)-2-oxoethyl)piperazin-1-yl)benzofuran-3-yl)(methyl) amino)-4-(4-fluorophenyl)thiazole-5-carbonitrile in the form of a white solid (30.3 mg, 32%). LCMS (ESI) [M+H]$^+$=593; $^1$H NMR (400 MHz, CD$_3$OD) δ 8.10-8.19 (m, 2H), 7.22-7.27 (m, 2H), 6.88-6.92 (m, 1H), 6.70-6.74 (m, 1H), 4.57-4.62 (m, 1H), 4.46-4.53 (m, 1H), 4.20-4.27 (m, 1H), 4.04-4.10 (m, 1H), 3.75-3.82 (m, 1H), 3.66 (s, 3H), 3.13-3.23 (m, 6H), 2.80-2.87 (m, 2H), 2.70-2.74 (m, 4H), 1.35-1.39 (m, 3H).

Example 7. S-0035: 2-((2-ethyl-5-(4-(2-(3-hydroxyazetidin-1-yl)-2-oxoethyl) piperazin-1-yl)-7-methylpyrazolo[1,5-a]pyrimidin-3-yl)(methyl)amino)-4-(4-fluorophenyl)thiazole-5-carbonitrile

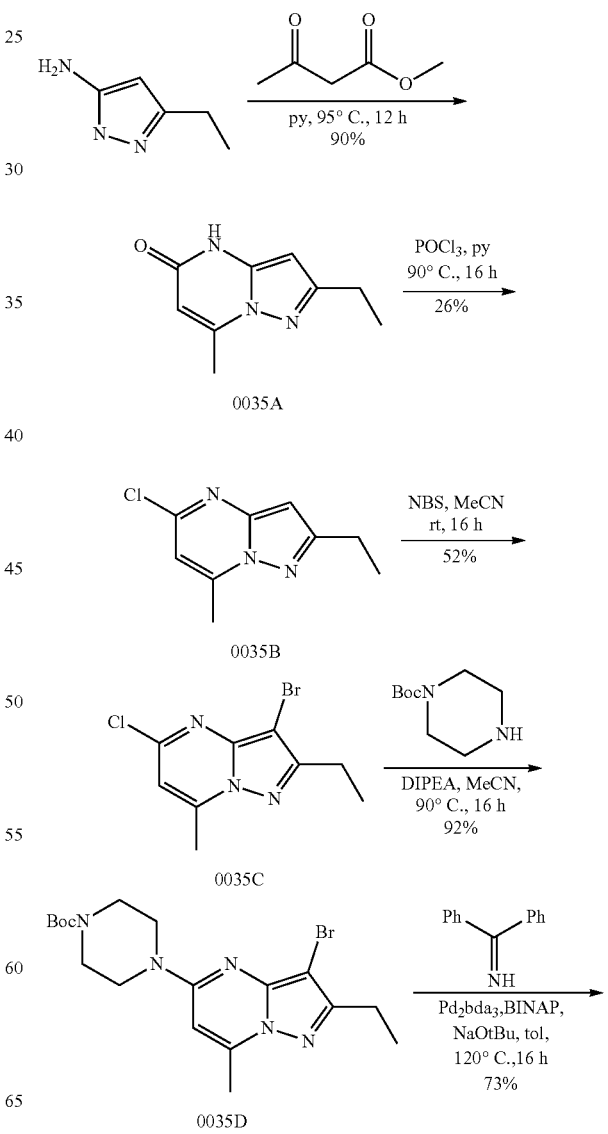

-continued

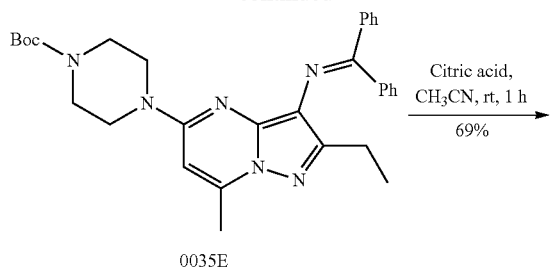
0035E

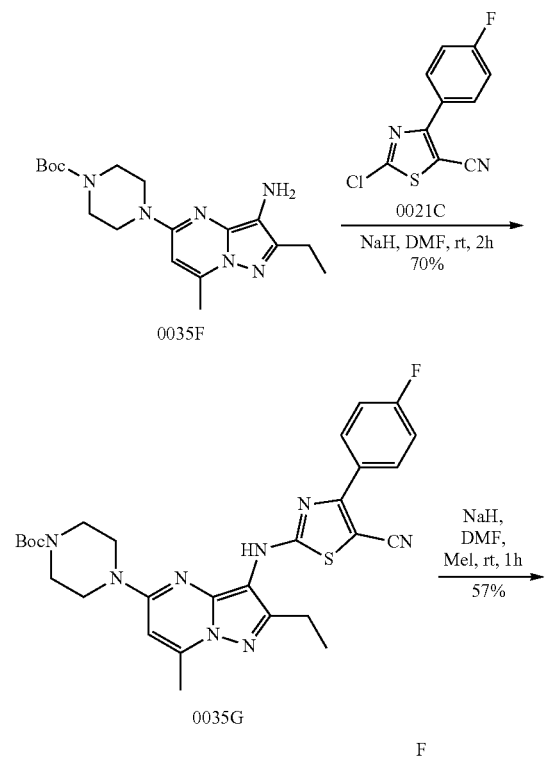
0035F
0035G
0035H

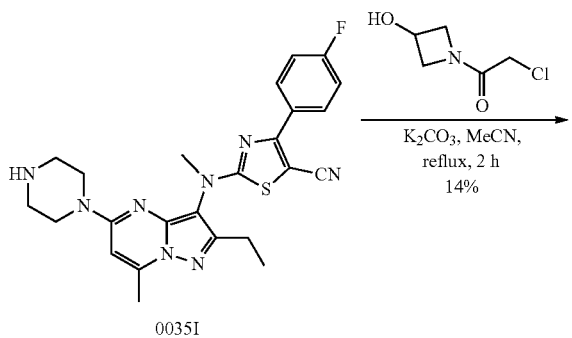
0035I

-continued

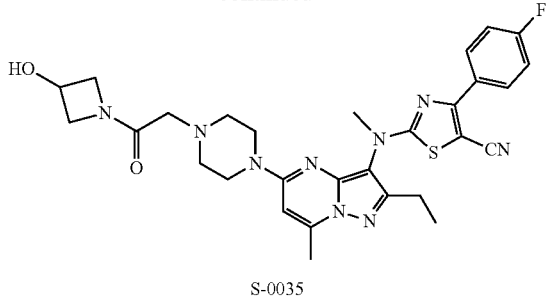
S-0035

Step 1: 2-ethyl-7-methylpyrazolo[1,5-a]pyrimidin-5 (4H)-one

A solution of 3-ethyl-1H-pyrazol-5-amine (400 mg, 3.6 mmol) and methyl 3-oxobutanoate (627 mg, 5.4 mmol) in pyridine (6 mL) was heated to 95° C., stirred for 12 h, and concentrated. The residue was purified by flash chromatography (methanol/dichloromethane=0%-10%) to give 2-ethyl-7-methylpyrazolo[1,5-a]pyrimidin-5(4H)-one in the form of a white solid (600 mg, 90%). LCMS (ESI) [M+H]$^+$=178.

Step 2: 5-chloro-2-ethyl-7-methylpyrazolo[1,5-a]pyrimidine

Pyridine (0.2 mL) was added to a solution of 2-ethyl-7-methylpyrazolo[1,5-a]pyrimidin-5(4H)-one (400 mg, 2.56 mmol) in phosphorus oxychloride (8 mL), and the reaction solution was stirred at 90° C. for 16 h, then cooled to room temperature, and concentrated. Ethyl acetate and water were added to the residue, and an organic phase was obtained. The organic phase was washed with a 1 μM sodium carbonate solution, dried over anhydrous sodium sulfate, filtered and concentrated. The residue was purified by flash chromatography (ethyl acetate/petroleum ether=0%-20%) to give 5-chloro-2-ethyl-7-methylpyrazolo[1,5-a]pyrimidine (130 mg, 26%). LCMS (ESI) [M+H]$^+$=196; $^1$H NMR (400 MHz, CDCl$_3$) δ 6.612 (s, 1H), 6.433 (s, 1H), 2.845 (q, 2H), 2.740 (s, 3H), 1.334 (t, 3H).

Step 3: 3-bromo-5-chloro-2-ethyl-7-methylpyrazolo[1,5-a]pyrimidine

A solution of 5-chloro-2-ethyl-7-methylpyrazolo[1,5-a]pyrimidine (40 mg, 0.205 mmol) and N-bromosuccinimide (40 mg, 0.225 mmol) in acetonitrile (5 mL) was stirred at room temperature for 16 h and then concentrated. The residue was purified by flash chromatography (ethyl acetate/petroleum ether=0%-20%) to give 3-bromo-5-chloro-2-ethyl-7-methylpyrazolo [1,5-a]pyrimidine in the form of a yellow solid (45 mg, 52%). LCMS (ESI) [M+H]$^+$=274; $^1$H NMR (400 MHz, CDCl$_3$) δ 6.665 (s, 1H), 2.857 (q, 2H), 2.736 (s, 3H), 1.329 (t, 3H).

Step 4: tert-butyl 4-(3-bromo-2-ethyl-7-methylpyrazolo[1,5-a]pyrimidin-5-yl) piperazine-1-carboxylate A solution of 3-bromo-5-chloro-2-ethyl-7-methylpyrazolo[1,5-a]pyrimidine (70 mg, 0.256 mmol), tert-butyl piperazine-1-carboxylate (71 mg, 0.385 mmol) and N,N-diisopropylethylamine (99 mg, 0.768 mmol) in acetonitrile (3 mL) was heated to 90° C., stirred for 16 h, and then concentrated. The residue was purified by flash chromatography (ethyl acetate/petroleum ether=0%-20%) to give tert-butyl 4-(3-bromo-2-ethyl-7-methylpyrazolo[1,5-a]pyrimidin-5-yl)piperazine-1-carboxylate in the form of a yellow solid (100 mg, 92%). LCMS (ESI) [M+H]$^+$=424.

Step 5: tert-butyl 4-(3-(diphenylmethyleneamino)-2-ethyl-7-methylpyrazolo[1,5-a]pyrimidin-5-yl)piperazine-1-carboxylate In the glove box, tert-butyl 4-(3-bromo-2-ethyl-7-methylpyrazolo[1,5-a]pyrimidin-5-yl) piperazine-1-carboxylate (100 mg, 0.236 mmol), diphenylmethanimine (80 mg, 0.472 mmol), tris(dibenzylideneacetone)dipalladium(0) (20 mg, 0.0236 mmol), (±)-2,2'-bis (diphenylphosphino)-1,1'-binaphthyl (30 mg, 0.0476 mmol), sodium tert-butoxide (70 mg, 0.708 mmol) and toluene (10 mL) were mixed in a microwave tube, and the reaction solution was heated to 120° C., stirred for 16 h, and then concentrated. The residue was purified by flash chromatography (ethyl acetate/petroleum ether=0%-20%) to give tert-butyl 4-(3-(diphenylmethyleneamino)-2-ethyl-7-methylpyrazolo[1,5-a]pyrimidin-5-yl)piperazine-1-carboxylate in the form of a yellow solid (90 mg, 73%). LCMS (ESI) [M+H]$^+$=525.

Step 6: tert-butyl 4-(3-amino-2-ethyl-7-methylpyrazolo[1,5-a]pyrimidin-5-yl) piperazine-1-carboxylate A solution of tert-butyl 4-(3-(diphenylmethyleneamino)-2-ethyl-7-methylpyrazolo[1,5-a]pyrimidin-5-yl)piperazine-1-carboxylate (200 mg, 0.382 mmol) and citric acid (146 mg, 0.764 mmol) in acetonitrile (5 mL) were stirred at room temperature for 2 h and then concentrated. The residue was purified by flash chromatography (ethyl acetate/petroleum ether=0%-60%) to give tert-butyl 4-(3-amino-2-ethyl-7-methylpyrazolo[1,5-a]pyrimidin-5-yl)piperazine-1-carboxylate in the form of a brown solid (200 mg, 69%). LCMS (ESI) [M+H]$^+$=361.

Step 7: tert-butyl 4-(3-(5-cyano-4-(4-fluorophenyl)thiazole-2-ylamino)-2-ethyl-7-methylpyrazolo[1,5-a]pyrimidin-5-yl)piperazine-1-carboxylate A solution of tert-butyl 4-(3-amino-2-ethyl-7-methylpyrazolo[1,5-a]pyrimidin-5-yl) piperazine-1-carboxylate (110 mg, 0.305 mmol) and sodium hydride (60% in oil, 15 mg, 0.61 mmol) in N, N-dimethylformamide (5 mL) was stirred at 0° C. for 10 min. Then 2-chloro-4-(4-fluorophenyl)thiazole-5-carbonitrile (87 mg, 0.367 mmol) was added, and the reaction solution was further stirred at room temperature for 2 h. The reaction was quenched with water, and ethyl acetate (20 mL×3) was added for extraction. The organic phases were combined, washed with saturated brine (30 mL×2), dried over anhydrous sodium sulfate, filtered and concentrated. The residue was purified by flash chromatography (methanol/dichloromethane=0%-10%) to give tert-butyl 4-(3-(5-cyano-4-(4-fluorophenyl)thiazole-2-ylamino)-2-ethyl-7-methylpyrazolo[1,5-a]pyrimidin-5-yl)piperazine-1-carboxylate (120 mg, 70%). LCMS (ESI) [M+H]$^+$=563.

Step 8: tert-butyl 4-(3-(5-cyano-4-(4-fluorophenyl)thiazole-2-yl)methylamino-2-ethyl-7-methylpyrazolo[1,5-a]pyrimidin-5-yl)piperazine-1-carboxylate A solution of tert-butyl 4-(3-(5-cyano-4-(4-fluorophenyl)thiazole-2-ylamino)-2-ethyl-7-methylpyrazolo[1,5-a]pyrimidin-5-yl)piperazine-1-carboxylate (120 mg, 0.213 mmol) and sodium hydride (60% in oil, 10 mg, 0.426 mmol) in N, N-dimethylformamide (5 mL) was stirred at 0° C. for 10 min. Then methyl iodide (33 mg, 0.235 mmol) was added, and the reaction solution was further stirred at room temperature for 2 h. The reaction was quenched with water, and ethyl acetate (20 mL×3) was added for extraction. The organic phases were combined, washed with saturated brine (30 mL×2), dried over anhydrous sodium sulfate, filtered and concentrated. The residue was purified by flash chromatography (methanol/dichloromethane=0%-10%) to give tert-butyl 4-(3-(5-cyano-4-(4-fluorophenyl)thiazole-2-yl)methylamino-2-ethyl-7-methylpyrazolo[1,5-a]pyrimidin-5-yl)piperazine-1-carboxylate (70 mg, 57%). LCMS (ESI) [M+H]$^+$=577.

Step 9: 2-((2-ethyl-7-methyl-5-(piperazin-1-yl)pyrazolo[1,5-a]pyrimidin-3-yl)(methyl) amino)-4-(4-fluorophenyl)thiazole-5-carbonitrile A mixture of tert-butyl 4-(3-(5-cyano-4-(4-fluorophenyl)thiazole-2-yl)methylamino-2-ethyl-7-methylpyrazolo[1,5-a]pyrimidin-5-yl)piperazine-1-carboxylate (70 mg, 0.121 mmol) and hydrogen chloride (4 N in dioxane, 5 mL) was stirred at room temperature for 1 h and then concentrated. A sodium carbonate solution (20 mL) was added to adjust pH to low alkalinity, and dichloromethane (20 mL×3) was added for extraction. The organic phases were combined, washed with saturated brine (10 mL×2), dried over anhydrous sodium sulfate, filtered, and concentrated to give 2-((2-ethyl-7-methyl-5-(piperazin-1-yl)pyrazolo[1,5-a]pyrimidin-3-yl)(methyl)amino)-4-(4-fluorophenyl)thiazole-5-carbonitrile in the form of a yellow solid (25 mg, 44%), which was directly used in the next step without purification. LCMS (ESI) [M+H]$^+$=477.

Step 10: 2-((2-ethyl-5-(4-(2-(3-hydroxyazetidin-1-yl)-2-oxoethyl)piperazin-1-yl)-7-methylpyrazolo[1,5-a]pyrimidin-3-yl)(methyl)amino)-4-(4-fluorophenyl)thiazole-5-carbonitrile (S-0035)

2-((2-ethyl-7-methyl-5-(piperazin-1-yl)pyrazolo[1,5-a]pyrimidin-3-yl)(methyl)amino)-4-(4-fluorophenyl)thiazole-5-carbonitrile (20 mg, 0.042 mmol), 2-chloro-1-(3-hydroxyazetidin-1-yl)acetyl (8 mg, 0.05 mmol) and potassium carbonate (17 mg, 0.126 mmol) were mixed in acetonitrile (3 mL), and the reaction solution was heated to reflux for 2 h, cooled to room temperature, filtered, and concentrated. The residue was purified by Pre-HPLC to give 2-((2-ethyl-5-(4-(2-(3-hydroxyazetidin-1-yl)-2-oxoethyl)piperazin-1-yl)-7-methylpyrazolo [1,5-a]pyrimidin-3-yl)(methyl) amino)-4-(4-fluorophenyl)thiazole-5-carbonitrile in the form of a white solid (3.5 mg, 14%). LCMS (ESI) [M+H]$^+$=590. $^1$H NMR (400 MHz, CD$_3$OD) δ 8.127 (m, 1H), 7.233 (t, 1H), 6.614 (s, 1H), 4.570 (m, 1H), 4.478 (m, 1H), 4.209 (m, 1H), 4.051 (m, 1H), 3.748 (m, 5H), 3.603 (s, 3H), 3.111 (d, J=3.6 Hz, 1H), 2.714 (q, 2H), 2.668 (s, 3H), 2.574 (m, 4H), 1.308 (t, 3H).

Example 8. S-0041: 2-((2-ethyl-5-(4-(2-(3-hydroxyazetidin-1-yl)-2-oxoethyl) piperazin-1-yl)pyrazolo[1,5-a]pyrimidin-3-yl)(methyl)amino)-4-(4-fluorophenyl)thiazole-5-carbonitrile
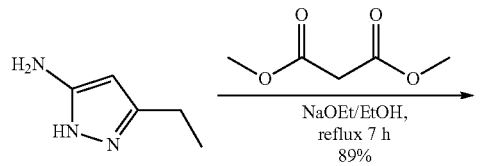
0041A
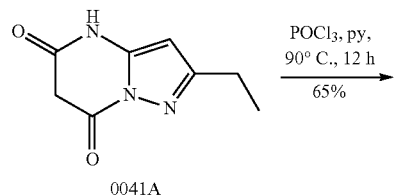
0041B
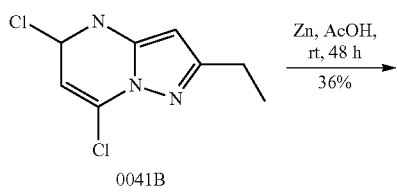
0041C
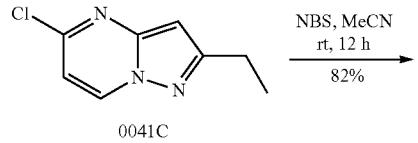
0041D
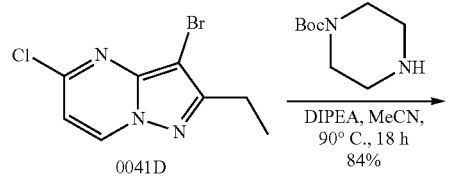
0041E
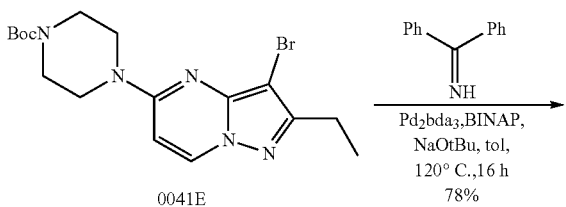
0041F
-continued
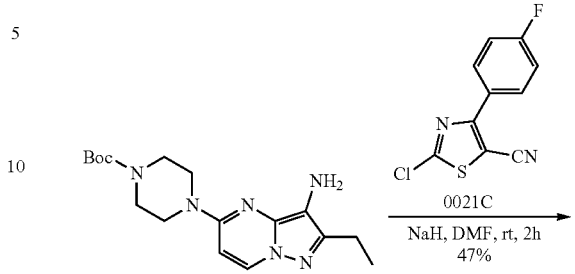
0041G
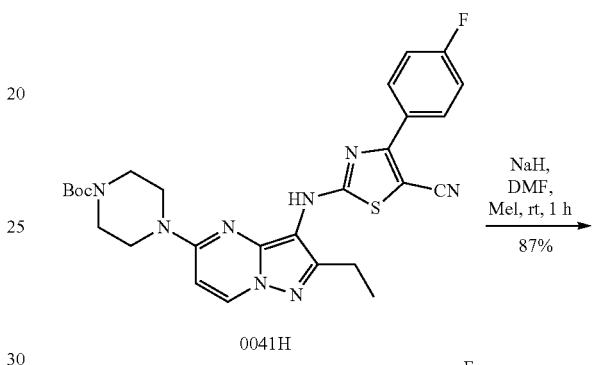
0041H
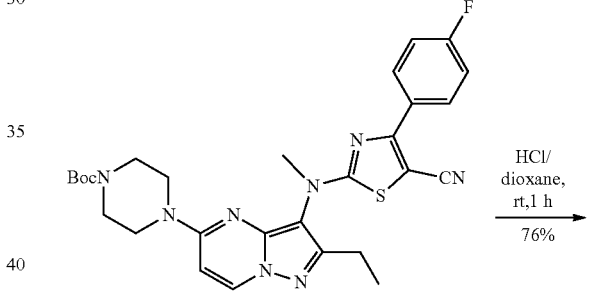
0041I
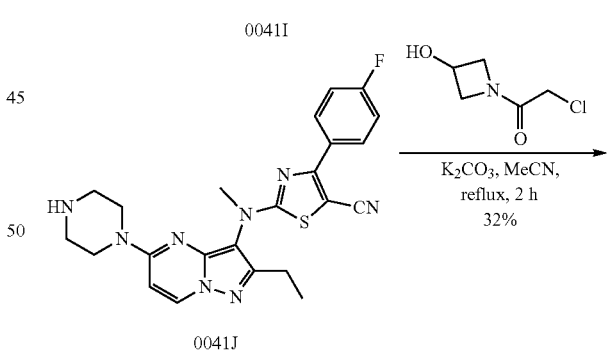
0041J
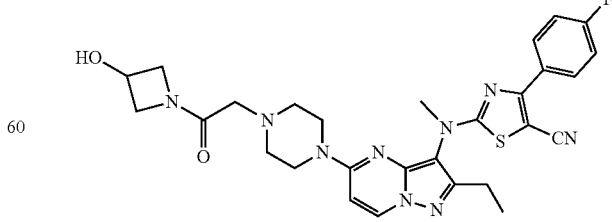
S-0041

Step 1: 2-ethylpyrazolo[1,5-a]pyrimidin-5,7(4H,6H)-dione 3-ethyl-1H-pyrazol-5-amine (180 mg, 1.62 mmol), dimethyl malonate (214 mg, 1.62 mmol) and sodium methoxide (17 mg, 0.324 mmol) were mixed in ethanol (6 mL), and the reaction solution was heated to reflux for 12 h and cooled to room temperature. A dilute hydrochloric acid solution was added to adjust pH to 5. The reaction solution was concentrated to give 2-ethylpyrazolo[1,5-a]pyrimidin-5,7(4H,6H)-dione in the form of a white solid (260 mg, 89%). LCMS (ESI) [M+H]$^+$=180.

Step 2: 5,7-dichloro-2-ethylpyrazolo[1,5-a]pyrimidine

N,N-dimethylaniline (1 mL) was added to a solution of 2-ethylpyrazolo[1,5-a]pyrimidin-5,7(4H,6H)-dione (1400 mg, 7.82 mmol) in phosphorus oxychloride (8 mL), and the reaction solution was heated to 100° C., stirred for 16 h, and then concentrated. The residue was diluted with ethyl acetate and water, an organic phase was obtained. The organic phase was washed with a 1 N sodium carbonate solution, dried over anhydrous sodium sulfate, filtered and concentrated. The residue was purified by flash chromatography (ethyl acetate/petroleum ether=0%-20%) to give 5,7-dichloro-2-ethylpyrazolo[1,5-a]pyrimidine (1100 mg, 65%). LCMS (ESI) [M+H]$^+$=216.

Step 3: 5-chloro-2-ethylpyrazolo[1,5-a]pyrimidine 5,7-dichloro-2-ethylpyrazolo[1,5-a]pyrimidine (500 mg, 2.32 mmol) and zinc powder (756 mg, 11.62 mmol) were mixed in acetic acid (15 mL), and the reaction solution was stirred at room temperature for 48 h and then concentrated. The residue was diluted with a sodium carbonate solution, and then ethyl acetate (20 mL×3) was added for extraction. The organic phases were combined, dried over anhydrous sodium sulfate, filtered and concentrated. The residue was purified by flash chromatography (methanol/dichloromethane=0%-10%) to give 5-chloro-2-ethylpyrazolo[1,5-a]pyrimidine in the form of a white solid (150 mg, 35.7%). LCMS (ESI) [M+H]$^+$=182.

Step 4: 3-bromo-5-chloro-2-ethylpyrazolo[1,5-a]pyrimidine

A solution of 5-chloro-2-ethylpyrazolo[1,5-a]pyrimidine (170 mg, 0.94 mmol) and N-bromosuccinimide (167 mg, 0.94 mmol) in acetonitrile (5 mL) was stirred at room temperature for 16 h and then concentrated. The residue was purified by flash chromatography (ethyl acetate/petroleum ether=0%-20%) to give 3-bromo-5-chloro-2-ethylpyrazolo[1,5-a]pyrimidine in the form of a yellow solid (200 mg, 82%). LCMS (ESI) [M+H]$^+$=260.

Step 5: tert-butyl 4-(3-bromo-2-ethylpyrazolo[1,5-a]pyrimidin-5-yl)piperazine-1-carboxylate A solution of 3-bromo-5-chloro-2-ethylpyrazolo[1,5-a]pyrimidine (150 mg, 0.579 mmol), tert-butyl piperazine-1-carboxylate (158 mg, 0.868 mmol) and N,N-diisopropylethylamine (224 mg, 1.737 mmol) in acetonitrile (3 mL) was heated to 90° C., stirred for 16 h, and then concentrated. The residue was purified by flash chromatography (ethyl acetate/petroleum ether=0%-60%) to give tert-butyl 4-(3-bromo-2-ethylpyrazolo[1,5-a]pyrimidin-5-yl)piperazine-1-carboxylate in the form of a yellow solid (200 mg, 84%). LCMS (ESI) [M+H]$^+$=410.

Step 6: tert-butyl 4-(3-(diphenylmethyleneamino)-2-ethylpyrazolo[1,5-a]pyrimidin-5-yl)piperazine-1-carboxylate In the glove box, tert-butyl 4-(3-bromo-2-ethylpyrazolo[1,5-a]pyrimidin-5-yl)piperazine-1-carboxylate (200 mg, 0.489 mmol), diphenylmethanimine (178 mg, 0.978 mmol), tris(dibenzylideneacetone)dipalladium(0) (44 mg, 0.0489 mmol), (±)-2,2'-bis (diphenylphosphino)-1,1'-binaphthyl (60 mg, 0.0978 mmol), sodium tert-butoxide (141 mg, 1.467 mmol) and toluene (8 mL) were mixed in a microwave tube, and the reaction solution was heated to 120° C., stirred for 16 h, and concentrated. The residue was purified by flash chromatography (ethyl acetate/petroleum ether 0%-60%) to give tert-butyl 4-(3-(diphenylmethyleneamino)-2-ethylpyrazolo[1,5-a]pyrimidin-5-yl)piperazine-1-carboxylate in the form of a yellow solid (200 mg, 78%). LCMS (ESI) [M+H]$^+$=511.

Step 7: tert-butyl 4-(3-amino-2-ethylpyrazolo[1,5-a]pyrimidin-5-yl)piperazine-1-carboxylate A solution of tert-butyl 4-(3-(diphenylmethyleneamino)-2-ethylpyrazolo[1,5-a]pyrimidin-5-yl)piperazine-1-carboxylate (200 mg, 0.392 mmol) and citric acid (150 mg, 0.784 mmol) in acetonitrile (5 mL) were stirred at room temperature for 2 h and then concentrated. The residue was purified by flash chromatography (ethyl acetate/petroleum ether=0%-60%) to give tert-butyl 4-(3-amino-2-ethylpyrazolo[1,5-a]pyrimidin-5-yl)piperazine-1-carboxylate in the form of a brown solid (120 mg, 89%). LCMS (ESI) [M+H]$^+$=347.

Step 8: tert-butyl 4-(3-(5-cyano-4-(4-fluorophenyl)thiazol-2-ylamino)-2-ethylpyrazolo[1,5-a]pyrimidin-5-yl)piperazine-1-carboxylate A solution of tert-butyl 4-(3-amino-2-ethylpyrazolo[1,5-a]pyrimidin-5-yl)piperazine-1-carboxylate (200 mg, 0.578 mmol) and sodium hydride (60% in oil, 46 mg, 1.156 mmol) in N, N-dimethylformamide (5 mL) was stirred at 0° C. for 10 min. Then 2-chloro-4-(4-fluorophenyl)thiazole-5-carbonitrile (165 mg, 0.693 mmol) was added, and the reaction solution was further stirred at room temperature for 2 h. The reaction was quenched with water, and ethyl acetate (20 mL×3) was added for extraction. The organic phases were combined, washed with saturated brine (30 mL×2), dried over anhydrous sodium sulfate, filtered and concentrated. The residue was purified by flash chromatography (methanol/dichloromethane=0%-10%) to give tert-butyl 4-(3-(5-cyano-4-(4-fluorophenyl)thiazol-2-ylamino)-2-ethylpyrazolo[1,5-a]pyrimidin-5-yl)piperazine-1-carboxylate (150 mg, 47%). LCMS (ESI) [M+H]$^+$=549.

Step 9: tert-butyl 4-(3-(5-cyano-4-(4-fluorophenyl)thiazol-2-yl)methylamino-2-ethylpyrazolo[1,5-a]pyrimidin-5-yl)piperazine-1-carboxylate A solution of tert-butyl 4-(3-(5-cyano-4-(4-fluorophenyl)thiazol-2-ylamino)-2-ethylpyrazolo[1,5-a]pyrimidin-5-yl)piperazine-1-carboxylate (90 mg, 0.164 mmol) and sodium hydride (60% in oil, 8 mg, 0.328 mmol) in N, N-dimethylformamide (5 mL) was stirred at 0° C. for 10 min. Then methyl iodide (28 mg, 0.197 mmol) was added, and the reaction solution was further stirred at room temperature for 2 h. The reaction was quenched with water, and ethyl acetate (20 mL×3) was added for extraction. The organic phases were combined, washed with saturated brine (30 mL×2), dried over anhydrous sodium sulfate, filtered and concentrated. The residue was purified by flash chromatography (methanol/dichloromethane=0%-10%) to give tert-butyl 4-(3-(5-cyano-4-(4-fluorophenyl)thiazol-2-yl)methylamino-2-ethylpyrazolo [1,5-a]pyrimidin-5-yl)piperazine-1-carboxylate (80 mg, 87%). LCMS (ESI) [M+H]⁺=563.

Step 10: 2-((2-ethyl-5-(piperazin-1-yl)pyrazolo[1,5-a]pyrimidin-3-yl)(methyl)amino)-4-(4-fluorophenyl)thiazole-5-carbonitrile A mixture of tert-butyl 4-(3-(5-cyano-4-(4-fluorophenyl)thiazol-2-yl)methylamino-2-ethylpyrazolo[1,5-a]pyrimidin-5-yl)piperazine-1-carboxylate (80 mg, 0.142 mmol) and hydrogen chloride (4 N in dioxane, 5 mL) was stirred at room temperature for 1 h, and then concentrated. A sodium carbonate solution (20 mL) was added to adjust pH to low alkalinity, and ethyl acetate (20 mL×3) was added for extraction. The organic phases were combined, washed with saturated brine (10 mL×2), dried over anhydrous sodium sulfate, filtered, and concentrated to give 2-((2-ethyl-5-(piperazin-1-yl)pyrazolo[1,5-a]pyrimidin-3-yl)(methyl)amino)-4-(4-fluorophenyl)thiazole-5-carbonitrile in the form of a yellow solid (50 mg, 76%), which was directly used in the next step without purification. LCMS (ESI) [M+H]⁺=463.

Step 11: 2-((2-ethyl-5-(4-(2-(3-hydroxyazetidin-1-yl)-2-oxoethyl)piperazin-1-yl)pyrazolo [1,5-a]pyrimidin-3-yl)(methyl)amino)-4-(4-fluorophenyl)thiazole-5-carbonitrile (S-0041)

2-((2-ethyl-5-(piperazin-1-yl)pyrazolo[1,5-a]pyrimidin-3-yl)(methyl)amino)-4-(4-fluorophenyl)thiazole-5-carbonitrile (50 mg, 0.108 mmol), 2-chloro-1-(3-hydroxyazetidin-1-yl)acetyl (24 mg, 0.162 mmol) and potassium carbonate (45 mg, 0.324 mmol) were mixed in acetonitrile (3 mL), and the reaction solution was heated to reflux for 2 h, cooled to room temperature, filtered, and concentrated. The residue was purified by Pre-HPLC to give 2-((2-ethyl-5-(4-(2-(3-hydroxyazetidin-1-yl)-2-oxoethyl)piperazin-1-yl)pyrazolo [1,5-a]pyrimidin-3-yl)(methyl)amino)-4-(4-fluorophenyl)thiazole-5-carbonitrile in the form of a white solid (21 mg, 32%). LCMS (ESI) [M+H]⁺=575. ¹H NMR (400 MHz, CD₃OD) δ 8.361 (d, J=8.0 Hz, 1H), 8.126 (m, 2H), 7.232 (t, 2H), 6.699 (d, J=8.0 Hz, 1H), 4.576 (m, 1H), 4.480 (m, 1H), 4.209 (m, 1H), 4.050 (m, 1H), 3.768 (m, 5H), 3.599 (s, 3H), 3.116 (d, J=4.0 Hz, 2H), 2.689 (q, 2H), 2.584 (t, 4H), 1.304 (t, 3H).

Example 9. S-0043: 2-((2-ethyl-5-(4-(2-(3-hydroxyazetidin-1-yl)-2-oxoethyl) piperazin-1-yl)-2H-pyrazolo[3,4-b]pyridin-3-yl)(methyl)amino)-4-(4-fluorophenyl)thiazole-5-carbonitrile

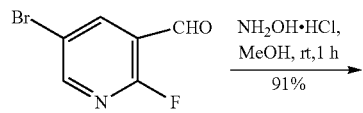

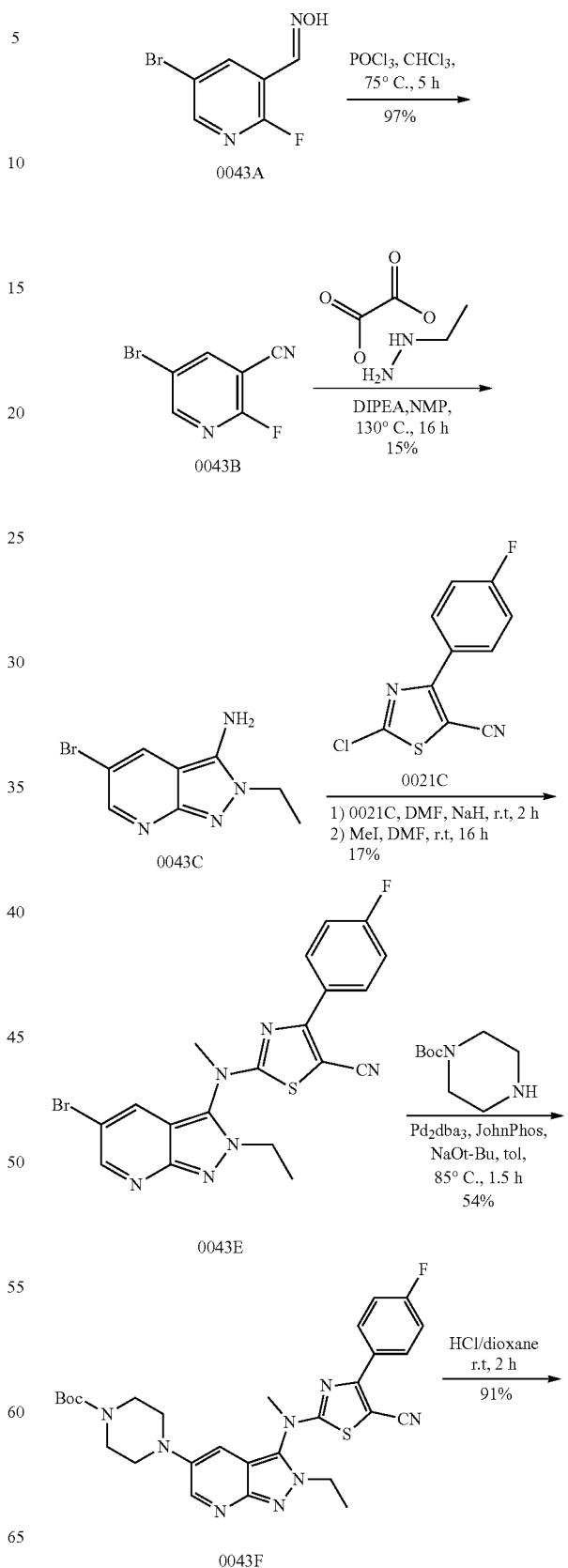

-continued

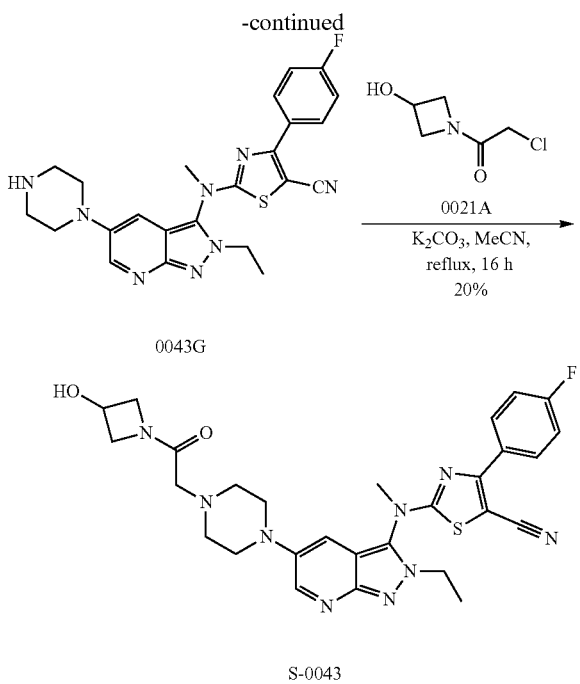

0043G

S-0043

Step 1: 5-Bromo-2-Fluoronicotinaldehyde Oxime

Hydroxylamine hydrochloride (1.11 g, 16.17 mmol) was added to a solution of 5-bromo-2-fluoronicotine (3.0 g, 14.70 mmol) in methanol (50 mL), and the reaction solution was stirred at room temperature for 1 h. The reaction was quenched with a sodium carbonate solution (200 mL), and ethyl acetate (500 mL×2) was added for extraction. The organic phases were combined, washed with saturated brine (100 mL×2), dried over anhydrous sodium sulfate, filtered and concentrated to give 5-bromo-2-fluoronicotinaldehyde oxime in the form of a white solid (2.9 g, 91%). LCMS (ESI) $[M+H]^+=219$.

Step 2: 5-bromo-2-fluoronicotinonitrile

Phosphorus oxychloride (15.5 g, 100 mmol) was added to a solution of 5-bromo-2-fluoronicotinaldehyde oxime (2.83 g, 12 mmol) in chloroform (50 mL), and the reaction solution was heated to 75° C. and stirred for 5 h. The reaction was quenched with a sodium bisulfite solution (20 mL), and ethyl acetate (150 mL×2) was added for extraction. The organic phases were combined, washed with saturated brine (100 mL×2), dried over anhydrous sodium sulfate, filtered and concentrated to give 5-bromo-2-fluoronicotinonitrile in the form of a brown solid (2.5 g, 97%). $^1$HNMR (400 MHz, DMSO-$d_6$) δ 8.85-8.87 (m, 1H) 8.67-8.68 (m, 1H) Step 3: 5-bromo-2-ethyl-2H-pyrazolo[3,4-b]pyridin-3-amine N, N-diisopropylethylamine (2.6 g, 20.5 mmol) was added to a solution of 5-bromo-2-fluoronicotinonitrile (1.0 g, 4.1 mmol) and ethylhydrazine oxalate (1.22 g, 8.2 mmol) in N-methyl-2-pyrrolidone (10 mL), and the reaction solution was heated to 130° C., stirred for 16 h, and then concentrated. Ethyl acetate (500 mL×3) was added for extraction. The organic phases were combined, washed with saturated brine (200 mL×3), dried over anhydrous sodium sulfate, filtered and concentrated. The residue was purified by flash chromatography (ethyl acetate/petroleum ether=0%-100%) to give 5-bromo-2-ethyl-2H-pyrazolo[3,4-b]pyridin-3-amine in the form of a yellow solid (180 mg, 15%). LCMS (ESI) $[M+H]^+=241$.

Step 4: 2-((5-bromo-2-ethyl-2H-pyrazolo[3,4-b]pyridin-3-yl)(methyl)amino)-4-(4-fluorophenyl)thiazole-5-carbonitrile Sodium hydride (60% in oil, 54 mg, 2.25 mmol) was slowly added to a solution of 5-bromo-2-ethyl-2H-pyrazolo[3,4-b]pyridin-3-amine (180 mg, 0.75 mmol) in N, N-dimethylformamide (3 mL), and the mixture was stirred at room temperature for 2 h. Then 2-chloro-4-(4-fluorophenyl)thiazole-5-carbonitrile (196 mg, 0.825 mmol) was added, and the mixture was further stirred at room temperature for 2 h. Then methyl iodide (105 mg, 0.75 mmol) was added, and the resulting reaction solution was further stirred at room temperature for 16 h. The reaction was quenched with water (30 mL), and ethyl acetate (50 mL×2) was added for extraction. The organic phases were combined, washed with saturated brine (10 mL×2), dried over anhydrous sodium sulfate, filtered and concentrated. The residue was purified by flash chromatography (ethyl acetate/petroleum ether=0%-30%) to give 2-((5-bromo-2-ethyl-2H-pyrazolo[3,4-b]pyridin-3-yl)(methyl)amino)-4-(4-fluorophenyl) thiazole-5-carbonitrile in the form of a brown solid (60 mg, 17%). LCMS (ESI) $[M+H]^+=457$.

Step 5: tert-butyl 4-(3-((5-cyano-4-(4-fluorophenyl)thiazol-2-yl)(methyl)amino)-2-ethyl-2H-pyrazolo[3,4-b]pyridin-5-yl)piperazine-1-carboxylate In a glove box, 2-((5-bromo-2-ethyl-2H-pyrazolo[3,4-b]pyridin-3-yl)(methyl)amino)-4-(4-fluorophenyl)thiazole-5-carbonitrile (60 mg, 0.13 mmol), tert-butyl piperazine-1-carboxylate (48.36 mg, 0.26 mmol), tris(dibenzylideneacetone)dipalladium(0) (11.8 mg, 0.013 mmol), 2-(di-tert-butylphosphino)biphenyl (7.7 mg, 0.026 mmol), sodium tert-butoxide (24.9 mg, 0.26 mmol) and toluene (3 mL) were mixed in a microwave tube. The reaction solution was heated to 85° C., stirred for 1.5 h, and then cooled to room temperature. Ethyl acetate (20 mL×3) was added for extraction. The organic phases were combined, washed with saturated brine (10 mL×2), dried over anhydrous sodium sulfate, filtered and concentrated. The residue was purified by flash chromatography (ethyl acetate/petroleum ether=0%-50%) to give tert-butyl 4-(3-((5-cyano-4-(4-fluorophenyl)thiazol-2-yl)(methyl)amino)-2-ethyl-2H-pyrazolo[3,4-b]pyridin-5-yl)piperazine-1-carboxylate in the form of a brown solid (40 mg, 54%). LCMS (ESI) $[M+H]^+=563$.

Step 6: 2-((2-ethyl-5-(piperazin-1-yl)-2H-pyrazolo[3,4-b]pyridin-3-yl)(methyl)amino)-4-(4-fluorophenyl)thiazole-5-carbonitrile Hydrogen chloride (4 N in dioxane, 4 mL) was added to a solution of tert-butyl 4-(3-((5-cyano-4-(4-fluorophenyl)thiazol-2-yl)(methyl)amino)-2-ethyl-2H-pyrazolo[3,4-b]pyridin-5-yl)piperazine-1-carboxylate (40 mg, 0.071 mmol) in dichloromethane (4 mL). The reaction solution was stirred at room temperature for 4 h and then concentrated. A sodium carbonate solution (20 mL) was added to adjust pH to low alkalinity, and dichloromethane (20 mL×3) was added for extraction. The organic phases were combined, washed with saturated brine (10 mL×2), dried over anhydrous sodium sulfate, filtered, and concentrated to give 2-((2-ethyl-5-

(piperazin-1-yl)-2H-pyrazolo[3,4-b]pyridin-3-yl)(methyl) amino)-4-(4-fluorophenyl)thiazole-5-carbonitrile in the form of a brown solid (30 mg, 91%). LCMS (ESI) [M+H]$^+$=463.

Step 7: 2-((2-ethyl-5-(4-(2-(3-hydroxyazetidin-1-yl)-2-oxoethyl)piperazin-1-yl)-2H-pyrazolo[3,4-b]pyridin-3-yl)(methyl)amino)-4-(4-fluorophenyl)thiazole-5-carbonitrile (S-0043)

2-chloro-1-(3-hydroxyazetidin-1-yl)acetyl (19.4 mg, 0.129 mmol) and potassium carbonate (26.4 mg, 0.192 mmol) were added to a solution of 2-((2-ethyl-5-(piperazin-1-yl)-2H-pyrazolo[3,4-b]pyridin-3-yl)(methyl)amino)-4-(4-fluorophenyl)thiazole-5-carbonitrile (30 mg, 0.064 mmol) in acetonitrile (3 mL), and the reaction solution was heated to reflux for 2 h and then concentrated. The residue was purified by Pre-HPLC to give 2-((2-ethyl-5-(4-(2-(3-hydroxyazetidin-1-yl)-2-oxoethyl)piperazin-1-yl)-2H-pyrazolo[3,4-b]pyridin-3-yl)(methyl)amino)-4-(4-fluorophenyl)thiazole-5-carbonitrile in the form of a yellow solid (7.9 mg, 20%). LCMS (ESI) [M+H]$^+$=575; $^1$H $^1$HNMR (400 MHz, DMSO-d$_6$) δ 8.66-8.68 (m, 1H), 8.05-8.10 (m, 2H), 7.38-7.45 (m, 2H), 8.28-7.32 (m, 1H), 5.65-5.68 (m, 1H), 4.28-4.47 (m, 4H), 4.01-4.06 (m, 1H), 3.89-3.92 (m, 1H), 3.64 (s, 3H), 3.54-3.61 (m, 1H), 3.15-3.18 (m, 4H), 2.98-3.05 (m, 2H), 2.55-2.61 (m, 4H), 1.45-1.50 (m, 3H).

Example 10. S-0044: 2-((2-ethyl-5-(4-(2-(3-hydroxyazetidin-1-yl)-2-oxoethyl) piperazin-1-yl)-2H-pyrazolo[3,4-c]pyridin-3-yl)(methyl)amino)-4-(4-fluorophenyl) thiazole-5-carbonitrile

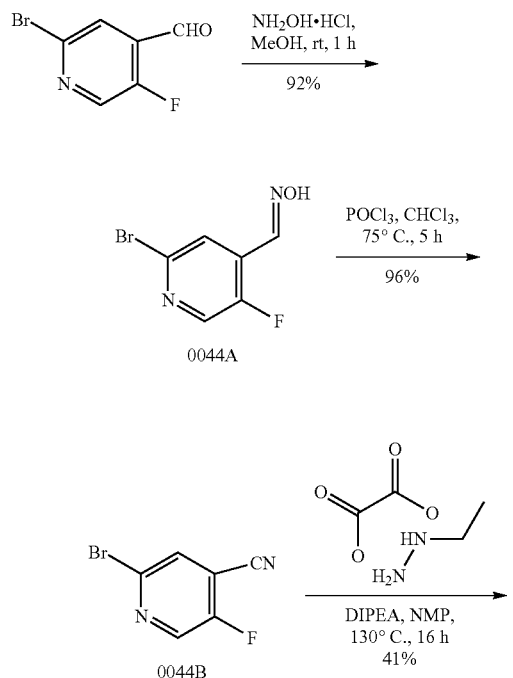

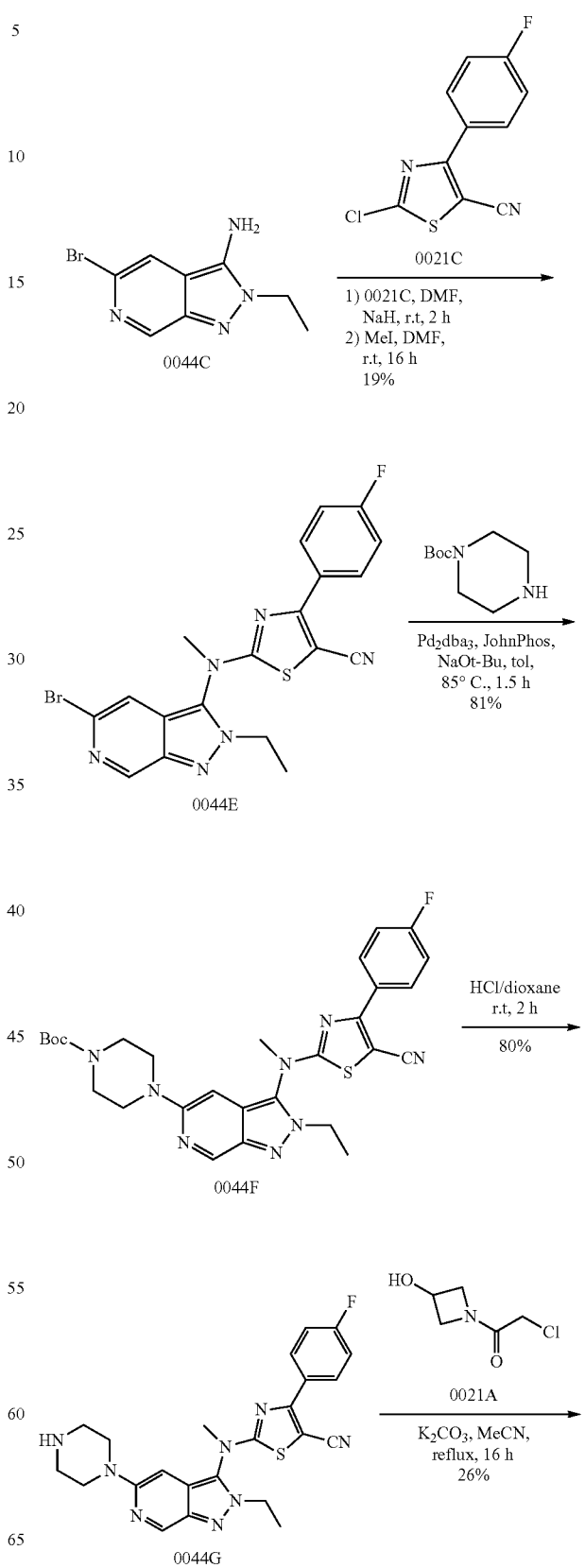

-continued

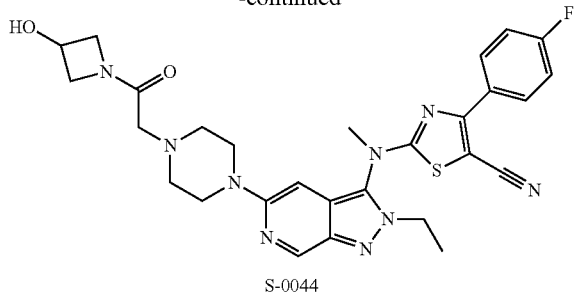

S-0044

Step 1: 2-bromo-5-fluoroisonicotinaldehyde Oxime

Hydroxylamine hydrochloride (185 mg, 2.69 mmol) was added to a solution of 2-bromo-5-fluoroisonicotine (500 mg, 2.45 mmol) in methanol (20 mL), and the reaction solution was stirred at room temperature for 1 h. The reaction was quenched with a sodium carbonate solution (200 mL), and ethyl acetate (100 mL×2) was added for extraction. The organic phases were combined, washed with saturated brine (50 mL×2), dried over anhydrous sodium sulfate, filtered and concentrated to give 2-bromo-5-fluoroisonicotinaldehyde oxime in the form of a white solid (497 mg, 92%). LCMS (ESI) [M+H]$^+$=219.

Step 2: 2-bromo-5-fluoroisonicotinonitrile

Phosphorus oxychloride (2.72 g, 18.16 mmol) was added to a solution of 2-bromo-5-fluoroisonicotinaldehyde oxime (497 mg, 2.27 mmol) in chloroform (20 mL), and the reaction solution was heated to 75° C. and stirred for 5 h. The reaction was quenched with a sodium bisulfite solution (20 mL), and ethyl acetate (100 mL×2) was added for extraction. The organic phases were combined, washed with saturated brine (10 mL×2), dried over anhydrous sodium sulfate, filtered and concentrated to give 2-bromo-5-fluoroisonicotinonitrile in the form of a brown solid (440 mg, 96%). $^1$HNMR (400 MHz, DMSO-d$_6$) δ 8.74 (s, 1H) 8.34-8.35 (m, 1H)

Step 3: 5-bromo-2-ethyl-2H-pyrazolo[3,4-c]pyridin-3-amine

N, N-diisopropylethylamine (1.4 g, 11 mmol) was added to a solution of 2-bromo-5-fluoroisonicotinonitrile (440 mg, 2.2 mmol) and ethylhydrazine oxalate (660 mg, 4.4 mmol) in N-methyl-2-pyrrolidone (10 mL), and the reaction solution was heated to 130° C., stirred for 16 h and then concentrated. Ethyl acetate (500 mL×3) was added for extraction. The organic phases were combined, washed with saturated brine (200 mL×3), dried over anhydrous sodium sulfate, filtered and concentrated. The residue was purified by flash chromatography (ethyl acetate/petroleum ether=0%-100%) to give 5-bromo-2-ethyl-2H-pyrazolo[3,4-c]pyridin-3-amine in the form of a yellow solid (220 mg, 41%). LCMS (ESI) [M+H]$^+$=241.

Step 4: 2-((5-bromo-2-ethyl-2H-pyrazolo[3,4-c]pyridin-3-yl)(methyl)amino)-4-(4-fluorophenyl)thiazole-5-carbonitrile Sodium hydride (60% in oil, 65 mg, 2.73 mmol) was slowly added to a solution of 5-bromo-2-ethyl-2H-pyrazolo[3,4-c]pyridin-3-amine (220 mg, 0.91 mmol) in N, N-dimethylformamide (3 mL), and the mixture was stirred at room temperature for 2 h. Then 2-chloro-4-(4-fluorophenyl)thiazole-5-carbonitrile (238 mg, 1.0 mmol) was added, and the mixture was further stirred at room temperature for 2 h. Then methyl iodide (127 mg, 0.91 mmol) was added, and the mixture was further stirred at room temperature for 16 h. The reaction was quenched with water (20 mL), and ethyl acetate (50 mL×2) was added for extraction. The organic phases were combined, washed with saturated brine (10 mL×2), dried over anhydrous sodium sulfate, filtered and concentrated. The residue was purified by flash chromatography (ethyl acetate/petroleum ether=0%-30%) to give 2-((5-bromo-2-ethyl-2H-pyrazolo[3,4-c]pyridin-3-yl)(methyl)amino)-4-(4-fluorophenyl)thiazole-5-carbonitrile in the form of a brown solid (80 mg, 19%). LCMS (ESI) [M+H]$^+$=457.

Step 5: tert-butyl 4-(3-((5-cyano-4-(4-fluorophenyl)thiazol-2-yl)(methyl)amino)-2-ethyl-2H-pyrazolo[3,4-c]pyridin-5-yl)piperazine-1-carboxylate In a glove box, 2-((5-bromo-2-ethyl-2H-pyrazolo[3,4-c]pyridin-3-yl)(methyl)amino)-4-(4-fluorophenyl)thiazole-5-carbonitrile (80 mg, 0.17 mmol), tert-butyl piperazine-1-carboxylate (64.47 mg, 0.34 mmol), tris(dibenzylideneacetone)dipalladium(0) (15.69 mg, 0.017 mmol), 2-(di-tert-butylphosphino)biphenyl (10.24 mg, 0.034 mmol), sodium tert-butoxide (33.11 mg, 0.34 mmol) and toluene (3 mL) were mixed in a microwave tube. The reaction solution was heated to 85° C., stirred for 1.5 h, and then cooled to room temperature. Ethyl acetate (30 mL×3) was added for extraction. The organic phases were combined, washed with saturated brine (10 mL×2), dried over anhydrous sodium sulfate, filtered and concentrated. The residue was purified by flash chromatography (ethyl acetate/petroleum ether=0%-50%) to give tert-butyl 4-(3-((5-cyano-4-(4-fluorophenyl)thiazol-2-yl)(methyl) amino)-2-ethyl-2H-pyrazolo[3,4-c]pyridin-5-yl)piperazine-1-carboxylate in the form of a brown solid (50 mg, 81%). LCMS (ESI) [M+H]$^+$=563.

Step 6: 2-((2-ethyl-5-(piperazin-1-yl)-2H-pyrazolo[3,4-c]pyridin-3-yl)(methyl)amino)-4-(4-fluorophenyl)thiazole-5-carbonitrile Hydrogen chloride (4 N in dioxane, 4 mL) was added to a solution of tert-butyl 4-(3-((5-cyano-4-(4-fluorophenyl)thiazol-2-yl)(methyl)amino)-2-ethyl-2H-pyrazolo[3,4-c]pyridin-5-yl)piper azine-1-carboxylate (50 mg, 0.071 mmol) in dichloromethane (4 mL). The reaction solution was stirred at room temperature for 4 h and then concentrated. A sodium carbonate solution (20 mL) was added to adjust pH to low alkalinity, and dichloromethane (20 mL×3) was added for extraction. The organic phases were combined, washed with saturated brine (10 mL×2), dried over anhydrous sodium sulfate, filtered, and concentrated to give 2-((2-ethyl-5-(piperazin-1-yl)-2H-pyrazolo[3,4-c]pyridin-3-yl)(methyl)amino)-4-(4-fluorophenyl)thiazole-5-carbonitrile in the form of a brown solid (33 mg, 80%). LCMS (ESI) [M+H]$^+$=463.

Step 7: 2-((2-ethyl-5-(4-(2-(3-hydroxyazetidin-1-yl)-2-oxoethyl)piperazin-1-yl)-2H-pyrazolo[3,4-c]pyridin-3-yl)(methyl)amino)-4-(4-fluorophenyl)thiazole-5-carbonitrile (S-0044)

2-chloro-1-(3-hydroxyazetidin-1-yl)acetyl (21.42 mg, 0.142 mmol) and potassium carbonate (29.3 mg, 0.213 mmol) were added to a solution of 2-((2-ethyl-5-(piperazin-1-yl)-2H-pyrazolo[3,4-c]pyridin-3-yl)(methyl)amino)-4-(4-fluorophenyl)thiazole-5-carbonitrile (33 mg, 0.071 mmol) in acetonitrile (3 mL), and the reaction solution was heated to reflux for 2 h and then concentrated. The residue was purified by Pre-HPLC to give 2-((2-ethyl-5-(4-(2-(3-hydroxyazetidin-1-yl)-2-oxoethyl)piperazin-1-yl)-2H-pyrazolo[3,4-c]pyridin-3-yl)(methyl)amino)-4-(4-fluorophenyl)thiazole-5-carbonitrile in the form of a yellow solid (10.7 mg, 26%). LCMS (ESI) [M+H]$^+$=575; $^1$H NMR (400 MHz, DMSO-d$_6$) δ 8.97-8.99 (m, 1H), 8.04-8.09 (m, 2H), 7.39-7.45 (m, 2H), 6.62-6.64 (m, 1H), 5.65-5.68 (m, 1H), 4.32-4.47 (m, 4H), 4.01-4.07 (m, 1H), 3.89-3.94 (m, 1H), 3.64 (s, 3H), 3.55-3.60 (m, 1H), 3.37-3.41 (m, 4H), 2.95-3.06 (m, 2H), 2.50-2.56 (m, 4H), 1.46-1.51 (m, 3H).

Example 11. S-0045: 2-((2-ethyl-5-(4-(2-(3-hydroxyazetidin-1-yl)-2-oxoethyl) piperazin-1-yl)furo[2,3-b]pyridin-3-yl)(methyl)amino)-4-(4-fluorophenyl)thiazole-5-carbonitrile

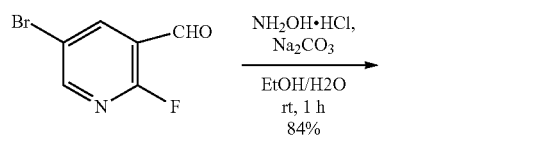

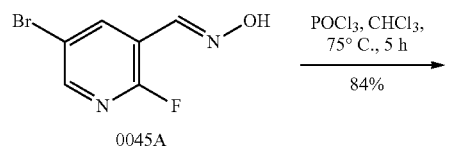

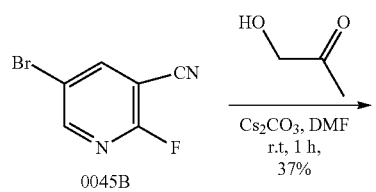

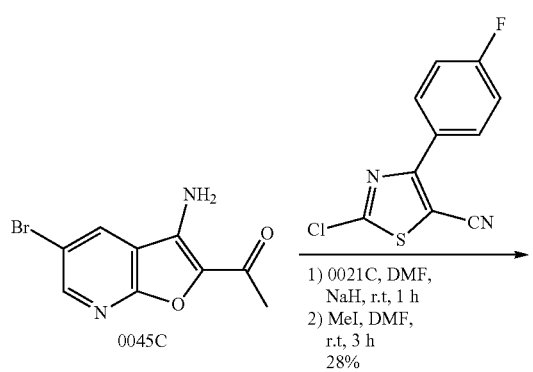

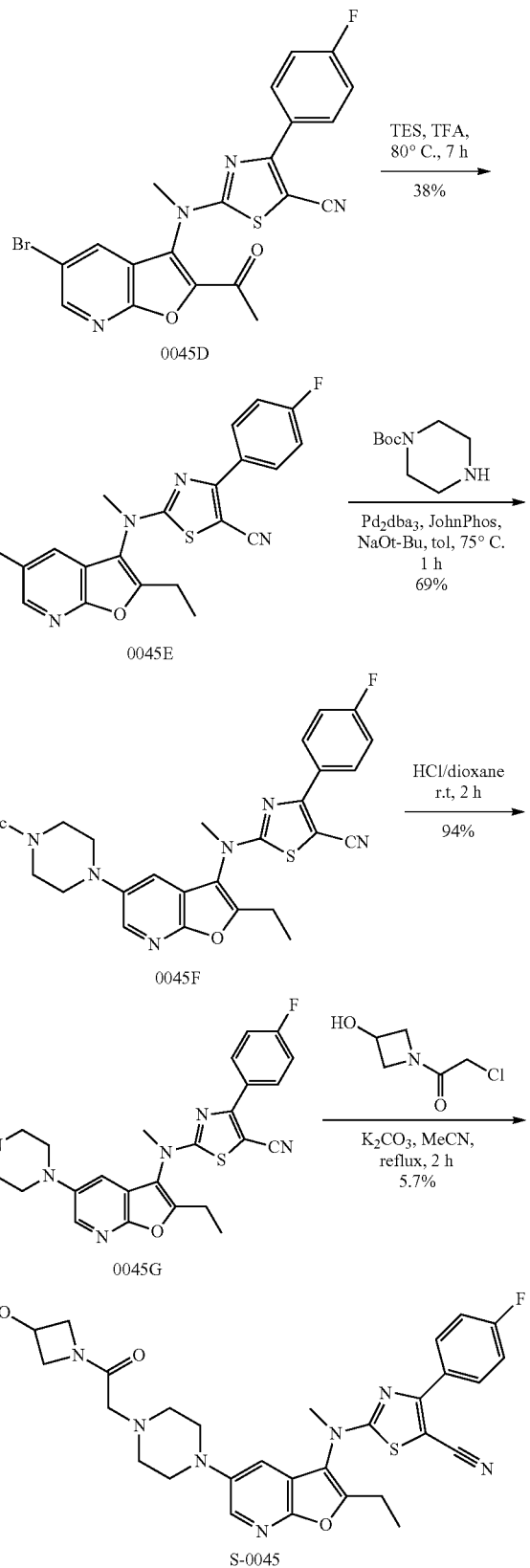

Step 1: 5-bromo-2-fluoronicotinaldehyde oxime

Hydroxylamine hydrochloride (383 mg, 5.5 mmol) and sodium carbonate (583 mg, 5.5 mmol) were dissolved in a mixture of ethanol (20 mL) and water (10 mL), and then 5-bromo-2-fluoronicotine (1.08 g, 5 mmol) was added. The reaction solution was stirred at room temperature for 1 h and diluted with water (100 mL), and ethyl acetate (150 mL×2) was added for extraction. The organic phases were combined, washed with saturated brine (100 mL×2), dried over anhydrous sodium sulfate, filtered, and concentrated to give 5-bromo-2-fluoronicotinaldehyde oxime in the form of a white solid (920 mg, 84%), which was directly used in the next step without purification. LCMS (ESI) $[M+H]^+$=218.9.

Step 2: 5-bromo-2-fluoronicotinonitrile

Phosphorus oxychloride (5.18 g, 33.79 mmol) was added to a solution of 5-bromo-2-fluoronicotinaldehyde oxime (920 mg, 4.22 mmol) in chloroform (50 mL), and the reaction solution was heated to 75° C., stirred for 5 h, and concentrated. A sodium carbonate solution was added to adjust pH of the residue to 7-8, and then ethyl acetate (100 mL×2) was added for extraction. The organic phases were combined, washed with saturated brine (100 mL×2), dried over anhydrous sodium sulfate, filtered, and concentrated to give 5-bromo-2-fluoronicotinonitrile in the form of a pink solid (710 mg, 84%), which was directly used in the next step without purification.

Step 3: 1-(3-amino-5-bromofuro[2,3-b]pyridin-2-yl)ethanone 1-hydroxyacetone (261 mg, 3.53 mmol) was added to a solution of 5-bromo-2-fluoronicotinonitrile (710 mg, 3.53 mmol) and cesium carbonate (2.30 g, 7 mmol) in N, N-dimethylformamide (8 mL), and the reaction solution was stirred at room temperature for 1 h. Then the reaction solution was diluted with ethyl acetate, washed with saturated brine (10 mL×2) and water (100 mL), dried over anhydrous sodium sulfate, filtered and concentrated. The residue was purified by flash chromatography (ethyl acetate/petroleum ether=0%-30%) to give 1-(3-amino-5-bromofuro [2,3-b]pyridin-2-yl)ethanone in the form of a yellow solid (332 mg, 37%). LCMS (ESI) $[M+H]^+$=256.9.

Step 4: 2-((2-acetyl-5-bromofuro[2,3-b]pyridin-3-yl)(methyl)amino)-4-(4-fluorophenyl) thiazole-5-carbonitrile Sodium hydride (60% in oil, 156 mg, 3.9 mmol) was slowly added to a solution of 1-(3-amino-5-bromofuro[2,3-b]pyridin-2-yl)ethanone (332 mg, 1.3 mmol) in N,N-dimethylformamide (4 mL), and the mixture was stirred at room temperature for 0.5 h. Then 2-chloro-4-(4-fluorophenyl) thiazole-5-carbonitrile (310 mg, 1.3 mmol) was added, and the mixture was further stirred at room temperature for 1 h. Then methyl iodide (370 mg, 2.6 mmol) was added, and the mixture was further stirred at room temperature for 3 h. The reaction was quenched with water (50 mL), and ethyl acetate (50 mL×2) was added for extraction. The organic phases were combined, washed with saturated brine (50 mL×2), dried over anhydrous sodium sulfate, filtered and concentrated. The residue was purified by flash chromatography (ethyl acetate/petroleum ether=0%-35%) to give 2-((2-acetyl-5-bromofuro[2,3-b]pyridin-3-yl) (methyl)amino)-4-(4-fluorophenyl)thiazole-5-carbonitrile in the form of a yellow solid (173 mg, 28%). LCMS (ESI) $[M+H]^+$=472.6.

Step 5: 2-((5-bromo-2-ethylfuro[2,3-b]pyridin-3-yl)(methyl)amino)-4-(4-fluorophenyl) thiazole-5-carbonitrile A mixture of 2-((2-acetyl-5-bromofuro[2,3-b]pyridin-3-yl)(methyl)amino)-4-(4-fluorophenyl)thiazole-5-carbonitrile (173 mg, 0.367 mmol), trifluoroacetic acid (1.5 mL) and triethylsilane (1.5 mL) was stirred at 80° C. for 7 h, and then concentrated under vacuum. The residue was diluted with ethyl acetate (50 mL), washed with water (50 mL×2), dried over anhydrous sodium sulfate, filtered and concentrated. The residue was purified by flash chromatography (ethyl acetate/petroleum ether=0%-35%) to give 2-((5-bromo-2-ethylfuro [2,3-b]pyridin-3-yl)(methyl)amino)-4-(4-fluorophenyl)thiazole-5-carbonitrile in the form of a yellow solid (64 mg, 38.1%). LCMS (ESI) $[M+H]^+$=456.8.

Step 6: tert-butyl 4-(3-((5-cyano-4-(4-fluorophenyl)thiazol-2-yl)(methyl)amino)-2-ethylfuro[2,3-b]pyridin-5-yl)piperazine-1-carboxylate In a glove box, 2-((5-bromo-2-ethylfuro[2,3-b]pyridin-3-yl)(methyl)amino)-4-(4-fluorophenyl)thiazole-5-carbonitrile (63 mg, 0.137 mmol), tert-butyl piperazine-1-carboxylate (51 mg, 0.275 mmol), tris(dibenzylideneacetone) dipalladium(0) (6.29 mg, 0.007 mmol), 2-(di-tert-butylphosphino)biphenyl (4.1 mg, 0.014 mmol), sodium tert-butoxide (33 mg, 0.344 mmol) and toluene (3 mL) were mixed in a microwave tube. The reaction solution was heated to 75° C., stirred for 1 h, and then cooled to room temperature. Then the reaction solution was diluted with ethyl acetate (50 mL), washed with saturated brine (50 mL×2), dried over anhydrous sodium sulfate, filtered and concentrated. The residue was purified by flash chromatography (ethyl acetate/petroleum ether=0%-30%) to give tert-butyl 4-(3-((5-cyano-4-(4-fluorophenyl)thiazol-2-yl)(methyl)amino)-2-ethylfuro[2,3-b]pyridin-5-yl) piperazine-1-carboxylate in the form of a yellow solid (53 mg, 69%). LCMS (ESI) $[M+H]^+$=563.0.

Step 7: 2-((2-ethyl-5-(piperazin-1-yl)furo[2,3-b]pyridin-3-yl)(methyl)amino)-4-(4-fluorophenyl)thiazole-5-carbonitrile A mixture solution of tert-butyl 4-(3-((5-cyano-4-(4-fluorophenyl)thiazol-2-yl)(methyl) amino)-2-ethylfuro[2,3-b] pyridin-5-yl)piperazine-1-carboxylate (53 mg, 0.094 mmol) and hydrogen chloride (4 N in dioxane, 1 mL) was stirred at room temperature for 2 h and then concentrated. A sodium carbonate solution (30 mL) was added to adjust pH to low alkalinity, and dichloromethane (30 mL×2) was added for extraction. The organic phases were combined, washed with saturated brine (10 mL×2), dried over anhydrous sodium sulfate, filtered, and concentrated to give 2-((2-ethyl-5-(piperazin-1-yl)furo[2,3-b]pyridin-3-yl)(methyl) amino)-4-(4-fluorophenyl)thiazole-5-carbonitrile in the form of a yellow solid (41 mg, 94%), which was directly used in the next step without purification. LCMS (ESI) $[M+H]^+$=463.0.

Step 8: 2-((2-ethyl-5-(4-(2-(3-hydroxyazetidin-1-yl)-2-oxoethyl)piperazin-1-yl)furo [2,3-b]pyridin-3-yl)(methyl)amino)-4-(4-fluorophenyl)thiazole-5-carbonitrile 2-chloro-1-(3-hydroxyazetidin-1-yl)acetyl (19.8 mg, 0.133 mmol) and potassium carbonate (37 mg, 0.266 mmol)

were added to a solution of 2-((2-ethyl-5-(piperazin-1-yl)furo[2,3-b]pyridin-3-yl)(methyl)amino)-4-(4-fluorophenyl)thiazole-5-carbonitrile (41 mg, 0.089 mmol) in acetonitrile (5 mL), and the reaction solution was heated to reflux for 2 h and then concentrated. The residue was purified by Pre-HPLC to give 2-((2-ethyl-5-(4-(2-(3-hydroxyazetidin-1-yl)-2-oxoethyl)piperazin-1-yl)furo[2,3-b]pyridin-3-yl)(methyl)amino)-4-(4-fluorophen yl)thiazole-5-carbonitrile in the form of a white solid (2.9 mg, 5.7%). LCMS (ESI) [M+H]+=576.0. H NMR (400 MHz, CD$_3$OD) δ 8.16-8.12 (m, 2H), 8.06 (d, J=2.4 Hz, 1H), 7.52 (d, J=2.4 Hz, 1H), 7.27-7.22 (m, 2H), 4.62-4.56 (m, 1H), 4.55-4.46 (m, 1H), 4.26-4.21 (m, 1H), 4.10-4.06 (m, 1H), 3.81-3.77 (m, 1H), 3.66 (s, 3H), 3.33-3.32 (m, 4H), 3.14 (d, J=3.6 Hz, 2H), 2.85 (q, J=7.5 Hz, 2H), 2.71-2.69 (m, 4H), 1.38 (t, J=7.6 Hz, 4H).

Example 12. S-0046: 2-((2-ethyl-5-(4-(2-(3-hydroxyazetidin-1-yl)-2-oxoethyl) piperazin-1-yl)furo[2,3-c]pyridin-3-yl)(methyl)amino)-4-(4-fluorophenyl)thiazole-5-carbonitrile

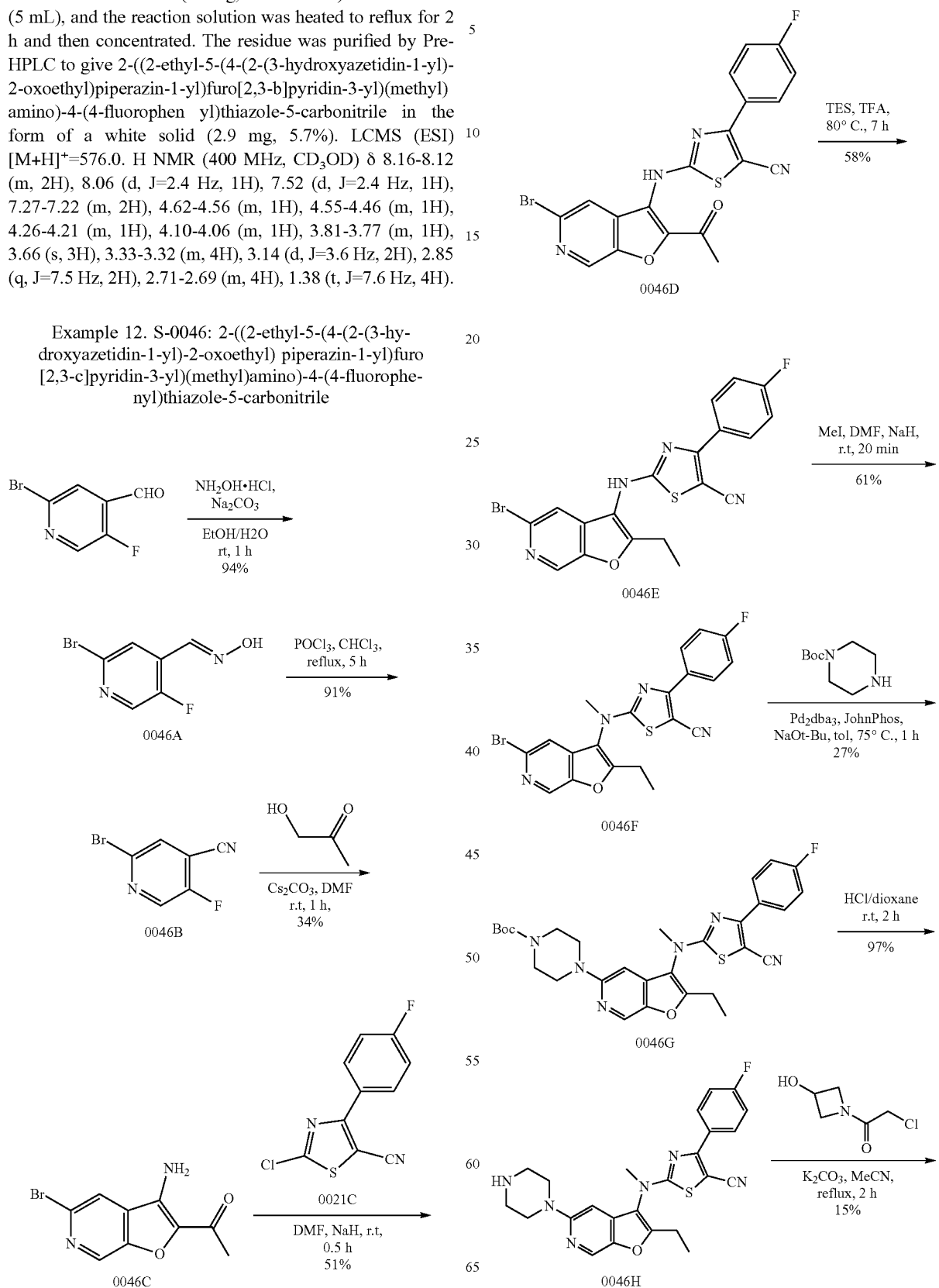

-continued

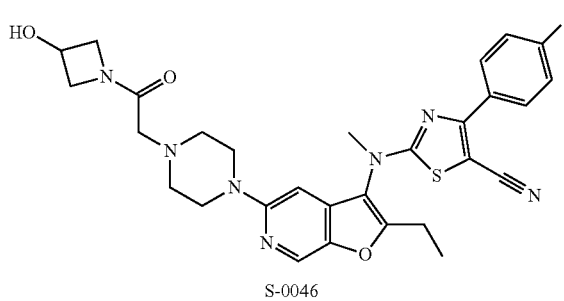

S-0046

Step 1: 2-bromo-5-fluoroisonicotinaldehyde oxime

Hydroxylamine hydrochloride (281 mg, 4.04 mmol) and sodium carbonate (429 mg, 4.04 mmol) were dissolved in a mixture of ethanol (20 mL) and water (10 mL), then 2-bromo-5-fluoroisonicotine (750 mg, 3.68 mmol) was added, and the mixture was stirred at room temperature for 1 h. The reaction solution was diluted with water (100 mL), and ethyl acetate (150 mL×2) was added for extraction. The organic phases were combined, washed with saturated brine (100 mL×2), dried over anhydrous sodium sulfate, filtered, and concentrated to give 2-bromo-5-fluoroisonicotinaldehyde oxime in the form of a yellow solid (754 mg, 94%), which was directly used in the next step without purification. LCMS (ESI) [M+H]$^+$=218.9.

Step 2: 2-bromo-5-fluoroisonicotinonitrile

Phosphorus oxychloride (4.24 g, 27.67 mmol) was added to a solution of 2-bromo-5-fluoroisonicotinaldehyde oxime (754 mg, 3.45 mmol) in chloroform (50 mL), and the reaction solution was heated to reflux for 5 h, and concentrated. A sodium carbonate solution was added to adjust pH of the residue to 7-8, and then ethyl acetate (100 mL×2) was added for extraction. The organic phases were combined, washed with saturated brine (100 mL×2), dried over anhydrous sodium sulfate, filtered, and concentrated to give 2-bromo-5-fluoroisonicotinonitrile in the form of a brown oil (637 mg, 91.8%), which was directly used in the next step without purification.

Step 3: 1-(3-amino-5-bromofuro[2,3-c]pyridin-2-yl) ethanone 1-hydroxyacetone (235 mg, 3.17 mmol) was added to a solution of 2-bromo-5-fluoroisonicotinonitrile (637 mg, 3.17 mmol) and cesium carbonate (2.06 g, 6.34 mmol) in N,N-dimethylformamide (5 mL), and the mixture was stirred at room temperature for 1 h. The reaction solution was diluted with ethyl acetate (150 mL), washed with saturated brine (100 mL×2) and water (100 mL), dried over anhydrous sodium sulfate, filtered and concentrated. The residue was purified by flash chromatography (ethyl acetate/petroleum ether=0%-30%) to give 1-(3-amino-5-bromofuro[2,3-c]pyridin-2-yl)ethanone in the form of a yellow solid (271 mg, 34%). LCMS (ESI) [M+H]$^+$=256.9.

Step 4: 2-(2-acetyl-5-bromofuro[2,3-c]pyridin-3-ylamino)-4-(4-fluorophenyl)thiazole-5-carbonitrile Sodium hydride (60% in oil, 85 mg, 2.13 mmol) was slowly added to a solution of 1-(3-amino-5-bromofuro[2,3-c]pyridin-2-yl)ethanone (271 mg, 1.07 mmol) in N,N-dimethylformamide (3 mL), and the mixture was stirred at room temperature for 15 min. Then 2-chloro-4-(4-fluorophenyl)thiazole-5-carbonitrile (255 mg, 1.07 mmol) was added, and the resulting mixture was further stirred at room temperature for 0.5 h. The reaction was quenched with water (50 mL), and ethyl acetate (50 mL×2) was added for extraction. The organic phases were combined, washed with saturated brine (50 mL×2), dried over anhydrous sodium sulfate, filtered and concentrated. The residue was purified by flash chromatography (ethyl acetate/petroleum ether=0%-40%) to give 2-(2-acetyl-5-bromofuro[2,3-c]pyridin-3-ylamino)-4-(4-fluorophenyl)thiazole-5-carbonitrile in the form of a yellow solid (251 mg, 51.4%). LCMS (ESI) [M+H]$^+$=458.8.

Step 5: 2-(5-bromo-2-ethylfuro[2,3-c]pyridin-3-ylamino)-4-(4-fluorophenyl)thiazole-5-carbonitrile A mixture of 2-(2-acetyl-5-bromofuro[2,3-c]pyridin-3-ylamino)-4-(4-fluorophenyl) thiazole-5-carbonitrile (251 mg, 0.548 mmol), trifluoroacetic acid (1.5 mL) and triethylsilane (1.5 mL) was stirred at 80° C. for 7 h, and then concentrated under vacuum. The residue was diluted with ethyl acetate (50 mL), washed with water (50 mL×2), dried over anhydrous sodium sulfate, filtered and concentrated. The residue was purified by flash chromatography (ethyl acetate/petroleum ether=0%-30%) to give 2-(5-bromo-2-ethylfuro[2,3-c]pyridin-3-ylamino)-4-(4-fluorophenyl)thiazole-5-carbonitrile in the form of a yellow solid (141 mg, 58%). LCMS (ESI) [M+H]$^+$=442.8.

Step 6: 2-((5-bromo-2-ethylfuro[2,3-c]pyridin-3-yl)(methyl)amino)-4-(4-fluorophenyl) thiazole-5-carbonitrile Sodium hydride (60% in oil, 13 mg, 0.328 mmol) was slowly added to a solution of 2-(5-bromo-2-ethylfuro[2,3-c]pyridin-3-ylamino)-4-(4-fluorophenyl)thiazole-5-carbonitrile (97 mg, 0.218 mmol) in N,N-dimethylformamide (4 mL), and the mixture was stirred at room temperature for 10 min. Then methyl iodide (31 mg, 0.218 mmol) was added, and the resulting mixture was further stirred at room temperature for 20 min. The reaction was quenched with water (50 mL), and ethyl acetate (50 mL×2) was added for extraction. The organic phases were combined, washed with saturated brine (50 mL×2), dried over anhydrous sodium sulfate, filtered and concentrated. The residue was purified by flash chromatography (ethyl acetate/petroleum ether=0%-35%) to give 2-((5-bromo-2-ethylfuro[2,3-c]pyridin-3-yl) (methyl)amino)-4-(4-fluorophenyl)thiazole-5-carbonitrile in the form of a yellow solid (61 mg, 61%). LCMS (ESI) [M+H]$^+$=456.8.

Step 7: tert-butyl 4-(3-((5-cyano-4-(4-fluorophenyl) thiazol-2-yl)(methyl)amino)-2-ethylfuro[2,3-c]pyridin-5-yl)piperazine-1-carboxylate In a glove box, 2-((5-bromo-2-ethylfuro[2,3-c]pyridin-3-yl)(methyl)amino)-4-(4-fluorophenyl)thiazole-5-carbonitrile (61 mg, 0.133 mmol), tert-butyl piperazine-1-carboxylate (50 mg, 0.269 mmol), tris(dibenzylideneacetone)dipalladium(0) (6.40 mg, 0.007 mmol), 2-(di-tert-butylphosphino)biphenyl (4.0 mg, 0.013 mmol), sodium tert-butoxide (32 mg, 0.333 mmol) and toluene (3 mL) were mixed in a microwave tube. The reaction solution was heated to 75° C., stirred for 1 h, and then cooled to room temperature. Then the reaction solution was diluted with ethyl acetate (50 mL), washed with saturated brine (50 mL×2), dried over anhydrous sodium sulfate, filtered and concentrated. The residue was purified by flash chromatography (ethyl acetate/petroleum ether=0%-30%) to give tert-butyl 4-(3-((5-cyano-4-(4-fluorophenyl)thiazol-2-yl)(methyl)amino)-2-ethylfuro[2,3-c]pyridin-5-yl) piperazine-1-carboxylate in the form of a yellow solid (20 mg, 27%). LCMS (ESI) [M+H]$^+$=563.3.

Step 8: 2-((2-ethyl-5-(piperazin-1-yl)furo[2,3-c]pyridin-3-yl)(methyl)amino)-4-(4-fluorophenyl)thiazole-5-carbonitrile A mixture solution of tert-butyl 4-(3-((5-cyano-4-(4-fluorophenyl)thiazol-2-yl)(methyl) amino)-2-ethylfuro[2,3-c]pyridin-5-yl)piperazine-1-carboxylate (20 mg, 0.036 mmol) and hydrogen chloride (4 N in dioxane, 1 mL) in dichloromethane (2 mL) was stirred at room temperature for 2 h and then concentrated. A sodium carbonate solution (30 mL) was added to adjust pH to low alkalinity. Dichloromethane (30 mL×2) was added for extraction. The organic phases were combined, washed with saturated brine (10 mL×2), dried over anhydrous sodium sulfate, filtered, and concentrated to give 2-((2-ethyl-5-(piperazin-1-yl)furo[2,3-c]pyridin-3-yl)(methyl)amino)-4-(4-fluorophenyl)thiazole-5-carbonitrile in the form of a yellow solid (16 mg, 97%), which was directly used in the next step without purification. LCMS (ESI) [M+H]$^+$=463.0.

Step 9: 2-((2-ethyl-5-(4-(2-(3-hydroxyazetidin-1-yl)-2-oxoethyl)piperazin-1-yl)furo [2,3-c]pyridin-3-yl)(methyl)amino)-4-(4-fluorophenyl)thiazole-5-carbonitrile 2-chloro-1-(3-hydroxyazetidin-1-yl)acetyl (10 mg, 0.0693 mmol) and potassium carbonate (14.4 mg, 0.104 mmol) were added to a solution of 2-((2-ethyl-5-(piperazin-1-yl) furo[2,3-c]pyridin-3-yl)(methyl)amino)-4-(4-fluorophenyl)thiazole-5-carbonitrile (16 mg, 0.035 mmol) in acetonitrile (5 mL), and the reaction solution was heated to reflux for 2 h and then concentrated. The residue was purified by Pre-HPLC to give 2-((2-ethyl-5-(4-(2-(3-hydroxyazetidin-1-yl)-2-oxoethyl)piperazin-1-yl)furo[2,3-c]pyridin-3-yl)(methyl)amino)-4-(4-fluorophenyl)thiazole-5-carbonitrile (S-0046) in the form of a white solid (3.0 mg, 15%). LCMS (ESI) [M+H]+=576.0. $^1$HNMR (400 MHz, CD$_3$OD) δ 8.43 (s, 1H), 8.14 (dd, J=8.7, 5.4 Hz, 2H), 7.25 (t, J=8.7 Hz, 2H), 6.78 (s, 1H), 4.60-4.57 (m, 1H), 4.53-4.49 (m, 1H), 4.26-4.22 (m, 1H), 4.10-4.07 (m, 1H), 3.81-3.77 (m, 1H), 3.65 (s, 3H), 3.52 (m, 4H), 3.11 (d, J=3.2 Hz, 2H), 2.84 (q, J=7.6 Hz, 2H), 2.65-2.63 (m, 4H), 1.37 (t, J=7.6 Hz, 3H).

Example 13. S-0027: 4-(3,4-difluorophenyl)-2-((2-ethyl-7-fluoro-5-(4-(2-(3-hydroxyazetidin-1-yl)-2-oxoethyl)piperazin-1-yl)-2H-indazol-3-yl)(methyl) amino) thiazole-5-carbonitrile

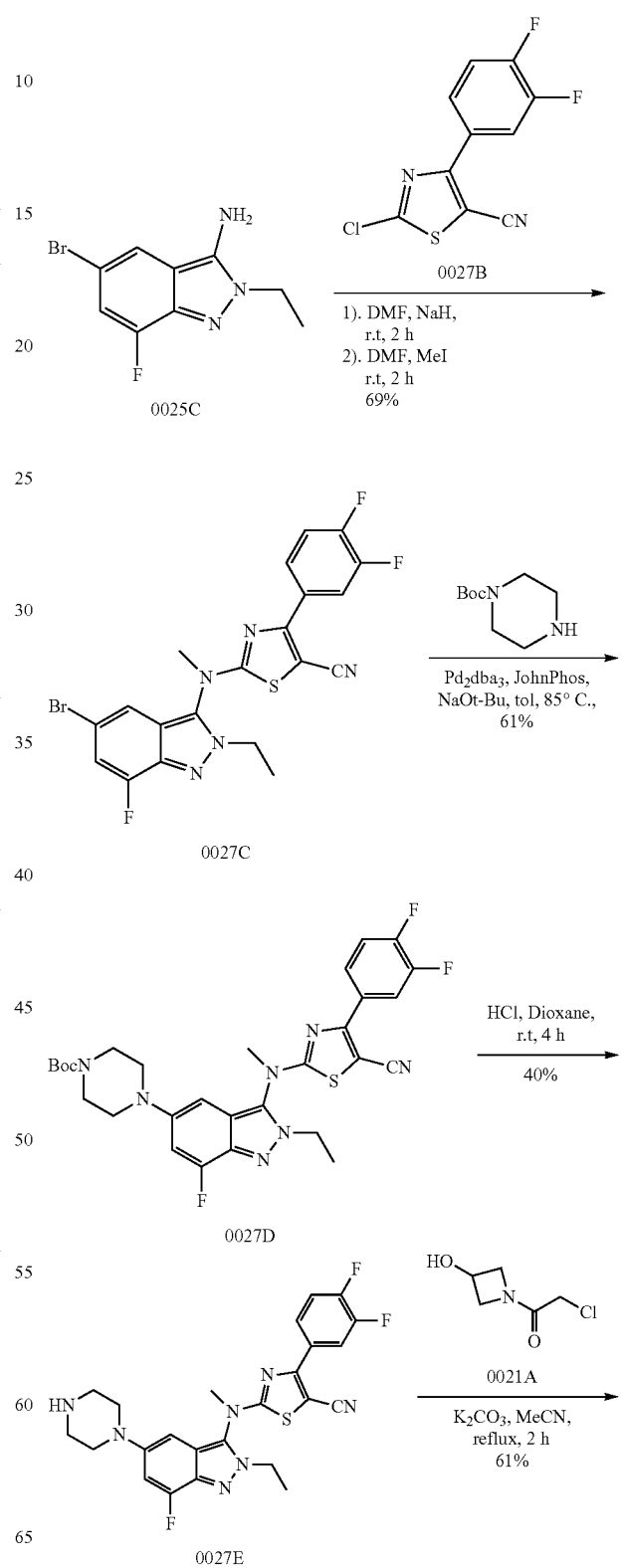

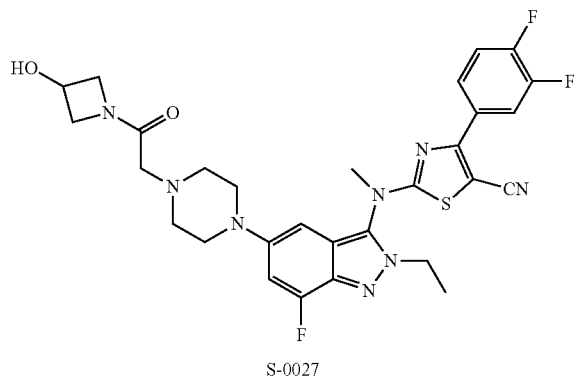

S-0027

The synthesis procedure is similar to S-0025. 0027C: LCMS (ESI) [M+H]$^+$=492, 0027D: LCMS (ESI) [M+H]$^+$=598, 0027E: LCMS (ESI) [M+H]$^+$=498, S-0027: LCMS (ESI) [M+H]$^+$=610; H NMR (400 MHz, CD$_3$OD) δ 7.97-8.01 (m, 2H), 7.43-7.45 (m, 1H), 7.02-7.06 (m, 1H), 6.55 (d, J=2.0 Hz, 1H), 4.06-4.58 (m, 6H), 3.79-3.80 (m, 1H), 3.71 (s, 3H), 3.13-3.21 (m, 6H), 2.66-2.69 (m, 4H), 1.57 (t, J=7.6 Hz, 3H).

Example 14. S-0029: 2-(4-(2-ethyl-7-fluoro-3-((3-(4-fluorophenyl)-1,2,4-thiadiazol-5-yl)(methyl)amino)-2H-indazol-5-yl)piperazin-1-yl)-1-(3-hydroxyazetidin-1-yl)ethyl-1-one

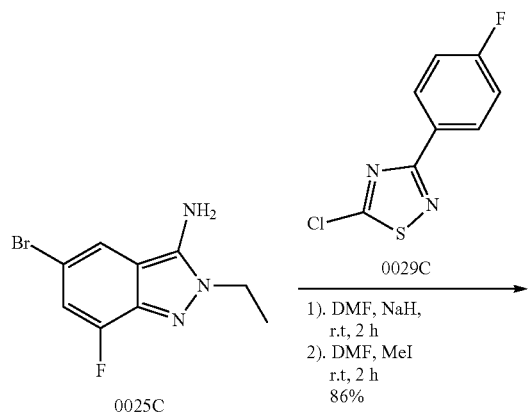

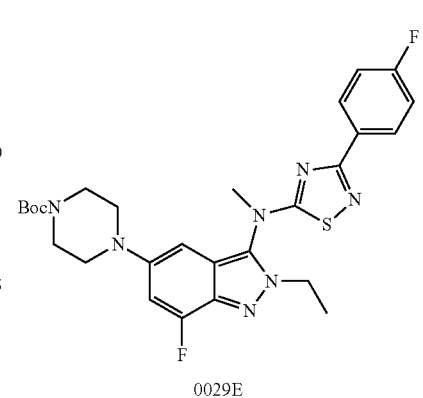

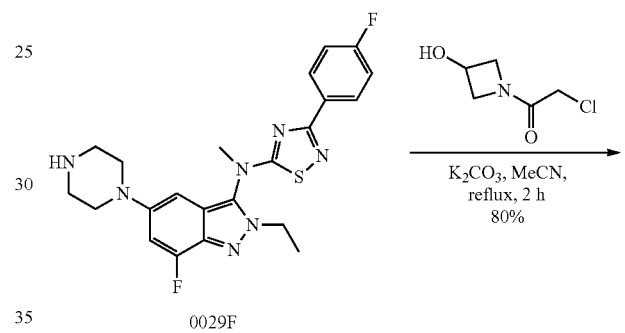

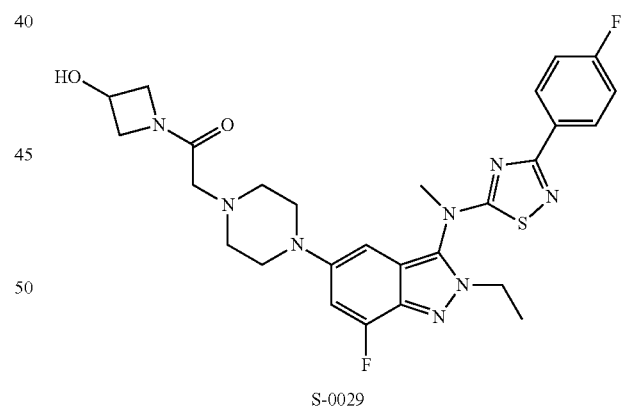

S-0029

The synthesis procedure is similar to S-0025. 0029D: LCMS (ESI) [M+H]$^+$=450, 0029E: LCMS (ESI) [M+H]$^+$=556, 0029F: LCMS (ESI) [M+H]$^+$=456, S-0029: LCMS (ESI) [M+H]$^+$=569; 1H NMR (400 MHz, CD$_3$OD) δ 8.19-8.26 (m, 2H), 7.15-7.27 (m, 2H), 7.01-7.06 (m, 1H), 6.55 (d, J=2.0 Hz, 1H), 4.05-4.59 (m, 6H), 3.75-3.80 (m, 1H), 3.74 (s, 3H), 3.11-3.21 (m, 6H), 2.65-2.69 (m, 4H), 1.56 (t, J=7.6 Hz, 3H).

155

Example 15. S-0080: 2-(4-(2-ethyl-7-fluoro-3-((4-(4-fluorophenyl)pyrimidin-2-yl) (methyl)amino)-2H-indazol-5-yl)piperazin-1-yl)-1-(3-hydroxyazetidin-1-yl)ethyl-1-one

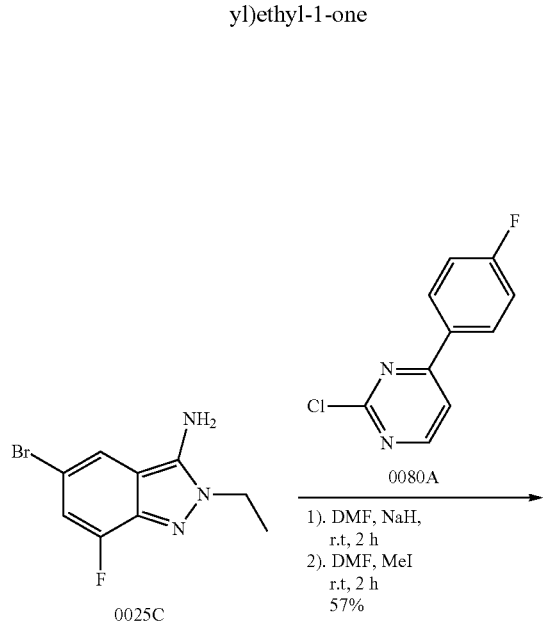

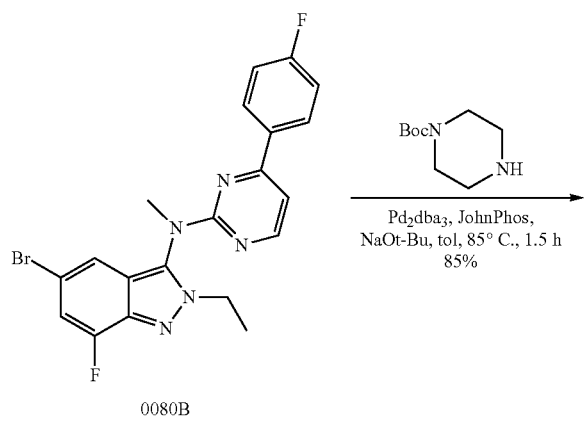

156

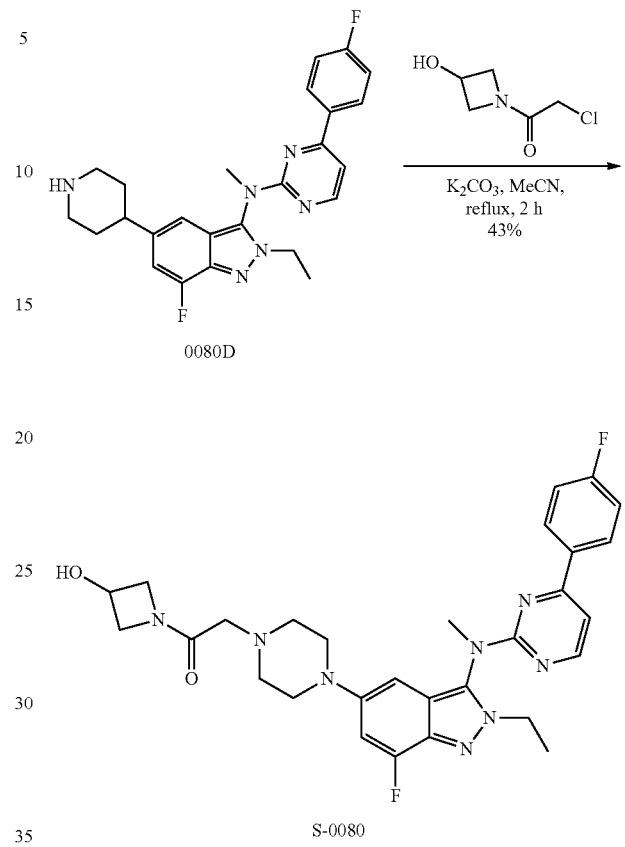

The synthesis procedure is similar to S-0025. 0080B: LCMS (ESI) [M+H]⁺=444, 0080C: LCMS (ESI) [M+H]⁺=550, 0080D: LCMS (ESI) [M+H]⁺=450, S-0080: LCMS (ESI) [M+H]⁺=563; 1H NMR (400 MHz, CD₃OD) δ 8.42-8.44 (m, 1H), 8.09-8.11 (m, 2H), 7.37-7.39 (m, 1H), 7.18-7.22 (m, 2H), 6.96-7.00 (m, 1H), 6.52-6.55 (m, 1H), 4.05-4.59 (m, 6H), 3.74-3.80 (m, 1H), 3.67 (s, 3H), 3.11-3.21 (m, 6H), 2.63-2.69 (m, 4H), 1.49 (t, J=7.6 Hz, 3H).

Example 16. S-0040: 2-((2-ethyl-5-(4-(2-(3-hydroxyazetidin-1-yl)-2-oxoethyl) piperazin-1-yl)pyrazolo[1,5-a]pyridin-3-yl)(methyl)amino)-4-(4-fluorophenyl)thiazole-5-carbonitrile

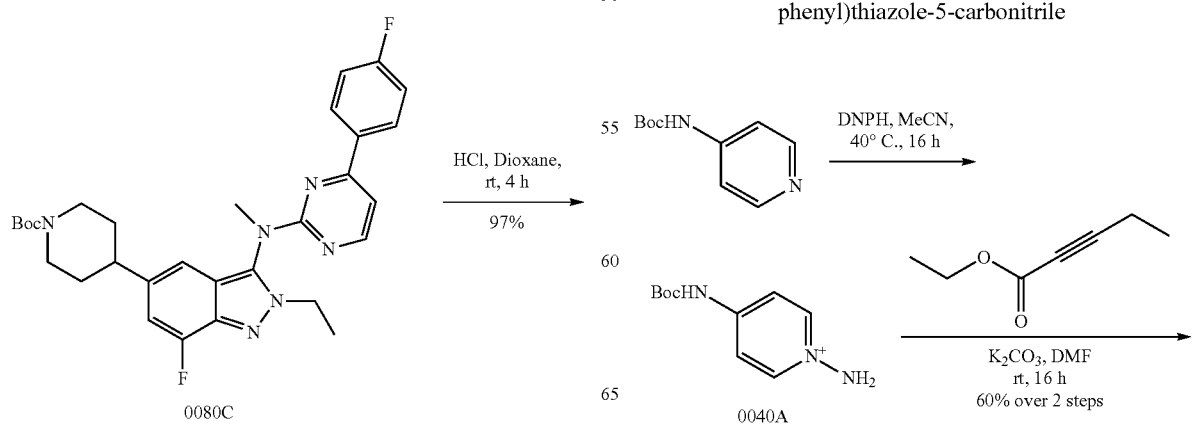

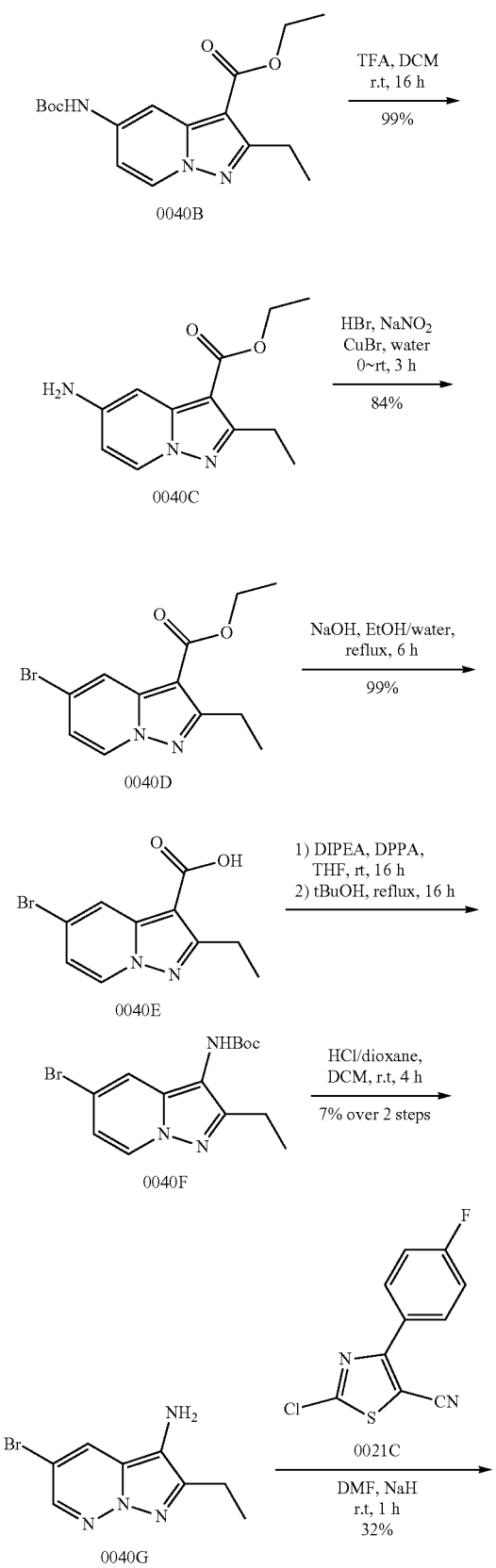
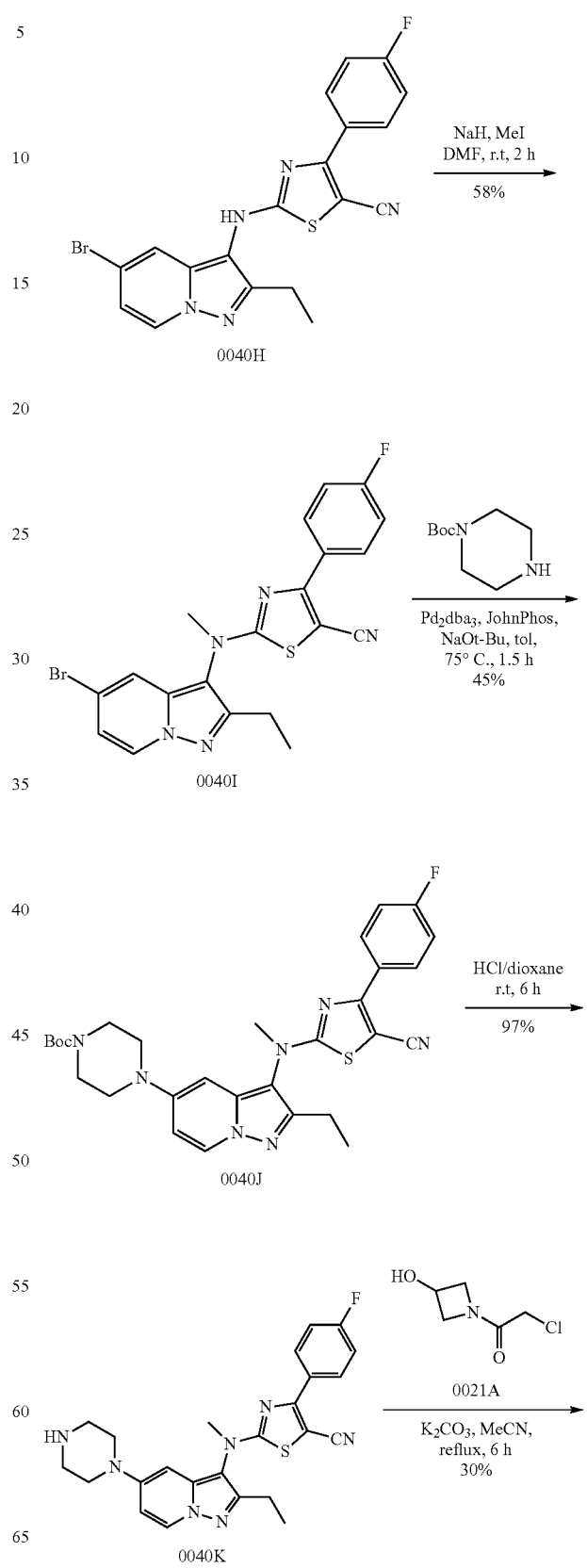

-continued

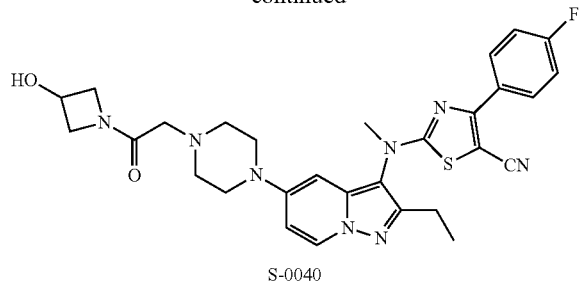

S-0040

Step 1: ethyl 5-(tert-butoxycarbonylamino)-2-ethylpyrazolo[1,5-a]pyridine-3-carboxylate 2,4-dinitrophenylhydroxylamine (199 mg, 1 mmol) was added to a solution of 4-tert-butoxycarbonylaminopyridine (194 mg, 1 mmol) in acetonitrile (10 mL), and the mixture was heated to 40° C., stirred for 16 h, and then concentrated. The residue was diluted with N,N-dimethylformamide (5 mL), then ethyl 2-pentynoate (126 mg, 1 mmol) and potassium carbonate (276 mg, 2 mmol) were added, and the resulting mixture was further stirred at room temperature for 16 h. Ethyl acetate (20 mL×3) was added for extraction, and the organic phases were combined, washed with water (20 mL×3), dried over anhydrous sodium sulfate, filtered and concentrated. The residue was purified by flash chromatography (ethyl acetate/petroleum ether=0%-30%) to give ethyl 5-(tert-butoxycarbonylamino)-2-ethylpyrazolo[1,5-a]pyridine-3-carboxylate in the form of a yellow solid (200 mg, 60%). LCMS (ESI) [M+H]$^+$=334.

Step 2: ethyl 5-amino-2-ethylpyrazolo[1,5-a]pyridine-3-carboxylate

Trifluoroacetic acid (2 mL) was added to a solution of ethyl 5-(tert-butoxycarbonylamino)-2-ethylpyrazolo[1,5-a]pyridine-3-carboxylate (200 mg, 0.6 mmol) in dichloromethane (10 mL), and the mixture was stirred at room temperature for 16 h. The reaction was quenched with a sodium carbonate solution (20 mL). Dichloromethane (30 mL×3) was added for extraction. The organic phases were combined, dried over anhydrous sodium sulfate, filtered, and concentrated to give ethyl 5-amino-2-ethylpyrazolo[1,5-a]pyridine-3-carboxylate in the form of a yellow solid (140 mg, 99%), which was directly used in the next step without purification. LCMS (ESI) [M+H]$^+$=234.

Step 3: ethyl 5-bromo-2-ethylpyrazolo[1,5-a]pyridine-3-carboxylate

At 0° C., water (2 mL) and cuprous bromide (255 mg, 1.8 mmol) were added to a mixture of ethyl 5-amino-2-ethylpyrazolo[1,5-a]pyridine-3-carboxylate (140 mg, 0.6 mmol) and hydrobromic acid (33% in acetic acid, 4 mL), and the reaction solution was heated to room temperature, stirred for 10 min, and then cooled to 0° C. A solution of sodium nitrite (69 mg, 1 mmol) in water (2 mL) was slowly added dropwise. The reaction solution was further stirred at room temperature for 3 h, then an aqueous sodium hydroxide solution was added to adjust pH to 10, and ethyl acetate (30 mL×3) was added for extraction. The organic phases were combined, washed with water (20 mL×3), dried over anhydrous sodium sulfate, filtered and concentrated. The residue was purified by flash chromatography (ethyl acetate/petroleum ether=0%-25%) to give ethyl 5-bromo-2-ethylpyrazolo[1,5-a]pyridine-3-carboxylate in the form of a yellow oil (150 mg, 84%). LCMS (ESI) [M+H]$^+$=297.

Step 4: 5-bromo-2-ethylpyrazolo[1,5-a]pyridine-3-carboxylic acid

Sodium hydroxide (60 mg, 1.5 mmol) was added to a solution of ethyl 5-bromo-2-ethylpyrazolo[1,5-a]pyridine-3-carboxylate (150 mg, 0.5 mmol) in ethanol (9 mL) and water (3 mL), and the reaction solution was heated to reflux for 6 h, and concentrated. The residue was neutralized with a hydrochloric acid solution (1 N, 15 mL). The precipitated solid was filtered out and washed with water (10 mL) to give 5-bromo-2-ethylpyrazolo[1,5-a]pyridine-3-carboxylic acid in the form of a yellow solid (135 mg, 99%). LCMS (ESI) [M+H]$^+$=269.

Step 5: 5-bromo-2-ethylpyrazolo[1,5-a]pyridin-3-tert-butoxycarbonylamino

Diphenylphosphoryl azide (2.15 g, 7.83 mmol) and N,N-diisopropylethylamine (1.01 g, 7.83 mmol) were added to a solution of 5-bromo-2-ethylpyrazolo[1,5-a]pyridine-3-carboxylic acid (700 mg, 2.61 mmol) in tetrahydrofuran (15 mL), and the mixture was stirred at room temperature for 16 h. Then the mixture was concentrated, added with tert-butanol (20 mL), and heated to reflux for 16 h. The reaction solution was concentrated to give crude 5-bromo-2-ethylpyrazolo[1,5-a]pyridin-3-tert-butoxycarbonylamino in the form of a yellow oil (885 mg), which was directly used in the next step. LCMS (ESI) [M+H]$^+$=340.

Step 6: 5-bromo-2-ethylpyrazolo[1,5-a]pyridin-3-amine

Hydrogen chloride (4 N in dioxane, 5 mL) was added to a solution of 5-bromo-2-ethylpyrazolo[1,5-a]pyridin-3-tert-butoxycarbonylamino (885 mg, 2.61 mmol) in dichloromethane (5 mL), and the mixture was stirred at room temperature for 4 h. The reaction solution was concentrated, the residue was neutralized with a sodium carbonate solution (20 mL), and then dichloromethane (30 mL×3) was added for extraction. The organic phases were combined, dried over anhydrous sodium sulfate, filtered and concentrated. The residue was purified by Pre-TLC (ethyl acetate/petroleum ether=1/1) to give 5-bromo-2-ethylpyrazolo[1,5-a]pyridin-3-amine in the form of a yellow solid (45 mg, 7%). LCMS (ESI) [M+H]$^+$=240.

Step 7: 2-(5-bromo-2-ethylpyrazolo[1,5-a]pyridin-3-ylamino)-4-(4-fluorophenyl) thiazole-5-carbonitrile A solution of 5-bromo-2-ethylpyrazolo[1,5-a]pyridin-3-amine (50 mg, 0.21 mmol) and sodium hydride (60% in oil, 25 mg, 0.63 mmol) in N,N-dimethylformamide (3 mL) was stirred at room temperature for 10 min, then 2-chloro-4-(4-fluorophenyl)thiazole-5-carbonitrile (50 mg, 0.21 mmol) was added, and the reaction solution was further stirred at room temperature for 2 h. The reaction was quenched with water (10 mL), and dichloromethane (10 mL×3) was added for extraction. The organic phases were combined, washed with saturated brine (10 mL×2), dried over anhydrous sodium sulfate, filtered and concentrated. The residue was purified by flash chromatography (ethyl acetate/petroleum ether=0%-50%) to give 2-(5-bromo-2-ethylpyrazolo[1,5-a]

pyridin-3-ylamino)-4-(4-fluorophenyl)thiazole-5-carbonitrile in the form of a yellow solid (30 mg, 32%). LCMS (ESI) [M+H]⁺=442.

Step 8: 2-((5-bromo-2-ethylpyrazolo[1,5-a]pyridin-3-yl)(methyl)amino)-4-(4-fluorophenyl)thiazole-5-carbonitrile Sodium hydride (60% in oil, 8 mg, 0.2 mmol) was slowly added to a solution of 2-(5-bromo-2-ethylpyrazolo[1,5-a]pyridin-3-ylamino)-4-(4-fluorophenyl)thiazole-5-carbonitrile (30 mg, 0.068 mmol) in N, N-dimethylformamide (1 mL), and the mixture was stirred at room temperature for 10 min. Then methyl iodide (10 mg, 0.068 mmol) was added, and the mixture was further stirred at room temperature for 2 h. The reaction was quenched with water (10 mL), and ethyl acetate (10 mL×3) was added for extraction. The organic phases were combined, washed with saturated brine (10 mL×2), dried over anhydrous sodium sulfate, filtered and concentrated. The residue was purified by flash chromatography (ethyl acetate/petroleum ether=0%-30%) to give 2-((5-bromo-2-ethylpyrazolo[1,5-a]pyridin-3-yl) methylamino)-4-(4-fluorophenyl)thiazole-5-carbonitrile in the form of a yellow solid (18 mg, 58%). LCMS (ESI) [M+H]⁺=456.

Step 9: tert-butyl 4-(3-(5-cyano-4-(4-fluorophenyl) thiazol-2-yl)methylamino-2-ethylpyrazolo[1,5-a] pyridin-5-yl)piperazine-1-carboxylate In a glove box, 2-((5-bromo-2-ethylpyrazolo[1,5-a]pyridin-3-yl)methylamino)-4-(4-fluorophenyl)thiazole-5-carbonitrile (18 mg, 0.039 mmol), tert-butyl piperazine-1-carboxylate (22 mg, 0.12 mmol), tris(dibenzylideneacetone) dipalladium(0) (4 mg, 0.004 mmol), (±)-2,2'-bis (diphenylphosphino)-1,1'-binaphthyl (3 mg, 0.01 mmol), sodium tert-butoxide (19 mg, 0.2 mmol) and toluene (2 mL) were mixed in a microwave tube, and the reaction solution was heated to 75° C., stirred for 1.5 h, and concentrated. The residue was purified by flash chromatography (ethyl acetate/ petroleum ether 0%-40%) to give tert-butyl 4-(3-(5-cyano-4-(4-fluorophenyl)thiazol-2-yl)methylamino-2-ethylpyrazolo[1,5-a]pyridin-5-yl)piperazine-1-carboxylate in the form of a yellow oil (10 mg, 45%). LCMS (ESI) [M+H]+=562.

Step 10: 2-((2-ethyl-5-(piperazin-1-yl)pyrazolo[1,5-a]pyridin-3-yl)(methyl)amino)-4-(4-fluorophenyl) thiazole-5-carbonitrile A mixture solution of tert-butyl 4-(3-(5-cyano-4-(4-fluorophenyl)thiazol-2-yl) methylamino-2-ethylpyrazolo[1,5-a]pyridin-5-yl)piperazine-1-carboxylate (10 mg, 0.018 mmol) and hydrogen chloride (4 N in dioxane, 1 mL) was stirred at room temperature for 6 h and then concentrated. A sodium carbonate solution (10 mL) was added to adjust pH to low alkalinity, and dichloromethane (10 mL×3) was added for extraction. The organic phases were combined, washed with saturated brine (10 mL×2), dried over anhydrous sodium sulfate, filtered, and concentrated to give 2-((2-ethyl-5-(piperazin-1-yl)pyrazolo[1,5-a]pyridin-3-yl) (methyl) amino)-4-(4-fluorophenyl)thiazole-5-carbonitrile in the form of a yellow oil (8 mg, 97%). LCMS (ESI) [M+H]⁺=462.

Step 11: 2-((2-ethyl-5-(4-(2-(3-hydroxyazetidin-1-yl)-2-oxoethyl)piperazin-1-yl) pyrazolo[1,5-a]pyridin-3-yl)(methyl)amino)-4-(4-fluorophenyl)thiazole-5-carbonitrile 2-((2-ethyl-5-(piperazin-1-yl)pyrazolo[1,5-a]pyridin-3-yl)(methyl)amino)-4-(4-fluorophenyl)thiazole-5-carbonitrile (8 mg, 0.017 mmol), 2-chloro-1-(3-hydroxyazetidin-1-yl) acetyl (8 mg, 0.05 mmol) and potassium carbonate (12 mg, 0.086 mmol) were mixed in acetonitrile (3 mL), and the reaction solution was heated to reflux for 6 h, cooled to room temperature, filtered, and concentrated. The residue was purified by flash chromatography (methanol/dichloromethane=0%-8%) to give 2-((2-ethyl-5-(4-(2-(3-hydroxyazetidin-1-yl)-2-oxoethyl)piperazin-1-yl)pyrazolo[1,5-a]pyridin-3-yl)(methyl)amino)-4-(4-fluorophenyl)thiazole-5-carbonitrile (3 mg, 30%) in the form of a yellow solid. LCMS (ESI) [M+H]⁺=575; ¹H NMR (400 MHz, CD₃OD) δ 8.15 (d, J=7.6 Hz, 1H), 8.02-8.05 (m, 2H), 7.12-7.16 (m, 2H), 6.73 (dd, J=7.6 Hz, 1H), 6.39 (d, J=2.4 Hz, 1H), 4.45-4.49 (m, 2H), 3.96-4.10 (m, 2H), 3.53-3.55 (m, 1H), 3.49 (s, 3H), 3.23-3.27 (m, 4H), 3.01-3.02 (m, 2H), 2.60 (q, J=7.6 Hz, 2H), 2.53-2.58 (m, 4H), 1.24 (q, J=7.6 Hz, 3H).

Example 17. S-0068: 4-(3,4-difluorophenyl)-2-((2-ethyl-5-(4-(2-(3-hydroxyazetidin-1-yl)-2-oxoethyl) piperazin-1-yl)-7-methylpyrazolo[1,5-a]pyrimidin-3-yl)(methyl)amino) thiazole-5-carbonitrile

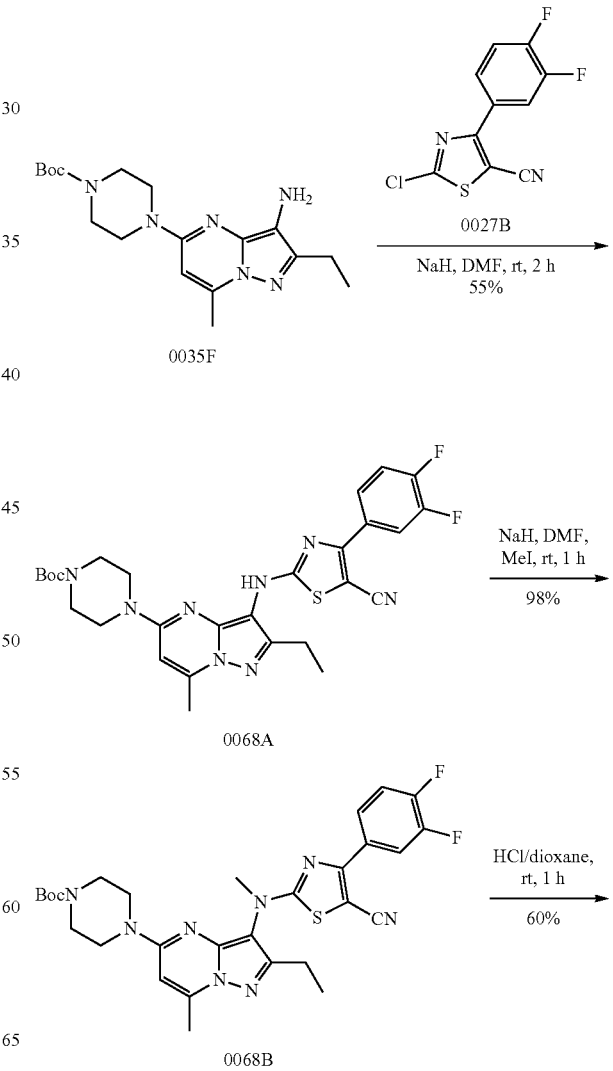

-continued
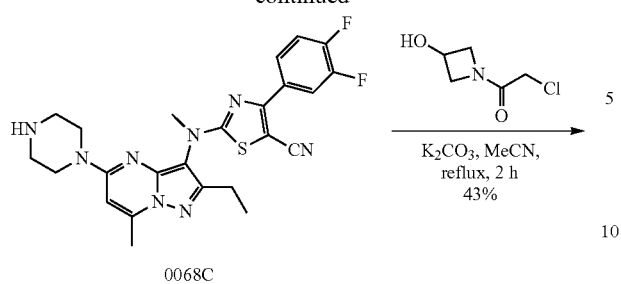
0068C
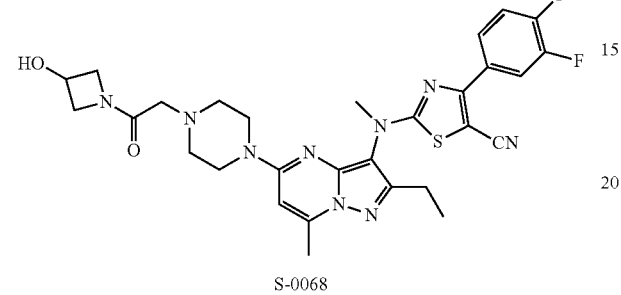
S-0068
The synthesis procedure is similar to S-0035. 0068A: LCMS (ESI) [M+H]⁺=581, 0068B: LCMS (ESI) [M+H]⁺=595, 0068C: LCMS (ESI) [M+H]⁺=495, S-0068: LCMS (ESI) [M+H]⁺=608. $^1$H NMR (400 MHz, CD$_3$OD) δ 7.950 (m, 1H), 7.415 (m, 1H), 6.613 (s, 1H), 4.570 (m, 1H), 4.522 (m, 1H), 4.211 (m, 1H), 4.050 (m, 1H), 3.745 (m, 5H), 3.605 (s, 3H), 3.113 (d, J=3.6 Hz, 1H), 2.714 (q, 2H), 2.668 (s, 3H), 2.575 (m, 4H), 1.306 (t, 3H).
Example 18. S-0030: 6-((2-ethyl-7-fluoro-5-(4-(2-(3-hydroxyazetidin-1-yl)-2-oxoethyl) piperazin-1-yl)-2H-indazol-3-yl)(methyl)amino)-2-(4-fluorophenyl)nicotinonitrile
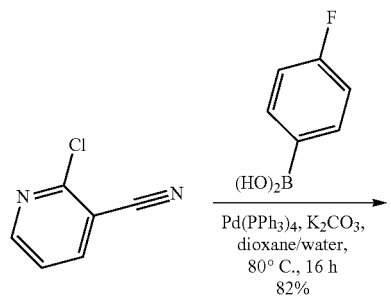
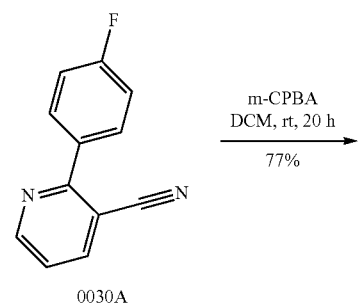
0030A
-continued
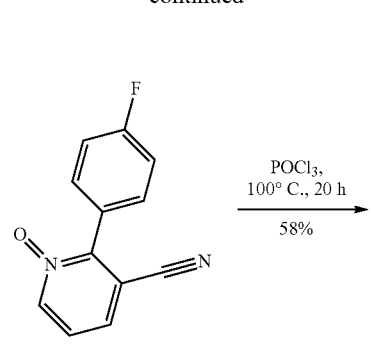
0030B
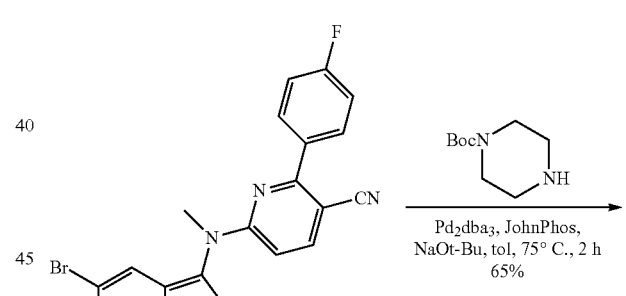
0030C
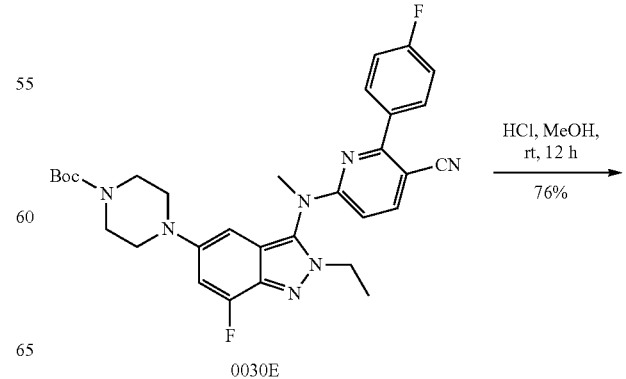
0030D
0030E

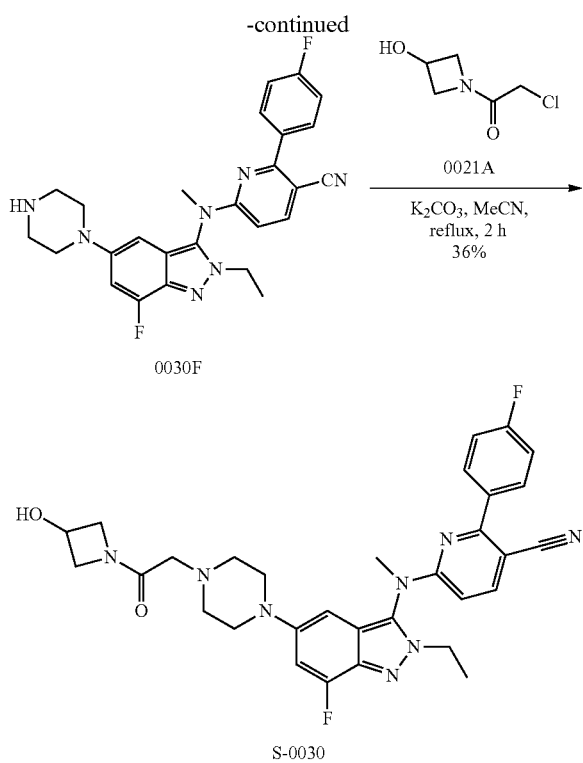

Step 1: 3-cyano-2-(4-fluorophenyl)pyridine

Under an argon atmosphere, 2-chloronicotinonitrile (1.38 g, 10.0 mmol, 1.0 eq.), (4-fluorophenyl)boronic acid (1.54 g, 11.0 mmol, 1.1 eq.), tetrakis(triphenylphosphine) palladium (0.6 g, 0.5 mmol, 0.05 eq.) and potassium carbonate (3.45 g, 25.0 mmol, 2.5 eq.) were mixed in a mixture of dioxane (24 mL) and water (5 mL), and the reaction solution was heated to 80° C., stirred overnight, cooled to room temperature and filtered. Ethyl acetate was added to the filtrate for extraction, and the organic phase was concentrated to give a crude product. The crude product was recrystallized with an ethyl acetate-n-heptane system to give 3-cyano-2-(4-fluorophenyl)pyridine in the form of a yellow solid (1.62 g, 82%). $^1$HNMR (400 MHz, DMSO-$d_6$) δ 8.94 (dd, J=2 Hz, J=5.2 Hz, 1H), 8.43 (dd, J=2 Hz, J=8.4 Hz, 1H), 7.92-7.96 (m, 2H), 7.62 (dd, J=4.8 Hz, J=7.6 Hz, 1H), 7.39-7.44 (m, 2H). LC-MS: 215.0 (M+H)$^+$.

Step 2: 3-cyano-2-(4-fluorophenyl)pyridine 1-oxide

At 0° C., 3-chloroperoxybenzoic acid (4.0 g, 16.0 mmol, 2.0 eq.) was added to a solution of 3-cyano-2-(4-fluorophenyl)pyridine (1.62 g, 8 mmol, 1.0 eq.) in dichloromethane (60 mL), and the mixture was stirred at 25° C. for 20 h. Sodium hyposulfite was added, and the resulting mixture was further stirred for 10 min. The reaction was quenched with water, and ethyl acetate was added for extraction. The organic phase was washed with a saturated sodium carbonate solution and brine, dried over anhydrous sodium sulfate, filtered and concentrated. The obtained crude product was recrystallized with an ethyl acetate-n-heptane system to give 3-cyano-2-(4-fluorophenyl)pyridine 1-oxide in the form of a gray solid (1.34 g, 76.6%). LC-MS: 214.9 (M+H)$^+$.

Step 3: 6-chloro-2-(4-fluorophenyl)nicotinonitrile

A mixture of 3-cyano-2-(4-fluorophenyl)pyridine 1-oxide (550 mg, 2.56 mmol) and phosphorus oxychloride (10 mL) was heated to 100° C. and stirred overnight. The reaction was quenched with ice water slowly added, and then a solid of sodium carbonate was added to adjust pH to 8. Ethyl acetate (100 mL×3) was added for extraction, and the organic phases were combined, dried over anhydrous sodium sulfate, filtered and concentrated. The residue was purified by flash chromatography (petroleum ether/ethyl acetate=20/1) to give 6-chloro-2-(4-fluorophenyl)nicotinonitrile in the form of a white solid (350 mg, 58%). LCMS (ESI) [M]$^+$=232; $^1$H NMR (400 MHz, CDCl$_3$) δ 8.11-7.92 (m, 3H), 7.72 (d, J=9.1 Hz, H), 7.41 (d, J=8.2 Hz, 1H), 7.26-7.20 (m, 2H).

Step 4: 6-((5-bromo-2-ethyl-7-fluoro-2H-indazol-3-yl)(methyl)amino)-2-(4-fluorophenyl) nicotinonitrile Sodium hydride (60% in oil, 34 mg, 1.395 mmol) was slowly added to a solution of 5-bromo-2-ethyl-7-fluoro-2H-indazol-3-amine (120 mg, 0.465 mmol) in N, N-dimethylformamide (8 mL), and the mixture was stirred at 0° C. for 15 min. Then 6-chloro-2-(4-fluorophenyl)nicotinonitrile (108 mg, 0.465 mmol) was added, and the mixture was further stirred at room temperature for 1 h. Methyl iodide (0.35 mL, 0.93 mmol) was added, and the mixture was further stirred at room temperature for 1 h. The reaction was quenched with water (20 mL), and ethyl acetate (30 mL×3) was added for extraction. The organic phases were combined, washed with saturated brine (10 mL×2), dried over anhydrous sodium sulfate, filtered and concentrated. The residue was purified by flash chromatography (ethyl acetate/petroleum ether=5/1) to give 6-((5-bromo-2-ethyl-7-fluoro-2H-indazol-3-yl) (methyl)amino)-2-(4-fluorophenyl)nicotinonitrile in the form of a yellow solid (100 mg, 46%). LCMS (ESI) [M+H]$^+$=468; $^1$H NMR (400 MHz, CD$_3$OD) δ 8.12-8.15 (m, 2H), 7.21-7.26 (m, 2H), 7.05 (s, 1H), 6.58 (s, 1H), 4.05-4.59 (m, 6H), 3.77-3.80 (m, 1H), 3.70 (s, 3H), 3.12-3.17 (m, 6H), 2.67-2.69 (m, 4H), 2.58 (s, 3H), 1.56 (t, J=7.6 Hz, 3H).

Step 5: tert-butyl 4-(3-((5-cyano-6-(4-fluorophenyl)pyridin-2-yl)(methyl)amino)-2-ethyl-7-fluoro-2H-indazol-5-yl)piperazine-1-carboxylate In a glove box, 6-((5-bromo-2-ethyl-7-fluoro-2H-indazol-3-yl)(methyl)amino)-2-(4-fluorophenyl)nicotinonitrile (100 mg, 0.214 mmol), tert-butyl piperazine-1-carboxylate (198.9 mg, 1.068 mmol), tris(dibenzylideneacetone)dipalladium(0) (9.8 mg, 0.011 mmol), 2-(di-tert-butylphosphino)biphenyl (6.4 mg, 0.021 mmol), sodium tert-butoxide (41.4 mg, 0.428 mmol) and toluene (3 mL) were mixed in a microwave tube. The reaction solution was heated to 75° C., stirred for 2 h, and then cooled to room temperature. Ethyl acetate (20 mL×3) was added for extraction. The organic phases were combined, washed with saturated brine (10 mL×2), dried over anhydrous sodium sulfate, filtered and concentrated. The residue was purified by flash chromatography (ethyl acetate/petroleum ether=1/1) to give tert-butyl 4-(3-((5-cyano-6-(4-fluorophenyl)pyridin-2-yl)(methyl)amino)-2-ethyl-7-fluoro-2H-indazol-5-yl)piperazine-1-carboxylate in the form of a yellow oil (80 mg, 65%). LCMS (ESI) [M+H]$^+$=574

Step 6: 6-((2-ethyl-7-fluoro-5-(piperazin-1-yl)-2H-indazol-3-yl)(methyl)amino)-2-(4-fluorophenyl) nicotinonitrile A mixture solution of tert-butyl 4-(3-((5-cyano-6-(4-fluorophenyl)pyridin-2-yl)(methyl) amino)-2-ethyl-7-fluoro- 2H-indazol-5-yl)piperazine-1-carboxylate (80 mg, 0.139 mmol) and hydrogen chloride (4 N in dioxane, 4 mL) was stirred at room temperature overnight and then concentrated. A sodium carbonate solution (20 mL) was added to adjust pH to low alkalinity, and dichloromethane (20 mL×3) was added for extraction. The organic phases were combined, washed with saturated brine (10 mL×2), dried over anhydrous sodium sulfate, filtered, and concentrated to give 6-((2-ethyl-7-fluoro-5-(piperazin-1-yl)-2H-indazol-3-yl)(methyl)amino)-2-(4-fluorophenyl)nicotinonitrile in the form of a yellow solid (50 mg, 76%). LCMS (ESI) [M+H]$^+$=474.

Step 7: 6-((2-ethyl-7-fluoro-5-(4-(2-(3-hydroxyazetidin-1-yl)-2-oxoethyl)piperazin-1-yl)-2H-indazol-3-yl)(methyl)amino)-2-(4-fluorophenyl)nicotinonitrile 2-chloro-1-(3-hydroxyazetidin-1-yl)acetyl (23.7 mol, 0.158 mmol) and potassium carbonate (43.9 mg, 0.318 mmol) were added to a solution of 6-((2-ethyl-7-fluoro-5-(piperazin-1-yl)-2H-indazol-3-yl)(methyl)amino)-2-(4-fluorophenyl)nicotinonitrile (50 mg, 0.106 mmol) in acetonitrile (3 mL), and the reaction solution was heated to 80° C., stirred for 2 h, and then concentrated. The residue was purified by flash chromatography (methanol/dichloromethane=1/10) to give 6-((2-ethyl-7-fluoro-5-(4-(2-(3-hydroxyazetidin-1-yl)-2-oxoethyl)piperazin-1-yl)-2H-indazol-3-yl)(methyl)amino)-2-(4-fluorophenyl)nicotinonitrile S-0030 in the form of a yellow solid (22.8 mg, 36%). LCMS (ESI) [M+H]$^+$=587.3@5.37 min; $^1$H NMR (400 MHz, CD$_3$OD) δ 8.01 (d, J=7.4 Hz, 2H), 7.87 (d, J=8.8 Hz, 1H), 7.25 (t, J=8.7 Hz, 2H), 7.01 (d, J=14.0 Hz, 1H), 6.51 (d, J=51.3 Hz, s, 2H), 6.40 (s, 1H), 4.87 (s, 72H), 5.04-4.41 (m, 2H), 4.41-4.15 (m, 4H), 3.78 (dd, J=10.7, 4.2 Hz, 1H), 3.65 (s, 3H), 3.47 (s, 14H), 3.24-2.77 (m, 6H), 2.66 (t, J=4.7 Hz, 4H), 1.57-1.44 (m, 3H).

Example 19. S-0058:2-(ethyl(2-ethyl-6-(4-(2-(3-hydroxyazetidin-1-yl)-2-oxoethyl) piperazin-1-yl) imidazo[1,2-a]pyrimidin-3-yl)amino)-4-(4-fluorophenyl)thiazole-5-carbonitrile

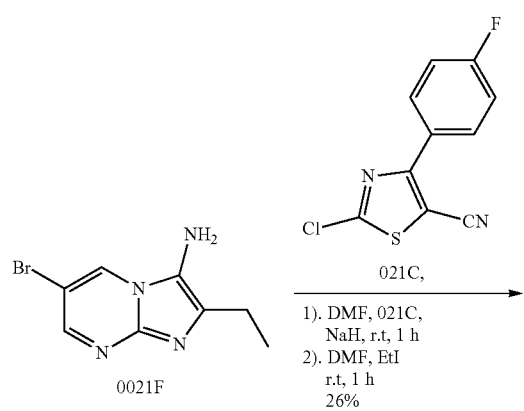

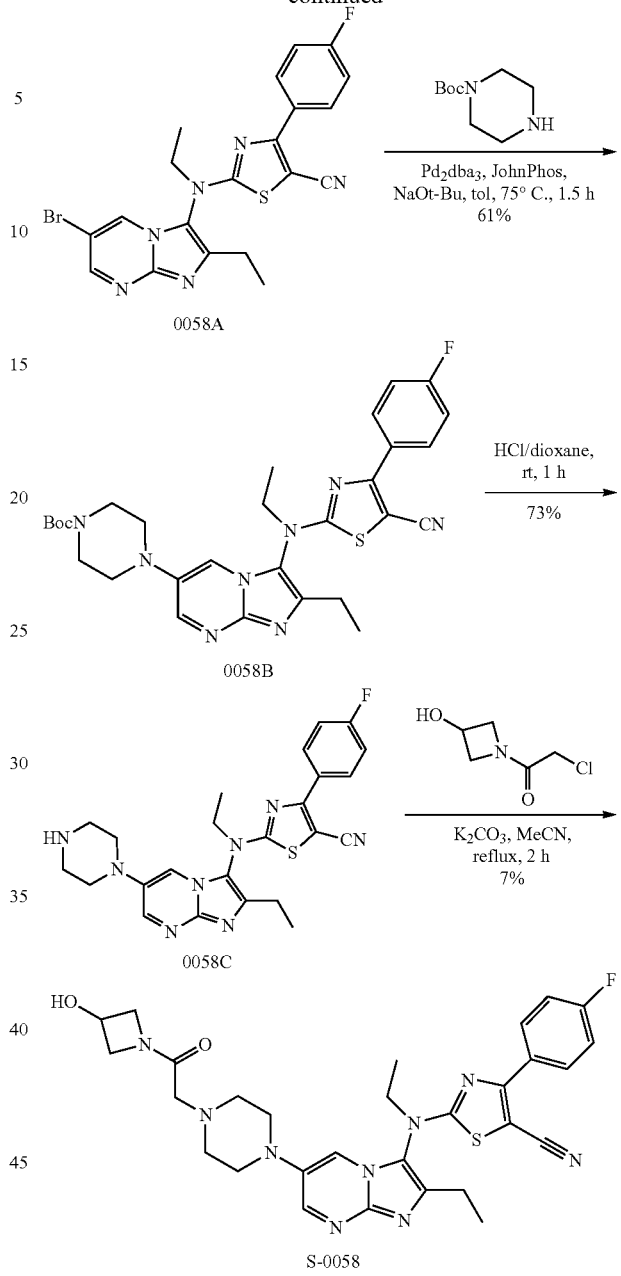

Step 1: 2-((6-bromo-2-ethylimidazo[1,2-a]pyrimidin-3-yl)(ethyl)amino)-4-(4-fluorophenyl)thiazole-5-carbonitrile Sodium hydride (60% in oil, 50 mg, 1.25 mmol) was slowly added to a solution of 6-bromo-2-ethylimidazo[1,2-a]pyrimidin-3-amine (100 mg, 0.415 mmol) in N,N-dimethylformamide (3 mL), and the reaction solution was stirred at 0° C. for 10 min. Then 2-chloro-4-(4-fluorophenyl)thiazole-5-carbonitrile (89 mg, 0.374 mmol) was added, and the resulting mixture was further stirred at room temperature for 1 h. Then iodoethane (71 mg, 0.456 mmol) was added, and the resulting mixture was further stirred at room temperature for 1 h. The reaction was quenched with water (30 mL), and ethyl acetate (15 mL×3) was added for extraction.

The organic phases were combined, washed with saturated brine (10 mL×2), dried over anhydrous sodium sulfate, filtered, and concentrated. The residue was purified by flash chromatography (methanol/dichloromethane=0%-10%) to give 2-((6-bromo-2-ethylimidazo [1,2-a]pyrimidin-3-yl)(ethyl)amino)-4-(4-fluorophenyl)thiazole-5-carbonitrile in the form of a yellow solid (51 mg, 26%). LCMS (ESI) [M+H]⁺=471.

Step 2: tert-butyl 4-(3-((5-cyano-4-(4-fluorophenyl)thiazol-2-yl)(ethyl)amino)-2-ethylimidazo[1,2-a]pyrimidin-6-yl)piperazine-1-carboxylate 2-((6-bromo-2-ethylimidazo[1,2-a]pyrimidin-3-yl)(ethyl)amino)-4-(4-fluorophenyl) thiazole-5-carbonitrile (40 mg, 0.085 mmol), tert-butyl piperazine-1-carboxylate (48 mg, 0.255 mmol), tris(dibenzylideneacetone)dipalladium(0) (9 mg, 0.009 mmol), 2-(di-tert-butylphosphino)biphenyl (3 mg, 0.009 mmol), sodium tert-butoxide (25 mg, 0.225 mmol) and toluene (4 mL) were added to a microwave tube. The reaction solution was heated to 80° C. under a nitrogen atmosphere, then stirred for 1.5 h, and cooled to room temperature. Ethyl acetate (20 mL×3) was added for extraction. The organic phases were combined, washed with saturated brine (10 mL×2), dried over anhydrous sodium sulfate, filtered and concentrated. The residue was purified by flash chromatography (ethyl acetate/petroleum ether=0%-60%) to give tert-butyl 4-(3-((5-cyano-4-(4-fluorophenyl)thiazol-2-yl)(ethyl)amino)-2-ethylimidazo [1,2-a]pyrimidin-6-yl)piperazine-1-carboxylate in the form of a yellow solid (30 mg, 61%). LCMS (ESI) [M+H]⁺=577.

Step 3: 2-(ethyl(2-ethyl-6-(piperazin-1-yl)imidazo [1,2-a]pyrimidin-3-yl)amino)-4-(4-fluorophenyl)thiazole-5-carbonitrile A mixture of tert-butyl 4-(3-((5-cyano-4-(4-fluorophenyl)thiazol-2-yl)(ethyl)amino)-2-ethylimidazo[1,2-a]pyrimidin-6-yl)piperazine-1-carboxylate (30 mg, 0.052 mmol) and hydrogen chloride (4 N in dioxane, 4 mL) was stirred at room temperature for 1 h, and concentrated. A sodium carbonate solution was added to adjust pH to low alkalinity. Ethyl acetate (10 mL×3) was added for extraction. The organic phases were combined, washed with saturated brine (10 mL×2), dried over anhydrous sodium sulfate, filtered, and concentrated to give 2-(ethyl(2-ethyl-6-(piperazin-1-yl)imidazo[1,2-a]pyrimidin-3-yl)amino)-4-(4-fluorophenyl)thiazole-5-carbonitrile in the form of a yellow solid (18 mg, 73%). LCMS (ESI) [M+H]⁺=477.

Step 4: 2-(ethyl(2-ethyl-6-(4-(2-(3-hydroxyazetidin-1-yl)-2-oxoethyl)piperazin-1-yl) imidazo[1,2-a]pyrimidin-3-yl)amino)-4-(4-fluorophenyl)thiazole-5-carbonitrile (S-0058)

2-chloro-1-(3-hydroxyazetidin-1-yl)acetyl (12 mg, 0.076 mmol) and potassium carbonate (16 mg, 0.114 mmol) were added to a solution of 2-(ethyl(2-ethyl-6-(piperazin-1-yl) imidazo [1,2-a]pyrimidin-3-yl)amino)-4-(4-fluorophenyl)thiazole-5-carbonitrile (18 mg, 0.038 mmol) in acetonitrile (3 mL), and the reaction solution was heated to reflux for 2 h, then cooled to room temperature, filtered and concentrated. The residue was purified by Pre-HPLC to give 2-(ethyl(2-ethyl-6-(4-(2-(3-hydroxyazetidin-1-yl)-2-oxoethyl)piperazin-1-yl)imidazo[1,2-a]pyrimidin-3-yl)amino)-4-(4-fluorophenyl)thiazole-5-carbonitrile S-0058 in the form of a white solid (1.5 mg, 7%). LCMS (ESI) [M+H]⁺ =590.0@5.49 min. ¹H NMR (400 MHz, CD₃OD) δ 8.71 (s, 1H), 8.17-8.14 (m, 2H), 7.89 (s, 1H), 7.29 (m, 2H), 4.60-4.48 (m, 2H), 4.31-4.21 (m, 2H), 4.09-3.99 (m, 2H), 3.80-3.77 (m, 1H), 3.23-3.14 (m, 6H), 2.74-2.68 (m, 6H), 1.39-1.28 (m, 6H).

Example 20. S-0069:2-(ethyl(2-ethyl-5-(4-(2-(3-hydroxyazetidin-1-yl)-2-oxoethyl) piperazine-1-yl)-7-methylpyrazolo[1,5-a]pyrimidin-3-yl)amino)-4-(4-fluorophenyl) thiazole-5-carbonitrile

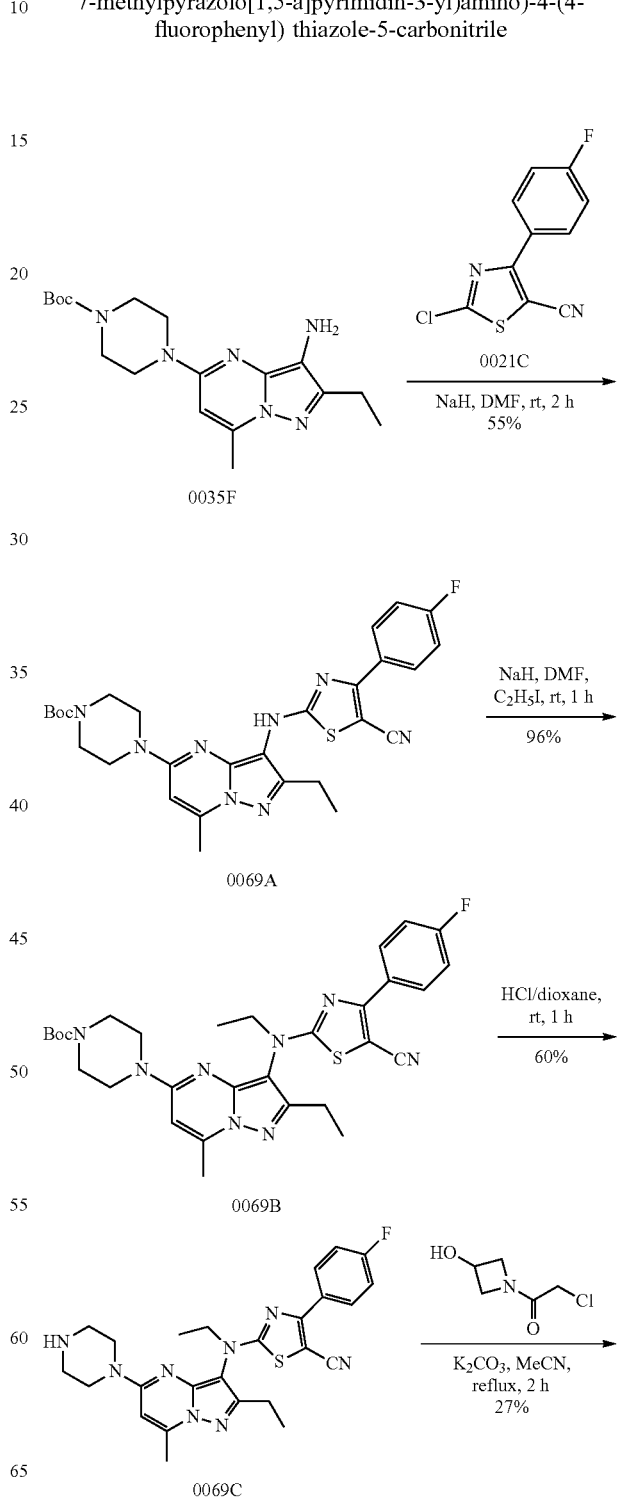

-continued

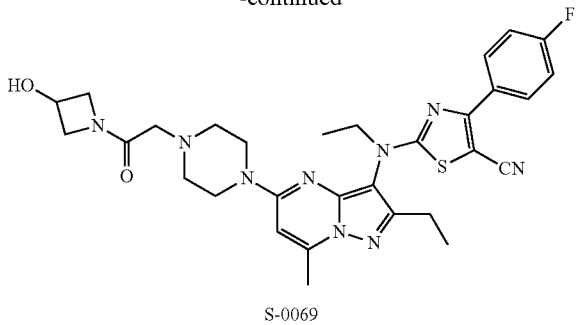

S-0069

Step 1: tert-butyl 4-(3-(5-cyano-4-(4-fluorophenyl) thiazole-2-ylamino)-2-ethyl-7-methylpyrazolo[1,5-a] pyrimidin-5-yl)piperazine-1-carboxylate A mixture of tert-butyl 4-(3-amino-2-ethyl-7-methylpyrazolo[1,5-a]pyrimidin-5-yl) piperazine-1-carboxylate (70 mg, 0.194 mmol) and sodium hydride (60% in oil, 9 mg, 0.388 mmol) in N,N-dimethylformamide (5 mL) was stirred at 0° C. for 10 min. Then 2-chloro-4-(4-fluorophenyl)thiazole-5-carbonitrile (55 mg, 0.233 mmol) was added and the reaction system was stirred at room temperature for 2 h. The reaction was quenched with water, and ethyl acetate (20 mL×3) was added for extraction. The organic phases were combined, washed with saturated brine (30 mL×2), dried over anhydrous sodium sulfate, filtered and concentrated. The residue was purified by flash chromatography (methanol/dichloromethane=0-10%) to give tert-butyl 4-(3-(5-cyano-4-(4-fluorophenyl)thiazole-2-ylamino)-2-ethyl-7-methylpyrazolo[1,5-a]pyrimidin-5-yl)piperazine-1-carboxylate (60 mg, 55%). LCMS (ESI) [M+H]$^+$=563.2.

Step 2: tert-butyl 4-(3-(5-cyano-4-(4-fluorophenyl) thiazol-2-yl)ethylamino)-2-ethyl-7-methylpyrazolo [1,5-a]pyrimidin-5-yl)piperazine-1-carboxylate A mixture of tert-butyl 4-(3-(5-cyano-4-(4-fluorophenyl) thiazole-2-ylamino)-2-ethyl-7-methylpyrazolo[1,5-a]pyrimidin-5-yl)piperazine-1-carboxylate (60 mg, 0.106 mmol) and sodium hydride (60% in oil, 5 mg, 0.206 mmol) in N,N-dimethylformamide (4 mL) was stirred at 0° C. for 10 min. Then methyl iodide (16 mg, 0.106 mmol) was added and the reaction system was stirred at room temperature for 2 h. The reaction was quenched with water, and ethyl acetate (20 mL×3) was added for extraction. The organic phases were combined, washed with saturated brine (30 mL×2), dried over anhydrous sodium sulfate, filtered and concentrated. The residue was purified by flash chromatography (methanol/dichloromethane=0-10%) to give tert-butyl 4-(3-(5-cyano-4-(4-fluorophenyl)thiazole-2-yl)ethylamino)-2-ethyl-7-methylpyrazolo[1,5-a]pyrimidin-5-yl)piperazine-1-carboxylate (60 mg, 96%). LCMS (ESI) [M+H]$^+$=591.

Step 3: 2-(ethyl(2-ethyl-7-methyl-5-(piperazine-1-yl)pyrazolo[1,5-a]pyrimidin-3-yl) amino)-4-(4-fluorophenyl)thiazole-5-carbonitrile A mixture of tert-butyl 4-(3-(5-cyano-4-(4-fluorophenyl)thiazole-2-yl)ethylamino)-2-ethyl-7-methylpyrazolo[1,5-a]pyrimidin-5-yl)piperazine-1-carboxylate (60 mg, 0.101 mmol) in hydrogen chloride (4 N in dioxane, 4 mL) was stirred at room temperature for 1 h. The mixture was concentrated, and a sodium bicarbonate solution (20 mL) was added to adjust pH to low alkalinity. Ethyl acetate (20 mL×3) was added for extraction. The organic phases were combined, washed with saturated brine (10 mL×2), dried over anhydrous sodium sulfate, filtered and concentrated to give 2-(ethyl(2-ethyl-7-methyl-5-(piperazine-1-yl)pyrazolo [1,5-a]pyrimidin-3-yl)amino)-4-(4-fluorophenyl)thiazole-5-carbonitrile (30 mg, 60%) in the form of a yellow solid, which was directly used in the next step without purification. LCMS (ESI) [M+H]$^+$=491.3.

Step 4: 2-(ethyl(2-ethyl-5-(4-(2-(3-hydroxyazetidin-1-yl)-2-oxoethyl)piperazine-1-yl)-7-methylpyrazolo [1,5-a]pyrimidin-3-yl)amino)-4-(4-fluorophenyl) thiazole-5-carbonitrile S-0069

A mixture of 2-(ethyl(2-ethyl-7-methyl-5-(piperazine-1-yl)pyrazolo[1,5-a]pyrimidin-3-yl)amino)-4-(4-fluorophenyl)thiazole-5-carbonitrile (30 mg, 0.061 mmol), 2-chloro-1-(3-hydroxyazetidin-1-yl)acetyl (14 mg, 0.091 mmol) and potassium carbonate (17 mg, 0.121 mmol) in acetonitrile (2 mL) was stirred at reflux for 2 h, and then cooled to room temperature and filtered. The filtrate was concentrated. The residue was purified by Pre-HPLC to give 2-(ethyl(2-ethyl-5-(4-(2-(3-hydroxyazetidin-1-yl)-2-oxoethyl)piperazine-1-yl)-7-methylpyrazolo[1,5-a]pyrimidin-3-yl)amino)-4-(4-fluorophenyl)thiazole-5-carbonitrile S-0069 in the form of a white solid (10 mg, 27%). LCMS (ESI) [M+H]$^+$=604.1@6.45 min. $^1$H NMR (400 MHz, CD$_3$OD) δ 8.121 (m, 2H), 7.231 (m, 2H), 6.614 (s, 1H), 4.568 (m, 1H), 4.477 (m, 1H), 4.208 (m, 2H), 4.049 (m, 1H), 3.846 (m, 1H), 3.752 (m, 5H), 3.108 (s, 2H), 2.717 (q, 2H), 2.677 (s, 3H), 2.573 (m, 4H), 1.3339 (t, 6H).

Example 21. S-0070: (R)-2-((2-ethyl-5-(4-(2-(3-hydroxyazetidin-1-yl)-2-oxoethyl)-2-methylpiperazine-1-yl)-7-methylpyrazolo[1,5-a]pyrimidin-3-yl) (methyl)amino)-4-(4-fluorophenyl)thiazole-5-carbonitrile

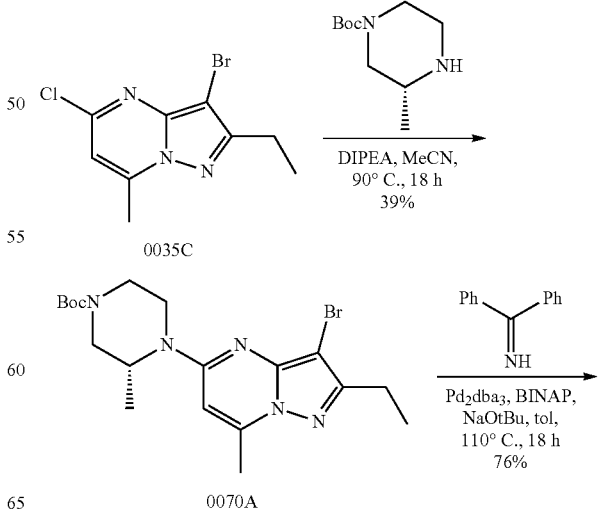

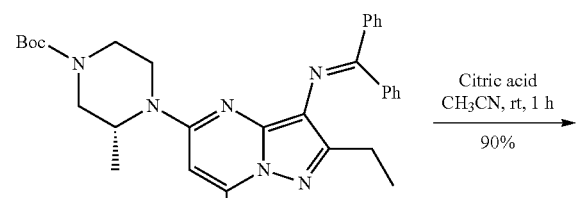

0070B

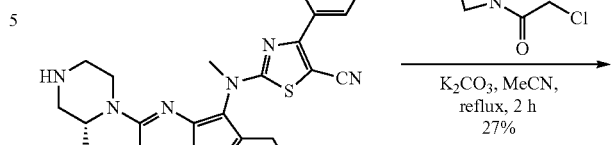

0070F

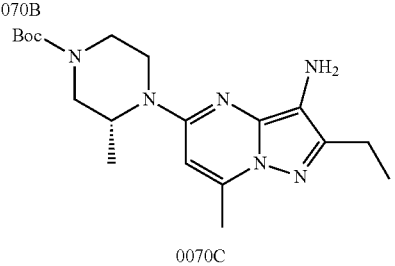

0070C

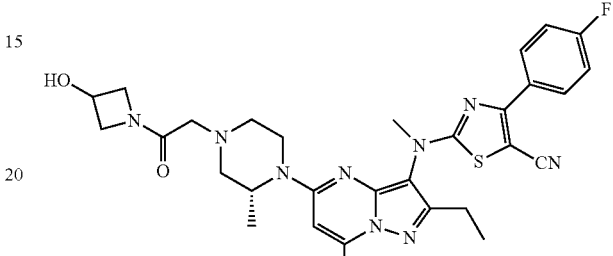

S-0070

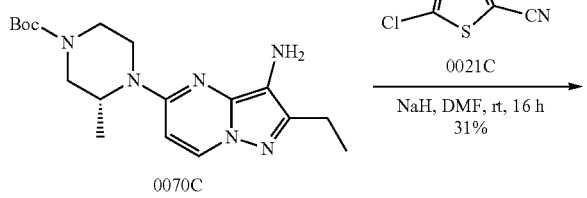

0070C

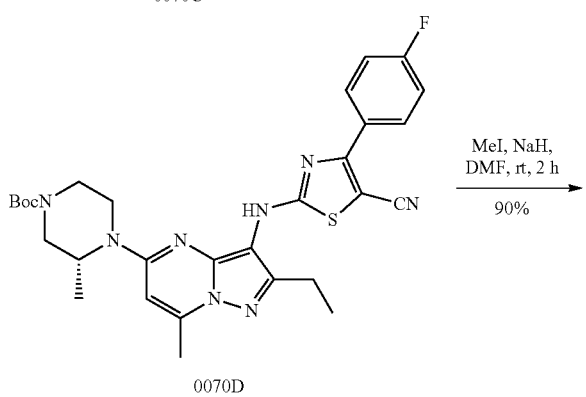

0070D

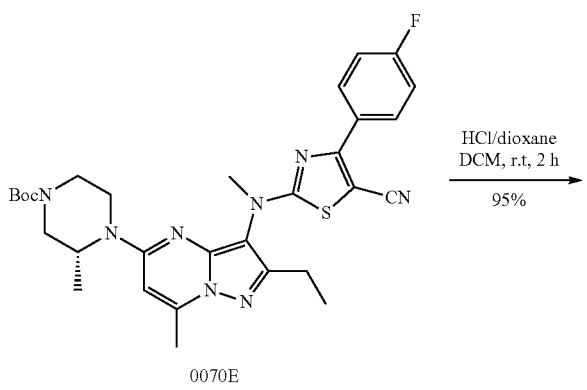

0070E

Step 1: (R)-tert-butyl 4-(3-bromo-2-ethyl-7-methylpyrazolo[1,5-a]pyrimidin-5-yl)-3-methylpiperazine-1-carboxylate A mixture of 3-bromo-5-chloro-2-ethyl-7-methylpyrazolo [1,5-a]pyrimidine (300 mg, 1.096 mmol), (R)-tert-butyl 3-methylpiperazine-1-carboxylate (657 mg, 3.288 mmol), and N,N-diisopropylethylamine (423 mg, 3.288 mmol) in acetonitrile (3 mL) was stirred at 90° C. for 18 h in a sealed tube. The reaction system was cooled to room temperature, filtered and concentrated. The residue was purified by flash chromatography (ethyl acetate/petroleum ether=1/3) to give (R)-tert-butyl 4-(3-bromo-2-ethyl-7-methylpyrazolo[1,5-a] pyrimidin-5-yl)-3-methylpiperazine-1-carboxylate (190 mg, 39%) in the form of a yellow oil. LCMS (ESI) [M+H]$^+$=439.

Step 2: (R)-tert-butyl 4-(3-(diphenylmethyleneamino)-2-ethyl-7-methylpyrazolo[1,5-a]pyrimidin-5-yl)-3-methylpiperazine-1-carboxylate To a microwave tube were added (R)-tert-butyl 4-(3-bromo-2-ethyl-7-methylpyrazolo [1,5-a]pyrimidin-5-yl)-3-methylpiperazine-1-carboxylate (190 mg, 0.433 mmol), diphenylmethanimine (156 mg, 0.866 mmol), tris(dibenzylideneacetone)dipalladium(0) (39 mg, 0.043 mmol), (±)-2,2'-bis(diphenylphosphino)-1,1'-binaphthyl (53 mg, 0.086 mmol), sodium tert-butoxide (82 mg, 0.866 mmol), and toluene (3 mL) in a glove box. The mixture was stirred at 100° C. for 16 h, then cooled to room temperature and filtered. The filtrate was concentrated. The residue was purified by flash chromatography (petroleum ether/ethyl acetate=2/1) to give (R)-tert-butyl 4-(3-(diphenylmethyleneamino)-2-ethyl-7-methylpyrazolo[1,5-a]pyrimidin-5-yl)-3-methylpiperazine-1-carboxylate (180 mg, 76%) in the form of a yellow oil. LCMS (ESI) [M+H]$^+$=539.3.

Step 3: (R)-tert-butyl 4-(3-amino-2-ethyl-7-methylpyrazolo[1,5-a]pyrimidin-5-yl)-3-methylpiperazine-1-carboxylate A mixture of (R)-tert-butyl 4-(3-(diphenylmethyleneamino)-2-ethyl-7-methylpyrazolo [1,5-a]pyrimidin-5- yl)-3-methylpiperazine-1-carboxylate (180 mg, 0.334 mmol) and citric acid (128 mg, 0.668 mmol) in acetonitrile (2 mL) was stirred at room temperature for 1 h, and then concentrated. The residue was purified by flash chromatography (petroleum ether/ethyl acetate=1/3) to give (R)-tert-butyl 4-(3-amino-2-ethyl-7-methylpyrazolo[1,5-a]pyrimidin-5-yl)-3-methylpiperazine-1-carboxylate (112 mg, 90%) in the form of a black oil. LCMS (ESI) [M+H]$^+$=375.3.

Step 4: (R)-tert-butyl 4-(3-(5-cyano-4-(4-fluorophenyl)thiazol-2-ylamino)-2-ethyl-7-methylpyrazolo[1,5-a]pyrimidin-5-yl)-3-methylpiperazine-1-carboxylate A mixture of (R)-tert-butyl 4-(3-amino-2-ethyl-7-methylpyrazolo[1,5-a]pyrimidin-5-yl)-3-methylpiperazine-1-carboxylate (112 mg, 0.298 mmol) and sodium hydride (60% in oil, 14 mg, 0.596 mmol) in N,N-dimethylformamide (5 mL) was stirred at 0° C. for 15 min. Then 2-chloro-4-(4-fluorophenyl)thiazole-5-carbonitrile (71 mg, 0.298 mmol) was added. The reaction system was stirred at room temperature for another 16 h. The reaction was quenched with water, and ethyl acetate (50 mL×3) was added for extraction. The organic phases were combined, washed with saturated brine (30 mL×2), dried over anhydrous sodium sulfate, filtered and concentrated. The residue was purified by flash chromatography (ethyl acetate/petroleum ether=2/1) to give (R)-tert-butyl 4-(3-(5-cyano-4-(4-fluorophenyl)thiazol-2-ylamino)-2-ethyl-7-methylpyrazolo[1,5-a]pyrimidin-5-yl)-3-methylpiperazine-1-carboxylate in the form of a yellow solid (60 mg, 31%). LCMS (ESI) [M+H]$^+$=576.8.

Step 5: (R)-tert-butyl 4-(3-(5-cyano-4-(4-fluorophenyl)thiazol-2-yl)methylamino-2-ethyl-7-methylpyrazolo[1,5-a]pyrimidin-5-yl)-3-methylpiperazine-1-carboxylate A solution of (R)-tert-butyl 4-(3-(5-cyano-4-(4-fluorophenyl)thiazol-2-ylamino)-2-ethyl-7-methylpyrazolo[1,5-a]pyrimidin-5-yl)-3-methylpiperazine-1-carboxylate (60 mg, 0.104 mmol) and sodium hydride (60% in oil, 5 mg, 0.208 mmol) in N,N-dimethylformamide (2 mL) was stirred at 0° C. for 15 min. Then methyl iodide (0.06 mL, 0.187 mmol) was added and the mixture was stirred at room temperature for another 1 h. The reaction was quenched with water, and ethyl acetate (50 mL×3) was added for extraction. The organic phases were combined, washed with saturated brine (30 mL×2), dried over anhydrous sodium sulfate, filtered and concentrated. The residue was purified by flash chromatography (ethyl acetate/petroleum ether=2/1) to give (R)-tert-butyl 4-(3-(5-cyano-4-(4-fluorophenyl)thiazol-2-yl)methylamino-2-ethyl-7-methylpyrazolo[1,5-a]pyrimidin-5-yl)-3-methylpiperazine-1-carboxylate (54 mg, 90%) in the form of a yellow oil. LCMS (ESI) [M+H]$^+$=591.0.

Step 6: (R)-2-((2-ethyl-7-methyl-5-(2-methylpiperazin-1-yl)pyrazolo[1,5-a]pyrimidin-3-yl)(methyl)amino)-4-(4-fluorophenyl)thiazole-5-carbonitrile A mixture of (R)-tert-butyl 4-(3-(5-cyano-4-(4-fluorophenyl)thiazol-2-yl)methylamino-2-ethyl-7-methylpyrazolo[1,5-a]pyrimidin-5-yl)-3-methylpiperazine-1-carboxylate (54 mg, 0.092 mmol) in hydrogen chloride (4 N in dioxane, 2 mL) was stirred at room temperature overnight, and then concentrated. A sodium carbonate solution (30 mL) was added to adjust pH to low alkalinity, and ethyl acetate (50 mL×3) was added for extraction. The organic phases were combined, washed with saturated brine (10 mL×2), dried over sodium sulfate, filtered and concentrated to give (R)-2-((2-ethyl-7-methyl-5-(2-methylpiperazin-1-yl)pyrazolo[1,5-a]pyrimidin-3-yl)(methyl)amino)-4-(4-fluorophenyl)thiazole-5-carbonitrile (40 mg, 90%) in the form of a yellow solid, which was directly used in the next step without purification. LCMS (ESI) [M+H]$^+$=491.

Step 7: (R)-2-((2-ethyl-5-(4-(2-(3-hydroxyazetidin-1-yl)-2-oxoethyl)-2-methylpiperazin-1-yl)-7-methylpyrazolo[1,5-a]pyrimidin-3-yl)(methyl)amino)-4-(4-fluorophenyl)thiazole-5-carbonitrile S-0070

(R)-2-((2-ethyl-7-methyl-5-(2-methylpiperazin-1-yl)pyrazolo[1,5-a]pyrimidin-3-yl)(methyl)amino)-4-(4-fluorophenyl)thiazole-5-carbonitrile (40 mg, 0.081 mol), 2-chloro-1-(3-hydroxyazetidin-1-yl)acetyl (17 mg, 0.122 mmol) and potassium carbonate (33.5 mg, 0.243 mmol) were mixed in acetonitrile (3 mL). The reaction system was stirred at reflux for 2 h, cooled to room temperature, and filtered. The filtrate was concentrated. The residue was purified by Pre-HPLC to give (R)-2-((2-ethyl-5-(4-(2-(3-hydroxyazetidin-1-yl)-2-oxoethyl)-2-methylpiperazin-1-yl)-7-methylpyrazolo[1,5-a]pyrimidin-3-yl)(methyl)amino)-4-(4-fluorophenyl)thiazole-5-carbonitrile S-0070 (15.3 mg, 27%) in the form of a white solid. LCMS (ESI) [M+H]$^+$=604.2@10.18 min; $^1$H NMR (400 MHz, CD$_3$OD) δ 8.15 (dd, J$_1$=8.8 Hz, J$_2$=5.4 Hz, 2H), 7.25 (t, J=8.8 Hz, 2H), 6.59 (s, 1H), 4.62-4.48 (m, 2H), 4.28-4.03 (m, 4H), 3.79-3.76 (m, 1H), 3.60 (s, 3H), 3.52-3.49 (m, 1H), 3.43-3.33 (m, 1H), 3.04-2.91 (m, 3H), 2.98 (q, J=7.6 Hz, 2H), 2.67 (s, 3H), 2.62-2.58 (m, 1H), 2.50-2.44 (m, 1H), 1.33 (t, J=7.6 Hz, 6H).

Example 22. S-0071: (S)-2-((2-ethyl-5-(4-(2-(3-hydroxyazetidin-1-yl)-2-oxoethyl)-2-methylpiperazin-1-yl)-7-methylpyrazolo[1,5-a]pyrimidin-3-yl)(methyl)amino)-4-(4-fluorophenyl)thiazole-5-carbonitrile

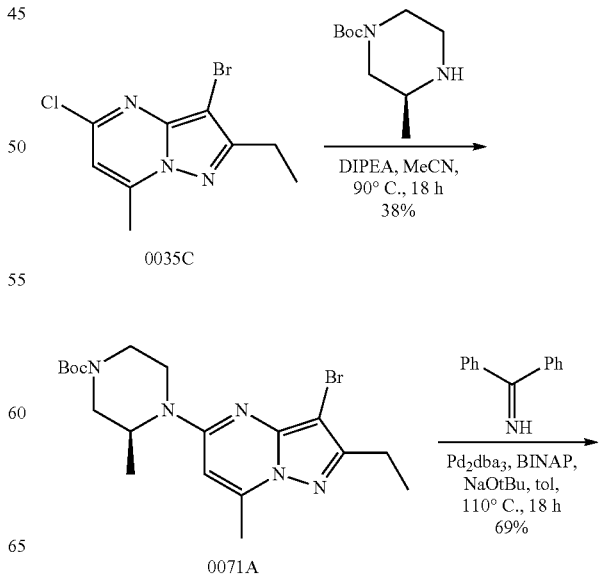

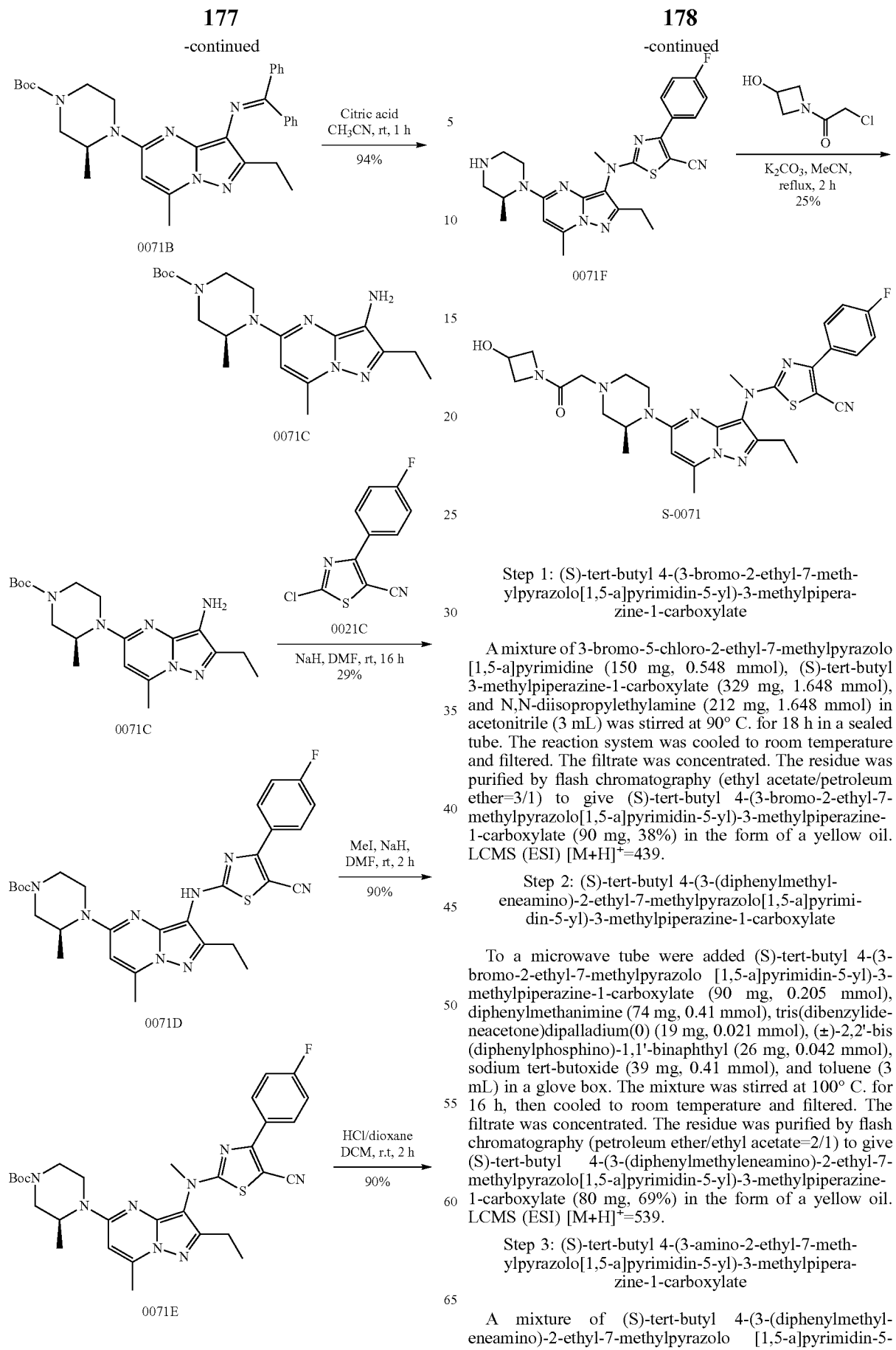

Step 1: (S)-tert-butyl 4-(3-bromo-2-ethyl-7-methylpyrazolo[1,5-a]pyrimidin-5-yl)-3-methylpiperazine-1-carboxylate A mixture of 3-bromo-5-chloro-2-ethyl-7-methylpyrazolo[1,5-a]pyrimidine (150 mg, 0.548 mmol), (S)-tert-butyl 3-methylpiperazine-1-carboxylate (329 mg, 1.648 mmol), and N,N-diisopropylethylamine (212 mg, 1.648 mmol) in acetonitrile (3 mL) was stirred at 90° C. for 18 h in a sealed tube. The reaction system was cooled to room temperature and filtered. The filtrate was concentrated. The residue was purified by flash chromatography (ethyl acetate/petroleum ether=3/1) to give (S)-tert-butyl 4-(3-bromo-2-ethyl-7-methylpyrazolo[1,5-a]pyrimidin-5-yl)-3-methylpiperazine-1-carboxylate (90 mg, 38%) in the form of a yellow oil. LCMS (ESI) [M+H]$^+$=439.

Step 2: (S)-tert-butyl 4-(3-(diphenylmethyleneamino)-2-ethyl-7-methylpyrazolo[1,5-a]pyrimidin-5-yl)-3-methylpiperazine-1-carboxylate To a microwave tube were added (S)-tert-butyl 4-(3-bromo-2-ethyl-7-methylpyrazolo[1,5-a]pyrimidin-5-yl)-3-methylpiperazine-1-carboxylate (90 mg, 0.205 mmol), diphenylmethanimine (74 mg, 0.41 mmol), tris(dibenzylideneacetone)dipalladium(0) (19 mg, 0.021 mmol), (±)-2,2'-bis(diphenylphosphino)-1,1'-binaphthyl (26 mg, 0.042 mmol), sodium tert-butoxide (39 mg, 0.41 mmol), and toluene (3 mL) in a glove box. The mixture was stirred at 100° C. for 16 h, then cooled to room temperature and filtered. The filtrate was concentrated. The residue was purified by flash chromatography (petroleum ether/ethyl acetate=2/1) to give (S)-tert-butyl 4-(3-(diphenylmethyleneamino)-2-ethyl-7-methylpyrazolo[1,5-a]pyrimidin-5-yl)-3-methylpiperazine-1-carboxylate (80 mg, 69%) in the form of a yellow oil. LCMS (ESI) [M+H]$^+$=539.

Step 3: (S)-tert-butyl 4-(3-amino-2-ethyl-7-methylpyrazolo[1,5-a]pyrimidin-5-yl)-3-methylpiperazine-1-carboxylate A mixture of (S)-tert-butyl 4-(3-(diphenylmethyleneamino)-2-ethyl-7-methylpyrazolo [1,5-a]pyrimidin-5- yl)-3-methylpiperazine-1-carboxylate (80 mg, 2.214 mmol) and citric acid (82 mg, 0.428 mmol) in acetonitrile (1 mL) was stirred at room temperature for 1 h, and then was concentrated. The residue was purified by flash chromatography (petroleum ether/ethyl acetate=1/3) to give (S)-tert-butyl 4-(3-amino-2-ethyl-7-methylpyrazolo[1,5-a]pyrimidin-5-yl)-3-methylpiperazine-1-carboxylate (50 mg, 94%) in the form of a black oil. LCMS (ESI) [M+H]$^+$=375.

Step 4: (S)-tert-butyl 4-(3-(5-cyano-4-(4-fluorophenyl)thiazol-2-ylamino)-2-ethyl-7-methylpyrazolo[1,5-a]pyrimidin-5-yl)-3-methylpiperazine-1-carboxylate A solution of (S)-tert-butyl 4-(3-amino-2-ethyl-7-methylpyrazolo[1,5-a]pyrimidin-5-yl)-3-methylpiperazine-1-carboxylate (50 mg, 0.087 mmol) and sodium hydride (60% in oil, 4 mg, 0.174 mmol) in N,N-dimethylformamide (5 mL) was stirred at 0° C. for 15 min, then 2-chloro-4-(4-fluorophenyl)thiazole-5-carbonitrile (21 mg, 0.087 mmol) was added and the reaction system was stirred at room temperature for another 16 h. The reaction was quenched with water, and ethyl acetate (50 mL×3) was added for extraction. The organic phases were combined, washed with saturated brine (30 mL×2), dried over anhydrous sodium sulfate, filtered and concentrated. The residue was purified by flash chromatography (ethyl acetate/petroleum ether=2/1) to give (S)-tert-butyl 4-(3-(5-cyano-4-(4-fluorophenyl)thiazol-2-ylamino)-2-ethyl-7-methylpyrazolo[1,5-a]pyrimidin-5-yl)-3-methylpiperazine-1-carboxylate in the form of a yellow solid (25 mg, 29%). LCMS (ESI) [M+H]$^+$=576.

Step 5: (S)-tert-butyl 4-(3-(5-cyano-4-(4-fluorophenyl)thiazol-2-yl)methylamino-2-ethyl-7-methylpyrazolo[1,5-a]pyrimidin-5-yl)-3-methylpiperazine-1-carboxylate A solution of (S)-tert-butyl 4-(3-(5-cyano-4-(4-fluorophenyl)thiazol-2-ylamino)-2-ethyl-7-methylpyrazolo[1,5-a]pyrimidin-5-yl)-3-methylpiperazine-1-carboxylate (25 mg, 0.043 mmol) and sodium hydride (60% in oil, 2 mg, 0.086 mmol) in N,N-dimethylformamide (2 mL) was stirred at 0° C. for 15 min. Then methyl iodide (0.02 mL, 0.039 mmol) was added and the reaction system was stirred at room temperature for another 1 h. The reaction was quenched with water, and ethyl acetate (50 mL×3) was added for extraction. The organic phases were combined, washed with saturated brine (30 mL×2), dried over anhydrous sodium sulfate, filtered and concentrated. The residue was purified by flash chromatography (ethyl acetate/petroleum ether=2/1) to give (S)-tert-butyl 4-(3-(5-cyano-4-(4-fluorophenyl)thiazol-2-yl)methylamino-2-ethyl-7-methylpyrazolo[1,5-a]pyrimidin-5-yl)-3-methylpiperazine-1-carboxylate (20 mg, 90%) in the form of a yellow oil. LCMS (ESI) [M+H]+=591.

Step 6: (S)-2-((2-ethyl-7-methyl-5-(2-methylpiperazin-1-yl)pyrazolo[1,5-a]pyrimidin-3-yl)(methyl)amino)-4-(4-fluorophenyl)thiazole-5-carbonitrile A mixture of (S)-tert-butyl 4-(3-(5-cyano-4-(4-fluorophenyl)thiazol-2-yl)methylamino-2-ethyl-7-methylpyrazolo[1,5-a]pyrimidin-5-yl)-3-methylpiperazine-1-carboxylate (20 mg, 0.034 mmol) in hydrogen chloride (4 N in dioxane, 1 mL) was stirred at room temperature overnight, and then concentrated. Sodium carbonate solution (30 mL) was added to adjust pH to low alkalinity, and ethyl acetate (50 mL×3) was added for extraction. The organic phases were combined, washed with saturated brine (10 mL×2), dried over anhydrous sodium sulfate, filtered and concentrated to give (S)-2-((2-ethyl-7-methyl-5-(2-methylpiperazin-1-yl)pyrazolo[1,5-a]pyrimidin-3-yl)(methyl)amino)-4-(4-fluorophenyl)thiazole-5-carbonitrile (15 mg, 90%) in the form of yellow solid, which was directly used in the next step without purification. LCMS (ESI) [M+H]$^+$=491.

Step 7: (S)-2-((2-ethyl-5-(4-(2-(3-hydroxyazetidin-1-yl)-2-oxoethyl)-2-methylpiperazin-1-yl)-7-methylpyrazolo[1,5-a]pyrimidin-3-yl)(methyl)amino)-4-(4-fluorophenyl)thiazole-5-carbonitrile (S)-2-((2-ethyl-7-methyl-5-(2-methylpiperazin-1-yl)pyrazolo[1,5-a]pyrimidin-3-yl) (methyl)amino)-4-(4-fluorophenyl)thiazole-5-carbonitrile (15 mg, 0.106 mmol), 2-chloro-1-(3-hydroxyazetidin-1-yl)acetyl (23.7 mol, 0.158 mmol) and potassium carbonate (43.9 mg, 0.318 mmol) were mixed in acetonitrile (3 mL). The reaction system was stirred at reflux for 2 h, cooled to room temperature, and filtered. The filtrate was concentrated. The residue was purified by Pre-HPLC to give (S)-2-((2-ethyl-5-(4-(2-(3-hydroxyazetidin-1-yl)-2-oxoethyl)-2-methylpiperazin-1-yl)-7-methylpyrazolo[1,5-a]pyrimidin-3-yl)(methyl)amino)-4-(4-fluorophenyl)thiazole-5-carbonitrile S-0071 (4.5 mg, 25%) in the form of a white solid. LCMS (ESI) [M+H]$^+$=604.0@10.14 min; $^1$H NMR (400 MHz, CD$_3$OD) δ 8.15 (dd, J$_1$=8.8 Hz, J$_2$=5.4 Hz, 2H), 7.25 (t, J=8.8 Hz, 2H), 6.59 (s, 1H), 4.62-4.48 (m, 2H), 4.28-4.03 (m, 4H), 3.79-3.76 (m, 1H), 3.60 (s, 3H), 3.52-3.49 (m, 1H), 3.43-3.33 (m, 1H), 3.04-2.91 (m, 3H), 2.98 (q, J=7.6 Hz, 2H), 2.67 (s, 3H), 2.62-2.58 (m, 1H), 2.50-2.44 (m, 1H), 1.33 (t, J=7.6 Hz, 6H).

Example 23. S-0074: (R)-2-((2-ethyl-5-(4-(2-(3-hydroxyazetidin-1-yl)-2-oxoethyl)-3-methylpiperazin-1-yl)-7-methylpyrazolo[1,5-a]pyrimidin-3-yl)(methyl)amino)-4-(4-fluorophenyl)thiazole-5-carbonitrile

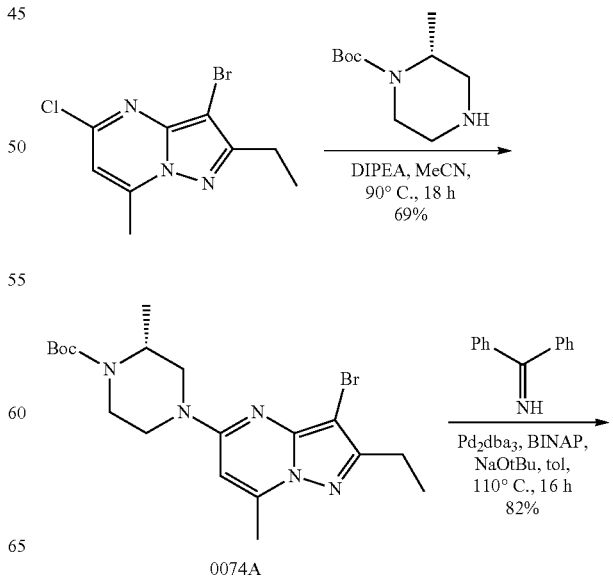

0074A

-continued

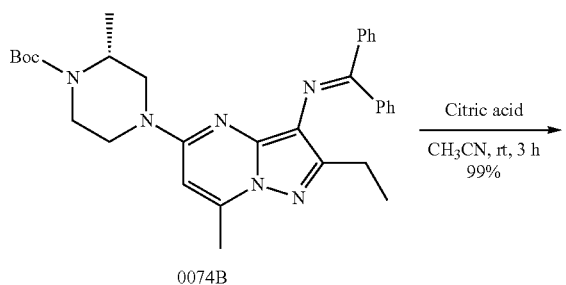

0074B

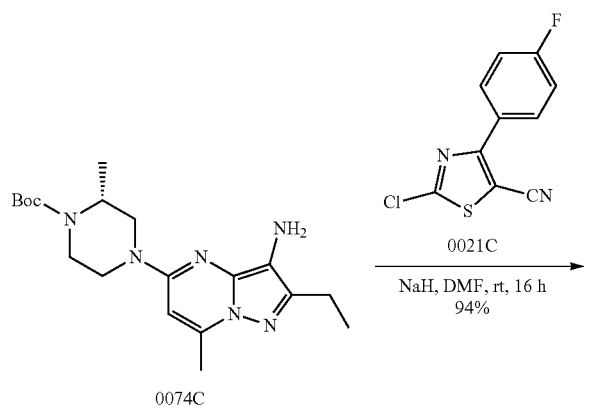

0074C

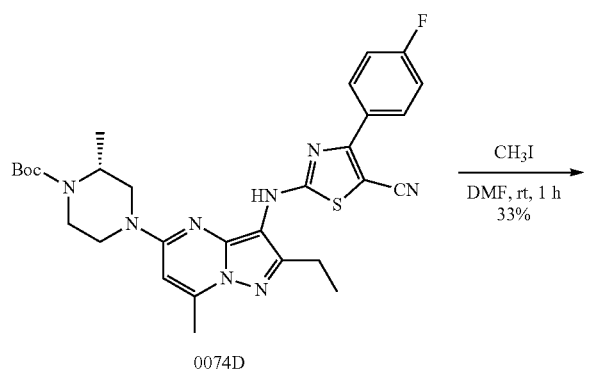

0074D

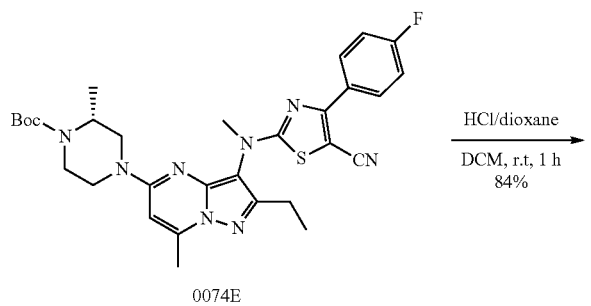

0074E

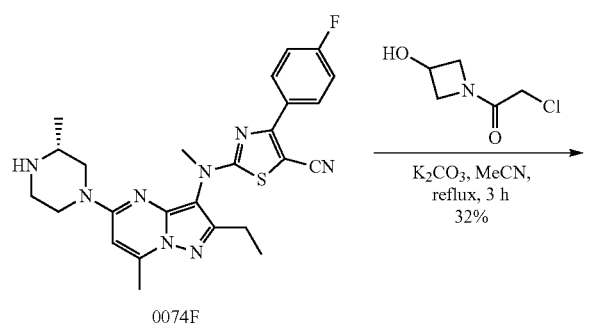

0074F

-continued

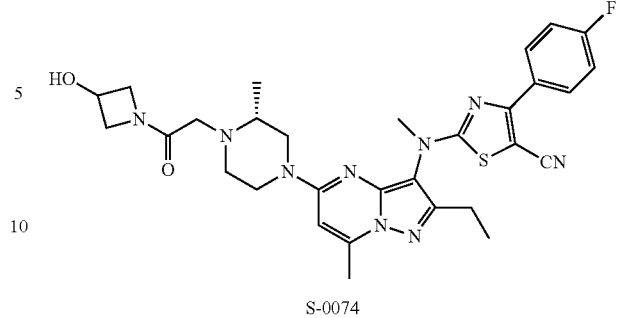

S-0074

Step 1: (R)-tert-butyl 4-(3-bromo-2-ethyl-7-methylpyrazolo[1,5-a]pyrimidin-5-yl)-2-methylpiperazine-1-carboxylate A solution of 3-bromo-5-chloro-2-ethyl-7-methylpyrazolo[1,5-a]pyrimidine (135 mg, 0.495 mmol), (R)-tert-butyl 2-methylpiperazine-1-carboxylate (494.5 mg, 2.47 mmol) and N,N-diisopropylethylamine (191 mg, 1.48 mmol) in acetonitrile (2 mL) was stirred at 90° C. in a sealed tube for 18 h, and concentrated. The residue was purified by flash chromatography (ethyl acetate/petroleum ether=0-30%) to give (R)-tert-butyl 4-(3-bromo-2-ethyl-7-methylpyrazolo[1,5-a]pyrimidin-5-yl)-2-methylpiperazine-1-carboxylate (150 mg, 69.3%) in the form of a colorless oil. LCMS (ESI) [M+H]$^+$=440.1.

Step 2: (R)-tert-butyl 4-(3-(diphenylmethyleneamino)-2-ethyl-7-methylpyrazolo [1,5-a]pyrimidin-5-yl)-2-methylpiperazine-1-carboxylate A mixture of (R)-tert-butyl 4-(3-bromo-2-ethyl-7-methylpyrazolo[1,5-a]pyrimidin-5-yl)-2-methylpiperazine-1-carboxylate (150 mg, 0.343 mmol), diphenylmethanimine (124 mg, 0.686 mmol), tris(dibenzylideneacetone)dipalladium(0) (31 mg, 0.0343 mmol), (±)-2,2'-bis (diphenylphosphino)-1,1'-binaphthyl (43 mg, 0.0686 mmol) and sodium tert-butoxide (99 mg, 1.031 mmol) in toluene (3 mL) was stirred at 110° C. for 16 h, and concentrated. The residue was purified by flash chromatography (ethyl acetate/petroleum ether=0-60%) to give (R)-tert-butyl 4-(3-(diphenylmethyleneamino)-2-ethyl-7-methylpyrazolo[1,5-a]pyrimidin-5-yl)-2-methylpiperazine-1-carboxylate (151 mg, 81.8%) in the form of a yellow oil. LCMS (ESI) [M+H]$^+$=539.3.

Step 3: (R)-tert-butyl 4-(3-amino-2-ethyl-7-methylpyrazolo[1,5-a]pyrimidin-5-yl)-2-methylpiperazine-1-carboxylate A mixture of (R)-tert-butyl 4-(3-(diphenylmethyleneamino)-2-ethyl-7-methylpyrazolo [1,5-a]pyrimidin-5-yl)-2-methylpiperazine-1-carboxylate (151 mg, 0.281 mmol) and citric acid (135 mg, 0.703 mmol) in acetonitrile (3 mL) was stirred at room temperature for 3 h, and concentrated. The residue was purified by flash chromatography (methanol/dichloromethane=0-40%) to give (R)-tert-butyl 4-(3-amino-2-ethyl-7-methylpyrazolo[1,5-a]pyrimidin-5-yl)-2-methylpiperazine-1-carboxylate in the form of a dark blue oil (104 mg, 99%). LCMS (ESI) [M+H]$^+$=375.2.

Step 4: (R)-tert-butyl 4-(3-(5-cyano-4-(4-fluorophenyl)thiazol-2-ylamino)-2-ethyl-7-methylpyrazolo[1,5-a]pyrimidin-5-yl)-2-methylpiperazine-1-carboxylate A mixture of (R)-tert-butyl 4-(3-amino-2-ethyl-7-methylpyrazolo[1,5-a]pyrimidin-5-yl)-2-methylpiperazine-1-carboxylate (104 mg, 0.278 mmol) and sodium hydride (60% in oil, 33.4 mg, 0.834 mmol) in N,N-dimethylformamide (5 mL) was stirred at 0° C. for 10 min. Then 2-chloro-4-(4-fluorophenyl)thiazole-5-carbonitrile (66 mg, 0.277 mmol) was added and the reaction system was stirred at room temperature for another 16 h. The reaction was quenched by adding water, and ethyl acetate (50 mL×3) was added for extraction. The organic phases were combined, washed with saturated brine (30 mL×2), dried over anhydrous sodium sulfate, filtered and concentrated. The residue was purified by flash chromatography (ethyl acetate/petroleum ether=0-40%) to give (R)-tert-butyl 4-(3-(5-cyano-4-(4-fluorophenyl) thiazol-2-ylamino)-2-ethyl-7-methylpyrazolo[1,5-a]pyrimidin-5-yl)-2-methylpiperazine-1-carboxylate in the form of a yellow oil (151 mg, 94%). LCMS (ESI) [M+H]$^+$=577.2.

Step 5: (R)-tert-butyl 4-(3-((5-cyano-4-(4-fluorophenyl)thiazol-2-yl)(methyl)amino)-2-ethyl-7-methylpyrazolo[1,5-a]pyrimidin-5-yl)-2-methylpiperazine-1-carboxylate A mixture of (R)-tert-butyl 4-(3-(5-cyano-4-(4-fluorophenyl)thiazol-2-ylamino)-2-ethyl-7-methylpyrazolo[1,5-a]pyrimidin-5-yl)-2-methylpiperazine-1-carboxylate (151 mg, 0.262 mmol) and sodium hydride (60% in oil, 21 mg, 0.524 mmol) in N,N-dimethylformamide (3 mL) was stirred at 0° C. for 10 min. Then methyl iodide (34 mg, 0.239 mmol) was added and the reaction system was stirred at room temperature for another 1 h, The reaction was quenched by adding water, and ethyl acetate (50 mL×3) was added for extraction. The organic phases were combined, washed with saturated brine (30 mL×2), dried over anhydrous sodium sulfate, filtered and concentrated. The residue was purified by flash chromatography (ethyl acetate/petroleum ether=0-35%) to give (R)-tert-butyl 4-(3-((5-cyano-4-(4-fluorophenyl) thiazol-2-yl)(methyl)amino)-2-ethyl-7-methylpyrazolo[1,5-a]pyrimidin-5-yl)-2-methylpiperazine-1-carboxylate in the form of a yellow oil (51 mg, 33%). LCMS (ESI) [M+H]$^+$=591.2.

Step 6: (R)-2-((2-ethyl-7-methyl-5-(3-methylpiperazin-1-yl)pyrazolo[1,5-a]pyrimidin-3-yl)(methyl) amino)-4-(4-fluorophenyl)thiazole-5-carbonitrile A mixture of (R)-tert-butyl 4-(3-((5-cyano-4-(4-fluorophenyl)thiazol-2-yl)(methyl) amino)-2-ethyl-7-methylpyrazolo[1,5-a]pyrimidin-5-yl)-2-methylpiperazine-1-carboxylate (50 mg, 0.085 mmol) and hydrogen chloride (4 N in dioxane, 1 mL) was stirred at room temperature for 1 h, and concentrated. A sodium carbonate solution (30 mL) was added to adjust pH to low alkalinity, and ethyl acetate (50 mL×3) was added for extraction. The organic phases were combined, washed with saturated brine (10 mL×2), dried over anhydrous sodium sulfate, filtered and concentrated to give (R)-2-((2-ethyl-7-methyl-5-(3-methylpiperazin-1-yl) pyrazolo[1,5-a]pyrimidin-3-yl)(methyl)amino)-4-(4-fluorophenyl) thiazole-5-carbonitrile (35 mg, 84%) in the form of a yellow oil, which was directly used in the next step without purification. LCMS (ESI) [M+H]$^+$=491.3.

Step 7: (R)-2-((2-ethyl-5-(4-(2-(3-hydroxyazetidin-1-yl)-2-oxoethyl)-3-methylpiperazin-1-yl)-7-methylpyrazolo[1,5-a]pyrimidin-3-yl)(methyl) amino)-4-(4-fluorophenyl)thiazole-5-carbonitrile (5-0074)

A mixture of (R)-2-((2-ethyl-7-methyl-5-(3-methylpiperazin-1-yl)pyrazolo[1,5-a]pyrimidin-3-yl)(methyl)amino)-4-(4-fluorophenyl)thiazole-5-carbonitrile (35 mg, 0.071 mmol), 2-chloro-1-(3-hydroxyazetidin-1-yl)acetyl (22 mg, 0.147 mmol) and potassium carbonate (30 mg, 0.217 mmol) in acetonitrile (3 mL) was stirred at reflux for 3 h, cooled to room temperature and filtered. The filtrate was concentrated. The residue was purified by flash chromatography (methanol/dichloromethane=0-10%) to give (R)-2-((2-ethyl-5-(4-(2-(3-hydroxyazetidin-1-yl)-2-oxoethyl)-3-methylpiperazin-1-yl)-7-methylpyrazolo[1,5-a]pyrimidin-3-yl)(methyl) amino)-4-(4-fluorophenyl)thiazole-5-carbonitrile S-0074 (14 mg, 32.5%) in the form of a white solid. LCMS (ESI) [M+H]$^+$=604.0@9.98 min. $^1$H NMR (400 MHz, CD$_3$OD) δ 8.15 (dd, J$_1$=8.8 Hz, J$_2$=5.4 Hz, 2H), 7.26 (t, J=8.8 Hz, 2H), 6.63 (s, 1H), 4.59-4.55 (m, 1H), 4.53-4.49 (m, 1H), 4.25-4.18 (m, 2H), 4.15-4.08 (m, 2H), 4.39-3.78 (m, 1H), 3.61 (s, 3H), 3.51-3.49 (m, 1H), 3.42-3.33 (m, 1H), 3.14-3.08 (m, 2H), 2.99-2.93 (m, 1H), 2.77-2.64 (m, 6H), 2.54-2.49 (m, 1H), 1.32 (t, J=7.6 Hz, 3H), 1.14 (d, J=3.6 Hz, 3H).

Example 24. S-0075: (S)-2-((2-ethyl-5-(4-(2-(3-hydroxyazetidin-1-yl)-2-oxoethyl)-3-methylpiperazin-1-yl)-7-methylpyrazolo[1,5-a]pyrimidin-3-yl) (methyl)amino)-4-(4-fluorophenyl)thiazole-5-carbonitrile

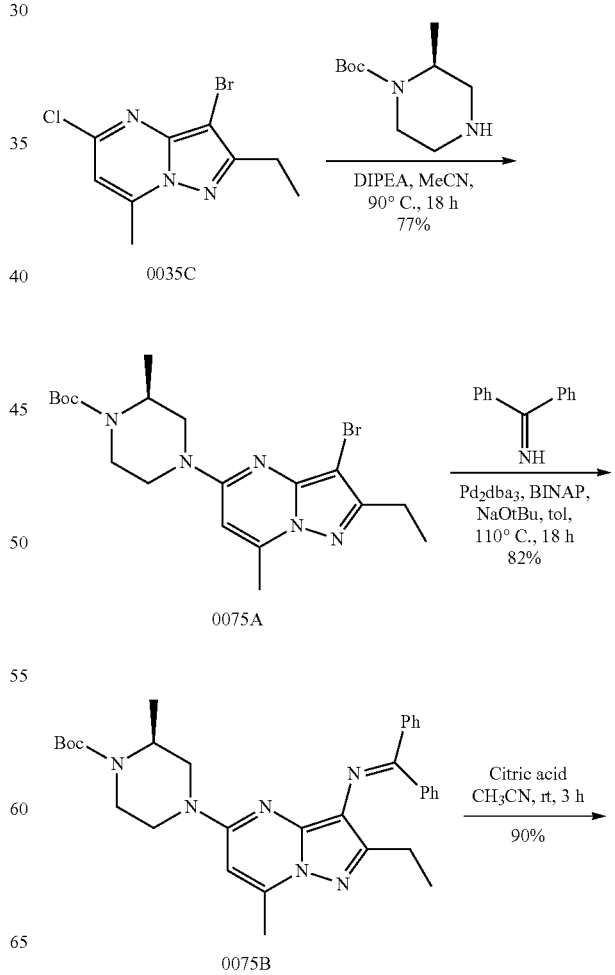

-continued

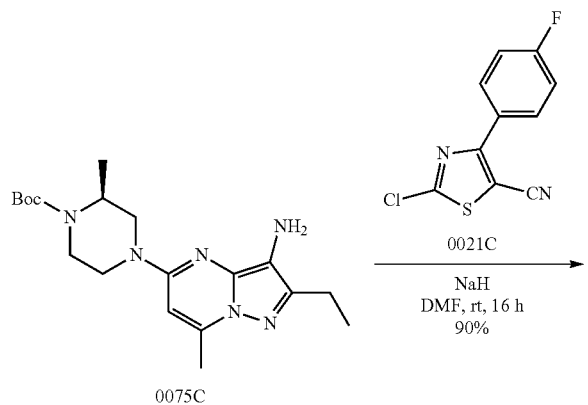

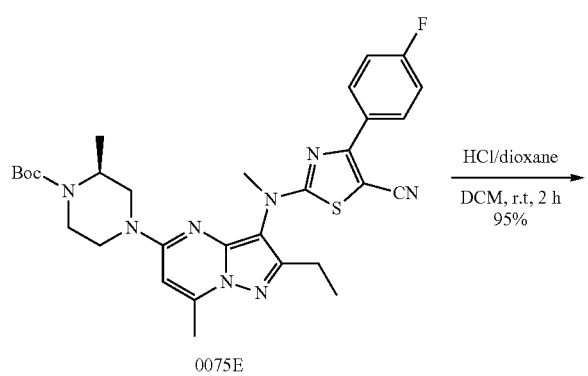

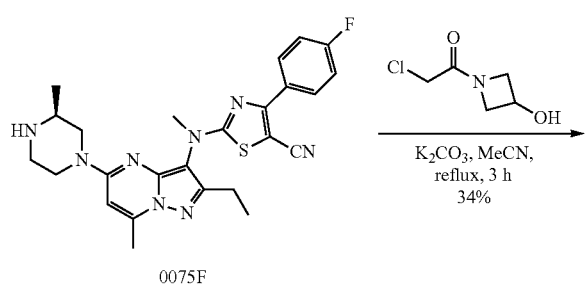

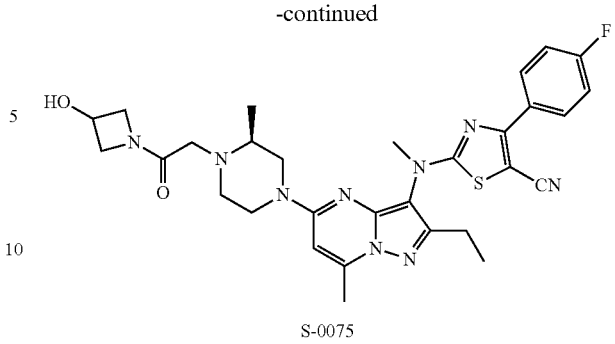

Step 1: (S)-tert-butyl 4-(3-bromo-2-ethyl-7-methylpyrazolo[1,5-a]pyrimidin-5-yl)-2-methylpiperazine-1-carboxylate A mixture of 3-bromo-5-chloro-2-ethyl-7-methylpyrazolo[1,5-a]pyrimidine (135 mg, 0.495 mmol), (S)-tert-butyl 2-methylpiperazine-1-carboxylate (494.5 mg, 2.47 mmol) and N,N-diisopropylethylamine (191 mg, 1.48 mmol) in acetonitrile (2 mL) was stirred at 90° C. in a sealed tube for 18 h and concentrated. The residue was purified by flash chromatography (ethyl acetate/petroleum ether=0-30%) to give (S)-tert-butyl 4-(3-bromo-2-ethyl-7-methylpyrazolo[1,5-a]pyrimidin-5-yl)-2-methylpiperazine-1-carboxylate (168 mg, 77.5%) in the form of a colorless oil. LCMS (ESI) [M+H]$^+$=440.1.

Step 2: (S)-tert-butyl 4-(3-(diphenylmethyleneamino)-2-ethyl-7-methylpyrazolo [1,5-a]pyrimidin-5-yl)-2-methylpiperazine-1-carboxylate A mixture of (S)-tert-butyl 4-(3-bromo-2-ethyl-7-methylpyrazolo[1,5-a]pyrimidin-5-yl)-2-methylpiperazine-1-carboxylate (168 mg, 0.384 mmol), diphenylmethanimine (139 mg, 0.768 mmol), tris(dibenzylideneacetone)dipalladium(0) (35 mg, 0.0382 mmol), (±)-2,2'-bis (diphenylphosphino)-1,1'-binaphthyl (48 mg, 0.0770 mmol), and sodium tert-butoxide (111 mg, 1.156 mmol) in toluene (3 mL) was stirred at 110° C. for 16 h, and concentrated. The residue was purified by flash chromatography (ethyl acetate/petroleum ether=0-60%) to give (S)-tert-butyl 4-(3-(diphenylmethyleneamino)-2-ethyl-7-methylpyrazolo[1,5-a]pyrimidin-5-yl)-2-methylpiperazine-1-carboxylate (170 mg, 82.3%) in the form of a yellow oil. LCMS (ESI) [M+H]$^+$=539.3.

Step 3: (S)-tert-butyl 4-(3-amino-2-ethyl-7-methylpyrazolo[1,5-a]pyrimidin-5-yl)-2-methylpiperazine-1-carboxylate A mixture of (S)-tert-butyl 4-(3-(diphenylmethyleneamino)-2-ethyl-7-methylpyrazolo [1,5-a]pyrimidin-5-yl)-2-methylpiperazine-1-carboxylate (170 mg, 0.316 mmol) and citric acid (152 mg, 0.791 mmol) in acetonitrile (3 mL) was stirred at room temperature for 3 h, and concentrated. The residue was purified by flash chromatography (methanol/dichloromethane=0-40%) to give (S)-tert-butyl 4-(3-amino-2-ethyl-7-methylpyrazolo[1,5-a]pyrimidin-5-yl)-2-methylpiperazine-1-carboxylate in the form of a dark blue oil (106 mg, 89.7%). LCMS (ESI) [M+H]$^+$=375.3.

Step 4: (S)-tert-butyl 4-(3-(5-cyano-4-(4-fluorophenyl)thiazol-2-ylamino)-2-ethyl-7-methylpyrazolo[1,5-a]pyrimidin-5-yl)-2-methylpiperazine-1-carboxylate A mixture of (S)-tert-butyl 4-(3-amino-2-ethyl-7-methylpyrazolo[1,5-a]pyrimidin-5-yl)-2-methylpiperazine-1-carboxylate (106 mg, 0.283 mmol) and sodium hydride (60% in oil, 34 mg, 0.850 mmol) in N,N-dimethylformamide (5 mL) was stirred at 0° C. for 10 min. Then 2-chloro-4-(4-fluorophenyl)thiazole-5-carbonitrile (67 mg, 0.282 mmol) was added and the reaction system was stirred at room temperature for another 16 h. The reaction was quenched by adding water, and ethyl acetate (50 mL×3) was added for extraction. The organic phases were combined, washed with saturated brine (30 mL×2), dried over anhydrous sodium sulfate, filtered and concentrated. The residue was purified by flash chromatography (ethyl acetate/petroleum ether=0-40%) to give (S)-tert-butyl 4-(3-(5-cyano-4-(4-fluorophenyl) thiazol-2-ylamino)-2-ethyl-7-methylpyrazolo[1,5-a]pyrimidin-5-yl)-2-methylpiperazine-1-carboxylate in the form of a yellow oil (147 mg, 90%). LCMS (ESI) [M+H]$^+$=577.2.

Step 5: (S)-tert-butyl 4-(3-((5-cyano-4-(4-fluorophenyl)thiazol-2-yl)(methyl)amino)-2-ethyl-7-methylpyrazolo[1,5-a]pyrimidin-5-yl)-2-methylpiperazine-1-carboxylate A mixture of (S)-tert-butyl 4-(3-(5-cyano-4-(4-fluorophenyl)thiazol-2-ylamino)-2-ethyl-7-methylpyrazolo[1,5-a]pyrimidin-5-yl)-2-methylpiperazine-1-carboxylate (147 mg, 0.255 mmol) and sodium hydride (60% in oil, 20.4 mg, 0.510 mmol) in N,N-dimethylformamide (3 mL) was stirred at 0° C. for 10 min. Then methyl iodide (32.6 mg, 0.230 mmol) was added and the reaction system was stirred at room temperature for another 1 h. The reaction was quenched by adding water, and ethyl acetate (50 mL×3) was added for extraction. The organic phases were combined, washed with saturated brine (30 mL×2), dried over anhydrous sodium sulfate, filtered and concentrated. The residue was purified by flash chromatography (ethyl acetate/petroleum ether=0-30%) to give (S)-tert-butyl 4-(3-((5-cyano-4-(4-fluorophenyl) thiazol-2-yl)(methyl)amino)-2-ethyl-7-methylpyrazolo[1,5-a]pyrimidin-5-yl)-2-methylpiperazine-1-carboxylate in the form of a yellow oil (63 mg, 41.9%). LCMS (ESI) [M+H]$^+$=591.2.

Step 6: (S)-2-((2-ethyl-7-methyl-5-(3-methylpiperazin-1-yl)pyrazolo[1,5-a]pyrimidin-3-yl)(methyl)amino)-4-(4-fluorophenyl)thiazole-5-carbonitrile A mixture of (S)-tert-butyl 4-(3-((5-cyano-4-(4-fluorophenyl)thiazol-2-yl)(methyl) amino)-2-ethyl-7-methylpyrazolo[1,5-a]pyrimidin-5-yl)-2-methylpiperazine-1-carboxylate (63 mg, 0.107 mmol) and hydrogen chloride (4 N in dioxane, 1 mL) was stirred at room temperature for 1 h, and concentrated. A sodium carbonate solution (30 mL) was added to adjust pH to low alkalinity, and ethyl acetate (50 mL×3) was added for extraction. The organic phases were combined, washed with saturated brine (10 mL×2), dried over anhydrous sodium sulfate, filtered and concentrated to give (S)-2-((2-ethyl-7-methyl-5-(3-methylpiperazin-1-yl) pyrazolo[1,5-a]pyrimidin-3-yl)(methyl)amino)-4-(4-fluorophenyl) thiazole-5-carbonitrile (50 mg, 95%) in the form of a yellow solid, which was directly used in the next step without purification. LCMS (ESI) [M+H]$^+$=491.3.

Step 7: (S)-2-((2-ethyl-5-(4-(2-(3-hydroxyazetidin-1-yl)-2-oxoethyl)-3-methylpiperazin-1-yl)-7-methylpyrazolo[1,5-a]pyrimidin-3-yl)(methyl)amino)-4-(4-fluorophenyl)thiazole-5-carbonitrile (S-0075)

A mixture of (S)-2-((2-ethyl-7-methyl-5-(3-methylpiperazin-1-yl)pyrazolo[1,5-a]pyrimidin-3-yl)(methyl)amino)-4-(4-fluorophenyl)thiazole-5-carbonitrile (50 mg, 0.102 mmol), 2-chloro-1-(3-hydroxyazetidin-1-yl)acetyl (30.4 mg, 0.204 mmol) and potassium carbonate (42.2 mg, 0.306 mmol) in acetonitrile (3 mL) was stirred at reflux for 3 h, cooled to room temperature and filtered. The filtrate was concentrated. The residue was purified by flash chromatography (methanol/dichloromethane=0-10%) to give (S)-2-((2-ethyl-5-(4-(2-(3-hydroxyazetidin-1-yl)-2-oxoethyl)-3-methylpiperazin-1-yl)-7-methylpyrazolo[1,5-a]pyrimidin-3-yl)(meth yl)amino)-4-(4-fluorophenyl)thiazole-5-carbonitrile S-0075 (21 mg, 34%) in the form of a white solid. LCMS (ESI) [M+H]$^+$=604.0@9.98 min. $^1$H NMR (400 MHz, CD$_3$OD) δ 8.15 (dd, J$_1$=8.8 Hz, J$_2$=5.4 Hz, 2H), 7.25 (t, J=8.8 Hz, 2H), 6.62 (s, 1H), 4.62-4.48 (m, 2H), 4.28-4.03 (m, 4H), 3.79-3.76 (m, 1H), 3.60 (s, 3H), 3.52-3.49 (m, 1H), 3.43-3.33 (m, 1H), 3.04-2.91 (m, 3H), 2.98 (q, J=7.6 Hz, 2H), 2.67 (s, 3H), 2.62-2.58 (m, 1H), 2.50-2.44 (m, 1H), 1.33 (t, J=7.6 Hz, 3H), 1.13 (d, J=4.8 Hz, 3H).

Example 25. S-0082: 2-(ethyl(2-ethyl-5-(4-(2-(3-hydroxyazetidin-1-yl)-2-2-oxoethyl) piperazin-1-yl) pyrazolo[1,5-a]pyrimidin-3-yl)amino)-4-(4-fluorophenyl)thiazole-5-carbonitrile

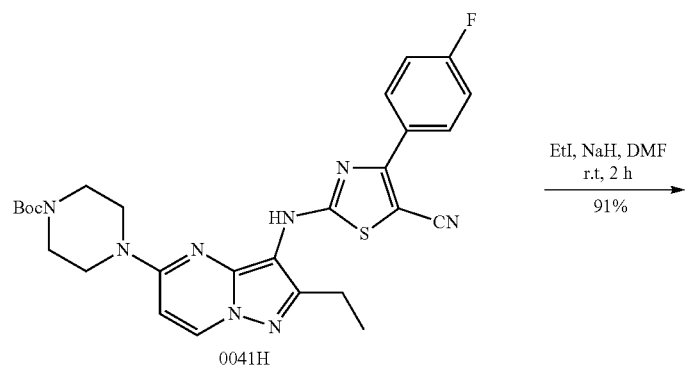

0041H

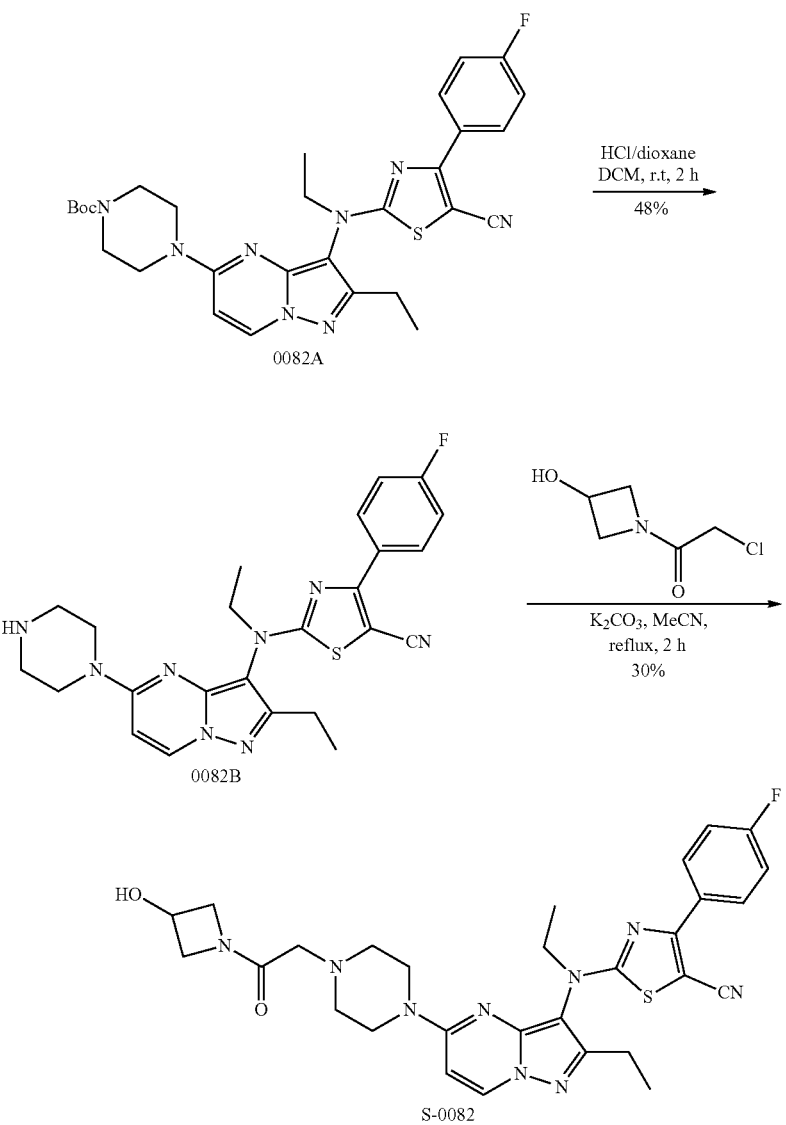

Step 1: tert-butyl 4-(3-((5-cyano-4-(4-fluorophenyl)thiazol-2-yl)(ethyl)amino)-2-ethylpyrazolo[1,5-a]pyrimidin-5-yl)piperazine-1-carboxylate A mixture of tert-butyl 4-(3-(5-cyano-4-(4-fluorophenyl)thiazol-2-ylamino)-2-ethylpyrazolo[1,5-a]pyrimidin-5-yl)piperazine-1-carboxylate (78 mg, 0.135 mmol) and sodium hydride (60% in oil, 11 mg, 0.270 mmol) in N,N-dimethylformamide (3 mL) was stirred at 0° C. for 10 min. Then iodoethane (19 mg, 0.12 mmol) was added and the reaction system was stirred at room temperature for another 2 h. The reaction was quenched by adding water, and ethyl acetate (15 mL×3) was added for extraction. The organic phases were combined, washed with saturated brine (30 mL×2), dried over anhydrous sodium sulfate, filtered and concentrated. The residue was purified by flash chromatography (methanol/dichloromethane=0-10%) to give tert-butyl 4-(3-((5-cyano-4-(4-fluorophenyl)thiazol-2-yl) (ethyl)amino)-2-ethylpyrazolo[1,5-a]pyrimidin-5-yl)piperazine-1-carboxylate (71 mg, 91%). LCMS (ESI) [M+H]$^+$=577.

Step 2: 2-(ethyl(2-ethyl-5-(piperazin-1-yl)pyrazolo[1,5-a]pyrimidin-3-yl)amino)-4-(4-fluorophenyl)thiazole-5-carbonitrile A mixture of 4-(3-((5-cyano-4-(4-fluorophenyl)thiazol-2-yl)(ethyl)amino)-2-ethylpyrazolo[1,5-a]pyrimidin-5-yl)piperazine-1-carboxylate (71 mg, 0.123 mmol) and hydrogen chloride (4 N in dioxane, 5 mL) was stirred at room temperature for 2 h, and concentrated. A sodium carbonate solution (20 mL) was added to adjust pH to low alkalinity. Ethyl acetate (20 mL×3) was added for extraction. The organic phases were combined, washed with saturated brine (10 mL×2), dried over anhydrous sodium sulfate, filtered and concentrated to give 2-(ethyl(2-ethyl-5-(piperazin-1-yl)pyrazolo[1,5-a]pyrimidin-3-yl) amino)-4-(4-fluorophenyl)thiazole-5-carbonitrile (28 mg, 48%) in the form of a yellow solid, which was directly used in the next step without purification. LCMS (ESI) [M+H]$^+$=477.

Step 3: 2-(ethyl(2-ethyl-5-(4-(2-(3-hydroxyazetidin-1-yl)-2-oxoethyl)piperazin-1-yl) pyrazolo[1,5-a]pyrimidin-3-yl)amino)-4-(4-fluorophenyl)thiazole-5-carbonitrile S-0082

A mixture of 2-(ethyl(2-ethyl-5-(piperazin-1-yl)pyrazolo[1,5-a]pyrimidin-3-yl) amino)-4-(4-fluorophenyl)thiazole-5-carbonitrile (28 mg, 0.059 mmol), 2-chloro-1-(3-hydroxyazetidin-1-yl)acetyl (11 mg, 0.07 mmol) and potassium carbonate (16 mg, 0.118 mmol) in acetonitrile (3 mL) was stirred at reflux for 2 h, cooled to room temperature and filtered. The filtrate was concentrated. The residue was purified by Pre-HPLC to give 2-(ethyl(2-ethyl-5-(4-(2-(3-hydroxyazetidin-1-yl)-2-oxoethyl)piperazin-1-yl)pyrazolo[1,5-a]pyrimidin-3-yl)amino)-4-(4-fluorophenyl)thiazole-5-carbonitrile S-0082 in the form of a white solid (10.5 mg, 30%). LCMS (ESI) [M+H]$^+$=590.1@6.27 min; $^1$H NMR (400 MHz, CD$_3$OD) δ 8.38 (d, J=8.0 Hz, 1H), 8.16-8.12 (m, 2H), 7.27-7.23 (m, 2H), 6.71 (d, J=8.0 Hz, 1H), 4.60-4.47 (m, 2H), 4.27-4.20 (m, 2H), 4.08-4.06 (m, 1H), 3.90-3.38 (m, 6H), 3.15 (m, 2H), 2.73-2.67 (q, J=7.2 Hz, 2H), 2.59 (m, 4H), 1.35-1.30 (m, 6H).

Example 26. S-0094: 2-((2-ethyl-5-(4-(2-(3-hydroxyazetidin-1-yl)-2-oxoethyl) piperazin-1-yl)-2H-pyrazolo[4,3-b]pyridin-3-yl)(methyl)amino)-4-(4-fluorophenyl) thiazole-5-carbonitrile

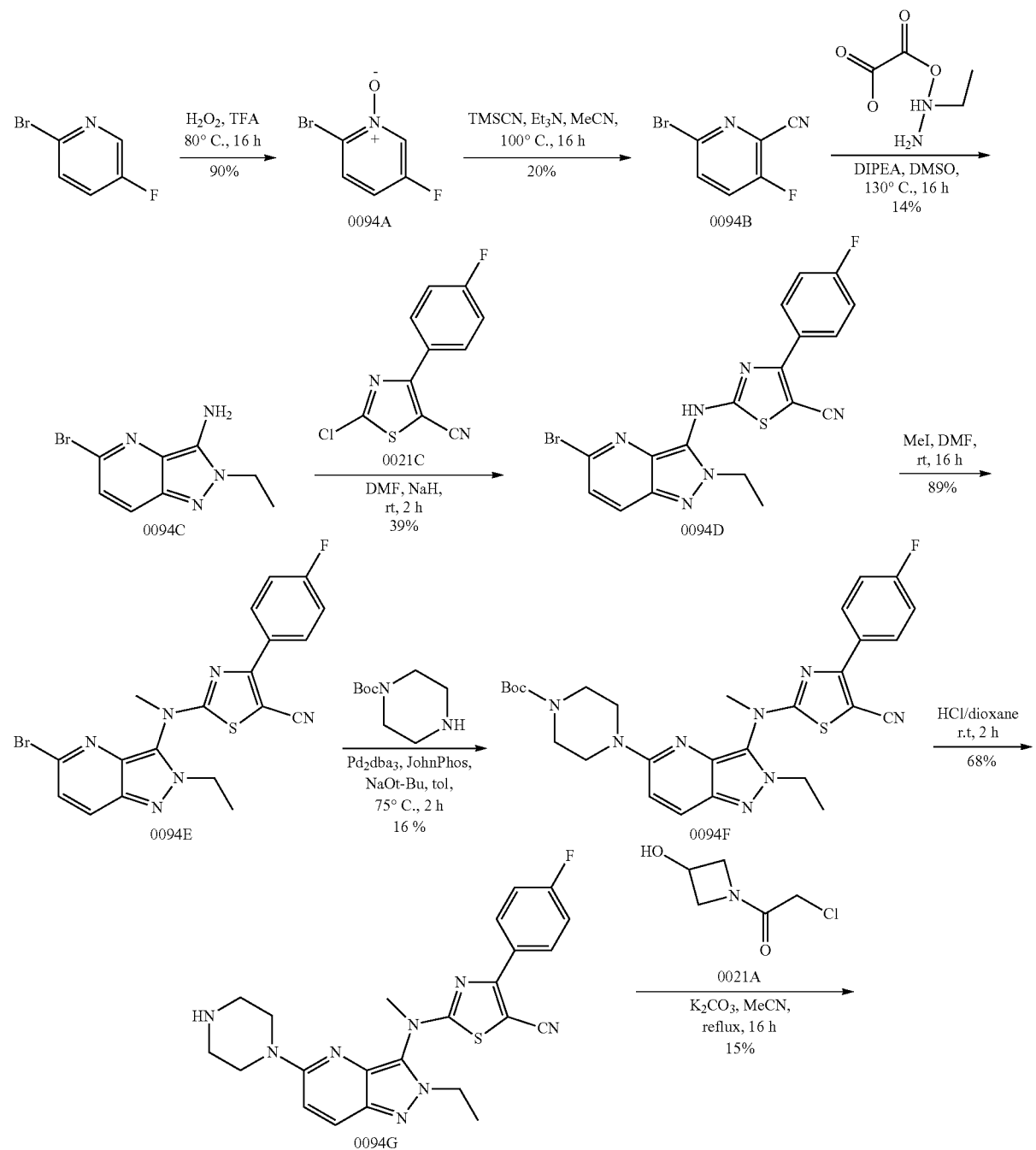

-continued

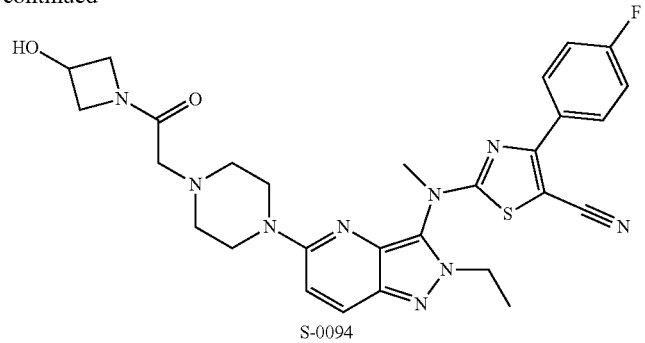

S-0094

Step 1: 2-bromo-5-fluoropyridin 1-oxide

To a solution of 2-bromo-5-fluoropyridine (3.0 g, 17.04 mmol) in 2,2,2-trifluoroacetic acid (25 mL) was added hydrogen peroxide (5 mL). The reaction solution was stirred at 80° C. for 16 h. Then the reaction was quenched with water (20 mL), and ethyl acetate (20 mL×3) was added for extraction. The organic phases were washed with saturated brine (20 mL×3), dried over anhydrous sodium sulfate, filtered and concentrated to give 2-bromo-5-fluoropyridin 1-oxide (2.98 g, 90%) in the form of a yellow oil, which was directly used in the next step without purification. LCMS (ESI) [M+H]+=193.7.

Step 2: 6-bromo-3-fluoro-2-cyanopyridine

To a solution of 2-bromo-5-fluoropyridin 1-oxide (500 mg, 2.6 mmol) in acetonitrile (2 mL) was added trimethylsilanecarbonitrile (1.28 g, 13 mmol) and triethylamine (1.3 g, 13 mmol). The reaction solution was stirred at 100° C. for 16 h, and then concentrated. The residue was purified by flash chromatography (ethyl acetate/petroleum ether=0-20%) to give 6-bromo-3-fluoro-2-cyanopyridine (100 mg, 20% yield). LCMS (ESI) [M+H]+=202.7.

Step 3: 5-bromo-2-ethyl-2H-pyrazolo[4,3-b]pyridin-3-amine

To a solution of 6-bromo-3-fluoro-2-cyanopyridine (600 mg, 3 mmol) and ethylhydrazine oxalate (2.25 g, 15 mmol) in dimethyl sulfoxide (10 mL) was added N,N-diisopropylethylamine (3.1 g, 24 mmol). The reaction solution was stirred at 130° C. for 16 h. After cooling to room temperature, ethyl acetate (50 mL×3) was added for extraction. The organic phases were washed with saturated brine (40 mL×3), dried with anhydrous sodium sulfate, filtered and concentrated. The residue was purified by flash chromatography (ethyl acetate/petroleum ether=0-60%) to give 5-bromo-2-ethyl-2H-pyrazolo[4,3-b]pyridin-3-amine (100 mg, 14%) in the form of a yellow solid. LCMS (ESI) [M+H]+=240.9. $^1$H NMR (400 MHz, DMSO-d$_6$) δ 7.67 (d, J=8.8 Hz, 1H), 7.21 (d, J=8.8 Hz, 1H), 4.52 (bs, 2H), 4.28 (q, J=7.2 Hz, 2H), 1.53 (t, J=7.2 Hz, 3H).

Step 4: 2-((5-bromo-2-ethyl-2H-pyrazolo[4,3-b]pyridin-3-yl)amino)-4-(4-fluorophenyl) thiazole-5-carbonitrile To a solution of 5-bromo-2-ethyl-2H-pyrazolo[4,3-b]pyridin-3-amine (100 mg, 0.41 mmol) in N,N-dimethylformamide (3 mL) was slowly added sodium hydride (60% in oil, 33 mg, 0.82 mmol). The reaction solution was stirred at room temperature for 10 min. Then 2-chloro-4-(4-fluorophenyl)thiazole-5-carbonitrile (98 mg, 0.41 mmol) was added, and the resulting reaction solution was stirred at room temperature for 30 min. The reaction was quenched with water (10 mL), and ethyl acetate (10 mL×3) was added for extraction. Then organic phases were dried over anhydrous sodium sulfate, filtered and concentrated. The residue was purified by flash chromatography (ethyl acetate/petroleum ether 0-35%) to give 2-((5-bromo-2-ethyl-2H-pyrazolo[4,3-b]pyridin-3-yl)amino)-4-(4-fluorophenyl)thiazole-5-carbonitrile (71 mg, 39%) in the form of a yellow oil. LCMS (ESI) [M+H]+=445.0.

Step 5: 2-((5-bromo-2-ethyl-2H-pyrazolo[4,3-b]pyridin-3-yl)(methyl)amino)-4-(4-fluorophenyl)thiazole-5-carbonitrile To a solution of 2-((5-bromo-2-ethyl-2H-pyrazolo[4,3-b]pyridin-3-yl)amino)-4-(4-fluorophenyl)thiazole-5-carbonitrile (71 mg, 0.16 mmol) in N,N-dimethylformamide (3 mL) was slowly added sodium hydride (60% in oil, 13 mg, 0.32 mmol). The reaction solution was stirred at room temperature for 30 min. Then methyl iodide (23 mg, 0.16 mmol) was added, and the resulting mixture solution was stirred at room temperature for 2 h. The reaction was quenched with water (10 mL), and ethyl acetate (10 mL×3) was added for extraction. The organic phases were washed with saturated brine (10 mL×3), dried over anhydrous sodium sulfate, filtered and concentrated. The residue was purified by flash chromatography (ethyl acetate/petroleum ether=0-30%) to give 2-((5-bromo-2-ethyl-2H-pyrazolo[4,3-b]pyridin-3-yl)(methyl)amino)-4-(4-fluorophenyl)thiazole-5-carbonitrile (65 mg, 89%) in the form of a brown oil. LCMS (ESI) [M+H]+=457.0.

Step 6: tert-butyl 4-(3-((5-cyano-4-(4-fluorophenyl)thiazole-2-yl)(methyl)amino)-2-ethyl-2H-pyrazolo[4,3-b]pyridin-5-yl)piperazine-1-carboxylate In a glove box, to a solution of 2-((5-bromo-2-ethyl-2H-pyrazolo[4,3-b]pyridin-3-yl) (methyl)amino)-4-(4-fluorophenyl)thiazole-5-carbonitrile (100 mg, 0.22 mmol), tert-butyl piperazine-1-carboxylate (205 mg, 1.1 mmol), tris(dibenzylideneacetone)dipalladium(0) (20 mg, 0.022 mmol), 2-(di-tert-butylphosphino)biphenyl (7 mg, 0.022 mmol), and sodium tert-butoxide (65 mg, 0.66 mmol) was added toluene (3 mL). The reaction solution was stirred at 75° C. for 2 h. After cooling to room temperature, ethyl acetate (10 mL) was added for dilution. Then the reaction solution was washed with water (10 mL×3), dried over anhydrous sodium sulfate, filtered and concentrated. The residue was purified by flash chromatography (ethyl acetate/petroleum ether=0-25%) to give tert-butyl 4-(3-((5-cyano-4-(4-fluorophenyl)thiazol-2-yl)(methyl)amino)-2-ethyl-2H-pyrazolo[4,3-b]pyridin-5-yl)piperazine-1-carboxylate (20 mg, 16% yield) in the form of a yellow solid. LCMS (ESI) [M+H]⁺=563.3.

Step 7: 2-((2-ethyl-5-(piperazin-1-yl)-2H-pyrazolo [4,3-b]pyridin-3-yl) (methyl)amino)-4-(4-fluorophenyl)thiazole-5-carbonitrile A solution of tert-butyl 4-(3-((5-cyano-4-(4-fluorophenyl)thiazol-2-yl) (methyl)amino)-2-ethyl-2H-pyrazolo[4,3-b]pyridin-5-yl)piperazine-1-carboxylate (20 mg, 0.035 mmol) in hydrogen chloride (4 N in 1,4-dioxane, 2 mL) was stirred at room temperature for 4 h, and then concentrated. Aqueous sodium bicarbonate (5 mL) was added to the reaction solution, and ethyl acetate (5 mL×3) was added for extraction. The organic phases were washed with saturated brine (4 mL×3), dried over anhydrous sodium sulfate, filtered and concentrated to give 2-((2-ethyl-5-(piperazin-1-yl)-2H-pyrazolo[4,3-b]pyridin-3-yl)(methyl)amino)-4-(4-fluorophenyl)thiazole-5-carbonitrile (11 mg, 68%) in the form of a yellow solid. LCMS (ESI) [M+H]⁺=463.2.

Step 8: 2-((2-ethyl-5-(4-(2-(3-hydroxyazetidin-1-yl)-2-oxoethyl)piperazin-1-yl)-2H-pyrazolo[4,3-b]pyridin-3-yl)(methyl)amino)-4-(4-fluorophenyl) thiazole-5-carbonitrile (S-0094)

A mixture of 2-((2-ethyl-5-(piperazin-1-yl)-2H-pyrazolo[4,3-b]pyridin-3-yl)(methyl) amino)-4-(4-fluorophenyl)thiazole-5-carbonitrile (11 mg, 0.024 mmol), 2-chloro-1-(3-hydroxyazetidin-1-yl)acetyl (7 mg, 0.048 mmol) and potassium carbonate (60 mg, 0.438 mmol) in acetonitrile (3 mL) was stirred at reflux for 2 h. The reaction solution was concentrated. The residue was purified by Pre-HPLC to give 2-((2-ethyl-5-(4-(2-(3-hydroxyazetidin-1-yl)-2-oxoethyl)piperazin-1-yl)-2H-pyrazolo[4,3-b]pyridin-3-yl)(methyl)amino)-4-(4-fluorophenyl)thiazole-5-carbonitrile S-0094 (2.1 mg, 15%) in the form of a white solid. LCMS (ESI) [M+H]⁺=576.0@7.46 min; ¹H NMR (400 MHz, CD₃OD) δ 8.16-8.12 (m, 2H), 7.87 (d, J=9.6 Hz, 1H), 7.28-7.23 (m, 2H), 7.17 (d, J=10.0 Hz, 1H), 4.60-4.55 (m, 1H), 4.53-4.48 (m, 1H), 4.32 (q, J=7.2 Hz, 2H), 4.27-4.20 (m, 1H), 4.09-4.05 (m, 1H), 3.81-3.76 (m, 1H), 3.71 (s, 3H), 3.69-3.66 (m, 4H), 3.11 (d, J=3.6 Hz, 2H), 2.61 (m, 4H), 1.55 (t, J=7.2 Hz, 3H).

Example 27. S-0095: 2-((2-ethyl-5-(4-(2-(3-hydroxyazetidin-1-yl)-2-oxoethyl) piperazine-1-yl)-7-methyl-2H-pyrazolo[4,3-b]pyridin-3-yl)(methyl) amino)-4-(4-fluorophenyl)thiazole-5-carbonitrile

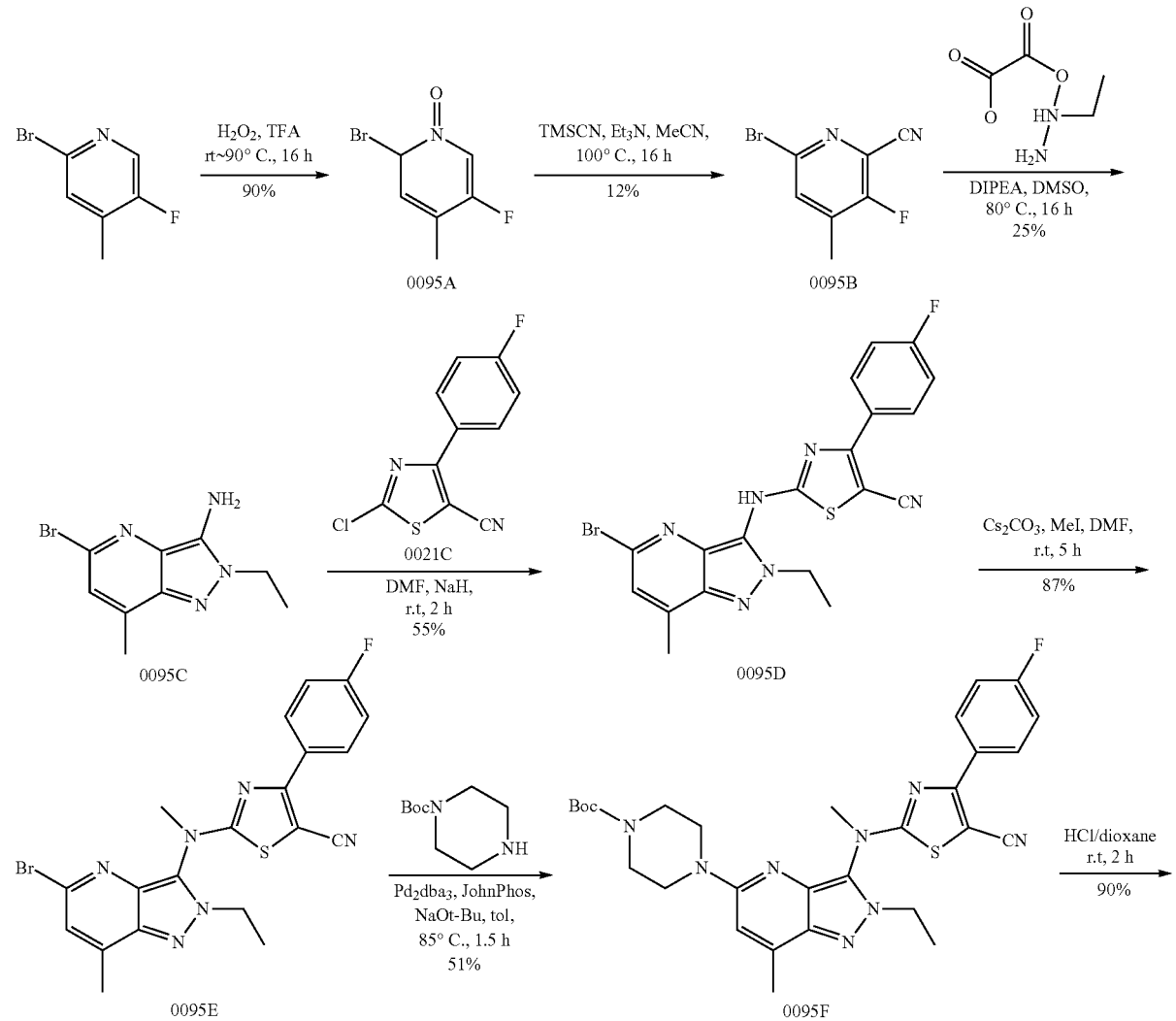

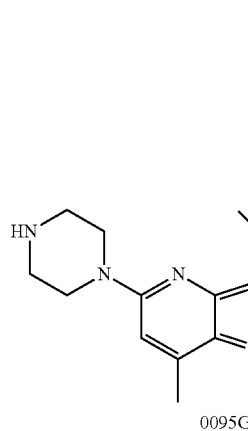

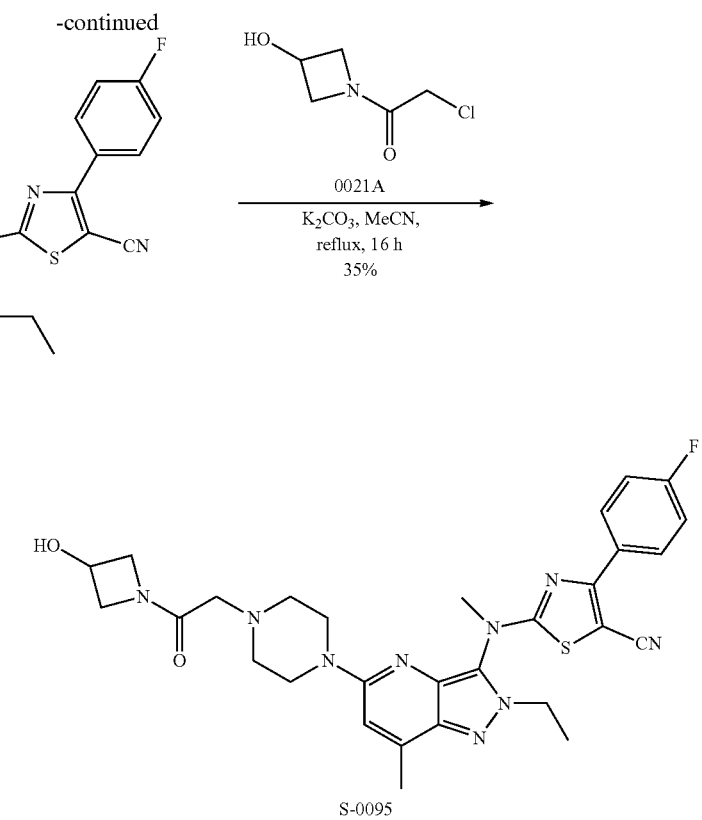

Step 1: 2-bromo-5-fluoro-4-methylpyridine 1-oxide

To a solution of 2-bromo-5-fluoro-4-methylpyridine (1.0 g, 5.29 mmol) in 2,2,2-trifluoroacetic acid (15 mL) was added hydrogen peroxide (4 mL). The reaction solution was stirred at 80° C. for 16 h. The reaction was quenched with water (20 mL), and ethyl acetate (20 mL×3) was added for extraction. The organic phases were washed with saturated brine (20 mL×3), dried over anhydrous sodium sulfate, filtered and concentrated to give 2-bromo-5-fluoro-4-methylpyridine 1-oxide 0095A (2.98 g, 90%) in the form of a yellow oil, which was directly used in the next step without purification. LCMS (ESI) $[M+H]^+$=207 (LC-MS Method A).

Step 2: 6-bromo-3-fluoro-4-methyl-2-cyanopyridine

To a solution of 2-bromo-5-fluoro-4-methylpyridine 1-oxide 0095A (2.5 g, 12.1 mmol) in acetonitrile (5 mL) was added trimethylsilanecarbonitrile (5.9 g, 60.6 mmol) and triethylamine (5.9 g, 60.6 mmol). The reaction solution was stirred at 100° C. for 16 h, and then concentrated to driness. The residue was purified by flash chromatography (ethyl acetate/petroleum ether=0-20%) to give 6-bromo-3-fluoro-4-methyl-2-cyanopyridine 0095B (500 mg, 12%). LCMS (ESI) $[M+H]^+$=214 (LC-MS Method A).

Step 3: 5-bromo-2-ethyl-7-methyl-2H-pyrazolo[4,3-b]pyridin-3-amine

To a solution of 6-bromo-3-fluoro-4-methyl-2-cyanopyridine 0095B (500 mg, 2.34 mmol) and ethylhydrazine oxalate (2.7 g, 18.7 mmol) in dimethyl sulfoxide (10 mL) was added N,N-diisopropylethylamine (2.4 g, 18.7 mmol). The reaction solution was stirred at 80° C. for 2 h. After cooling to room temperature, ethyl acetate (50 mL×3) was added for extraction. The organic phases were washed with saturated brine (40 mL×3), dried over anhydrous sodium sulfate, filtered and concentrated. The residue was purified by flash chromatography (ethyl acetate/petroleum ether=0-60%) to give 5-bromo-2-ethyl-7-methyl-2H-pyrazolo[4,3-b]pyridin-3-amine 0095C (150 mg, 25%) in the form of a yellow solid. LCMS (ESI) $[M+H]^+$=255 (LC-MS Method B).

Step 4: 2-(5-bromo-2-ethyl-7-methyl-2H-pyrazolo[4,3-b]pyridin-3-ylamino)-4-(4-fluorophenyl)thiazole-5-carbonitrile To a solution of 5-bromo-2-ethyl-7-methyl-2H-pyrazolo[4,3-b]pyridin-3-amine 0095C (140 mg, 0.55 mmol) in N,N-dimethylformamide (4 mL) was added sodium hydride (60% in mineral oil, 20 mg, 0.82 mmol). The reaction solution was stirred at room temperature for 10 min. Then 2-chloro-4-(4-fluorophenyl)thiazole-5-carbonitrile (196 mg, 0.82 mmol) was added, and the resulting reaction solution was stirred at room temperature for 2 h. The reaction was quenched with ice water (10 mL), and ethyl acetate (10 mL×3) was added for extraction. The organic phases were washed with saturated brine (10 mL×3), dried over anhydrous sodium sulfate, filtered and concentrated. The residue was purified by flash chromatography (ethyl acetate/petroleum ether=0-35%) to give 2-(5-bromo-2-ethyl-7-methyl-2H-pyrazolo [4,3-b]pyridin-3-ylamino)-4-(4-fluorophenyl)thiazole-5-carbonitrile 0095D (140 mg, 55%) in the form of a yellow solid. LCMS (ESI) $[M+H]^+$=457 (LC-MS Method A).

Step 5: 2-((5-bromo-2-ethyl-7-methyl-2H-pyrazolo[4,3-b]pyridin-3-yl)(methyl)amino)-4-(4-fluorophenyl)thiazole-5-carbonitrile To a solution of 2-(5-bromo-2-ethyl-7-methyl-2H-pyrazolo[4,3-b]pyridin-3-ylamino)-4-(4-fluorophenyl)thiazole-5-carbonitrile 0095D (130 mg, 0.285 mmol) in N,N-dimethylformamide (3 mL) was added cesium carbonate (278 mg, 0.855 mmol). The reaction solution was stirred at room temperature for 30 min. Then methyl iodide (40 mg, 0.285 mmol) was added, and the resulting mixture was stirred at room temperature for 2 h. The reaction was quenched with water (10 mL), and ethyl acetate (10 mL×3) was added for extraction. The organic phases were washed with saturated brine (10 mL×3), dried over anhydrous sodium sulfate, filtered and concentrated. The residue was purified by flash chromatography (ethyl acetate/petroleum ether=0-30%) to give 2-((5-bromo-2-ethyl-7-methyl-2H-pyrazolo[4,3-b]pyridin-3-yl)(methyl)amino)-4-(4-fluorophenyl)thiazole-5-carbonitrile 0095E (100 mg, 87%) in the form of a yellow solid. LCMS (ESI) [M+H]$^+$=471, (LC-MS Method B).

Step 6: tert-butyl 4-(3-((5-cyano-4-(4-fluorophenyl)thiazol-2-yl)(methyl)amino)-2-ethyl-7-methyl-2H-pyrazolo[4,3-b]pyridin-5-yl)piperidine-1-carboxylate In a glove box, to a sealed tube were added 2-((5-bromo-2-ethyl-7-methyl-2H-pyrazolo [4,3-b]pyridin-3-yl)(methyl)amino)-4-(4-fluorophenyl)thiazole-5-carbonitrile 0095E (100 mg, 0.21 mmol), tris(dibenzylideneacetone)dipalladium(0) (19 mg, 0.021 mmol), tert-butyl piperazine-1-carboxylate (396 mg, 2.13 mmol), 2-(di-tert-butylphosphino)biphenyl (13 mg, 0.042 mmol), sodium tert-butoxide (61 mg, 0.64 mmol) and toluene (3 mL). The reaction solution was stirred at 85° C. for 2 h. After cooling to room temperature, ethyl acetate (10 mL) was added for extraction. The organic phases were washed with water (10 mL×3), dried over anhydrous sodium sulfate, filtered and concentrated. The residue was purified by flash chromatography (ethyl acetate/petroleum ether=0-25%) to give tert-butyl 4-(3-((5-cyano-4-(4-fluorophenyl)thiazol-2-yl)(methyl)amino)-2-ethyl-7-methyl-2H-pyrazolo[4,3-b]pyridin-5-yl)piperidine-1-carboxylate 0095F (55 mg, 51% yield) in the form of a yellow solid. LCMS (ESI) [M+H]$^+$=577, (LC-MS Method B).

Step 7: 2-((2-ethyl-7-methyl-5-(piperazin-1-yl)-2H-pyrazolo[4,3-b]pyridin-3-yl)(methyl) amino)-4-(4-fluorophenyl)thiazole-5-carbonitrile A solution of tert-butyl 4-(3-((5-cyano-4-(4-fluorophenyl)thiazol-2-yl)(methyl)amino)-2-ethyl-7-methyl-2H-pyrazolo[4,3-b]pyridin-5-yl)piperidine-1-carboxylate 0095F (55 mg, 0.095 mmol) in hydrogen chloride (4 N in 1,4-dioxane, 3 mL) was stirred at room temperature for 1 h. The reaction solution was concentrated. Then aqueous sodium bicarbonate (5 mL) was added, and dichloromethane (5 mL×3) was added for extraction. The organic phases were washed with saturated brine (5 mL×3), dried over anhydrous sodium sulfate, filtered and concentrated to give 2-((2-ethyl-7-methyl-5-(piperazin-1-yl)-2H-pyrazolo[4,3-b]pyridin-3-yl)(methyl)amino)-4-(4-fluorophenyl)thiazole-5-carbonitrile 0095G (40 mg, 90%) in the form of a yellow solid. LCMS (ESI) [M+H]$^+$=477, (LC-MS Method A).

Step 8: 2-((2-ethyl-5-(4-(2-(3-hydroxyazetidin-1-yl)-2-oxoethyl)piperazin-1-yl)-7-methyl-2H-pyrazolo[4,3-b]pyridin-3-yl)(methyl)amino)-4-(4-fluorophenyl)thiazole-5-carbonitrile A solution of 2-((2-ethyl-7-methyl-5-(piperazin-1-yl)-2H-pyrazolo[4,3-b]pyridin-3-yl)(methyl)amino)-4-(4-fluorophenyl)thiazole-5-carbonitrile 0095G (40 mg, 0.084 mmol), 2-chloro-1-(3-hydroxyazetidin-1-yl)ethanone (25 mg, 0.168 mmol) and potassium carbonate (34 mg, 0.252 mmol) in acetonitrile (3 mL) was stirred at reflux for 2 h. The reaction solution was concentrated. The residue was purified by flash chromatography (methanol/dichloromethane=0-15%) to give 2-((2-ethyl-5-(4-(2-(3-hydroxyazetidin-1-yl)-2-oxoethyl) piperazin-1-yl)-7-methyl-2H-pyrazolo[4,3-b]pyridin-3-yl)(methyl)amino)-4-(4-fluorophenyl) thiazole-5-carbonitrile S-0095 (17.3 mg, 35%) in the form of a yellow solid. LCMS (ESI) [M+H]$^+$=590.0@7.857 min (Method B); $^1$H NMR (400 MHz, CD$_3$OD) δ 8.14 (dd, J=8.8, 5.4 Hz, 2H), 7.25 (t, J=8.8 Hz, 2H), 6.99 (d, J=20.6 Hz, 1H), 4.89-4.42 (m, 2H), 4.42-4.16 (m, 3H), 4.07 (dd, J=9.4, 3.6 Hz, 1H), 3.87-3.67 (m, 1H), 3.65 (d, J=4.7 Hz, 3H), 3.34-2.97 (m, 2H), 2.61 (dd, J=15.0, 10.4 Hz, 6H), 1.46 (s, 3H), 1.40 (s, 7H).

Example 28. S-0097: 2-((2-ethyl-5-(4-(2-(3-hydroxyazetidin-1-yl)-2-oxoethyl) piperazin-1-yl)furo[3,2-b]pyridin-3-yl)(methyl)amino)-4-(4-fluorophenyl)thiazole-5-carbonitrile

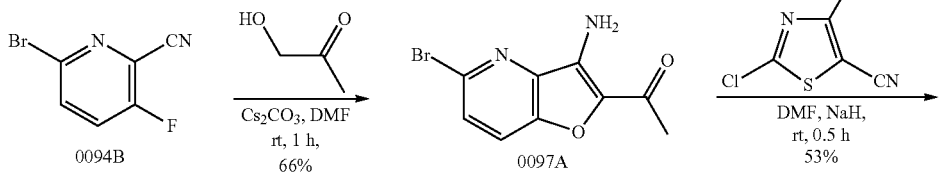

-continued
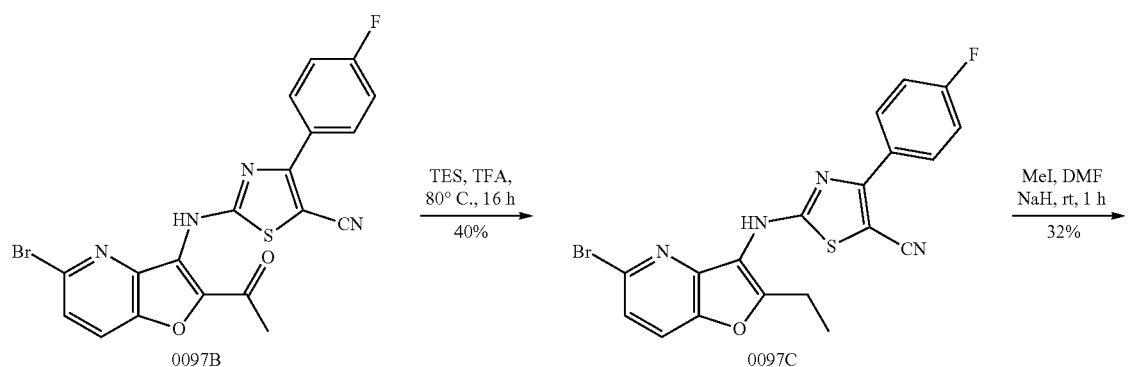
0097B
TES, TFA,
80° C., 16 h
40%
0097C
MeI, DMF
NaH, rt, 1 h
32%
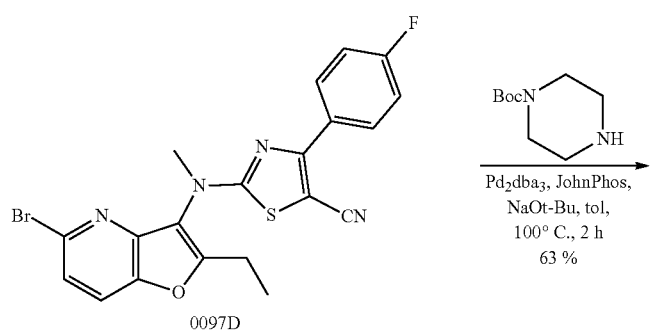
0097D
BocN⌒NH
Pd₂dba₃, JohnPhos,
NaOt-Bu, tol,
100° C., 2 h
63 %
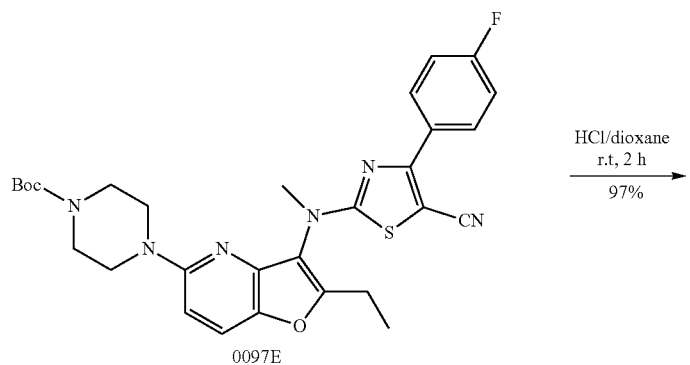
0097E
HCl/dioxane
r.t, 2 h
97%
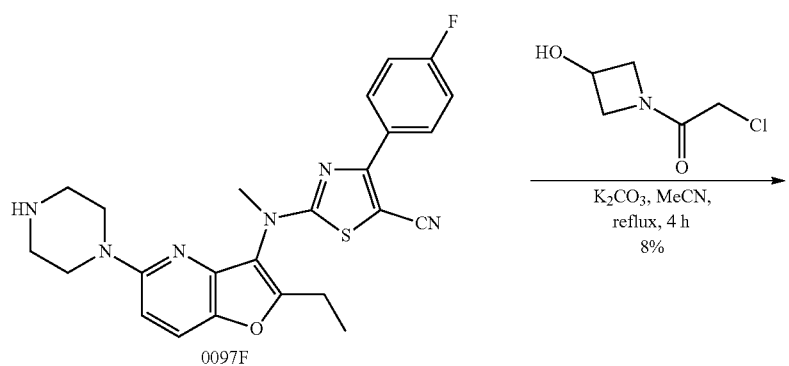
0097F
K₂CO₃, MeCN,
reflux, 4 h
8%

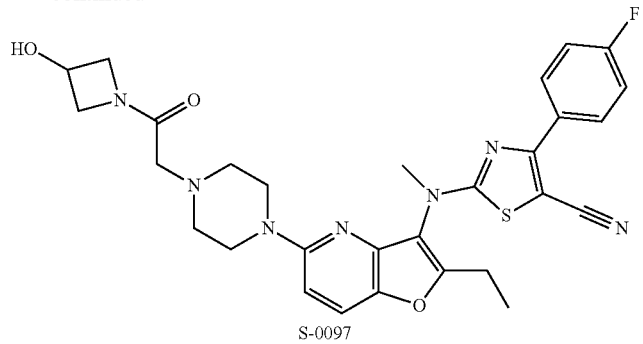

S-0097

Step 1: 1-(3-amino-5-bromofuro[3,2-b]pyridin-2-yl)ethanone

To a solution of 6-bromo-3-fluoroisonicotinonitrile (1200 mg, 6 mmol) and cesium carbonate (1956 mg, 12 mmol) in N,N-dimethylformamide (5 mL) was added 1-hydroxyacetone (444 mg, 6 mmol). The reaction solution was stirred at room temperature for 1 h, and ethyl acetate (150 mL) was added for dilution. The reaction solution was washed with saturated brine (100 mL×2) and water (100 mL), dried over anhydrous sodium sulfate, filtered and concentrated. The residue was purified by flash chromatography (ethyl acetate/petroleum ether=0-30%) to give 1-(3-amino-5-bromofuro[3,2-b]pyridin-2-yl)ethanone (1000 mg, 66%) in the form of a yellow solid. $^1$H NMR (400 MHz, CDCl3) δ 7.62 (dd, J=8.4, 26 Hz, 2H), 5.74 (br, 2H), 2.51 (s, 3H).

Step 2: 2-((2-acetyl-5-bromofuro[2,3-b]pyridin-3-yl)amino)-4-(4-fluorophenyl) thiazole-5-carbonitrile To a solution of 1-(3-amino-5-bromofuro[3,2-b]pyridin-2-yl)ethanone (1000 mg, 3.94 mmol) in N,N-dimethylformamide (6 mL) was slowly added sodium hydride (60% in oil, 315 mg, 7.88 mmol). The reaction solution was stirred at room temperature for 15 min. Then 2-chloro-4-(4-fluorophenyl)thiazole-5-carbonitrile (937 mg, 3.94 mmol) was added, and the resulting reaction solution was stirred at room temperature for 30 min. The reaction was quenched with water (50 mL), and ethyl acetate (50 mL×2) was added for extraction. The organic phases were washed with saturated brine (50 mL×2), dried over anhydrous sodium sulfate, filtered and concentrated. The residue was purified by flash chromatography (ethyl acetate/petroleum ether=0-40%) to give 2-((2-acetyl-5-bromofuro[2,3-b]pyridin-3-yl) amino)-4-(4-fluorophenyl)thiazole-5-carbonitrile (950 mg, 53%) in the form of a brown solid. LCMS (ESI) [M+H]$^+$=457.9.

Step 3: 2-((5-bromo-2-ethylfuro[2,3-b]pyridin-3-yl)amino)-4-(4-fluorophenyl)thiazole-5-carbonitrile A solution of 2-((2-acetyl-5-bromofuro[2,3-b]pyridin-3-yl)amino)-4-(4-fluorophenyl) thiazole-5-carbonitrile (950 mg, 2.08 mmol) and triethylsilane (6 mL) in trifluoroacetic acid (6 mL) was stirred at 80° C. for 16 h. The reaction solution was concentrated. The residue was diluted with ethyl acetate (50 mL), washed with water (50 mL×2), dried over anhydrous sodium sulfate, filtered and concentrated. The residue was purified by flash chromatography (ethyl acetate/petroleum ether=0-30%) to give 2-((5-bromo-2-ethylfuro[2,3-b]pyridin-3-yl) amino)-4-(4-fluorophenyl)thiazole-5-carbonitrile (375 mg, 40%) in the form of a yellow solid. LCMS (ESI) [M+H]$^+$=443.0.

Step 4: 2-((5-bromo-2-ethylfuro[2,3-b]pyridin-3-yl)(methyl)amino)-4-(4-fluorophenyl) thiazole-5-carbonitrile To a solution of 2-((5-bromo-2-ethylfuro[2,3-b]pyridin-3-yl)amino)-4-(4-fluorophenyl) thiazole-5-carbonitrile (135 mg, 0.305 mmol) in N,N-dimethylformamide (5 mL) was slowly added sodium hydride (60% in oil, 18 mg, 0.458 mmol). The reaction solution was stirred at room temperature for 30 min. Then methyl iodide (42 mg, 0.3 mmol) was added, and the resulting reaction solution was stirred at room temperature for 2 h. The reaction was quenched with water (50 mL), and ethyl acetate (50 mL×2) was added for extraction. The organic phases were washed with saturated brine (50 mL×2), dried over anhydrous sodium sulfate, filtered and concentrated. The residue was purified by flash chromatography (ethyl acetate/petroleum ether=0-35%) to give 2-((5-bromo-2-ethylfuro[2,3-b]pyridin-3-yl)(methyl)amino)-4-(4-fluorophenyl)thiazole-5-carbonitrile (44 mg, 32%) in the form of a brown liquid. LCMS (ESI) [M+H]$^+$=456.9.

Step 5: tert-butyl 4-(3-((5-cyano-4-(4-fluorophenyl)thiazol-2-yl)(methyl)amino)-2-ethylfuro[2,3-b]pyridin-5-yl)piperazine-1-carboxylate In a glove box, to a solution of 2-((5-bromo-2-ethylfuro[2,3-b]pyridin-3-yl)(methyl) amino)-4-(4-fluorophenyl)thiazole-5-carbonitrile (44 mg, 0.096 mmol), tert-butyl piperazine-1-carboxylate (94 mg, 0.48 mmol), tris(dibenzylideneacetone)dipalladium(0) (4 mg, 0.0048 mmol), 2-(di-tert-butylphosphino)biphenyl (3 mg, 0.0096 mmol), and sodium tert-butoxide (28 mg, 0.288 mmol) were added toluene (3 mL). The reaction solution was stirred at 100° C. for 2 h. After cooling to room temperature, ethyl acetate was added for extraction. The reaction solution was washed with water (50 mL×2), dried over anhydrous sodium sulfate, filtered and concentrated. The residue was purified by flash chromatography (ethyl acetate/petroleum ether=30%) to give tert-butyl 4-(3-((5-cyano-4-(4-fluorophenyl) thiazol-2-yl)(methyl)amino)-2-ethylfuro[2,3-b]pyridin-5-yl)piperazine-1-carboxylate (34 mg, 63%) in the form of a yellow solid. LCMS (ESI) [M+H]$^+$=563.0.

Step 6: 2-((2-ethyl-5-(piperazin-1-yl)furo[2,3-b]pyridin-3-yl)(methyl)amino)-4-(4-fluorophenyl)thiazole-5-carbonitrile To a solution of tert-butyl 4-(3-((5-cyano-4-(4-fluorophenyl)thiazol-2-yl)(methyl)amino)-2-ethylfuro[2,3-b]pyridin- 5-yl)piperazine-1-carboxylate (34 mg, 0.06 mmol) in dichloromethane (4 mL) was added hydrogen chloride (4 N in 1,4-dioxane, 2 mL). The reaction solution was stirred at room temperature for 2 h, and then concentrated. Aqueous sodium bicarbonate (30 mL) was added to adjust pH to low alkalinity, and ethyl acetate (30 mL×2) was added for extraction. The organic phases were dried over anhydrous sodium sulfate, filtered and concentrated to give 2-((2-ethyl-5-(piperazin-1-yl)furo[2,3-b]pyridin-3-yl) (methyl)amino)-4-(4-fluorophenyl)thiazole-5-carbonitrile (27 mg, 97% yield) in the form of a yellow solid, which was directly used in the next reaction without purification. LCMS (ESI) [M+H]$^+$=463.1.

Step 7: 2-((2-ethyl-5-(4-(2-(3-hydroxyazetidin-1-yl)-2-oxoethyl)piperazin-1-yl)furo[2,3-b]pyridin-3-yl)(methyl)amino)-4-(4-fluorophenyl)thiazole-5-carbonitrile (S-0097)

To a solution of 2-((2-ethyl-5-(piperazin-1-yl)furo[2,3-b]pyridin-3-yl)(methyl)amino)-4-(4-fluorophenyl)thiazole-5-carbonitrile (27 mg, 0.058 mmol) in acetonitrile (5 mL) were added 2-chloro-1-(3-hydroxyazetidin-1-yl)acetyl (17 mg, 0.117 mmol) and potassium carbonate (24 mg, 0.175 mmol). The reaction solution was stirred at reflux for 4 h, and then concentrated. The residue was purified by Pre-HPLC to give 2-((2-ethyl-5-(4-(2-(3-hydroxyazetidin-1-yl)-2-oxoethyl)piperazin-1-yl)furo[2,3-b]pyridin-3-yl)(methyl)amino)-4-(4-fluorophenyl)thiazole-5-carbonitrile S-0097 (2.8 mg, 8%) in the form of a white solid. LCMS (ESI) [M+H]$^+$=576.0@8.92 min. $^1$H NMR (400 MHz, CD$_3$OD) δ 8.12 (m, J=8.8 Hz, 2H), 7.67 (d, J=9.2 Hz, 1H), 7.23 (t, J=8.8 Hz, 2H), 6.81 (d, J=9.2 Hz, 1H), 4.59-4.45 (m, 2H), 4.21 (m, 1H), 4.05 (m, 1H), 3.78 (m, 1H), 3.65 (s, 3H), 3.52 (m, 4H), 3.10 (d, J=2.8 Hz, 2H), 2.82 (q, J=7.2 Hz, 2H), 2.61 (m, 4H), 1.33 (t, J=7.6 Hz, 3H).

Example 29. S-0098: 2-((2-ethyl-5-(4-(2-(3-hydroxyazetidin-1-yl)-2-oxoethyl) piperazin-1-yl)-1H-pyrrolo[3,2-b]pyridin-3-yl)(methyl)amino)-4-(4-fluorophenyl) thiazole-5-carbonitrile

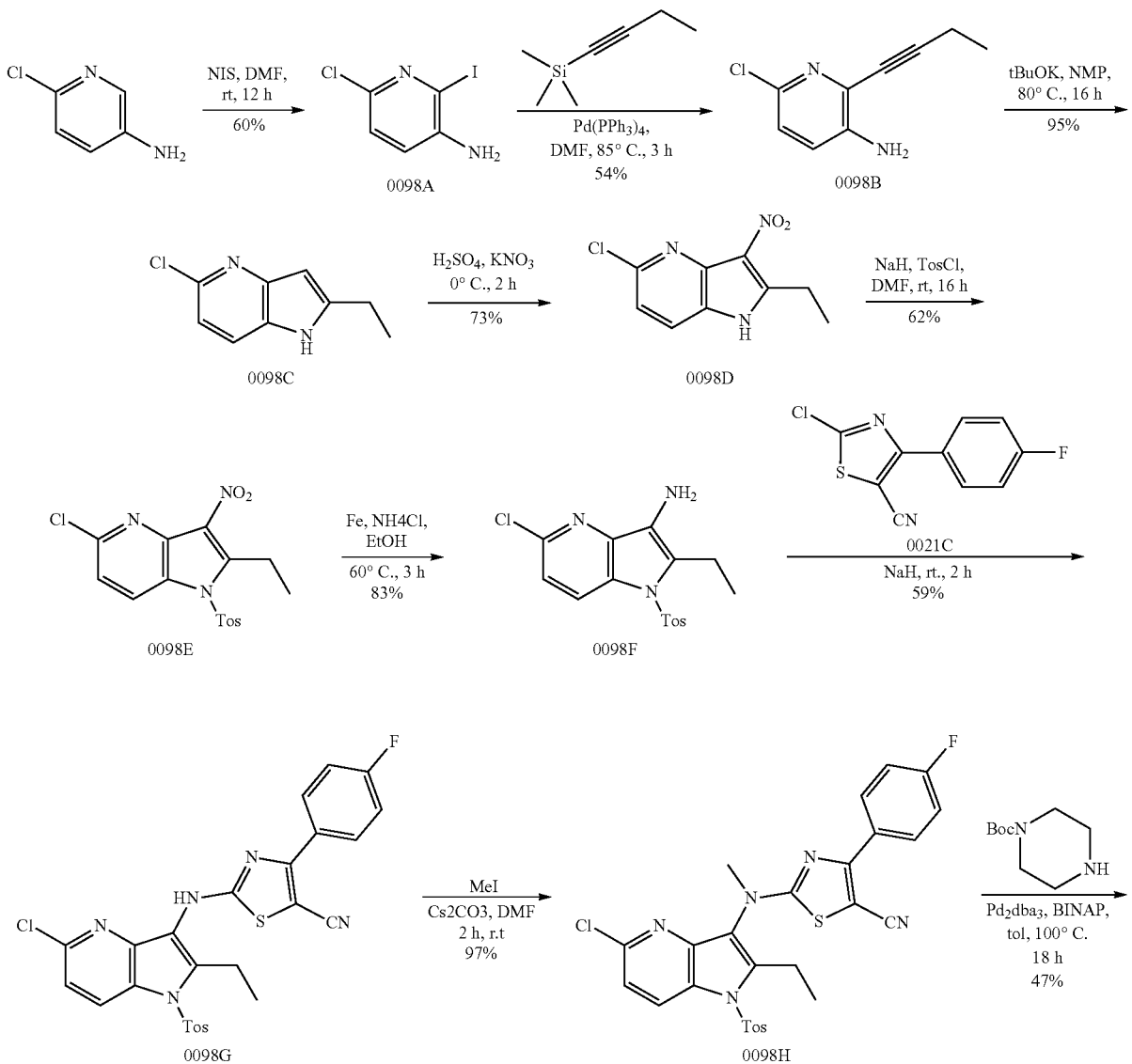

-continued

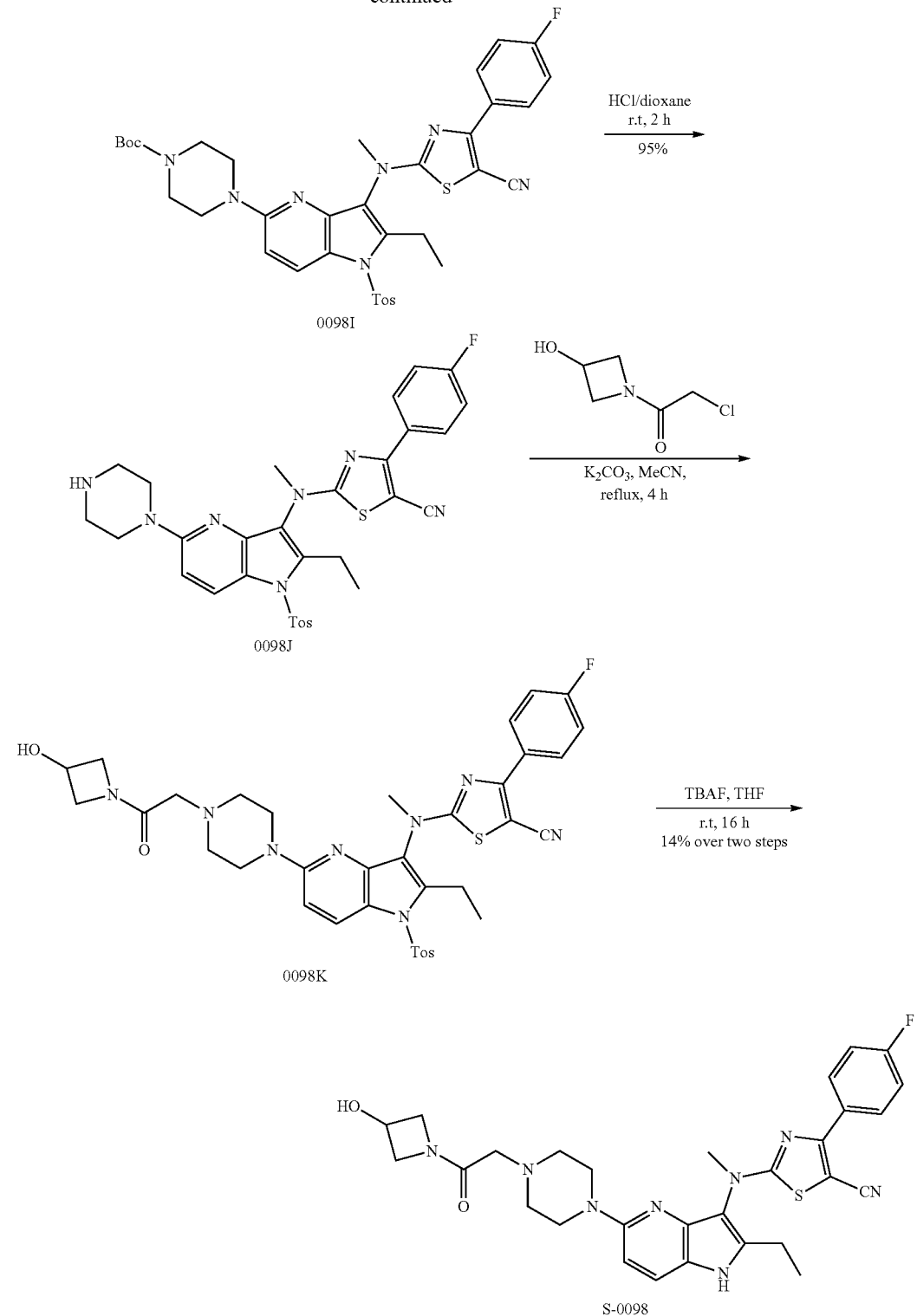

Step 1: 6-chloro-2-iodopyridin-3-amine

A mixture solution of 6-chloropyridin-3-amine (5.0 g, 38.9 mmol) and 1-iodopyrrolidine-2,5-dione (9.65 g, 42.8 mmol) in N,N-dimethylforamide (50 mL) was stirred at room temperature for 16 h. The reaction solution was diluted with ethyl acetate (200 mL), washed sequentially with water and saturated brine, dried over anhydrous sodium sulfate, filtered and concentrated. The residue was purified by flash chromatography (ethyl acetate/petroleum ether=0-10%) to give 6-chloro-2-iodopyridin-3-amine 0098A (6.0 g, 600%). LCMS (ESI) [M+H]$^+$=255.0@1.57 min (LC-MS Method A).

Step 2: 2-(but-1-ynyl)-6-chloropyridin-3-amine

A mixture of 6-chloro-2-iodopyridin-3-amine 0098A (6.0 g, 23.6 mmol), but-1-ynyl trimethylsilane(5.95 g, 47.2 mmol), triethylamine (7.16 g, 70.8 mmol), bis(triphenylphosphine) palladium(II) chloride (828 mg, 1.18 mmol) and copper(I) iodide (448 mg, 2.36 mmol) in N,N-dimethylformamide (20 mL) and water (2 mL) was stirred at 85° C. for 3 h. After cooling to room temperature, ethyl acetate (200 mL) was added for dilution. The organic phases were washed sequentially with water and saturated brine, dried over anhydrous sodium sulfate, filtered and concentrated The residue was purified by flash chromatography (ethyl acetate/petroleum ether=0-10%) to give 2-(but-1-ynyl)-6-chloropyridin-3-amine 0098B (2.3 g, 54%) in the form of a yellow solid. LCMS (ESI) [M+H]$^+$=181.1. @1.59 min (LC-MS Method A).

Step 3: 5-chloro-2-ethyl-1H-pyrrolo[3,2-b]pyridine

A mixture of 2-(but-1-ynyl)-6-chloropyridin-3-amine 0098B (2.3 g, 12.7 mmol) and potassium tert-butoxide (2.8 g, 25.5 mmol) in 1-methylpyrrolidin-2-one (15 mL) was stirred at 85° C. for 16 h. After cooling to room temperature, ethyl acetate (150 mL) was added for dilution. The organic phases were washed sequentially with water and saturated brine, dried over anhydrous sodium sulfate, filtered and concentrated to give 5-chloro-2-ethyl-1H-pyrrolo [3,2-b]pyridine 0098C (2.2 g, 95%) in the form of a brown solid. LCMS (ESI) [M+H]$^+$=181.2@1.51 min (LC-MS Method A).

Step 4: 5-chloro-2-ethyl-3-nitro-1H-pyrrolo[3,2-b]pyridine

A solution of 5-chloro-2-ethyl-1H-pyrrolo[3,2-b]pyridine 0098C (1.1 g, 6.09 mmol) and potassium nitrate (1.2 g, 12.18 mmol) in sulfuric acid (10 mL) was stirred at 0° C. for 2 h. Aqueous sodium bicarbonate solution was added to adjust pH to 7-8. The reaction solution was filtered. The filter cake was washed with water, and dried in vacuo to give 5-chloro-2-ethyl-3-nitro-1H-pyrrolo[3,2-b]pyridine 0098D (1.0 g, 73%) in the form of a yellow solid. LCMS (ESI) [M+H]$^+$=226.1 @ 1.47 min (LC-MS Method A).

Step 5: 5-chloro-2-ethyl-3-nitro-1-tosyl-1H-pyrrolo[3,2-b]pyridine

A solution of 5-chloro-2-ethyl-3-nitro-1H-pyrrolo[3,2-b]pyridine 0098D (500 mg, 2.22 mmol), sodium hydride (107 mg, 2.66 mmol) and 4-methylbenzene-1-sulfonylchloride (507 mg, 2.66 mmol) in N,N-dimethylformamide (10 mL) was stirred at room temperature for 16 h. The reaction solution was diluted with ethyl acetate (100 mL). The organic phases were washed sequentially with water and saturated brine, dried over anhydrous sodium sulfate, filtered and concentrated. The residue was purified by flash chromatography (ethyl acetate/petroleum ether=0-20%) to give 5-chloro-2-ethyl-3-nitro-1-tosyl-1H-pyrrolo[3,2-b]pyridine 0098E (520 mg, 62%) in the form of a yellow solid. LCMS (ESI) [M+H]$^+$=380.1 @ 1.93 min (LC-MS Method A).

Step 6: 5-chloro-2-ethyl-1-tosyl-1H-pyrrolo[3,2-b]pyridin-3-amine

A solution of 5-chloro-2-ethyl-3-nitro-1-tosyl-1H-pyrrolo[3,2-b]pyridine 0098E (520 mg, 1.37 mmol), iron powder (306 mg, 5.48 mmol), saturated ammonium chloride solution (2 mL) in ethanol (10 mL) was stirred for 2 h at 60° C. After cooling to room temperature, the reaction solution was filtered. The filtrate was concentrated. The residue was redissolved in ethyl acetate (150 mL), washed sequentially with water and saturated brine, dried over anhydrous sodium sulfate, filtered and concentrated to give 5-chloro-2-ethyl-1-tosyl-1H-pyrrolo[3,2-b]pyridin-3-amine 0098F (400 mg, 83%) in the form of a yellow solid. LCMS (ESI) [M+H]=350.1 @ 1.85 min (LC-MS Method A).

Step 7: 2-(5-chloro-2-ethyl-1-tosyl-1H-pyrrolo[3,2-b]pyridin-3-ylamino)-4-(4-fluorophenyl)thiazole-5-carbonitrile A solution of 5-chloro-2-ethyl-1-tosyl-1H-pyrrolo[3,2-b]pyridin-3-amine 0098F (160 mg, 0.46 mmol) and sodium hydride (28 mg, 0.69 mmol) in N,N-dimethylformamide (4 mL) was stirred at room temperature for 10 min. Then 2-chloro-4-(4-fluorophenyl)thiazole-5-carbonitrile (164 mg, 0.69 mmol) was added, and the resulting reaction solution was stirred at room temperature for 2 h. The reaction was quenched with water, and ethyl acetate (20 mL×3) was added for extraction. The organic phases were dried over anhydrous sodium sulfate, filtered and concentrated. The residue was purified by flash chromatography (methanol/dichloromethane=10-25%) to give 2-(5-chloro-2-ethyl-1-tosyl-1H-pyrrolo[3,2-b]pyridin-3-ylamino)-4-(4-fluorophenyl)thiazole-5-carbonitrile 0098G (150 mg, 59%). LCMS (ESI) [M+H]$^+$=552.0. @ 2.04 min (LC-MS Method A).

Step 8: 2-((5-chloro-2-ethyl-1-tosyl-1H-pyrrolo[3,2-b]pyridin-3-yl)(methyl)amino)-4-(4-fluorophenyl)thiazole-5-carbonitrile A mixture of 2-(5-chloro-2-ethyl-1-tosyl-1H-pyrrolo[3,2-b]pyridin-3-ylamino)-4-(4-fluorophenyl)thiazole-5-carbonitrile 0098G (180 mg, 0.33 mmol), methyl iodide (70 mg, 0.49 mmol) and cesium carbonate (160 mg, 0.49 mmol) in N,N-dimethylformamide (3 mL) was stirred at room temperature for 1 h. The reaction was quenched with water, and ethyl acetate (20 mL×3) was added for extraction. The organic phases were dried over anhydrous sodium sulfate, filtered and concentrated to give 2-((5-chloro-2-ethyl-1-tosyl-1H-pyrrolo[3,2-b]pyridin-3-yl)(methyl)amino)-4-(4-fluorophenyl)thiazole-5-carbonitrile 0098H (180 mg, 97%). LCMS (ESI) [M+H]$^+$=566 @ 2.41 min (LC-MS Method A).

Step 9: tert-butyl 4-(3-((5-cyano-4-(4-fluorophenyl)thiazol-2-yl)(methyl)amino)-2-amino-1-tosyl-1H-pyrrolo[3,2-b]pyridin-5-yl)piperazine-1-carboxylate A mixture of 2-((5-chloro-2-ethyl-1-tosyl-1H-pyrrolo[3,2-b]pyridin-3-yl)(methyl) amino)-4-(4-fluorophenyl)thiazole-5-carbonitrile 0098H (140 mg, 0.25 mmol), tert-butyl piperazine-1-carboxylate (69 mg, 0.37 mmol), tris(dibenzylideneacetone)dipalladium(0) (23 mg, 0.05 mmol), (±)-2,2'-bis(diphenylphosphino)-1,1'-binaphthyl (32 mg, 0.0978 mmol) and cesium carbonate (204 mg, 0.63 mmol) in toluene (5 mL) was stirred at 90° C. for 16 h. The reaction was concentrated. The residue was purified by flash chromatography (ethyl acetate/petroleum ether=10-35%) to give tert-butyl 4-(3-((5-cyano-4-(4-fluorophenyl) thiazol-2-yl)(methyl)amino)-2-amino-1-tosyl-1H-pyrrolo[3,2-b]pyridin-5-yl)piperazine-1-carboxylate 0098I (90 mg, 47%) in the form of a yellow solid. LCMS (ESI) [M+H]⁺=716.1. @ 2.38 min (LC-MS Method A).

Step 10: 2-((2-ethyl-5-(piperazin-1-yl)-1-tosyl-1H-pyrrolo[3,2-b]pyridin-3-yl)(methyl) amino)-4-(4-fluorophenyl)thiazole-5-carbonitrile A solution of tert-butyl 4-(3-((5-cyano-4-(4-fluorophenyl)thiazol-2-yl)(methyl)amino)-2-amino-1-tosyl-1H-pyrrolo[3,2-b]pyridin-5-yl)piperazine-1-carboxylate 00981 (48 mg, 0.067 mmol) in hydrogen chloride (4 N in dioxane, 4 mL) was stirred at room temperature for 1 h. The reaction solution was concentrated to give 2-((2-ethyl-5-(piperazin-1-yl)-1-tosyl-1H-pyrrolo[3,2-b]pyridin-3-yl)(methyl) amino)-4-(4-fluorophenyl)thiazole-5-carbonitrile 0098J (45 mg, 95%) in the form of a yellow solid, which was directly used in the next step without purification. LCMS (ESI) [M+H]⁺=616.1. @ 1.73 min (LC-MS Method A).

Step 11: 2-((2-ethyl-5-(4-(2-(3-hydroxyazetidin-1-yl)-2-oxoethyl)piperazin-1-yl)-1-tosyl-1H-pyrrolo[3,2-b]pyridin-3-yl)(methyl)amino)-4-(4-fluorophenyl)thiazole-5-carbonitrile A mixture of 2-((2-ethyl-5-(piperazin-1-yl)-1-tosyl-1H-pyrrolo[3,2-b]pyridin-3-yl) (methyl)amino)-4-(4-fluorophenyl)thiazole-5-carbonitrile 0098J (45 mg, 0.067 mmol), 2-chloro-1-(3-hydroxyazetidin-1-yl)ethanone (20 mg, 0.13 mmol) and potassium carbonate (18 mg, 0.13 mmol) in acetonitrile (2 mL) was stirred at reflux for 4 h. The reaction solution was filtered. The filtrate was concentrated to give 2-((2-ethyl-5-(4-(2-(3-hydroxyazetidin-1-yl)-2-oxoethyl)piperazin-1-yl)-1-tosyl-1H-pyrrolo[3,2-b]pyridin-3-yl)(methyl)amino)-4-(4-fluorophenyl)thiazole-5-carbonitrile 0098K (crude product) in the form of a brown solid, which was directly used in the next step without purification. LCMS (ESI) [M+H]⁺=729.1@1.66 min (LC-MS Method A).

Step 12: 2-((2-ethyl-5-(4-(2-(3-hydroxyazetidin-1-yl)-2-oxoethyl)piperazin-1-yl)-1H-pyrrolo[3,2-b]pyridin-3-yl)(methyl)amino)-4-(4-fluorophenyl)thiazole-5-carbonitrile A mixture of 2-((2-ethyl-5-(4-(2-(3-hydroxyazetidin-1-yl)-2-oxoethyl)piperazin-1-yl)-1-tosyl-1H-pyrrolo[3,2-b]pyridin-3-yl)(methyl)amino)-4-(4-fluorophenyl)thiazole-5-carbonitrile 0098K (crude product) and tetrabutylammonium fluoride (1M in tetrahydrofuran, 2 mL) was stirred at room temperature for 16 h. The residue was purified by high-pressure reversed-phase column chromatography to give 2-((2-ethyl-5-(4-(2-(3-hydroxyazetidin-1-yl)-2-oxoethyl) piperazin-1-yl)-1H-pyrrolo[3,2-b]pyridin-3-yl)(methyl)amino)-4-(4-fluorophenyl)thiazole-5-carbonitrile S-0098 (5.5 mg, 14.5% yield over two steps) in the form of a white solid. LCMS (ESI) [M+H]⁺=575.3 @8.61 min (LC-MS Method D). ¹H NMR (400 MHz, CD₃OD) δ 8.17-8.13 (m, 2H), 7.62 (s, J=8.8 Hz, 1H), 7.28-7.23 (m, 2H), 7.39 (d, J=8.8 Hz, 1H), 4.58-4.57 (m, 1H), 4.53-4.51 (m, 1H), 4.26-4.21 (m, 1H), 4.09-4.07 (m, 1H)), 3.80-3.77 (m, 1H), 3.67 (s, 3H), 3.53-3.51 (m, 4H), 3.12 (s, 2H), 2.81 (q, 2H), 2.66-2.63 (m, 4H), 1.38 (t, 3H).

Example 30. S-0099: 2-((2-ethyl-5-(4-(2-(3-hydroxyazetidin-1-yl)-2-oxoacetyl) piperazin-1-yl)-7-methylpyrazolo[1,5-a]pyrimidin-3-yl)(methyl)amino)-4-(4-fluorophenyl)thiazole-5-carbonitrile

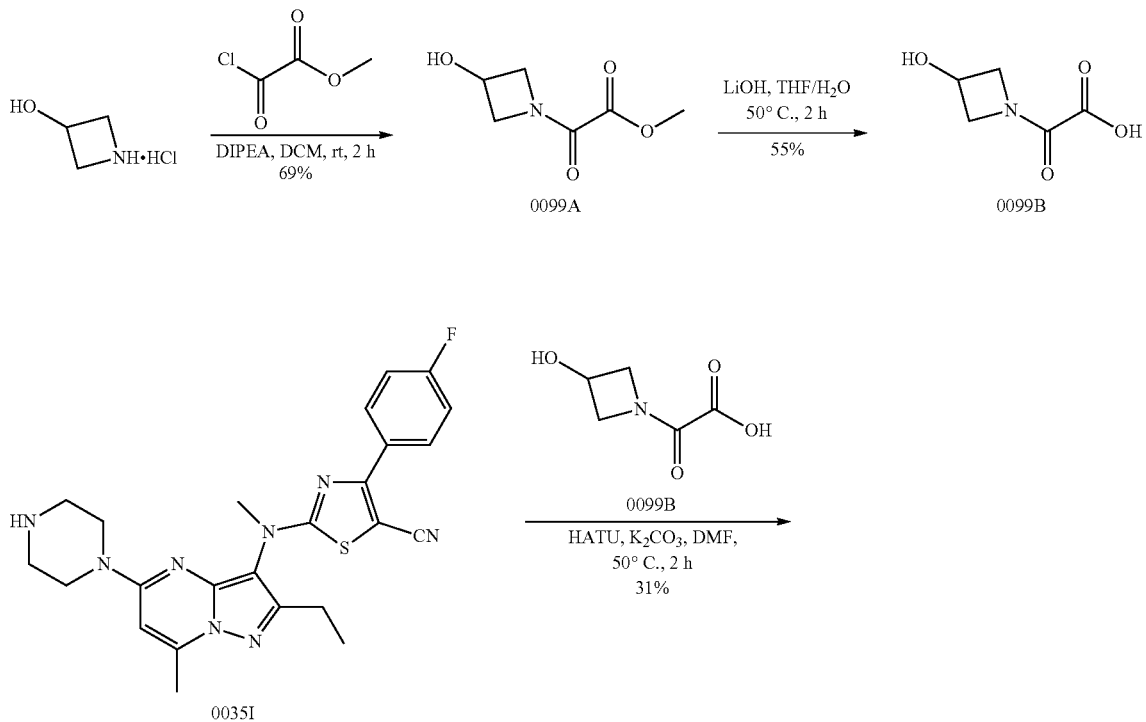

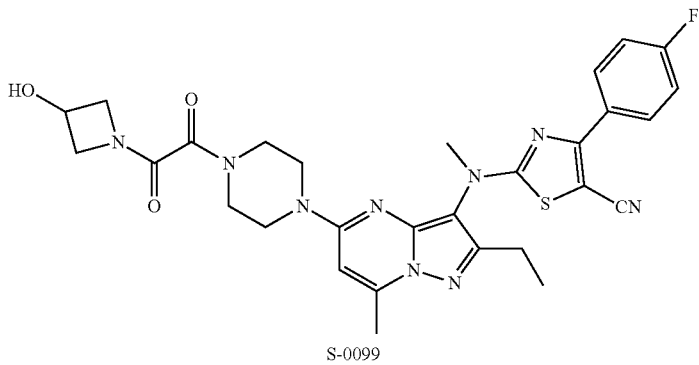

S-0099

Step 1: methyl 2-(3-hydroxyazetidin-1-yl)-2-oxoacetate

A mixture of azetidin-3-ol hydrochloride (800 mg, 7.3 mmol), methyl chloroglyoxylate (895 mg, 7.3 mmol) and N,N-diisopropylethylamine (1883 mg, 14.6 mmol) in dichloromethane (10 mL) was stirred at room temperature for 2 h. The reaction solution was concentrated. The residue was purified by flash chromatography (ethyl acetate/petroleum ether=0-30%) to give methyl 2-(3-hydroxyazetidin-1-yl)-2-oxoacetate (600 mg, 69%). LCMS (ESI) [M+H]$^+$=160.

Step 2: 2-(3-hydroxyazetidin-1-yl)-2-oxoacetic acid

A mixture of methyl 2-(3-hydroxyazetidin-1-yl)-2-oxoacetate (600 mg, 1.886 mmol) and lithium hydroxide (90 mg, 3.77 mmol) in tetrahydrofuran/water (5 mL/1 mL) was stirred at 50° C. for 1 h. After cooling to room temperature, hydrochloric acid (1 mol/L) was added to adjust pH to 5. Then the reaction solution was concentrated to give 2-(3-hydroxyazetidin-1-yl)-2-oxoacetic acid (300 mg, 55%). LCMS (ESI) [M+H]$^+$=146.

Step 3: 2-((2-ethyl-5-(4-(2-(3-hydroxyazetidin-1-yl)-2-oxoacetyl)piperazin-1-yl)-7-methylpyrazolo[1,5-a]pyrimidin-3-yl)(methyl)amino)-4-(4-fluorophenyl)thiazole-5-carbonitrile (S-0099)

A mixture of 2-(3-hydroxyazetidin-1-yl)-2-oxoacetic acid (35 mg, 0.21 mmol), 2-((2-ethyl-7-methyl-5-(piperazin-1-yl)pyrazolo[1,5-a]pyrimidin-3-yl)(methyl)amino)-4-(4-fluorophenyl)thiazole-5-carbonitrile (50 mg, 0.105 mmol), O-(7-azabenzotriazole-1-yl)-N,N,N',N'-tetramethylurea hexafluorophosphate (80 mg, 0.21 mmol) and potassium carbonate (29 mg, 0.21 mmol) in N,N-dimethylformamide (5 mL) was stirred at 50° C. for 2 h. The reaction was quenched with water (15 mL), and ethyl acetate (20 mL×3) was added for extraction. The organic phases were combined, washed with saturated brine (10 mL×2), dried over anhydrous sodium sulfate, filtered and concentrated. The residue was purified by flash chromatography (methanol/dichloromethane=0-10%) to give 2-((2-ethyl-5-(4-(2-(3-hydroxyazetidin-1-yl)-2-oxoacetyl)piperazin-1-yl)-7-methylpyrazolo[1,5-a]pyrimidin-3-yl)(methyl)amino)-4-(4-fluorophenyl)thiazole-5-carbonitrile (S-0099) (20 mg, 32%) in the form of a white solid. LCMS (ESI) [M+H]$^+$=604@9.13 min. $^1$H NMR (400 MHz, CD$_3$OD) δ 8.132 (m, 2H), 7.239 (m, 2H), 6.669 (s, 1H), 4.637 (m, 1H), 4.418 (m, 1H), 4.301 (m, 2H), 4.013 (m, 1H), 3.3.798 (m, 5H), 3.692 (m, 2H), 3.638 (m, 2H), 3.612 (s, 3H), 2.727 (q, 2H), 2.696 (s, 3H), 1.315 (t, 3H).

Example 31. S-0100CP: 2-((2-ethyl-5-(4-(2-(3-hydroxyazetidin-1-yl)acetyl)piperazin-1-yl)-7-methylpyrazolo[1,5-a]pyrimidin-3-yl)(methyl)amino)-4-(4-fluorophenyl)thiazole-5-carbonitrile

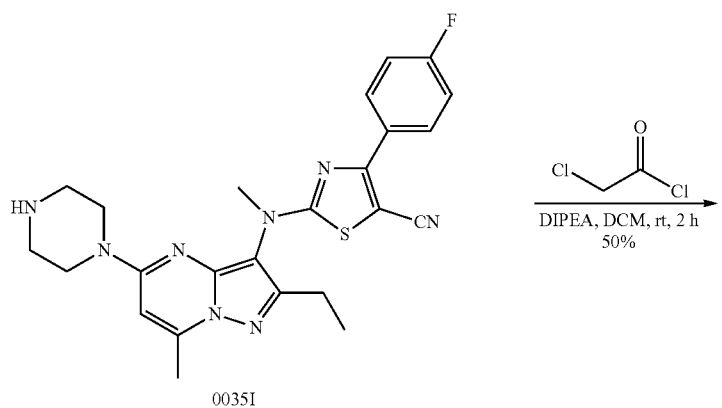

00351

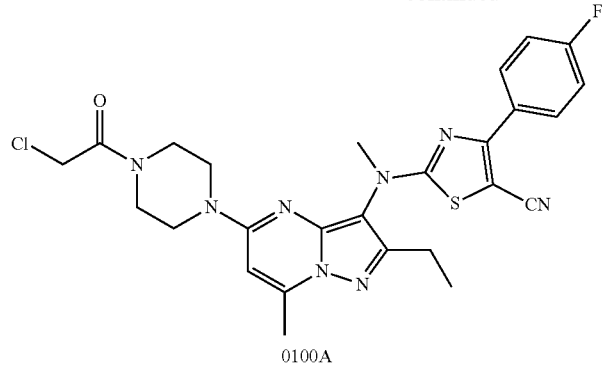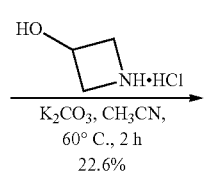

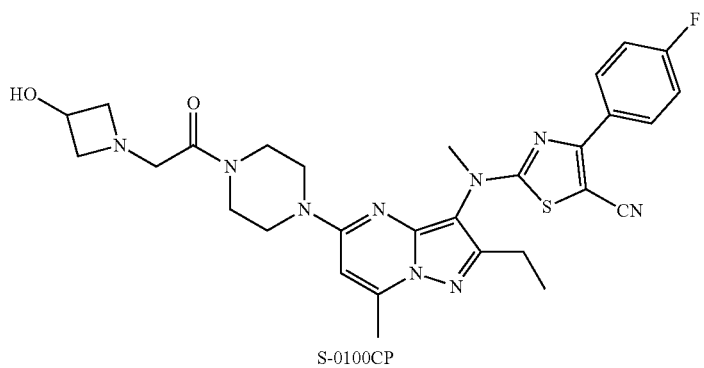

Step 1: 2-((5-(4-(2-chloroacetyl)piperazin-1-yl)-2-ethyl-7-methylpyrazolo[1,5-a]pyrimidin-3-yl)(methyl)amino)-4-(4-fluorophenyl)thiazole-5-carbonitrile A mixture of 2-((2-ethyl-7-methyl-5-(piperazin-1-yl)pyrazolo[1,5-a]pyrimidin-3-yl)(methyl)amino)-4-(4-fluorophenyl)thiazole-5-carbonitrile (100 mg, 0.21 mmol), 2-chloroacetyl chloride (28 mg, 0.25 mmol) and N,N-diisopropylethylamine (81 mg, 0.63 mmol) in dichloromethane (3 mL) was stirred at room temperature for 2 h. The reaction solution was concentrated. The residue was purified by flash chromatography (ethyl acetate/petroleum ether=0-80%) to give 2-((5-(4-(2-chloroacetyl)piperazin-1-yl)-2-ethyl-7-methylpyrazolo[1,5-a]pyrimidin-3-yl)(methyl)amino)-4-(4-fluorophenyl)thiazole-5-carbonitrile (60 mg, 50%). LCMS (ESI) [M+H]$^+$=553.

Step 2: 2-((2-ethyl-5-(4-(2-(3-hydroxyazetidin-1-yl)acetyl)piperazin-1-yl)-7-methylpyrazolo[1,5-a]pyrimidin-3-yl)(methyl)amino)-4-(4-fluorophenyl)thiazole-5-carbonitrile S-0100 CP A mixture of 2-((5-(4-(2-chloroacetyl)piperazin-1-yl)-2-ethyl-7-methyl pyrazolo[1,5-a]pyrimidin-3-yl)(methyl)amino)-4-(4-fluorophenyl)thiazole-5-carbonitrile (60 mg, 0.108 mmol), azetidin-3-ol hydrochloride (24 mg, 0.216 mmol) and potassium carbonate (45 mg, 0.324 mmol) in acetonitrile (5 mL) was stirred at 60° C. for 2 h, and then cooled to room temperature. The reaction solution was filtered. The filtrate was concentrated. The residue was purified by Pre-HPLC to give 2-((2-ethyl-5-(4-(2-(3-hydroxyazetidin-1-yl)acetyl)piperazin-1-yl)-7-methylpyrazolo[1,5-a]pyrimidin-3-yl)(methyl)amino)-4-(4-fluorophenyl)thiazole-5-carbonitrile S-0100 CP (14.5 mg, 22.6%) in the form of a white solid. LCMS (ESI) [M+H]$^+$=590@7.74 min. $^1$H NMR (400 MHz, CD$_3$OD) δ 8.135 (m, 2H), 7.242 (m, 2H), 6.641 (s, 1H), 4.376 (m, 1H), 3.767 (m, 4H), 3.723 (m, 2H), 3.662 (m, 2H), 3.611 (s, 3H), 3.572 (m, 2H), 3.489 (s, 2H), 2.996 (m, 2H), 2.725 (q, 2H), 2.689 (s, 3H), 1.315 (t, 3H).

Example 32. S-0102CP: 2-((2-ethyl-5-(4-(2-hydroxyethylsulfonyl)piperazin-1-yl) pyrazolo[1,5-a]pyrimidin-3-yl)(methyl)amino)-4-(4-fluorophenyl)thiazole-5-carbonitrile

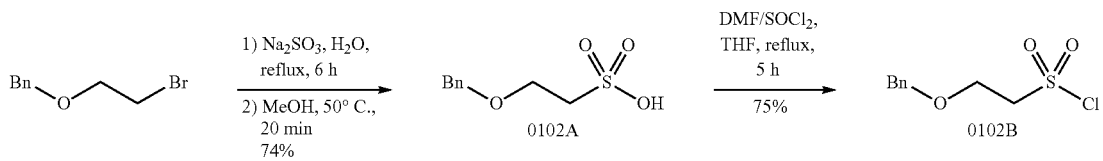

-continued

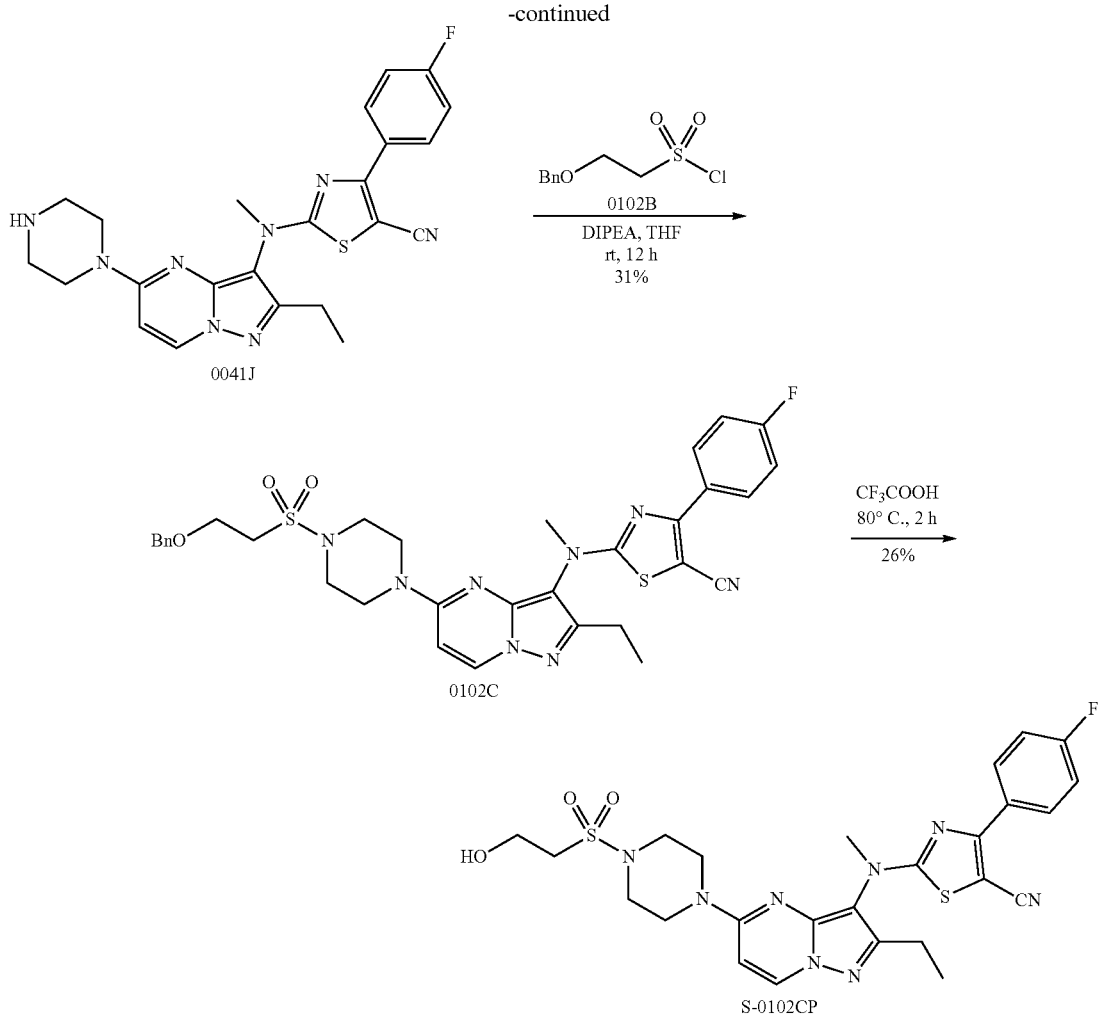

Step 1: 2-(benzyloxy)ethanesulfonic acid

A mixture of ((2-bromoethoxy)methyl)benzene (600 mg, 2.79 mmol) and sodium sulfite (434 mg, 3.44 mmol) in water (20 mL) was stirred at 100° C. for 6 h and concentrated to give a white solid. Methanol (20 mL) was added to the white solid. The reaction solution was stirred at 50° C. for 20 min. The reaction solution was filtered. The filtrate was concentrated to give 2-(benzyloxy)ethanesulfonic acid (490 mg, 74%) in the form of a white solid. H NMR (400 MHz, DMSO-d$_6$) δ 7.38-7.24 (m, 5H), 4.44 (s, 2H), 3.66-3.60 (m, 2H), 2.76 (m, 2H).

Step 2: 2-(benzyloxy)ethanesulfonyl Chloride

To a solution of 2-(benzyloxy)ethanesulfonic acid (490 mg, 2.26 mmol) in tetrahydrofuran (2 mL) was added N,N-dimethylformamide (16 mg, 0.226 mmol) and thionyl chloride (0.5 mL, 8.90 mmol). The reaction solution was stirred at 65° C. for 5 h, and then filtered. The filtrate was concentrated to give 2-(benzyloxy)ethanesulfonyl chloride (400 mg, 75%) in the form of a yellow oil, which was used in next step without purification.

Step 3: 2-((5-(4-(2-(benzyloxy)ethylsulfonyl)piperazin-1-yl)-2-ethyl pyrazolo[1,5-a]pyrimidin-3-yl)(methyl)amino)-4-(4-fluorophenyl)thiazole-5-carbonitrile A mixture of 2-((2-ethyl-5-(piperazin-1-yl)pyrazolo[1,5-a]pyrimidin-3-yl)(methyl) amino)-4-(4-fluorophenyl)thiazole-5-carbonitrile (100 mg, 0.216 mmol), 2-(benzyloxy)ethanesulfonyl chloride (253 mg, 1.082 mmol) and N,N-diisopropylethylamine (83 mg, 0.648 mmol) in tetrahydrofuran (2 mL) was stirred at 25° C. for 2 h. The reaction solution was concentrated. The residue was purified by flash chromatography (ethyl acetate/petroleum ether=0-60%) to give 2-((5-(4-(2-(benzyloxy)ethylsulfonyl)piperazin-1-yl)-2-ethylpyrazolo [1,5-a]pyrimidin-3-yl)(methyl)amino)-4-(4-fluorophenyl)thiazole-5-carbonitrile (45 mg, 31%) in the form of a yellow solid. LCMS (ESI) [M+H]$^+$=660.9.

Step 4: 2-((2-ethyl-5-(4-(2-hydroxyethylsulfonyl)piperazin-1-yl)pyrazolo[1,5-a]pyrimidin-3-yl)(methyl)amino)-4-(4-fluorophenyl)thiazole-5-carbonitrile S-0102CP A solution of 2-((5-(4-(2-(benzyloxy)ethylsulfonyl)piperazin-1-yl)-2-ethylpyrazolo [1,5-a]pyrimidin-3-yl)(methyl) amino)-4-(4-fluorophenyl)thiazole-5-carbonitrile (45 mg, 0.068 mmol) in trifluoroacetic acid (2 mL) was stirred at 80° C. for 3 h. The reaction solution was concentrated. The residue was purified by Pre-HPLC to give 2-((2-ethyl-5-(4-(2-hydroxyethylsulfonyl)piperazin-1-yl)pyrazolo[1,5-a]pyrimidin-3-yl)(methyl)amino)-4-(4-fluorophenyl)thiazole-5-carbonitrile S-0102CP (10.1 mg, 26%) in the form of a white solid. LCMS (ESI) [M+H]$^+$=570.8@8.88 min. $^1$H NMR (400 MHz, CDCl$_3$) δ 8.27 (d, J=7.8 Hz, 1H), 8.20-8.10 (m, 2H), 7.16 (t, J=8.7 Hz, 2H), 6.36 (d, J=7.8 Hz, 1H), 4.15-4.00 (m, 2H), 3.77-3.61 (m, 4H), 3.59 (s, 3H), 3.40 (t, J=5.0 Hz, 4H), 3.22-3.13 (m, 2H), 3.02-2.79 (m, 2H), 2.78-2.54 (m, 1H), 1.31 (dd, J=19.3, 11.7 Hz, 3H).

Example 33. S-0103CP: 2-((2-ethyl-5-(4-(ethylsulfonyl)piperazin-1-yl)pyrazolo [1,5-a]pyrimidin-3-yl)(methyl)amino)-4-(4-fluorophenyl)thiazole-5-carbonitrile

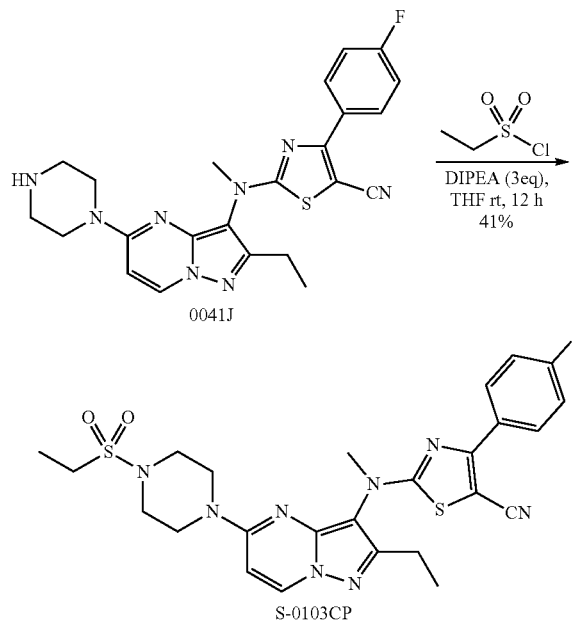

Step 1: 2-((2-ethyl-5-(4-(ethylsulfonyl)piperazin-1-yl)pyrazolo[1,5-a]pyrimidin-3-yl) (methyl)amino)-4-(4-fluorophenyl)thiazole-5-carbonitrile A mixture of 2-((2-ethyl-5-(piperazin-1-yl)pyrazolo[1,5-a]pyrimidin-3-yl)(methyl) amino)-4-(4-fluorophenyl)thiazole-5-carbonitrile (30 mg, 0.065 mmol), ethanesulfonyl chloride (13 mg, 0.098 mmol), and N,N-diisopropylethylamine (25 mg, 0.195 mmol) in tetrahydrofuran (2 mL) was stirred at room temperature for 2 h, and then concentrated. The residue was purified by Pre-HPLC to give 2-((2-ethyl-5-(4-(ethylsulfonyl)piperazin-1-yl) pyrazolo[1,5-a]pyrimidin-3-yl)(methyl)amino)-4-(4-fluorophenyl)thiazole-5-carbonitrile S-0103CP (14.7 mg, 41%) in the form of a white solid. LCMS (ESI) [M+H]$^+$=555.1@10.53 min. $^1$H NMR (400 MHz, DMSO-d$_6$) δ 8.70 (d, J=7.9 Hz, 1H), 8.09 (s, 2H), 7.41 (t, J=8.7 Hz, 2H), 6.81 (d, J=8.2 Hz, 1H), 3.76 (s, 4H), 3.53 (s, 3H), 3.29-2.80 (m, 6H), 2.67-2.59 (m, 2H), 1.22 (dd, J=16.2, 7.5 Hz, 6H).

Example 34. S-0104CP: 2-((2-ethyl-5-(4-(2-(3-hydroxyazetidin-1-yl)-2-oxoethyl)-3-oxopiperazin-1-yl)pyrazolo[1,5-a]pyrimidin-3-yl)(methyl)amino)-4-(4-fluorophenyl)thiazole-5-carbonitrile

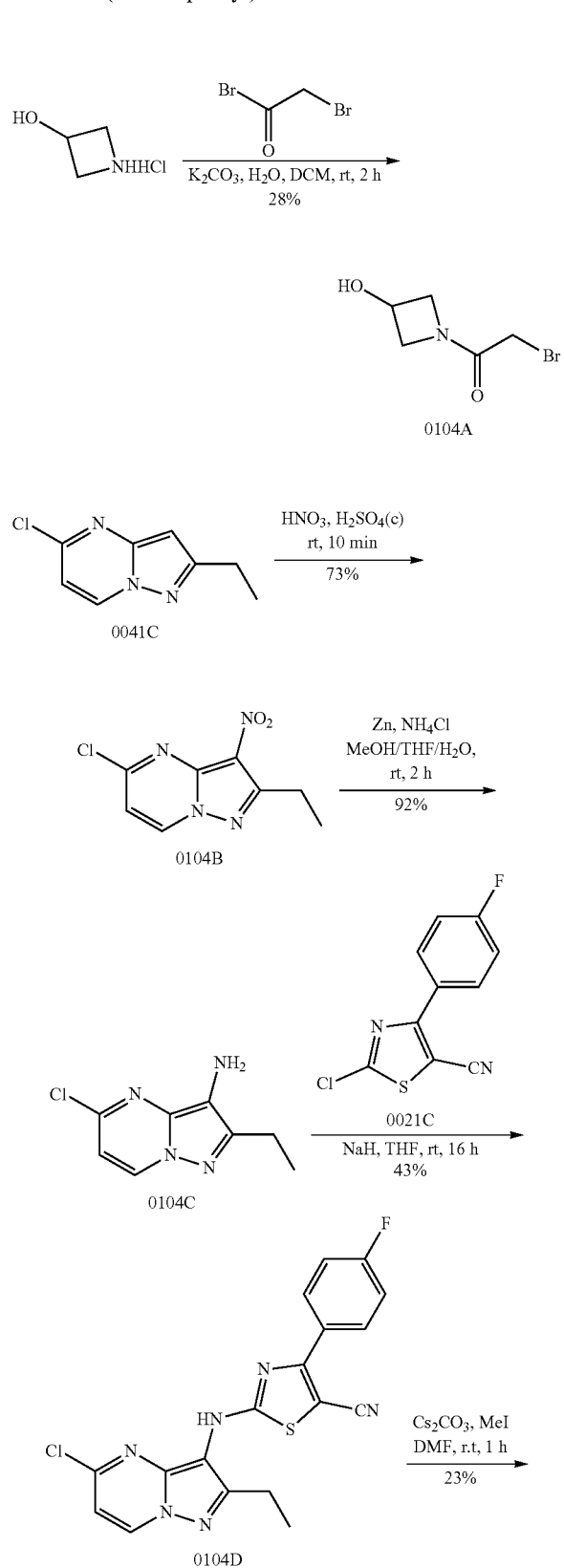

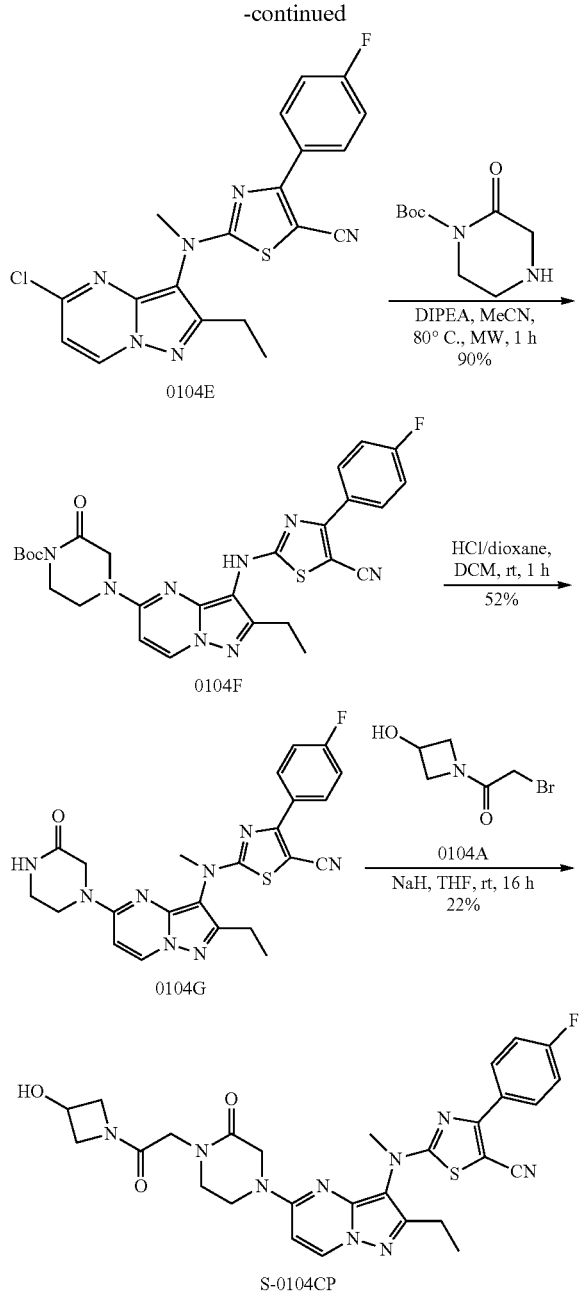

Step 1: 2-bromo-1-(3-hydroxyazetidin-1-yl)ethanone

To a solution of potassium carbonate (1391 mg, 10.08 mmol) in water (4 mL) was added azetidin-3-ol hydrochloride (550 mg, 5.04 mmol). The reaction solution was stirred at room temperature for 10 min. Then 2-bromoacetyl bromide (1014 mg, 5.04 mmol) was slowly added at 0° C., and the resulting reaction solution was stirred at room temperature for 1 h. Dichloromethane (10 mL×3) was added for extraction. The organic phases were dried over anhydrous sodium sulfate, filtered and concentrated to give 2-bromo-1-(3-hydroxyazetidin-1-yl)ethanone (280 mg, 28%). LCMS (ESI) [M+H]$^+$=194, (LC-MS Method B).

Step 2: 5-chloro-2-ethyl-3-nitropyrazolo[1,5-a]pyrimidine

A solution of 5-chloro-2-ethylpyrazolo[1,5-a]pyrimidine 0041C (550 mg, 3.03 mmol) in concentrated sulfuric acid (8 mL) was cooled to 0° C. Then concentrated nitric acid (210 mg, 3.34 mmol) was slowly added. The reaction solution was stirred at room temperature for 10 min. The reaction solution was poured into ice-water (50 mL), and ethyl acetate (50 mL×3) was added for extraction. The organic phases were washed with 1 N aqueous sodium bicarbonate (20 mL×3), dried over sodium sulfate and concentrated. The residue was purified by flash chromatography (ethyl acetate/petroleum ether=0-20%) to give 5-chloro-2-ethyl-3-nitropyrazolo[1,5-a]pyrimidine 0041D (500 mg, 73%). LCMS (ESI) [M+H]$^+$=227. (LC-MS Method B).

Step 3: 5-chloro-2-ethylpyrazolo[1,5-a]pyrimidin-3-amine

A mixture of 5-chloro-2-ethyl-3-nitropyrazolo[1,5-a]pyrimidine 0041D (500 mg, 2.2 mmol), zinc (286 mg, 4.4 mmol) and ammonium chloride (238 mg, 4.4 mmol) in methanol/tetrahydrofuran/water (25 mL) was stirred at room temperature for 2 h. The reaction solution was filtered. The filtrate was concentrated. The residue was purified by flash chromatography (ethyl acetate/petroleum ether=0-60%) to give 5-chloro-2-ethylpyrazolo[1,5-a]pyrimidin-3-amine 0104A (400 mg, 92%). LCMS (ESI) [M+H]$^+$=197 (LC-MS Method B).

Step 4: 2-((5-chloro-2-ethylpyrazolo[1,5-a]pyrimidin-3-yl)amino)-4-(4-fluorophenyl) thiazole-5-carbonitrile To a solution of 5-chloro-2-ethylpyrazolo[1,5-a]pyrimidin-3-amine 0104A (80 mg, 0.408 mmol) in tetrahydrofuran (3 mL) was slowly added sodium hydride (60% in oil, 33 mg, 0.82 mmol). The reaction solution was stirred at room temperature for 10 min. Then 2-chloro-4-(4-fluorophenyl)thiazole-5-carbonitrile (196 mg, 0.82 mmol) was added and the resulting reaction solution was stirred at room temperature for 16 h. The reaction was quenched with ice water (10 mL), and ethyl acetate (10 mL×3) was added for extraction. The organic phases were washed with saturated brine (10 mL×3), dried over anhydrous sodium sulfate, filtered and concentrated. The residue was purified by flash chromatography (ethyl acetate/petroleum ether=0-35%) to give 2-((5-chloro-2-ethylpyrazolo[1,5-a]pyrimidin-3-yl)amino)-4-(4-fluorophenyl)thiazole-5-carbonitrile 0104B (70 mg, 43%) in the form of a yellow solid. LCMS (ESI) [M+H]$^+$=399, (LC-MS Method A).

Step 5: 2-((5-chloro-2-ethylpyrazolo[1,5-a]pyrimidin-3-yl)(methyl)amino)-4-(4-fluorophenyl)thiazole-5-carbonitrile To a solution of 2-((5-chloro-2-ethylpyrazolo[1,5-a]pyrimidin-3-yl)amino)-4-(4-fluorophenyl)thiazole-5-carbonitrile 0104B (70 mg, 0.176 mmol) in N,N-dimethylforma mide (3 mL) was added cesium carbonate (171 mg, 0.528 mmol). The reaction solution was stirred at room temperature for 30 min. Then methyl iodide (40 mg, 0.285 mmol) was added and the resulting reaction solution was stirred at room temperature for 2 h. The reaction was quenched with water (10 mL), and ethyl acetate (10 mL×3) was added for extraction. The organic phases were washed with saturated brine (10 mL×3), dried over anhydrous sodium sulfate, filtered and concentrated. The residue was purified by flash chromatography (ethyl acetate/petroleum ether=0-50%) to give 2-((5-chloro-2-ethylpyrazolo [1,5-a]pyrimidin-3-yl)(methyl)amino)-4-(4-fluorophenyl)thiazole-5-carbonitrile 0104C (17 mg, 23%) in the form of a yellow solid. LCMS (ESI) [M+H]$^+$=413, (LC-MS Method A).

Step 6: tert-butyl 4-(3-((5-cyano-4-(4-fluorophenyl)thiazol-2-yl)amino)-2-ethylpyrazolo [1,5-a]pyrimidin-5-yl)-2-oxopiperazine-1-carboxylate A mixture of 2-((5-chloro-2-ethylpyrazolo[1,5-a]pyrimidin-3-yl)(methyl)amino)-4-(4-fluorophenyl)thiazole-5-carbonitrile 0104C (80 mg, 0.194 mmol), tert-butyl 2-oxopiperazine-1-carboxylate (58 mg, 0.291 mmol) and diisopropylethylamine (75 mg, 0.582 mmol) in acetonitrile (3 mL) was stirred at 80° C. for 1 h under microwave. The reaction solution was concentrated. The residue was purified by flash chromatography (ethyl acetate/petroleum ether=0-60%) to give tert-butyl 4-(3-((5-cyano-4-(4-fluorophenyl)thiazol-2-yl) amino)-2-ethylpyrazolo[1,5-a]pyrimidin-5-yl)-2-oxopiperazine-1-carboxylate 0104D (130 mg, 90%). LCMS (ESI) [M+H]+=577, (LC-MS Method A).

Step 7: 2-((2-ethyl-5-(3-oxopiperazin-1-yl)pyrazolo[1,5-a]pyrimidin-3-yl)(methyl) amino)-4-(4-fluorophenyl)thiazole-5-carbonitrile A mixture of tert-butyl 4-(3-((5-cyano-4-(4-fluorophenyl)thiazol-2-yl)amino)-2-ethylpyrazolo[1,5-a]pyrimidin-5-yl)-2-oxopiperazine-1-carboxylate 0104D (130 mg, 0.225 mmol) in hydrogen chloride (4 N in 1,4-dioxane, 3 mL) was stirred at room temperature for 1 h. The reaction solution was concentrated. Then aqueous sodium bicarbonate (5 mL) was added, and dichloromethane (5 mL×3) was added for extraction. The organic phases were washed with saturated brine (5 mL×3), dried over anhydrous sodium sulfate, filtered and concentrated. The residue was purified by flash chromatography (methanol/dichloromethane=0-10%) to give 2-((2-ethyl-5-(3-oxopiperazin-1-yl)pyrazolo[1,5-a]pyrimidin-3-yl)(methyl) amino)-4-(4-fluorophenyl)thiazole-5-carbonitrile 0104E (50 mg, 52%). LCMS (ESI) [M+H]$^+$=477, (LC-MS Method B).

Step 8: 2-((2-ethyl-5-(4-(2-(3-hydroxyazetidin-1-yl)-2-oxoethyl)-3-oxopiperazin-1-yl) pyrazolo[1,5-a]pyrimidin-3-yl)(methyl)amino)-4-(4-fluorophenyl)thiazole-5-carbonitrile (S-0104CP)

To a solution of 2-((2-ethyl-5-(3-oxopiperazin-1-yl)pyrazolo[1,5-a]pyrimidin-3-yl) (methyl)amino)-4-(4-fluorophenyl)thiazole-5-carbonitrile 0104E (50 mg, 0.105 mmol) in tetrahydrofuran (3 mL) was added sodium hydride (60% in mineral oil, 13 mg, 0.315 mmol). The reaction solution was stirred at room temperature for 30 min. Then 2-bromo-1-(3-hydroxyazetidin-1-yl)ethanone (31 mg, 0.157 mmol) was added and the resulting reaction solution was stirred at room temperature for 16 h. The reaction was quenched with ice water (10 mL), and ethyl acetate (10 mL×3) was added for extraction. The organic phases were washed with saturated brine (10 mL: 3), dried over anhydrous sodium sulfate, filtered and concentrated. The residue was purified by flash chromatography (methanol/dichloromethane=0-15%) to give 2-((2-ethyl-5-(4-(2-(3-hydroxyazetidin-1-yl)-2-oxoethyl)piperazin-1-ylpyrazolo [1,5-a]pyrimidin-3-yl)(methyl)amino)-4-(4-fluorophenyl)thiazole-5-carbonitrile 5-0104 CP (14 mg, 22%). LCMS (ESI) [M+H]$^+$=590.1 @ 7.650 min (Method B). $^1$H NMR (400 MHz, DMSO-d$_6$) δ 8.706 (d, J=8.0 Hz, 1H), 8.069 (m, 2H), 7.379 (t, 2H), 6.780 (d, J=8.0 Hz, 1H), 5.741 (d, J=6.0 Hz, 1H), 4.458 (m, 1H), 4.248 (m, 3H), 4.015 (m, 3H), 3.861 (m, 3H), 3.585 (m, 3H), 3.539 (s, 3H), 3.432 (m, 2H), 2.616 (m, 2H), 1.212 (t, 3H).

Example 35. S-0105CP: 2-((2-ethyl-5-(4-(2-(3-hydroxyazetidin-1-yl)-2-oxoethyl) piperazin-1-yl)furo[3,2-b]pyridin-3-yl)amino)-4-(4-fluorophenyl)thiazole-5-carbonitrile

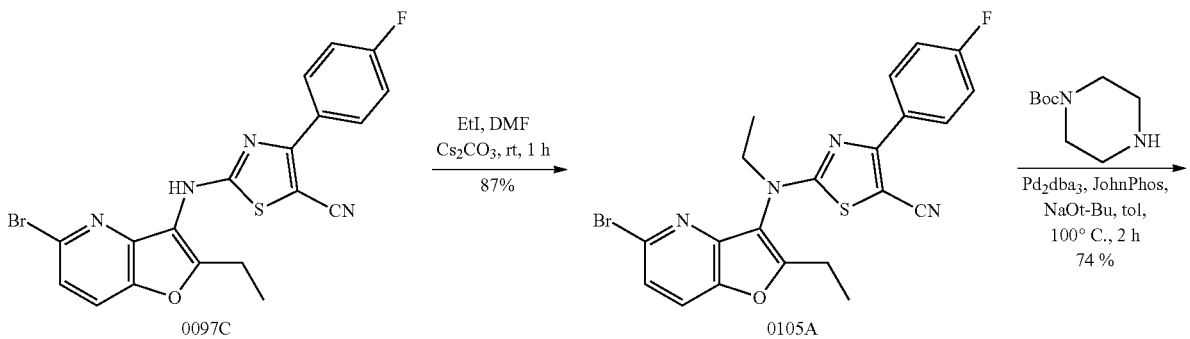

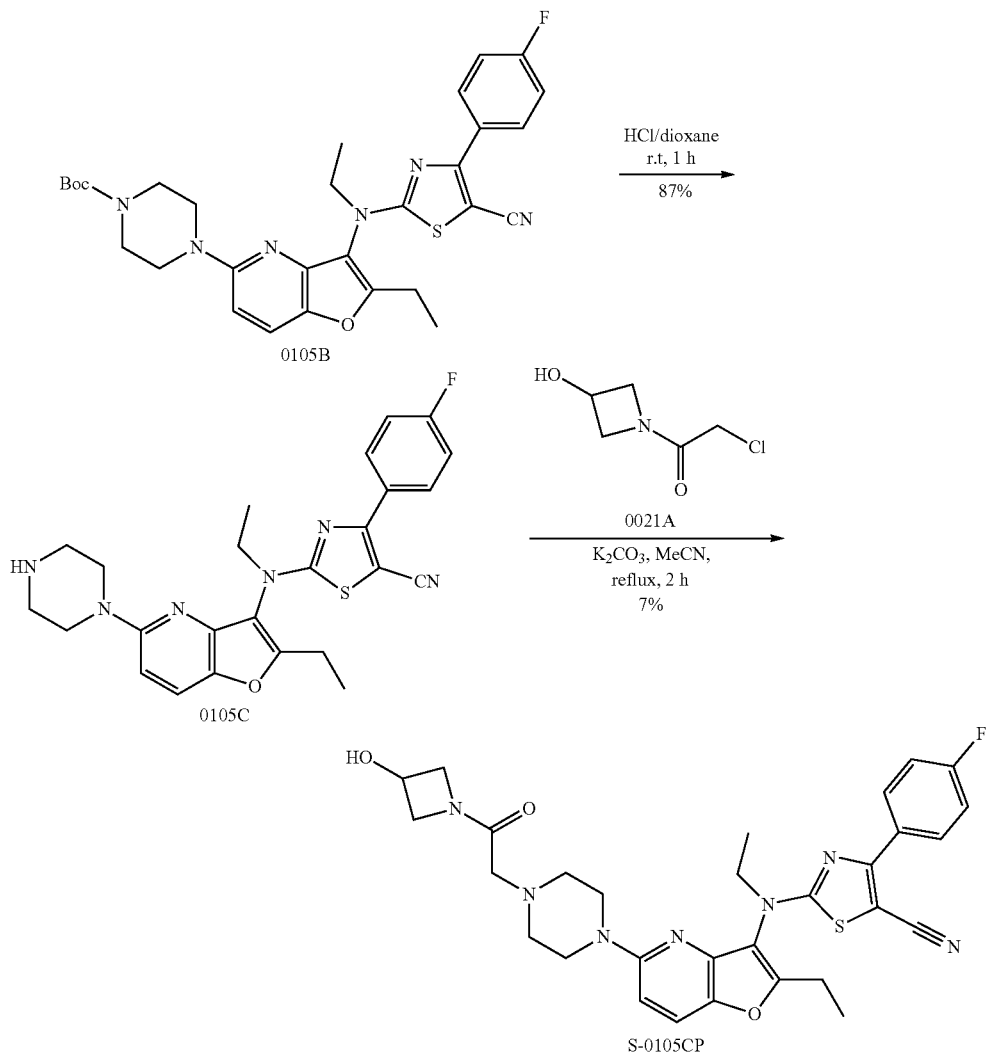

Step 1: 2-((5-bromo-2-ethylfuro[3,2-b]pyridin-3-yl)(ethyl)amino)-4-(4-fluorophenyl) thiazole-5-carbonitrile To a solution of 2-((5-bromo-2-ethylfuro[3,2-b]pyridin-3-yl)amino)-4-(4-fluorophenyl) thiazole-5-carbonitrile (100 mg, 0.23 mmol) in N,N-dimethylformamide (3 mL) was added cesium carbonate (225 mg, 0.69 mmol). The reaction solution was stirred at room temperature for 10 min and then iodoethane (42 mg, 0.27 mmol) was added. The resulting reaction solution was stirred at room temperature for 1 h. Water (10 mL) was added and ethyl acetate (10 mL×3) was added for extraction. The organic phases were washed with saturated brine (10 mL×3), dried over anhydrous sodium sulfate, filtered and concentrated. The residue was purified by flash chromatography (ethyl acetate/petroleum ether=0-20%) to give 2-((5-bromo-2-ethylfuro [3,2-b]pyridin-3-yl)(ethyl)amino)-4-(4-fluorophenyl)thiazole-5-carbonitrile (94 mg, 87%) in the form of a brown oil. LCMS (ESI) [M+H]$^+$=471.0.

Step 2: tert-butyl 4-(3-((5-cyano-4-(4-fluorophenyl)thiazol-2-yl)(ethyl)amino)-2-ethylfuro [3,2-b]pyridin-5-yl)piperazine-1-carboxylate In a glove box, to a solution of 2-((5-bromo-2-ethylfuro [2,3-b]pyridin-3-yl)(ethyl) amino)-4-(4-fluorophenyl)thiazole-5-carbonitrile (90 mg, 0.19 mmol), tert-butyl piperazine-1-carboxylate (177 mg, 0.95 mmol), tris(dibenzylideneacetone)dipalladium (0) (17 mg, 0.019 mmol), 2-(di-tert-butylphosphino)biphenyl (6 mg, 0.019 mmol), and sodium tert-butoxide (28 mg, 0.288 mmol) was added toluene (3 mL). The reaction solution was stirred at 100° C. for 2 h. After cooling to room temperature, ethyl acetate (10 mL) was added for dilution. Then the reaction solution was washed with water (10 mL×2), dried over anhydrous sodium sulfate, filtered and concentrated. The residue was purified by flash chromatography (ethyl acetate/petroleum ether=0-25%) to give tert-butyl 4-(3-((5-cyano-4-(4-fluorophenyl)thiazol-2-yl)(ethyl)amino)-2-ethylfuro[3,2-b]pyridin-5-yl)piperazine-1-carboxylate (81 mg, 74%) in the form of a yellow solid. LCMS (ESI) [M+H]$^+$=577.2.

Step 3: 2-(ethyl(2-ethyl-5-(piperazin-1-yl)furo[3,2-b]pyridin-3-yl)amino)-4-(4-fluorophenyl)thiazole-5-carbonitrile A mixture of tert-butyl 4-(3-((5-cyano-4-(4-fluorophenyl)thiazol-2-yl)(ethyl)amino)-2-ethylfuro[3,2-b]pyridin-5-yl)piperazine-1-carboxylate (100 mg, 0.17 mmol) in hydrogen chloride (4 N in 1,4-dioxane, 3 mL) was stirred at room temperature for 1 h, and then concentrated. Saturated aqueous sodium bicarbonate (5 mL) was added to the residue to adjust pH to low alkalinity, and ethyl acetate (10 mL×3) was added for extraction. The organic phases were washed with saturated brine (10 mL×3), dried over anhydrous sodium sulfate, filtered and concentrated to give 2-(ethyl(2-ethyl-5-(piperazin-1-yl)furo[3,2-b]pyridin-3-yl)amino)-4-(4-fluorophenyl)thiazole-5-carbonitrile (70 mg, 87%) in the form of a yellow solid, which was used in the next step without purification. LCMS (ESI) [M+H]⁺=477.0.

Step 4: 2-(ethyl(2-ethyl-5-(4-(2-(3-hydroxyazetidin-1-yl)-2-oxoethyl)piperazin-1-yl)furo [3,2-b]pyridin-3-yl)amino)-4-(4-fluorophenyl)thiazole-5-carbonitrile To a mixture of 2-(ethyl(2-ethyl-5-(piperazin-1-yl)furo[3,2-b]pyridin-3-yl)amino)-4-(4-fluorophenyl)thiazole-5-carbonitrile (70 mg, 0.147 mmol) in acetonitrile (3 mL) was added 2-chloro-1-(3-hydroxyazetidin-1-yl)ethanone (50 mg, 0.336 mmol) and potassium carbonate (69 mg, 0.5 mmol). The reaction solution was stirred at reflux for 2 h, and then concentrated. The residue was purified by pre-HPLC to give 2-(ethyl(2-ethyl-5-(4-(2-(3-hydroxyazetidin-1-yl)-2-oxoethyl)piperazin-1-yl)furo[3,2-b]pyridin-3-yl)amino)-4-(4-fluorophenyl)thiazole-5-carbonitrile S-0105CP (6.2 mg, 7%) in the form of a white solid. LCMS (ESI) [M+H]⁺=590.1@6.66 min; ¹H NMR (400 MHz, CD₃OD) δ 8.16-8.12 (m, 2H), 7.72 (d, J=8.4 Hz, 1H), 7.28-7.23 (m, 2H), 6.83 (d, J=9.2 Hz, 1H), 4.80-4.47 (m, 2H), 4.26-4.05 (m, 4H), 3.80-43.76 (m, 1H), 3.59 (s, 4H), 3.14 (m, 2H), 2.83 (q, J=7.6 Hz, 2H), 2.65 (m, 4H), 1.37 (t, J=7.6 Hz, 6H).

Example 36. S-0117: 2-(ethyl(2-ethyl-5-(4-(2-(3-hydroxyazetidin-1-yl)-2-oxoethyl) piperazin-1-yl)-2H-pyrazolo[4,3-b]pyridin-3-yl)amino)-4-(4-fluorophenyl)thiazole-5-carbonitrile

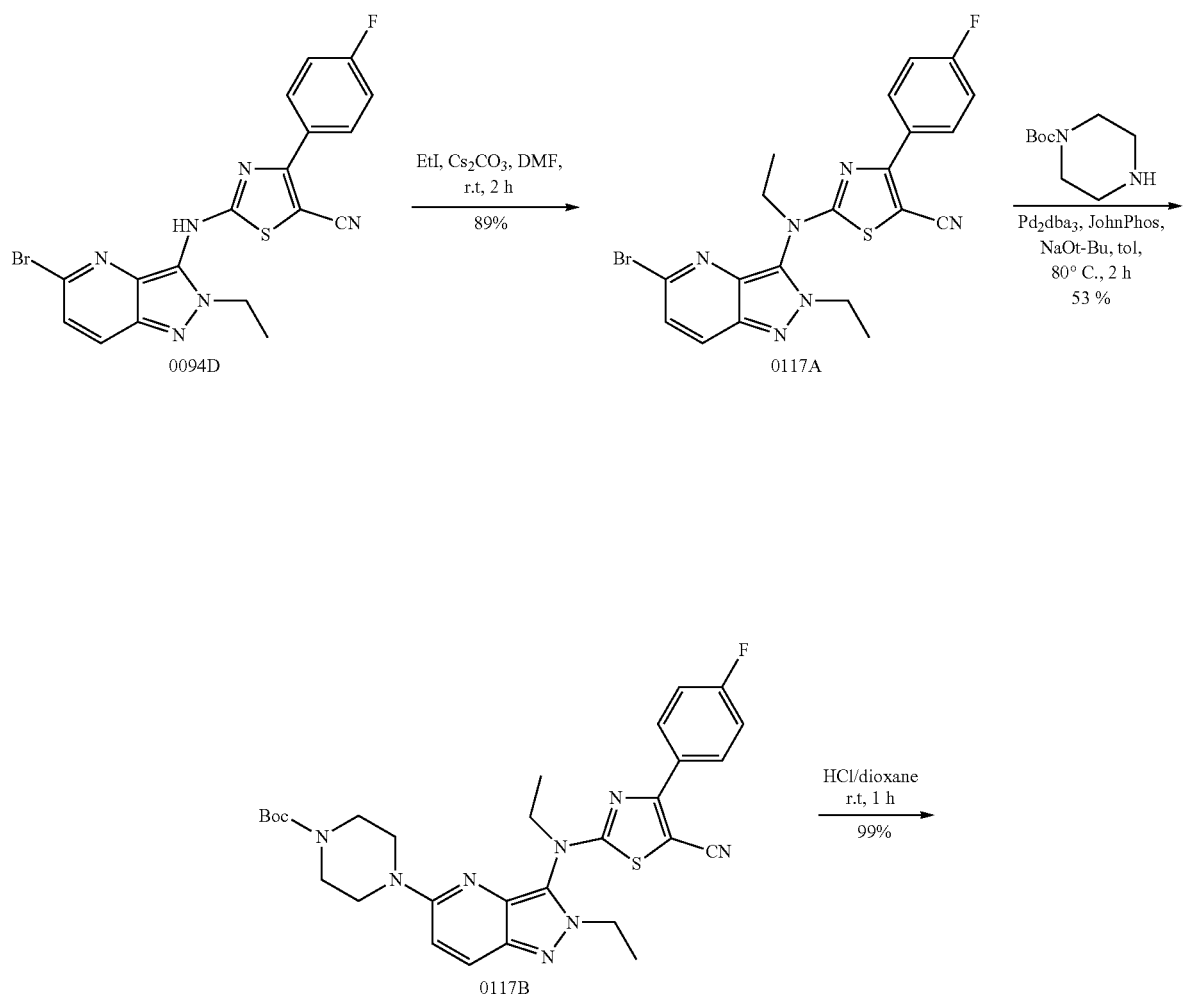

-continued

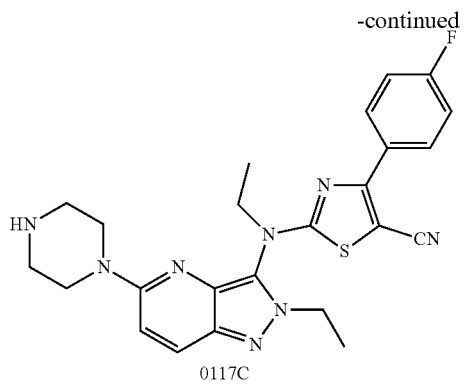
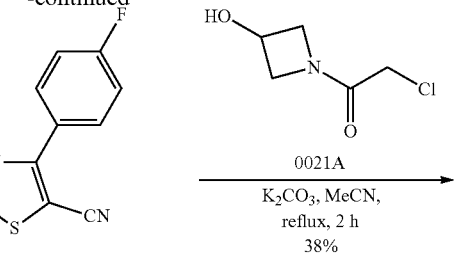

0117C

0021A
K₂CO₃, MeCN,
reflux, 2 h
38%

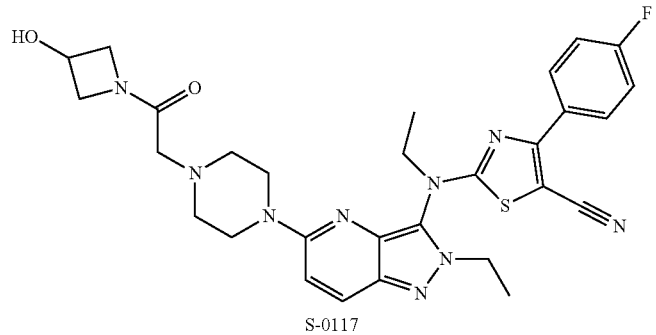

S-0117

Step 1: 2-((5-bromo-2-ethyl-2H-pyrazolo[4,3-b]pyridin-3-yl)(ethyl)amino)-4-(4-fluorophenyl)thiazole-5-carbonitrile To a solution of 2-((5-bromo-2-ethyl-2H-pyrazolo[4,3-b]pyridin-3-yl)amino)-4-(4-fluorophenyl)thiazole-5-carbonitrile 0094D (220 mg, 0.5 mmol) in N,N-dimethylformamide (4 mL) was added sodium hydride (60% in mineral oil, 40 mg, 1.0 mmol). The reaction solution was stirred at room temperature for 30 min. Then iodoethane (78 mg, 0.5 mmol) was added, and the resulting reaction solution was stirred at room temperature for 2 h. The reaction was quenched with water (10 mL), and ethyl acetate (20 mL×3) was added for extraction. The organic phases were washed with water and saturated brine (20 mL×3), dried over anhydrous sodium sulfate, filtered and concentrated. The residue was purified by flash chromatography (ethyl acetate/petroleum ether=0-30%) to give 2-((5-bromo-2-ethyl-2H-pyrazolo[4,3-b]pyridin-3-yl)(ethyl)amino)-4-(4-fluorophenyl) thiazole-5-carbonitrile 0117A (210 mg, 89%) in the form of a brown oil. LCMS (ESI) [M+H]$^+$=471.0 @ 2.26 min (LC-MS Method A).

Step 2: tert-butyl 4-(3-((5-cyano-4-(4-fluorophenyl)thiazol-2-yl)(ethyl)amino)-2-ethyl-2H-pyrazolo[4,3-b]pyridin-5-yl)piperazine-1-carboxylate In a glove box, to a sealed tube were added 2-((5-bromo-2-ethyl-2H-pyrazolo[4,3-b]pyridin-3-yl)(ethyl)amino)-4-(4-fluorophenyl)thiazole-5-carbonitrile 0117A (335 mg, 1.8 mmol), tert-butyl piperazine-1-carboxylate (335 mg, 1.8 mmol), tris(dibenzylideneacetone) dipalladium(0) (66 mg, 0.072 mmol), 2-(di-tert-butylphosphino)biphenyl (22 mg, 0.072 mmol), sodium tert-butoxide (104 mg, 1.08 mmol) and toluene (3 mL). The reaction solution was stirred at 80° C. for 2 h. The organic phases were washed with water (10 mL×3), dried over anhydrous sodium sulfate, filtered and concentrated. The residue was purified by flash chromatography (ethyl acetate/petroleum ether=0-30%) to give tert-butyl 4-(3-((5-cyano-4-(4-fluorophenyl)thiazol-2-yl)(ethyl)amino)-2-ethyl-2H-pyrazolo[4,3-b]pyridin-5-yl)piperazine-1-carboxylate 0117B (110 mg, 53%) in the form of a yellow solid. LCMS (ESI) [M+H]$^+$=577.2 @ 2.57 min (LC-MS Method B).

Step 3: 2-(ethyl(2-ethyl-5-(piperazin-1-yl)-2H-pyrazolo[4,3-b]pyridin-3-yl)amino)-4-(4-fluorophenyl)thiazole-5-carbonitrile A solution of tert-butyl 4-(3-((5-cyano-4-(4-fluorophenyl)thiazol-2-yl)(ethyl)amino)-2-ethyl-2H-pyrazolo[4,3-b]pyridin-5-yl)piperazine-1-carboxylate 0117B (140 mg, 0.24 mmol) in hydrogen chloride (4 N in dioxane, 2 mL) was stirred at room temperature for 1 h. Then aqueous sodium bicarbonate (10 mL) was added, and dichloromethane (20 mL×3) was added for extraction. The organic phases were washed with saturated brine (20 mL×3), dried over sodium sulfate, filtered and concentrated to give 2-(ethyl(2-ethyl-5-(piperazin-1-yl)-2H-pyrazolo[4,3-b]pyridin-3-yl) amino)-4-(4-fluorophenyl)thiazole-5-carbonitrile 0117C (115 mg, 99%) in the form of a yellow solid. LCMS (ESI) [M+H]$^+$=477.1 @ 1.88 min (LC-MS Method B).

Step 4: 2-(ethyl(2-ethyl-5-(4-(2-(3-hydroxyazetidin-1-yl)-2-oxoethyl)piperazin-1-yl)-2H-pyrazolo[4,3-b]pyridin-3-yl)amino)-4-(4-fluorophenyl)thiazole-5-carbonitrile To a solution of 2-(ethyl(2-ethyl-5-(piperazin-1-yl)-2H-pyrazolo[4,3-b]pyridin-3-yl) amino)-4-(4-fluorophenyl)thiazole-5-carbonitrile 0117C (115 mg, 0.24 mmol) in acetonitrile (3 mL) was added 2-chloro-1-(3-hydroxyazetidin-1-yl)ethanone (71 mg, 0.48 mmol) and potassium carbonate (99 mg, 0.72 mmol), and then the resulting solution was stirred at reflux for 2 h. The reaction solution was concentrated. The residue was purified by flash chromatography (methanol/dichloromethane=0-8%) to give 2-(ethyl(2-ethyl-5-(4-(2-(3-hydroxyazetidin-1-yl)-2-oxoethyl)piperazin-1-yl)-2H-pyrazolo[4,3-b]pyridin-3-yl)amino)-4-(4-fluorophenyl)thiazole-5-carbonitrile S-0117 (53.6 mg, 38%) in the form of a white solid. LCMS (ESI) [M+H]⁺=590.1 @5.93 min (LC-MS Method C). H NMR (400 MHz, (CD$_3$)$_2$SO) δ 8.09-8.05 (m, 2H), 7.92 (d, J=9.6 Hz, 1H), 7.44-7.40 (m, 2H), 7.18 (d, J=9.2 Hz, 1H), 5.68 (d, 1H), 4.43-4.32 (m, 2H), 4.53-4.48 (m, 1H), 4.24 (q, J=7.2, 2H), 4.02 (m, 1H), 3.92-3.81 (m, 2H), 3.58-3.54 (m, 5H), 2.99 (q, J=3.6 Hz, 2H), 2.50 (s, 4H), 1.46 (t, J=7.6 Hz, 3H), 1.32 (t, J=7.6 Hz, 3H).

Example 37. S-0120: 2-((2-ethyl-5-(4-(2-(3-hydroxy-3-methylazetidin-1-yl)-2-oxoethyl)piperazin-1-yl)pyrazolo[1,5-a]pyrimidin-3-yl)(methyl)amino)-4-(4-fluorophenyl)thiazole-5-carbonitrile

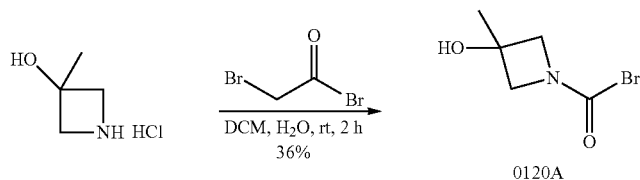

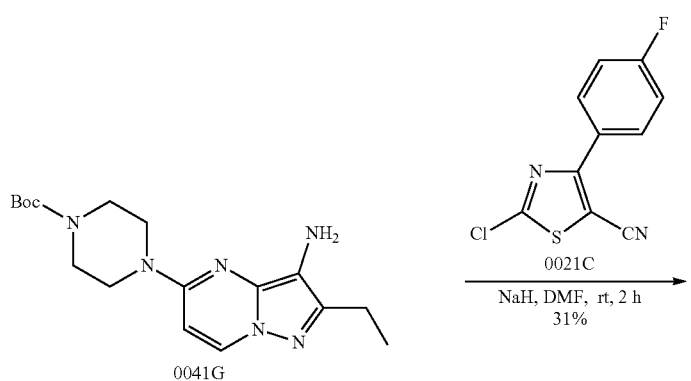

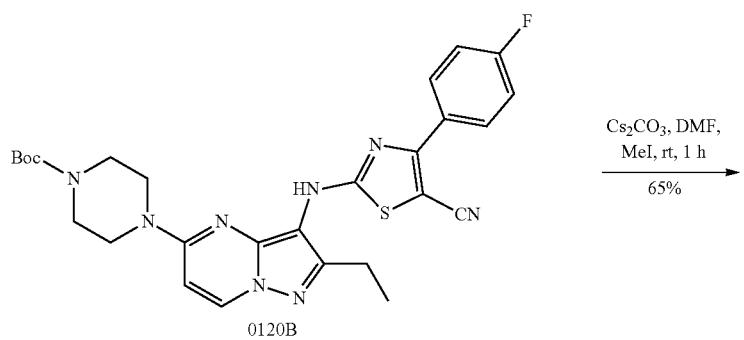

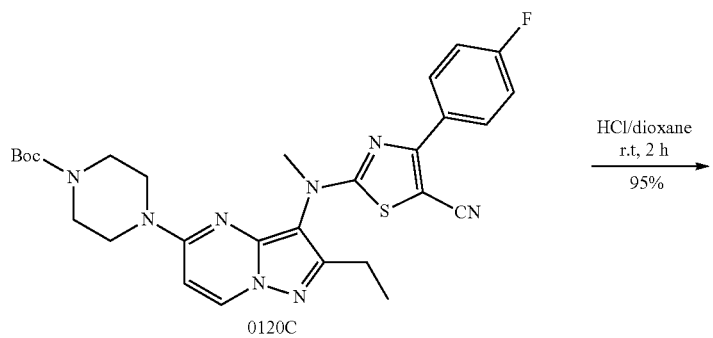

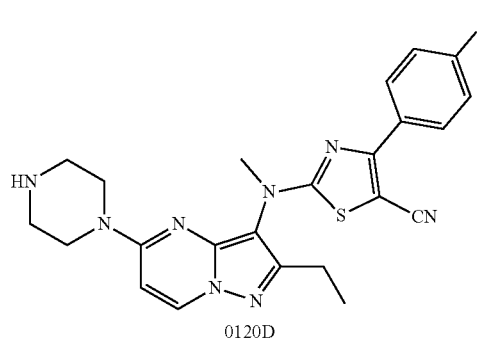
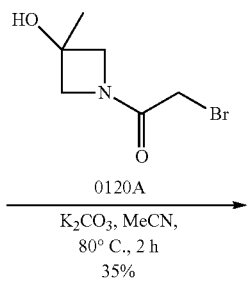

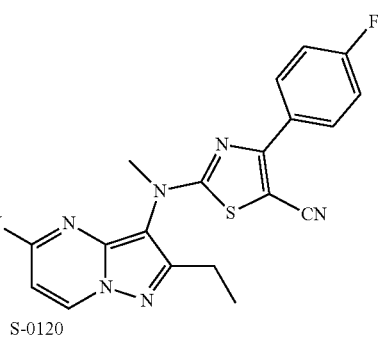

Step 1: 2-bromo-1-(3-hydroxy-3-methylazetidin-1-yl)ethanone

To a mixture of potassium carbonate (803 mg, 5.82 mmol) in water (4 mL) was added 3-methylazetidin-3-ol hydrochloride (360 mg, 2.91 mmol). The mixture was stirred at room temperature for 10 min. Then 2-bromoacetyl bromide (586 mg, 2.91 mmol) was added at 0° C., and the resulting solution was stirred at room temperature for 1 h. Dichloromethane (10 mL×3) was added for extraction. The organic phases were dried over anhydrous sodium sulfate, filtered and concentrated to give 2-bromo-1-(3-hydroxy-3-methylazetidin-1-yl)ethanone 0120A (220 mg, 36%). LCMS (ESI) $[M+H]^+$=208.0@ 1.18 min (Method A).

Step 2: tert-butyl 4-(3-((5-cyano-4-(4-4-fluorophenyl)thiazol-2-yl)amino)-2-ethylpyrazolo [1,5-a]pyrimidin-5-yl)piperazine-1-carboxylate To a solution of tert-butyl 4-(3-amino-2-ethylpyrazolo[1,5-a]pyrimidin-5-yl)piperazine-1-carboxylate 0041G (60 mg, 0.173 mmol) in N,N-dimethylformamide (3 mL) was added sodium hydride (60% in oil, 33 mg, 0.82 mmol). The reaction solution was stirred at room temperature for 10 min. Then 2-chloro-4-(4-fluorophenyl)thiazole-5-carbonitrile (196 mg, 0.82 mmol) was added, and the resulting reaction solution was stirred at room temperature for 16 h. The reaction was quenched with ice water (10 mL), and ethyl acetate (10 mL×3) was added for extraction. The organic phases were washed with saturated brine (10 mL: 3), dried over anhydrous sodium sulfate, filtered and concentrated. The residue was purified by flash chromatography (ethyl acetate/petroleum ether=0-35%) to give tert-butyl 4-(3-((5-cyano-4-(4-4-fluorophenyl)thiazol-2-yl)amino)-2-ethylpyrazolo[1,5-a]pyrimidin-5-yl)piperazine-1-carboxylate 0120B (30 mg, 31%) in the form of a yellow solid. LCMS (ESI) $[M+H]^+$=549.2 @ 2.16 min (Method B).

Step 3: tert-butyl 4-(3-((5-cyano-4-(4-4-fluorophenyl)thiazol-2-yl)(methyl)amino)-2-ethylpyrazolo[1,5-a]pyrimidin-5-yl)piperazine-1-carboxylate To a solution of tert-butyl 4-(3-((5-cyano-4-(4-4-fluorophenyl)thiazol-2-yl)amino)-2-ethylpyrazolo[1,5-a]pyrimidin-5-yl)piperazine-1-carboxylate 0120B (60 mg, 0.109 mmol) in N,N-dimethylformamide (3 mL) was added cesium carbonate (71 mg, 0.218 mmol). The mixture was stirred at room temperature for 30 min. Then methyl iodide (27 mg, 0.193 mmol) was added, and the resulting reaction solution was stirred at room temperature for 2 h. The reaction was quenched with water (10 mL), and ethyl acetate (10 mL×3) was added for extraction. The organic phases were washed with saturated brine (10 mL×3), dried over anhydrous sodium sulfate, filtered and concentrated. The residue was purified by flash chromatography (ethyl acetate/petroleum ether=0-50%) to give tert-butyl 4-(3-((5-cyano-4-(4-4-fluorophenyl)thiazol-2-yl)(methyl)amino)-2-ethylpyrazolo[1,5-a]pyrimidin-5-yl)piperazine-1-carboxylate 0120C (40 mg, 65%) in the form of a yellow solid. LCMS (ESI) $[M+H]^+$=563.1@ 2.09 min (Method A).

Step 4: 2-((2-ethyl-5-(piperazin-1-yl)pyrazolo[1,5-a]pyrimidin-3-yl)(methyl)amino)-4-(4-fluorophenyl)thiazole-5-carbonitrile A mixture of tert-butyl 4-(3-((5-cyano-4-(4-4-fluorophenyl)thiazol-2-yl)(methyl) amino)-2-ethylpyrazolo[1,5-a]pyrimidin-5-yl)piperazine-1-carboxylate 0120C (40 mg, 0.071 mmol) in hydrogen chloride (4 N in 1,4-dioxane, 3 mL) was stirred at room temperature for 1 h. The reaction solution was concentrated. Then aqueous sodium bicarbonate (5 mL) was added, and dichloromethane (5 mL×3) was added for extraction. The organic phases were washed with saturated brine (5 mL×3), dried over anhydrous sodium sulfate, filtered and concentrated to give 2-((2-ethyl-5-(piperazin-1-yl)

pyrazolo[1,5-a]pyrimidin-3-yl)(methyl) amino)-4-(4-fluorophenyl)thiazole-5-carbonitrile 0120D (4 mg, 95%). LCMS (ESI) [M+H]⁺=463.2@ 1.69 min (Method A).

Step 5: 2-((2-ethyl-5-(4-(2-(3-hydroxy-3-methylazetidin-1-yl)-2-oxoethyl)piperazin-1-yl) pyrazolo[1,5-a]pyrimidin-3-yl)(methyl)amino)-4-(4-fluorophenyl)thiazole-5-carbonitrile To a solution of 2-((2-ethyl-5-(piperazin-1-yl)pyrazolo[1,5-a]pyrimidin-3-yl)(methyl) amino)-4-(4-fluorophenyl)thiazole-5-carbonitrile 0120D (40 mg, 0.0865 mmol) in acetonitrile (2 mL) was added 2-bromo-1-(3-hydroxy-3-methylazetidin-1-yl)ethanone 0120A (27 mg, 0.129 mmol) and potassium carbonate (36 mg, 0.259 mmol). The mixture was stirred at 80° C. for 2 h, and then concentrated. The residue was purified by flash chromatography (methanol/dichloromethane=0-15%) to give 2-((2-ethyl-5-(4-(2-(3-hydroxy-3-methylazetidin-1-yl)-2-oxoethyl)piperazin-1-yl) pyrazolo[1,5-a]pyrimidin-3-yl)(methyl)amino)-4-(4-fluorophenyl) thiazole-5-carbonitrile S-0120 (18 mg, 35%) in the form of a white solid. LCMS (ESI) [M+H]⁺=590.1@7.49 min (Method C). H NMR (400 MHz, DMSO-d₆) δ 8.628 (d, J=8.0 Hz, 1H), 8.065 (m, 2H), 7.383 (t, 2H), 6.757 (d, J=7.6 Hz, 1H), 5.599 (s, 1H), 3.996 (m, 2H), 3.648 (m, 6H), 3.327 (s, 3H), 3.008 (d, J=5.6 Hz, 1H), 2.615 (m, 2H), 2.501 (m, 4H), 1.341 (d, J=4.0 Hz, 3H), 1.202 (t, 3H).

Example 38. S-0121: 4-(3,4-difluorophenyl)-2-((2-ethyl-5-(4-(2-(3-hydroxyazetidin-1-yl)-2-oxoethyl) piperazin-1-yl)pyrazolo[1,5-a]pyrimidin-3-yl) (methyl)amino)thiazole-5-carbonitrile

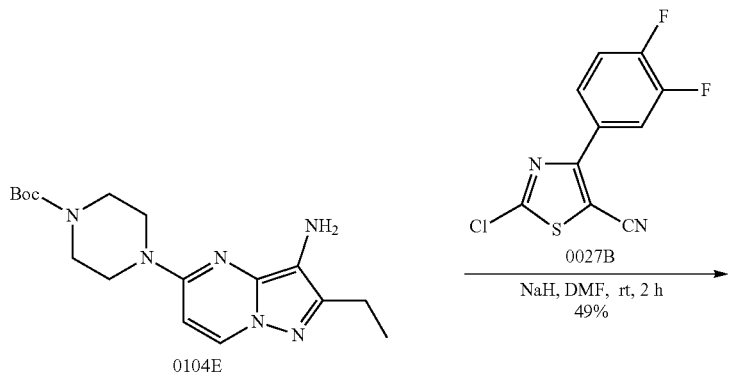

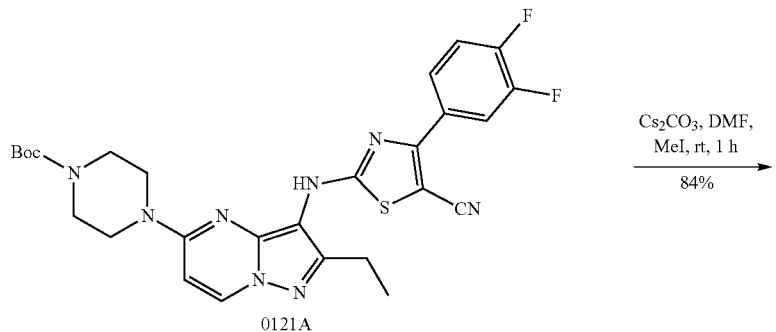

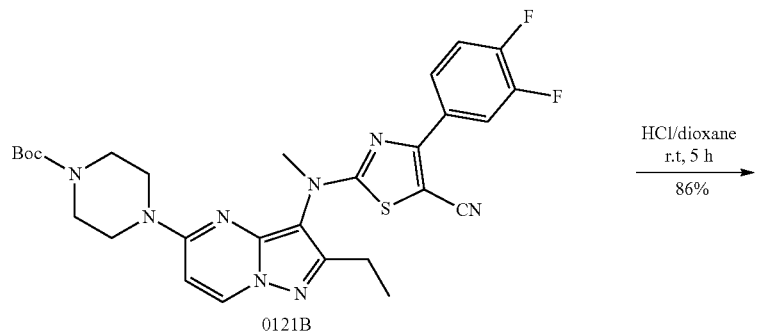

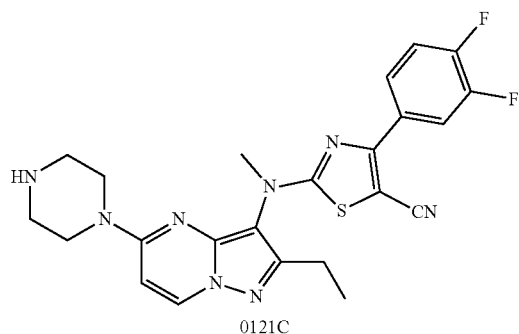
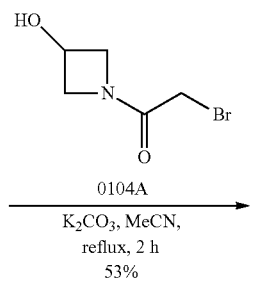

Step 1: tert-butyl 4-(3-((5-cyano-4-(3,4-difluorophenyl)thiazol-2-yl)amino)-2-ethylpyrazolo[1,5-a]pyrimidin-5-yl)piperazine-1-carboxylate Sodium hydride (60% in mineral oil, 23 mg, 0.578 mmol) was added to a solution of tert-butyl 4-(3-amino-2-ethylpyrazolo[1,5-a]pyrimidin-5-yl)piperazine-1-carboxylate 0104E (100 mg, 0.289 mmol) in tetrahydrofuran (3 mL). The mixture was stirred at room temperature for 10 min. 2-chloro-4-(3,4-difluorophenyl)thiazole-5-carbonitrile (111 mg, 0.433 mmol) was added and the resulting mixture was stirred at room temperature for 16 h. The reaction was quenched by adding ice water (10 mL), and ethyl acetate (10 mL×3) was added for extraction. The organic phases were washed with saturated brine (10 mL×3), dried over anhydrous sodium sulfate, filtered and concentrated. The residue was purified by flash chromatography (ethyl acetate/petroleum ether=0-35%) to give tert-butyl 4-(3-((5-cyano-4-(3,4-difluorophenyl)thiazol-2-yl)amino)-2-ethylpyrazolo[1,5-a]pyrimidin-5-yl)piperazine-1-carboxylate 0121A (80 mg, 49%) in the form of a yellow solid. LCMS (ESI) [M+H]$^+$=567.2 @2.23 min (Method B).

Step 2: tert-butyl 4-(3-((5-cyano-4-(3,4-difluorophenyl)thiazol-2-yl)(methyl)amino)-2-ethylpyrazolo[1,5-a]pyrimidin-5-yl)piperazine-1-carboxylate Cesium carbonate (94 mg, 0.288 mmol) was added to a solution of tert-butyl 4-(3-((5-cyano-4-(3,4-difluorophenyl)thiazol-2-yl)amino)-2-ethylpyrazolo[1,5-a]pyrimidin-5-yl)piperazine-1-carboxylate 0121A (80 mg, 0.144 mmol) in N,N-dimethylformamide (3 mL), and the mixture was stirred at room temperature for 30 min. Then methyl iodide (24 mg, 0.172 mmol) was added, and the resulting mixture was stirred at room temperature for 2 h. The reaction was quenched by adding water (10 mL) and ethyl acetate (10 mL×3) was added for extraction. The organic phases were washed with saturated brine (10 mL×3), dried over anhydrous sodium sulfate, filtered and concentrated. The residue was purified by flash chromatography (ethyl acetate/petroleum ether=0-50%) to give tert-butyl 4-(3-((5-cyano-4-(3,4-difluorophenyl)thiazol-2-yl)(methyl)amino)-2-ethylpyrazolo[1,5-a]pyrimidin-5-yl)piperazine-1-carboxylate 0121B (70 mg, 84%) in the form of a yellow solid. LCMS (ESI) [M+H]$^+$=581.3@2.63 min (Method B).

Step 3: 4-(3,4-difluorophenyl)-2-((2-ethyl-5-(piperazin-1-yl)pyrazolo[1,5-a]pyrimidin-3-yl)(methyl)amino)thiazole-5-carbonitrile A solution of tert-butyl 4-(3-((5-cyano-4-(3,4-difluorophenyl)thiazol-2-yl)(methyl)amino)-2-ethylpyrazolo[1,5-a]pyrimidin-5-yl)piperazine-1-carboxylate 0121B (70 mg, 0.121 mmol) in hydrogen chloride (4 N in 1,4-dioxane, 3 mL) was stirred at room temperature for 1 h. The reaction system was concentrated. Aqueous sodium bicarbonate (5 mL) was added. Dichloromethane (5 mL×3) was added for extraction. The organic phases were washed with saturated brine (5 mL×3), dried over anhydrous sodium sulfate, filtered and concentrated to give 4-(3,4-difluorophenyl)-2-((2-ethyl-5-(piperazin-1-yl)pyrazolo[1,5-a]pyrimidin-3-yl)(methyl)amino)thiazole-5-carbonitrile 0121C (50 mg, 86%). LCMS (ESI) [M+H]$^+$=481.0 @ 1.83 min (Method A).

Step 4: 4-(3,4-difluorophenyl)-2-((2-ethyl-5-(4-(2-(3-hydroxyazetidin-1-yl)-2-oxoethyl) piperazin-1-yl) pyrazolo[1,5-a]pyrimidin-3-yl)(methyl)amino)thiazole-5-carbonitrile 2-chloro-1-(3-hydroxyazetidin-1-yl)ethanone 0021A (30 mg, 0.156 mmol) and potassium carbonate (43 mg, 0.312 mmol) were added to a solution of 4-(3,4-difluorophenyl)-2-((2-ethyl-5-(piperazin-1-yl)pyrazolo[1,5-a]pyrimidin-3-yl)(methyl)amino)thiazole-5-carbonitrile 0121C (50 mg, 0.104 mmol) in acetonitrile (2 mL). The reaction system was stirred at 80° C. for 2 h, and concentrated. The residue was purified by flash chromatography (methanol/dichloromethane=0-15%) to give 4-(3,4-difluorophenyl)-2-((2-ethyl-5-(4-(2-(3-hydroxyazetidin-1-yl)-2-oxoethyl) piperazin-1-yl) pyrazolo[1,5-a]pyrimidin-3-yl)(methyl) amino)thiazole-5-carbonitrile S-0121 (33 mg, 53%) in the form of a white solid. LCMS (ESI) [M+H]⁺=594.3@7.57 min (Method C). ¹H NMR (400 MHz, CD₃OD) δ 8.361 (d, J=8.0 Hz, 1H), 7.94 (m, 2H), 7.395 (q, 2H), 6.700 (d, J=8.0 Hz, 1H), 4.588 (m, 1H), 4.227 (m, 1H), 4.053 (dd, 1H), 3.767 (m, 5H), 3.3602 (s, 3H), 3.119 (d, J=3.2 Hz, 2H), 2.678 (q, 2H), 2.585 (t, 4H), 1.303 (t, 3H).

Example 39. S-0122: 2-(ethyl(2-ethyl-7-fluoro-5-(4-(2-(3-hydroxyazetidin-1-yl)-2-oxoethyl)piperazin-1-yl)-2H-indazol-3-yl)amino)-4-(4-fluorophenyl)thiazole-5-carbonitrile

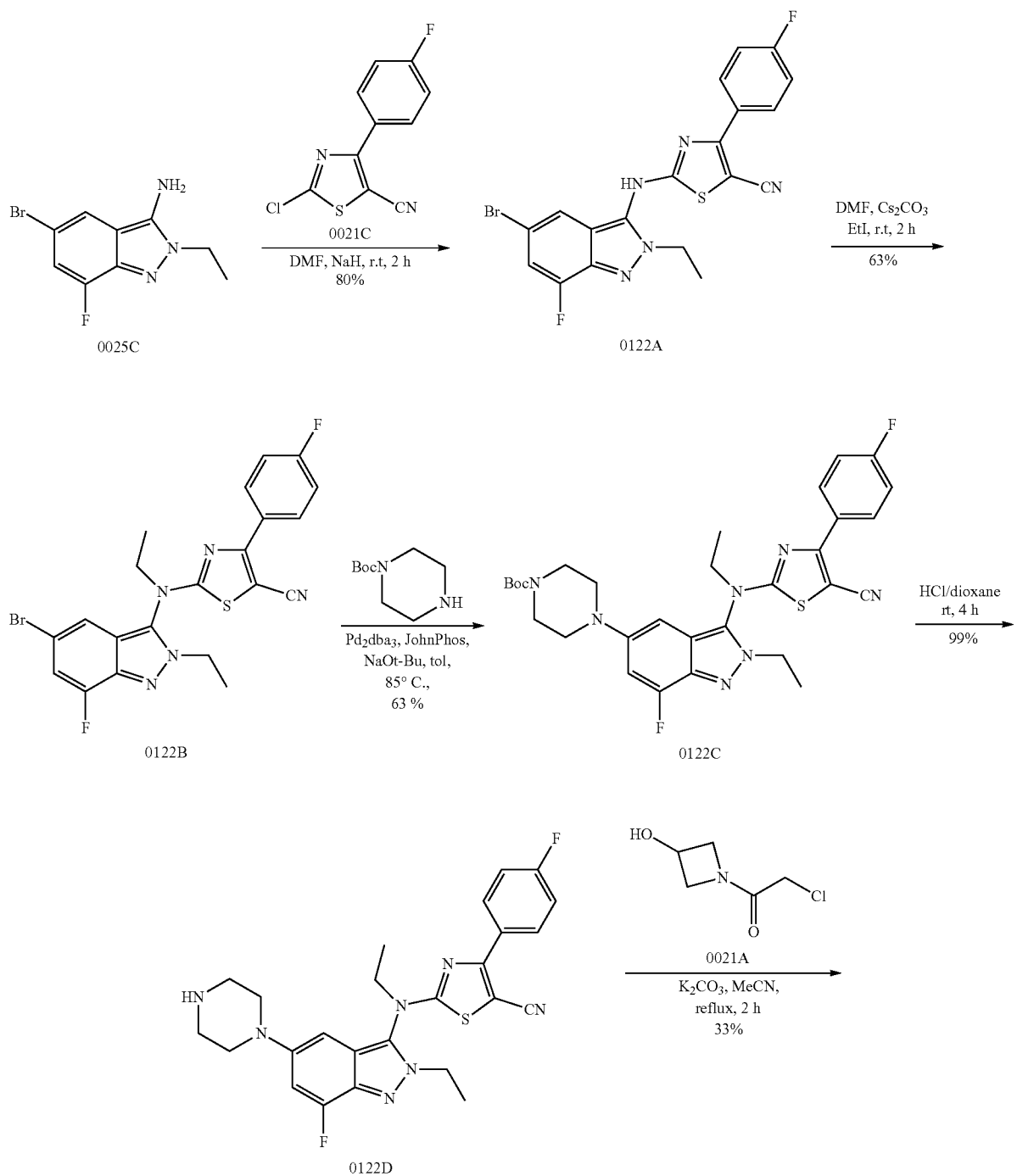

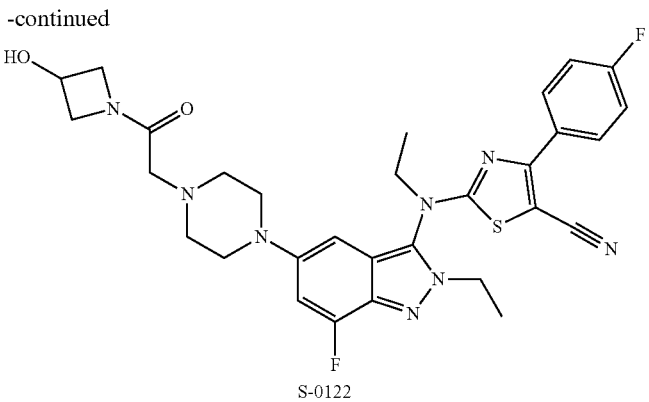

S-0122

Step 1: 2-(5-bromo-2-ethyl-7-fluoro-2H-indazol-3-ylamino)-4-(4-fluorophenyl)thiazole-5-carbonitrile Sodium hydride (60% in oil, 278 mg, 11.6 mmol) was added to a solution of 5-bromo-2-ethyl-7-fluoro-2H-indazol-3-amine 0025C (1 g, 3.89 mmol) in N,N-dimethylformamide (20 mL), and the mixture was stirred at room temperature for 15 min. 2-chloro-4-(4-fluorophenyl) thiazole-5-carbonitrile 0021C (111 mg, 0.433 mmol) was added and the mixture was stirred at room temperature for 16 h. The reaction was quenched by adding water (30 mL) and ethyl acetate (30 mL×5) was added for extraction. The organic phases were washed with saturated brine (10 mL×2), dried over anhydrous sodium sulfate, filtered and concentrated. The residue was purified by flash chromatography (ethyl acetate/petroleum ether=0-50%) to give 2-(5-bromo-2-ethyl-7-fluoro-2H-indazol-3-ylamino)-4-(4-fluorophenyl) thiazole-5-carbonitrile 0122A (1.0 g, 80%) in the form of a yellow solid. LCMS (ESI) [M+H]$^+$=460.0@1.71 min (Method B).

Step 2: 2-((5-bromo-2-ethyl-7-fluoro-2H-indazol-3-yl)(ethyl)amino)-4-(4-fluorophenyl) thiazole-5-carbonitrile Cesium carbonate (637 mg, 2.0 mmol) was added to a solution of 2-((5-bromo-2-ethyl-7-fluoro-2H-indazol-3-yl) amino)-4-(4-fluorophenyl)thiazole-5-carbonitrile 0122A (300 mg, 0.7 mmol) in N,N-dimethylformamide (10 mL) and the mixture was stirred at room temperature for 30 min. Then iodoethane (305 mg, 2.0 mmol) was added and the resulting mixture was stirred at room temperature for 2 h. The reaction was quenched by adding water (10 mL) and ethyl acetate (30 mL×2) was added for extraction. The organic phases were washed with saturated brine (30 mL×2), dried over anhydrous sodium sulfate, filtered and concentrated. The residue was purified by flash chromatography (ethyl acetate/petroleum ether=0-50%) to give 2-((5-bromo-2-ethyl-7-fluoro-2H-indazol-3-yl)(ethyl) amino)-4-(4-fluorophenyl)thiazole-5-carbonitrile 0122B (200 mg, 63%) in the form of a red solid. LCMS (ESI) [M+H]$^+$=488@1.96 min (Method B).

Step 3: tert-butyl 4-(3-((5-cyano-4-(4-fluorophenyl)thiazol-2-yl)(ethyl)amino)-2-ethyl-7-fluoro-2H-indazol-5-yl)piperazine-1-carboxylate In a glove box, 2-((5-bromo-2-ethyl-7-fluoro-2H-indazol-3-yl)(ethyl)amino)-4-(4-fluorophenyl)thiazole-5-carbonitrile 0122B (150 mg, 0.3 mmol), tert-butyl piperazine-1-carboxylate (285 mg, 1.5 mmol), tris(dibenzylideneacetone) dipalladium(0) (30 mg, 0.03 mmol), 2-(di-tert-butylphosphino)biphenyl (18 mg, 0.06 mmol), sodium tert-butoxide (90 mg, 0.9 mmol) and toluene (3 mL) were added to a microwave tube. The mixture was stirred at 85° C. for 1.5 h, and then cooled to room temperature. Ethyl acetate (20 mL×3) was added for extraction. The organic phases were washed with water (10 mL×2), dried over anhydrous sodium sulfate, filtered and concentrated. The residue was purified by flash chromatography (ethyl acetate/petroleum ether=0-50%) to give tert-butyl 4-(3-((5-cyano-4-(4-fluorophenyl)thiazol-2-yl)(ethyl)amino)-2-ethyl-7-fluoro-2H-indazol-5-yl)piperazine-1-carboxylate 0122C (152 mg, 63%) in the form of a red solid. LCMS (ESI) [M+H]$^+$=594.2 @2.31 min (Method A).

Step 4: 2-(ethyl(2-ethyl-7-fluoro-5-(piperazin-1-yl)-2H-indazol-3-yl)amino)-4-(4-fluorophenyl)thiazole-5-carbonitrile A mixture of tert-butyl 4-(3-((5-cyano-4-(4-fluorophenyl)thiazol-2-yl)(ethyl)amino)-2-ethyl-7-fluoro-2H-indazol-5-yl)piperazine-1-carboxylate 0122C (152 mg, 0.26 mmol) in hydrogen chloride (4 N in dioxane, 3 mL) was stirred at room temperature for 1 h, added with a sodium bicarbonate solution (10 mL) and then stirred. Dichloromethane (20 mL×3) was added for extraction. The organic phases were washed with saturated brine (10 mL×2), dried over anhydrous sodium sulfate, filtered and concentrated to give 2-(ethyl(2-ethyl-7-fluoro-5-(piperazin-1-yl)-2H-indazol-3-yl)amino)-4-(4-fluorophenyl)thiazole-5-carbonitrile 0122D (125 mg, 99%) in the form of a yellow solid. LCMS (ESI) [M+H]$^+$=494.2@2.09 min (Method B).

Step 5: 2-(ethyl(2-ethyl-7-fluoro-5-(4-(2-(3-hydroxyazetidin-1-yl)-2-oxoethyl)piperazin-1-yl)-2H-indazol-3-yl)amino)-4-(4-fluorophenyl)thiazole-5-carbonitrile 2-chloro-1-(3-hydroxyazetidin-1-yl)ethanone (57 mg, 0.38 mmol) and potassium carbonate (105 mg, 0.76 mmol) were added to a solution of 2-(ethyl(2-ethyl-7-fluoro-5-(piperazin-1-yl)-2H-indazol-3-yl)amino)-4-(4-fluorophenyl)thiazole-5-carbonitrile 0122D (125 mg, 0.25 mmol) in acetonitrile (3 mL). The mixture was stirred at reflux for 2 h. The reaction system was concentrated and the residue was purified by flash chromatography (methanol/dichloromethane=0-8%) to give 2-(ethyl(2-ethyl-7-fluoro-5-(4-(2-(3-hydroxyazetidin-1-yl)-2-oxoethyl)piperazin-1-yl)-2H-indazol-3-yl)amino)-4-(4-fluorophenyl) thiazole-5-carbonitrile S-0122 (51.6 mg, 33%) in the form of a white solid. LCMS (ESI) [M+H]$^+$=607.2@8.24 min(Method D); $^1$H NMR (400 MHz, CD$_3$OD) δ 8.13-8.17 (m, 2H), 7.24-7.29 (m, 2H), 7.02-7.06 (m, 1H), 6.51 (s, 1H), 4.42-4.58 (m, 3H), 4.33-4.39 (m, 2H), 4.21-4.25 (m, 1H), 4.06-4.09 (m, 1H), 3.92-3.97 (m, 1H), 3.76-3.80 (m, 1H), 3.18-3.21 (m, 4H), 3.13 (s, 2H), 3.66-3.69 (m, 4H), 1.57-1.60 (m, 3H), 1.35-1.39 (m, 3H).
Example 40. S-0123: 4-(3,4-difluorophenyl)-2-(ethyl(2-ethyl-7-fluoro-5-(4-(2-(3-hydroxyazetidin-1-yl)-2-oxoethyl)piperazin-1-yl)-2H-indazol-3-yl)amino)thiazole-5-carbonitrile
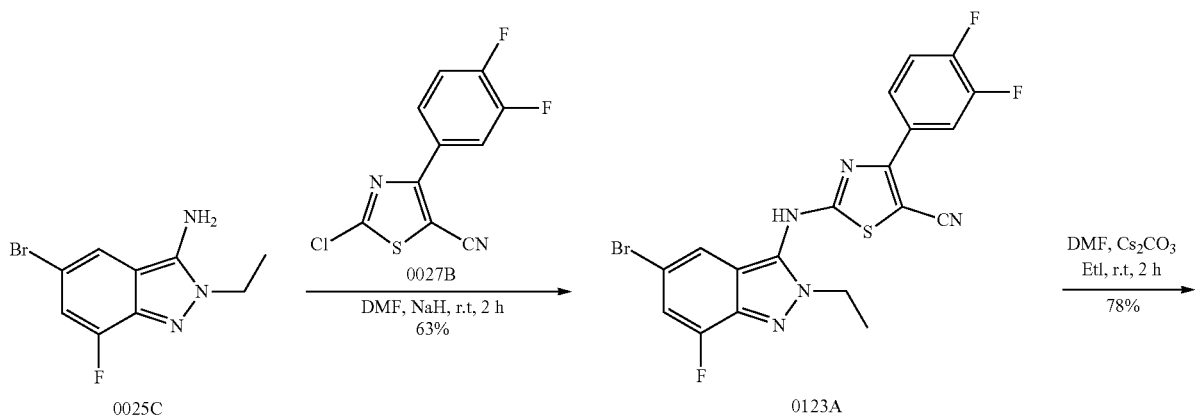
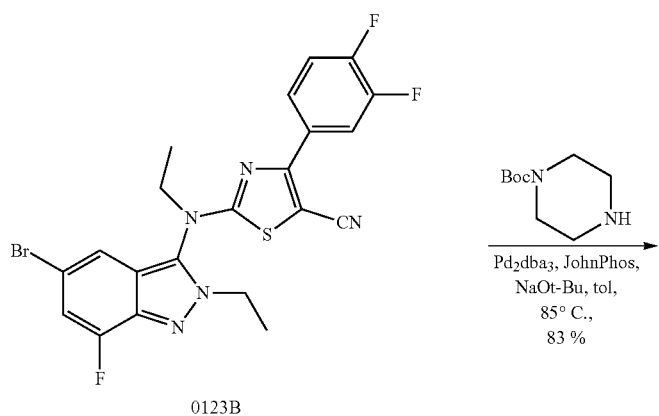
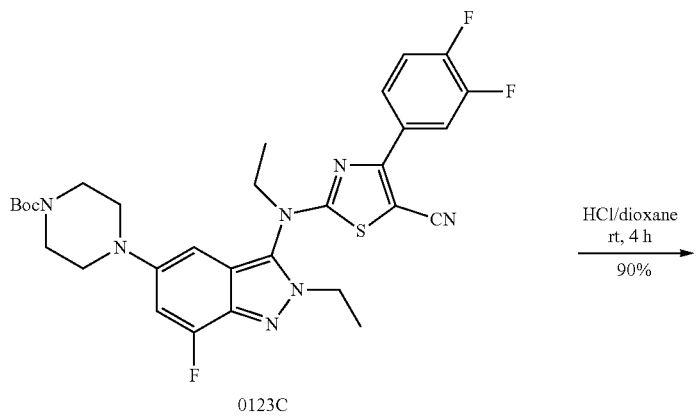

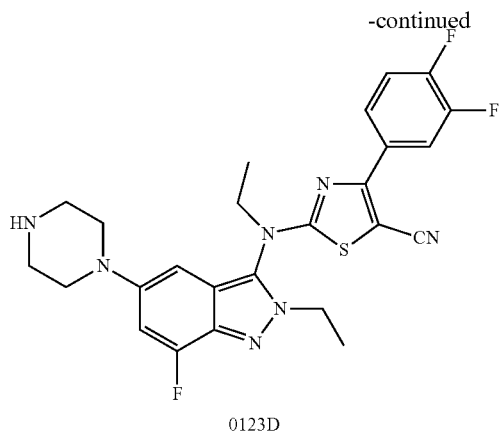

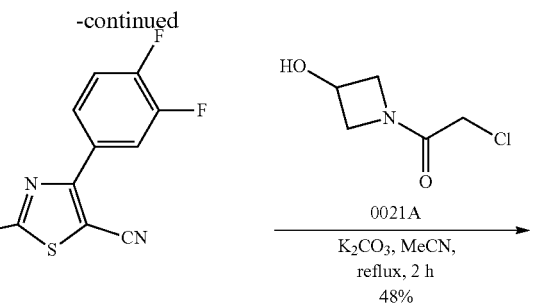

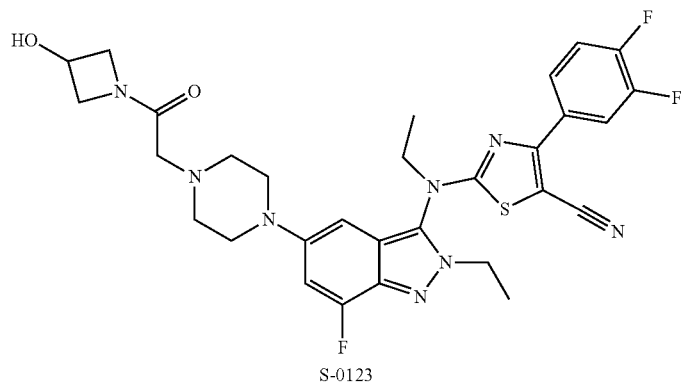

Step 1: 2-(5-bromo-2-ethyl-7-fluoro-2H-indazol-3-ylamino)-4-(3,4-difluorophenyl) thiazole-5-carbonitrile Sodium hydride (60% in oil, 74 mg, 3.112 mmol) was added to a solution of 5-bromo-2-ethyl-7-fluoro-2H-indazol-3-amine 0025C (200 mg, 0.778 mmol) in N,N-dimethylformamide (5 mL), and the mixture was stirred at room temperature for 15 min. 2-chloro-4-(3,4-difluorophenyl)thiazole-5-carbonitrile (258 mg, 1.011 mmol) was added and the resulting mixture was stirred at room temperature for 2 h. The reaction was quenched by adding water (30 mL), and ethyl acetate (30 mL×5) was added for extraction. The organic phases were washed with saturated brine (10 mL×2), dried over anhydrous sodium sulfate, filtered and concentrated. The residue was purified by flash chromatography (ethyl acetate/petroleum ether=0-50%) to give 2-(5-bromo-2-ethyl-7-fluoro-2H-indazol-3-ylamino)-4-(3,4-difluorophenyl)thiazole-5-carbonitrile 0123A (220 mg, 63%) in the form of a yellow solid. LCMS (ESI) [M+H]$^+$=478.0 @1.95 min (Method B).

Step 2: 2-((5-bromo-2-ethyl-7-fluoro-2H-indazol-3-yl)(ethyl)amino)-4-(3,4-difluorophenyl)thiazole-5-carbonitrile Cesium carbonate (350 mg, 1.38 mmol) was added to a solution of 2-(5-bromo-2-ethyl-7-fluoro-2H-indazol-3-ylamino)-4-(3,4-difluorophenyl)thiazole-5-carbonitrile 0123A (220 mg, 0.46 mmol) in N,N-dimethylformamide (10 mL). The mixture was stirred at room temperature for 30 min and then iodoethane (269 mg, 1.38 mmol) was added. The resulting mixture was stirred at room temperature for 2 h. The reaction was quenched by adding water (10 mL), and ethyl acetate (10 mL×3) was added for extraction. The organic phases were washed with saturated brine (10 mL×3), dried over anhydrous sodium sulfate, filtered and concentrated. The residue was purified by flash chromatography (ethyl acetate/petroleum ether=0-30%) to give 2-((5-bromo-2-ethyl-7-fluoro-2H-indazol-3-yl)(ethyl)amino)-4-(3,4-difluorophenyl) thiazole-5-carbonitrile 0123B (200 mg, 78%) in the form of a yellow solid. LCMS (ESI) [M+H]$^+$=506.0 @2.33 min (Method A).

Step 3: tert-butyl 4-(3-((5-cyano-4-(3,4-difluorophenyl)thiazol-2-yl)(ethyl)amino)-2-ethyl-7-fluoro-2H-indazol-5-yl)piperazine-1-carboxylate In a glove box, 2-((5-bromo-2-ethyl-7-fluoro-2H-indazol-3-yl)(ethyl)amino)-4-(3,4-difluorophenyl)thiazole-5-carbonitrile 0123B (190 mg, 0.376 mmol), tert-butyl piperazine-1-carboxylate (699 mg, 3.76 mmol), tris (dibenzylideneacetone)dipalladium(0) (34 mg, 0.038 mmol), 2-(di-tert-butylphosphino)biphenyl (22 mg, 0.072 mmol), sodium tert-butoxide (110 mg, 1.128 mmol) and toluene (3 mL) were added to a microwave tube. The reaction system was stirred at 85° C. for 1.5 h and then cooled to room temperature. Ethyl acetate (20 mL×3) was added for extraction. The organic phases were washed with water (10 mL×2), dried over anhydrous sodium sulfate, filtered and concentrated. The residue was purified by flash chromatography (ethyl acetate/petroleum ether=0-30%) to give tert-butyl 4-(3-((5-cyano-4-(3,4-difluorophenyl)thiazol-2-yl)(ethyl)amino)-2-ethyl-7-fluoro-2H-indazol-5-yl) piperazine-1-carboxylate 0123C (190 mg, 83%) in the form of a yellow solid. LCMS (ESI) [M+H]$^+$=612.3 @2.66 min (LC-MS Method B).

Step 4: 4-(3,4-difluorophenyl)-2-(ethyl(2-ethyl-7-fluoro-5-(piperazin-1-yl)-2H-indazol-3-yl)amino)thiazole-5-carbonitrile A solution of tert-butyl 4-(3-((5-cyano-4-(3,4-difluorophenyl)thiazol-2-yl)(ethyl)amino)-2-ethyl-7-fluoro-2H-indazol-5-yl)piperazine-1-carboxylate 0123C (190 mg, 0.311 mmol) in hydrogen chloride (4 N in dioxane, 5 mL) was stirred at room temperature for 1 h. A sodium bicarbonate solution (20 mL) was added, and dichloromethane (20 mL×3) was added for extraction. The organic phases were washed with saturated brine (10 mL×2), dried over anhydrous sodium sulfate, filtered and concentrated to give 4-(3,4-difluorophenyl)-2-(ethyl (2-ethyl-7-fluoro-5-(piperazin-1-yl)-2H-indazol-3-yl)amino)thiazole-5-carbonitrile 0123D (150 mg, 90%) in the form of a yellow solid. LCMS (ESI) [M+H]$^+$=512.1 @2.13 min (LC-MS Method B).

Step 5: 4-(3,4-difluorophenyl)-2-(ethyl(2-ethyl-7-fluoro-5-(4-(2-(3-hydroxyazetidin-1-yl)-2-oxoethyl)piperazin-1-yl)-2H-indazol-3-yl)amino)thiazole-5-carbonitrile 2-chloro-1-(3-hydroxyazetidin-1-yl)ethanone (65 mg, 0.44 mmol) and potassium carbonate (121 mg, 0.882 mmol) were added to a solution of 4-(3,4-difluorophenyl)-2-(ethyl(2-ethyl-7-fluoro-5-(piperazin-1-yl)-2H-indazol-3-yl)amino)thiazole-5-carbonitrile 0123D (150 mg, 0.294 mmol) in acetonitrile (4 mL). The mixture was stirred at reflux for 2 h. The reaction system was concentrated and the residue was purified by flash chromatography (methanol/dichloromethane=0-6%) to give 4-(3,4-difluorophenyl)-2-(ethyl(2-ethyl-7-fluoro-5-(4-(2-(3-hydroxyazetidin-1-yl)-2-oxoethyl)piperazin-1-yl)-2H-indazol-3-yl)amino)thiazole-5-carbo nitrile S-0123 (82 mg, 48%) in the form of a white solid. LCMS (ESI) [M+H]$^+$=625.0@8.44 min (Method D); $^1$H NMR (400 MHz, CD$_3$OD) δ 8.08-7.91 (m, 2H), 7.44 (dd, J=18.7, 8.4 Hz, 1H), 7.11-6.99 (m, 1H), 6.52 (d, J=1.5 Hz, 1H), 4.73-4.29 (m, 3H), 4.23 (dd, J=10.4, 6.9 Hz, 3H), 4.09 (d, J=4.2 Hz, 2H), 3.98 (ddd, J=21.4, 20.8, 5.3 Hz, 2H), 3.16 (dt, J=18.5, 9.8 Hz, 6H), 2.76-2.61 (m, 4H), 1.59 (t, J=7.3 Hz, 3H), 1.43-1.18 (m, 3H).

Example 41. S-0124: 2-(ethyl(2-ethyl-5-(4-(2-(3-hydroxyazetidin-1-yl)-2-oxoethyl) piperazin-1-yl)-7-methyl-2H-pyrazolo[4,3-b]pyridin-3-yl)amino)-4-(4-fluorophenyl) thiazole-5-carbonitrile

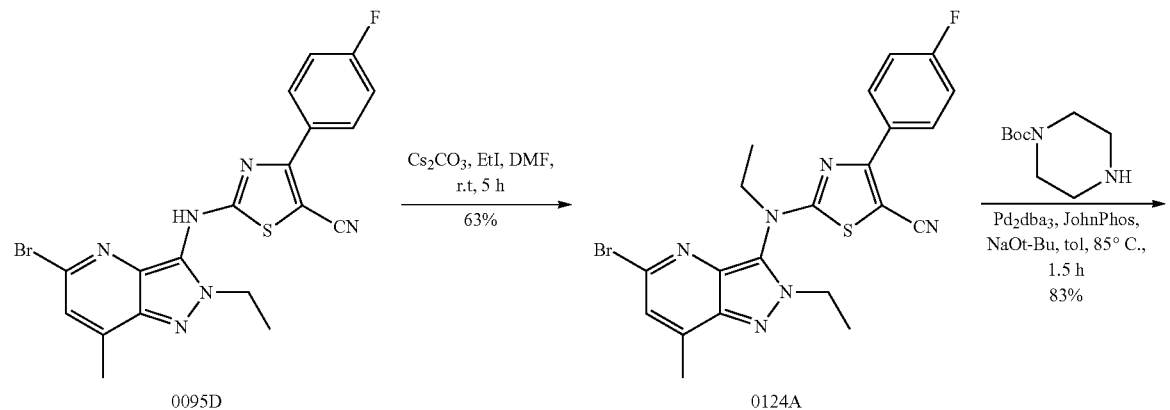

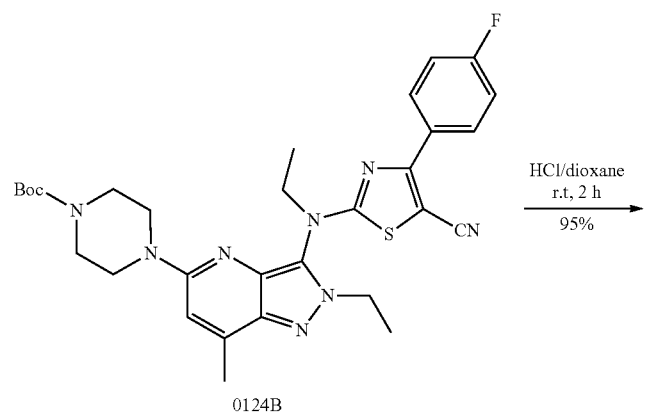

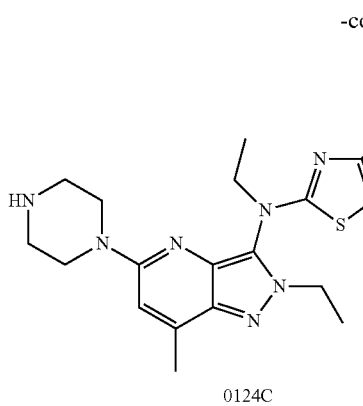

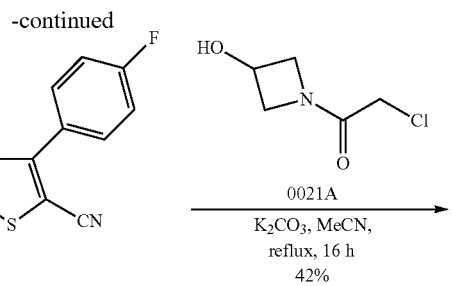

0124C

K₂CO₃, MeCN,
reflux, 16 h
42%

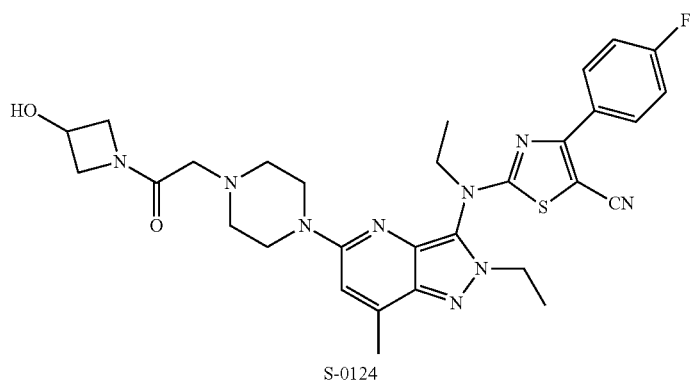

S-0124

Step 1: 2-((5-bromo-2-ethyl-7-methyl-2H-pyrrolo[4,3-b]pyridin-3-yl)(ethyl)amino)-4-(4-fluorophenyl)thiazole-5-carbonitrile Cesium carbonate (249 mg, 0.99 mmol) was added to a solution of 2-(5-bromo-2-ethyl-7-methyl-2H-pyrrolo[4,3-b]pyridin-3-ylamino)-4-(4-fluorophenyl)thiazole-5-carbonitrile 0095D (150 mg, 0.33 mmol) in N,N-dimethylformamide (3 mL). The mixture was stirred at room temperature for 30 min and then iodoethane (193 mg, 0.99 mmol) was added. The resulting mixture was stirred at room temperature for 2 h. The reaction was quenched by adding water (10 mL) and ethyl acetate (10 mL×3) was added for extraction. The organic phases were washed with saturated brine (10 mL×3), dried over anhydrous sodium sulfate, filtered and concentrated. The residue was purified by flash chromatography (ethyl acetate/petroleum ether=0-30%) to give 2-((5-bromo-2-ethyl-7-methyl-2H-pyrrolo[4,3-b]pyridin-3-yl)(ethyl)amino)-4-(4-fluorophenyl)thiazole-5-carbonitrile 0124A (100 mg, 63%) in the form of a yellow solid. LCMS (ESI) [M+H]⁺=485.0 @ 2.17 min (Method A).

Step 2: tert-butyl 4-(3-((5-cyano-4-(4-fluorophenyl)thiazol-2-yl)(ethyl)amino)-2-ethyl-7-methyl-2H-pyrrolo[4,3-b]pyridin-5-yl)piperazine-1-carboxylate In a glove box, 2-((5-bromo-2-ethyl-7-methyl-2H-pyrrolo[4,3-b]pyridin-3-yl)(methyl) amino)-4-(4-fluorophenyl)thiazole-5-carbonitrile 0124A (80 mg, 0.165 mmol), tris(dibenzylideneacetone)dipalladium(0) (15 mg, 0.017 mmol), tert-butylpiperazine-1-carboxylate (308 mg, 1.65 mmol), 2-(di-tert-butylphosphino)biphenyl (10 mg, 0.033 mmol), sodium tert-butoxide (49 mg, 0.50 mmol) and toluene (3 mL) were added to a sealed tube. The reaction system was stirred at 85° C. for 2 h, cooled to room temperature, and diluted by adding ethyl acetate (10 mL). The organic phases were washed with water (10 mL×3), dried over anhydrous sodium sulfate, filtered and concentrated. The residue was purified by flash chromatography (ethyl acetate/petroleum ether=0-25%) to give tert-butyl 4-(3-((5-cyano-4-(4-fluorophenyl)thiazol-2-yl)(ethyl)amino)-2-ethyl-7-methyl-2H-pyrrolo[4,3-b]pyridin-5-yl) piperazine-1-carboxylate 0124B (100 mg, 83%) in the form of a yellow solid. LCMS (ESI) [M+H]⁺=591.2 @2.66 min (Method B).

Step 3: 2-(ethyl(2-ethyl-7-methyl-5-(piperazin-1-yl)-2H-pyrrolo[4,3-b]pyridin-3-yl) amino)-4-(4-fluorophenyl)thiazole-5-carbonitrile A mixture of tert-butyl 4-(3-((5-cyano-4-(4-fluorophenyl)thiazol-2-yl)(ethyl)amino)-2-ethyl-7-methyl-2H-pyrrolo[4,3-b]pyridin-5-yl)piperazine-1-carboxylate 0124B (100 mg, 0.169 mmol) in hydrogen chloride (4 N in 1,4-dioxane, 3 mL) was stirred at room temperature for 1 h. The reaction system was concentrated. Aqueous sodium bicarbonate (5 mL) was added, and dichloromethane (5 mL×3) was added for extraction. The organic phases were washed with saturated brine (5 mL×3), dried over anhydrous sodium sulfate, filtered and concentrated to give 2-(ethyl(2-ethyl-7-methyl-5-(piperazin-1-yl)-2H-pyrrolo[4,3-b]pyridin-3-yl)amino)-4-(4-fluorophenyl)thiazole-5-carbonitrile 0124C (80 mg, 95%) in the form of a yellow solid. LCMS (ESI) [M+H]⁺=491.1 @1.50 min (Method A).

Step 4: 2-(ethyl(2-ethyl-5-(4-(2-(3-hydroxyazetidin-1-yl)-2-oxoethyl)piperazin-1-yl)-7-methyl-2H-pyrazolo[4,3-b]pyridin-3-yl)amino)-4-(4-fluorophenyl)thiazole-5-carbonitrile A solution of 2-(ethyl(2-ethyl-7-methyl-5-(piperazin-1-yl)-2H-pyrrolo[4,3-b]pyridin-3-yl) amino)-4-(4-fluorophenyl)thiazole-5-carbonitrile 0124C (80 mg, 0.163 mmol), 2-chloro-1-(3-hydroxyazetidin-1-yl)ethanone (36 mg, 0.245 mmol) and potassium carbonate (67 mg, 0.489 mmol) in acetonitrile (3 mL) was stirred at reflux for 2 h. The reaction system was concentrated and the residue was purified by flash chromatography (methanol/dichloromethane=0-15%) to give 2-(ethyl(2-ethyl-5-(4-(2-(3-hydroxyazetidin-1-yl)-2-oxoethyl)piperazin-1-yl)-7-methyl-2H-pyrazolo[4,3-b]pyridin-3-yl)amino)-4-(4-fluorophenyl)thiazole-5-carbonitrile S-0124 (40 mg, 42%) in the form of a yellow solid. LCMS (ESI) [M+H]$^+$=604.0@8.36 min (Method D); $^1$H NMR (400 MHz, CD$_3$OD) δ 8.14 (dd, J=8.8, 5.3 Hz, 2H), 7.26 (t, J=8.8 Hz, 2H), 6.96 (s, 1H), 4.90-4.41 (m, 2H), 4.41-4.14 (m, 5H), 4.14-3.99 (m, 2H), 3.24-2.96 (m, 2H), 2.67-2.54 (m, 7H), 1.61-1.46 (m, 3H), 1.44-1.07 (m, 3H).

Example 42. S-0125: 2-((7-fluoro-5-(4-(2-(3-hydroxyazetidin-1-yl)-2-oxoethyl) piperazin-1-yl)-2-isopropyl-2H-indazol-3-yl)(methyl)amino)-4-(4-fluorophenyl)thiazole-5-carbonitrile

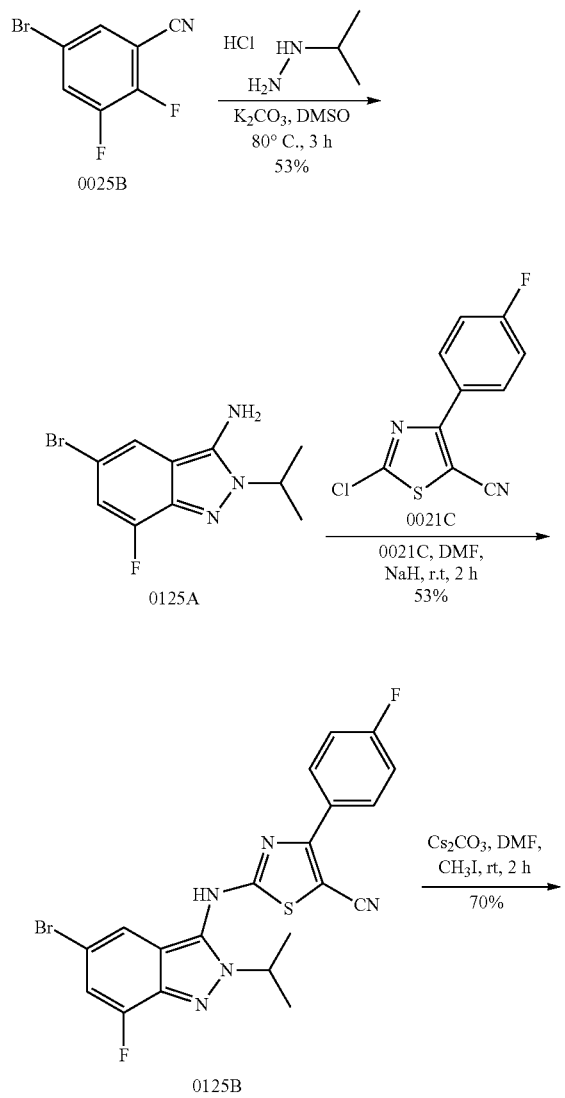

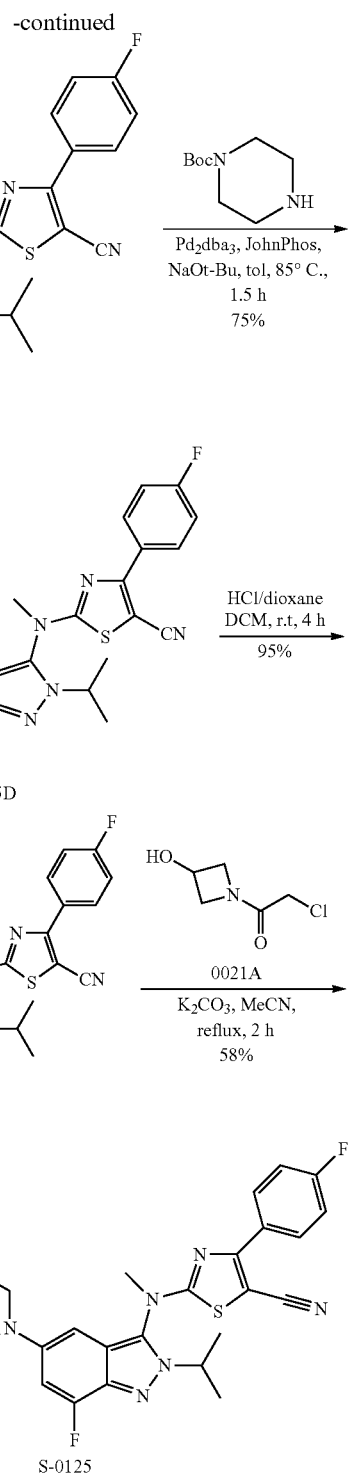

Step 1: 5-bromo-7-fluoro-2-isopropyl-2H-indazol-3-amine

Potassium carbonate (3.8 g, 27.6 mmol) was added to a solution of 5-bromo-2,3-difluorobenzonitrile 0025B (1.2 g, 5.53 mmol) and isopropylhydrazine hydrochloride (3.0 g, 27.6 mmol) in dimethyl sulfoxide (15 mL). The reaction system was stirred at 80° C. for 3 h and cooled to room temperature. Ethyl acetate (100 mL×3) was added for extraction. The organic phases were combined, washed with saturated brine (50 mL×3), dried over anhydrous sodium sulfate, filtered and concentrated. The residue was purified by flash chromatography (ethyl acetate/petroleum ether=0-60%) to give 5-bromo-7-fluoro-2-isopropyl-2H-indazol-3-amine 0125A (800 mg, 53%) in the form of a yellow solid. LCMS (ESI) [M+H]$^+$=272.1@1.56 min (Method A).

Step 2: 2-(5-bromo-7-fluoro-2-isopropyl-2H-indazol-3-ylamino)-4-(4-fluorophenyl) thiazole-5-carbonitrile Sodium hydride (60% in mineral oil, 142 mg, 5.90 mmol) was slowly added to a solution of 5-bromo-7-fluoro-2-isopropyl-2H-indazol-3-amine 0125A (400 mg, 1.47 mmol) in N,N-dimethylformamide (4 mL). The mixture was stirred at room temperature for 10 min. 2-chloro-4-(4-fluorophenyl)thiazole-5-carbonitrile (454 mg, 1.91 mmol) was added and the resulting mixture was stirred at room temperature for 2 h. The reaction was quenched by adding water (30 mL), and ethyl acetate (10 mL×3) was added for extraction. The organic phases were combined, washed with saturated brine (10 mL×3), dried over anhydrous sodium sulfate, filtered and concentrated. The residue was purified by flash chromatography (ethyl acetate/petroleum ether=0-35%) to give 2-(5-bromo-7-fluoro-2-isopropyl-2H-indazol-3-ylamino)-4-(4-fluorophenyl)thiazole-5-carbonitrile 0125B (370 mg, 53%) in the form of a yellow solid. LCMS (ESI) [M+H]$^+$=473.0@2.03 min (Method A).

Step 3: 2-((5-bromo-7-fluoro-2-isopropyl-2H-indazol-3-yl)(methyl)amino)-4-(4-fluorophenyl)thiazole-5-carbonitrile Cesium carbonate (409 mg, 1.26 mmol) was added to a solution of 2-(5-bromo-7-fluoro-2-isopropyl-2H-indazol-3-ylamino)-4-(4-fluorophenyl)thiazole-5-carbonitrile 0125B (200 mg, 0.42 mmol) in N,N-dimethylformamide (3 mL), and the mixture was stirred at room temperature for 30 min. Then methyl iodide (60 mg, 0.42 mmol) was added, and the resulting mixture was stirred at room temperature for 2 h. The reaction was quenched by adding water (10 mL), and ethyl acetate (10 mL×3) was added for extraction. The organic phases were combined, washed with saturated brine (10 mL×3), dried over anhydrous sodium sulfate, filtered and concentrated. The residue was purified by flash chromatography (ethyl acetate/petroleum ether=0-30%) to give 2-((5-bromo-7-fluoro-2-isopropyl-2H-indazol-3-yl)(methyl)amino)-4-(4-fluorophenyl)thiazole-5-carbonitrile 0125C (130 mg, 70%) in the form of a yellow solid. LCMS (ESI) [M+H]$^+$=488.0@2.12 min (Method A).

Step 4: tert-butyl 4-(3-((5-cyano-4-(4-fluorophenyl)thiazol-2-yl)(methyl)amino)-7-fluoro-2-isopropyl-2H-indazol-5-yl)piperazine-1-carboxylate In a glove box, 2-((5-bromo-7-fluoro-2-isopropyl-2H-indazol-3-yl)(methyl)amino)-4-(4-fluorophenyl)thiazole-5-carbonitrile 0125C (130 mg, 0.267 mmol), tris(dibenzylideneacetone)dipalladium(0) (24 mg, 0.027 mmol), tert-butyl piperazine-1-carboxylate (496 mg, 2.67 mmol), 2-(di-tert-butylphosphino)biphenyl (16 mg, 0.054 mmol), sodium tert-butoxide (78 mg, 0.801 mmol) and toluene (3 mL) were mixed in a sealed tube. The reaction system was stirred at 85° C. for 2 h, cooled to room temperature, and diluted by adding ethyl acetate (10 mL). The organic phases were washed with water (10 mL×3), dried over anhydrous sodium sulfate, filtered and concentrated. The residue was purified by flash chromatography (ethyl acetate/petroleum ether=0-25%) to give tert-butyl 4-(3-((5-cyano-4-(4-fluorophenyl)thiazol-2-yl)(methyl)amino)-7-fluoro-2-isopropyl-2H-indazol-5-yl)piperazine-1-carboxylate 0125D (110 mg, 75%) in the form of a yellow solid. LCMS (ESI) [M+H]$^+$=594.2.@2.09 min (Method A).

Step 5: 2-((7-fluoro-2-isopropyl-5-(piperazin-1-yl)-2H-indazol-3-yl)(methyl)amino)-4-(4-fluorophenyl)thiazole-5-carbonitrile A mixture of tert-butyl 4-(3-((5-cyano-4-(4-fluorophenyl)thiazol-2-yl)(methyl)amino)-7-fluoro-2-isopropyl-2H-indazol-5-yl)piperazine-1-carboxylate 0125D (110 mg, 0.185 mmol) in hydrogen chloride (4 N in dioxane, 3 mL) was stirred at room temperature for 1 h and then concentrated. A sodium carbonate solution (5 mL) was added and dichloromethane (5 mL×3) was added for extraction. The organic phases were combined, washed with saturated brine (4 mL×3), dried over sodium sulfate, filtered and concentrated to give 2-((7-fluoro-2-isopropyl-5-(piperazin-1-yl)-2H-indazol-3-yl)(methyl)amino)-4-(4-fluorophenyl)thiazole-5-carbonitrile 0125E (86 mg, 95%) in the form of a yellow solid. LCMS (ESI) [M+H]$^+$=494.2.@2.10 min (Method B).

Step 6: 2-((7-fluoro-5-(4-(2-(3-hydroxyazetidin-1-yl)-2-oxoethyl)piperazin-1-yl)-2-isopropyl-2H-indazol-3-yl)(methyl)amino)-4-(4-fluorophenyl)thiazole-5-carbonitrile A solution of 2-((7-fluoro-2-isopropyl-5-(piperazin-1-yl)-2H-indazol-3-yl)(methyl) amino)-4-(4-fluorophenyl)thiazole-5-carbonitrile 0125E (86 mg, 0.174 mmol), 2-chloro-1-(3-hydroxyazetidin-1-yl)ethanone (38 mg, 0.261 mmol) and potassium carbonate (72 mg, 0.522 mmol) in acetonitrile (3 mL) was stirred at reflux for 2 h. The reaction system was concentrated and the residue was purified by flash chromatography (methanol/dichloromethane=0-15%) to give 2-((7-fluoro-5-(4-(2-(3-hydroxyazetidin-1-yl)-2-oxoethyl) piperazin-1-yl)-2-isopropyl-2H-indazol-3-yl)(methyl)amino)-4-(4-fluorophenyl)thiazole-5-carbonitrile S-0125 (62 mg, 58%) in the form of a yellow solid. LCMS (ESI) [M+H]$^+$=607.0@8.37 min (Method D); $^1$H NMR (400 MHz, CD$_3$OD) δ 8.15 (dd, J=8.5, 5.5 Hz, 2H), 7.26 (t, J=8.7 Hz, 2H), 7.03 (d, J=14.1 Hz, 1H), 6.55 (s, 1H), 4.85-4.42 (m, 3H), 4.23 (dd, J=10.4, 6.8 Hz, 1H), 4.07 (dd, J=9.6, 3.9 Hz, 1H), 3.80-3.76 (m, 1H), 3.71 (s, 3H), 3.27-3.11 (m, 6H), 2.66-2.68 (m, 4H), 1.63-1.59 (m, 6H).

Example 43. S-0126: 2-((2-cyclopropyl-7-fluoro-5-(4-(2-(3-hydroxyazetidin-1-yl)-2-oxoethyl)piperazin-1-yl)-2H-indazol-3-yl)(methyl)amino)-4-(4-fluorophenyl)thiazole-5-carbonitrile

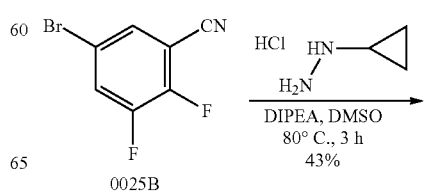

255
-continued

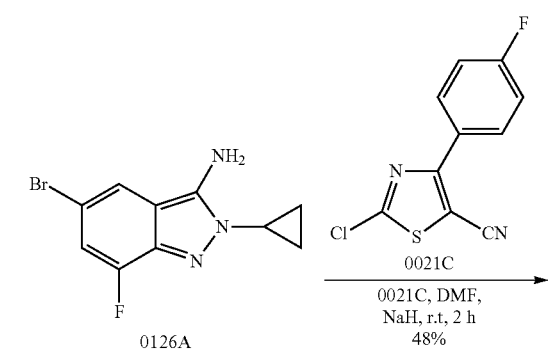

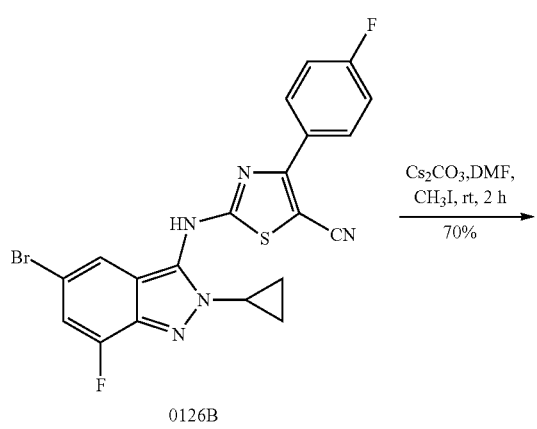

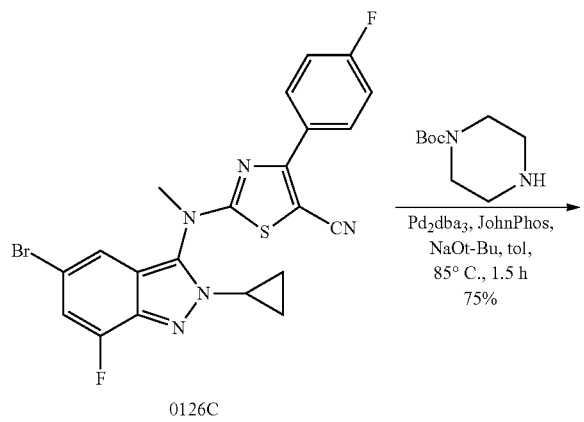

256
-continued

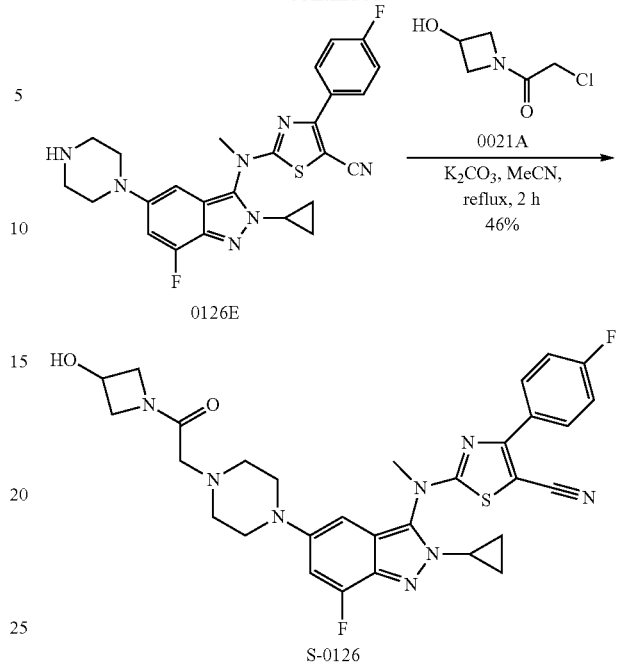

Step 1:
5-bromo-2-cyclopropyl-7-fluoro-2H-indazol-3-amine

N,N-diisopropylethylamine (2.7 g, 27.6 mmol) was added to a solution of 5-bromo-2,3-difluorobenzonitrile 0025B (1.2 g, 5.53 mmol) and cyclopropylhydrazine hydrochloride (2.9 g, 27.6 mmol) in dimethyl sulfoxide (15 mL). The mixture was stirred at 80° C. for 3 h and cooled to room temperature. Ethyl acetate (100 mL×3) was added for extraction. The organic phases were combined, washed with saturated brine (50 mL×3), dried over sodium sulfate, filtered and concentrated. The residue was purified by flash chromatography (ethyl acetate/petroleum ether=0-60%) to give 5-bromo-2-cyclopropyl-7-fluoro-2H-indazol-3-amine 0126A (700 mg, 43%) in the form of a yellow solid. LCMS (ESI) $[M+H]^+$=270.0@1.59 min (Method B).

Step 2: 2-(5-bromo-2-cyclopropyl-7-fluoro-2H-indazol-3-ylamino)-4-(4-fluorophenyl) thiazole-5-carbonitrile Sodium hydride (60% in oil, 89 mg, 3.72 mmol) was slowly added to a solution of 5-bromo-2-cyclopropyl-7-fluoro-2H-indazol-3-amine 0126A (200 mg, 0.74 mmol) in N,N-dimethylformamide (4 mL), and the mixture was stirred at room temperature for 10 min. 2-chloro-4-(4-fluorophenyl)thiazole-5-carbonitrile (229 mg, 0.96 mmol) was added and the resulting mixture was stirred at room temperature for 2 h. The reaction was quenched by adding ice water (10 mL) and ethyl acetate (10 mL×3) was added for extraction. The organic phases were combined, washed with saturated brine (10 mL×3), dried over anhydrous sodium sulfate, filtered and concentrated. The residue was purified by flash chromatography (ethyl acetate/petroleum ether=0-35%) to give 2-(5-bromo-2-cyclopropyl-7-fluoro-2H-indazol-3-ylamino)-4-(4-fluorophenyl)thiazole-5-carbonitrile 0126B (168 mg, 48%) in the form of a yellow solid. LCMS (ESI) $[M+H]^+$=472.0@2.26 min (Method A).

Step 3: 2-((5-bromo-2-cyclopropyl-7-fluoro-2H-indazol-3-yl)(methyl)amino)-4-(4-fluorophenyl)thiazole-5-carbonitrile Cesium carbonate (347 mg, 1.06 mmol) was added to a solution of 2-(5-bromo-2-cyclopropyl-7-fluoro-2H-indazol-3-ylamino)-4-(4-fluorohenyl)thiazole-5-carbonitrile 0126B (168 mg, 0.35 mmol) in N,N-dimethylformamide (3 mL), and the mixture was stirred at room temperature for 30 min. Then methyl iodide (49 mg, 0.35 mmol) was added, and the resulting mixture was stirred at room temperature for 2 h. The reaction was quenched by adding water (10 mL) and ethyl acetate (10 mL×3) was added for extraction. The organic phases were combined, washed with saturated brine (10 mL×3), dried over anhydrous sodium sulfate, filtered and concentrated. The residue was purified by flash chromatography (ethyl acetate/petroleum ether=0-30%) to give 2-((5-bromo-2-cyclopropyl-7-fluoro-2H-indazol-3-yl)(methyl)amino)-4-(4-fluorophenyl)thiazole-5-carbonitrile 0126C (120 mg, 70%) in the form of a yellow solid. LCMS (ESI) $[M+H]^+$=486.0@2.35 min (Method A).

Step 4: tert-butyl 4-(3-((5-cyano-4-(4-fluorophenyl)thiazol-2-yl)(methyl)amino)-2-cyclopropyl-7-fluoro-2H-indazol-5-yl)piperazine-1-carboxylate In a glove box, 2-((5-bromo-2-cyclopropyl-7-fluoro-2H-indazol-3-yl)(methyl)amino)-4-(4-fluorophenyl)thiazole-5-carbonitrile 0126C (120 mg, 0.247 mmol), tris(dibenzylideneacetone)dipalladium(0) (23 mg, 0.025 mmol), tert-butylpiperazine-1-carboxylate (461 mg, 2.47 mmol), 2-(di-tert-butylphosphino)biphenyl (15 mg, 0.050 mmol), sodium tert-butoxide (72 mg, 0.741 mmol) and toluene (3 mL) were mixed in a sealed tube. The reaction system was stirred at 85° C. for 2 h, cooled to room temperature and diluted by adding ethyl acetate (10 mL). The organic phases were washed with water (10 mL×3), dried over anhydrous sodium sulfate, filtered and concentrated. The residue was purified by flash chromatography (ethyl acetate/petroleum ether=0-25%) to give tert-butyl 4-(3-((5-cyano-4-(4-fluorophenyl)thiazol-2-yl)(methyl)amino)-2-cyclopropyl-7-fluoro-2H-indazol-5-yl) piperazine-1-carboxylate 0126D (110 mg, 75%) in the form of a yellow solid. LCMS (ESI) $[M+H]^+$=592.2.@2.43 min (Method B).

Step 5: 2-((2-cyclopropyl-7-fluoro-5-(piperazin-1-yl)-2H-indazol-3-yl)(methyl)amino)-4-(4-fluorophenyl)thiazole-5-carbonitrile A mixture of tert-butyl 4-(3-((5-cyano-4-(4-fluorophenyl)thiazol-2-yl)(methyl)amino)-2-cyclopropyl-7-fluoro-2H-indazol-5-yl)piperazine-1-carboxylate 0126D (110 mg, 0.22 mmol) in hydrogen chloride (4 N in dioxane, 3 mL) was stirred at room temperature for 1 h and then concentrated. A sodium carbonate solution (5 mL) was added, and dichloromethane (5 mL×3) was added for extraction. The organic phases were combined, washed with saturated brine (4 mL×3), dried over sodium sulfate, filtered and concentrated to give 2-((2-cyclopropyl-7-fluoro-5-(piperazin-1-yl)-2H-indazol-3-yl)(methyl)amino)-4-(4-fluorophenyl)thiazole-5-carbonitrile 0126E (82 mg, 90%) in the form of a yellow solid. LCMS (ESI) $[M+H]^+$=492.1.@1.48 min (Method A).

Step 6: 2-((2-cyclopropyl-7-fluoro-5-(4-(2-(3-hydroxyazetidin-1-yl)-2-oxoethyl) piperazin-1-yl)-2H-indazol-3-yl)(methyl)amino)-4-(4-fluorophenyl)thiazole-5-carbonitrile A solution of 2-((2-cyclopropyl-7-fluoro-5-(piperazin-1-yl)-2H-indazol-3-yl)(methyl) amino)-4-(4-fluorophenyl)thiazole-5-carbonitrile 0126E (82 mg, 0.167 mmol), 2-chloro-1-(3-hydroxyazetidin-1-yl)ethanone (37 mg, 0.250 mmol) and potassium carbonate (69 mg, 0.501 mmol) in acetonitrile (3 mL) was stirred at reflux for 2 h. The reaction system was concentrated and the residue was purified by flash chromatography (methanol/dichloromethane=0-15%) to give 2-((2-cyclopropyl-7-fluoro-5-(4-(2-(3-hydroxyazetidin-1-yl)-2-oxoethyl) piperazin-1-yl)-2H-indazol-3-yl)(methyl)amino)-4-(4-fluorophenyl)thiazole-5-carbonitrile S-0126 (46 mg, 46%) in the form of a yellow solid. LCMS (ESI) $[M+H]^+$=605.0@5.99 min (Method C); $^1$H NMR (400 MHz, CD$_3$OD) δ 8.16 (dd, J=8.6, 5.4 Hz, 2H), 7.27 (t, J=8.7 Hz, 2H), 7.02 (d, J=14.0 Hz, 1H), 6.54 (s, 1H), 4.55 (ddd, J=30.0, 12.4, 5.6 Hz, 2H), 4.23 (dd, J=10.1, 7.0 Hz, 1H), 4.08 (dd, J=9.6, 3.9 Hz, 1H), 3.91-3.74 (m, 2H), 3.33 (s, 3H), 3.28-3.13 (m, 6H), 2.68-2.66 (m, 4H), 1.36-1.33 (m, 4H).

Example 44. S-0128: 2-((2-ethyl-5-(4-(2-(3-hydroxyazetidin-1-yl)-2-oxoethyl) piperazin-1-yl)-1-methyl-1H-pyrrolo[3,2-b]pyridin-3-yl)(methyl) amino)-4-(4-fluorophenyl)thiazole-5-carbonitrile

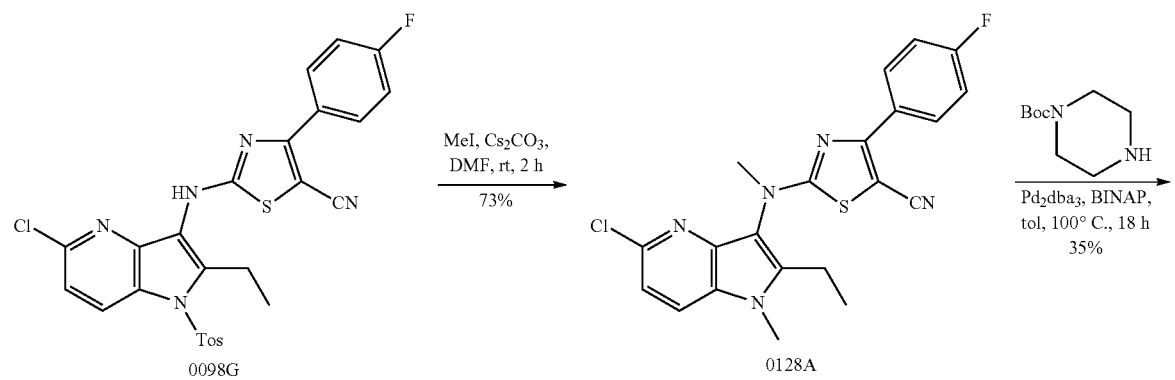

-continued

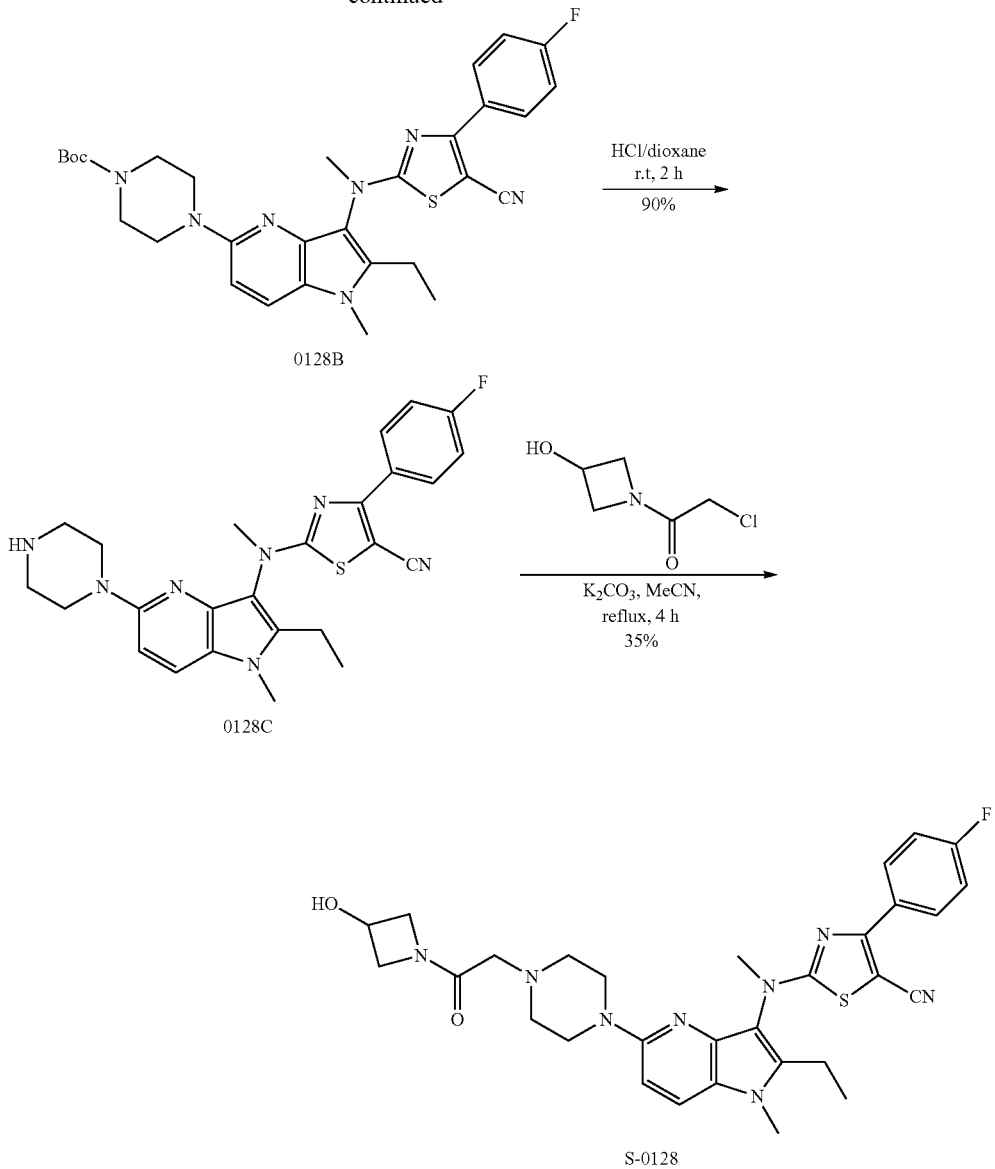

Step 1: 2-((5-chloro-2-ethyl-1-methyl-1H-pyrrolo[3,2-b]pyridin-3-yl)(methyl)amino)-4-(4-fluorophenyl)thiazole-5-carbonitrile A mixture of 2-(5-chloro-2-ethyl-1-tosyl-1H-pyrrolo[3,2-b]pyridin-3-ylamino)-4-(4-fluorophenyl)thiazole-5-carbonitrile 0098G (600 mg, 1.17 mmol), methyl iodide (332 mg, 2.34 mmol) and cesium carbonate (760 mg, 2.34 mmol) in N,N-dimethylformamide (3 mL) was stirred for 1 h at room temperature. The reaction was quenched by adding water and ethyl acetate (20 mL×3) was added for extraction. Organic phases were dried over anhydrous sodium sulfate, filtered and concentrated. The residue was purified by flash chromatography (ethyl acetate/petroleum ether=0-40%) to give 2-((5-chloro-2-ethyl-1-methyl-1H-pyrrolo [3,2-b]pyridin-3-yl)(methyl)amino)-4-(4-fluorophenyl)thiazole-5-carbonitrile 0128A (340 mg, 73%). LCMS (ESI) [M+H]$^+$=426.1 @2.18 min (LC-MS Method A).

Step 2: tert-butyl 4-(3-((5-cyano-4-(4-fluorophenyl)thiazol-2-yl)(methyl)amino)-2-ethyl-1-methyl-1H-pyrrolo[3,2-b]pyridin-5-yl)piperazine-1-carboxylate A mixture of 2-((5-chloro-2-ethyl-1-methyl-1H-pyrrolo[3,2-b]pyridin-3-yl)(methyl) amino)-4-(4-fluorophenyl)thiazole-5-carbonitrile 0128A (340 mg, 0.80 mmol), tert-butyl piperazine-1-carboxylate (712 mg, 4.0 mmol), tris(dibenzylideneacetone)dipalladium(0) (73 mg, 0.08 mmol), (±)-2,2'-bis(diphenylphosphino)-1,1'-binaphthyl (99 mg, 0.16 mmol) and cesium carbonate (780 mg, 2.4 mmol) in toluene (5 mL) was stirred at 90° C. for 16 h under nitrogen atmosphere. The reaction system was concentrated and the residue was purified by flash chromatography (ethyl acetate/petroleum ether=10-35%) to give tert-butyl 4-(3-((5-cyano-4-(4-fluorophenyl)thiazol-2-yl)(methyl)amino)-2-ethyl-1-methyl-1H-pyrrolo[3,2-b]pyridin-5-yl)piperazine-1-carboxylate 0128B (160 mg, 35%) in the form of a yellow solid. LCMS (ESI) [M+H]$^+$=576.3 @2.11 min (LC-MS Method B).

Step 3: 2-((2-ethyl-1-methyl-5-(piperazin-1-yl)-1H-pyrrolo[3,2-b]pyridin-3-yl)(methyl) amino)-4-(4-fluorophenyl)thiazole-5-carbonitrile A mixture of tert-butyl 4-(3-((5-cyano-4-(4-fluorophenyl) thiazol-2-yl)(methyl)amino)-2-ethyl-1-methyl-1H-pyrrolo [3,2-b]pyridin-5-yl)piperazine-1-carboxylate 0128B (48 mg, 0.067 mmol) in hydrogen chloride (4 N in dioxane, 4 mL) was stirred at room temperature for 1 h. The reaction system was concentrated to give 2-((2-ethyl-1-methyl-5-(piperazin-1-yl)-1H-pyrrolo[3,2-b]pyridin-3-yl)(methyl) amino)-4-(4-fluorophenyl)thiazole-5-carbonitrile 0128C (120 mg, 90%) in the form of a yellow solid, which was directly used in the next step without purification. LCMS (ESI) [M+H]$^+$=476.2 @1.59 min (LC-MS Method A).

Step 4: 2-((2-ethyl-5-(4-(2-(3-hydroxyazetidin-1-yl)-2-oxoethyl)piperazin-1-yl)-1-methyl-1H-pyrrolo[3,2-b]pyridin-3-yl)(methyl)amino)-4-(4-fluorophenyl) thiazole-5-carbonitrile A mixture of 2-((2-ethyl-1-methyl-5-(piperazin-1-yl)-1H-pyrrolo[3,2-b]pyridin-3-yl) (methyl)amino)-4-(4-fluorophenyl)thiazole-5-carbonitrile 0128C (120 mg, 0.253 mmol), 2-chloro-1-(3-hydroxyazetidin-1-yl)ethanone (56 mg, 0.378 mmol) and potassium carbonate (104 mg, 0.759 mmol) in acetonitrile (2 mL) was stirred at reflux for 4 h. The mixture was concentrated and the residue was purified by flash chromatography (methanol/dichloromethane=0-15%) to give 2-((2-ethyl-5-(4-(2-(3-hydroxyazetidin-1-yl)-2-oxoethyl)piperazin-1-yl)-1-methyl-1H-pyrrolo[3,2-b]pyridin-3-yl)(methyl)amino)-4-(4-fluorophenyl)thiazole-5-carbonitrile S-0128 (52 mg, 35%) in the form of a white solid. LCMS (ESI) [M+H]$^+$=589.0@8.46 min (Method D); $^1$H NMR (400 MHz, CD$_3$OD) δ 8.05-8.02 (m, 2H), 7.62 (d, J=9.0 Hz, 1H), 7.14 (dd, J=12.2, 5.4 Hz, 2H), 6.69 (d, J=9.1 Hz, 1H), 4.48-4.37 (m, 2H), 4.12 (dd, J=10.0, 6.7 Hz, 2H), 4.00-3.58 (m, 7H), 3.42 (d, J=2.2 Hz, 4H), 3.21-2.84 (m, 2H), 2.81-2.65 (m, 6H), 1.26-1.14 (m, 3H).

Example 45. S-0129: 2-((2-ethyl-5-(4-(2-(3-hydroxyazetidin-1-yl)-2-oxoethyl) piperazin-1-yl) thieno[3,2-b]pyridin-3-yl)(methyl)amino)-4-(4-fluorophenyl)thiazole-5-carbonitrile

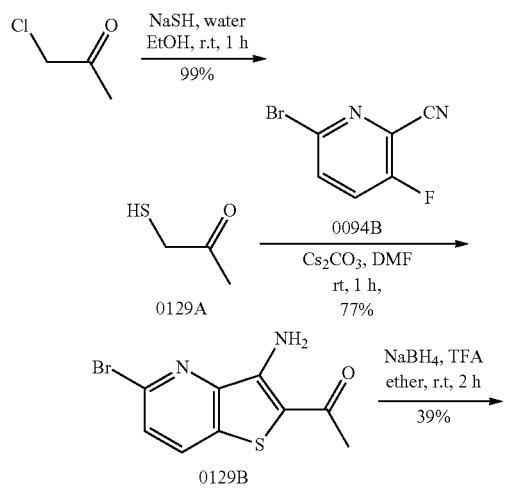

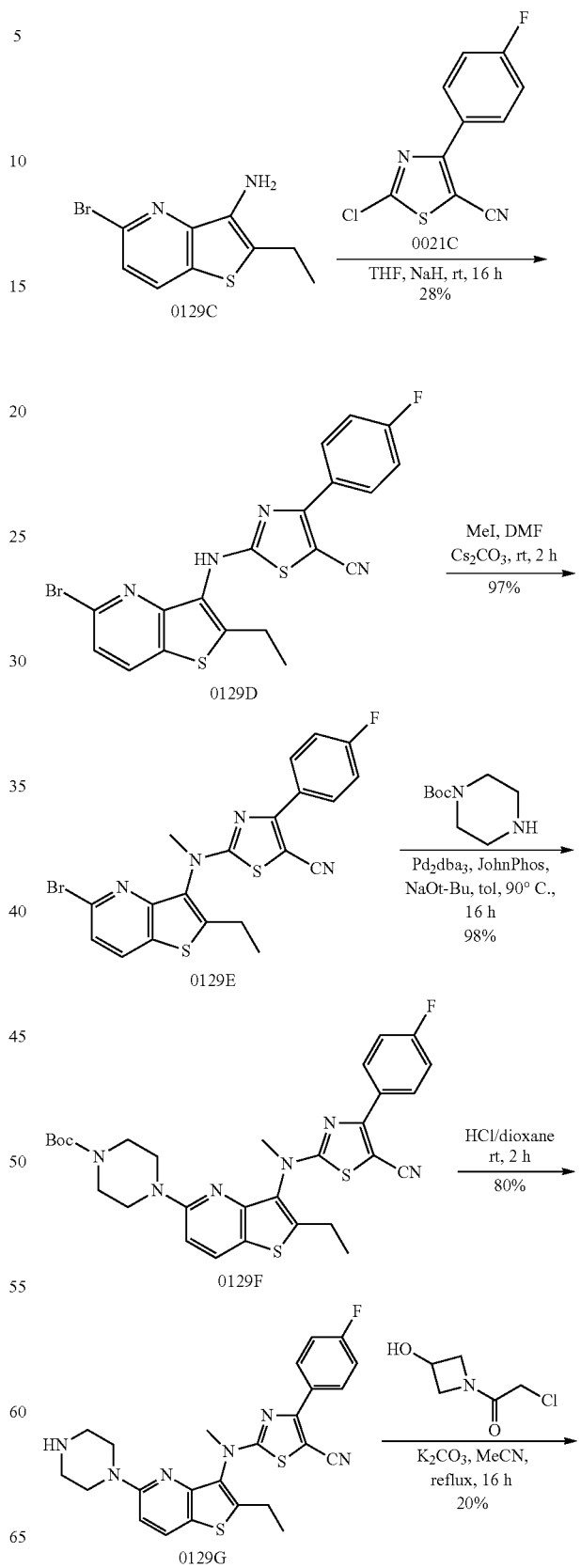

-continued

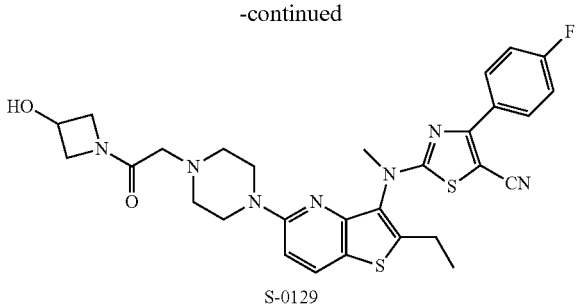

S-0129

Step 1: 1-mercaptopropan-2-one 1-chloropropan-2-one (92 mg, 1 mmol) was added to a solution of sodium hydrogensulfide (160 mg, 2 mmol, 70%) in ethanol (1 mL) and water (1 mL) at 10° C. The reaction system was stirred at 20° C. for 1 h. The reaction was quenched by adding water (20 mL) and dichloromethane (10 mL×3) was added for extraction. The organic phases were combined, washed with saturated brine (50 mL×3), dried over anhydrous sodium sulfate, filtered and concentrated to give 1-mercaptopropan-2-one 0129A (90 mg, 99%) in the form of a colorless oil, which was directly used in the next step. $^1$H NMR (400 MHz, CDCl$_3$) δ 3.31 (s, 2H), 2.28 (s, 3H).

Step 2: 1-(3-amino-5-bromothieno[3,2-b]pyridin-2-yl)ethanone

Cesium carbonate (3.25 g, 10 mmol) was added to a solution of 6-bromo-3-fluoropicolinonitrile 0094B (1 g, 5 mmol) and 1-mercaptopropan-2-one 0129A (0.45 g, 5 mmol) in N,N-dimethylformamide (15 mL). The reaction system was stirred at 25° C. for 2 h. The reaction was quenched by adding water (20 mL) and the mixture was stirred for 10 min. The reaction system was filtered and the filter cake was washed with water (20 mL). The filter cake was dried to give 1-(3-amino-5-bromothieno[3,2-b]pyridin-2-yl)ethanone 0129B (1.04 g, 77%) in the form of a yellow solid. LCMS (ESI) [M+H]$^+$=271.0@1.70 min (Method A).

Step 3: 5-bromo-2-ethylthieno[3,2-b]pyridin-3-amine

Sodium borohydride (111 mg, 3 mmol) was slowly added to a solution of 1-(3-amino-5-bromothieno[3,2-b]pyridin-2-yl)ethanone 0129B (270 mg, 1 mmol) in ether (10 mL). The mixture was stirred at room temperature for 30 min. Trifluoroacetic acid (342 mg, 3 mmol) was added and the resulting mixture was stirred at room temperature for 2 h. The reaction was quenched by adding ice water (10 mL) and ethyl acetate (10 mL×3) was added for extraction. The combined organic phases were washed with saturated brine (10 mL×3), dried over anhydrous sodium sulfate, filtered and concentrated. The residue was purified by flash chromatography (ethyl acetate/petroleum ether=0-35%) to give 5-bromo-2-ethylthieno[3,2-b]pyridin-3-amine 0129C (100 mg, 39%) in the form of a yellow solid. LCMS (ESI) [M+H]$^+$=257.0@1.93 min (Method B).

Step 4: 2-(5-bromo-2-ethylthieno[3,2-b]pyridin-3-ylamino)-4-(4-fluorophenyl)thiazole-5-carbonitrile Sodium hydride (60% in mineral oil, 47 mg, 1.17 mmol) was slowly added to a solution of 5-bromo-2-ethylthieno[3,2-b]pyridin-3-amine 0129C (100 mg, 0.39 mmol) in tetrahydrofuran (5 mL). The mixture was stirred at room temperature for 20 min. 2-chloro-4-(4-fluorophenyl)thiazole-5-carbonitrile (186 mg, 0.87 mmol) was added and the resulting mixture was stirred at room temperature for 16 h. The reaction was quenched by adding water (10 mL) and ethyl acetate (10 mL×3) was added for extraction. The organic phases were washed with saturated brine (10 mL×3), dried over anhydrous sodium sulfate, filtered and concentrated. The residue was purified by flash chromatography (ethyl acetate/petroleum ether=0-50%) to give 2-(5-bromo-2-ethylthieno[3,2-b]pyridin-3-ylamino)-4-(4-fluorophenyl)thiazole-5-carbonitrile 0129D (50 mg, 28%) in the form of a yellow solid. LCMS (ESI) [M+H]$^+$=459.0@2.27 min (Method B).

Step 5: 2-((5-bromo-2-ethylthieno[3,2-b]pyridin-3-yl)(methyl)amino)-4-(4-fluorophenyl) thiazole-5-carbonitrile Cesium carbonate (72 mg, 0.22 mmol) was added to a solution of 2-(5-bromo-2-ethylthieno[3,2-b]pyridin-3-ylamino)-4-(4-fluorophenyl)thiazole-5-carbonitrile 0129D (50 mg, 0.11 mmol) in N,N-dimethylformamide (2 mL). The mixture was stirred at room temperature for 30 min and then methyl iodide (19 mg, 0.13 mmol) was added. The resulting mixture was stirred at room temperature for 2 h. The reaction was quenched by adding water (10 mL) and ethyl acetate (10 mL×3) was added for extraction. The combined organic phases were washed with saturated brine (10 mL×3), dried over anhydrous sodium sulfate, filtered and concentrated. The residue was purified by flash chromatography (ethyl acetate/petroleum ether=0-30%) to give 2-((5-bromo-2-ethylthieno[3,2-b]pyridin-3-yl)(methyl)amino)-4-(4-fluorophenyl)thiazole-5-carbonitrile 0129E (50 mg, 97%) in the form of a yellow solid. LCMS (ESI) [M+H]$^+$=473.0@2.66 min (Method B).

Step 6: tert-butyl 4-(3-((5-cyano-4-(4-fluorophenyl)thiazol-2-yl)(methyl)amino)-2-ethylthieno[3,2-b]pyridin-5-yl)piperazine-1-carboxylate In a glove box, 2-((5-bromo-2-ethylthieno[3,2-b]pyridin-3-yl)(methyl)amino)-4-(4-fluorophenyl)thiazole-5-carbonitrile 0129E (50 mg, 0.1 mmol), tris(dibenzylideneacetone)dipalladium(0) (9 mg, 0.01 mmol), tert-butyl piperazine-1-carboxylate (99 mg, 0.52 mmol), 2-(di-tert-butylphosphino)biphenyl (6 mg, 0.02 mmol), sodium tert-butoxide (29 mg, 0.3 mmol) and toluene (3 mL) were mixed in a sealed tube. The reaction system was stirred at 90° C. for 16 h, cooled to room temperature and diluted by adding ethyl acetate (10 mL). The organic phases were washed with water (10 mL×3), dried over anhydrous sodium sulfate, filtered and concentrated. The residue was purified by flash chromatography (ethyl acetate/petroleum ether=0-35%) to give tert-butyl 4-(3-((5-cyano-4-(4-fluorophenyl)thiazol-2-yl)(methyl)amino)-2-ethylthieno[3,2-b]pyridin-5-yl)piperazine-1-carboxylate 0129F (60 mg, 98%) in the form of a yellow solid. LCMS (ESI) [M+H]$^+$=579.2.@2.51 min (Method A).

Step 7: 2-((2-ethyl-5-(piperazin-1-yl)thieno[3,2-b]pyridin-3-yl)(methyl)amino)-4-(4-fluorophenyl)thiazole-5-carbonitrile A mixture of tert-butyl 4-(3-((5-cyano-4-(4-fluorophenyl)thiazol-2-yl)(methyl)amino)-2-ethylthieno[3,2-b]pyridin-5- yl)piperazine-1-carboxylate 0129F (60 mg, 0.1 mmol) in hydrogen chloride (4 N in dioxane, 2 mL) was stirred at room temperature for 2 h and then concentrated. A sodium carbonate solution (5 mL) was added, and dichloromethane (5 mL×3) was added for extraction. The organic phases were combined, washed with saturated brine (4 mL×3), dried over anhydrous sodium sulfate, filtered and concentrated to give 2-((2-ethyl-5-(piperazin-1-yl)thieno[3,2-b]pyridin-3-yl)(methyl)amino)-4-(4-fluorophenyl)thiazole-5-carbonitrile 0129G (40 mg, 80%) in the form of a yellow solid. LCMS (ESI) [M+H]$^+$=479.0.@1.41 min (Method A).

Step 8: 2-((2-ethyl-5-(4-(2-(3-hydroxyazetidin-1-yl)-2-oxoethyl)piperazin-1-yl)thieno [3,2-b]pyridin-3-yl)(methyl)amino)-4-(4-fluorophenyl)thiazole-5-carbonitrile A solution of 2-((2-ethyl-5-(piperazin-1-yl)thieno[3,2-b]pyridin-3-yl)(methyl)amino)-4-(4-fluorophenyl)thiazole-5-carbonitrile 0129G (40 mg, 0.08 mmol), 2-chloro-1-(3-hydroxyazetidin-1-yl)ethanone (19 mg, 0.12 mmol) and potassium carbonate (33 mg, 0.24 mmol) in acetonitrile (5 mL) was stirred at reflux for 16 h. The reaction system was concentrated and the residue was purified by flash chromatography (methanol/dichloromethane=0-8%) to give 2-((2-ethyl-5-(4-(2-(3-hydroxyazetidin-1-yl)-2-oxoethyl)piperazin-1-yl) thieno[3,2-b]pyridin-3-yl)(methyl) amino)-4-(4-fluorophenyl)thiazole-5-carbonitrile S-0129 (10 mg, 20%) in the form of a yellow solid. LCMS (ESI) [M+H]$^+$=592.0@9.52 min (Method D); $^1$H NMR (400 MHz, CD$_3$OD) δ 813-8.16 (m, 2H), 7.99 (d, J=9.2 Hz, 1H), 7.24-7.28 (m, 2H), 6.93 (d, J=8.8 Hz, 1H), 4.46-4.59 (m, 2H), 4.20-4.24 (m, 1H), 4.03-4.08 (m, 1H), 3.76-3.79 (m, 1H), 3.67 (s, 3H), 3.58-3.63 (m, 4H), 3.13-3.15 (m, 2H), 2.94-2.99 (m, 2H), 2.55-2.60 (m, 4H), 1.39 (t, J=7.6 Hz, 3H).

Example 46. S-0131 (S-0131A and S-0131B): 2-((2-ethyl-7-fluoro-5-(4-(2-(3-hydroxyazetidin-1-yl)-2-oxoethyl)-2-(trifluoromethyl)piperazin-1-yl)-2H-indazol-3-yl) (methyl)amino)-4-(4-fluorophenyl) thiazole-5-carbonitrile

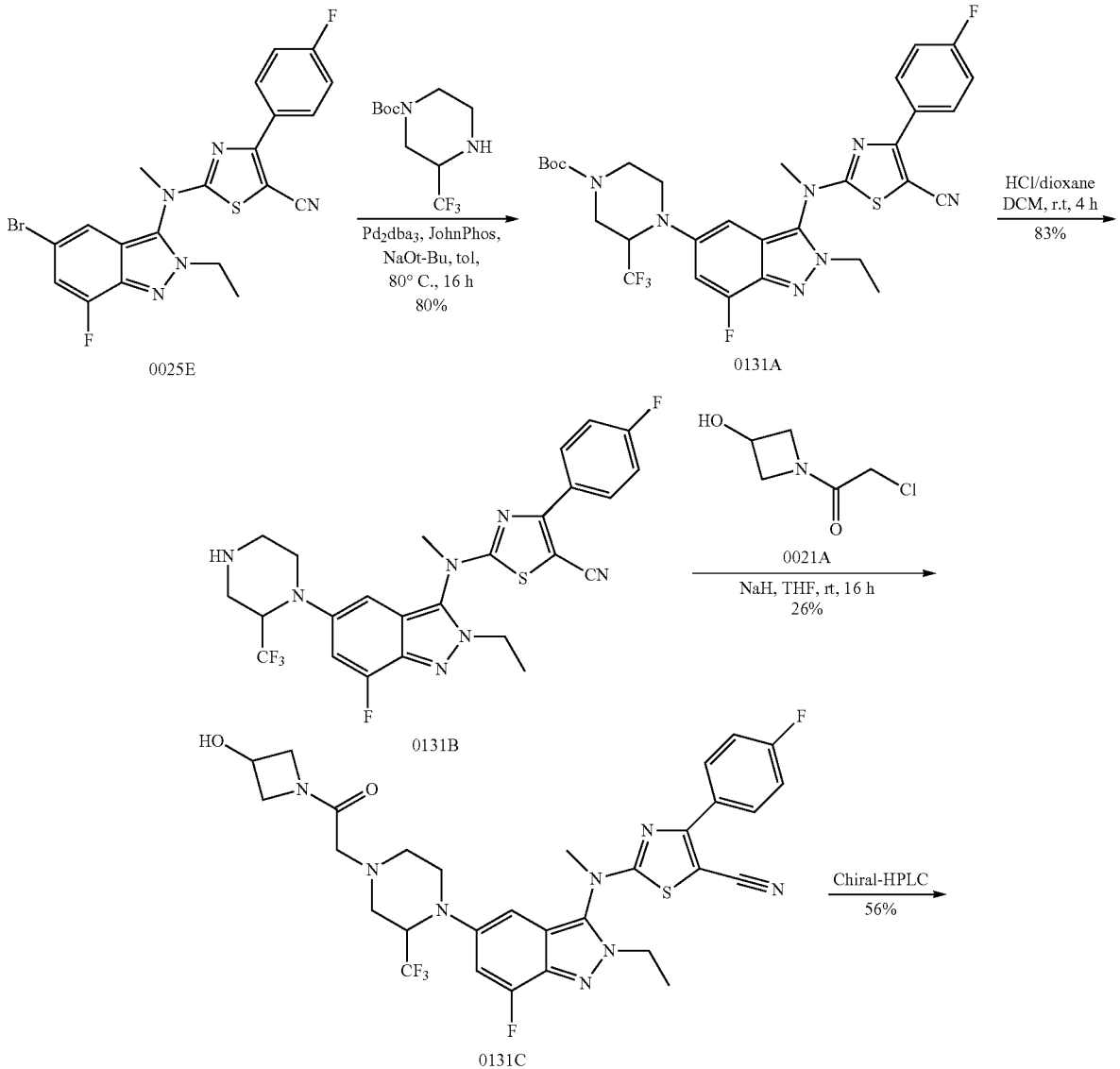

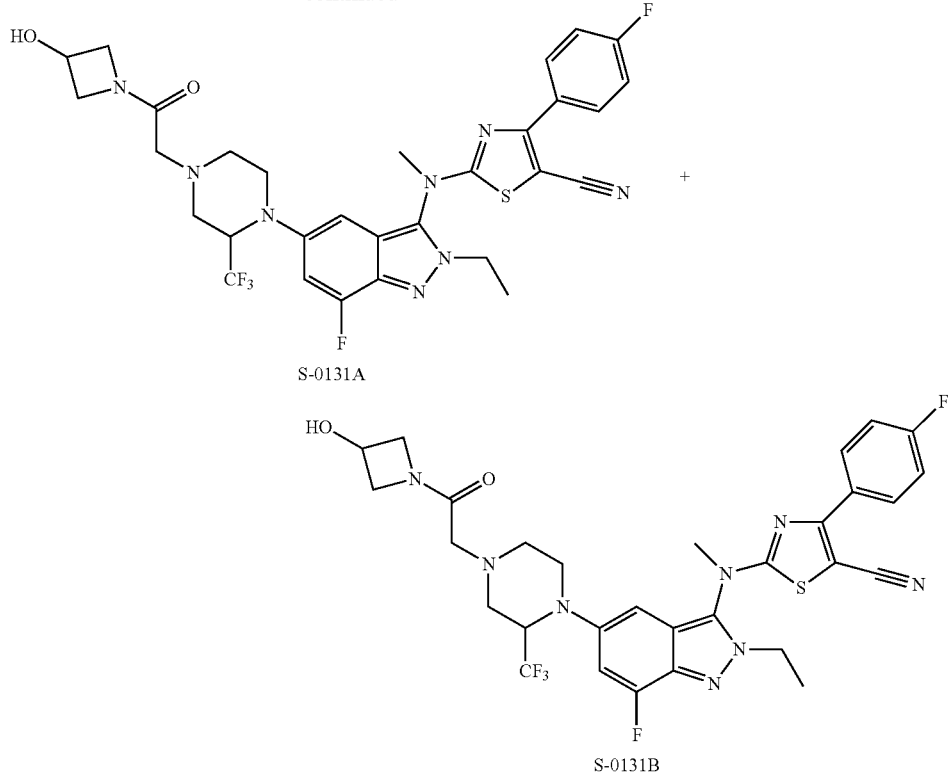

Step 1: tert-butyl 4-(3-((5-cyano-4-(4-fluorophenyl)thiazol-2-yl)(methyl)amino)-2-ethyl-7-fluoro-2H-indazol-5-yl)-3-(trifluoromethyl)piperazine-1-carboxylate In a glove box, 2-((5-bromo-2-ethyl-7-fluoro-2H-indazol-3-yl)(methyl)amino)-4-(4-fluorophenyl)thiazole-5-carbonitrile 0025E (100 mg, 0.211 mmol), tert-butyl 3-(trifluoromethyl)piperazine-1-carboxylate (80 mg, 0.361 mmol), tris(dibenzylideneacetone) dipalladium(0) (19 mg, 0.021 mmol), 2-(di-tert-butyl phosphine)biphenyl (13 mg, 0.042 mmol), sodium tert-butoxide (61 mg, 0.633 mmol) and toluene (3 mL) were added to a sealed tube. The reaction solution was heated to 80° C., stirred for 16 h, and then cooled to room temperature. The reaction solution was concentrated. The residue was purified by flash chromatography (ethyl acetate/petroleum ether=0-40%) to give tert-butyl 4-(3-((5-cyano-4-(4-fluorophenyl)thiazol-2-yl)(methyl)amino)-2-ethyl-7-fluoro-2H-indazol-5-yl)-3-(trifluoromethyl)piperazine-1-carboxylate 0131A (110 mg, 80%). LCMS (ESI) [M+H]$^+$=648.2@2.005 min (Method B).

Step 2: 2-((2-ethyl-7-fluoro-5-(2-(trifluoromethyl)piperazin-1-yl)-2H-indazol-3-yl) (methyl)amino)-4-(4-fluorophenyl)thiazole-5-carbonitrile A solution of tert-butyl 4-(3-((5-cyano-4-(4-fluorophenyl)thiazol-2-yl)(methyl)amino)-2-ethyl-7-fluoro-2H-indazol-5-yl)-3-(trifluoromethyl)piperazine-1-carboxylate 0131A (100 mg, 0.154 mmol) in hydrogen chloride (4 N in dioxane, 5 mL) was stirred at room temperature for 2 h and then concentrated. Aqueous sodium carbonate (20 mL) was added, and dichloromethane (20 mL×3) was added for extraction. The organic phases were combined, washed with saturated brine (10 mL×2), dried over anhydrous sodium sulfate, filtered and concentrated to give 2-((2-ethyl-7-fluoro-5-(2-(trifluoromethyl)piperazin-1-yl)-2H-indazol-3-yl)(methyl)amino)-4-(4-fluorophenyl)thiazole-5-carbonitrile 0131B (70 mg, 83%). LCMS (ESI) [M+H]$^+$=548.2@1.474 min (Method A).

Step 3: 2-((2-ethyl-7-fluoro-5-(4-(2-(3-hydroxyazetidin-1-yl)-2-oxoethyl)-2-(trifluoromethyl)piperazin-1-yl)-2H-indazol-3-yl)(methyl)amino)-4-(4-fluorophenyl)thiazole-5-carbonitrile A solution of 2-((2-ethyl-7-fluoro-5-(2-(trifluoromethyl)piperazin-1-yl)-2H-indazol-3-yl) (methyl)amino)-4-(4-fluorophenyl)thiazole-5-carbonitrile 0131B (80 mg, 0.146 mmol) and sodium hydride (60% in mineral oil, 12 mg, 0.292 mmol) in tetrahydrofuran (2 mL) was stirred at room temperature for 10 min. Then 2-bromo-1-(3-hydroxyazetidin-1-yl)ethanone (34 mg, 0.175 mmol) was added, and the mixture was stirred at room temperature for 16 h. The reaction was quenched with water (10 mL) and ethyl acetate (10 mL×3) was added for extraction. The organic phases were combined, washed with saturated brine (10 mL×2), dried over anhydrous sodium sulfate, filtered and concentrated. The residue was purified by flash chromatography (methanol/dichloromethane=0-8%) to give 2-((2-ethyl-7-fluoro-5-(4-(2-(3-hydroxyazetidin-1-yl)-2-oxoethyl)-2-(trifluoromethyl)piperazin-1-yl)-2H-indazol-3-yl) (methyl)amino)-4-(4-fluorophenyl)thiazole-5-carbonitrile 0131C (25 mg, 26%) in the form of a yellow solid. LCMS (ESI) [M+H]$^+$=661.2@ 1.978 min (Method B).

Step 4: (S)-2-((2-ethyl-7-fluoro-5-(4-(2-(3-hydroxyazetidin-1-yl)-2-oxoethyl)-2-(trifluoromethyl)piperazin-1-yl)-2H-indazol-3-yl)(methyl)amino)-4-(4-fluorophenyl)thiazole-5-carbonitrile and (R)-2-((2-ethyl-7-fluoro-5-(4-(2-(3-hydroxyazetidin-1-yl)-2-oxoethyl)-2-(trifluoromethyl)piperazin-1-yl)-2H-indazol-3-yl)(methyl)amino)-4-(4-fluorophenyl)thiazole-5-carbonitrile 2-((2-ethyl-7-fluoro-5-(4-(2-(3-hydroxyazetidin-1-yl)-2-oxoethyl)-2-(trifluoromethyl)piperazin-1-yl)-2H-indazol-3-yl)(methyl)amino)-4-(4-fluorophenyl)thiazole-5-carbonitrile 0131C (25 mg, 0.0378 mmol) was separated by chiral HPLC (column: AD-H, 4.6*100 mm, 5 μm; mobile phase: ethanol (containing 1% of a solution of ammonia in methanol)) to give 2-((2-ethyl-7-fluoro-5-(4-(2-(3-hydroxyazetidin-1-yl)-2-oxoethyl)-2-(trifluoromethyl)piperazin-1-yl)-2H-indazol-3-yl)(methyl)amino)-4-(4-fluorophenyl)thiazole-5-carbonitrile S-0131A (isomer-1) (7.0 mg, 35%) in the form of a white solid and 2-((2-ethyl-7-fluoro-5-(4-(2-(3-hydroxyazetidin-1-yl)-2-oxoethyl)-2-(trifluoromethyl)piperazin-1-yl)-2H-indazol-3-yl) (methyl)amino)-4-(4-fluorophenyl)thiazole-5-carbonitrile S-0131B (isomer-2) (7.0 mg, 35%) in the form of a white solid.

S-0131A (isomer-1): chiral HPLC: $t_R$=3.87 min, LCMS (ESI) [M+H]$^+$=661.2@8.460 min (Method D); $^1$H NMR (400 MHz, CD$_3$OD) δ 8.002 (m, 2H), 7.115 (t, 2H), 7.001 (m, 1H), 6.503 (d, J=4.8 Hz, 1H), 4.460 (m, 1H), 4.423 (m, 2H), 4.224 (m, 2H), 4.110 (m, 1H), 3.980 (m, 1H), 3.652 (m, 1H), 3.579 (m, 3H), 3.360 (m, 1H), 3.125 (m, 1H), 3.031 (m, 1H), 2.898 (m, 1H), 2.807 (d, J=10.4 Hz, 1H), 2.421 (m, 1H), 2.110 (m, 1H), 2.072 (m, 1H), 1.921 (m, 1H), 1.44 (t, 3H).

S-0131B (isomer-2): chiral HPLC: $t_R$=5.09 min, LCMS (ESI) [M+H]$^+$=661.2@8.459 min (Method D); $^1$H NMR (400 MHz, CD$_3$OD) δ 8.001 (m, 2H), 7.113 (t, 2H), 7.000 (m, 1H), 6.502 (d, J=4.8 Hz, 1H), 4.531 (m, 1H), 4.405 (m, 2H), 4.224 (m, 2H), 4.092 (m, 1H), 3.979 (m, 1H), 3.652 (m, 1H), 3.597 (m, 3H), 3.360 (m, 1H), 3.123 (m, 1H), 3.031 (m, 1H), 2.897 (m, 1H), 2.805 (d, J=10.4 Hz, 1H), 2.419 (m, 1H), 2.117 (m, 1H), 2.071 (m, 1H), 1.911 (m, 1H), 1.44 (t, 3H).

Example 47. S-0134 (S-0134A and S-0134B): 2-(ethyl(2-ethyl-7-fluoro-5-(4-(2-(3-hydroxyazetidin-1-yl)-2-oxoethyl)-2-(trifluoromethyl)piperazin-1-yl)-2H-indazol-3-yl)amino)-4-(4-fluorophenyl)thiazole-5-carbonitrile

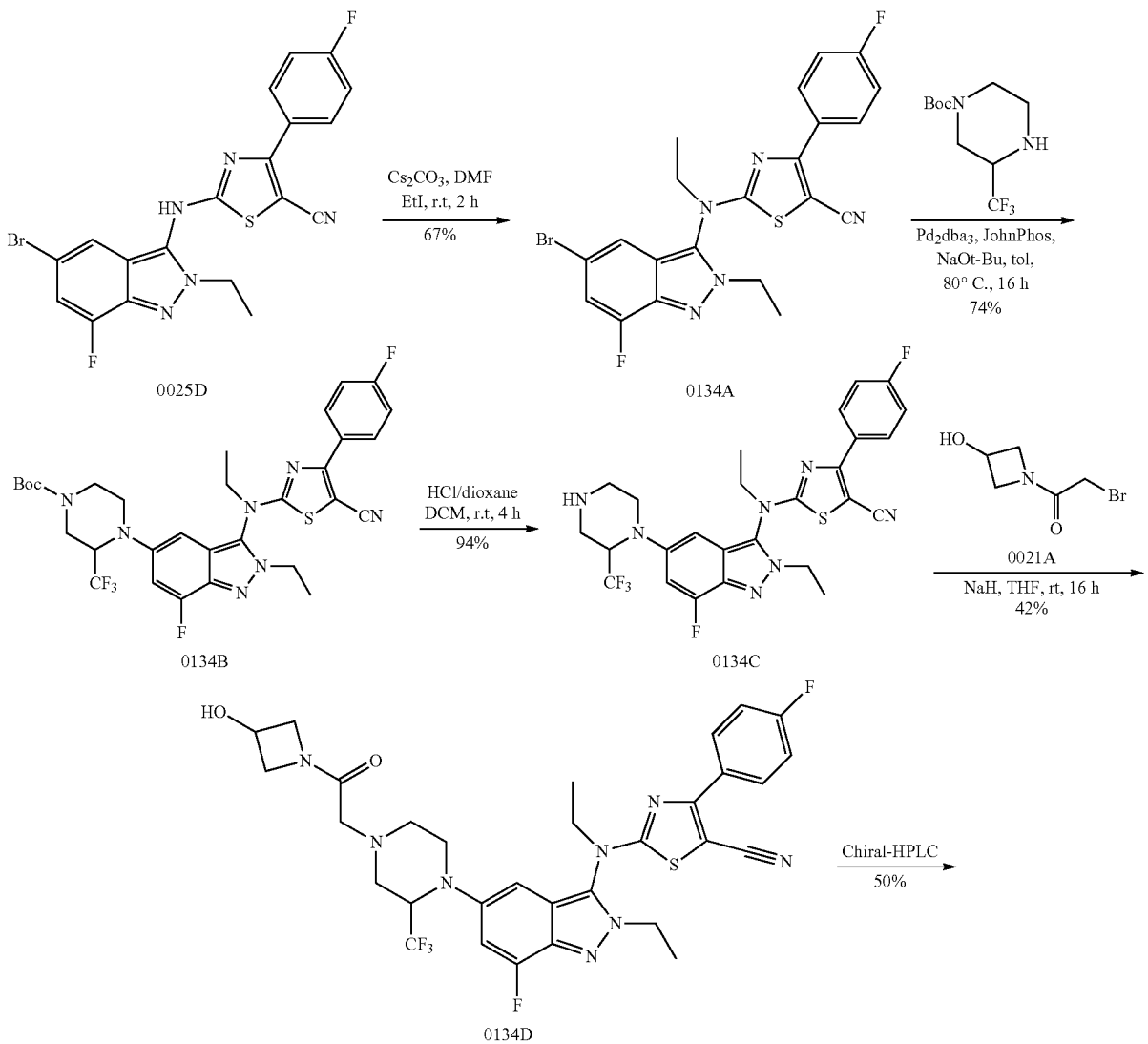

-continued

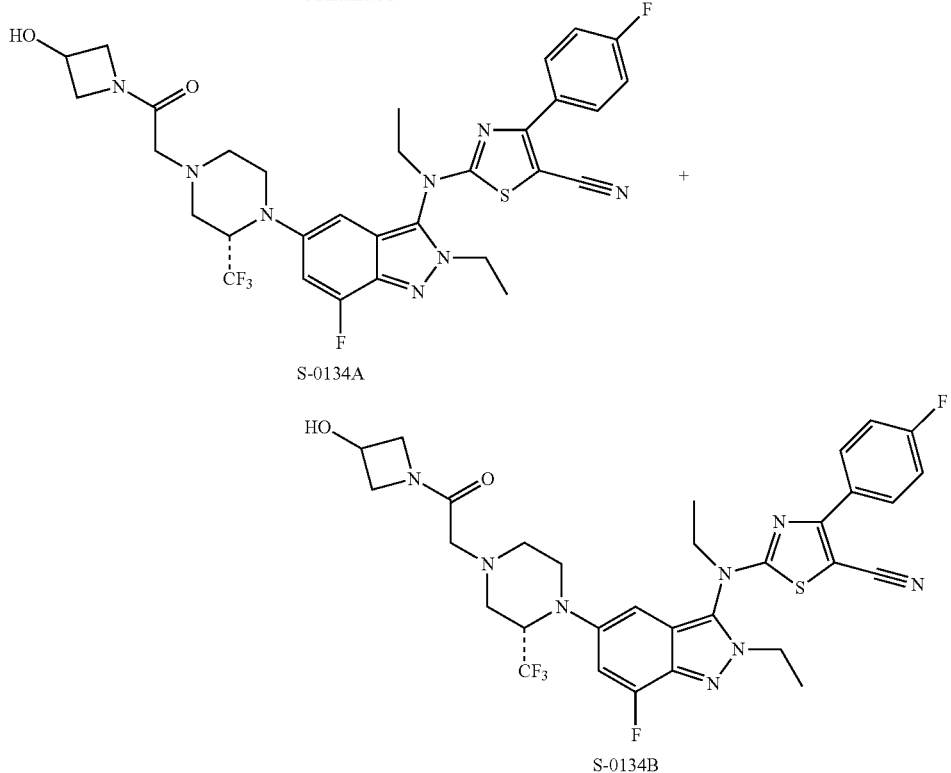

S-0134A

S-0134B

Step 1: 2-((5-bromo-2-ethyl-7-fluoro-2H-indazol-3-yl)(ethyl)amino)-4-(4-fluorophenyl) thiazole-5-carbonitrile Cesium carbonate (991 mg, 3.05 mmol) was added to a solution of 2-((5-bromo-2-ethyl-7-fluoro-2H-indazol-3-yl)amino)-4-(4-fluorophenyl)thiazole-5-carbonitrile 0025D (700 mg, 1.525 mmol) in N,N-dimethylformamide (15 mL), and the mixture was stirred at room temperature for 30 min. Then iodoethane (285 mg, 1.83 mmol) was added, and the resulting mixture was stirred at room temperature for 2 h. The reaction was quenched with water (50 mL) and ethyl acetate (50 mL×3) was added for extraction. The organic phases were combined, washed with saturated brine (50 mL×3), dried over anhydrous sodium sulfate, filtered and concentrated. The residue was purified by flash chromatography (ethyl acetate/petroleum ether=0-30%) to give 2-((5-bromo-2-ethyl-7-fluoro-2H-indazol-3-yl) (ethyl)amino)-4-(4-fluorophenyl)thiazole-5-carbonitrile 0134A (500 mg, 67%) in the form of a yellow solid. LCMS (ESI) [M+H]$^+$=488.0@ 2.13 min (Method A).

Step 2: tert-butyl 4-(3-((5-cyano-4-(4-fluorophenyl) thiazol-2-yl)(ethyl)amino)-2-ethyl-7-fluoro-2H-indazol-5-yl)-3-(trifluoromethyl)piperazine-1-carboxylate In a glove box, 2-((5-bromo-2-ethyl-7-fluoro-2H-indazol-3-yl)(ethyl) amino)-4-(4-fluorophenyl)thiazole-5-carbonitrile 0134A (100 mg, 0.205 mmol), tert-butyl 3-(trifluoromethyl)piperazine-1-carboxylate (78 mg, 0.308 mmol), tris (dibenzylideneacetone) dipalladium(0) (19 mg, 0.021 mmol), 2-(di-tert-butylphosphine)biphenyl (13 mg, 0.042 mmol), sodium tert-butoxide (59 mg, 0.615 mmol) and toluene (3 mL) were added to a sealed tube. The reaction solution was heated to 80° C., stirred for 16 h and then cooled to room temperature. The reaction solution was concentrated. The residue was purified by flash chromatography (ethyl acetate/petroleum ether=0-40%) to give tert-butyl 4-(3-((5-cyano-4-(4-fluorophenyl)thiazol-2-yl)(ethyl) amino)-2-ethyl-7-fluoro-2H-indazol-5-yl)-3-(trifluoromethyl)piperazine-1-carboxylate 0134B (100 mg, 74%). LCMS (ESI) [M+H]=662.2@1.711 min (Method A).

Step 3: 2-(ethyl(2-ethyl-7-fluoro-5-(2-(trifluoromethyl)piperazin-1-yl)-2H-indazol-3-yl) amino)-4-(4-fluorophenyl)thiazole-5-carbonitrile A solution of tert-butyl 4-(3-((5-cyano-4-(4-fluorophenyl) thiazol-2-yl)(ethyl)amino)-2-ethyl-7-fluoro-2H-indazol-5-yl)-3-(trifluoromethyl)piperazine-1-carboxylate 0134B (100 mg, 0.151 mmol) in hydrogen chloride (4 N in dioxane, 5 mL) was stirred at room temperature for 2 h and then concentrated. Aqueous sodium carbonate (20 mL) was added, and dichloromethane (20 mL×3) was added for extraction. The organic phases were combined, washed with saturated brine (10 mL×2), dried over anhydrous sodium sulfate, filtered and concentrated to give 2-(ethyl(2-ethyl-7-fluoro-5-(2-(trifluoromethyl)piperazin-1-yl)-2H-indazol-3-yl)amino)-4-(4-fluorophenyl)thiazole-5-carbonitrile 0134C (80 mg, 94%). LCMS (ESI) [M+H]$^+$=562.2@2.201 min (Method B).

Step 4: 2-(ethyl(2-ethyl-7-fluoro-5-(4-(2-(3-hydroxyazetidin-1-yl)-2-oxoethyl)-2-(trifluoromethyl) piperazin-1-yl)-2H-indazol-3-yl)amino)-4-(4-fluorophenyl)thiazole-5-carbonitrile A solution of 2-(ethyl(2-ethyl-7-fluoro-5-(2-(trifluoromethyl)piperazin-1-yl)-2H-indazol-3-yl)amino)-4-(4-fluorophenyl)thiazole-5-carbonitrile 0134C (80 mg, 0.142 mmol) and sodium hydride (60% in oil, 12 mg, 0.292 mmol) in tetrahydrofuran (2 mL) was stirred at room temperature for 10 min. Then 2-bromo-1-(3-hydroxyazetidin-1-yl)ethanone (34 mg, 0.175 mmol) was added, and the mixture was stirred at room temperature for 16 h. The reaction was quenched with water (10 mL) and ethyl acetate (10 mL×3) was added for extraction. The organic phases were combined, washed with saturated brine (10 mL×2), dried over anhydrous sodium sulfate, filtered and concentrated. The residue was purified by flash chromatography (methanol/dichloromethane=0-8%) to give 2-(ethyl(2-ethyl-7-fluoro-5-(4-(2-(3-hydroxyazetidin-1-yl)-2-oxoethyl)-2-(trifluoromethyl)piperazin-1-yl)-2H-indazol-3-yl)amino)-4-(4-fluoro phenyl) thiazole-5-carbonitrile 0134D (40 mg, 42%) in the form of a yellow solid. LCMS (ESI) [M+H]$^+$=675.3@ 1.914 min (Method B).

Step 5: (S)-2-(ethyl(2-ethyl-7-fluoro-5-(4-(2-(3-hydroxyazetidin-1-yl)-2-oxoethyl)-2-(trifluoromethyl)piperazin-1-yl)-2H-indazol-3-yl)amino)-4-(4-fluorophenyl)thiazole-5-carbonitrile and (R)-2-(ethyl (2-ethyl-7-fluoro-5-(4-(2-(3-hydroxyazetidin-1-yl)-2-oxoethyl)-2-(trifluoromethyl)piperazin-1-yl)-2H-indazol-3-yl)amino)-4-(4-fluorophenyl)thiazole-5-carbonitrile 2-(ethyl(2-ethyl-7-fluoro-5-(4-(2-(3-hydroxyazetidin-1-yl)-2-oxoethyl)-2-(trifluoromethyl)piperazin-1-yl)-2H-indazol-3-yl)amino)-4-(4-fluorophenyl)thiazole-5-carbonitrile 0134D (40 mg, 0.0593 mmol) was separated by chiral-HPLC (column: AD-H, 4.6*100 mm, 5 μm; mobile phase: ethonal (containing 1% of a solution of ammonia in methanol)) to give 2-(ethyl(2-ethyl-7-fluoro-5-(4-(2-(3-hydroxyazetidin-1-yl)-2-oxoethyl)-2-(trifluoromethyl)piperazin-1-yl)-2H-indazol-3-yl)amino)-4-(4-fluorophenyl) thiazole-5-carbonitrile S-0134A (isomer-1) (10.0 mg, 25%) in the form of a white solid and 2-(ethyl (2-ethyl-7-fluoro-5-(4-(2-(3-hydroxyazetidin-1-yl)-2-oxoethyl)-2-(trifluoromethyl)piperazin-1-yl)-2H-indazol-3-yl)amino)-4-(4-fluorophenyl)thiazole-5-carbonitrile S-0134B (isomer-2) (10.0 mg, 25%) in the form of a white solid.

S-0134A (isomer-1): chiral HPLC: $t_R$=3.05 min, LCMS (ESI) [M+H]$^+$=675.1@8.79 min (Method C); $^1$H NMR (400 MHz, CD$_3$OD) δ 8.011 (m, 2H), 7.127 (t, 2H), 6.996 (dd, J=13.2 Hz and 4.0 Hz, 1H), 6.477 (d, J=4.0 Hz, 1H), 4.469 (m, 1H), 4.407 (m, 2H), 4.322 (m, 1H), 4.223 (q, 2H), 4.092 (m, 1H), 3.980 (m, 1H), 3.813 (m, 1H), 3.652 (m, 1H), 3.381 (m, 1H), 3.122 (m, 1H), 3.040 (m, 1H), 2.900 (m, 1H), 2.809 (m, 1H), 2.428 (d, J=11.2 Hz, 1H), 1.455 (t, 3H), 1.187 (q, 3H).

S-0134B (isomer-2): chiral HPLC: $t_R$=4.26 min, LCMS (ESI) [M+H]$^+$=675.1@8.81 min (Method D); $^1$H NMR (400 MHz, CD$_3$OD) δ 8.130 (m, 2H), 7.246 (t, 2H), 7.115 (dd, J=13.6 Hz and 4.0 Hz, 1H), 6.603 (s, 1H), 4.657 (m, 1H), 4.548 (m, 2H), 4.433 m, 1H), 4.342 (m, 2H), 4.219 (m, 1H), 4.152 (m, 1H), 3.934 (m, 1H), 3.773 (m, 1H), 3.515 (m, 1H), 3.324 (m, 1H), 3.152 (m, 1H), 2.931 (d, J=10.4 Hz, 1H), 2.542 (m, 1H), 2.307 (m, 1H), 1.575 (t, 3H), 1.348 (q, 3H).

Example 48. S-0140: 2-((2-ethyl-5-(4-(2-(3-hydroxyazetidin-1-yl)-2-oxoethyl) piperazin-1-yl)-7-methyl-2H-pyrazolo[4,3-b]pyridin-3-yl)(2,2,2-trifluoroethyl)amino)-4-(4-fluorophenyl)thiazole-5-carbonitrile

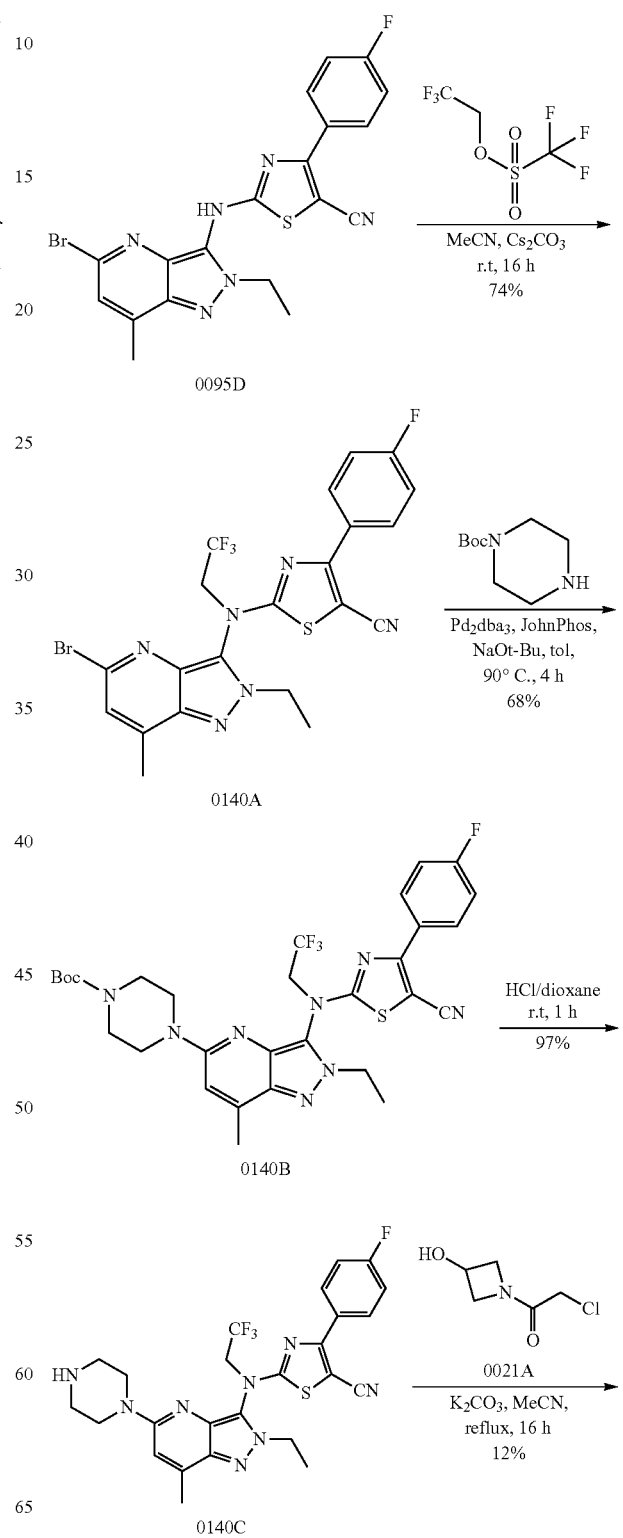

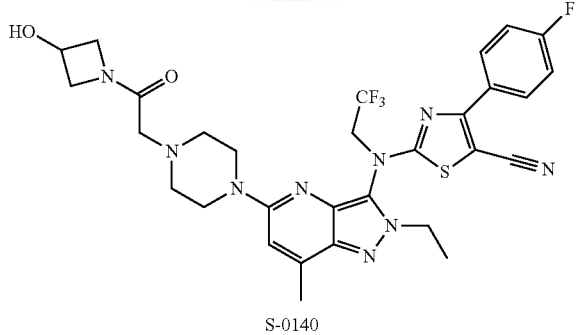 [SMILES: CCN(c1nc(-c2ccc(F)cc2)cs1)c1c2nc(N3CCN(CC(=O)N4CC(O)C4)CC3)cc(C)c2nn1CC]

S-0140

Step 1: 2-((5-bromo-2-ethyl-7-methyl-2H-pyrazolo[4,3-b]pyridin-3-yl)(2,2,2-trifluoroethyl)amino)-4-(4-fluorophenyl)thiazole-5-carbonitrile Cesium carbonate (488 mg, 1.5 mmol) was added to a solution of 2-(5-bromo-2-ethyl-7-methyl-2H-pyrazolo[4,3-H]pyridin-3-ylamino)-4-(4-fluorophenyl)thiazole-5-carbonitrile 0095D (228 mg, 0.5 mmol) and 2,2,2-trifluoroethyl trifluoromethanesulfonate (696 mg, 3 mmol) in acetonitrile (15 mL), and the mixture was stirred at room temperature for 16 h. The reaction was quenched with water (10 mL) and ethyl acetate (10 mL×3) was added for extraction. The organic phases were combined, washed with saturated brine (10 mL×3), dried over anhydrous sodium sulfate, filtered and concentrated. The residue was purified by flash chromatography (ethyl acetate/petroleum ether=0-30%) to give 2-((5-bromo-2-ethyl-7-methyl-2H-pyrazolo[4,3-b]pyridin-3-yl)(2,2,2-trifluoroethyl)amino)-4-(4-fluorophenyl) thiazole-5-carbonitrile 0140A (200 mg, 74%) in the form of a yellow solid. LCMS (ESI) [M+H]$^+$=539.0 @2.49 min (Method B).

Step 2: tert-butyl 4-(3-((5-cyano-4-(4-fluorophenyl)thiazol-2-yl)(2,2,2-trifluoroethyl) amino)-2-ethyl-7-methyl-2H-pyrazolo[4,3-b]pyridin-5-yl)piperazine-1-carboxylate In a glove box, 2-((5-bromo-2-ethyl-7-methyl-2H-pyrazolo[4,3-b]pyridin-3-yl)(2,2,2-trifluoroethyl)amino)-4-(4-fluorophenyl)thiazole-5-carbonitrile 0140A (269 mg, 0.5 mmol), tris(dibenzylideneacetone)dipalladium(0) (46 mg, 0.05 mmol), tert-butyl piperazine-1-carboxylate (465 mg, 2.5 mmol), 2-(di-tert-butylphosphine)biphenyl (30 mg, 0.1 mmol), sodium tert-butoxide (144 mg, 1.5 mmol) and toluene (10 mL) were mixed in a sealed tube. The reaction solution was heated to 90° C., stirred for 4 h, and then cooled to room temperature. The mixture was diluted with ethyl acetate (10 mL). Organic phases were washed with water (10 mL×3), dried over anhydrous sodium sulfate, filtered and concentrated. The residue was purified by flash chromatography (ethyl acetate/petroleum ether=0-35%) to give tert-butyl 4-(3-((5-cyano-4-(4-fluorophenyl)thiazol-2-yl)(2,2,2-trifluoroethyl)amino)-2-ethyl-7-methyl-2H-pyrazolo[4,3-b]pyridin-5-yl)piperazine-1-carboxylate 0140B (220 mg, 68%) in the form of a yellow solid. LCMS (ESI) [M+H]$^+$=645.2.@1.99 min (Method A).

Step 3: 2-((2-ethyl-7-methyl-5-(piperazin-1-yl)-2H-pyrazolo[4,3-b]pyridin-3-yl)(2,2,2-trifluoroethyl)amino)-4-(4-fluorophenyl)thiazole-5-carbonitrile A solution of tert-butyl 4-(3-((5-cyano-4-(4-fluorophenyl)thiazol-2-yl)(2,2,2-trifluoroethyl)amino)-2-ethyl-7-methyl-2H-pyrazolo[4,3-b]pyridin-5-yl)piperazine-1-carboxylate 0140B (220 mg, 0.34 mmol) and hydrogen chloride (4 N in dioxane, 2 mL) in dichloromethane (3 mL) was stirred at room temperature for 1 h and then concentrated. Aqueous sodium carbonate (5 mL) was added and the mixture was stirred, and dichloromethane (5 mL×3) was added for extraction. The organic phases were combined, washed with saturated brine (4 mL×3), dried over anhydrous sodium sulfate, filtered and concentrated to give 2-((2-ethyl-7-methyl-5-(piperazin-1-yl)-2H-pyrazolo[4,3-b]pyridin-3-yl)(2,2,2-trifluoroethyl)amino)-4-(4-fluorophenyl)thiazole-5-carbonitrile 0140C (180 mg, 97%) in the form of a yellow solid. LCMS (ESI) [M+H]$^+$=545.2 @2.23 min (Method B).

Step 4: 2-((2-ethyl-5-(4-(2-(3-hydroxyazetidin-1-yl)-2-oxoethyl)piperazin-1-yl)-7-methyl-2H-pyrazolo[4,3-b]pyridin-3-yl)(2,2,2-trifluoroethyl)amino)-4-(4-fluorophenyl)thiazole-5-carbonitrile A solution of 2-((2-ethyl-7-methyl-5-(piperazin-1-yl)-2H-pyrazolo[4,3-b]pyridin-3-yl) (2,2,2-trifluoroethyl)amino)-4-(4-fluorophenyl)thiazole-5-carbonitrile 0140C (80 mg, 0.33 mmol), 2-chloro-1-(3-hydroxyazetidin-1-yl)ethanone (74 mg, 0.5 mmol) and potassium carbonate (138 mg, 1 mmol) in acetonitrile (5 mL) was heated to reflux for 16 h. The reaction solution was concentrated and the residue was purified by flash chromatography (methanol/dichloromethane=0-8%) to give 2-((2-ethyl-5-(4-(2-(3-hydroxyazetidin-1-yl)-2-oxoethyl) piperazin-1-yl)-7-methyl-2H-pyrazolo[4,3-b]pyridin-3-yl)(2,2,2-trifluoroethyl)amino)-4-(4-fluorophenyl)thiazole-5-carbonitrile 0140 (26 mg, 12%) in the form of a yellow solid. LCMS (ESI) [M+H]$^+$=658.2@8.79 min (Method D); $^1$H NMR (400 MHz, CD$_3$OD) δ 8.09-8.14 (m, 2H), 7.22-7.29 (m, 2H), 6.94-6.98 (m, 1H), 5.14-5.16 (m, 1H), 4.01-4.71 (m, 7H), 3.57-3.74 (m, 5H), 3.01-3.13 (m, 2H), 2.48-2.56 (m, 7H), 1.49-1.57 (m, 3H).

Example 49. S-0141: 2-((2,2-difluoroethyl)(2-ethyl-5-(4-(2-(3-hydroxyazetidin-1-yl)-2-oxoethyl)piperazin-1-yl)-7-methyl-2H-pyrazolo[4,3-b]pyridin-3-yl)amino)-4-(4-fluorophenyl)thiazole-5-carbonitrile

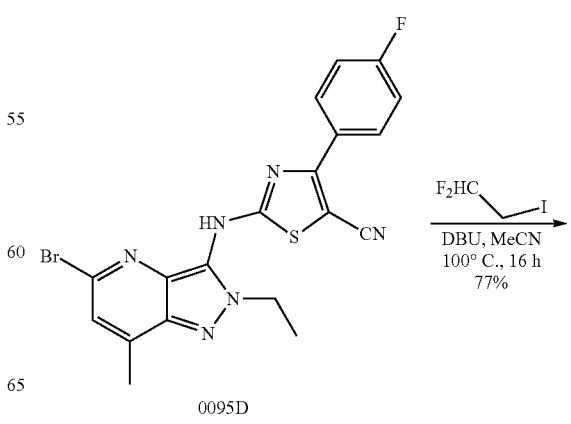

0095D

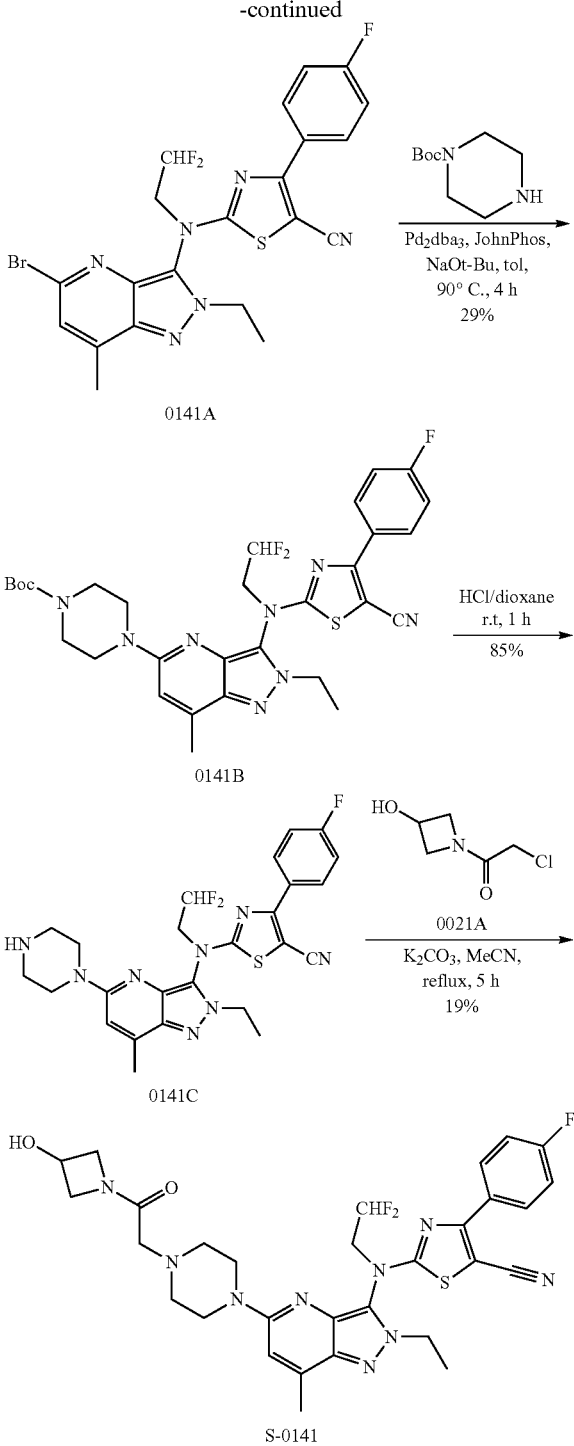

Step 1: 2-((5-bromo-2-ethyl-7-methyl-2H-pyrazolo[4,3-b]pyridin-3-yl)(2,2-difluoroethyl) amino)-4-(4-fluorophenyl)thiazole-5-carbonitrile To a solution of 2-(5-bromo-2-ethyl-7-methyl-2H-pyrazolo[4,3-b]pyridin-3-ylamino)-4-(4-fluorophenyl)thiazole-5-carbonitrile 0095D (228 mg, 0.5 mmol) and 1,1-difluoro-2-iodoethane (288 mg, 1.5 mmol) in acetonitrile (5 mL) was added 1,8-diazabicyclo[5.4.0]undec-7-ene (380 mg, 2.5 mmol). The mixture was stirred at 100° C. for 16 h and concentrated. The residue was purified by flash chromatography (ethyl acetate/petroleum ether=0-30%) to give 2-((5-bromo-2-ethyl-7-methyl-2H-pyrazolo[4,3-b]pyridin-3-yl)(2,2-difluoroethyl)amino)-4-(4-fluorophenyl)thiazole-5-carbonitrile 0141A (200 mg, 77%) in the form of a yellow solid. LCMS (ESI) [M+H]⁺=521.0@2.34 min (Method B).

Step 2: tert-butyl 4-(3-((5-cyano-4-(4-fluorophenyl)thiazol-2-yl)(2,2-difluoroethyl) amino)-2-ethyl-7-methyl-2H-pyrazolo[4,3-b]pyridin-5-yl)piperazine-1-carboxylate In a glove box, 2-((5-bromo-2-ethyl-7-methyl-2H-pyrazolo[4,3-b]pyridin-3-yl) (2,2-difluoroethyl)amino)-4-(4-fluorophenyl)thiazole-5-carbonitrile 0141A (200 mg, 0.38 mmol), tris(dibenzylideneacetone)dipalladium(0) (35 mg, 0.038 mmol), tert-butyl piperazine-1-carboxylate (358 mg, 1.92 mmol), 2-(di-tert-butylphosphino)biphenyl (23 mg, 0.076 mmol), sodium tert-butoxide (109 mg, 1.14 mmol) and toluene (5 mL) were mixed in a sealed tube. The mixture was stirred at 90° C. for 4 h, cooled to room temperature, and diluted with ethyl acetate (10 mL). The organic phase was washed with water (10 mL×3), dried over anhydrous sodium sulfate, filtered and concentrated. The residue was purified by flash chromatography (ethyl acetate/petroleum ether=0-35%) to give tert-butyl 4-(3-((5-cyano-4-(4-fluorophenyl)thiazol-2-yl)(2,2-difluoroethyl)amino)-2-ethyl-7-methyl-2H-pyrazolo [4,3-b]pyridin-5-yl)piperazine-1-carboxylate 0141B (70 mg, 29%) in the form of a yellow solid. LCMS (ESI) [M+H]⁺=627.2.@2.57 min (Method B).

Step 3: 2-((2,2-difluoroethyl)(2-ethyl-7-methyl-5-(piperazin-1-yl)-2H-pyrazolo[4,3-b]pyridin-3-yl) amino)-4-(4-fluorophenyl)thiazole-5-carbonitrile A solution of tert-butyl 4-(3-((5-cyano-4-(4-fluorophenyl)thiazol-2-yl)(2,2-difluoroethyl) amino)-2-ethyl-7-methyl-2H-pyrazolo[4,3-b]pyridin-5-yl)piperazine-1-carboxylate 0141B (70 mg, 0.11 mmol) and hydrogen chloride (4 N in dioxane, 2 mL) in dichloromethane (2 mL) was stirred at room temperature for 1 h and concentrated. Aqueous sodium carbonate (5 mL) was added, and then dichloromethane (5 mL×3) was added for extraction. The organic phases were combined, washed with saturated brine (4 mL×3), dried over anhydrous sodium sulfate, filtered and concentrated to give 2-((2,2-difluoroethyl)(2-ethyl-7-methyl-5-(piperazin-1-yl)-2H-pyrazolo[4,3-b]pyridin-3-yl)amino)-4-(4-fluorophenyl)thiazole-5-carbonitrile 0141C (50 mg, 85%) in the form of a yellow solid. LCMS (ESI) [M+H]⁺=527.2@2.10 min (Method B).

Step 4:2-((2,2-difluoroethyl)(2-ethyl-5-(4-(2-(3-hydroxyazetidin-1-yl)-2-oxoethyl) piperazin-1-yl)-7-methyl-2H-pyrazolo[4,3-b]pyridin-3-yl)amino)-4-(4-fluorophenyl)thiazole-5-carbonitrile A mixture of 2-((2,2-difluoroethyl)(2-ethyl-7-methyl-5-(piperazin-1-yl)-2H-pyrazolo [4,3-b]pyridin-3-yl)amino)-4-(4-fluorophenyl)thiazole-5-carbonitrile 0141C (50 mg, 0.095 mmol), 2-chloro-1-(3-hydroxyazetidin-1-yl)ethanone (42 mg, 0.285 mmol) and potassium carbonate (39 mg, 0.285 mmol) in acetonitrile (5 mL) was stirred at reflux for 16 h. The mixture was concentrated and the residue was purified by flash chromatography (methanol/dichloromethane=0-8%) to give 2-((2,2-difluoroethyl)(2-ethyl-5-(4-(2-

(3-hydroxyazetidin-1-yl)-2-oxoethyl)piperazin-1-yl)-7-methyl-2H-pyrazolo[4,3-b]pyridin-3-yl)amino)-4-(4-fluorophenyl)thiazole-5-carbonitrile S-0141 (12 mg, 19%) in the form of a yellow solid. LCMS (ESI) [M+H]+=640.2@8.29 min (Method D); ¹H NMR (400 MHz, CD₃OD) δ 8.09-8.13 (m, 2H), 7.22-7.29 (m, 2H), 6.92-6.95 (m, 1H), 6.27-6.56 (m, 1H), 4.17-4.54 (m, 8H), 3.57-3.76 (m, 5H), 3.12-3.19 (m, 2H), 2.55-2.57 (m, 7H), 1.48-1.57 (m, 3H).

Example 50. S-0135: (S)-2-(ethyl(2-ethyl-7-fluoro-5-(4-(2-(3-hydroxyazetidin-1-yl)-2-oxoethyl)-3-(trifluoromethyl)piperazin-1-yl)-2H-indazol-3-yl)amino)-4-(4-fluorophenyl) thiazole-5-carbonitrile and (R)-2-(ethyl(2-ethyl-7-fluoro-5-(4-(2-(3-hydroxyazetidin-1-yl)-2-oxoethyl)-3-(trifluoromethyl)piperazin-1-yl)-2H-indazol-3-yl)amino)-4-(4-fluorophenyl)thiazole-5-carbonitrile

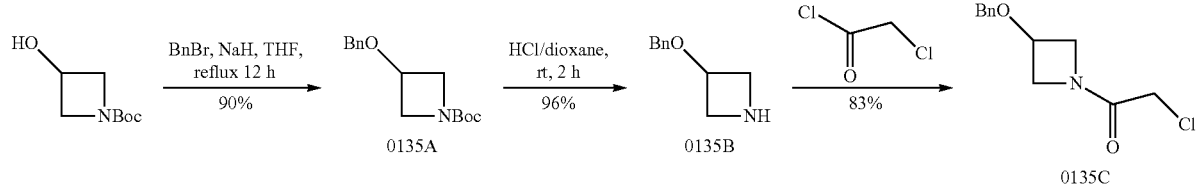

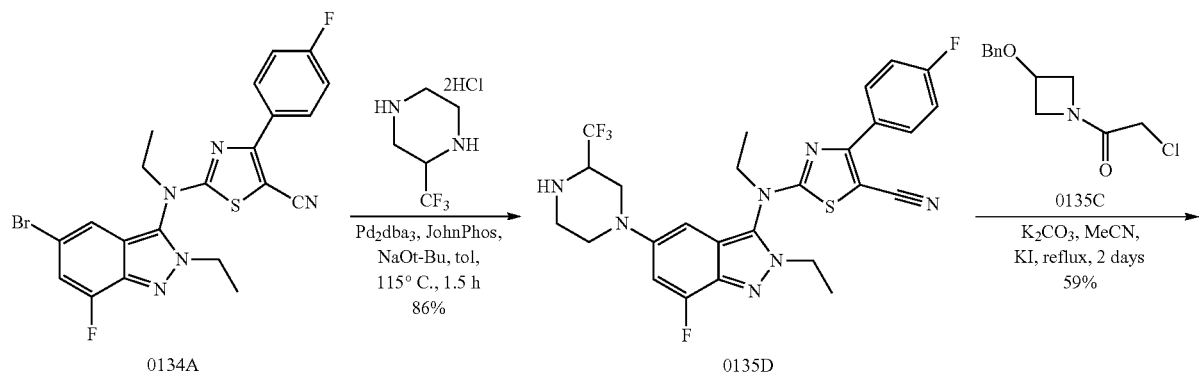

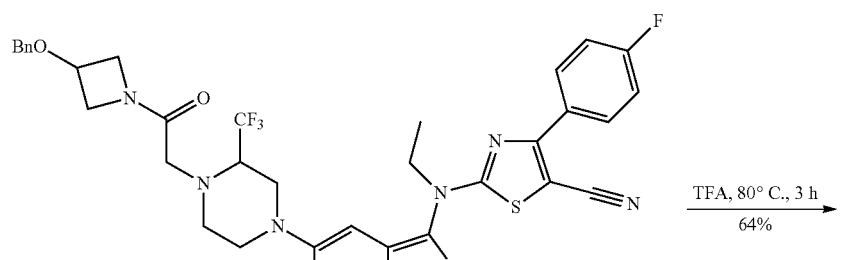

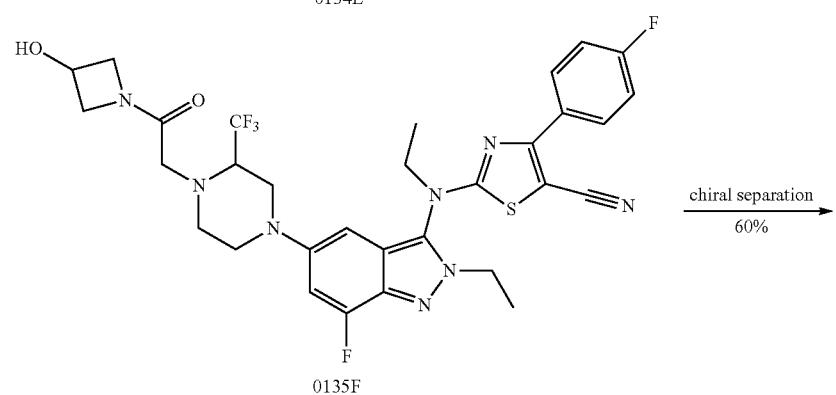

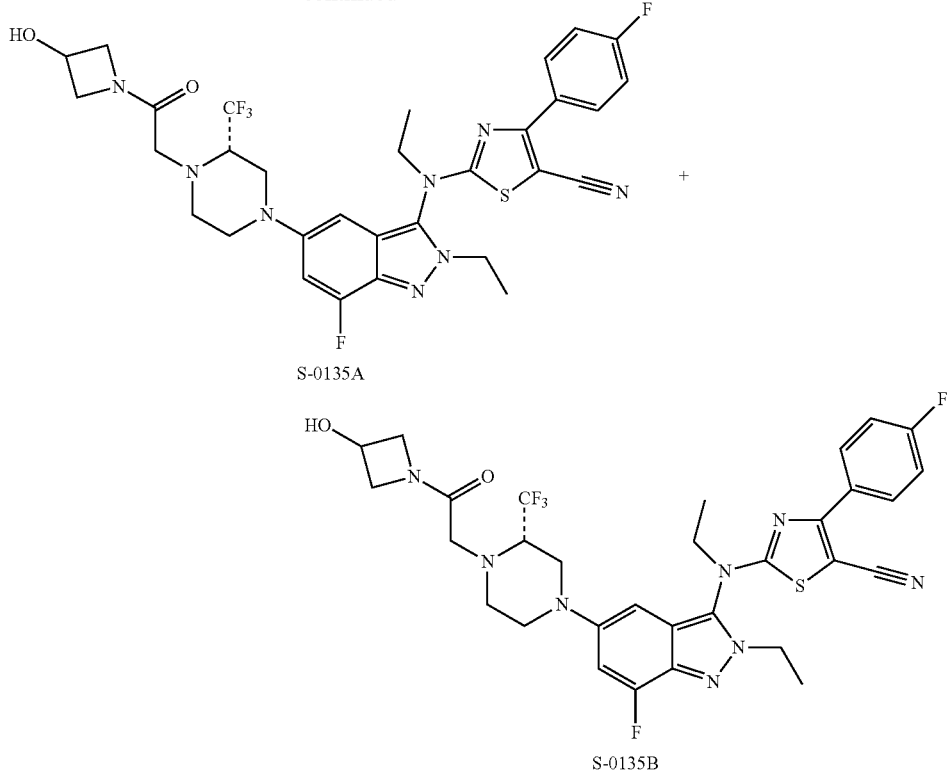

S-0135A

S-0135B

Step 1: tert-butyl 3-(benzyloxy)azetidine-1-carboxylate

A mixture of tert-butyl 3-hydroxyazetidine-1-carboxylate (3.0 g, 17.32 mmol), benzyl bromide (3.55 g, 20.78 mmol) and sodium hydride (60% in mineral oil, 1.04 g, 25.98 mmol) in tetrahydrofuran (30 mL) was stirred at room temperature for 16 h. The reaction was quenched with water (20 ml), and ethyl acetate (50 mL×3) was added for extraction. The organic phase was washed with saturated brine, dried over anhydrous sodium sulfate, and concentrated. The residue was purified by flash chromatography (ethyl acetate/petroleum ether=0-30%) to give tert-butyl 3-(benzyloxy)azetidine-1-carboxylate 0135A (4.1 g, 89.9%) in the form of a colorless oil. LCMS (ESI) [M−56+H]$^+$=208.2; [M+Na]$^+$=286.2@1.837 min (Method A).

Step 2: 3-(benzyloxy)azetidine Hydrochloride

A mixture of tert-butyl 3-(benzyloxy)azetidine-1-carboxylate 0135A (4.1 g, 15.57 mmol) in hydrogen chloride (4 N in dioxane, 20 mL) was stirred at room temperature for 2 h and then concentrated to give 3-(benzyloxy)azetidine hydrochloride 0135B (3.0 g, 96.5%). LCMS (ESI) [M+H]$^+$=164.3 @1.108 min (Method A).

Step 3: 1-(3-(benzyloxy)azetidin-1-yl)-2-chloroethanone

To a solution of potassium carbonate (1.38 g, 10.02 mmol) in water (10 mL) was added 3-(benzyloxy)azetidine hydrochloride (1.0 g, 5.01 mmol). The mixture was stirred at room temperature for 10 min and then diluted with dichloromethane (10 mL). 2-chloroacetyl chloride (622 mg, 5.51 mmol) was added at 0° C., and the reaction system was stirred at room temperature for 2 h. Ethyl acetate (60 mL×3) was added for extraction. The organic phase was dried over anhydrous sodium sulfate and concentrated to give 1-(3-(benzyloxy)azetidin-1-yl)-2-chloroethanone 0135C (1.0 g, 83.3%) in the form of a yellow oil. LCMS (ESI) [M+H]$^+$=240.1. @1.549 min (Method A).

Step 4: 2-(ethyl(2-ethyl-7-fluoro-5-(3-(trifluoromethyl)piperazin-1-yl)-2H-indazol-3-yl) amino)-4-(4-fluorophenyl)thiazole-5-carbonitrile In a glove box, a mixture of 2-((5-bromo-2-ethyl-7-fluoro-2H-indazol-3-yl)(ethyl)amino)-4-(4-fluorophenyl)thiazole-5-carbonitrile 0134A (100 mg, 0.205 mmol), 2-(trifluoromethyl) piperazine hydrochloride (71 mg, 0.312 mmol), tris(dibenzylidene acetone)dipalladium(0) (19 mg, 0.021 mmol), 2-(di-tert-butylphosphino)biphenyl (13 mg, 0.042 mmol), sodium tert-butoxide (60 mg, 0.615 mmol), and toluene (3 mL) was stirred at 80° C. for 16 h, and then cooled to room temperature. The mixture was concentrated, and the residue was purified by flash chromatography (ethyl acetate/petroleum ether=0-40%) to give 2-(ethyl(2-ethyl-7-fluoro-5-(3-(trifluoromethyl)piperazin-1-yl)-2H-indazol-3-yl)amino)-4-(4-fluorophenyl) thiazole-5-carbonitrile 0135D (100 mg, 86%). LCMS (ESI) [M+H]$^+$=562.0@2.233 min. (Method B).

Step 5: 2-((5-(4-(2-(3-(benzyloxy)azetidin-1-yl)-2-oxoethyl)-3-(trifluoromethyl)piperazin-1-yl)-2-ethyl-7-fluoro-2H-indazol-3-yl)(ethyl)amino)-4-(4-fluorophenyl)thiazole-5-carbonitrile A mixture of 2-(ethyl(2-ethyl-7-fluoro-5-(3-(trifluoromethyl)piperazin-1-yl)-2H-indazol-3-yl)amino)-4-(4-fluorophenyl)thiazole-5-carbonitrile 0135D (100 mg, 0.178 mmol), 1-(3-(benzyloxy)azetidin-1-yl)-2-chloroethanone 0135C (64 mg, 0.267 mmol), potassium iodide (44 mg, 0.267 mmol) and potassium carbonate (74 mg, 0.534 mmol) in acetonitrile (2 mL) was stirred at 80° C. for 48 h, and then cooled and concentrated. The residue was purified by flash chromatography (ethyl acetate/petroleum ether 0-40%) to give 2-((5-(4-(2-(3-(benzyloxy)azetidin-1-yl)-2-oxoethyl)-3-(trifluoromethyl) piperazin-1-yl)-2-ethyl-7-fluoro-2H-indazol-3-yl)(ethyl)amino)-4-(4-fluorophenyl)thiazole-5-carbonitrile 0135E (80 mg, 59%). LCMS (ESI) [M+H]$^+$=765.3@2.128 min (Method B).

Step 6: 2-(ethyl(2-ethyl-7-fluoro-5-(4-(2-(3-hydroxyazetidin-1-yl)-2-oxoethyl)-3-(trifluoromethyl) piperazin-1-yl)-2H-indazol-3-yl)amino)-4-(4-fluorophenyl)thiazole-5-carbonitrile A solution of 2-((5-(4-(2-(3-(benzyloxy)azetidin-1-yl)-2-oxoethyl)-3-(trifluoromethyl) piperazin-1-yl)-2-ethyl-7-fluoro-2H-indazol-3-yl)(ethyl)amino)-4-(4-fluorophenyl) thiazole-5-carbonitrile 0135E (70 mg, 0.0916 mmol) in trifluoroacetic acid (2 mL) was stirred at 80° C. for 3 h, and was cooled and concentrated. The residue was purified by flash chromatography (methanol/dichloromethane=0-8%) to give 2-(ethyl(2-ethyl-7-fluoro-5-(4-(2-(3-hydroxyazetidin-1-yl)-2-oxoethyl)-3-(trifluoromethyl) piperazin-1-yl)-2H-indazol-3-yl) amino)-4-(4-fluorophenyl)thiazole-5-carbonitrile 0135F (40 mg, 64%) in the form of a yellow solid. LCMS (ESI) [M+H]$^+$=675.2@1.830 min (Method A).

Step 7: (S)-2-(ethyl(2-ethyl-7-fluoro-5-(4-(2-(3-hydroxyazetidin-1-yl)-2-oxoethyl)-3-(trifluoromethyl)piperazin-1-yl)-2H-indazol-3-yl)amino)-4-(4-fluorophenyl)thiazole-5-carbonitrile and (R)-2-(ethyl(-2-ethyl-7-fluoro-5-(4-(2-(3-hydroxyazetidin-1-yl)-3-oxoethyl)-2-(trifluoromethyl)piperazin-1-yl)-2H-indazol-3-yl)amino)-4-(4-fluorophenyl)thiazole-5-carbonitrile 2-(ethyl(2-ethyl-7-fluoro-5-(4-(2-(3-hydroxyazetidin-1-yl)-2-oxoethyl)-3-(trifluoromethyl)piperazin-1-yl)-2H-indazol-3-yl)amino)-4-(4-fluorophenyl)thiazole-5-carbonitrile 0135F (40 mg, 0.0593 mmol) was separated by chiral-HPLC (Column: OD-H (250*4.6 mm, 5 um), mobile phase: Hexane (0.1% DEA):EtOH (0.1% DEA)=80:20) to give (S)-2-(ethyl(2-ethyl-7-fluoro-5-(4-(2-(3-hydroxyazetidin-1-yl)-2-oxoethyl)-3-(trifluoromethyl)piperazin-1-yl)-2H-indazol-3-yl)amino)-4-(4-fluorophenyl)thiazole-5-carbonitrile S-0135A (isomer-1) (16 mg, 40%) in the form of a white solid and (R)-2-(ethyl (2-ethyl-7-fluoro-5-(4-(2-(3-hydroxyazetidin-1-yl)-2-oxoethyl)-3-(trifluoromethyl)piperazin-1-yl)-2H-indazol-3-yl)amino)-4-(4-fluorophenyl)thiazole-5-carbonitrile S-0135B (isomer-2) (8.0 mg, 20% yield) in the form of a white solid.

S-0135A (isomer-1): chiral HPLC: $t_R$=10.04 min, LCMS (ESI) [M+H]$^+$=675.0@2.058 min (Method B); $^1$H NMR (400 MHz, CD$_3$OD) δ 8.017 (m, 2H), 7.131 (t, 2H), 6.859 (d, J=4.0 Hz, 1H), 6.408 (s, 1H), 4.469 (m, 1H), 4.316 (m, 2H), 4.222 (m, 2H), 4.117 (m, 1H), 3.928 (m, 2H), 33.837 (m, 2H), 3.655 (m, 1H), 3.497 (m, 12H), 3.431 (m, 2H), 3.3670 (m, 1H), 2.994 (m, 2H), 2.791 (m, 1H), 2.599 (m, 2H), 1.455 (t, 3H), 1.255 (t, 3H).

S-0135B (isomer-2): chiral HPLC: $t_R$=11.09 min, LCMS (ESI) [M+H]$^+$=675.2@2.0791 min (Method B); $^1$H NMR (400 MHz, CD$_3$OD) δ 8.017 (m, 2H), 7.131 (t, 2H), 6.837 (d, J=13.6 Hz, 1H), 6.407 (s, 1H), 4.469 (m, 1H), 4.370 (m, 2H), 4.297 (q, 2H), 4.118 (m, 1H), 3.958 (m, 1H), 3.820 (m, 1H), 3.663 (m, 1H), 3.527 (m, 1H), 3.432 (m, 2H), 2.993 (m, 1H), 2.807 (m, 1H), 1.455 (t, 3H), 1.255 (t, 3H).

Example 51. S-0144: 2-((2-ethyl-5-(4-(2-(3-hydroxyazetidin-1-yl)-2-oxoethyl) piperazin-1-yl)-7-methyl-2H-pyrazolo[4,3-b]pyridin-3-yl)(2-fluoroethyl)amino)-4-(4-fluorophenyl)thiazole-5-carbonitrile

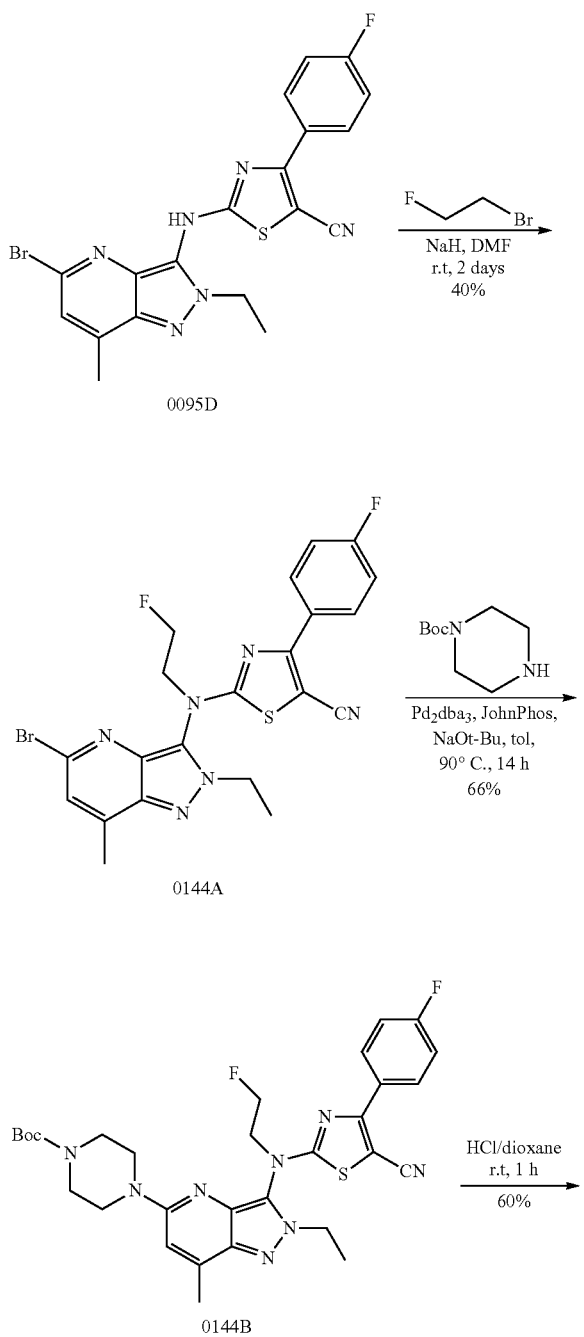

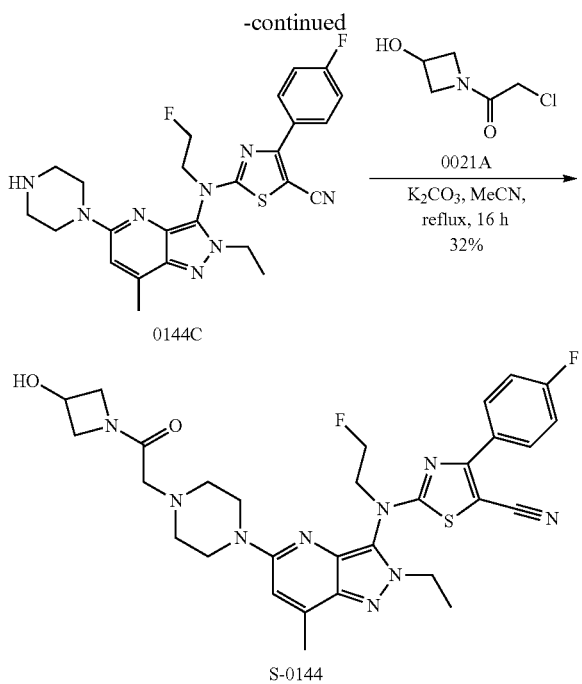

Step 1: 2-((5-bromo-2-ethyl-7-methyl-2H-pyrazolo[4,3-b]pyridin-3-yl)(2-fluoroethyl) amino)-4-(4-fluorophenyl)thiazole-5-carbonitrile To a solution of 2-(5-bromo-2-ethyl-7-methyl-2H-pyrazolo[4,3-b]pyridin-3-ylamino)-4-(4-fluorophenyl)thiazole-5-carbonitrile 0095D (46 mg, 0.1 mmol) in N,N-dimethylformamide (2 mL) was added sodium hydride (12 mg, 0.3 mmol, 60%) and the mixture was stirred at room temperature for 10 min. 1-bromo-2-fluoroethane (25 mg, 0.2 mmol) was added and the mixture was stirred at room temperature for 2 days. The reaction was quenched with water (10 mL) and ethyl acetate (10 mL×3) was added for extraction. The organic phases were combined, washed with saturated brine (10 mL×3), dried over anhydrous sodium sulfate, filtered and concentrated. The residue was purified by flash chromatography (ethyl acetate/petroleum ether=0-25%) to give 2-((5-bromo-2-ethyl-7-methyl-2H-pyrazolo[4,3-b]pyridin-3-yl)(2-fluoroethyl)amino)-4-(4-fluorophenyl)thiazole-5-carbonitrile 0144A (20 mg, 40%) in the form of a yellow solid. LCMS (ESI) [M+H]$^+$=503.0@2.36 min (Method B).

Step 2: tert-butyl 4-(3-(((5-cyano-4-(4-fluorophenyl)thiazol-2-yl)(2-fluoroethyl)amino)-2-ethyl-7-methyl-2H-pyrazolo[4,3-b]pyridin-5-yl)piperazine-1-carboxylate In a glove box, 2-((5-bromo-2-ethyl-7-methyl-2H-pyrazolo[4,3-b]pyridin-3-yl) (2-fluoroethyl)amino)-4-(4-fluorophenyl)thiazole-5-carbonitrile 0144A (50 mg, 0.1 mmol), tris(dibenzylideneacetone)dipalladium(0) (9 mg, 0.01 mmol), tert-butyl piperazine-1-carboxylate (93 mg, 0.5 mmol), 2-(di-tert-butylphosphino)biphenyl (6 mg, 0.02 mmol), sodium tert-butoxide (29 mg, 0.3 mmol) and toluene (2 mL) were mixed in a sealed tube. The mixture was stirred at 90° C. for 14 h and then cooled to room temperature. The mixture was concentrated, and the residue was purified by flash chromatography (ethyl acetate/petroleum ether=0-40%) to give tert-butyl 4-(3-((5-cyano-4-(4-fluorophenyl)thiazol-2-yl)(2-fluoroethyl) amino)-2-ethyl-7-methyl-2H-pyrazolo[4,3-b]pyridin-5-yl)piperazine-1-carboxylate 0144B (40 mg, 66%) in the form of a yellow solid. LCMS (ESI) [M+H]$^+$=609.2.@2.49 min (Method B).

Step 3: 2-((2-ethyl-7-methyl-5-(piperazin-1-yl)-2H-pyrazolo[4,3-b]pyridin-3-yl) (2-fluoroethyl)amino)-4-(4-fluorophenyl)thiazole-5-carbonitrile A mixture of tert-butyl 4-(3-((5-cyano-4-(4-fluorophenyl)thiazol-2-yl)(2-fluoroethyl) amino)-2-ethyl-7-methyl-2H-pyrazolo[4,3-b]pyridin-5-yl)piperazine-1-carboxylate 0144B (40 mg, 0.078 mmol) in hydrogen chloride (4 N in dioxane, 2 mL) and dichloromethane (2 mL) was stirred at room temperature for 1 h and then concentrated. Aqueous sodium carbonate (5 mL) was added, and then dichloromethane (5 mL×3) was added for extraction. The organic phases were combined, washed with saturated brine (4 mL×3), dried over anhydrous sodium sulfate, filtered and concentrated to give 2-((2-ethyl-7-methyl-5-(piperazin-1-yl)-2H-pyrazolo [4,3-b]pyridin-3-yl)(2-fluoroethyl)amino)-4-(4-fluorophenyl)thiazole-5-carbonitrile 0144C (20 mg, 60%) in the form of a yellow solid. LCMS (ESI) [M+H]$^+$=509.1@2.05 min (Method B).

Step 4: 2-((2-ethyl-5-(4-(2-(3-hydroxyazetidin-1-yl)-2-oxoethyl)piperazin-1-yl)-7-methyl-2H-pyrazolo[4,3-b]pyridin-3-yl)(2-fluoroethyl)amino)-4-(4-fluorophenyl)thiazole-5-carbonitrile A mixture of 2-((2-ethyl-7-methyl-5-(piperazin-1-yl)-2H-pyrazolo[4,3-b]pyridin-3-yl) (2-fluoroethyl)amino)-4-(4-fluorophenyl)thiazole-5-carbonitrile 0144C (30 mg, 0.06 mmol), 2-chloro-1-(3-hydroxyazetidin-1-yl)ethanone 0021A (17 mg, 0.12 mmol) and potassium carbonate (25 mg, 0.18 mmol) in acetonitrile (3 mL) was stirred at reflux for 16 h. The mixture was concentrated, and the residue was purified by flash chromatography (methanol/dichloromethane 0-8%) to give 2-((2-ethyl-5-(4-(2-(3-hydroxyazetidin-1-yl)-2-oxoethyl)piperazin-1-yl)-7-methyl-2H-pyrazolo[4,3-b]pyridin-3-yl)(2-fluoroethyl)amino)-4-(4-fluorophenyl)thiazole-5-carbonitrile S-0144 (11.8 mg, 32% yield) in the form of a yellow solid. LCMS (ESI) [M+H]$^+$=622.2@8.11 min (Method D); $^1$H NMR (400 MHz, CD$_3$OD) δ 8.13-8.17 (m, 2H), 7.25-7.29 (m, 2H), 6.97 (s, 1H), 4.92-5.04 (m, 1H), 4.55-4.77 (m, 2H), 4.47-4.54 (m, 2H), 4.42-4.46 (m, 1H), 4.29-4.38 (m, 2H), 4.20-4.27 (m, 1H), 4.05-4.11 (m, 1H), 3.76-3.82 (m, 1H), 3.63-3.70 (m, 4H), 3.06-3.17 (m, 2H), 2.58-2.64 (m, 4H), 2.57 (s, 3H), 1.58 (t, J=7.2 Hz, 3H).

Example 52. S-0149: 2-(4-(2-ethyl-3-(ethyl(4-(4-fluorophenyl)thiazol-2-yl)amino)-7-fluoro-2H-indazol-5-yl)piperazin-1-yl)-1-(3-hydroxyazetidin-1-yl)ethanone

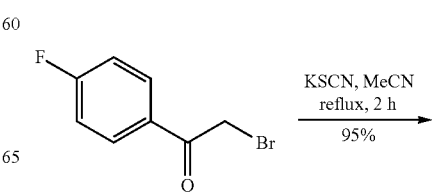

287
-continued

288
-continued

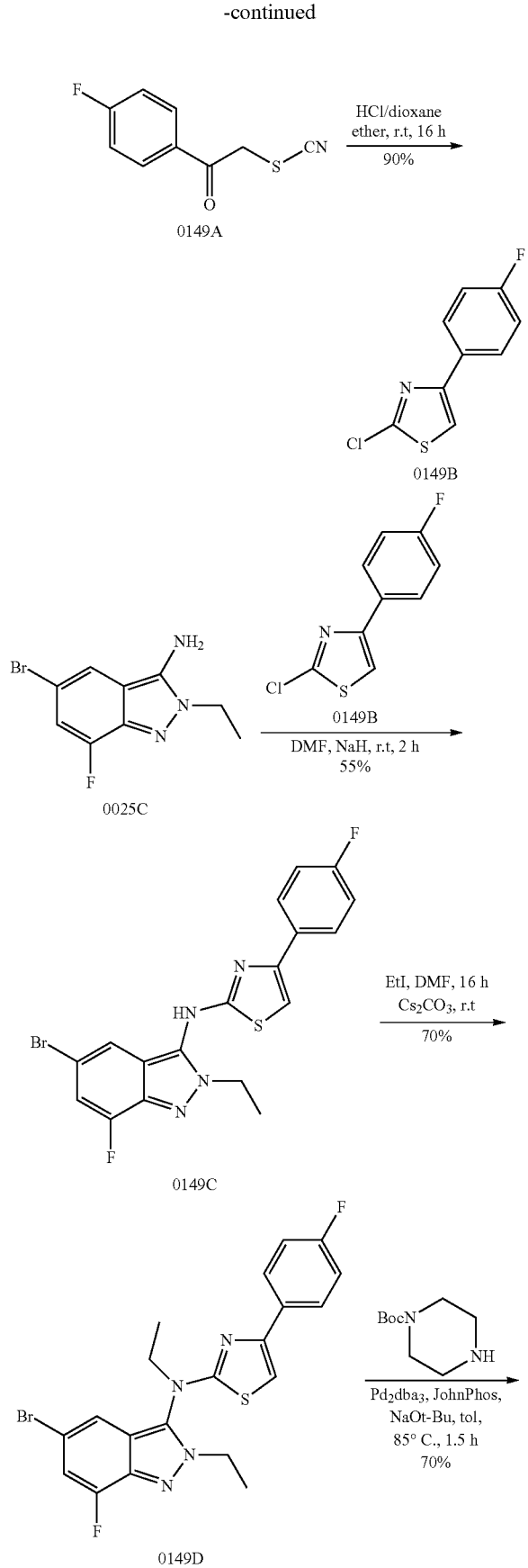

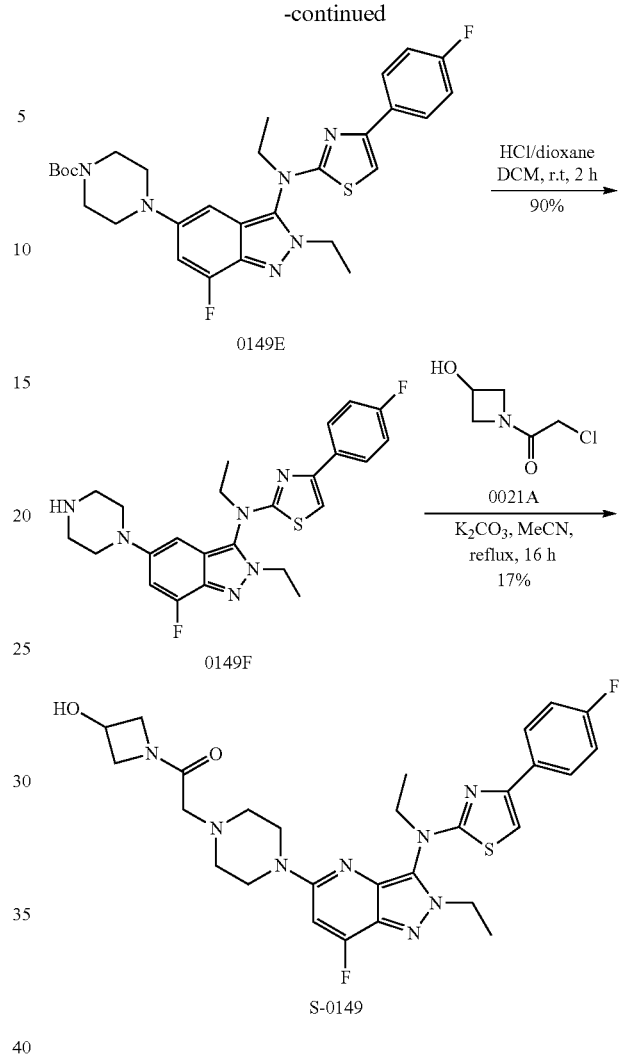

Step 1: 1-(4-fluorophenyl)-2-thiocyanatoethanone

Potassium thiocyanate (2.7 g, 27.7 mmol) was added to a solution of 2-bromo-1-(4-fluorophenyl)ethanone (3 g, 13.8 mmol) in acetonitrile (30 mL), and the mixture was heated to reflux for 2 h. The reaction solution was concentrated to give 1-(4-fluorophenyl)-2-thiocyanatoethanone 0149A in the form of a white solid (2.5 g, 95%). LCMS (ESI) [M+H]⁺=196.1@1.80 min (Method B).

Step 2: 2-chloro-4-(4-fluorophenyl)thiazole

A mixture of 1-(4-fluorophenyl)-2-thiocyanatoethanone 0149A (1 g, 5.12 mmol) and hydrogen chloride (4 N in dioxane, 15 mL) was stirred at room temperature overnight and then concentrated. The residue was purified by flash chromatography (ethyl acetate/petroleum ether=0%-20%) to give 2-chloro-4-(4-fluorophenyl)thiazole 0149B in the form of a yellow solid (50 mg, 27%). LCMS (ESI) [M+H]⁺=214.1.@1.88 min (Method A).

Step 3: N-(5-bromo-2-ethyl-7-fluoro-2H-indazol-3-yl)-4-(4-fluorophenyl)thiazol-2-amine Sodium hydride (60% in mineral oil, 278 mg, 11.6 mmol) was slowly added to a solution of 5-bromo-2-ethyl-7-fluoro- 2H-indazol-3-amine 0025C (300 mg, 1.16 mmol) in N,N-dimethylformamide (8 mL), and the mixture was stirred at room temperature for 15 min. Then 2-chloro-4-(4-fluorophenyl)thiazole 0149B (325 mg, 1.51 mmol) was added, and the mixture was stirred at room temperature for 2 h. The reaction was quenched with water (30 mL), and ethyl acetate (30 mL×5) was added for extraction. The organic phases were washed with saturated brine (10 mL×2), dried over anhydrous sodium sulfate, filtered and concentrated. The residue was purified by flash chromatography (ethyl acetate/petroleum ether=0%-50%) to give N-(5-bromo-2-ethyl-7-fluoro-2H-indazol-3-yl)-4-(4-fluorophenyl)thiazol-2-amine 0149C (278 mg, 55%). LCMS (ESI) [M+H]$^+$=437.0@1.95 min (LC-MS Method A).

Step 4: N-(5-bromo-2-ethyl-7-fluoro-2H-indazol-3-yl)-N-ethyl-4-(4-fluorophenyl) thiazol-2-amine Cesium carbonate (673 mg, 2.07 mmol) was added to a solution of N-(5-bromo-2-ethyl-7-fluoro-2H-indazol-3-yl)-4-(4-fluorophenyl)thiazol-2-amine 0149C (300 mg, 0.69 mmol) in N,N-dimethylformamide (10 mL), and the mixture was stirred at room temperature for 30 min. Then iodoethane (70 mg, 0.49 mmol) was added, and the resulting mixture was stirred at room temperature for 2 h. The reaction was quenched with water (10 mL) and ethyl acetate (10 mL×3) was added for extraction. The organic phases were washed with saturated brine (10 mL×3), dried over anhydrous sodium sulfate, filtered and concentrated. The residue was purified by flash chromatography (ethyl acetate/petroleum ether=0%-30%) to give N-(5-bromo-2-ethyl-7-fluoro-2H-indazol-3-yl)-N-ethyl-4-(4-fluorophenyl)thiazol-2-amine 0149D (240 mg, 75%) in the form of a yellow solid. $^1$H NMR (400 MHz, DMSO-d$_6$) δ 8.07-7.78 (m, 2H), 7.71 (s, 1H), 7.34 (dd, J=34.2, 20.7 Hz, 2H), 7.23 (d, J=8.6 Hz, 2H), 4.29 (dt, J=129.1, 64.6 Hz, 2H), 4.01-4.00 (m, 2H), 1.50 (t, J=7.2 Hz, 3H), 1.32-1.10 (m, 3H).

Step 5: tert-butyl 4-(2-ethyl-3-(ethyl(4-(4-fluorophenyl)thiazol-2-yl)amino)-7-fluoro-2H-indazol-5-yl)piperazine-1-carboxylate In a glove box, N-(5-bromo-2-ethyl-7-fluoro-2H-indazol-3-yl)-N-ethyl-4-(4-fluorophenyl)thiazol-2-amine 0149D (200 mg, 0.43 mmol), tert-butyl piperazine-1-carboxylate (765 mg, 4.3 mmol), tris(dibenzylideneacetone)dipalladium (0) (39 mg, 0.043 mmol), (=O)-2,2'-bis(diphenylphosphino)-1,1'-binaphthyl (26 mg, 0.086 mmol), sodium tert-butoxide (126 mg, 1.29 mmol) and toluene (3 mL) were added to a microwave tube, and the mixture was stirred at 85° C. for 1.5 h, and then cooled to room temperature. Ethyl acetate (20 mL×3) was added for extraction. The organic phases were washed with saturated brine (10 mL×2), dried over anhydrous sodium sulfate, filtered and concentrated. The residue was purified by flash chromatography (ethyl acetate/petroleum ether=0%-40%) to give tert-butyl 4-(2-ethyl-3-(ethyl(4-(4-fluorophenyl)thiazol-2-yl)amino)-7-fluoro-2H-indazol-5-yl)piperazine-1-carboxylat e 0149E (170 mg, 70%) in the form of a yellow solid. LCMS (ESI) [M+H]$^+$=569.2@2.13 min (Method A).

Step 6: N-ethyl-N-(2-ethyl-7-fluoro-5-(piperazin-1-yl)-2H-indazol-3-yl)-4-(4-fluoro) thiazol-2-amine A mixture of tert-butyl 4-(2-ethyl-3-(ethyl(4-(4-fluorophenyl)thiazol-2-yl)amino)-7-fluoro-2H-indazol-5-yl)piperazine-1-carboxylate 0149E (100 mg, 0.17 mmol) and hydrogen chloride (4 N in dioxane, 5 mL) was stirred at room temperature for 4 h, concentrated, and added with a saturated sodium bicarbonate solution (20 mL). Dichloromethane (20 mL×3) was added for extraction. The organic phases were washed with saturated brine (10 mL×2), dried over anhydrous sodium sulfate, filtered and concentrated to give N-ethyl-N-(2-ethyl-7-fluoro-5-(piperazin-1-yl)-2H-indazol-3-yl)-4-(4-fluoro)thiazol-2-amine 0149F (70 mg, 90%) in the form of a yellow solid. LCMS (ESI) [M+H]$^+$=469.2@1.49 min (LC-MS Method A).

Step 7: 2-(4-(2-ethyl-3-(ethyl(4-(4-fluorophenyl)thiazol-2-yl)amino)-7-fluoro-2H-indazol-5-yl)piperazin-1-yl)-1-(3-hydroxyazetidin-1-yl)ethanone 2-chloro-1-(3-hydroxyazetidin-1-yl)ethanone (33 mg, 0.22 mmol) and potassium carbonate (60 mg, 0.44 mmol) were added to a solution of N-ethyl-N-(2-ethyl-7-fluoro-5-(piperazin-1-yl)-2H-indazol-3-yl)-4-(4-fluoro)thiazol-2-amine 0149F (50 mg, 0.15 mmol) in acetonitrile (2 mL), and the mixture was heated to reflux for 2 h, and concentrated to dryness. The residue was purified by flash chromatography (methanol/dichloromethane=0%-8%) to give 2-(4-(2-ethyl-3-(ethyl(4-(4-fluorophenyl)thiazol-2-yl) amino)-7-fluoro-2H-indazol-5-yl)piperazin-1-yl)-1-(3-hydroxyazetidin-1-yl) ethanone S-0149 (15 mg, 17%) in the form of a white solid. LCMS (ESI) [M+H]$^+$=582.0@8.17 min (Method B); $^1$H NMR (400 MHz, CD$_3$OD) δ 7.89 (m, 2H), 7.16 (m, 2H), 7.07 (d, J=53.0 Hz, 2H), 6.51 (s, 1H), 4.57 (m, 2H), 4.50 (m, 2H), 4.35 (m, 2H), 4.22 (m, 2H), 3.78 (t, J=89.2 Hz, 1H), 3.14 (d, J=13.4 Hz, 6H), 2.66 (m, 4H), 1.79-1.38 (m, 3H), 1.36 (d, J=6.2 Hz, 3H).

Example 53. S-0151: 2-(4-(2-ethyl-3-(ethyl(4-(4-fluorophenyl)thiazol-2-yl)amino)-7-methyl-2H-pyrazolo[4,3-b]pyridin-5-yl)piperazin-1-yl)-1-(3-hydroxyazetidin-1-yl) ethanone

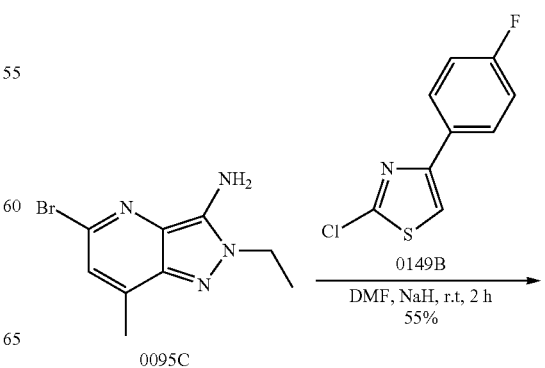

-continued

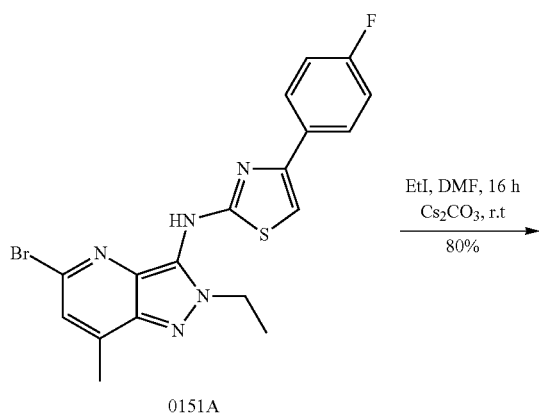

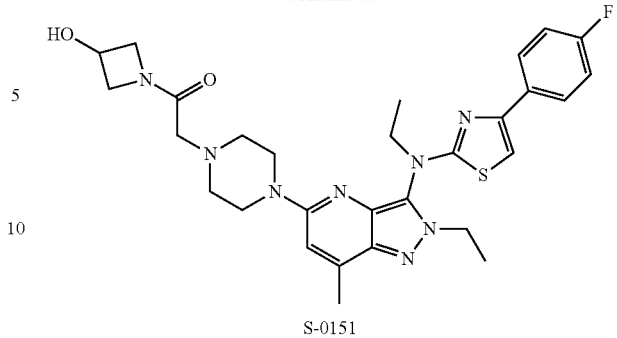

S-0151

Step 1: N-(5-bromo-2-ethyl-7-methyl-2H-pyrazolo[4,3-b]pyridin-3-yl)-4-(4-fluorophenyl) thiazol-2-amine Sodium hydride (60% in oil, 278 mg, 11.6 mmol) was slowly added to a solution of 5-bromo-2-ethyl-7-methyl-2H-pyrazolo[4,3-b]pyridin-3-amine 0095C (300 mg, 1.18 mmol) in N,N-dimethylformamide (8 mL), and the mixture was stirred at room temperature for 15 min. Then 2-chloro-4-(4-fluorophenyl)thiazole 0149B (325 mg, 1.51 mmol) was added, and the mixture was stirred at room temperature for 2 h. The reaction was quenched with water (30 mL) and ethyl acetate (30 mL×5) was added for extraction. The organic phases were washed with saturated brine (10 mL×2), dried over anhydrous sodium sulfate, filtered and concentrated. The residue was purified by flash chromatography (ethyl acetate/petroleum ether=0%-50%) to give N-(5-bromo-2-ethyl-7-methyl-2H-pyrazolo[4,3-b]pyridin-3-yl)-4-(4-fluorophenyl)thiazol-2-amine 0151A (280 mg, 55%) in the form of a yellow solid. LCMS (ESI) [M+H]$^+$=432.0@2.13 min (LC-MS Method A).

Step 2: N-(5-bromo-2-ethyl-7-methyl-2H-pyrazolo[4,3-b]pyridin-3-yl)-N-ethyl-4-(4-fluorophenyl)thiazol-2-amine Cesium carbonate (448 mg, 1.38 mmol) was added to a solution of N-(5-bromo-2-ethyl-7-methyl-2H-pyrazolo[4,3-b]pyridin-3-yl)-4-(4-fluorophenyl)thiazol-2-amine 0151A (200 mg, 0.46 mmol) in N,N-dimethylformamide (10 mL), and the mixture was stirred at room temperature for 30 min. Then iodoethane (215 mg, 1.38 mmol) was added, and the resulting mixture was stirred at room temperature for 2 h. The reaction was quenched with water (10 mL) and ethyl acetate (10 mL×3) was added for extraction. The organic phases were washed with saturated brine (10 mL×3), dried over anhydrous sodium sulfate, filtered and concentrated. The residue was purified by flash chromatography (ethyl acetate/petroleum ether=0%-30%) to give N-(5-bromo-2-ethyl-7-methyl-2H-pyrazolo[4,3-b]pyridin-3-yl)-N-ethyl-4-(4-fluorophenyl)thiazol-2-amine 0151B (170 mg, 80%) in the form of a yellow solid. LCMS (ESI) [M+H]$^+$=460.0@2.02 min (Method A).

Step 3: tert-butyl 4-(2-ethyl-3-(ethyl(4-(4-fluorophenyl)thiazol-2-yl)amino)-7-methyl-2H-pyrazolo[4,3-b]pyridin-5-yl)piperazine-1-carboxylate In a glove box, N-(5-bromo-2-ethyl-7-methyl-2H-pyrazolo[4,3-b]pyridin-3-yl)-N-ethyl-4-(4-fluorophenyl)thiazol-2-amine 0151B (150 mg, 0.33 mmol), tert-butyl piperazine- 1-carboxylate (587 mg, 3.3 mmol), tris(dibenzylideneacetone)dipalladium(0) (30 mg, 0.033 mmol), (±)-2,2'-bis(diphenylphosphino)-1,1'-binaphthyl (19 mg, 0.066 mmol), sodium tert-butoxide (97 mg, 0.99 mmol) and toluene (3 mL) were added to a microwave tube, and the mixture was stirred at 85° C. for 1.5 h, and then cooled to room temperature. Ethyl acetate (20 mL×3) was added for extraction. The organic phases were washed with saturated brine (10 mL×2), dried over anhydrous sodium sulfate, filtered and concentrated. The residue was purified by flash chromatography (ethyl acetate/petroleum ether=0%-40%) to give tert-butyl 4-(2-ethyl-3-(ethyl(4-(4-fluorophenyl)thiazol-2-yl)amino)-7-methyl-2H-pyrazolo[4,3-b]pyridin-5-yl)piperazine-1-carboxylate 0151C (130 mg, 75%) in the form of a yellow solid. LCMS (ESI) [M+H]$^+$=566.3@1.80 min (Method A).

Step 4: N-ethyl-N-(2-ethyl-7-methyl-5-(piperazin-1-yl)-2H-pyrazolo[4,3-b]pyridin-3-yl)-4-(4-fluorophenyl)thiazol-2-amine A mixture of tert-butyl 4-(2-ethyl-3-(ethyl(4-(4-fluorophenyl)thiazol-2-yl)amino)-7-methyl-2H-pyrazolo[4,3-b]pyridin-5-yl)piperazine-1-carboxylate 0151C (130 mg, 0.23 mmol) and hydrogen chloride (4 N in dioxane, 5 mL) was stirred at room temperature for 4 h, concentrated, and added with a saturated sodium bicarbonate solution (20 mL). Dichloromethane (20 mL×3) was added for extraction. The organic phases were washed with saturated brine (10 mL×2), dried over anhydrous sodium sulfate, filtered and concentrated to give N-ethyl-N-(2-ethyl-7-methyl-5-(piperazin-1-yl)-2H-pyrazolo[4,3-b]pyridin-3-yl)-4-(4-fluorophenyl)thiazol-2-amine 0151D (90 mg, 90%) in the form of a yellow solid. LCMS (ESI) [M+H]$^+$=466.2@1.52 min (LC-MS Method A).

Step 5: 2-(4-(2-ethyl-3-(ethyl(4-(4-fluorophenyl)thiazol-2-yl)amino)-7-methyl-2H-pyrazolo[4,3-b]pyridin-5-yl)piperazin-1-yl)-1-(3-hydroxyazetidin-1-yl)ethanone 2-chloro-1-(3-hydroxyazetidin-1-yl)ethanone (37 mg, 0.24 mmol) and potassium carbonate (100 mg, 0.72 mmol) were added to a solution of N-ethyl-N-(2-ethyl-7-methyl-5-(piperazin-1-yl)-2H-pyrazolo[4,3-b]pyridin-3-yl)-4-(4-fluorophenyl)thiazol-2-amine 0151D (90 mg, 0.19 mmol) in acetonitrile (4 mL), and the mixture was heated to reflux for 2 h and concentrated. The residue was purified by flash chromatography (methanol/dichloromethane=0%-8%) to give 2-(4-(2-ethyl-3-(ethyl(4-(4-fluorophenyl)thiazol-2-yl)amino)-7-methyl-2H-pyrazolo[4,3-b]pyridin-5-yl)piperazin-1-yl)-1-(3-hydroxyazetidin-1-yl)ethanone S-0151 (56 mg, 50%) in the form of a white solid. LCMS (ESI) [M+H]$^+$=579.0@8.21 min (Method B); $^1$H NMR (400 MHz, CD$_3$OD) S 7.98-7.85 (m, 2H), 7.12 (t, J=8.8 Hz, 2H), 6.95 (d, J=3.4 Hz, 2H), 4.89-4.42 (m, 2H), 4.26 (ddd, J=18.1, 13.0, 7.3 Hz, 4H), 4.14 (s, 2H), 3.72-3.56 (m, 1H), 4.11-3.09 (m, 4H), 3.35-2.84 (m, 2H), 2.67-2.55 (m, 7H), 1.55 (t, J=7.3 Hz, 3H), 1.37 (dd, J=23.1, 15.9 Hz, 3H).

Effect Example 1 Bioactivity Assay

Preparation and Treatment
Stock Solution Preparation
A 10 mM DMSO stock solution was formulated for each compound. A 30 mM DMSO stock solution was formulated for positive control HA130.

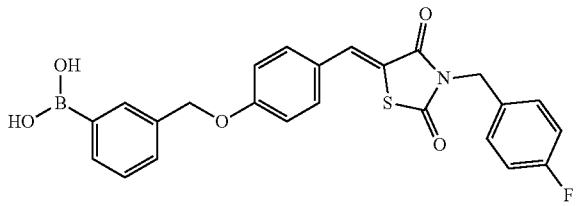

HA130

Preservation
The DMSO stock solutions were stored at room temperature in a desiccator for a short period of time or at −20° C. for a long period of time.
Preparation
All compounds were serially 3-fold diluted in DMSO from 10 μM to the 10th concentration.
A 1000× positive control (10 mM, HA130) and a 1000× negative control (100% DMSO) were prepared.
The plates were shaken for 5 min.
Preparation of 1× Reaction Buffer:
5× reaction buffer and cold water were mixed well in a volume ratio of 1:4.
Preparation of 20 U/mL Choline Oxidase Stock Solution:
1 tube of choline oxide in a kit was dissolved in 1× reaction buffer. The aliquots were frozen at −20° C.
Preparation of 200 U/mL Horseradish Peroxidase (HRP) Stock Solution:
1 tube of HRP in a kit was dissolved in 1 mL of 1× reaction buffer. The aliquots were frozen at −20° C.
Preparation of 20 mM Amplex® Red Reagent (for Detection) Stock Solution
Amplex Red reagent and DMSO were equilibrated at room temperature. 1 tube of Amplex Red reagent in a kit was dissolved in 200 μL of DMSO.
Detection:
a) 2×ATX (2 ng/L), 2×HRP (2 U/L), 2× choline oxidase (0.2 U/mL) were added to 1× reaction buffer.
b) 20 μL of the reaction mixture was added to the plate (PE, 6007270) (refer to step a).
c) 40 nL of diluent was added to the plate using Echo (refer to "Preparation").
d) 2×LPC (16:0) (60 mM) and 2× Amplex® Red (400 M) were prepared using 1× reaction buffer.
e) 20 μL of the mixture was added to the plate (refer to step d).
f) The plate was shaken for 30 s and allowed to stand at room temperature for 30 min.
g) The plate was examined using Envision, and the procedure was as follows: Excitation at 530 nm; and Emission at 590 nm.
Data Analysis:
Formula for Calculating % Inhibition (Percent Inhibition Rate) as Follows:

$$\% \text{ Inhibition} = \left\{1 - \frac{FLU_{cmpd} - \overline{FLU}_{positive}}{\overline{FLU}_{vehicle} - \overline{FLU}_{positive}}\right\} \times 100\%$$

FLU: Fluorescence (fluorescence reading)
$\overline{FLU}_{positive}$: Average fluorescence value in positive control wells (10 μM HA130) in the plate.

FLU$_{vehicle}$: Average fluorescence value in negative control wells (0.1% DMSO) in the plate.

Calculation of IC$_{50}$ and Dose-Response Curve:

IC$_{50}$ of the compounds was calculated via a non-linear regression line (dose-variable slope) fitted using % inhibition and log of compound concentration. The software used was Graphpad 5.0.

$$Y=\text{Bottom}+(\text{Top}-\text{Bottom})/(1+10^{((\text{Log } IC_{50}-X)\times\text{Hill Slope})})$$

X: log of inhibitor concentration
Y: % inhibition

The results are shown in Table 1.

TABLE 1

| Compound No. | IC$_{50}$ (μM) |
|---|---|
| HA130 (positive control) | 0.024 |
| GLPG1690 | 0.245 |
| S-0021 | 0.102 |
| S-0024 | 0.188 |
| S-0025 | 0.088 |
| S-0027 | 0.165 |
| S-0035 | 0.062 |
| S-0040 | 0.767 |
| S-0041 | 0.039 |
| S-0043 | 0.648 |
| S-0044 | 5.531 |
| S-0045 | 0.261 |
| S-0046 | >10 |
| S-0030 | 0.407 |
| S-0058 | 0.040 |
| S-0068 | 0.107 |
| S-0069 | 0.043 |
| S-0070 | 0.036 |
| S-0071 | 0.046 |
| S-0074 | 0.207 |
| S-0075 | 0.088 |
| S-0082 | 0.020 |
| S-0094 | 0.023 |
| S-0095 | 0.119 |
| S-0097 | 0.160 |
| S-0098 | 0.031 |
| S-0104CP | 0.256 |
| S-0105CP | 0.049 |
| S-0117 | 0.012 |
| S-0120 | 0.041 |
| S-0121 | 0.061 |
| S-0122 | 0.025 |
| S-0123 | 0.032 |
| S-0124 | 0.024 |
| S-0125 | 0.178 |
| S-0126 | 0.100 |
| S-0128 | 0.142 |
| S-0129 | 0.264 |
| S-0131A | 0.047 |
| S-0131B | 0.036 |
| S-0134A | 0.020 |
| S-0134B | 0.011 |
| S-0135A | 0.132 |
| S-0140 | 0.325 |
| S-0141 | 0.043 |
| S-0144 | 0.027 |

Effect Example 2. Inhibition of LPA in Mouse Plasma by Compounds

Preparation:

20 mM stock solutions of the compounds were prepared with DMSO and then diluted to 1 mM, which was subjected to a serial 3-fold dilution to yield 10 working solutions.

Collection of Fresh Mouse Plasma:

CD1 mice were euthanized by CO$_2$ inhalation. Approximately 1 mL of whole blood was taken by cardiac puncture, with EDTA-K$_2$ for anticoagulation. The blood was centrifuged at 3220 g for 10 min at 4° C. for plasma collection.

Plasma LPA18:2 Assay:

Reactions were performed in a 96-well plate, and the samples were tested in duplicate. 1 μL of each working solution was added to 100 μL of plasma, with the final concentrations of 10, 3.33, 1.11, 0.37, 0.12, 0.041, 0.014, 0.046, 0.015 and 0.0005 M. 1 μL of DMSO was added to plasma to serve as blank. The samples were incubated in a water bath at 37° C. for 120 min, and 600 μL of 10 μM tolbutamide in methanol was added to terminate the reaction. Tolbutamide also served as an internal standard. After 5 min of vortex mixing, the samples were centrifuged at 3220 g for 45 min at 4° C. to precipitate the protein. 100 μL of the supernatant was transferred to a new plate, diluted with water based on LC-MS response and peak shapes, mixed well and analyzed by LC-MS/MS.

Data Processing:

LPA18:2 was quantified using peak area ratio (LPA18:2/internal standard), requiring no standard curve. For test compounds of different concentrations, LPA data was represented by a percentage decrease of LPA: 100-[((LPA peak area ratio of compound)/(LPA peak area ratio of control))× 100]. IC$_{50}$ was calculated using Graphpad Prism 6.0 software.

The results are shown in Table 2.

TABLE 2

| Compound No. | LPA inhibition in plasma IC$_{50}$ (μM) |
|---|---|
| GLPG1690 | 1.061 |
| S-0021 | 0.790 |
| S-0025 | 0.131 |
| S-0035 | 0.300 |
| S-0041 | 0.036 |
| S-0058 | 0.373 |
| S-0094 | 0.013 |
| S-0095 | 0.309 |
| S-0097 | 0.160 |
| S-0098 | 0.002 |
| S-0105CP | 0.111 |
| S-0117 | 0.038 |
| S-0122 | 0.061 |
| S-0124 | 0.096 |
| S-0128 | 0.057 |
| S-0131A | 0.236 |
| S-0131B | 0.091 |
| S-0129 | 0.268 |
| S-0141 | 0.153 |
| S-0134A | 0.116 |
| S-0134B | 0.098 |
| S-0144 | 0.067 |
| S-0135A | 0.442 |
| S-0135B | 0.167 |
| S-0149 | 0.160 |
| S-0151 | 1.398 |

Effect Example 3. Time-Dependent Inhibition of CYP3A4

SYSTEM for TDI Assay

| CYP | Substrates cocktail | Stock Conc. | Final Concentration (μM) | Selective Inhibitors | Stock Conc. | Final Concentration (μM) | Microsomes Concentration (mg/mL) | Recombinant human enzymes (pmol/mL) | Internal Standards |
|---|---|---|---|---|---|---|---|---|---|
| 3A4 | Midazolam | 10 mM in ACN | 10 | Mifepristone | 10 inM in DMSO | 10 | 1 | — | 1'-OH-Midazolam-$^{13}C_3$ (100×) |

1. Preheating potassium phosphate buffer (K-buffer), pH 7.4: 100 mM potassium phosphate buffer (K-buffer) was prepared by mixing 9.5 mL of solution A with 40.5 mL of solution B, diluting to 500 mL with ultrapure water, and then adjusting to pH 7.4 with KOH or $H_3PO_4$, wherein the solution A (1M potassium dihydrogenphosphate) was prepared by dissolving 136.5 g of potassium dihydrogenphosphate in 1 μL of ultrapure water.

2. Preparation of human liver microsome suspension (1.3 mg/mL, 1.3×, stock: 20 mg/mL): 100 μL of human liver microsome suspension (20 mg/mL) was added into 1438 mL of K-buffer.

3. Preparation of NADPH solution (4.167 mg/mL, 5 mM): 8.3 mg of NADPH was added into 2 mL of buffer.

4. Preparation of substrate solution (1.5× final): 1.5 μL of 10 mM Midazolam was added to 998.5 μL of K-buffer to yield the substrate mixture.

5. Preparation of 100× test compound, reference and blank control solutions: 3 μL of 10 mM stock solution of test compound was added to 27 μL of ACN; 3 μL of positive control stock solution was added to 27 μL of ACN; and 3 μL of DMSO was added to 27 μL of ACN to serve as blank control.

6. Primary preheating system: An NADPH-free system for 0 min incubation: 78 μL of 1.3× human liver microsome solution (step 2) was mixed with 1 μL of the 100× stock solutions of positive control, test compound, or blank control (step 5); A system containing NADPH for 30 min incubation: 78 μL of 1.3× human liver microsome solution (step 2) was mixed with 1 μL of the 100× stock solutions of positive control, test compound, or blank control (step 5).

7. Secondary preheating system: 150 μL of the substrate solution prepared in step 4 was added into a deep well plate together with the NADPH solution from step 3

8. The samples were preheated for 10 min in a 37° C. water bath.

9. Reaction procedure: (1) reaction for 0 min: 21 μL of K-buffer was added to the primary preheating system and mixed well without incubation; 20 μL of the mixture was immediately transferred into the plate of the secondary preheating system; after mixing, the secondary system was incubated in a 37° C. water bath for 15 min, and 60 μL of the reaction mixture was added into 120 μL of acetonitrile containing internal standard to terminate the reaction; and (2) reaction for 30 min: 21 μL of NADPH was added into the primary preheating system for a 30-min incubation after mixing; 20 μL of the mixture was added into the secondary preheating system prior to mixing; the mixture was incubated in a 37° C. water bath for 15 min, and 60 μL of the reaction mixture was added into 120 μL of acetonitrile containing internal standard to terminate the reaction.

10. After termination, the samples were shaken on a shaker at 600 rpm for 10 min and centrifuged at 5594 g for 15 min prior to LC-MS/MS analysis.

The results are shown in Table 3.

TABLE 3

| Compound No. | CYP3A4 TDI % @ 10 μM |
|---|---|
| S-0021 | 1.67 |
| GLPG1690 | 21.57 |
| S-0024 | 4.8 |
| S-0025 | 34.21 |
| S-0035 | −4.84 |
| S-0027 | 42.12 |
| S-0041 | −4.00 |
| S-0043 | 12.38 |
| S-0044 | 15.3 |
| S-0045 | 2.68 |
| S-0046 | 10.38 |
| S-0094 | 20.88 |
| S-0095 | 2.91 |
| S-0097 | 12.51 |
| S-0098 | 37.19 |
| S-0105CP | 0 |
| S-0117 | 15.2 |
| S-0122 | 38.25 |
| S-0124 | 8.74 |
| S-0129 | 14.42 |
| S-0128 | 33.64 |
| S-0134B | 41.82 |

It's concluded that compounds S-0021, S-0024, S-0035, S-0041, S-0043, S-0044, S-0045, S-0046, S-0094, S-0095, S-0097, S-0105CP, S-0117, S-0124 and S-0129 demonstrate no time-dependent inhibition on CYP3A4, and compounds S-0025, S-0027, S-0098, S-0128, S-0134B and S-0122 show weak time-dependent inhibition on CYP3A4.

Although specific embodiments of the present invention have been described above, it will be appreciated by those skilled in the art that these embodiments are merely illustrative and that many changes or modifications can be made to these embodiments without departing from the principles and spirit of the invention. The scope of protection of the invention is therefore defined by the appended claims.

The invention claimed is:

1. A heterocyclic compound of formula I or a pharmaceutically acceptable salt thereof, wherein,

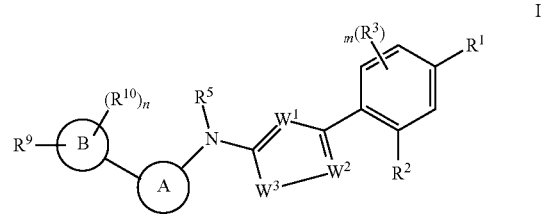

$R^1$ is hydrogen, cyano, halogen, $C_1$-$C_4$ alkyl;

m is 0, 1, 2, or 3, and $R^3$ is independently selected from halogen, cyano, $R^{3-1}$-substituted or unsubstituted $C_1$-$C_4$ alkyl, and $R^{3-2}$-substituted or unsubstituted $C_1$-$C_4$ alkoxy; $R^{3-1}$ and $R^{3-2}$ are each independently selected from halogens;

$W^1$ is =CH— or =N—;

$W^2$ is =CR$^4$— or =N—;

$W^3$ is —O—, —S—, —NH—, —N=CH—, —CH=N—, or —CH=CH—;

when $W^2$ is =N—, $R^2$ is hydrogen, cyano, halogen, $R^{2-1}$-substituted or unsubstituted $C_1$-$C_4$ alkyl, —C(=O)CH$_3$, —C(=O)CF$_3$, —C(=O)OCH$_3$, —C(=O)NH$_2$, or —NHC(=O)CH$_3$; $R^{2-1}$ is independently selected from hydroxy and cyano;

when $W^2$ is =CR$^4$—, one of $R^2$ and $R^4$ is hydrogen, cyano, halogen, $R^{2-2}$-substituted or unsubstituted $C_1$-$C_4$ alkyl, —C(=O)CH$_3$, —C(=O)CF$_3$, —C(=O)OCH$_3$, —C(=O)NH$_2$, or —NHC(=O)CH$_3$, and the other one is hydrogen or $C_1$-$C_4$ alkyl; $R^{2-2}$ is independently selected from hydroxy and cyano;

$R^5$ is $C_1$-$C_4$ alkyl;

ring A is $R^{6-3}$ is selected from hydrogen and $R^{6-1-1}$-substituted or unsubstituted $C_1$-$C_4$ alkyl; and $R^{6-1-1}$ is independently selected from hydroxy, cyano, halogen, and —C(=O)NH$_2$;

$R^{7-3}$ is selected from hydrogen, cyano, halogen, and $C_1$-$C_4$ alkyl;

$R^{8-3}$ is selected from hydrogen, cyano, halogen, and $C_1$-$C_4$ alkyl ring B is a $C_3$-$C_{10}$ cycloalkyl, a $C_4$-$C_7$ cycloalkenyl, a "4-10 membered monocyclic or bicyclic heterocycloalkyl having 1-3 heteroatoms selected from one or more of O, N, and S", or a "4-7 membered heterocycloalkenyl having 1 double bond and 1-3 heteroatoms selected from one or more of O, N, and S";

$R^9$ is -$L^1$-$L^2$-$L^3$;

$L^1$ is a single bond or $C_1$-$C_4$ alkylene;

$L^2$ is —O—, —C(=O)—, —C(=O)O—, —OC(=O)—, —C(=O)—C(=O)—, —C(=O)—C(=O)NR$^{L-3}$—, —NR$^{L-2}$—, —C(=O)NR$^{L-3}$—, —NR$^{L-4}$C(=O)—, —NR$^{L-5}$C(=O)O—, —SO$_2$—, —SO$_2$NR$^{L-6}$— or —NR$^{L-7}$SO$_2$—; $R^{L-1}$, $R^{L-2}$, $R^{L-3}$, $R^{L-4}$, $R^{L-5}$, $R^{L-6}$, and $R^{L-7}$ are each independently selected from hydrogen and $C_1$-$C_4$ alkyl;

$L^3$ is hydrogen, cyano, $R^{L-8}$-substituted or unsubstituted $C_1$-$C_4$ alkyl, amino-substituted or unsubstituted $C_3$-$C_7$ cycloalkyl, $R^{L-9}$-substituted or unsubstituted "4-10 membered monocyclic, bicyclic, or spirocyclic heterocycloalkyl having 1-3 heteroatoms selected from one or more of O, N, and S", $R^{L-10}$-substituted or unsubstituted "5-6 membered heterocycloalkenyl having 1 double bond and 1-3 heteroatoms selected from one or more of O, N, and S", or, $R^{L-11}$-substituted or unsubstituted" 5-6 membered heteroaryl having 1-3 heteroatoms selected from one or more of O, N, and S";

$R^{L-8}$ is independently selected from hydroxy, cyano, halogen, and phenyl;

$R^{L-9}$ is independently selected from oxo, hydroxy, cyano, halogen, phenyl, hydroxy-substituted $C_1$-$C_4$ alkyl, —SO$_2$CH$_3$, —C(=O)R$^{L-9-1}$, and —NR$^{L-9-2}$C(=O)R$^{L-9-3}$; $R^{L-9-1}$ is independently selected from $C_1$-$C_4$ alkyl and $C_1$-$C_4$ alkoxy; $R^{L-9-2}$ is independently selected from hydrogen and $C_1$-$C_4$ alkyl; $R^{L-9-3}$ is independently selected from $C_1$-$C_4$ alkyl;

$R^{L-10}$ is independently selected from oxo, hydroxy, cyano, halogen, phenyl, —SO$_2$CH$_3$, —C(=O)R$^{L-10-1}$, and is independently selected from $C_1$-$C_4$ alkyl and $C_1$-$C_4$ alkoxy; $R^{L-10-2}$ is independently selected from hydrogen and $C_1$-$C_4$ alkyl; $R^{L-10-3}$ is independently selected from $C_1$-$C_4$ alkyl;

$R^{L-11}$ is independently selected from hydroxy, cyano, halogen, phenyl, —SO$_2$CH$_3$, —C(=O)R$^{L-11-1}$, and —NR$^{L-11-2}$(=O)R$^{L-11-3}$; $R^{L-11-1}$ is independently selected from $C_1$-$C_4$ alkyl and $C_1$-$C_4$ alkoxy; $R^{L-11-2}$ is independently selected from hydrogen and $C_1$-$C_4$ alkyl; $R^{L-11-3}$ is independently selected from $C_1$-$C_4$ alkyl; and n is 0, 1, 2, 3, or 4, $R^{10}$ is independently selected from hydroxy, halogen, oxo, and $R^{10-1}$-substituted or unsubstituted $C_1$-$C_4$ alkyl; and $R^{10-1}$ is independently selected from hydroxy, and $C_1$-$C_4$ alkoxy.

2. The heterocyclic compound of formula I or the pharmaceutically acceptable salt thereof according to claim 1, wherein, when $R^1$ is halogen, the halogen is fluorine, chlorine, bromine, or iodine;

and/or, when $R^3$ is halogen, the halogen is fluorine, chlorine, bromine, or iodine;

and/or, when $R^3$ is $R^{3-1}$-substituted $C_1$-$C_4$ alkyl, there are one or more $R^{3-1}$, and in case that there are a plurality of $R^{3-1}$, the plurality of $R^{3-1}$ are the same or different;

and/or, when $R^3$ is $R^{3-1}$-substituted or unsubstituted $C_1$-$C_4$ alkyl, the $C_1$-$C_4$ alkyl is methyl, ethyl, n-propyl, isopropyl, n-butyl, isobutyl, sec-butyl, or tert-butyl;

and/or, when $R^3$ is $R^{3-2}$-substituted $C_1$-$C_4$ alkoxy, there are one or more $R^{3-2}$, and in case that there are a plurality of $R^{3-2}$, the plurality of $R^{3-2}$ are the same or different;

and/or, when $W^2$ is =N— and $R^2$ is halogen, the halogen is fluorine, chlorine, bromine, or iodine;

and/or, when $R^2$ is $R^{2-1}$-substituted $C_1$-$C_4$ alkyl, there are one or more $R^{2-1}$, and in case that there are a plurality of $R^{2-1}$, the plurality of $R^{2-1}$ are the same or different;

and/or, when $R^2$ is $R^{2-1}$-substituted or unsubstituted $C_1$-$C_4$ alkyl, the $C_1$-$C_4$ alkyl is methyl, ethyl, n-propyl, isopropyl, n-butyl, isobutyl, sec-butyl, or tert-butyl;

and/or, when $W^2$ is =CR$^4$— and one of $R^2$ and $R^4$ is halogen, the halogen is fluorine, chlorine, bromine, or iodine;

and/or, when one of $R^2$ and $R^4$ is $R^{2-2}$-substituted $C_1$-$C_4$ alkyl, there are one or more $R^{2-2}$, and in case that there are a plurality of $R^{2-2}$, the plurality of $R^{2-2}$ are the same or different;

and/or, when $R^5$ is $C_1$-$C_4$ alkyl, the $C_1$-$C_4$ alkyl is methyl, ethyl, n-propyl, isopropyl, n-butyl, isobutyl, sec-butyl, or tert-butyl;

and/or, when $R^{6-3}$ is selected from $R^{6-1-1}$-substituted $C_1$-$C_4$ alkyl, there are one or more $R^{6-1-1}$, and in case that there are a plurality of $R^{6-1-1}$, the plurality of $R^{6-1-1}$ are the same or different;

and/or, when $R^{6-3}$ is selected from $R^{6-1-1}$-substituted or unsubstituted $C_1$-$C_4$ alkyl, the $C_1$-$C_4$ alkyl is methyl, ethyl, n-propyl, isopropyl, n-butyl, isobutyl, sec-butyl, or tert-butyl;

and/or, when $R^{7-3}$ is selected from halogen, the halogen is fluorine, chlorine, bromine, or iodine;

and/or, when $R^{7-3}$ is selected from $C_1$-$C_4$ alkyl, the $C_1$-$C_4$ alkyl is methyl, ethyl, n-propyl, isopropyl, n-butyl, isobutyl, sec-butyl, or tert-butyl;

and/or, when $R^{8-3}$ is selected from halogen, the halogen is fluorine, chlorine, bromine, or iodine;

and/or, when $R^{8-3}$ is selected from $C_1$-$C_4$ alkyl, the $C_1$-$C_4$ alkyl is methyl, ethyl, n-propyl, isopropyl, n-butyl, isobutyl, sec-butyl, or tert-butyl;

and/or, when ring B is $C_3$-$C_{10}$ cycloalkyl, the $C_3$-$C_{10}$ cycloalkyl is $C_3$-$C_6$ cycloalkyl;

and/or, when ring B is $C_4$-$C_7$ cycloalkenyl, the $C_4$-$C_7$ cycloalkenyl is $C_5$-$C_6$ cycloalkenyl;

and/or, when ring B is "4-10 membered monocyclic or bicyclic heterocycloalkyl having 1-3 heteroatoms selected from one or more of O, N, and S", the "4-10 membered monocyclic or bicyclic heterocycloalkyl having 1-3 heteroatoms selected from one or more of O, N, and S" is "4-7 membered monocyclic heterocycloalkyl having 1-2 heteroatoms selected from one or more of O, N, and S";

and/or, when ring B is "4-10 membered monocyclic or bicyclic heterocycloalkyl having 1-3 heteroatoms selected from one or more of O, N, and S", the "4-10 membered monocyclic or bicyclic heterocycloalkyl having 1-3 heteroatoms selected from one or more of O, N, and S" is linked to ring A via a carbon atom or a nitrogen atom;

and/or, when ring B is "4-7 membered heterocycloalkenyl having 1 double bond and 1-3 heteroatoms selected from one or more of O, N, and S", the "4-7 membered heterocycloalkenyl having 1 double bond and 1-3 heteroatoms selected from one or more of O, N, and S" is "5-6 membered heterocycloalkenyl having 1 double bond and 1-2 heteroatoms selected from one or more of O, N, and S";

and/or, when ring B is "4-7 membered heterocycloalkenyl having 1 double bond and 1-3 heteroatoms selected from one or more of O, N, and S", the "4-7 membered heterocycloalkenyl having 1 double bond and 1-3 heteroatoms selected from one or more of O, N, and S" is linked to ring A via a carbon atom or a nitrogen atom;

and/or, $R^9$ is linked to a carbon atom or a nitrogen atom of ring B;

and/or, when $L^1$ is $C_1$-$C_4$ alkylene, the $C_1$-$C_4$ alkylene is —$CH_2$—, —$CH_2CH_2$—, —$CH(CH_3)$—, —$CH_2CH_2CH_2$—, or —$CH_2CH(CH_3)$—;

and/or, when $R^{L-1}$, $R^{L-2}$, $R^{L-3}$, $R^{L-4}$, $R^{L-5}$, $R^{L-6}$, and are each independently selected from $C_1$-$C_4$ alkyl, the $C_1$-$C_4$ alkyl is methyl, ethyl, n-propyl, isopropyl, n-butyl, isobutyl, sec-butyl, or tert-butyl;

and/or, when $L^3$ is $R^{L-8}$-substituted $C_1$-$C_4$ alkyl, there are one or more $R^{L-8}$, and in case that there are a plurality of $R^{L-8}$, the plurality of $R^{L-8}$ are the same or different;

and/or, when $L^3$ is $R^{L-8}$-substituted or unsubstituted $C_1$-$C_4$ alkyl, the $C_1$-$C_4$ alkyl is methyl, ethyl, n-propyl, isopropyl, n-butyl, isobutyl, sec-butyl, or tert-butyl;

and/or, when $L^3$ is amino-substituted $C_3$-$C_7$ cycloalkyl, there are one or more aminos;

and/or, when $L^3$ is "4-10 membered monocyclic, bicyclic, or spirocyclic heterocycloalkyl having 1-3 heteroatoms selected from one or more of O, N, and S" which is substituted with $R^{L-9}$, there are one or more $R^{L-9}$, and in case that there are a plurality of $R_{L-9}$, the plurality of $R^{L-9}$ are the same or different;

and/or, when $L^3$ is "4-10 membered monocyclic, bicyclic, or spirocyclic heterocycloalkyl having 1-3 heteroatoms selected from one or more of O, N, and S" which is substituted with $R^{L-9}$, $R^{L-9}$ is linked to a carbon atom or a nitrogen atom of the heterocycloalkyl;

and/or, when $L^3$ is "4-10 membered monocyclic, bicyclic, or spirocyclic heterocycloalkyl having 1-3 heteroatoms selected from one or more of O, N, and S" which is substituted or unsubstituted with $R^{L-9}$, the "4-10 membered monocyclic, bicyclic, or spirocyclic heterocycloalkyl having 1-3 heteroatoms selected from one or more of O, N, and S" is "4-10 membered monocyclic heterocycloalkyl having 1-2 heteroatoms selected from one or more of O, N, and S";

and/or, when $L^3$ is "4-10 membered monocyclic, bicyclic, or spirocyclic heterocycloalkyl having 1-3 heteroatoms selected from one or more of O, N, and S" which is substituted or unsubstituted with $R^{L-9}$, the heterocycloalkyl is linked to $L^2$ via a carbon atom or a nitrogen atom;

and/or, when $R^{L-9}$ is halogen, the halogen is fluorine, chlorine, bromine, or iodine;

and/or, when $R^{L-9}$ is independently selected from hydroxy-substituted $C_1$-$C_4$ alkyl, there are one or more hydroxys;

and/or, when $R^{L-9}$ is independently selected from hydroxy-substituted $C_1$-$C_4$ alkyl, the $C_1$-$C_4$ alkyl is methyl, ethyl, n-propyl, isopropyl, n-butyl, isobutyl, sec-butyl, or tert-butyl;

and/or, when $L^3$ is "5-6 membered heterocycloalkenyl having 1 double bond and 1-3 heteroatoms selected from one or more of O, N, and S" which is substituted with $R^{L-10}$, there are one or more $R^{L-10}$, and in case that there are a plurality of $R^{L-10}$, the plurality of $R^{L-10}$ are the same or different;

and/or, when $L^3$ is "5-6 membered heterocycloalkenyl having 1 double bond and 1-3 heteroatoms selected from one or more of O, N, and S" which is substituted with $R^{L-10}$, $R^{L-10}$ is linked to a carbon atom or a nitrogen atom of the heterocycloalkenyl;

and/or, when $L^3$ is "5-6 membered heterocycloalkenyl having 1 double bond and 1-3 heteroatoms selected from one or more of O, N, and S" which is substituted or unsubstituted with $R^{L-10}$, the "5-6 membered heterocycloalkenyl having 1 double bond and 1-3 heteroatoms selected from one or more of O, N, and S" is "5-6 membered heterocycloalkenyl having 1 double bond and 1-2 heteroatoms selected from one or more of O, N, and S";

and/or, when $L^3$ is "5-6 membered heterocycloalkenyl having 1 double bond and 1-3 heteroatoms selected from one or more of O, N, and S" which is substituted or unsubstituted with $R^{L-10}$, the heterocycloalkenyl is linked to $L^2$ via a carbon atom or a nitrogen atom;

and/or, when $L^3$ is "5-6 membered heteroaryl having 1-3 heteroatoms selected from one or more of O, N, and S" which is substituted with $R^{L-11}$, there are one or more $R^{L-11}$, and in case that there are a plurality of $R^{L-11}$, the plurality of $R^{L-11}$ are the same or different;

and/or, when $L^3$ is "5-6 membered heteroaryl having 1-3 heteroatoms selected from one or more of O, N, and S" which is substituted or unsubstituted with $R^{L-11}$, the "5-6 membered heteroaryl having 1-3 heteroatoms selected from one or more of O, N, and S" is "5-6 membered heteroaryl having 1-2 heteroatoms selected from one or more of O, N, and S";

and/or, when $L^3$ is "5-6 membered heteroaryl having 1-3 heteroatoms selected from one or more of O, N, and S" which is substituted or unsubstituted with $R^{L-11}$, the "5-6 membered heteroaryl having 1-3 heteroatoms selected from one or more of O, N, and S" is linked to $L^2$ via a carbon atom or a nitrogen atom;

and/or, when $R^{10}$ is independently selected from halogens, the halogen is fluorine, chlorine, bromine, or iodine;

and/or, when $R^{10}$ is independently selected from $R^{10-1}$-substituted $C_1$-$C_4$ alkyl, there are one or more $R^{10-1}$, and in case that there are a plurality of $R^{10-1}$, the plurality of $R^{10-1}$ are the same or different;

and/or, when $R^{10}$ is independently selected from $R^{10-1}$-substituted or unsubstituted $C_1$-$C_4$ alkyl, the $C_1$-$C_4$ alkyl is methyl, ethyl, n-propyl, isopropyl, n-butyl, isobutyl, sec-butyl, or tert-butyl;

and/or, $R^{10}$ is independently located at the ortho, meta or para position relative to ring A;

and/or, $R^{10}$ is linked to a carbon atom or a nitrogen atom of ring B.

3. The heterocyclic compound of formula I or the pharmaceutically acceptable salt thereof according to claim 2, wherein, when $R^1$ is halogen, the halogen is fluorine;

and/or, when $R^3$ is halogen, the halogen is fluorine;

and/or, when $R^3$ is $R^{3-1}$-substituted or -unsubstituted $C_1$-$C_4$ alkyl, the $C_1$-$C_4$ alkyl is methyl;

and/or, when $W^2$ is =N— and $R^2$ is halogen, the halogen is fluorine;

and/or, when $R^2$ is $R^{2-1}$-substituted or -unsubstituted $C_1$-$C_4$ alkyl, the $C_1$-$C_4$ alkyl is methyl;

and/or, when $W^2$ is =$CR^4$—, and one of $R^2$ and $R^4$ is halogen, the halogen is fluorine;

and/or, when $R^5$ is $C_1$-$C_4$ alkyl, the $C_1$-$C_4$ alkyl is methyl or ethyl;

and/or, when $R^{6-3}$ is selected from $R^{6-1-1}$-substituted or unsubstituted $C_1$-$C_4$ alkyl, the $C_1$-$C_4$ alkyl is methyl, ethyl, or isopropyl;

and/or, when $R^{7-3}$ is selected from halogens, the halogen is fluorine;

and/or, when $R^{7-3}$ is selected from $C_1$-$C_4$ alkyl, the $C_1$-$C_4$ alkyl is methyl;

and/or, when $R^{8-3}$ is selected from halogens, the halogen is fluorine;

and/or, when $R^{8-3}$ is selected from $C_1$-$C_4$ alkyl, the $C_1$-$C_4$ alkyl is methyl;

and/or, when ring B is $C_3$-$C_{10}$ cycloalkyl, the $C_3$-$C_{10}$ cycloalkyl is $C_5$-$C_6$ cycloalkyl;

and/or, when ring B is $C_4$-$C_7$ cycloalkenyl, the $C_4$-$C_7$ cycloalkenyl is cyclohexenyl;

and/or, when ring B is "4-10 membered monocyclic or bicyclic heterocycloalkyl having 1-3 heteroatoms selected from one or more of O, N, and S", the "4-10 membered monocyclic or bicyclic heterocycloalkyl having 1-3 heteroatoms selected from one or more of O, N, and S" is "5-6 membered monocyclic heterocycloalkyl having 1-2 heteroatoms selected from one or more of O, N, and S";

and/or, when ring B is "4-10 membered monocyclic or bicyclic heterocycloalkyl having 1-3 heteroatoms selected from one or more of O, N, and S", the "4-10 membered monocyclic or bicyclic heterocycloalkyl having 1-3 heteroatoms selected from one or more of O, N, and S" is linked to ring A via a nitrogen atom;

and/or, when ring B is "4-7 membered heterocycloalkenyl having 1 double bond and 1-3 heteroatoms selected from one or more of O, N, and S", the "4-7 membered heterocycloalkenyl having 1 double bond and 1-3 heteroatoms selected from one or more of O, N, and S" is

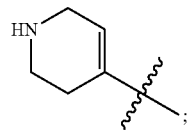

and/or, $R^9$ is linked to a nitrogen atom of ring B;

and/or, when $L^1$ is $C_1$-$C_4$ alkylene, the $C_1$-$C_4$ alkylene is —$CH_2$—;

and/or, when $R^{L-1}$, $R^{L-2}$, $R^{L-3}$, $R^{L-4}$, $R^{L-5}$, $R^{L-6}$, and are each independently selected from $C_1$-$C_4$ alkyl, the $C_1$-$C_4$ alkyl is methyl;

and/or, when $L^3$ is $R^{L-8}$-substituted or unsubstituted $C_1$-$C_4$ alkyl, the $C_1$-$C_4$ alkyl is methyl or ethyl;

and/or, when $L^3$ is "4-10 membered monocyclic, bicyclic or spirocyclic heterocycloalkyl having 1-3 heteroatoms selected from one or more of O, N, and S" which is substituted with $R^{L-9}$, there are one or more $R^{L-9}$, such as 2, 3, or 4 $R^{L-9}$;

and/or, when $L^3$ is "4-10 membered monocyclic, bicyclic or spirocyclic heterocycloalkyl having 1-3 heteroatoms selected from one or more of O, N, and S" which is substituted with $R^{L-9}$, and $R^{L-9}$ is linked to a carbon atom in the heterocycloalkyl, the carbon atom in the heterocycloalkyl, linked to $R^{L-9}$, is independently in R or S configuration;

and/or, when $L^3$ is "4-10 membered monocyclic, bicyclic, or spirocyclic heterocycloalkyl having 1-3 heteroatoms selected from one or more of O, N and S" which is substituted or unsubstituted with $R^{L-9}$, the "4-10 membered monocyclic, bicyclic, or spirocyclic heterocycloalkyl having 1-3 heteroatoms selected from one or more of O, N, and S" is "4-6 membered monocyclic heterocycloalkyl having 1-2 heteroatoms selected from one or more of O, N, and S";

and/or, when $L^3$ is "4-10 membered monocyclic, bicyclic, or spirocyclic heterocycloalkyl having 1-3 heteroatoms selected from one or more of O, N, and S" which is substituted or unsubstituted with $R^{L-9}$, the heterocycloalkyl is linked to $L^2$ via a nitrogen atom;

and/or, when $R^{L-9}$ is independently selected from halogens, the halogen is fluorine;

and/or, when $R^{L-9}$ is independently selected from hydroxy-substituted $C_1$-$C_4$ alkyl, the hydroxy-substituted $C_1$-$C_4$ alkyl is hydroxymethyl;

and/or, when $L^3$ is "5-6 membered heterocycloalkenyl having 1 double bond and 1-3 heteroatoms selected from one or more of O, N, and S" which is substituted with $R^{L-10}$, and $R^{L-10}$ is linked to a carbon atom in the heterocycloalkenyl, the carbon in the heterocycloalkenyl, linked to $R^{L-10}$, is independently in R configuration or S configuration;

and/or, when $L^3$ is "5-6 membered heterocycloalkenyl having 1 double bond and 1-3 heteroatoms selected from one or more of O, N, and S" which is substituted or unsubstituted with $R^{L-10}$, the heterocycloalkenyl is linked to $L^2$ via a nitrogen atom;

and/or, when $L^3$ is "5-6 membered heteroaryl having 1-3 heteroatoms selected from one or more of O, N, and S"

which is substituted or unsubstituted with $R^{L-11}$, the "5-6 membered heteroaryl having 1-3 heteroatoms selected from one or more of O, N and S" is linked to $L^2$ via a nitrogen atom;

and/or, when $R^{10}$ is independently selected from halogens, the halogen is fluorine;

and/or, when $R^{10}$ is independently selected from $R^{10-1}$-substituted or unsubstituted $C_1$-$C_4$ alkyl, the $C_1$-$C_4$ and/or, $R^{10}$ is linked to a carbon atom in ring B.

4. The heterocyclic compound of formula I or the pharmaceutically acceptable salt thereof according to claim 3, wherein, when $R^5$ is $C_1$-$C_4$ alkyl, the $C_1$-$C_4$ alkyl is ethyl;

and/or, when $R^{6-3}$ is selected from $R^{6-1-1}$-substituted or unsubstituted $C_1$-$C_4$ alkyl, the $C_1$-$C_4$ alkyl is methyl or ethyl;

and/or, when ring B is $C_4$-$C_7$ cycloalkenyl, the $C_4$-$C_7$ cycloalkenyl is

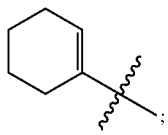

and/or, when ring B is "4-10 membered monocyclic or bicyclic heterocycloalkyl having 1-3 heteroatoms selected from one or more of O, N, and S", the "4-10 membered monocyclic or bicyclic heterocycloalkyl having 1-3 heteroatoms selected from one or more of O, N, and S" is

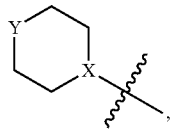

wherein X is N or CH, Y is NH or $CH_2$, but X and Y are not both carbon;

and/or, when $L^3$ is "4-10 membered monocyclic, bicyclic, or spirocyclic heterocycloalkyl having 1-3 heteroatoms selected from one or more of O, N, and S" which is substituted or unsubstituted with $R^{L-9}$, the "4-10 membered monocyclic, bicyclic, or spirocyclic heterocycloalkyl having 1-3 heteroatoms selected from one or more of O, N, and S" is

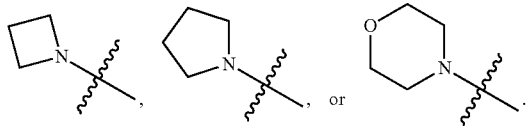 [SMILES: *N1CCC1 ; *N1CCCC1 ; *N1CCOCC1]

5. The heterocyclic compound of formula I or the pharmaceutically acceptable salt thereof according to claim 4, wherein, when ring B is "4-10 membered monocyclic or bicyclic heterocycloalkyl having 1-3 heteroatoms selected from one or more of O, N, and S", the "4-10 membered monocyclic or bicyclic heterocycloalkyl having 1-3 heteroatoms selected from one or more of O, N, and S" is

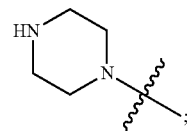 [SMILES: *N1CCNCC1]

and/or, when $L^3$ is "4-10 membered monocyclic, bicyclic, or spirocyclic heterocycloalkyl having 1-3 heteroatoms selected from one or more of O, N, and S" which is substituted or unsubstituted with $R^{L-9}$, the "4-10 membered monocyclic, bicyclic, or spirocyclic heterocycloalkyl having 1-3 heteroatoms selected from one or more of O, N, and S" which is substituted with $R^{L-9}$ is

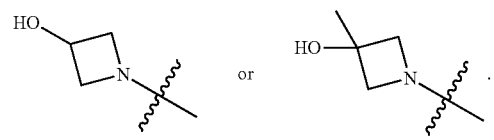

6. The heterocyclic compound of formula I or the pharmaceutically acceptable salt thereof according to claim 1, wherein ring A is

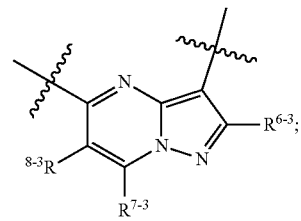

$R^{6-3}$ is $C_1$-$C_4$ alkyl; $R^{7-3}$ is hydrogen, halogen, or $C_1$-$C_4$ alkyl; and $R^{8-3}$ is hydrogen.

7. The heterocyclic compound of formula I or the pharmaceutically acceptable salt thereof according to claim 1, wherein, $R^1$ is halogen;

and/or, m is 0 or 1, and $R^3$ is halogen;

and/or, $W^1$ is =N—;

and/or, $W^2$ is =$CR^4$—;

and/or, when $W^2$ is =$CR^4$—, one of $R^2$ and $R^4$ is hydrogen or cyano, and the other is hydrogen;

and/or, $W^3$ is —O—, —S—, or —NH—;

and/or, $R^5$ is methyl, or ethyl;

and/or, ring A is

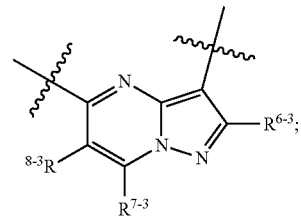

$R^{6-3}$ is $C_1$-$C_4$ alkyl; $R^{7-3}$ is selected from hydrogen, halogen, and $C_1$-$C_4$ alkyl; $R^{8-3}$ is hydrogen;

and/or, ring B is "4-10 membered monocyclic or bicyclic heterocycloalkyl having 1-3 heteroatoms selected from one or more of O, N, and S"; n is 0 or 1, $R^{10}$ is oxo or $R^{10-1}$-substituted or unsubstituted $C_1$-$C_4$ alkyl, and $R^{10-1}$ is independently selected from halogens;

and/or, $L^1$ is $C_1$-$C_4$ alkylene;

and/or, $L^2$ is —C(=O)—, —C(=O)—C(=O)—, or —SO$_2$—;

and/or, $L^3$ is $R^{L-8}$-substituted or unsubstituted $C_1$-$C_4$ alkyl, or "4-10 membered monocyclic, bicyclic or spirocyclic heterocycloalkyl having 1-3 heteroatoms selected from one or more of O, N, and S" which is substituted or unsubstituted with $R^{L-9}$; $R^{L-8}$ is independently selected from hydroxy, and $R^{L-9}$ is independently selected from hydroxy and $C_1$-$C_4$ alkyl.

8. The heterocyclic compound of formula I or the pharmaceutically acceptable salt thereof according to claim 7, wherein, $R^1$ is halogen;

and/or, when $W^2$ is =CR$^4$—, one of $R^2$ and $R^4$ is cyano and the other is hydrogen;

and/or, $W^3$ is —S—;

and/or, $R^5$ is ethyl;

and/or, ring A is

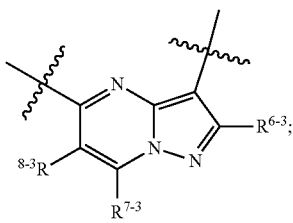

$R^{6-3}$ is $C_1$-$C_4$ alkyl; $R^{7-3}$ is selected from hydrogen, fluorine, and $C_1$-$C_4$ alkyl; $R^{8-3}$ is hydrogen;

and/or, ring B is "4-7 membered monocyclic heterocycloalkyl having 1-2 heteroatoms selected from one or more of O, N, and S"; n is 0 or 1, $R^{10}$ is $R^{10-1}$-substituted or unsubstituted $C_1$-$C_4$ alkyl, and $R^{10-1}$ is independently selected from halogens;

and/or, $L^2$ is —C(=O)—;

and/or, $L^3$ is "4-10 membered monocyclic, bicyclic, or spirocyclic heterocycloalkyl having 1-3 heteroatoms selected from one or more of O, N, and S" which is substituted or unsubstituted with $R^{L-9}$; $R^{L-9}$ is independently selected from hydroxy and $C_1$-$C_4$ alkyl.

9. The heterocyclic compound of formula I or the pharmaceutically acceptable salt thereof according to claim 8, wherein, when $W^2$ is =CR$^4$—, $R^2$ is hydrogen, and $R^4$ is cyano;

and/or, ring A is

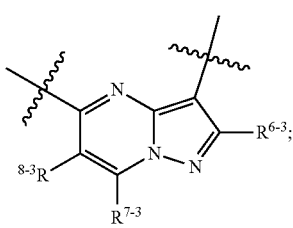

$R^{6-3}$ is $C_1$-$C_4$ alkyl; $R^{7-3}$ is selected from hydrogen, fluorine, and $C_1$-$C_4$ alkyl; and $R^{8-3}$ is hydrogen;

and/or, $L^3$ is "4-6 membered monocyclic heterocycloalkyl having 1-2 heteroatoms selected from one or more of O, N, and S" which is substituted or unsubstituted with $R^{L-9}$; $R^{L-9}$ is independently selected from hydroxy and $C_1$-$C_4$ alkyl.

10. The heterocyclic compound of formula I or the pharmaceutically acceptable salt thereof according to claim 1, wherein, $R^1$ is halogen, halogen-substituted $C_1$-$C_4$ alkyl, or halogen-substituted $C_1$-$C_4$ alkoxy;

m is 0 or 1, and $R^3$ is halogen;

$W^1$ is =N—;

$W^2$ is =CR$^4$—;

$W^3$ is —O—, —S—, or —NH—;

when $W^2$ is =CR$^4$—, one of $R^2$ and $R^4$ is cyano, and the other is hydrogen;

$R^5$ is $C_1$-$C_4$ alkyl;

ring A is

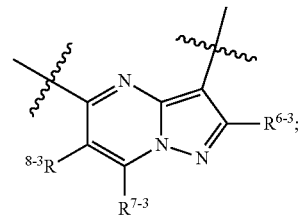

$R^{6-3}$ is $C_1$-$C_4$ alkyll;

$R^{7-3}$ is selected from hydrogen, fluorine, and $C_1$-$C_4$ alkyl;

$R^{8-3}$ is hydrogen;

ring B is "4-10 membered monocyclic or bicyclic heterocycloalkyl having 1-3 heteroatoms selected from one or more of O, N, and S";

$R^9$ is -$L^1$-$L^2$-$L^3$;

$L^1$ is $C_1$-$C_4$ alkylene;

$L^2$ is —C(=O)—;

$L^3$ is "4-10 membered monocyclic, bicyclic, or spirocyclic heterocycloalkyl having 1-3 heteroatoms selected from one or more of O, N, and S" which is substituted or unsubstituted with $R^{L-9}$;

$R^{L-9}$ is hydroxy; and n is 0 or 1, $R^{10}$ is unsubstituted $C_1$-$C_4$ alkyl.

11. The heterocyclic compound of formula I or the pharmaceutically acceptable salt thereof according to claim 1, wherein, $R^1$ is halogen;

m is 0 or 1, and $R^3$ is halogen;

$W^1$ is =N—;

$W^2$ is =CR$^4$—;

$W^3$ is —O—, —S—, or —NH—;

when $W^2$ is =CR$^4$—, one of $R^2$ and $R^4$ is cyano, and the other is hydrogen;

$R^5$ is methyl, or ethyl;

ring A is

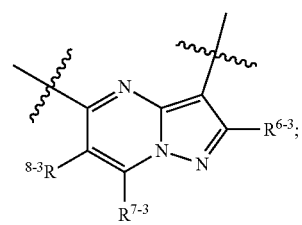

$R^{6-3}$ is $C_1$-$C_4$ alkyl;

$R^{7-3}$ is selected from hydrogen, fluorine, and $C_1$-$C_4$ alkyl;

$R^{8-3}$ is hydrogen;

ring B is "4-7 membered monocyclic heterocycloalkyl having 1-2 heteroatoms selected from one or more of O, N, and S";
$R^9$ is $-L^1-L^2-L^3$;
$L^1$ is $C_1$-$C_4$ alkylene;
$L^2$ is $-C(=O)-$;
$L^3$ is "4-6 membered monocyclic heterocycloalkyl having 1-2 heteroatoms selected from one or more of O, N, and S" which is substituted or unsubstituted with $R^{L-9}$;
$R^{L-9}$ is independently selected from hydroxy and $C_1$-$C_4$ alkyl; and
n is 0 or 1, $R^{10}$ is unsubstituted $C_1$-$C_4$ alkyl.

12. The heterocyclic compound of formula I or the pharmaceutically acceptable salt thereof according to claim 1, wherein $R^1$ is cyano or halogen;
m is 0;
$W^1$ is $=N-$;
$W^2$ is $=CR^4-$ or $=N-$;
$W^3$ is $-S-$;
when $W^2$ is $=N-$, $R^2$ is hydrogen, cyano, or methyl;
when $W^2$ is $=CR^4-$, "$R^4$ is cyano and $R^2$ is hydrogen", or, "$R^4$ is hydrogen and $R^2$ is cyano";
$R^5$ is $C_1$-$C_4$ alkyl;
ring A is

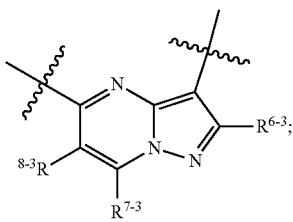

$R^{6-3}$ is $R^{6-1-1}$-substituted or unsubstituted $C_1$-$C_4$ alkyl, and $R^{6-1-1}$ is independently selected from hydroxy, cyano, halogen, and $-C(=O)NH_2$;
$R^{7-3}$ is hydrogen, fluorine, or $C_1$-$C_4$ alkyl;
$R^{8-3}$ is hydrogen or fluorine;
ring B is "4-10 membered monocyclic or bicyclic heterocycloalkyl having 1-3 heteroatoms selected from one or more of O, N, and S";
$R^9$ is $-L^1-L^2-L^3$;
$L^1$ is $C_1$-$C_4$ alkylene;
$L^2$ is $-C(=O)-$;
$L^3$ is "4-10 membered monocyclic, bicyclic, or spirocyclic heterocycloalkyl having 1-3 heteroatoms selected from one or more of O, N, and S" which is substituted or unsubstituted with $R^{L-9}$;
$R^{L-9}$ is independently selected from oxo, hydroxy, cyano, halogen, phenyl, hydroxy-substituted $C_1$-$C_4$ alkyl, $-SO_2CH_3$, $-C(=O)R^{L-9-1}$, and $-NR^{L-9-2}C(=O)R^{L-9-3}$; $R^{L-9-1}$ is independently selected from $C_1$-$C_4$ alkyl and $C_1$-$C_4$ alkoxy, $R^{L-9-2}$ is independently selected from hydrogen and $C_1$-$C_4$ alkyl, and $R^{L-9-3}$ is independently selected from $C_1$-$C_4$ alkyl; and
n is 0.

13. A heterocyclic compound of formula I or a pharmaceutically acceptable salt thereof, wherein, the heterocyclic compound of formula I is any one of the following compounds:

S-0035: 2-((2-ethyl-5-(4-(2-(3-hydroxyazetidin-1-yl)-2-oxoethyl)piperazin-1-yl)-7-methylpyrazolo[1,5-a]pyrimidin-3-yl)(methyl)amino)-4-(4-fluorophenyl)thiazole-5-carbonitrile S-0068: 4-(3,4-difluorophenyl)-2-((2-ethyl-5-(4-(2-(3-hydroxyazetidin-1-yl)-2-oxoethyl) piperazin-1-yl)-7-methylpyrazolo[1,5-a]pyrimidin-3-yl)(methyl)amino) thiazole-5-carbonitrile S-0069: 2-(ethyl(2-ethyl-5-(4-(2-(3-hydroxyazetidin-1-yl)-2-oxoethyl)piperazine-1-yl)-7-methylpyrazolo[1,5-a]pyrimidin-3-yl)amino)-4-(4-fluorophenyl)thiazole-5-carbonitrile S-0070: (R)-2-((2-ethyl-5-(4-(2-(3-hydroxyazetidin-1-yl)-2-oxoethyl)-2-methylpiperazin-1-yl)-7-methylpyrazolo[1,5-a]pyrimidin-3-yl)(methyl)amino)-4-(4-fluorophenyl)thiazole-5-carbonitrile S-0071: (S)-2-((2-ethyl-5-(4-(2-(3-hydroxyazetidin-1-yl)-2-oxoethyl)-2-methylpiperazin-1-yl)-7-methylpyrazolo[1,5-a]pyrimidin-3-yl)(methyl)amino)-4-(4-fluorophenyl)thiazole-5-carbonitrile S-0074: (R)-2-((2-ethyl-5-(4-(2-(3-hydroxyazetidin-1-yl)-2-oxoethyl)-3-methylpiperazin-1-yl)-7-methylpyrazolo[1,5-a]pyrimidin-3-yl)(methyl)amino)-4-(4-fluorophenyl)thiazole-5-carbonitrile S-0075: (S)-2-((2-ethyl-5-(4-(2-(3-hydroxyazetidin-1-yl)-2-oxoethyl)-3-methylpiperazin-1-yl)-7-methylpyrazolo[1,5-a]pyrimidin-3-yl)(methyl)amino)-4-(4-fluorophenyl)thiazole-5-carbonitrile S-0041: 2-((2-ethyl-5-(4-(2-(3-hydroxyazetidin-1-yl)-2-oxoethyl)piperazin-1-yl)pyrazolo [1,5-a]pyrimidin-3-yl)(methyl)amino)-4-(4-fluorophenyl)thiazole-5-carbonitrile S-0082: 2-(ethyl(2-ethyl-5-(4-(2-(3-hydroxyazetidin-1-yl)-2-oxoethyl)piperazin-1-yl) pyrazolo[1,5-a]pyrimidin-3-yl)amino)-4-(4-fluorophenyl)thiazole-5-carbonitrile S-0104CP: 2-((2-ethyl-5-(4-(2-(3-hydroxyazetidin-1-yl)-2-oxoethyl)-3-oxopiperazin-1-yl)pyrazolo[1,5-a]pyrimidin-3-yl)(methyl)amino)-4-(4-fluorophenyl)thiazole-5-carbonitrile S-0120: 2-((2-ethyl-5-(4-(2-(3-hydroxy-3-methylazetidin-1-yl)-2-oxoethyl)piperazin-1-yl)pyrazolo[1,5-a]pyrimidin-3-yl)(methyl)amino)-4-(4-fluorophenyl)thiazole-5-carbonitrile; and S-0121: 4-(3,4-difluorophenyl)-2-((2-ethyl-5-(4-(2-(3-hydroxyazetidin-1-yl)-2-oxoethyl) piperazin-1-yl) pyrazolo[1,5-a]pyrimidin-3-yl)(methyl)amino)thiazole-5-carbonitrile.

14. A pharmaceutical composition, comprising the heterocyclic compound of formula I or the pharmaceutically acceptable salt thereof according to claim 1, and a pharmaceutical excipient.

* * * * *